(12) United States Patent
Jung et al.

(10) Patent No.: US 11,450,806 B2
(45) Date of Patent: Sep. 20, 2022

(54) COMPOSITION FOR ORGANIC OPTOELECTRONIC ELEMENT, ORGANIC OPTOELECTRONIC ELEMENT, AND DISPLAY DEVICE

(71) Applicant: SAMSUNG SDI CO., LTD., Yongin-si (KR)

(72) Inventors: Ho Kuk Jung, Suwon-si (KR); Giwook Kang, Suwon-si (KR); Eui Su Kang, Suwon-si (KR); Byungku Kim, Suwon-si (KR); Youngkwon Kim, Suwon-si (KR); Hun Kim, Suwon-si (KR); Eun Sun Yu, Suwon-si (KR); Sangshin Lee, Suwon-si (KR); Sung-Hyun Jung, Suwon-si (KR); Pyeongseok Cho, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 720 days.

(21) Appl. No.: 15/517,206

(22) PCT Filed: May 2, 2016

(86) PCT No.: PCT/KR2016/004610
§ 371 (c)(1),
(2) Date: Apr. 6, 2017

(87) PCT Pub. No.: WO2016/208865
PCT Pub. Date: Dec. 29, 2016

(65) Prior Publication Data
US 2017/0309829 A1    Oct. 26, 2017

(30) Foreign Application Priority Data

Jun. 26, 2015 (KR) .......................... 10-2015-0091331

(51) Int. Cl.
*H01L 51/00* (2006.01)
*C07D 403/10* (2006.01)
(Continued)

(52) U.S. Cl.
CPC ........ *H01L 51/0067* (2013.01); *C07D 209/86* (2013.01); *C07D 251/24* (2013.01);
(Continued)

(58) Field of Classification Search
None
See application file for complete search history.

(56) References Cited

U.S. PATENT DOCUMENTS

2011/0240983 A1    10/2011   Sekiguchi et al.
2011/0309338 A1*   12/2011   Iwakuma ............. C07D 401/04
                                                        257/40
(Continued)

FOREIGN PATENT DOCUMENTS

CN    101654430 A    2/2010
CN    103619986 A    3/2014
(Continued)

OTHER PUBLICATIONS

Chinese Office Action dated Oct. 8, 2018, of the corresponding Patent Application No. 201680003688.6.

*Primary Examiner* — Jay Yang
(74) *Attorney, Agent, or Firm* — Lee IP Law, P.C.

(57) ABSTRACT

The present invention relates to: a composition for an organic optoelectronic element, containing at least one first compound represented by chemical formula 1, at least one second compound among compounds represented by chemical formula 2 and compounds composed of combinations of moieties represented by chemical formula 3 and moieties represented by chemical formula 4, and at least one third compound represented by chemical formula 5; an organic
(Continued)

optoelectronic element comprising the same; and a display device comprising the organic optoelectronic element. Chemical formulas 1 to 5 are as described in the specification.

14 Claims, 1 Drawing Sheet

(51) Int. Cl.
  *C07D 495/04* (2006.01)
  *C09K 11/06* (2006.01)
  *H01L 51/50* (2006.01)
  *C07D 209/86* (2006.01)
  *C07D 251/24* (2006.01)

(52) U.S. Cl.
  CPC ......... *C07D 403/10* (2013.01); *C07D 495/04* (2013.01); *C09K 11/06* (2013.01); *H01L 51/0054* (2013.01); *H01L 51/0071* (2013.01); *H01L 51/0072* (2013.01); *C09K 2211/1007* (2013.01); *C09K 2211/1011* (2013.01); *C09K 2211/1018* (2013.01); *C09K 2211/1029* (2013.01); *C09K 2211/185* (2013.01); *H01L 51/0052* (2013.01); *H01L 51/0058* (2013.01); *H01L 51/0061* (2013.01); *H01L 51/0085* (2013.01); *H01L 51/5016* (2013.01); *H01L 2251/308* (2013.01); *H01L 2251/5384* (2013.01)

(56) References Cited

U.S. PATENT DOCUMENTS

| | | | |
|---|---|---|---|
| 2015/0207082 A1* | 7/2015 | Dyatki | ................ H01L 51/0071 257/40 |
| 2016/0126472 A1* | 5/2016 | Oh | ....................... C07D 251/24 257/40 |

FOREIGN PATENT DOCUMENTS

| | | | |
|---|---|---|---|
| KR | 10-2010-0131745 | A | 12/2010 |
| KR | 10-2012-0116282 | A | 10/2012 |
| KR | 10-2014-0014959 | A | 2/2014 |
| KR | 10-2014-0135525 | A | 11/2014 |
| KR | 10-2015-0028579 | A | 3/2015 |
| KR | 10-2015-0083787 | A | 3/2015 |
| KR | 10-2016-0150000 | A | 12/2016 |
| TW | 201444951 | A | 12/2014 |
| TW | I500604 | B | 9/2015 |
| WO | WO 2010-067894 | A1 | 6/2010 |
| WO | WO 2012-163465 | A1 | 12/2012 |
| WO | WO 2014-185595 | A1 | 11/2014 |
| WO | WO 2015-034125 | A1 | 3/2015 |

* cited by examiner

[Figure 1]
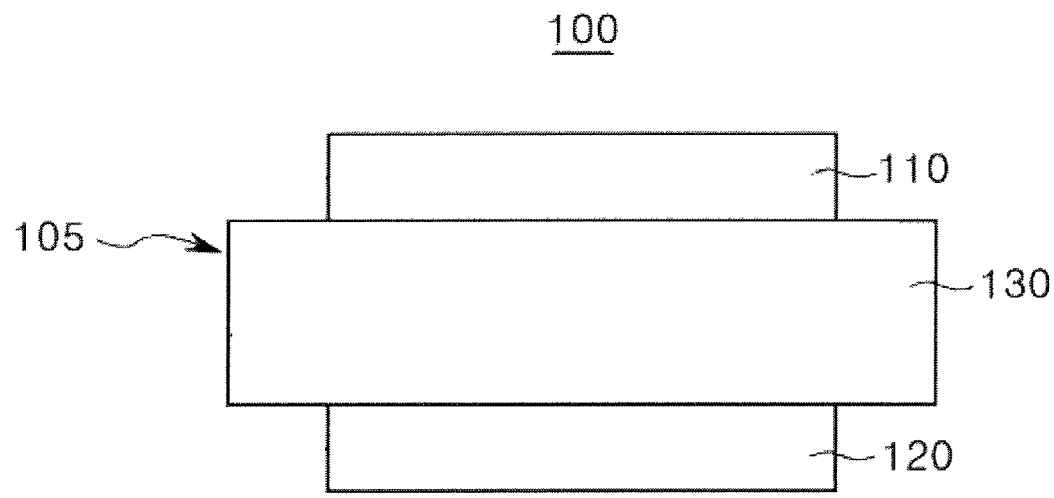
[Figure 2]
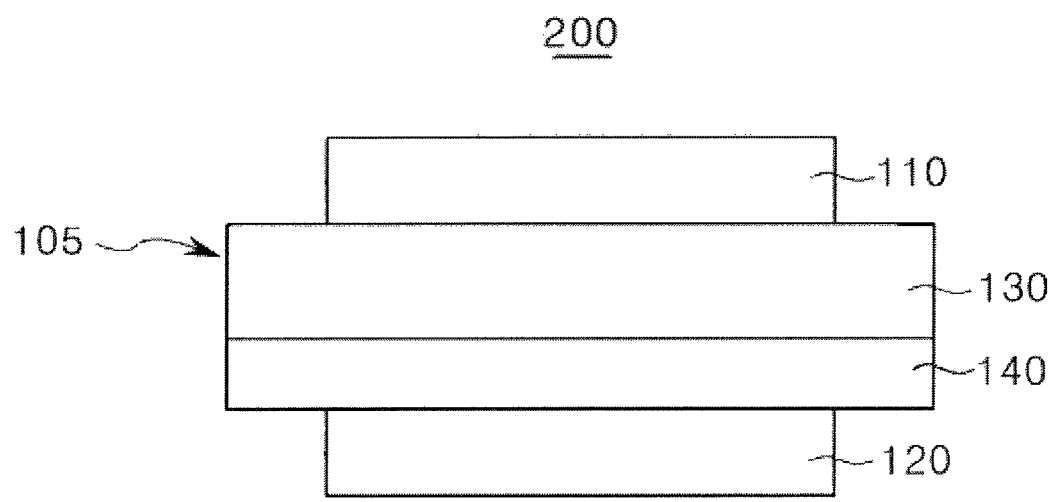

COMPOSITION FOR ORGANIC OPTOELECTRONIC ELEMENT, ORGANIC OPTOELECTRONIC ELEMENT, AND DISPLAY DEVICE

CROSS REFERENCE TO RELATED APPLICATIONS

This is the U.S. national phase application based on PCT Application No. PCT/KR2016/004610 filed, filed May 2, 2016, which is based on Korean Patent Application No. 10-2015-0091331, filed Jun. 26, 2015, the entire contents of all of which are hereby incorporated by reference.

TECHNICAL FIELD

A composition for an organic optoelectronic device, an organic optoelectronic device and a display device are disclosed.

BACKGROUND ART

An organic optoelectronic device is a device that converts electrical energy into photoenergy, and vice versa. An organic optoelectronic device may be classified as follows in accordance with its driving principles. One is an optoelectronic device where excitons are generated by photoenergy, separated into electrons and holes, and are transferred to different electrodes to generate electrical energy, and the other is a light emitting device where a voltage or a current is supplied to an electrode to generate photoenergy from electrical energy. Examples of the organic optoelectronic device may be an organic photoelectric device, an organic light emitting diode, an organic solar cell, and an organic photo conductor drum. Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode. Efficiency of a light emitting diode is considered to be one of the critical factors for realizing a long life-span full color display. Accordingly, development of a high efficient organic light emitting diode using a phosphorescent material has been actively researched. In the present invention, in order to solve this problem, an organic light emitting diode using a high efficient phosphorescent material is provided.

DISCLOSURE

Technical Problem

An embodiment provides a composition for an organic optoelectronic device having high efficiency and long life-span characteristics.

Another embodiment provides an organic optoelectronic device including the composition for an organic optoelectronic device.

Yet another embodiment provides a display device including the organic optoelectronic device.

Technical Solution

According to an embodiment, a composition for an organic optoelectronic device includes at least one first compound represented by Chemical Formula 1, at least one second compound selected from a compound represented by Chemical Formula 2, and a compound consisting of a combination of a moiety represented by Chemical Formula 3 and a moiety represented by Chemical Formula 4, and at least one third compound represented by Chemical Formula 5.

[Chemical Formula 1]

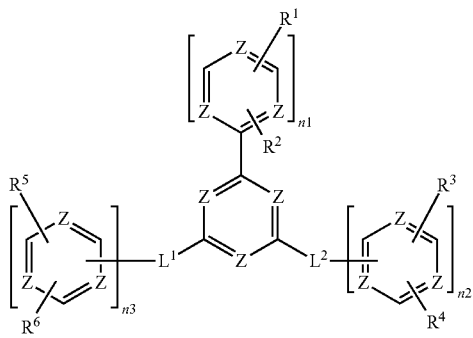

In Chemical Formula 1,
Z is independently N, C, or $CR^a$,
at least one of Z is N,
$R^1$ to $R^6$ and $R^a$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof,
$R^1$ to $R^6$ and $R^a$ are independently present or adjacent groups are linked to each other to form a ring,
$L^1$ and $L^2$ are independently a single bond, a substituted or unsubstituted C6 to C30 arylene group, a substituted or unsubstituted C2 to C30 heteroarylene group, or a combination thereof,
n1 is 1,
n2 and n3 are independently an integer of 0 or 1, and
$1 \leq n2+n3 \leq 2$;

[Chemical Formula 2]

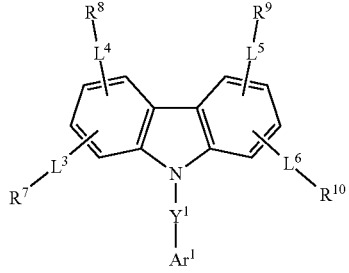

wherein, in Chemical Formula 2,
$L^3$ to $L^6$ and $Y^1$ are independently, a single bond, a substituted or unsubstituted C6 to C30 arylene group, a substituted or unsubstituted C2 to C30 heteroarylene group, or a combination thereof,
$Ar^1$ is a substituted or unsubstituted C6 to C30 aryl group, a substituted or unsubstituted C2 to C30 heterocyclic group, or a combination thereof,
$R^7$ to $R^{10}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and at least one of $R^7$ to $R^{10}$ and $Ar^1$ includes a substituted or unsubstituted triphenylene group or a substituted or unsubstituted carbazole group,

[Chemical Formula 3]

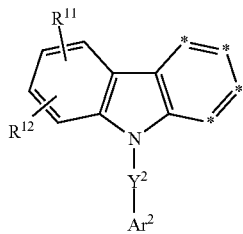

[Chemical Formula 4]

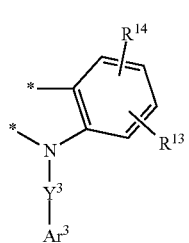

wherein, in Chemical Formulae 3 and 4, $Y^2$ and $Y^3$ are independently a single bond, a substituted or unsubstituted C6 to C30 arylene group, a substituted or unsubstituted C2 to C30 heteroarylene group, or a combination thereof, $Ar^2$ and $Ar^3$ are independently substituted or unsubstituted C6 to C30 aryl group, a substituted or unsubstituted C2 to C30 heterocyclic group, or a combination thereof, $R^{11}$ to $R^{14}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, two adjacent *'s of Chemical Formula 3 is combined with two *'s of Chemical Formula 4 to form a fused ring and in Chemical Formula 3, *'s not forming the fused ring are independently $CR^c$, and $R^c$ is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;

[Chemical Formula 5]

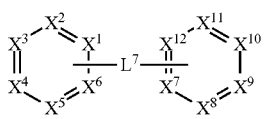

wherein, in Chemical Formula 5, $X^1$ to $X^{12}$ are independently N, C or $CR^d$, at least one of $X^1$ to $X^6$ is N, at least one of $X^7$ to $X^{12}$ is N, $R^d$ is independently, hydrogen, deuterium, a substituted or unsubstituted C1 to C30 alkyl group, a substituted or unsubstituted C1 to C30 alkenyl group, a substituted or unsubstituted C1 to C30 alkynyl group, a substituted or unsubstituted C6 to C30 aryl group, a substituted or unsubstituted C6 to C30 aryloxy group, a substituted or unsubstituted C6 to C30 arylthio group, a substituted or unsubstituted C2 to C30 heterocyclic group, a hydroxyl group, thiol group, or a combination thereof, $R^d$ is independently present, or adjacent $R^d$'s are linked to each other to form a ring, $L^7$ is a single bond, a substituted or unsubstituted C6 to C30 arylene group, a substituted or unsubstituted C2 to C30 heteroarylene group, or a combination thereof, and the "substituted" refers to replacement of at least one hydrogen by deuterium, a halogen, a hydroxyl group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group. According to another embodiment, an organic optoelectronic device including the composition for an organic optoelectronic device is provided. Yet according to another embodiment, a display device including the organic optoelectronic device is provided.

Advantageous Effects

An organic optoelectronic device having high efficiency and long life-span may be realized.

DESCRIPTION OF THE DRAWINGS

FIGS. 1 and 2 are cross-sectional views showing organic light emitting diodes according to an embodiment.

DESCRIPTION OF SYMBOLS

100, 200: organic light emitting diode
105: organic layer
110: cathode
120: anode
130: emission layer
140: auxiliary layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, the term "substituted" refers to one substituted with a substituent selected from deuterium, a halogen, a hydroxyl group, an amino group, a C1 to C30 amine group, a nitro group, a C1 to C40 silyl group, a C1 to C30 alkyl group, a C1 to C30 alkenyl group, a C1 to C30 alkynyl group, a C1 to C10 alkylsilyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group such as a trifluoromethyl group, or a cyano group, instead of at least one hydrogen of a substituent or a compound.

In addition, two adjacent substituents of the substituted C1 to C30 amine group, C1 to C40 silyl group, C1 to C30 alkyl group, C1 to C10 alkylsilyl group, C3 to C30 cycloalkyl group, C2 to C30 heterocycloalkyl group, C6 to C30 aryl group, C2 to C30 heterocyclic group, or C1 to C20 alkoxy group may be linked with each other to form a fused ring. For example, the substituted C6 to C30 aryl group may be linked with another adjacent substituted C6 to C30 aryl group to form a substituted or unsubstituted fluorene ring, or the substituted C6 to C30 aryl group may be linked with adjacent substituted C1 to C30 alkenyl group to form a triphenylene ring, a naphthalene ring, a pyrazine ring, a quinazoline ring, a quinoxaline ring, a phenanthroline ring, and the like.

In the present specification, when specific definition is not otherwise provided, the term "hetero" refers to one including 1 to 3 hetero atoms selected from N, O, S, P, and Si, and remaining carbons in one compound or substituent.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one hetero atom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to aryl group including at least one hetero atom selected from N, O, S, P, and Si instead of carbon (C). Two or more heteroaryl groups are linked by a sigma bond directly, or when the C2 to C60 heteroaryl group includes two or more rings, the two or more rings may be fused. When the heteroaryl group is a fused ring, each ring may include 1 to 3 hetero atoms.

Specific examples of the heteroaryl group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C50 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but are not limited thereto.

In the present specification, the single bond refers to a direct bond not by carbon or a hetero atom except carbon, and specifically the meaning that L is a single bond means that a substituent linked to L directly bonds with a central core. That is, in the present specification, the single bond does not refer to methylene that is bonded via carbon.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

Hereinafter, a composition for an organic optoelectronic device according to an embodiment is described.

A composition for an organic optoelectronic device according to an embodiment includes at least one first compound represented by Chemical Formula 1, at least one second compound selected from a compound represented by Chemical Formula 2, and a compound consisting of a combination of a moiety represented by Chemical Formula 3 and a moiety represented by Chemical Formula 4 and at least one third compound represented by Chemical Formula 5.

[Chemical Formula 1]

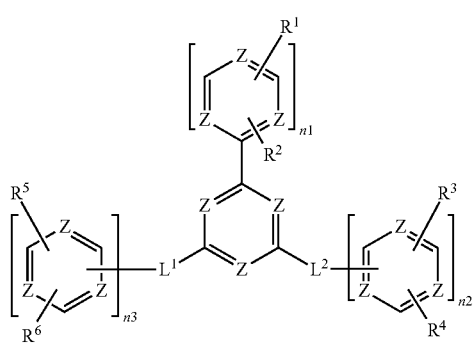

In Chemical Formula 1, Z is independently N, C, or $CR^a$, at least one of Z is N, $R^1$ to $R^6$ and $R^a$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^1$ to $R^6$ and $R^a$ are independently present or adjacent groups are linked to each other to form a ring, $L^1$ and $L^2$ are independently a single bond, a substituted or unsubstituted C6 to C30 arylene group, a substituted or unsubstituted C2 to C30 heteroarylene group, or a combination thereof, n1 is 1, n2 and n3 are independently an integer of 0 or 1, and $1 \leq n2+n3 \leq 2$;

[Chemical Formula 2]

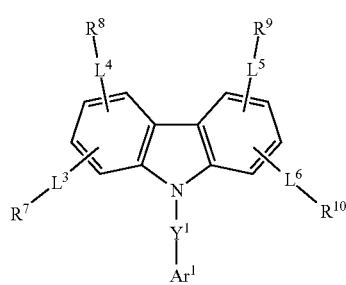

wherein, in Chemical Formula 2, $L^3$ to $L^6$ and $Y^1$ are independently, a single bond, a substituted or unsubstituted C6 to C30 arylene group, a substituted or unsubstituted C2 to C30 heteroarylene group, or a combination thereof, $Ar^1$ is a substituted or unsubstituted C6 to C30 aryl group, a substituted or unsubstituted C2 to C30 heterocyclic group, or a combination thereof, $R^7$ to $R^{10}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and at least one of $R^7$ to $R^{10}$ and $Ar^1$ includes a substituted or unsubstituted triphenylene group or a substituted or unsubstituted carbazole group,

[Chemical Formula 3]

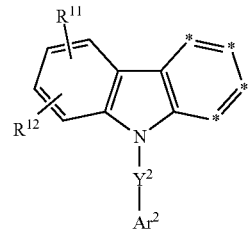

[Chemical Formula 4]

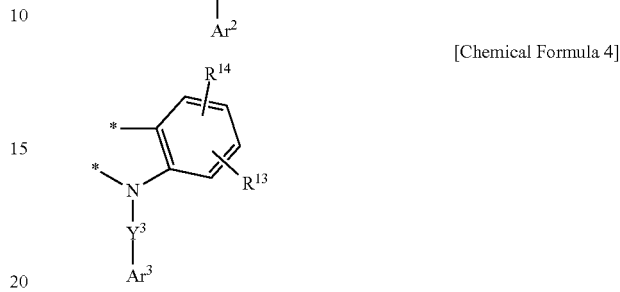

wherein, in Chemical Formulae 3 and 4, $Y^2$ and $Y^3$ are independently a single bond, a substituted or unsubstituted C6 to C30 arylene group, a substituted or unsubstituted C2 to C30 heteroarylene group, or a combination thereof, $Ar^2$ and $Ar^3$ are independently substituted or unsubstituted C6 to C30 aryl group, a substituted or unsubstituted C2 to C30 heterocyclic group, or a combination thereof, $R^{11}$ to $R^{14}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, two adjacent *'s of Chemical Formula 3 is combined with two *'s of Chemical Formula 4 to form a fused ring and in Chemical Formula 3, *'s not forming the fused ring are independently $CR^c$, $R^c$ is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;

[Chemical Formula 5]

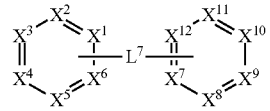

wherein, in Chemical Formula 5, $X^1$ to $X^{12}$ are independently N, C or $CR^d$, at least one of $X^1$ to $X^6$ is N, at least one of $X^7$ to $X^{12}$ is N, $R^d$ is independently, hydrogen, deuterium, a substituted or unsubstituted C1 to C30 alkyl group, a substituted or unsubstituted C1 to C30 alkenyl group, a substituted or unsubstituted C1 to C30 alkynyl group, a substituted or unsubstituted C6 to C30 aryl group, a substituted or unsubstituted C6 to C30 aryloxy group, a substituted or unsubstituted C6 to C30 arylthio group, a substituted or unsubstituted C2 to C30 heterocyclic group, a hydroxyl group, thiol group, or a combination thereof, $R^d$ is independently present, or adjacent $R^d$'s are linked to each other to form a ring, $L^7$ is a single bond, a substituted or unsubstituted C6 to C30 arylene group, a substituted or unsubstituted C2 to C30 heteroarylene group, or a combination thereof, and "substituted" of Chemical Formulae 1 to 5 refers to replacement of at least one hydrogen by deuterium, a halogen, a hydroxyl group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, C1 to C20 alkoxy group, a C1 to C10 trifluoroalkyl group, or a cyano group.

The first compound may include a ring containing at least one nitrogen and thereby has a structure easily receiving electrons when an electric field is applied thereto and accordingly, may increase the injection amount of electrons and have bipolar characteristics in which electron characteristics are relatively strong. The second compound may include a carbazole moiety and thereby may have bipolar characteristics in which hole characteristics are relatively strong.

When the first compound along with the second compound is used to form an emission layer, the first compound may increase charge mobility and stability and resultantly, improve luminous efficiency and life-span characteristics.

On the other hand, the the first compound has a problem of sharply deteriorating electron transport capability due to a trap phenomenon according to a HOMO energy level difference between a dopant and a host and thus increasing a driving voltage of the organic optoelectronic device.

Accordingly, the third compound having excellent electron injection and electron transport capability may be added thereto to decrease or minimize the trap phenomenon between a dopant and a host and resultantly not only sharply lower the driving voltage of the organic optoelectronic device but also provide an organic optoelectronic device having excellent efficiency and life-span.

The third compound having excellent electron injection and electron transport capability may solve the problem of the driving voltage increase that happens when only the first and second compounds are included and thus effectively improve power efficiency performance of the device.

$L^1$ and $L^2$ of Chemical Formula 1 according to an embodiment of the present invention may independently be a single bond, a substituted or unsubstituted C6 to C30 arylene group, a substituted or unsubstituted C2 to C30 heteroarylene group as described above, and specifically a substituted or unsubstituted C6 to C30 arylene group. For example, $L^1$ and $L^2$ may be a single bond, a substituted or unsubstituted phenylene group, a substituted or unsubstituted biphenylene group, a substituted or unsubstituted terphenylene group, a substituted or unsubstituted quarterphenylene group, a substituted or unsubstituted naphthylene group, a substituted or unsubstituted anthracenylene group, a substituted or unsubstituted triphenylenyl group, or a substituted or unsubstituted phenanthrenylene group.

Specific structures of the linking group are the same as Group 2 in the present specification.

$R^1$ and $R^2$ of Chemical Formula 1 according to an embodiment of the present invention are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof as described above, specifically, they may be hydrogen, deuterium, or a substituted or unsubstituted C6 to C30 aryl group. For example, $R^1$ and $R^2$ may independently be selected from hydrogen, a substituted or unsubstituted phenyl group, or a substituted or unsubstituted biphenyl group, or a combination thereof, but are not limited thereto.

$R^3$ to $R^6$ of Chemical Formula 1 according to an embodiment of the present invention may be hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof as described above, and $R^3$ to $R^6$ may independently be present or adjacent groups are linked to each other to form a fused ring, specifically, they may be hydrogen, deuterium, a substituted or unsubstituted C6 to C30 aryl group, or a substituted or unsubstituted C2 to C30 heteroaryl group, examples of the substituted or unsubstituted C6 to C30 aryl group may be a substituted or unsubstituted phenyl group, a substituted or unsubstituted biphenyl group, a substituted or unsubstituted quarterphenyl group, a substituted or unsubstituted naphthyl group, a substituted or unsubstituted phenanthrenyl group, or a combination thereof, and examples of the the substituted or unsubstituted C2 to C30 heteroaryl group may be a substituted or unsubstituted pyridinyl group, a substituted or unsubstituted pyrimidinyl group, a substituted or unsubstituted quinolinyl group, a substituted or unsubstituted isoquinolinyl group, a substituted or unsubstituted quinazolinyl group, a substituted or unsubstituted phenanthrolinyl group, or a combination thereof.

Adjacent groups of $R^3$ to $R^6$ may be linked to each other to form a substituted or unsubstituted naphthyl group, a substituted or unsubstituted quinolinyl group, a substituted or unsubstituted isoquinolinyl group, a substituted or unsubstituted quinazolinyl group, a substituted or unsubstituted phenanthrolinyl group, a substituted or unsubstituted triphenylenyl group, and the like.

Specific examples of the $R^3$ to $R^6$ may be hydrogen, or may be selected from substituents of Group 1 but are not limited thereto.

For example, the first compound may be represented by one of Chemical Formula 1-I to Chemical Formula 1-III.

[Chemical Formula 1-II]

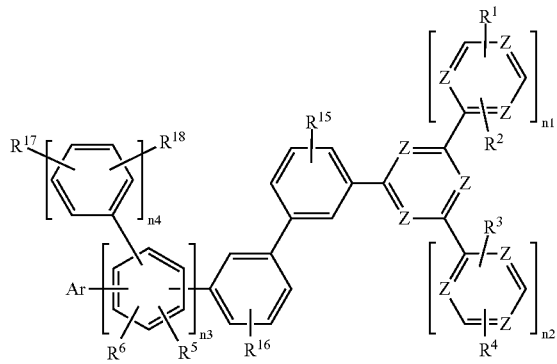

According to an embodiment, Chemical Formula 1-I may be represented by one of Chemical Formulae 1-IA to 1-IC.

[Chemical Formula 1-II]

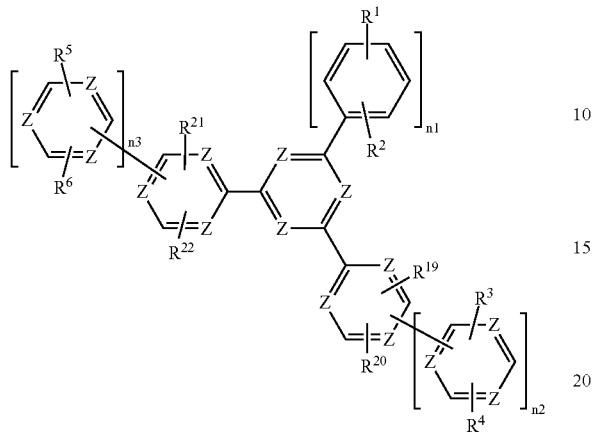

[Chemical Formula 1-IA]

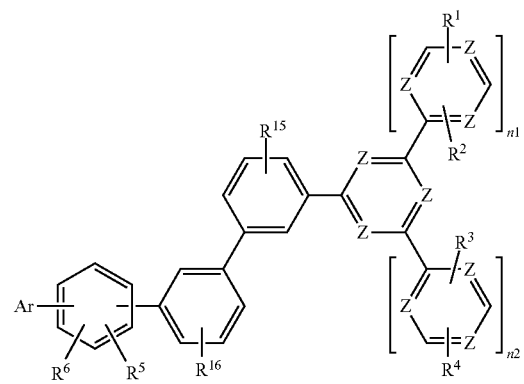

[Chemical Formula 1-III]

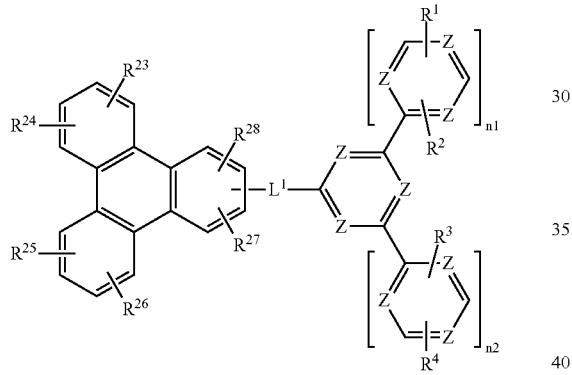

[Chemical Formula 1-IB]

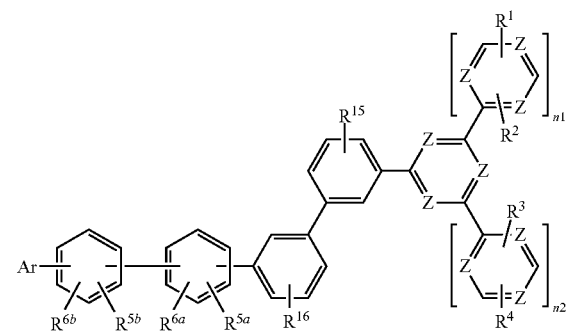

[Chemical Formula 1-IC]

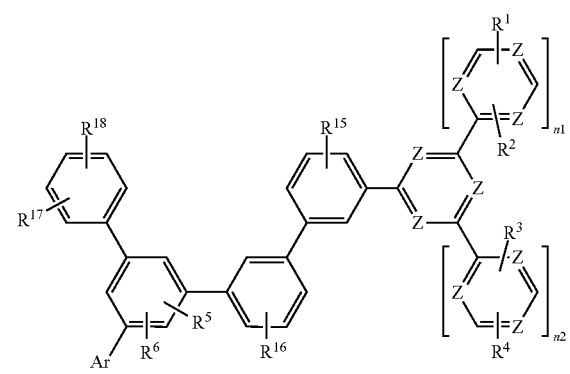

In Chemical Formulae 1-I to 1-III, Z, $R^1$ to $R^6$, $L^1$ and n1 to n3 are the same as defined above, $R^{15}$ to $R^{28}$ are independently hydrogen, deuterium, a substituted or unsubstituted C1 to C10 alkyl group, a substituted or unsubstituted C6 to C12 aryl group, a substituted or unsubstituted C2 to C30 heteroaryl group, or a combination thereof, Ar is a substituted or unsubstituted C6 to C30 aryl group, a substituted or unsubstituted C2 to C30 heterocyclic group, or a combination thereof, $R^1$ to $R^6$, $R^a$, $R^{17}$, and $R^{18}$ are independently present or adjacent groups are linked to each other to form a ring, n4 is an integer ranging from 0 to 2, and "substituted" is the same as defined above.

According to an embodiment, in Chemical Formula 1 and Chemical Formulae 1-I to 1-III, at least two Z which are not included in [ ] n1, [ ] n2 and [ ] n3 are "N" (nitrogen atom). For example, in Chemical Formula 1 and Chemical Formulae 1-I to 1-III, all of three Z which are not included in [ ] n1, [ ] n2 and [ ] n3 are "N" (nitrogen atom).

In Chemical Formulae 1-IA to 1-IC, Z, $R^1$ to $R^6$, $R^{15}$ to $R^{18}$, n1 and n2 are the same as above, $R^{5a}$ and $R^{5b}$, $R^{6a}$ and $R^{6b}$ and Ar are the same as $R^5$ and $R^6$, and "substituted" is the same as defined above.

Specifically, herein Ar is a substituted or unsubstituted C6 to C30 aryl group, a substituted or unsubstituted C2 to C30 heterocyclic group, or a combination thereof.

Specifically, Chemical Formula 1-IA may be represented by Chemical Formula 1-I-1a or 1-I-2a according to a substituting position of Ar, but is not limited thereto.

[Chemical Formula 1-I-1a]
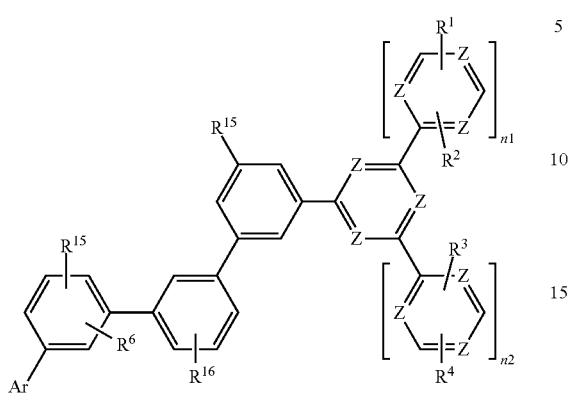
[Chemical Formula 1-I-2a]
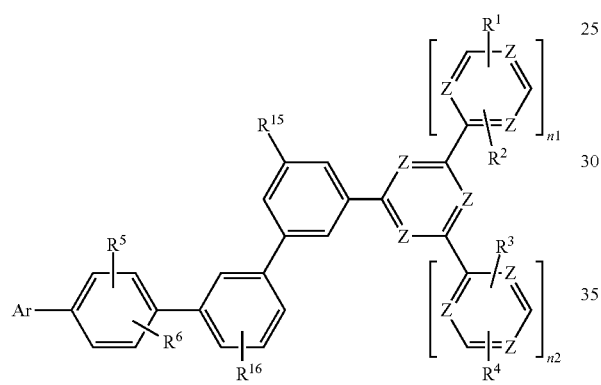
Specifically, Chemical Formula 1-IB may be represented by Chemical Formulae 1-I-1 b to 1-I-7b according to a linking group of aryl group moiety and Substituting position of Ar, but is not limited thereto.
[Chemical Formula 1-I-1b]
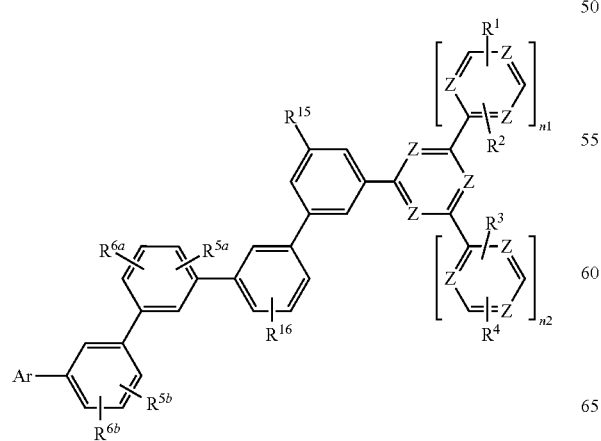
[Chemical Formula 1-I-2b]
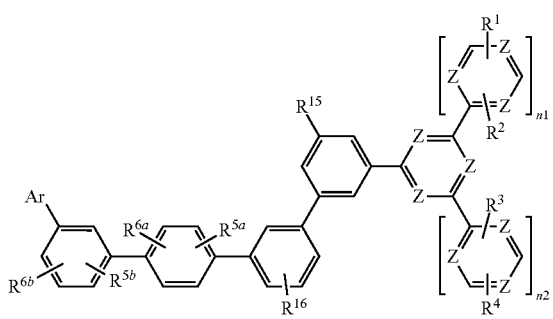
[Chemical Formula 1-I-3b]
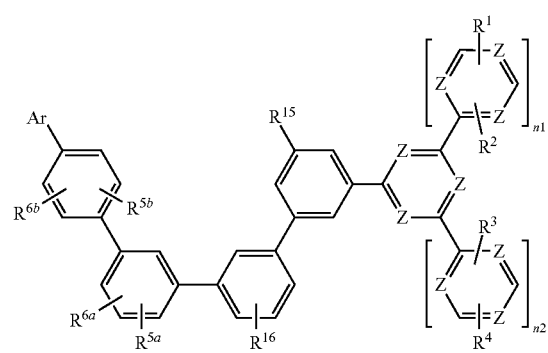
[Chemical Formula 1-I-4b]
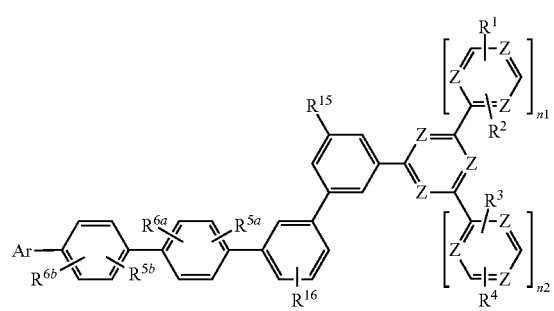
[Chemical Formula 1-I-5b]
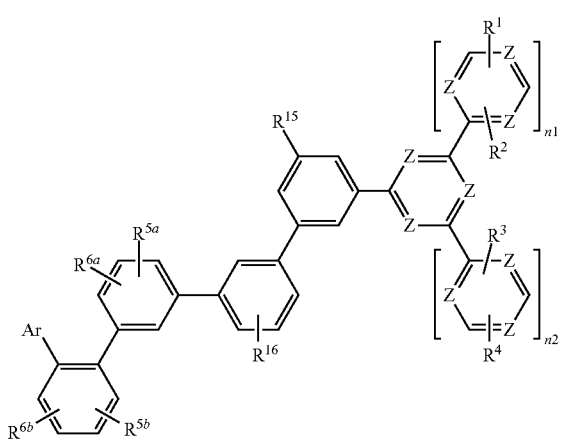

[Chemical Formula 1-I-6b]

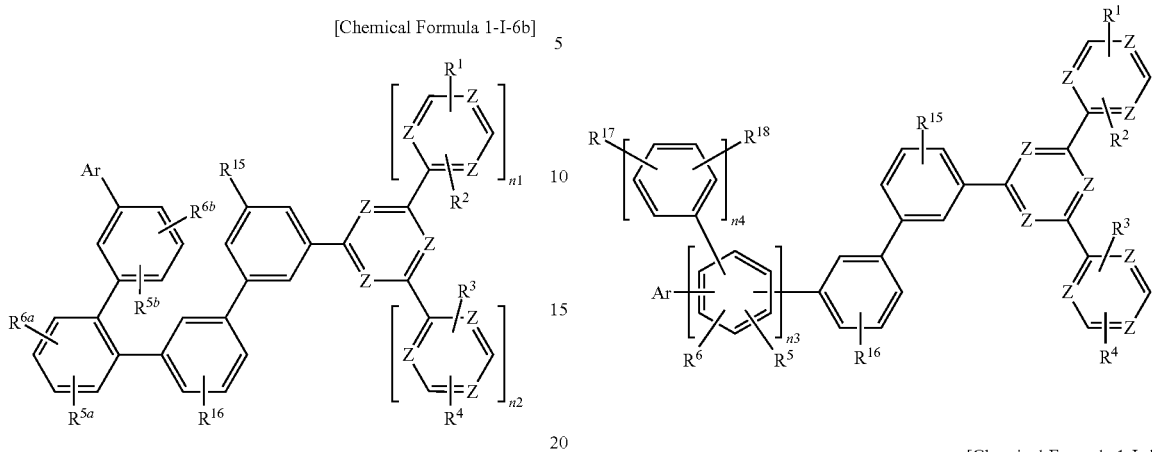

[Chemical Formula 1-I-7b]

[Chemical Formula 1-I-c]

[Chemical Formula 1-I-d]

Specifically, Chemical Formula 1-IC may be represented by Chemical Formula 1-I-1c where a linking position of R$^{15}$ is fixed, but is not limited thereto.

[Chemical Formula 1-I-1c]

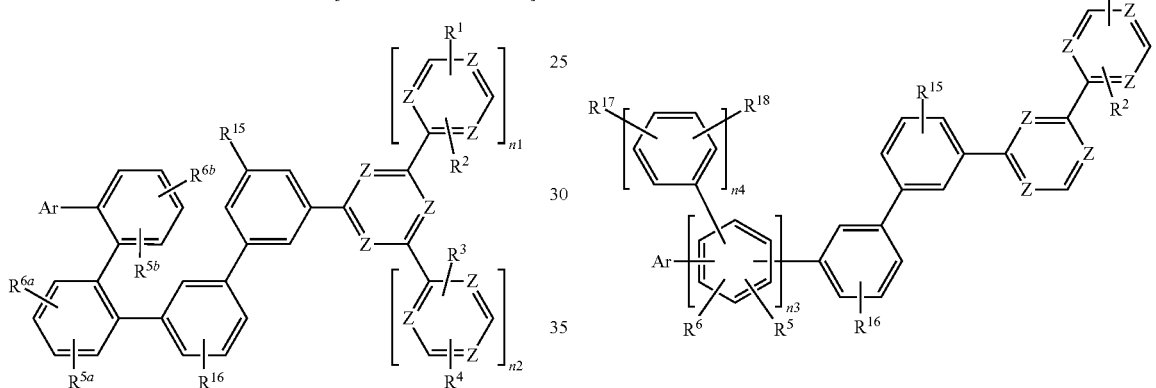

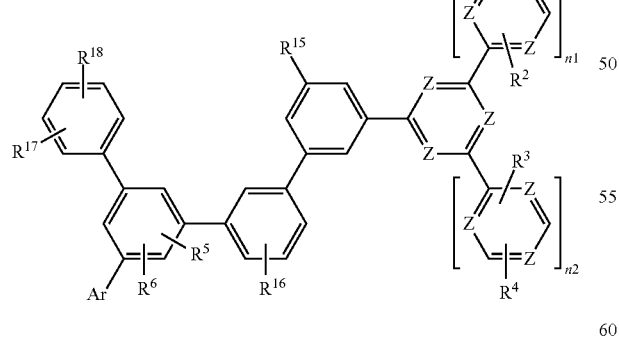

In Chemical Formulae 1-I-1a to 1-I-2a, 1-I-1 b to 1-I-7b and 1-I-1c, Z, R$^1$ to R$^6$, R$^{5a}$, R$^{5b}$, R$^{6a}$, R$^{6b}$, R$^{15}$ to R$^{18}$, n1, n2, and Ar are the same as described above.

Meanwhile, in Chemical Formula 1-I, n1 may be, for example an integer of 1 and n2 is an integer of 1 and Chemical Formula 1-1 may be represented by Chemical Formulae 1-I-c or 1-I-d, but is not limited thereto.

The Ar may be, for example, a substituted or unsubstituted phenyl group, a substituted or unsubstituted biphenyl group, a substituted or unsubstituted terphenyl group, a substituted or unsubstituted naphthyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted phenanthrolinyl group, or a substituted or unsubstituted quinazolinyl group.

More specifically, the Ar may be selected from substituted or unsubstituted groups of Group 1 but is not limited thereto.

[Group 1]

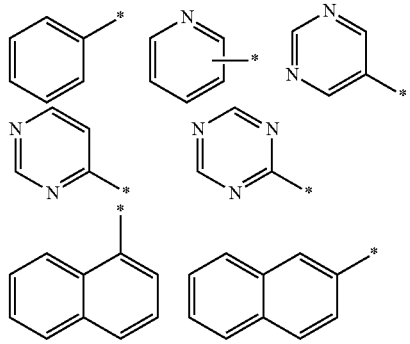

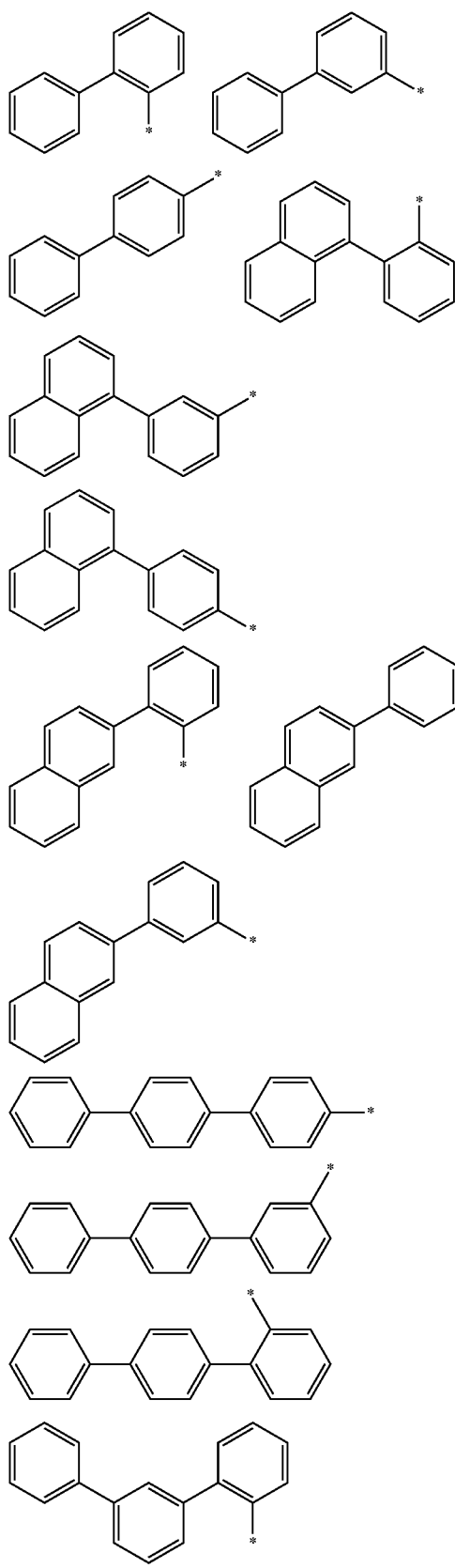
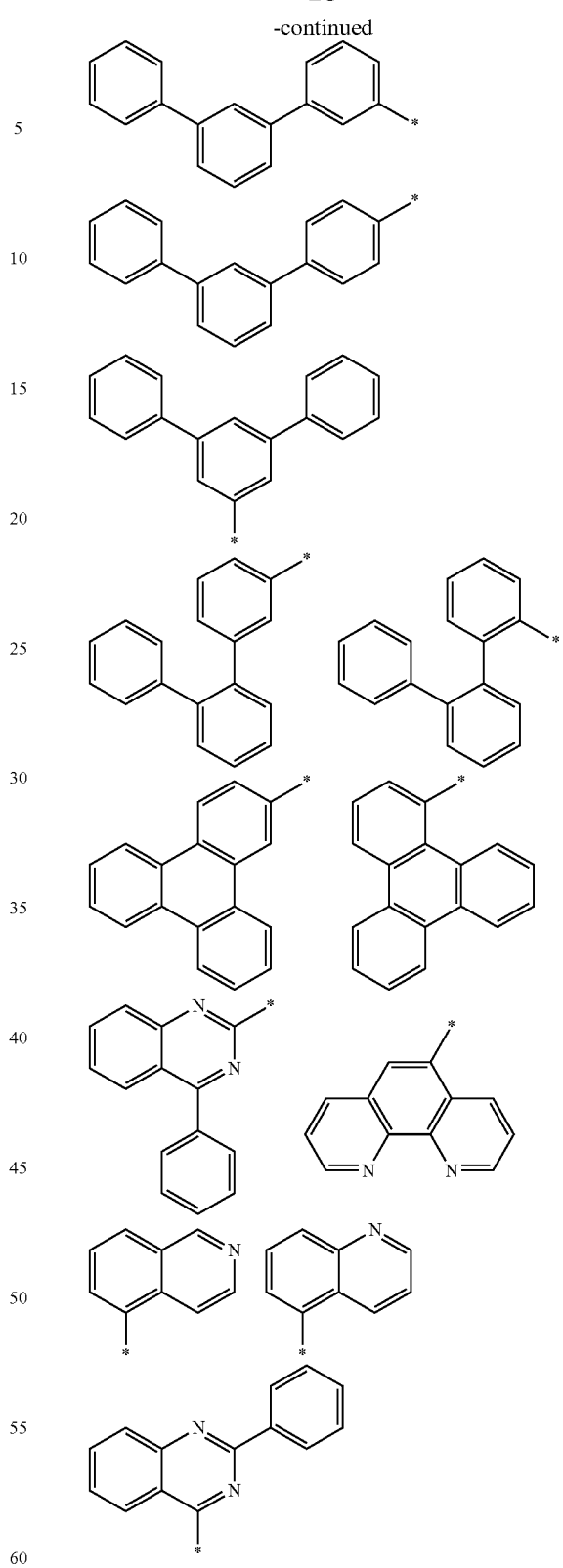
In Group 1, * is a linking point.
Chemical Formula 1-I may be, for example represented by one of Chemical Formulae 1-I-e to 1-I-n according to a position and the number of nitrogen, but is not limited thereto.

[Chemical Formula 1-I-e]
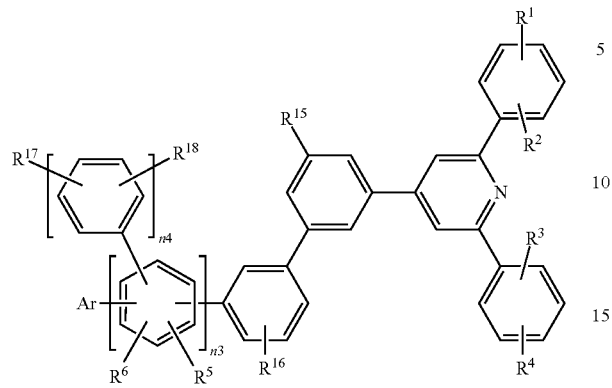
[Chemical Formula 1-I-f]
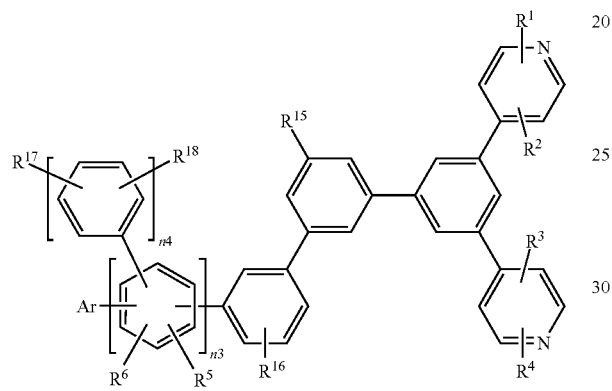
[Chemical Formula 1-I-g]
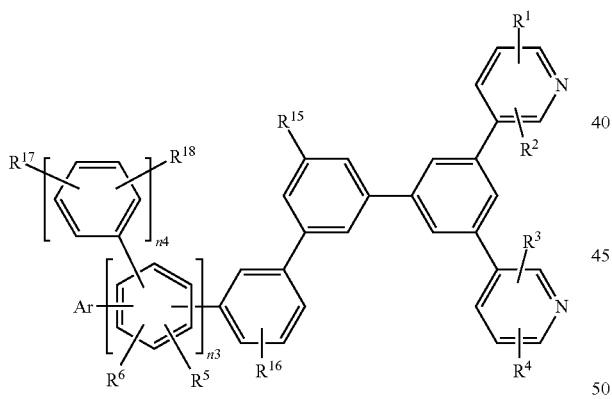
[Chemical Formula 1-I-h]
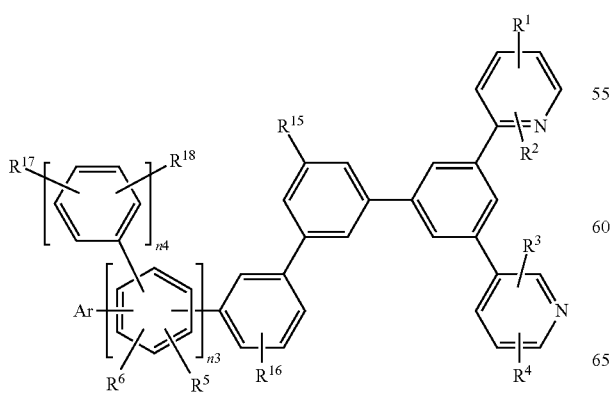
[Chemical Formula 1-I-i]
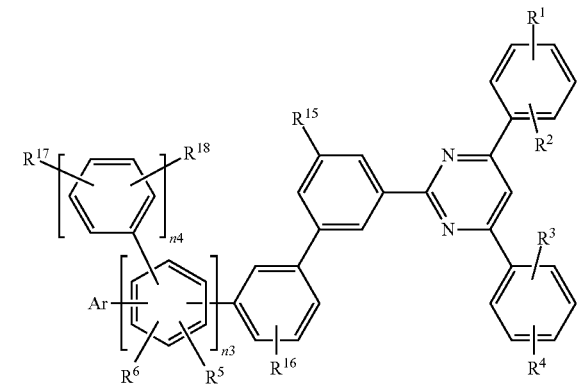
[Chemical Formula 1-I-j]
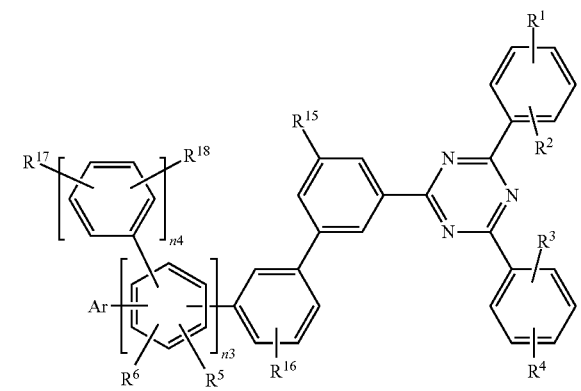
[Chemical Formula 1-I-k]
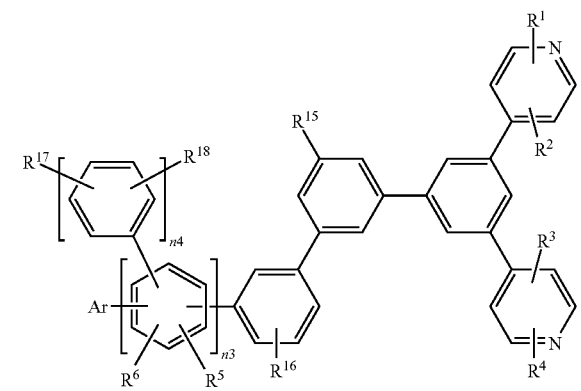
[Chemical Formula 1-I-l]
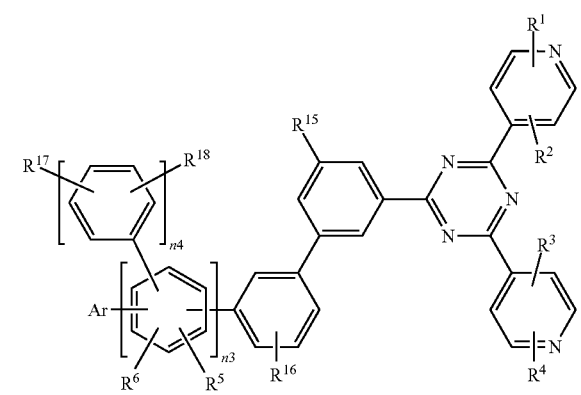

[Chemical Formula 1-I-m]

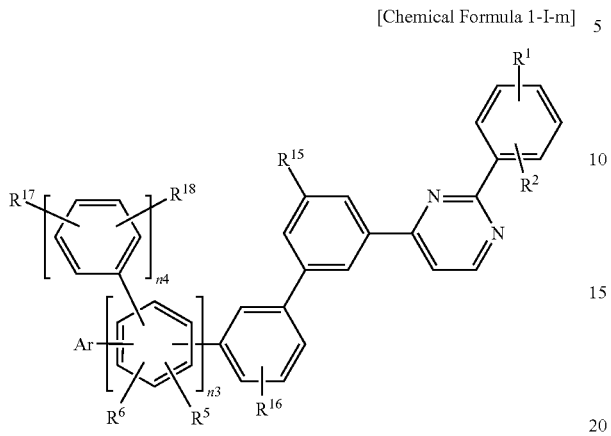

[Chemical Formula 1-I-n]

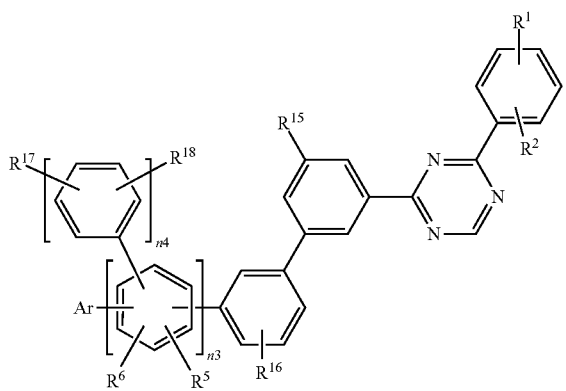

In Chemical Formulae 1-I-e to 1-1-n, $R^1$ to $R^6$, $R^{15}$ to $R^{18}$, Ar, and n1 to n4 are the same as described above.

According to an embodiment, Chemical Formula 1-I may be represented by Chemical Formula 1-IIA or 1-IIB.

[Chemical Formula 1-IIA]

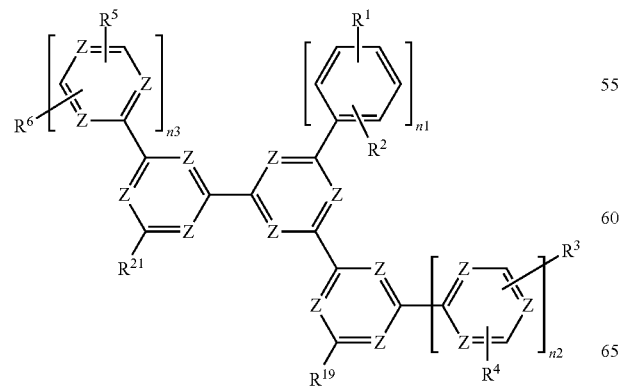

[Chemical Formula 1-IIB]

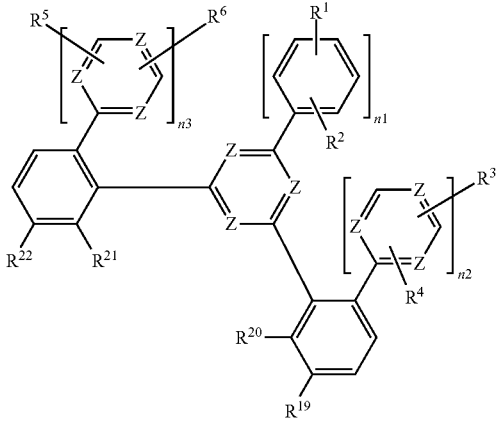

In Chemical Formulae 1-IIA and 1-IIB, Z, $R^1$ to $R^6$, $R^{19}$ to $R^{22}$, and n1 to n3 are the same as described above, specifically, $R^1$ and $R^2$ of Chemical Formula 1-II may be hydrogen, deuterium, or a substituted or unsubstituted C6 to C12 aryl group. For example, they may be hydrogen, but are not limited thereto.

Specifically, $R^3$ to $R^6$ of Chemical Formula 1-II may independently be a substituted or unsubstituted phenyl group, a substituted or unsubstituted biphenyl group, a substituted or unsubstituted terphenyl group, a substituted or unsubstituted naphthyl group, a substituted or unsubstituted pyridyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted phenanthrolinyl group, or a substituted or unsubstituted quinazolinyl group. For example, they may be selected from the substituted or unsubstituted groups of Group 1, but are not limited thereto.

Specifically, $R^{19}$ to $R^{22}$ of Chemical Formula 1-II may independently be hydrogen, a substituted or unsubstituted phenyl group, a substituted or unsubstituted biphenyl group, a substituted or unsubstituted naphthyl group, or a substituted or unsubstituted pyridyl group. For example, they may be selected from the substituted or unsubstituted groups of Group 1.

Herein, "substituted" is the same as defined above.

Chemical Formula 1-II may be, for example represented by one of Chemical Formulae 1-II-a to 1-II-h according to a position and the number of nitrogen, but is not limited thereto.

[Chemical Formula 1-II-a]

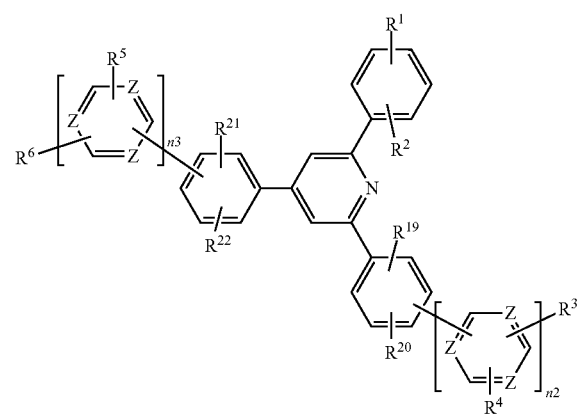

[Chemical Formula 1-II-b]
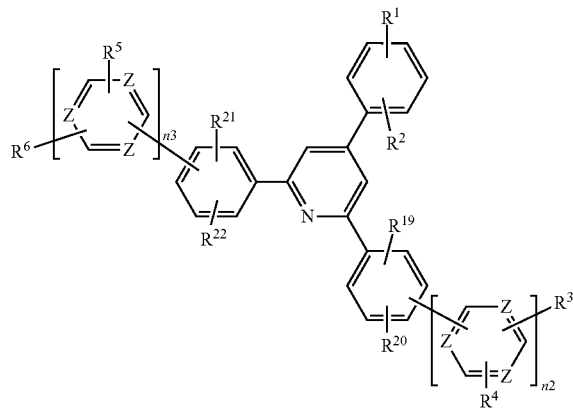
[Chemical Formula 1-II-c]
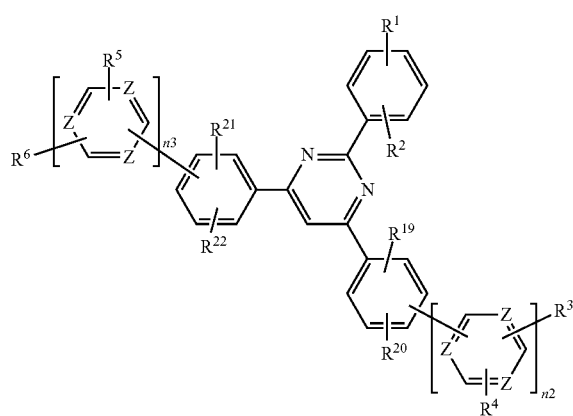
[Chemical Formula 1-II-d]
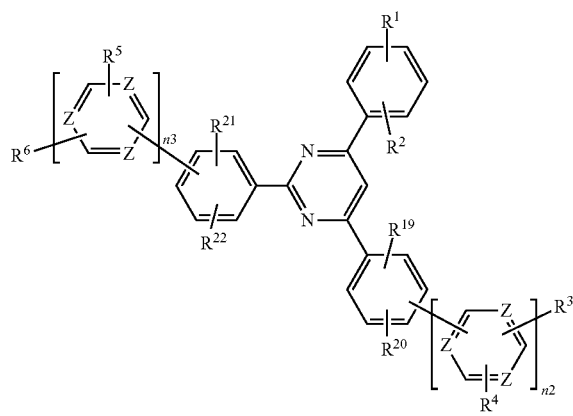
[Chemical Formula 1-II-e]
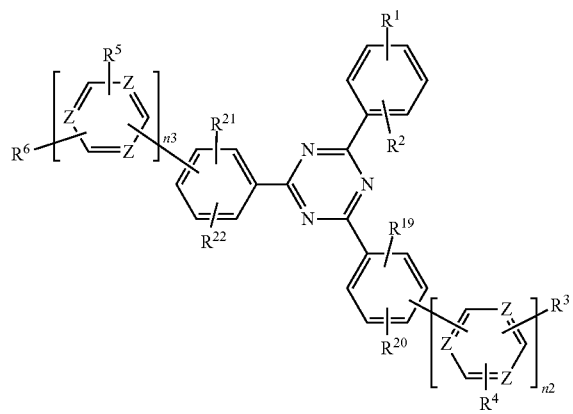
[Chemical Formula 1-II-f]
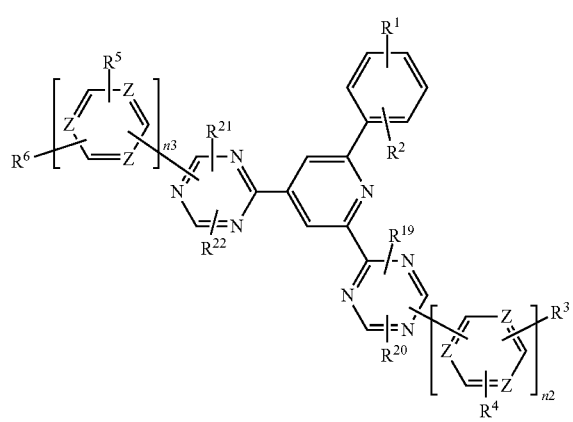
[Chemical Formula 1-II-g]
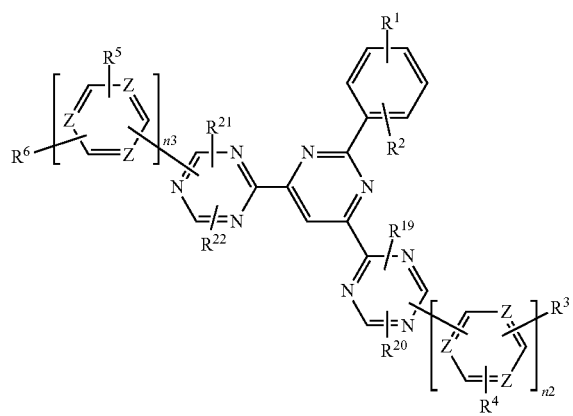

-continued

[Chemical Formula 1-II-h]

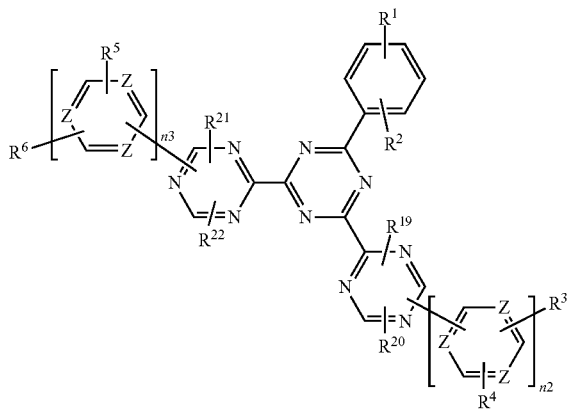

In Chemical Formulae 1-II-a to 1-II-h, Z, $R^1$ to $R^6$, $R^{19}$ to $R^{22}$, and n2 and n3 are the same as described above.

According to an embodiment, Chemical Formula 1-III may be represented by Chemical Formulae 1-IIIA or 1-IIIB according to a binding position of a triphenylene group.

[Chemical Formula 1-IIIA]

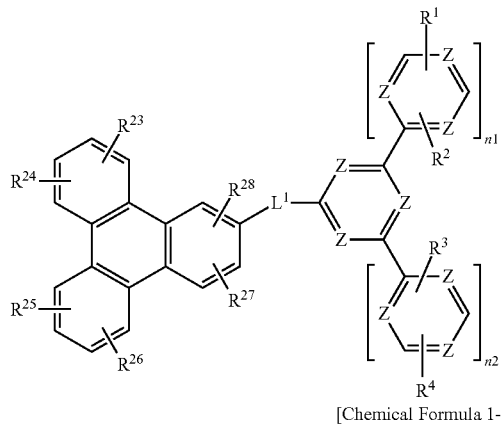

[Chemical Formula 1-IIIB]

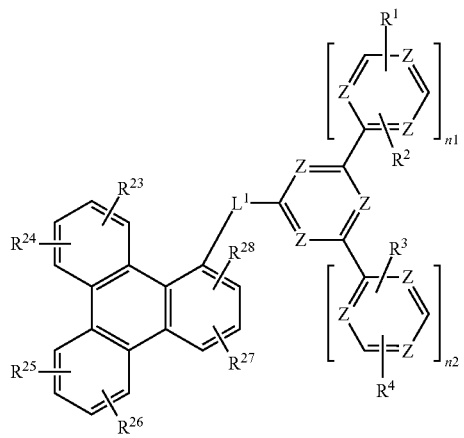

In Chemical Formulae 1-IIIA and 1-IIIB, Z, $R^1$ to $R^4$, $R^{23}$ to $R^{28}$, $L^1$, n1, and n2 are the same as described above.

Specifically, $R^1$ to $R^4$ and $R^{23}$ to $R^{28}$ of Chemical Formula 1-III may independently be hydrogen, deuterium, a substituted or unsubstituted C1 to C10 alkyl group, a substituted or unsubstituted C6 to C12 aryl group, or a combination thereof, and $L^1$ is a substituted or unsubstituted phenylene group, a substituted or unsubstituted biphenylene group, or a substituted or unsubstituted terphenylene group.

A 6-membered ring substituting the triphenylene group indicates all 6-membered rings directly or indirectly connected with the triphenylene group and consists of a carbon atom, a nitrogen atom, or a combination thereof In Chemical Formula 1-III, the total number of the 6-membered ring substituting the triphenylene group may be less than or equal to 6.

The first compound represented by Chemical Formula 1-III includes a triphenylene group and at least one nitrogen-containing heteroaryl group.

The first compound may include a ring containing at least one nitrogen and thereby has a structure easily receiving electrons when an electric field is applied thereto and accordingly an organic optoelectronic device including the compound has a lowered driving voltage.

In addition, the first compound represented by Chemical Formula 1-III has a triphenylene structure easily accepting a hole and a nitrogen-containing cyclic moiety easily accepting an electron and thus, a bipolar structure and accordingly may appropriately balance hole and electron flows and thus improve efficiency of the organic optoelectronic device.

For example, Chemical Formula 1-III without a linking group ($L^1$) may be for example represented by Chemical Formula 1-III-a or 1-III-b.

[Chemical Formula 1-III-a]

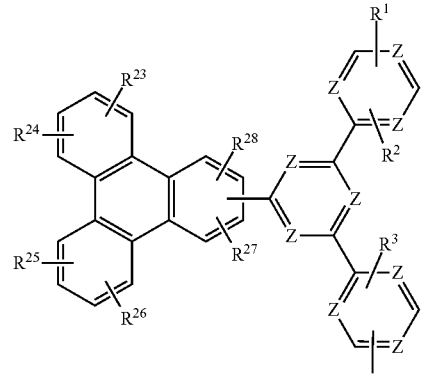

[Chemical Formula 1-III-b]

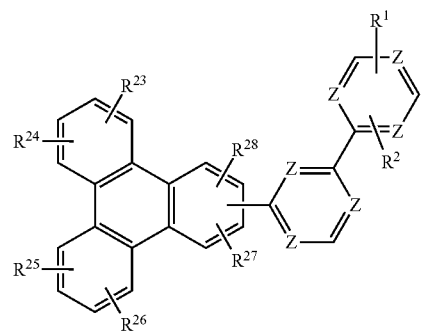

In Chemical Formulae 1-III-a and 1-III-b, Z, $R^1$ to $R^4$, and $R^{23}$ to $R^{28}$ are the same as described above.

For example, in Chemical Formula 1-III having a linking group ($L^1$), $L^1$ may be a substituted or unsubstituted phenylene group substituted or unsubstituted biphenylene group or a substituted or unsubstituted terphenylene group, a substituted or unsubstituted quarterphenylene group. The $L^1$ may be, for example a group selected from substituted or unsubstituted groups of Group 2.

[Group 2]

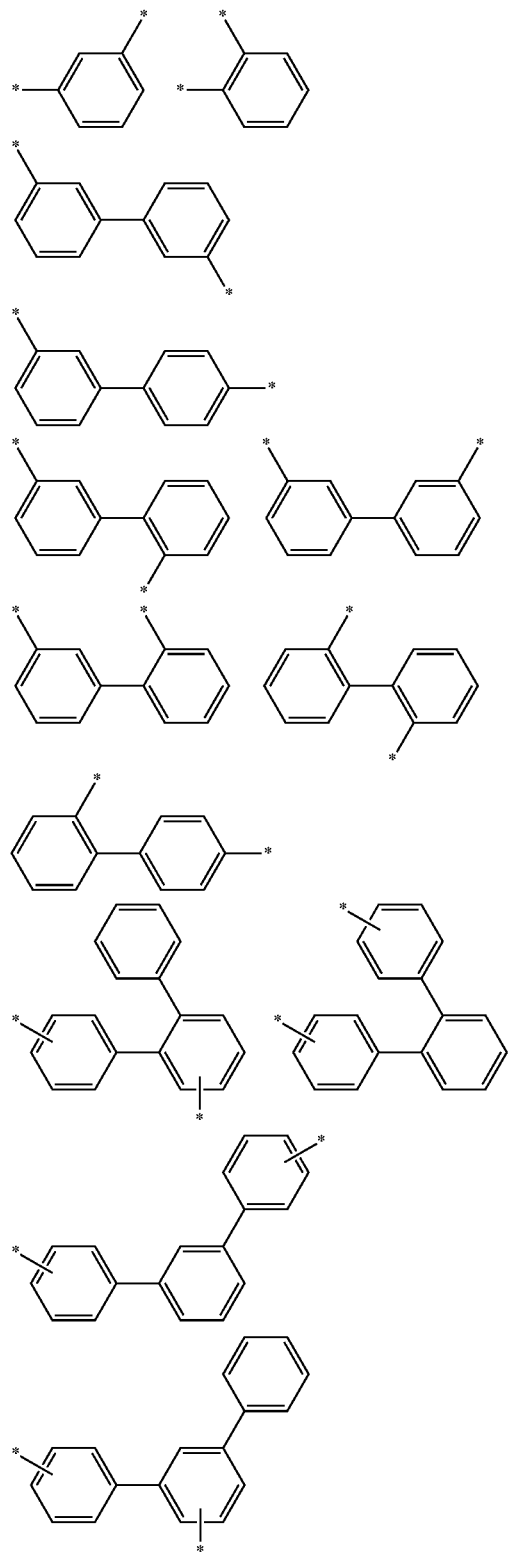

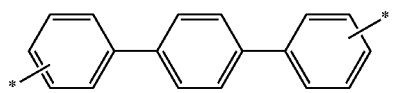

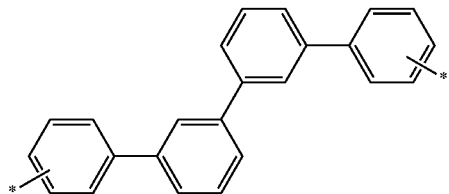

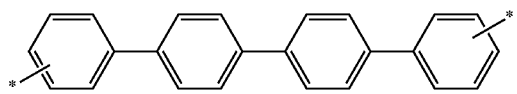

In Group 2, * is a linking point.

A first compound represented by Chemical Formula 1-III may have at least two kink structures, for example, at least two or four kink structures.

The first compound represented by Chemical Formula 1-III has the above kink structure and thus may appropriately localize a triphenylene structure easily accepting a hole and a nitrogen-containing cyclic moiety easily accepting an electron and control a flow of a conjugation system in the compound having the above bipolar structure and resultantly show excellent bipolar characteristics. In addition, the first compound represented by Chemical Formula 1-III may effectively prevent stacking of the organic compounds according to the structure and thus decrease process stability and simultaneously, a deposition temperature. This effect of preventing stacking may be further increased, when the first compound represented by Chemical Formula 1-III includes a linking group L1.

In the first compound represented by Chemical Formula 1-III, a structure having a linking group ($L^1$) may be, for example represented by Chemical Formulae 1-III-c to 1-III-t.

[Chemical Formula 1-III-c]

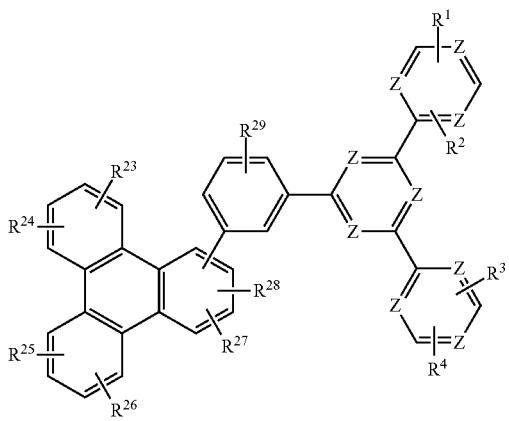

[Chemical Formula 1-III-d]
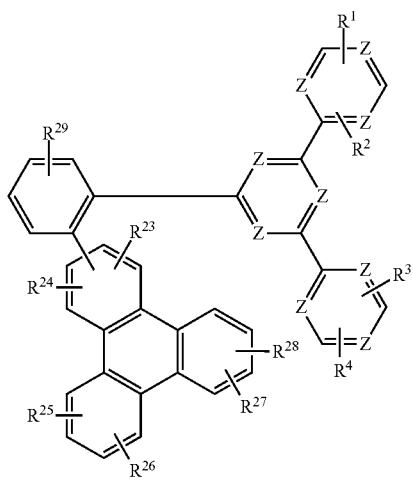
[Chemical Formula 1-III-e]
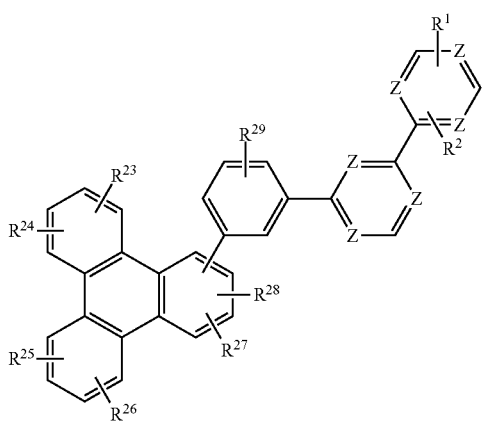
[Chemical Formula 1-III-f]
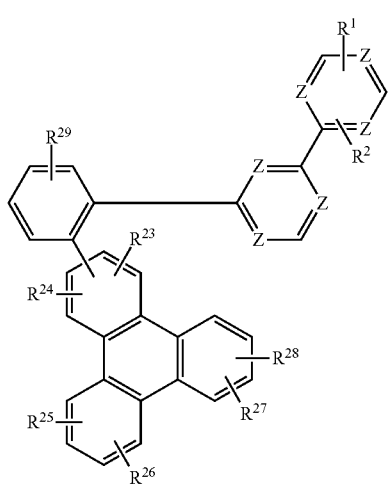
[Chemical Formula 1-III-g]
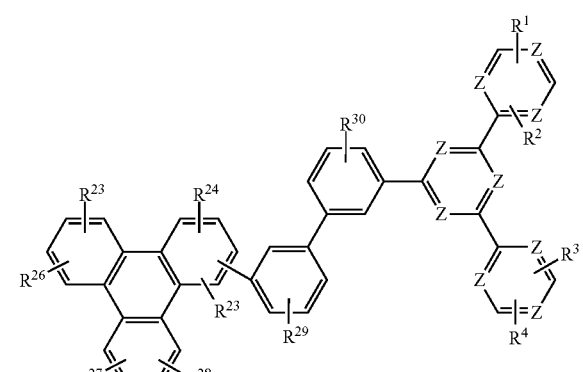
[Chemical Formula 1-III-h]
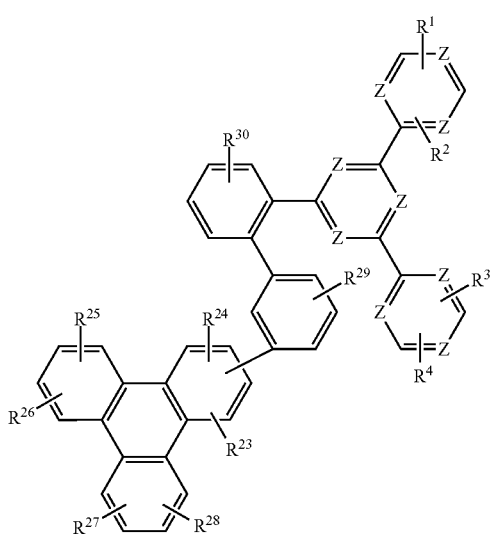
[Chemical Formula 1-III-i]
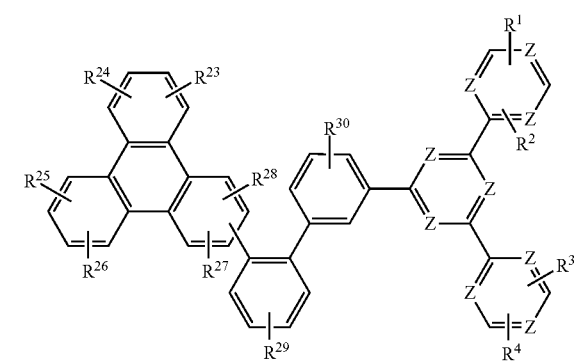

-continued
[Chemical Formula 1-III-j]
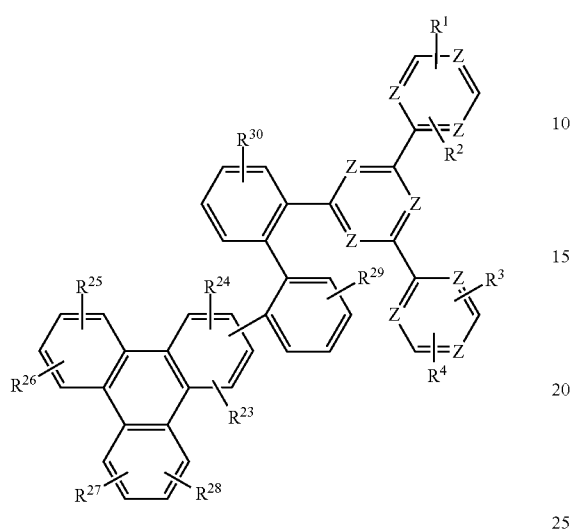
[Chemical Formula 1-III-k]
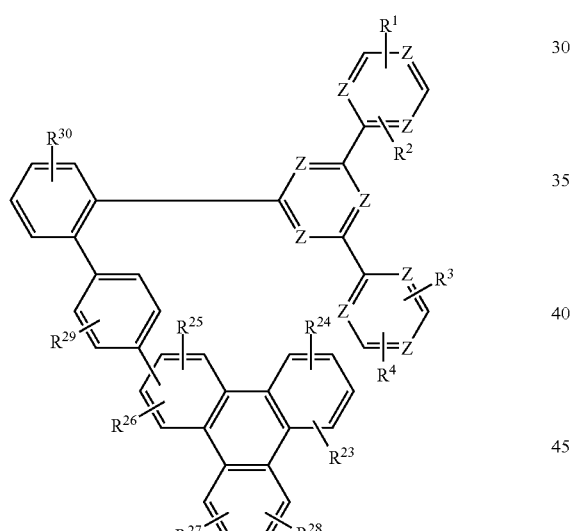
[Chemical Formula 1-III-l]
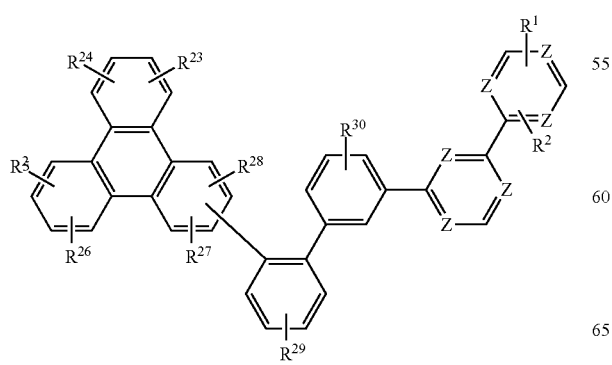
[Chemical Formula 1-III-m]
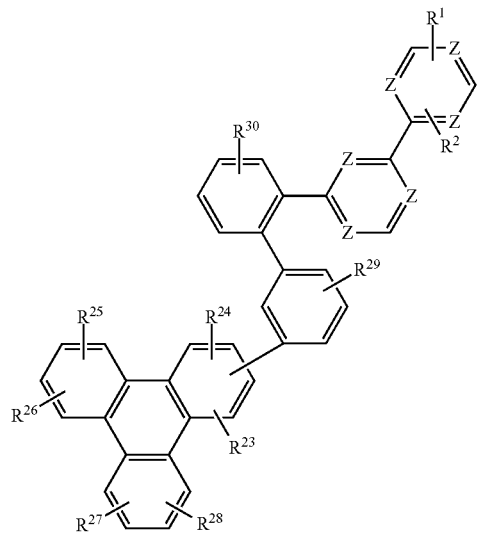
[Chemical Formula 1-III-n]
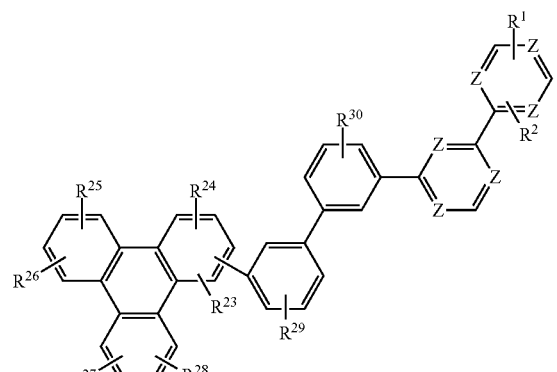
[Chemical Formula 1-III-o]
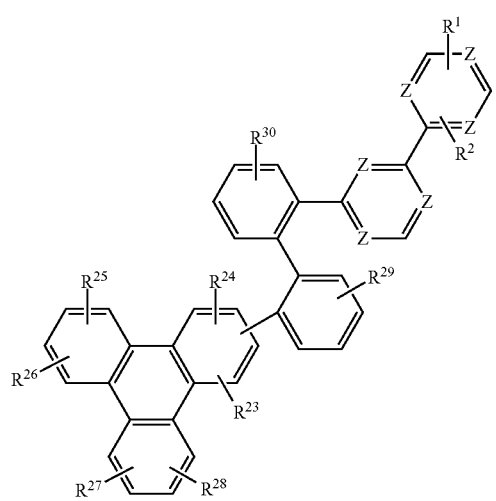

[Chemical Formula 1-III-p]
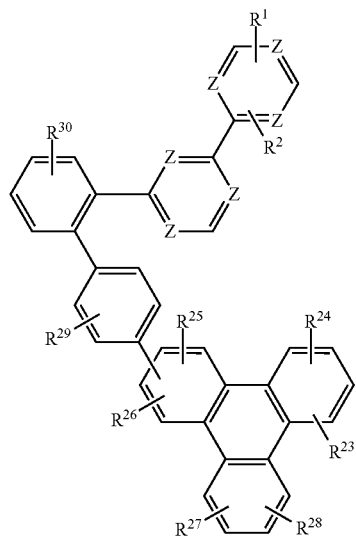
[Chemical Formula 1-III-q]
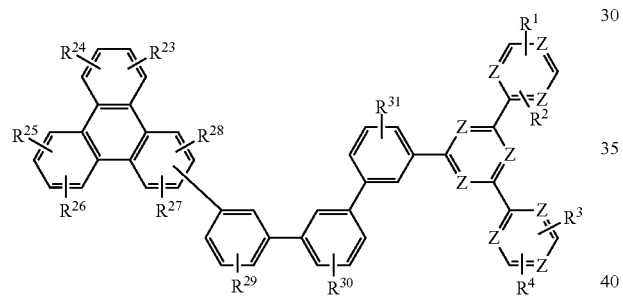
[Chemical Formula 1-III-r]
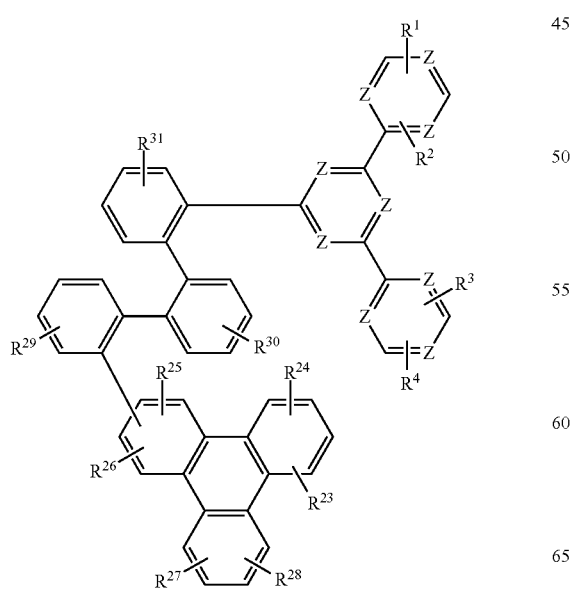
[Chemical Formula 1-III-s]
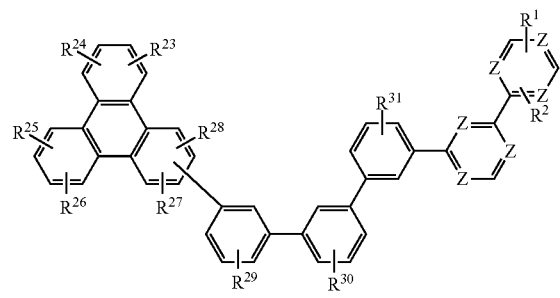
[Chemical Formula 1-III-t]
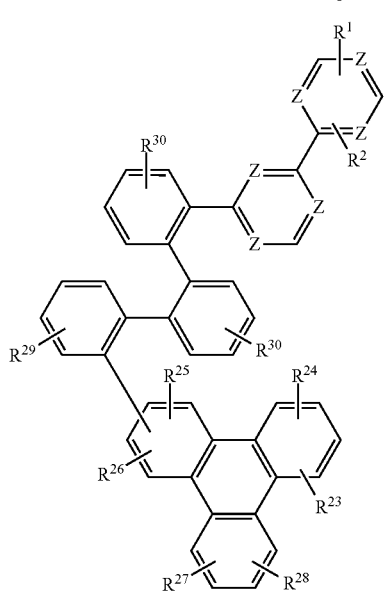
In Chemical Formulae 1-III-c to 1-III-t, Z, $R^1$ to $R^4$ and $R^{23}$ to $R^{28}$ are the same as above and $R^{29}$ to $R^{31}$ are the same as $R^{23}$ to $R^{28}$.
The first compound represented by Chemical Formula 1 may be, for example compounds of Group A, but is not limited thereto.

[Group A]
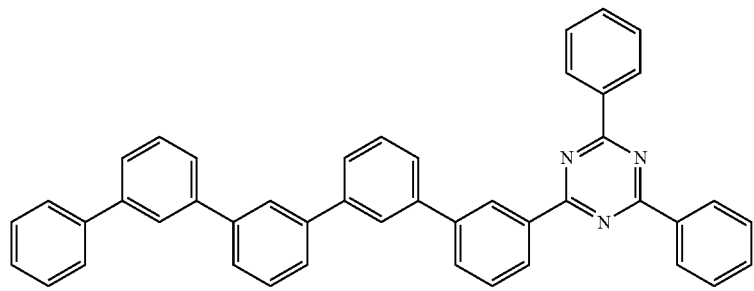
[A-1]
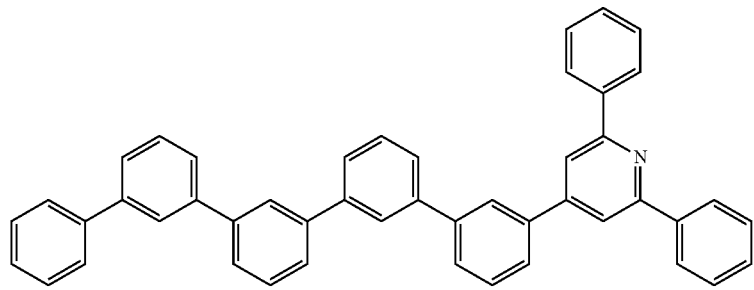
[A-2]
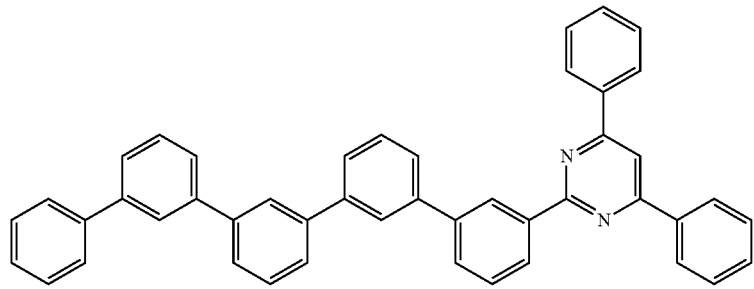
[A-3]
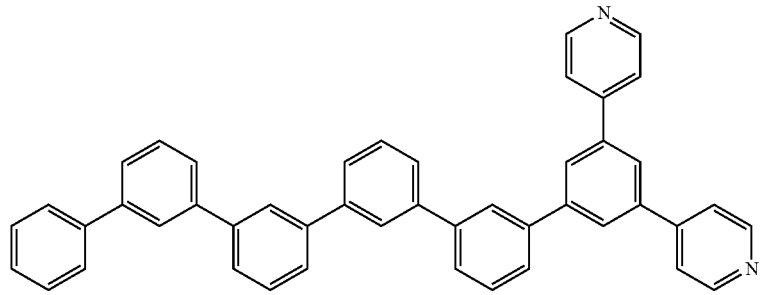
[A-4]
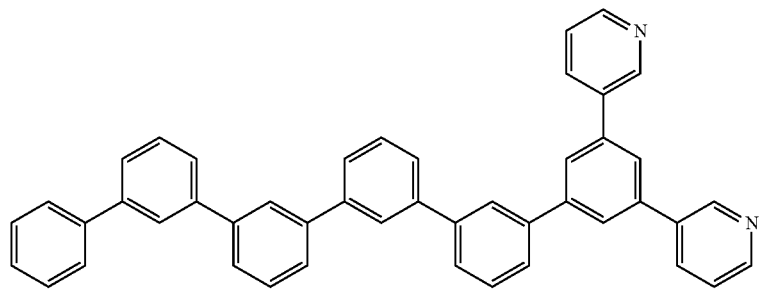
[A-5]

[A-6]
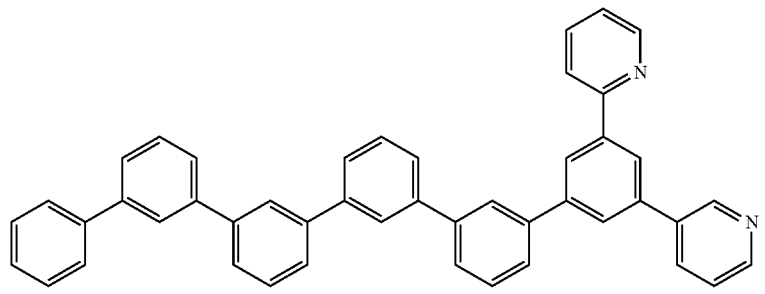
[A-7]
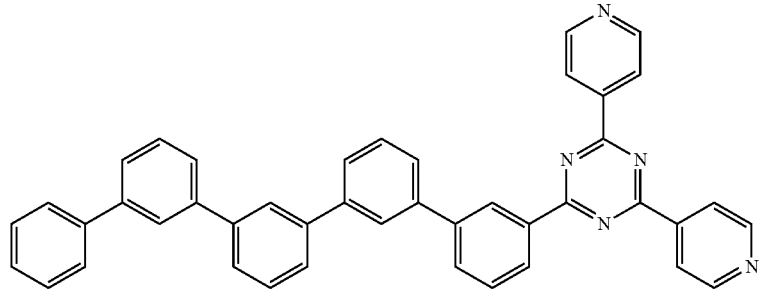
[A-8]
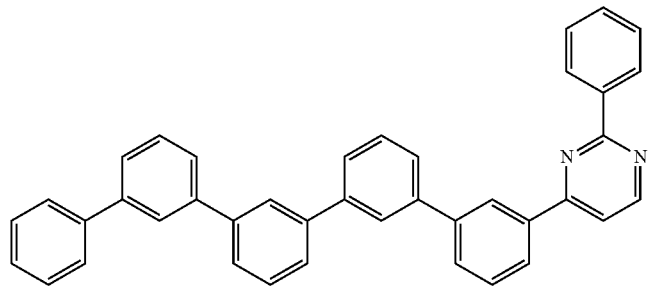
[A-9]
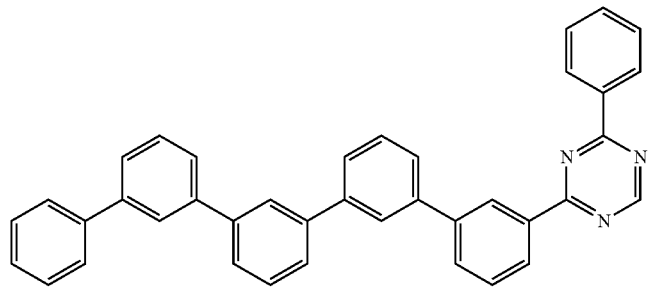
[A-10]
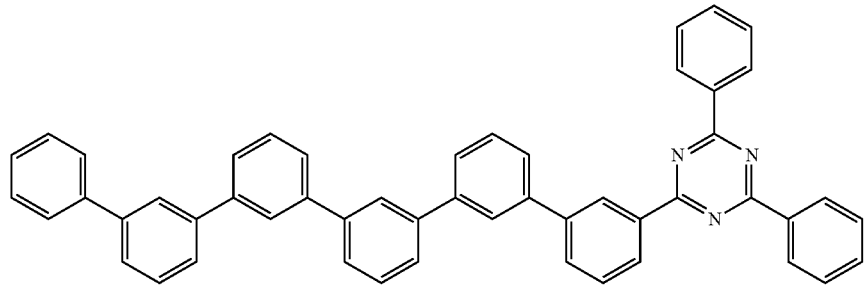

-continued
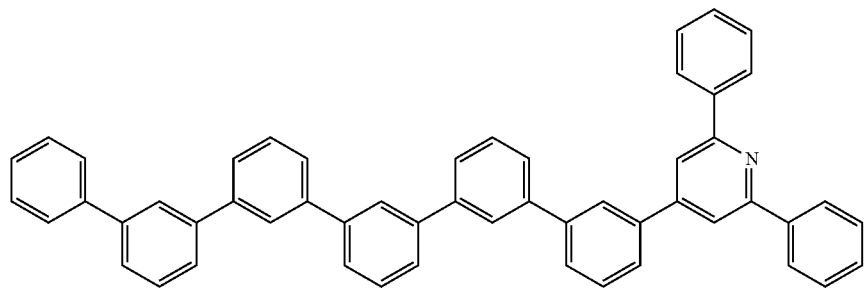
[A-11]
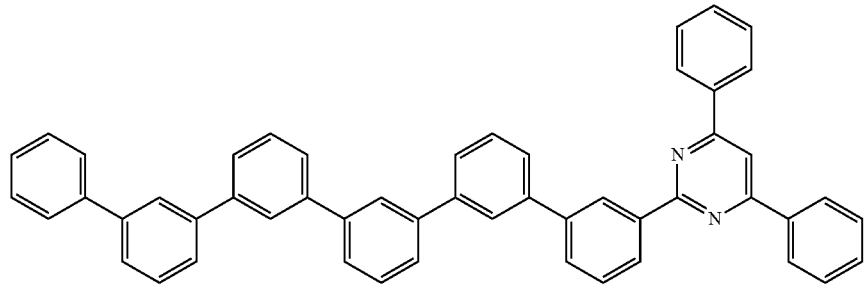
[A-12]
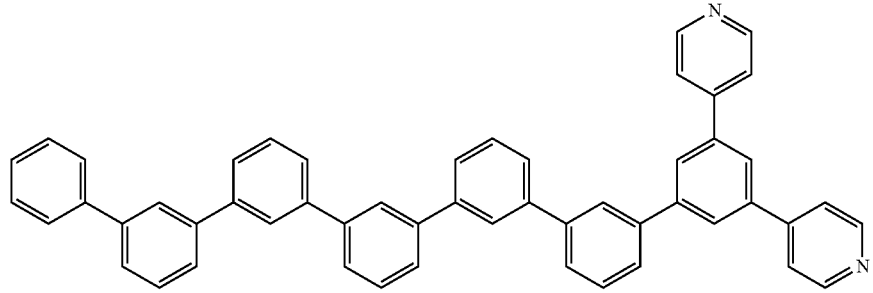
[A-13]
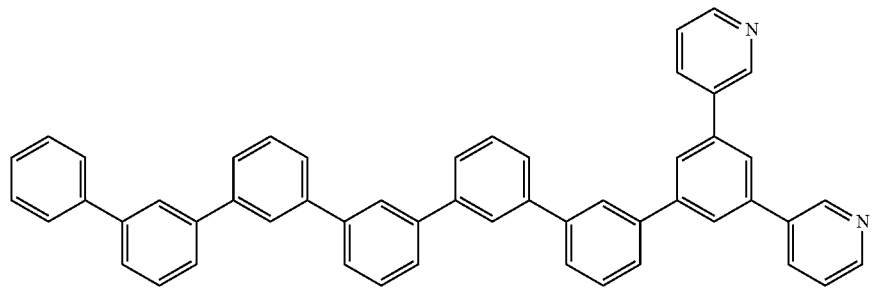
[A-14]
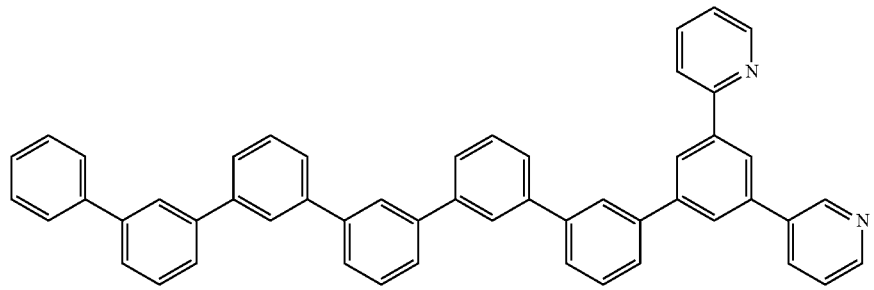
[A-15]

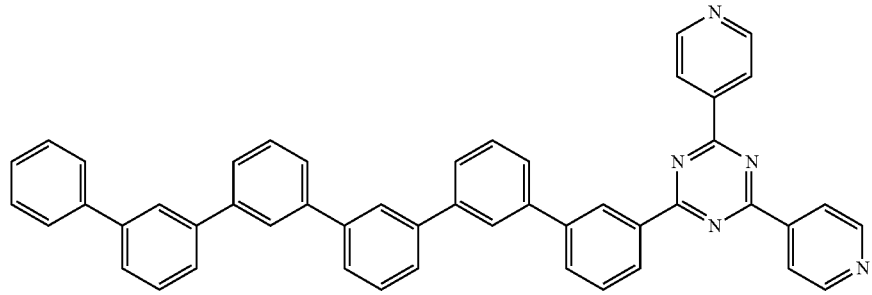
[A-16]
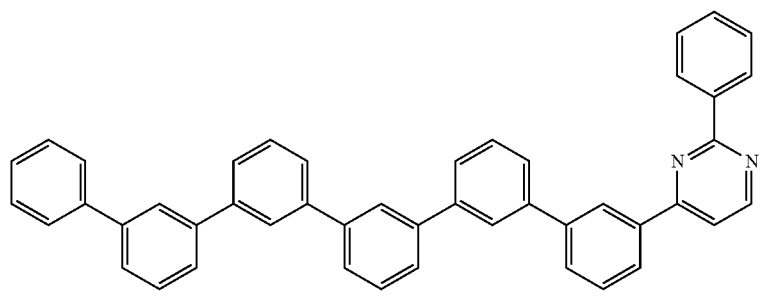
[A-17]
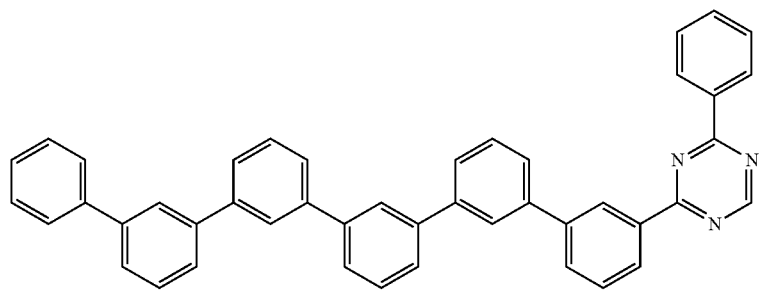
[A-18]
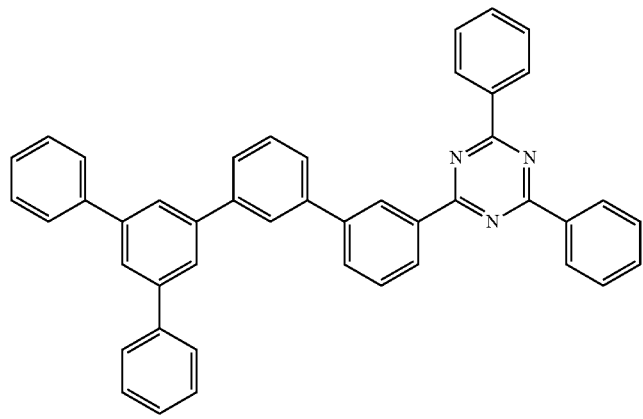
[A-19]

-continued
[A-20]
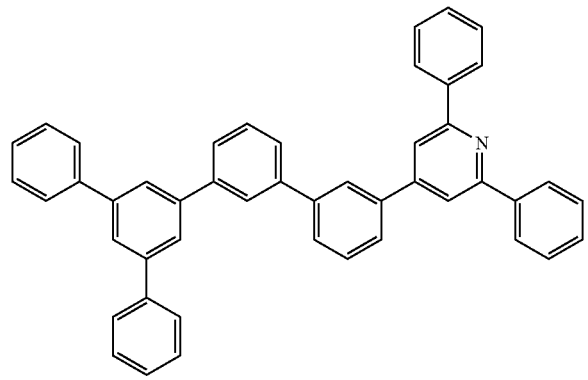
[A-21]
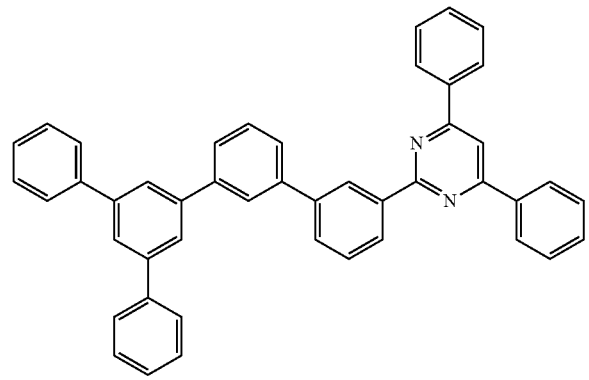
[A-22]
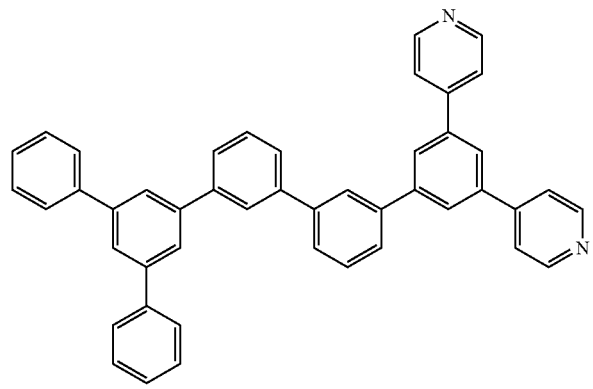
[A-23]
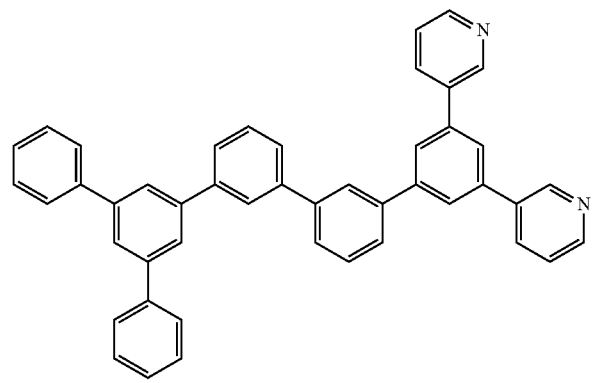
[A-24]
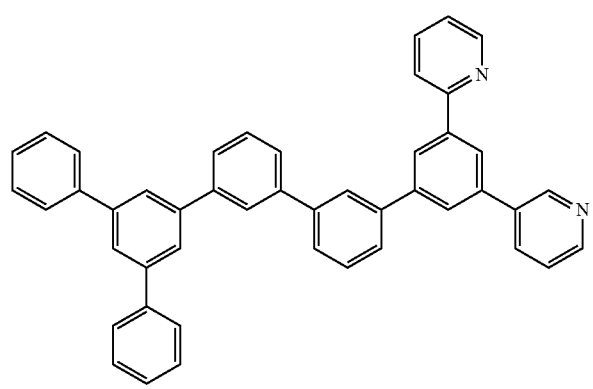
[A-25]
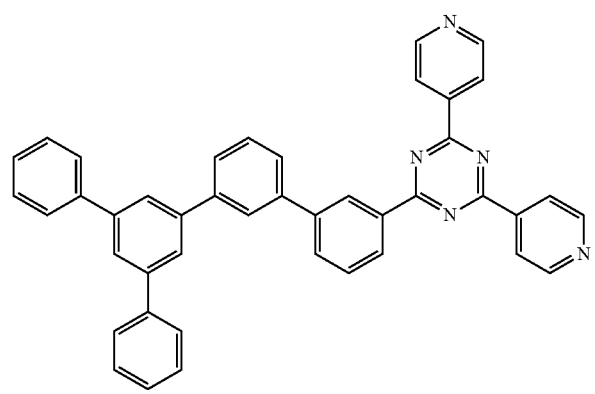
[A-26]
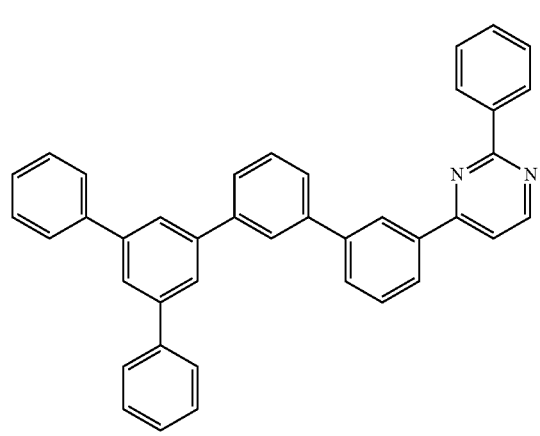
[A-27]
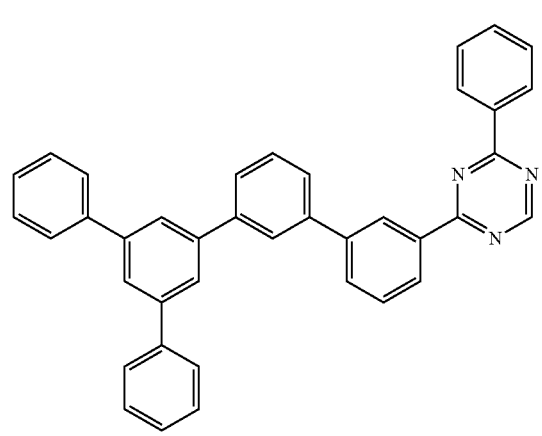

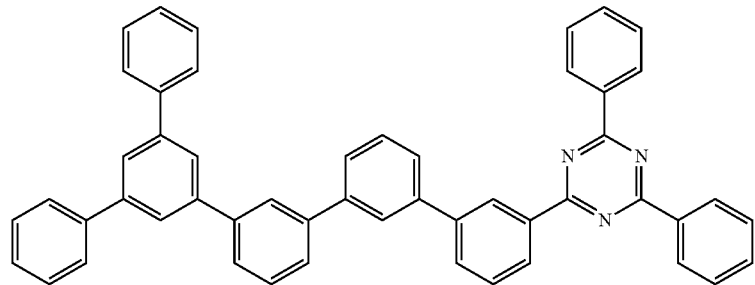
[A-28]
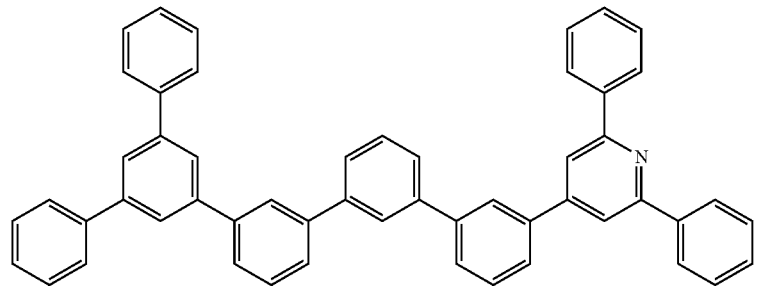
[A-29]
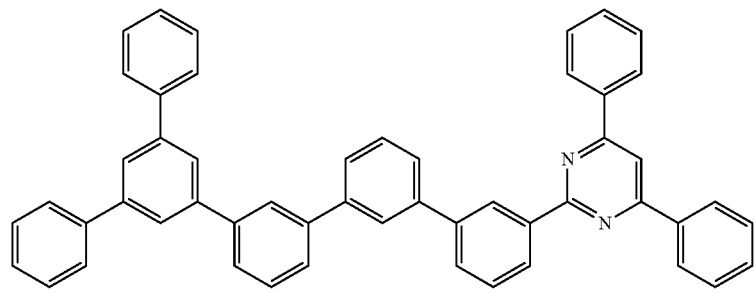
[A-30]
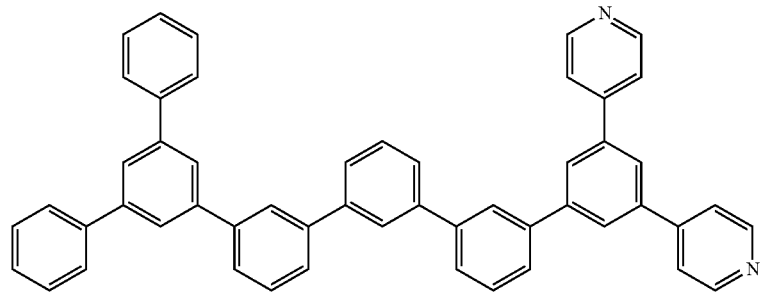
[A-31]
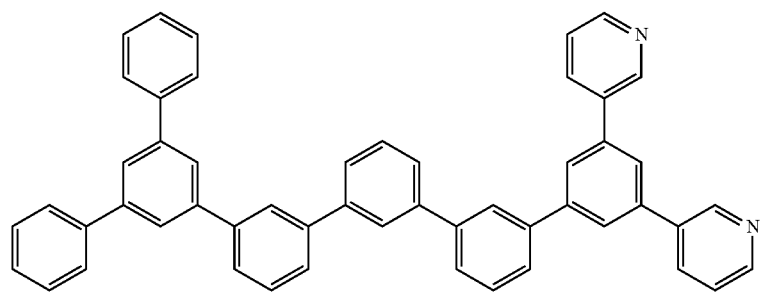
[A-32]

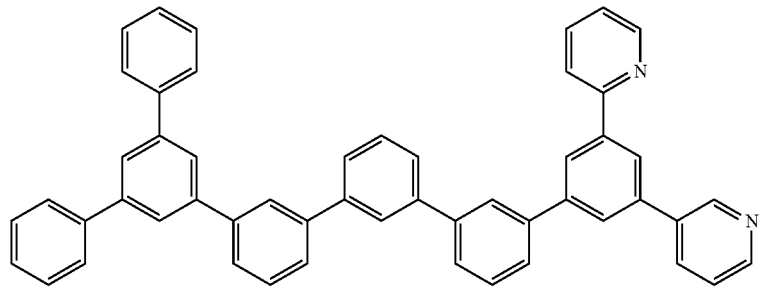
[A-33]
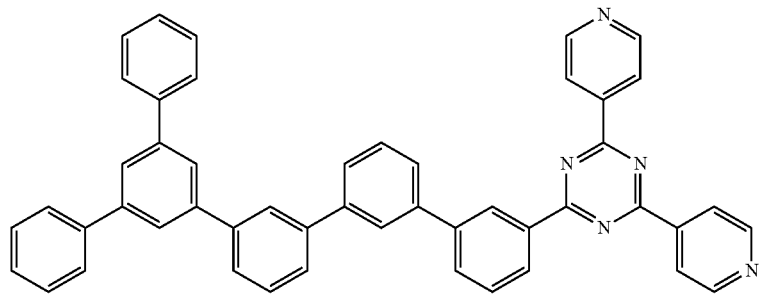
[A-34]
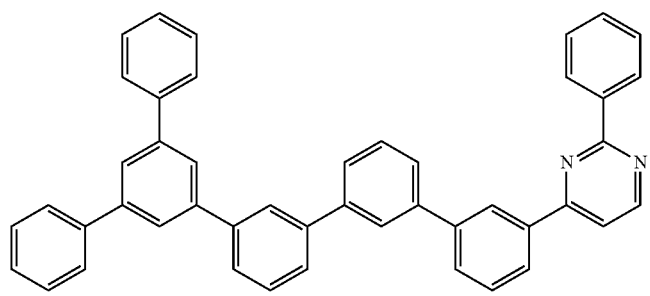
[A-35]
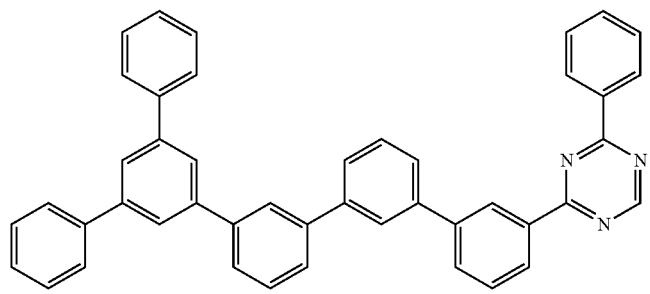
[A-36]

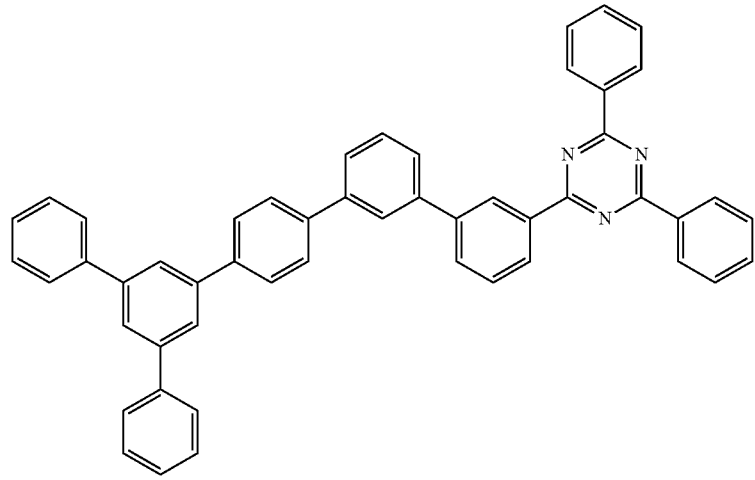
[A-37]
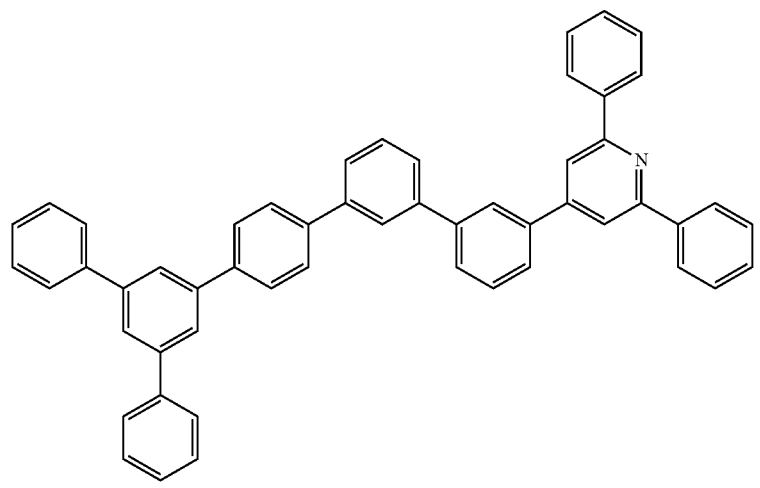
[A-38]
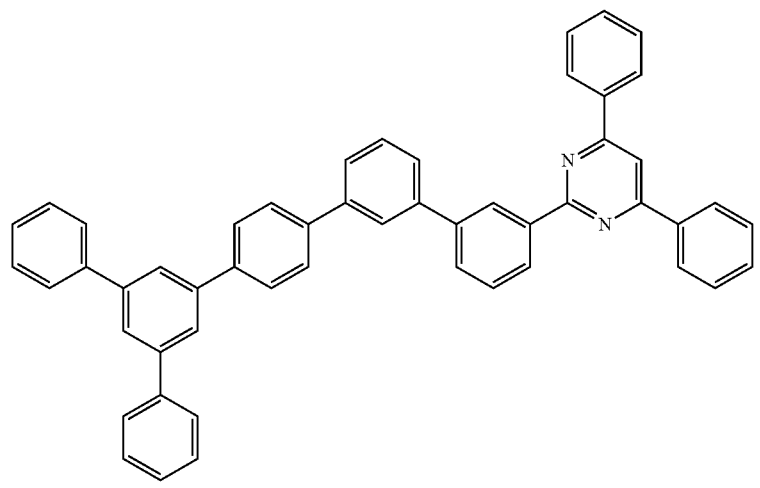
[A-39]

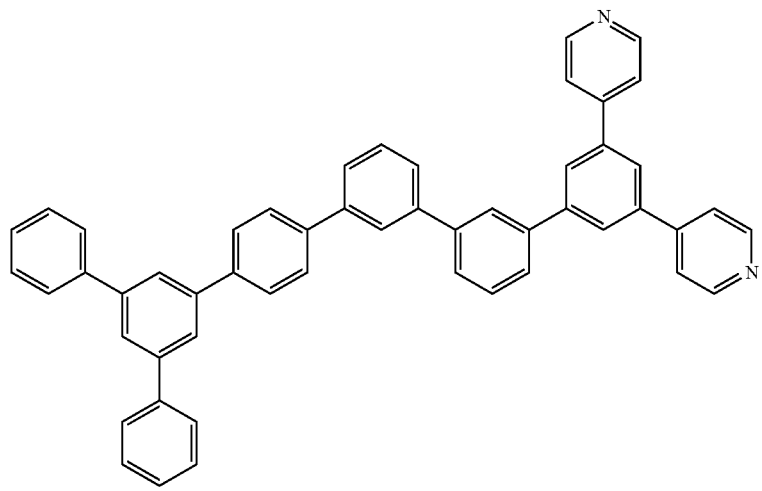
[A-40]
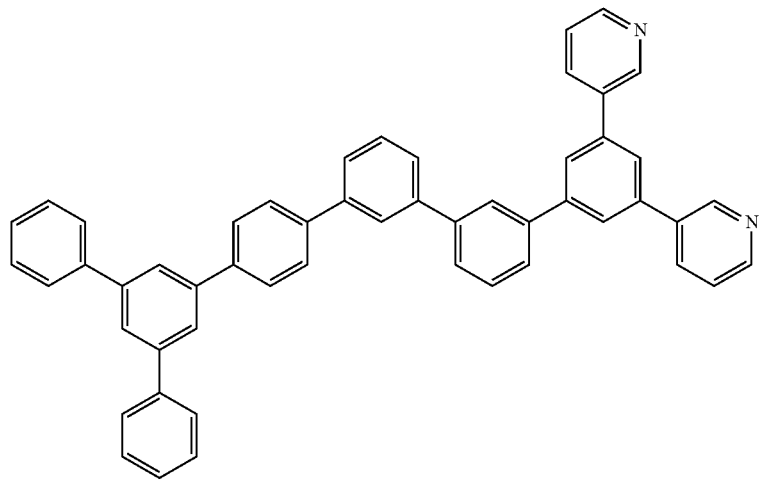
[A-41]
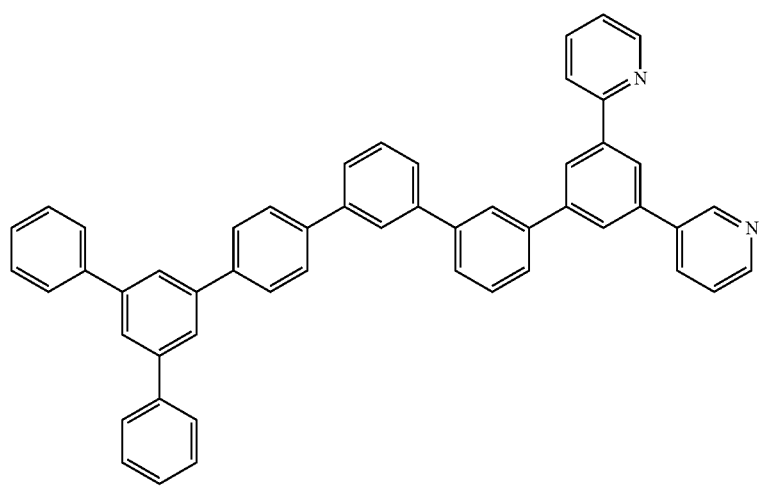
[A-42]

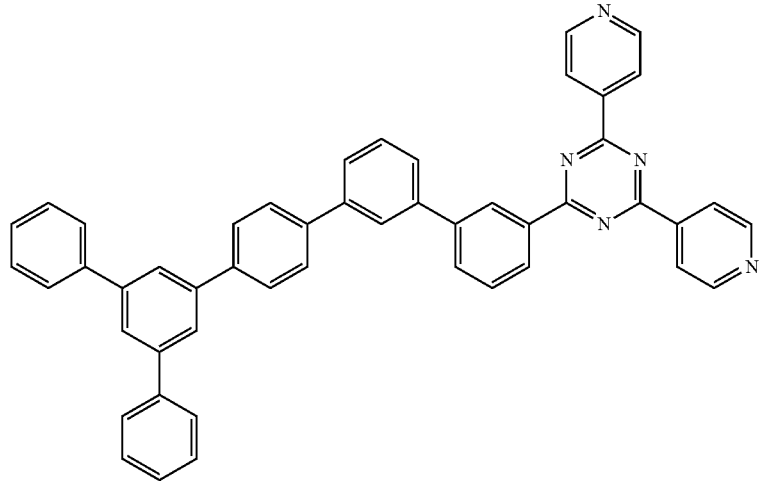
[A-43]
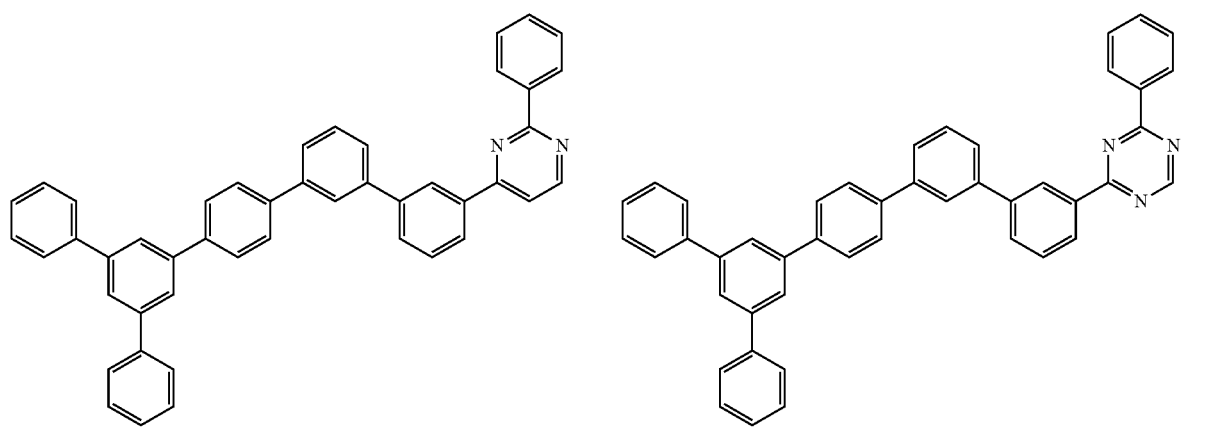
[A-44] [A-45]
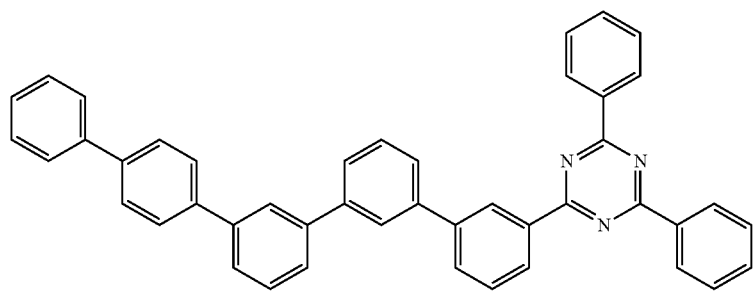
[A-46]
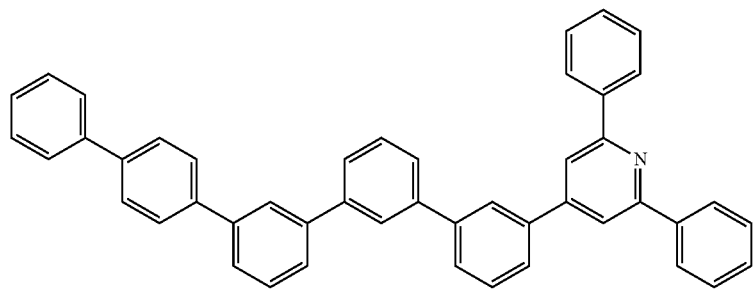
[A-47]

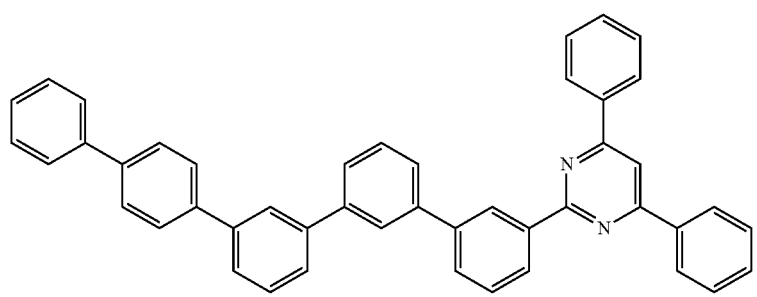
[A-48]
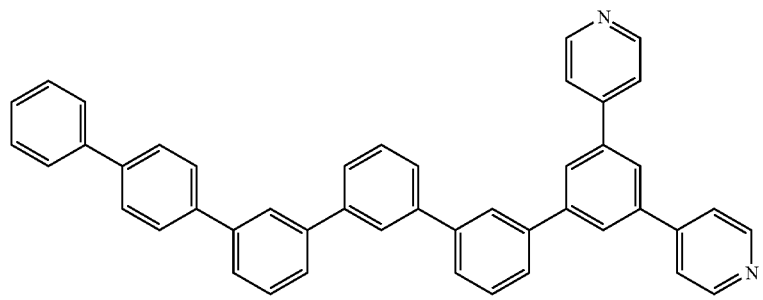
[A-49]
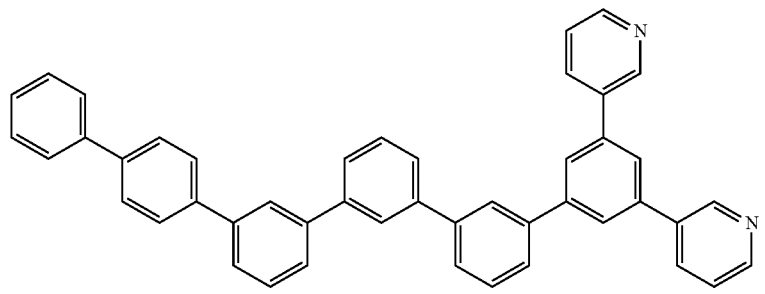
[A-50]
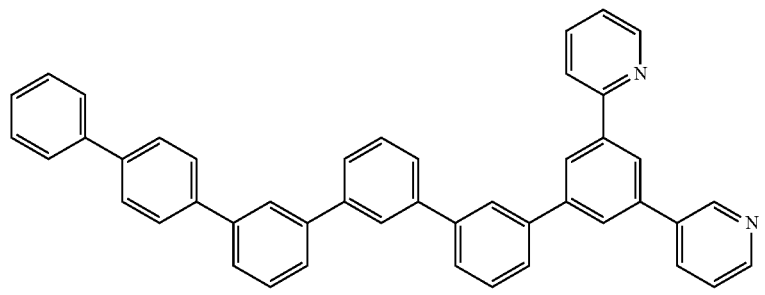
[A-51]
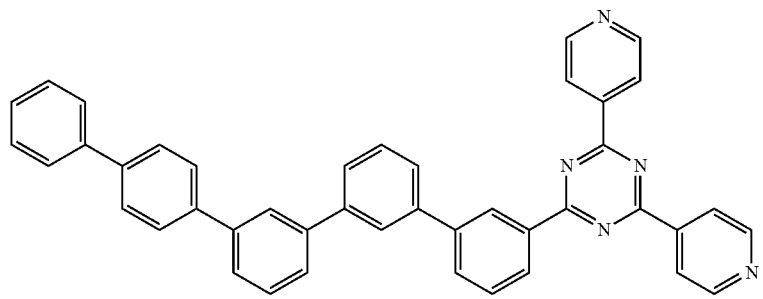
[A-52]

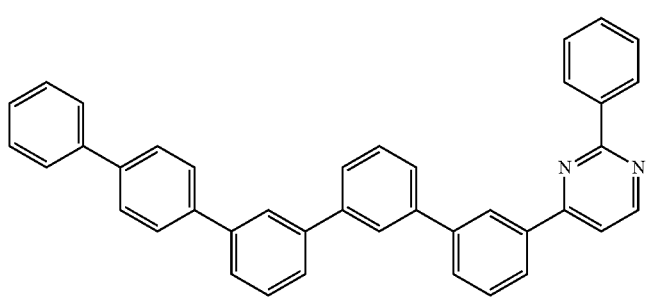
[A-53]
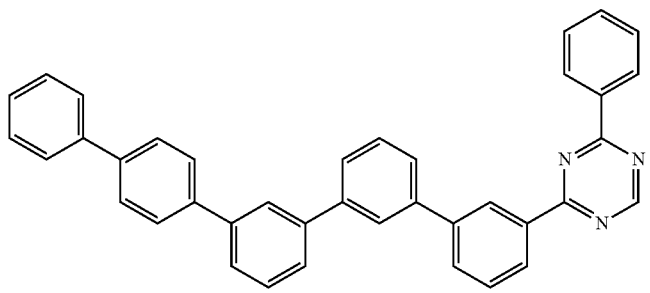
[A-54]
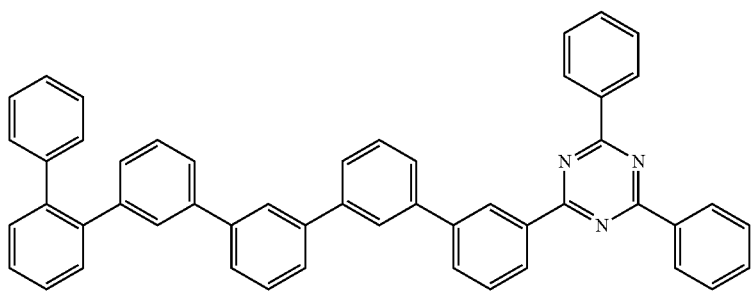
[A-55]
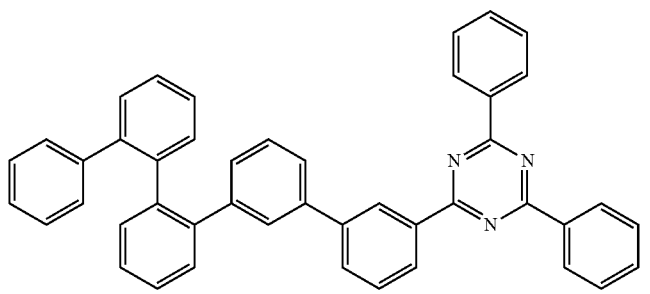
[A-56]
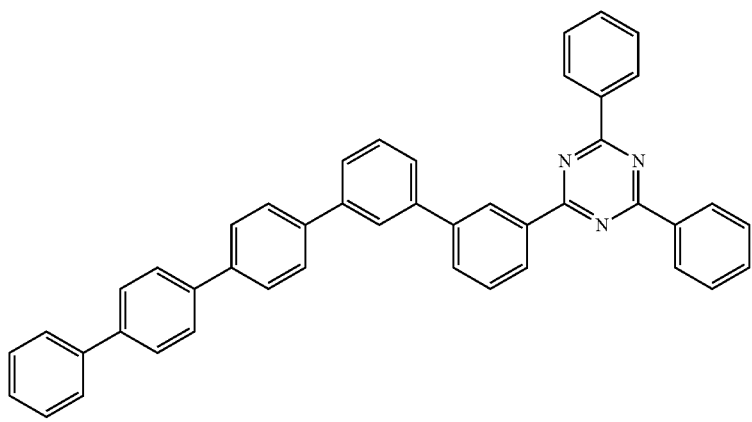
[A-57]

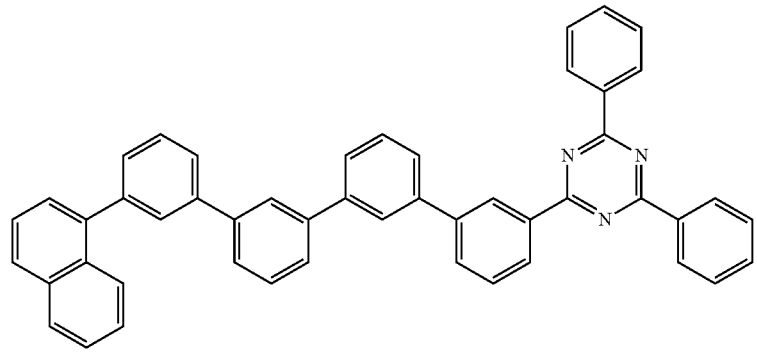
[A-58]
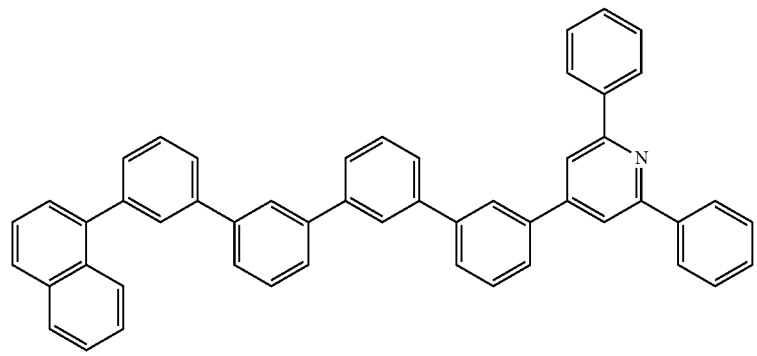
[A-59]
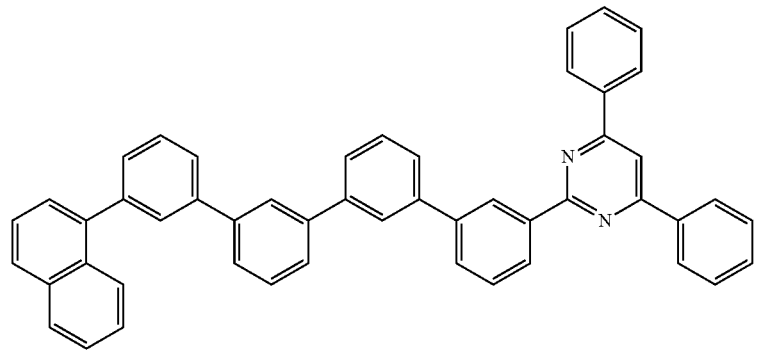
[A-60]
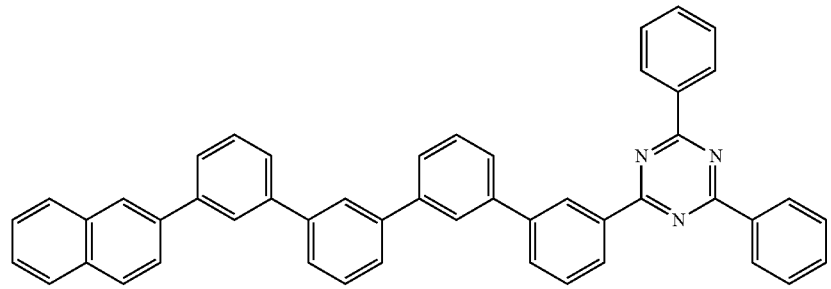
[A-61]

-continued
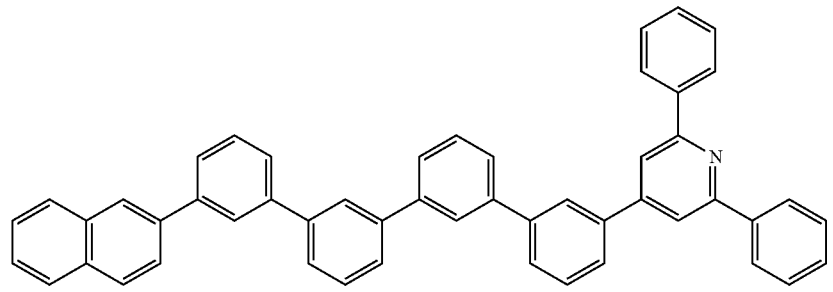
[A-62]

[A-63]
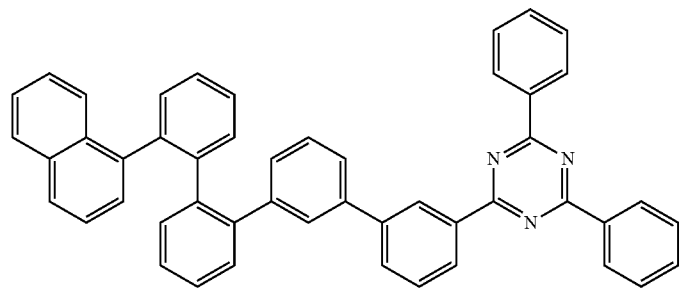
[A-64]
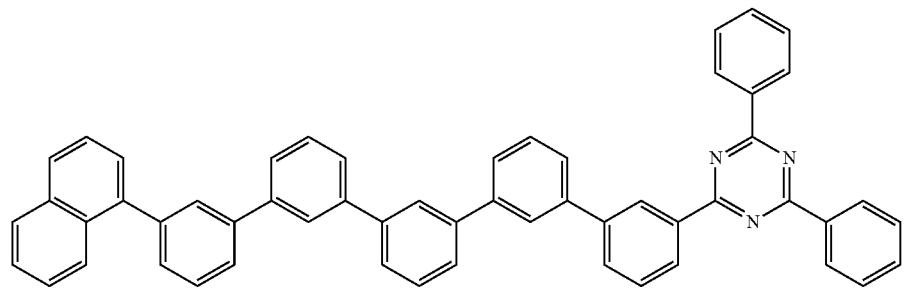
[A-65]
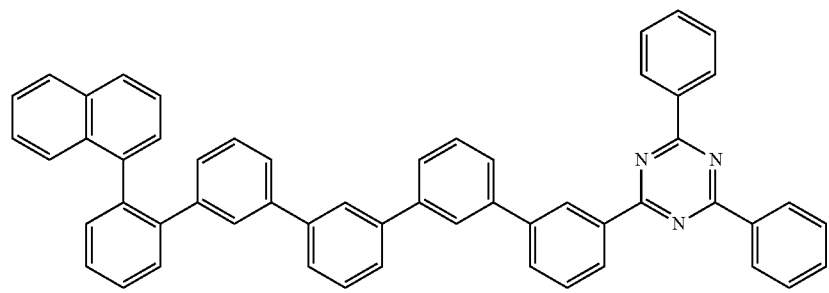
[A-66]

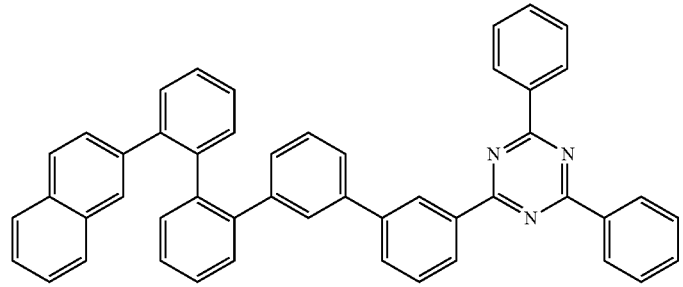
[A-67]
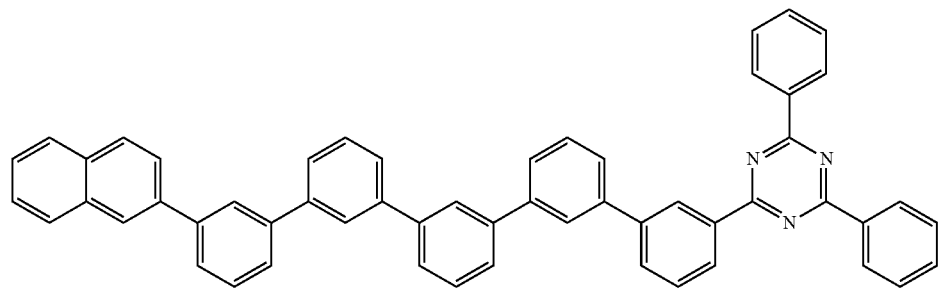
[A-68]
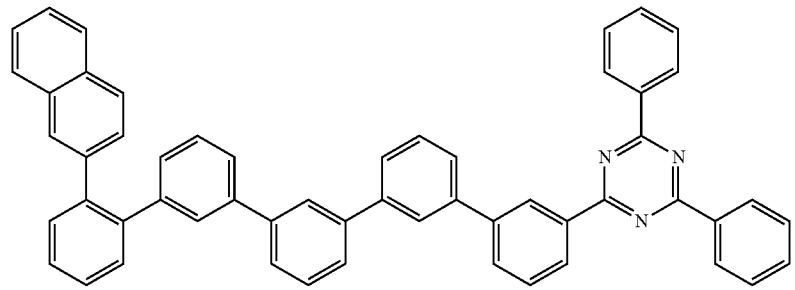
[A-69]
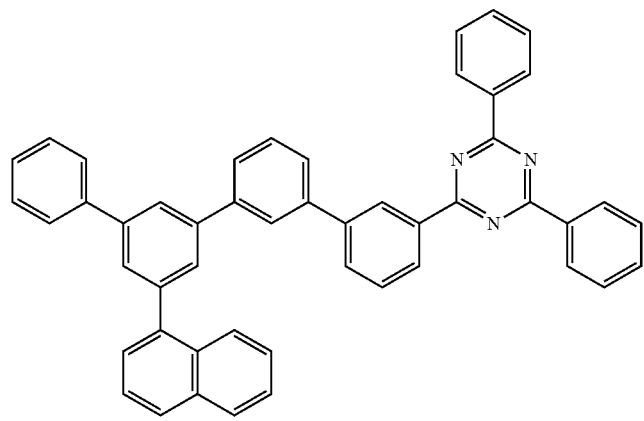
[A-70]

[A-71]
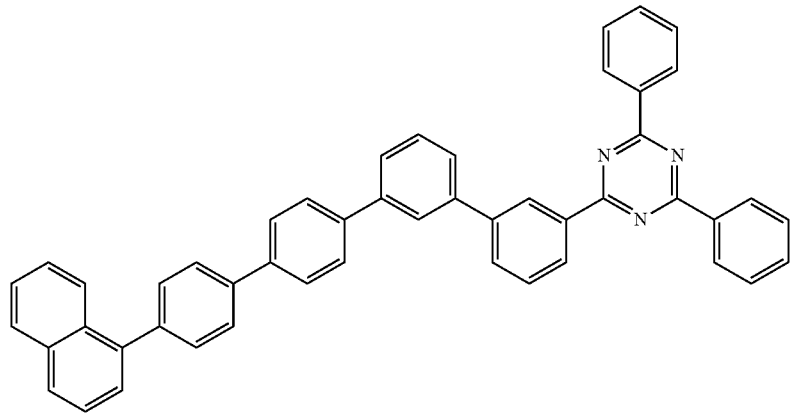
[A-72]
[A-73]
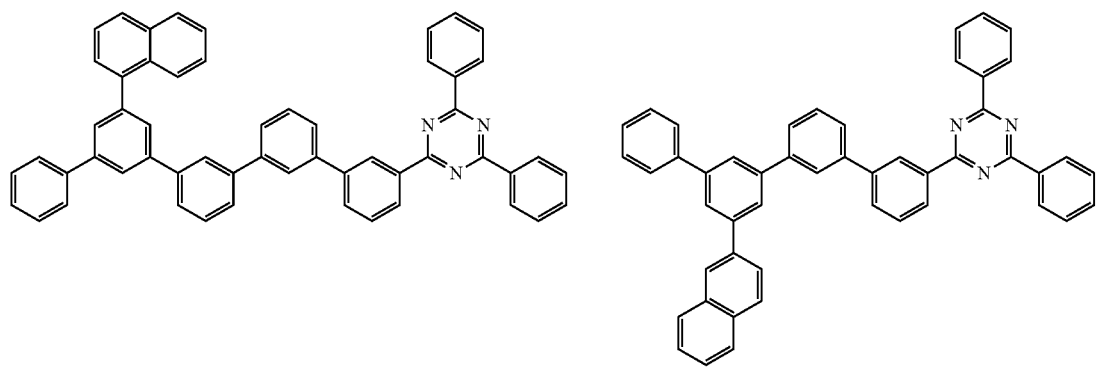
[A-74]
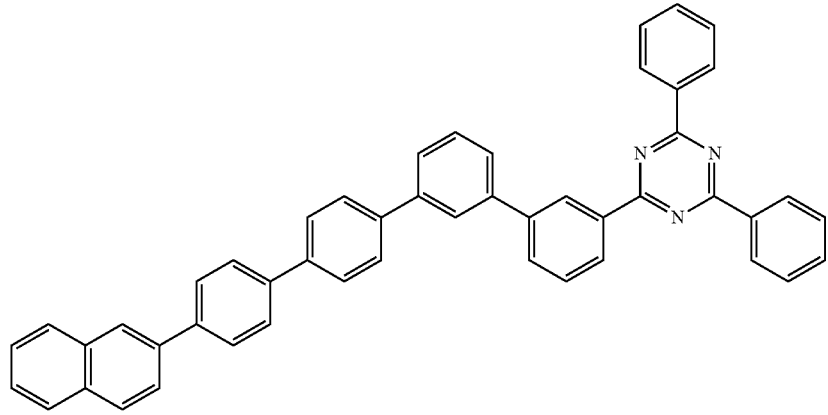
[A-75]
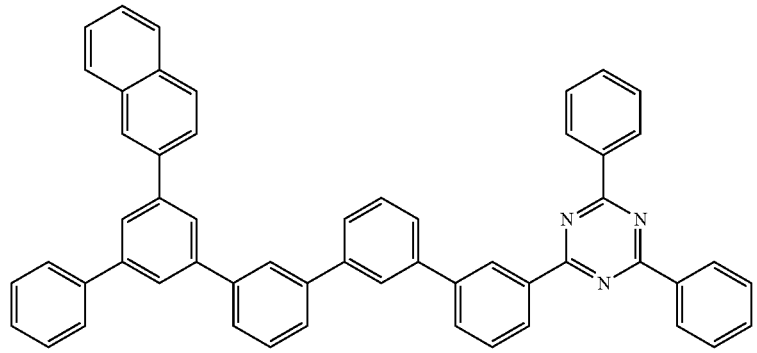

-continued
[A-76]
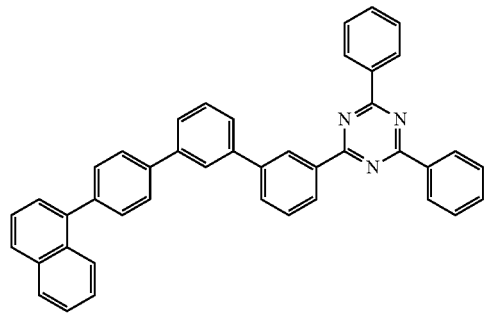
[A-77]
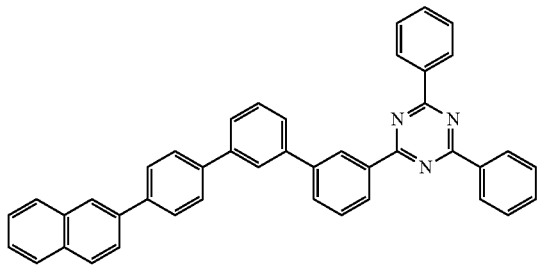
[A-78]
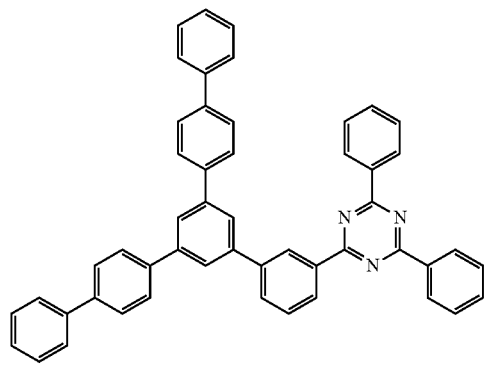
[A-79]
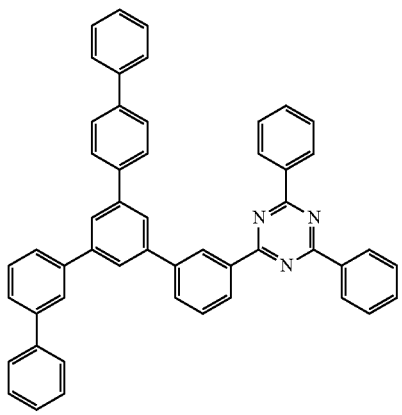
[A-80]
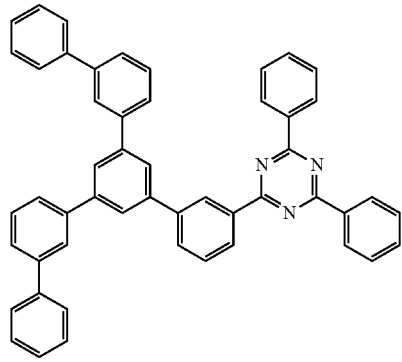
[A-81]
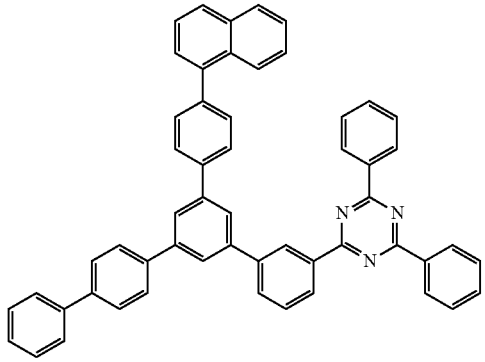
[A-82]
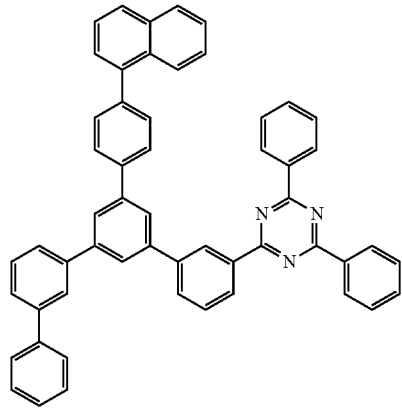
[A-83]
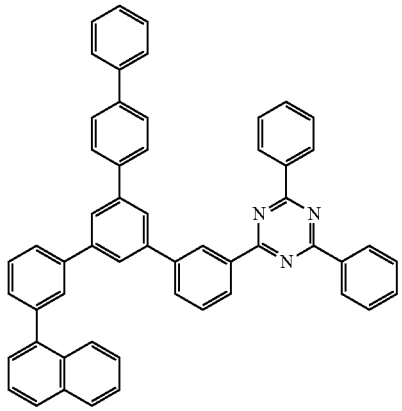

[A-84]
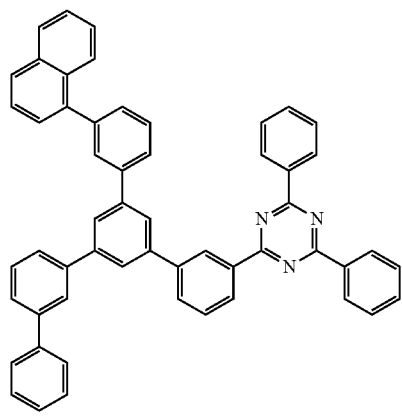
[A-85]
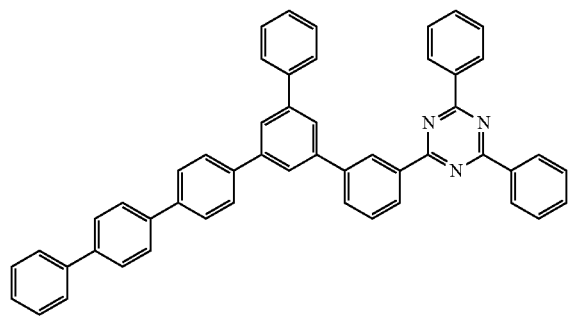
[A-86]
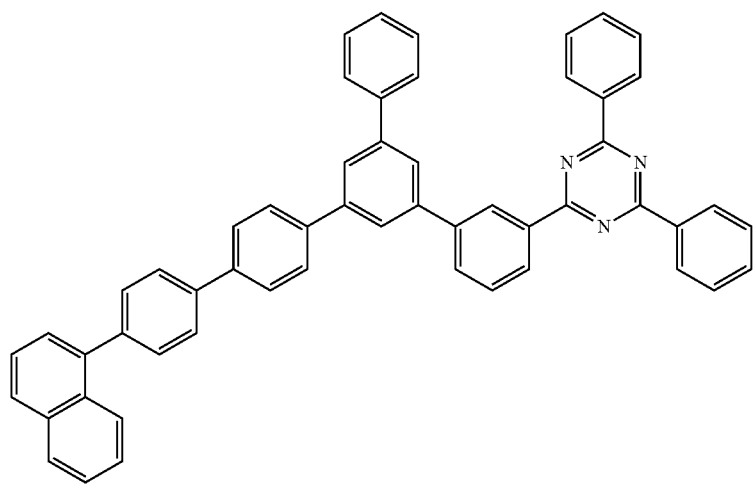
[A-87]
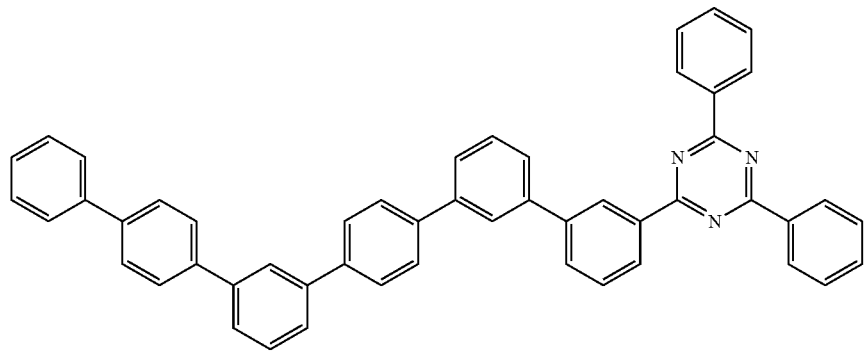
[A-88]
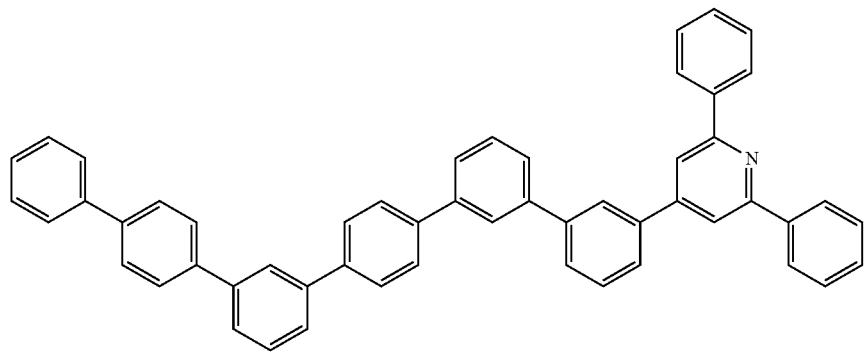

-continued
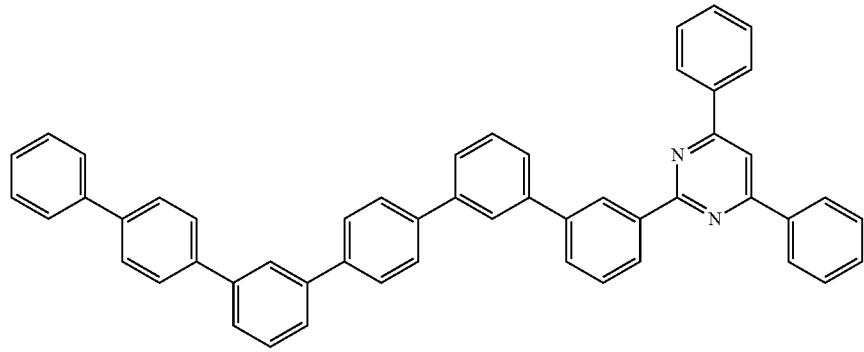
[A-89]
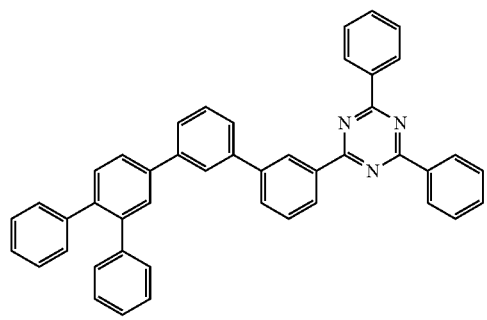
[A-90]
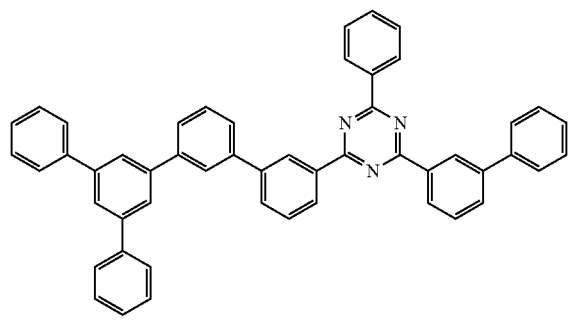
[A-91]
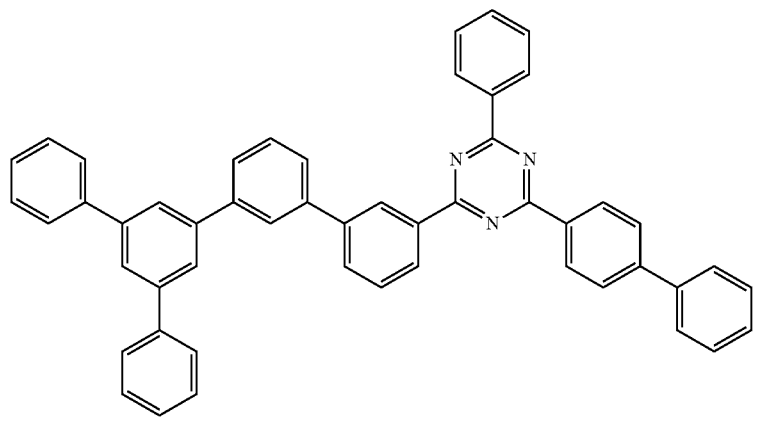
[A-92]
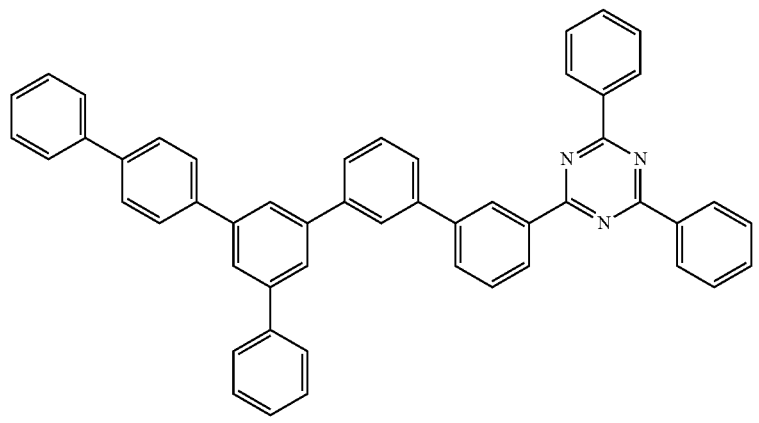
[A-93]

[A-94]
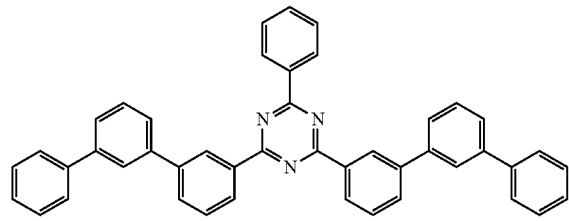
[A-95]
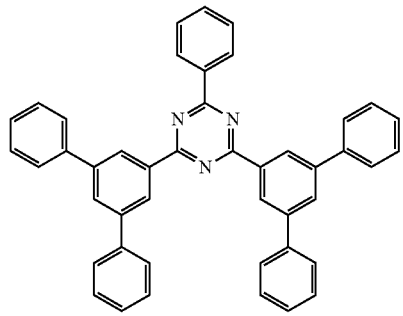
[A-96]
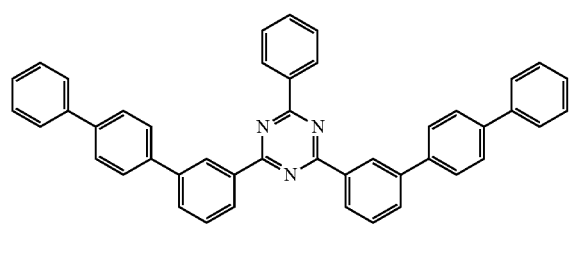
[A-97]
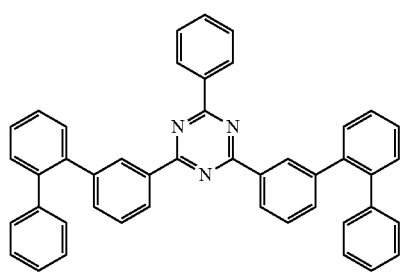
[A-98]
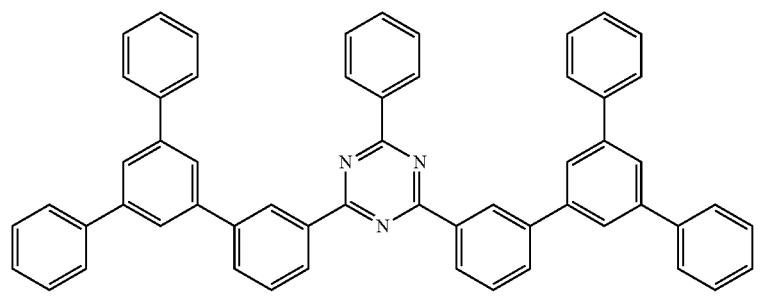
[A-99]
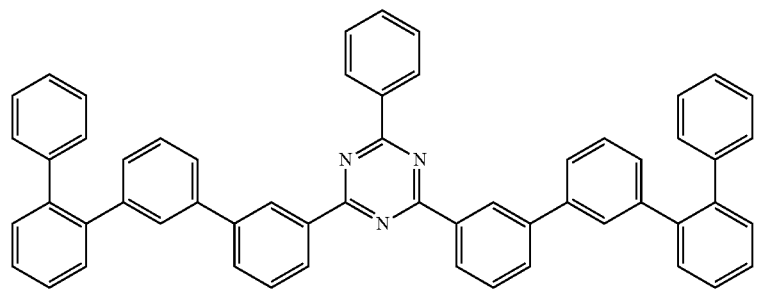
[A-100]
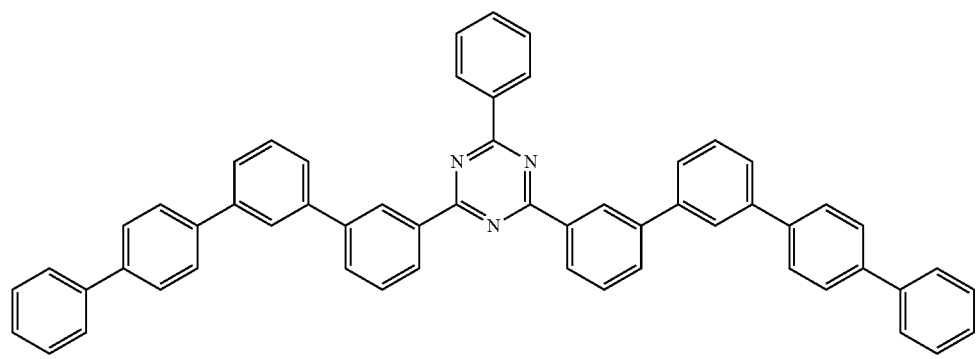

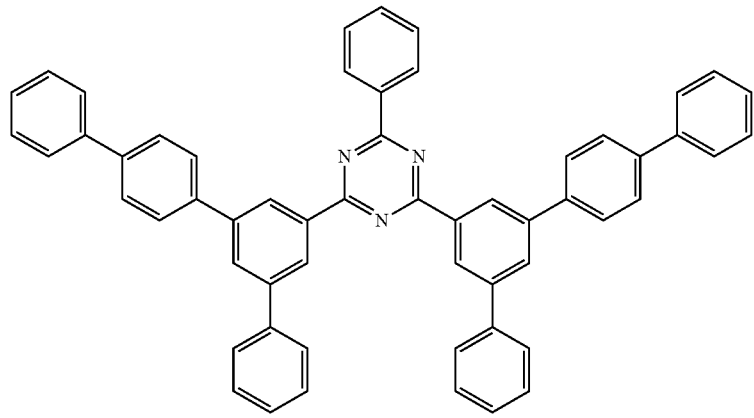
[A-101]
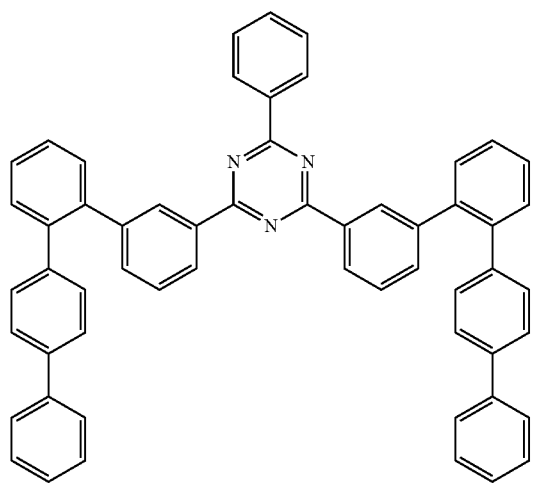
[A-102]
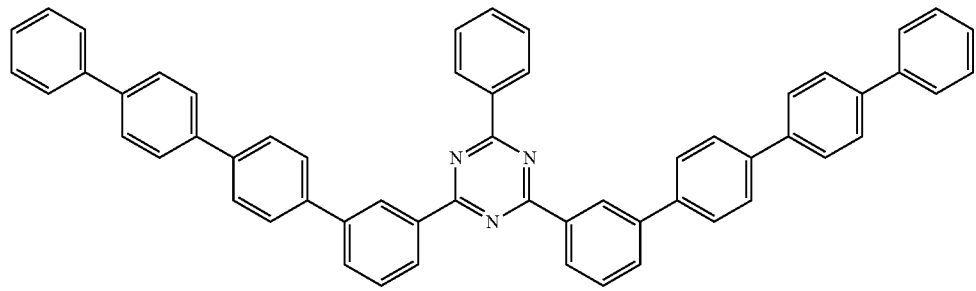
[A-103]

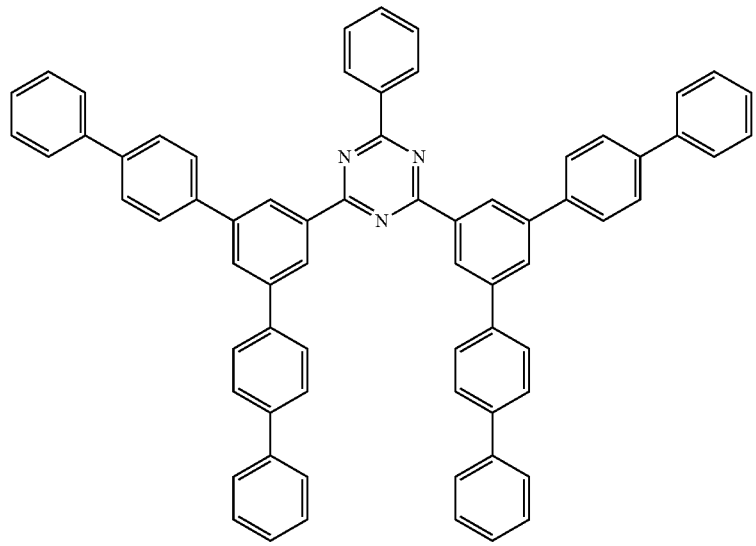
[A-104]
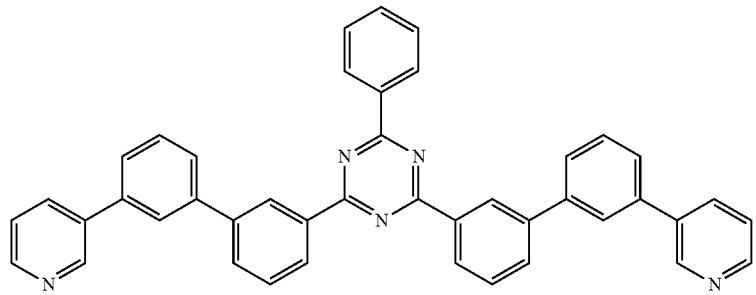
[A-105]
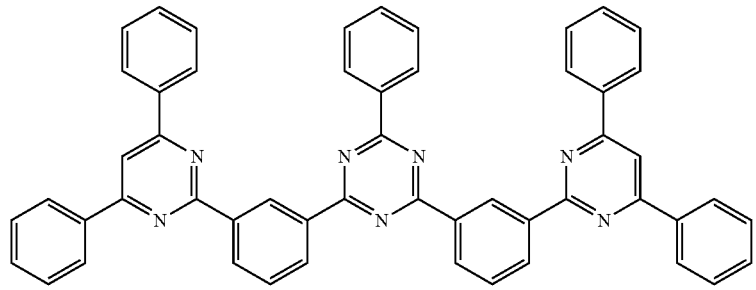
[A-106]
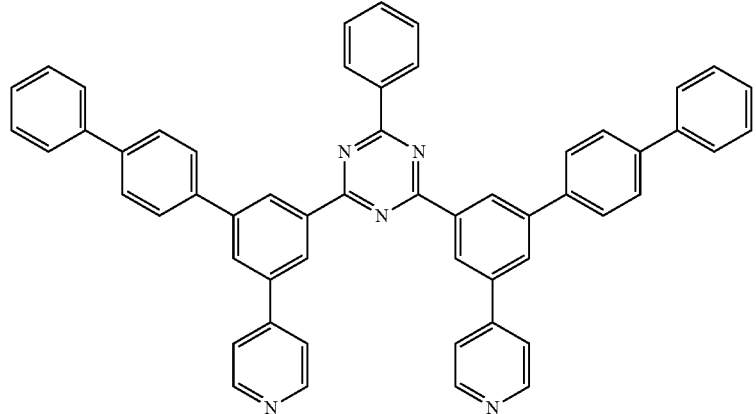
[A-107]

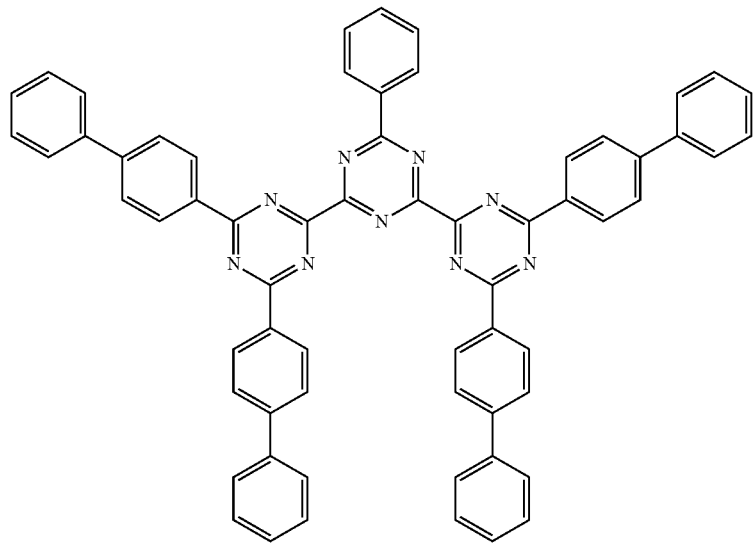
[A-108]
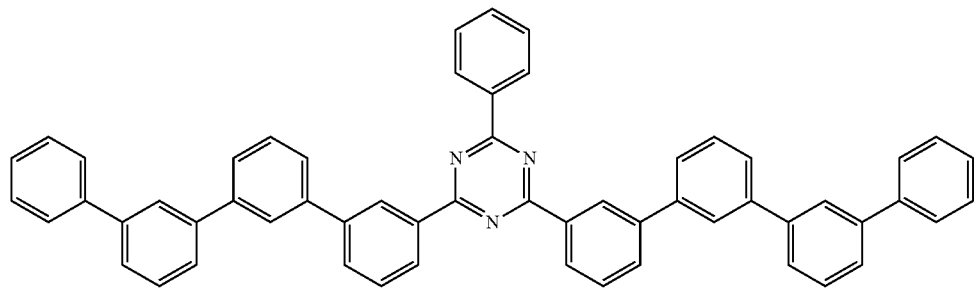
[A-109]
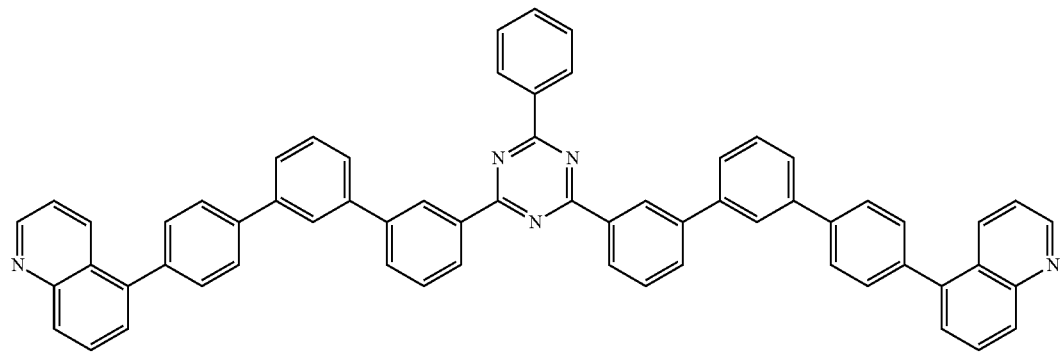
[A-110]
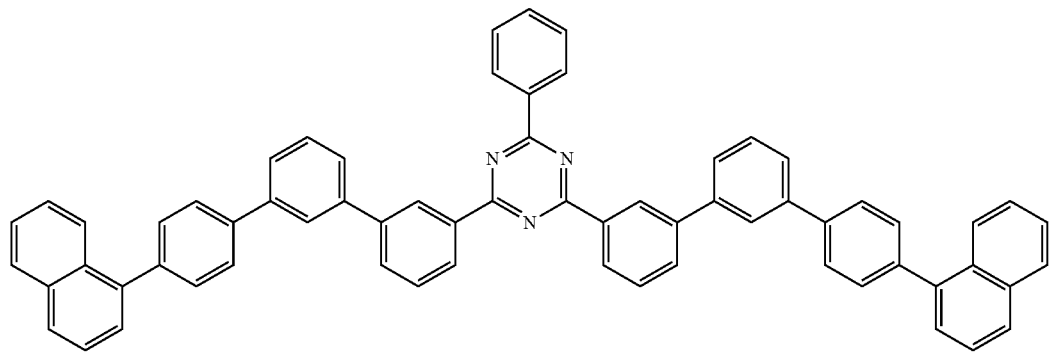
[A-111]

[A-112]
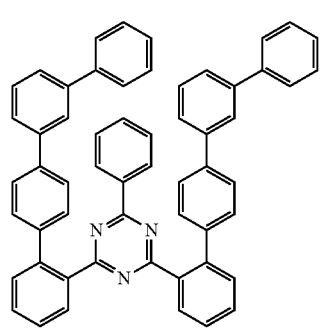
[A-113]
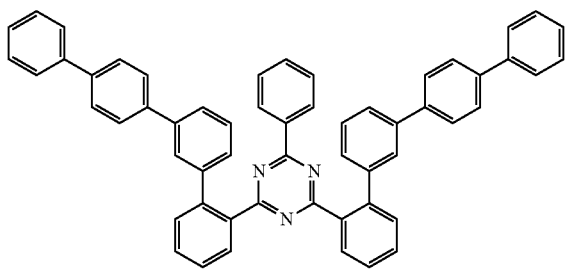
[A-114]
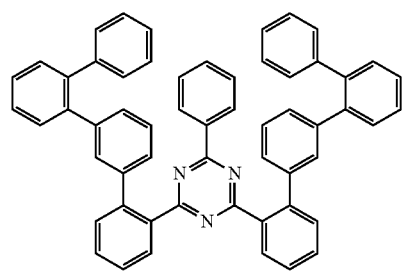
[A-115]
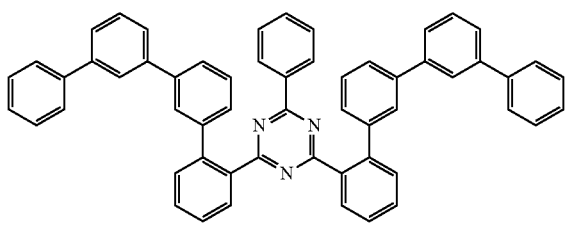
[A-116]
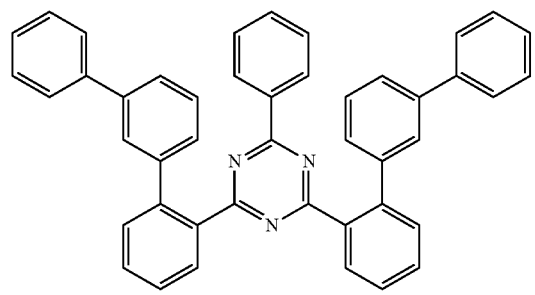
[A-117]
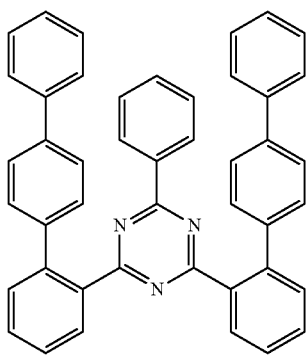
[A-118]
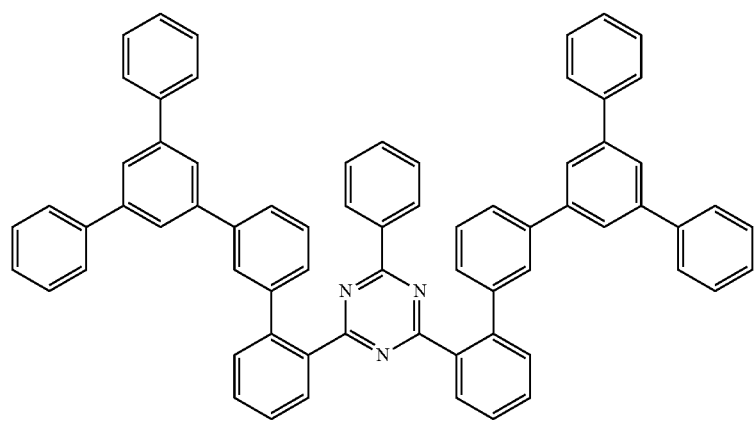

-continued
[A-119]
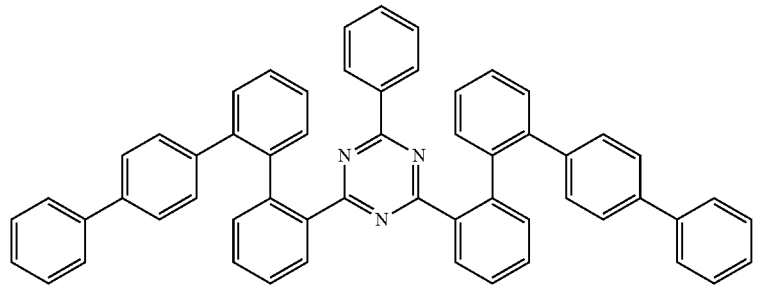
[A-120]
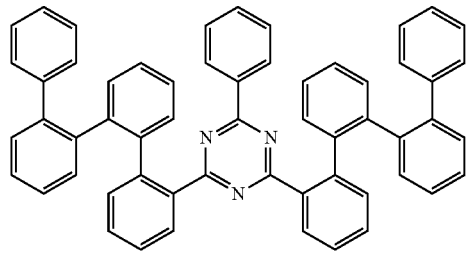
[A-121]
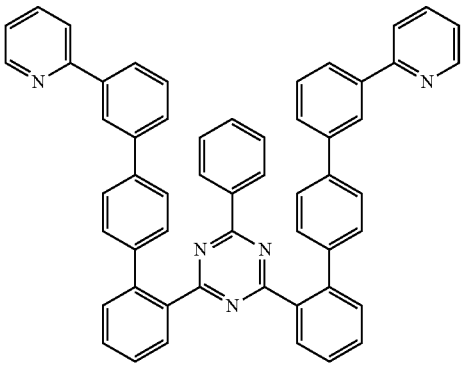
[A-122]
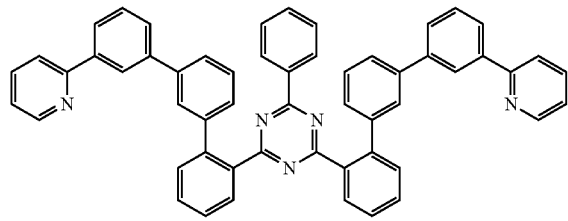
[A-123]
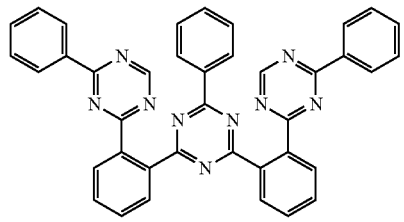
[A-124]
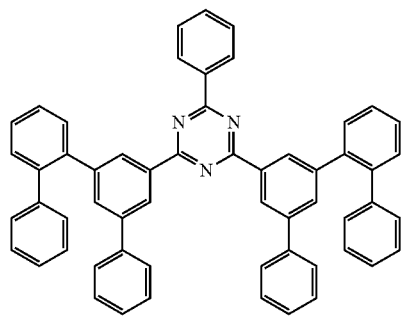
[A-125]
[A-126]
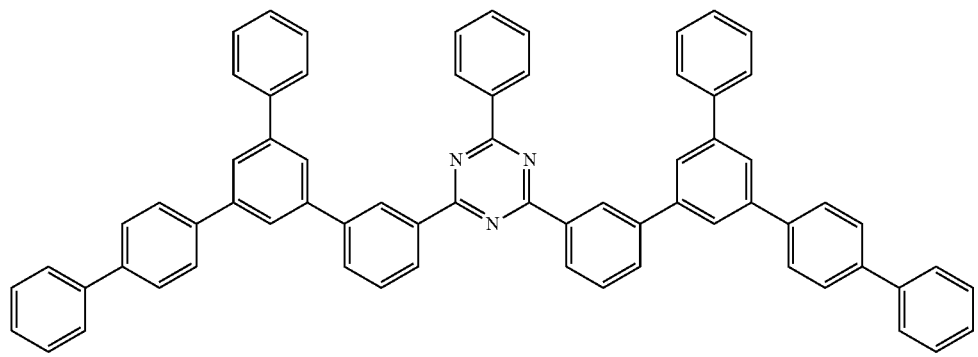

-continued
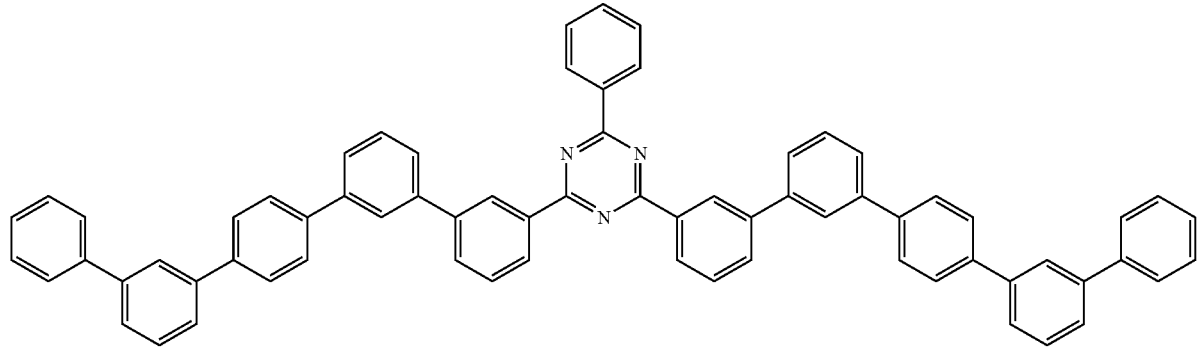
[A-127]
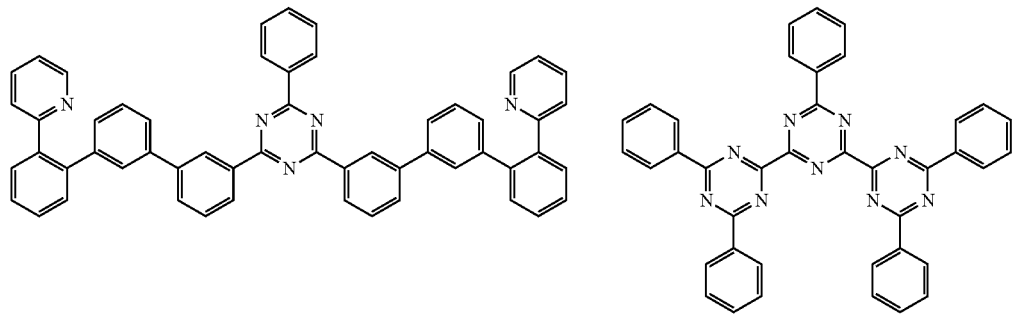
[A-128]  [A-129]
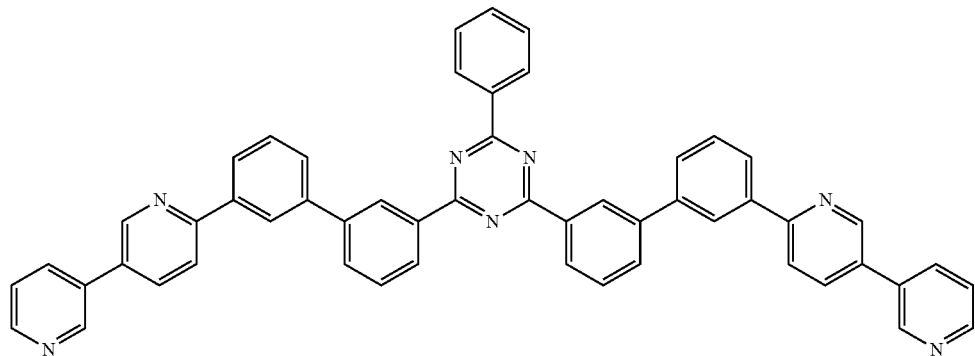
[A-130]
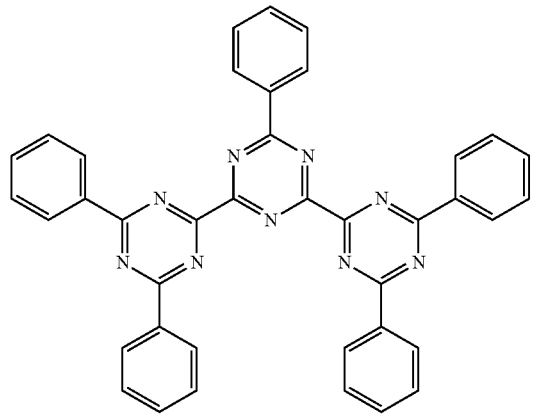
[A-131]

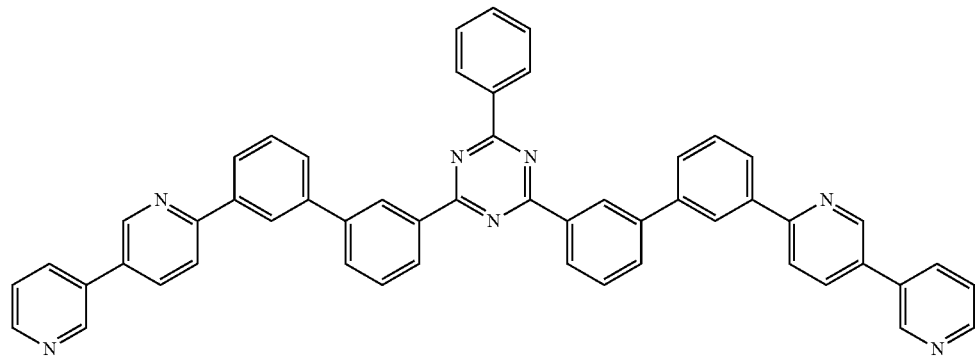
[A-132]
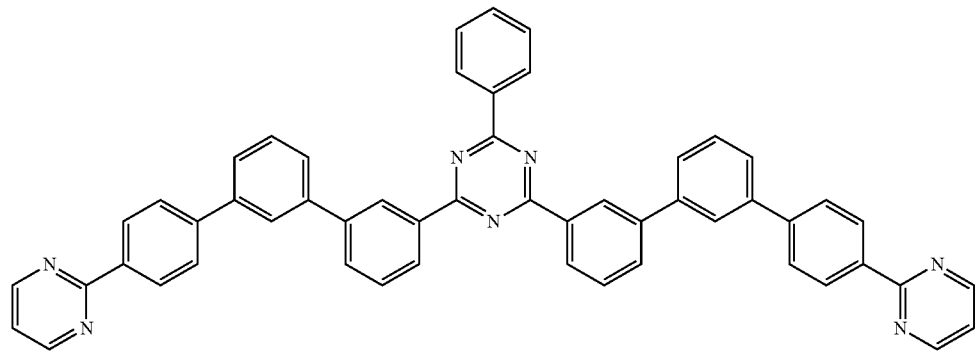
[A-133]
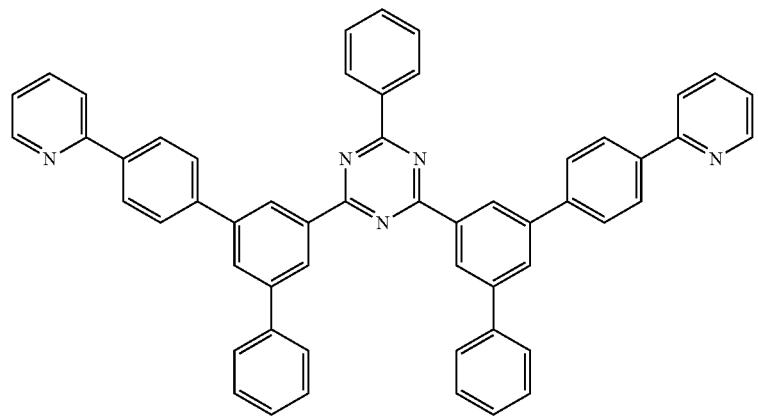
[A-134]
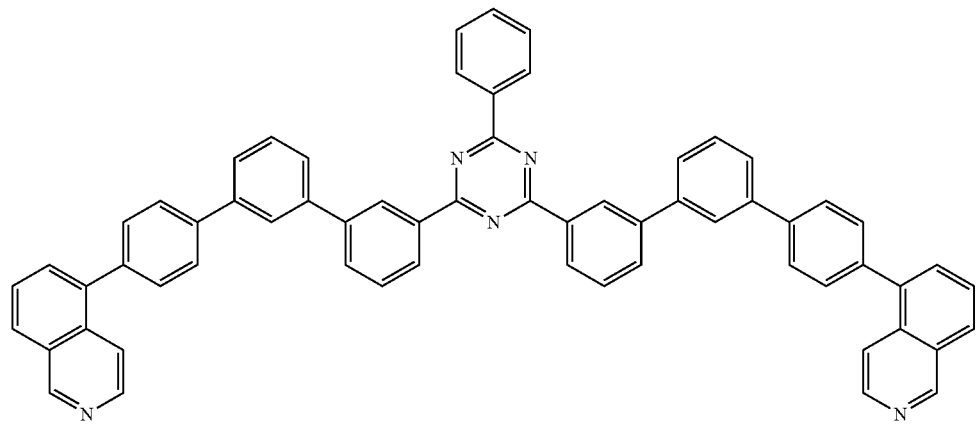
[A-135]

-continued
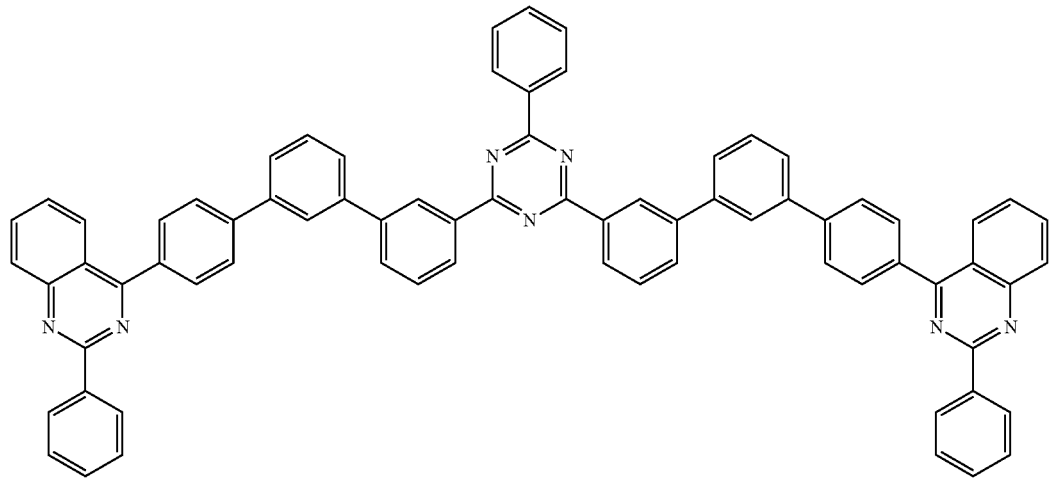
[A-138]
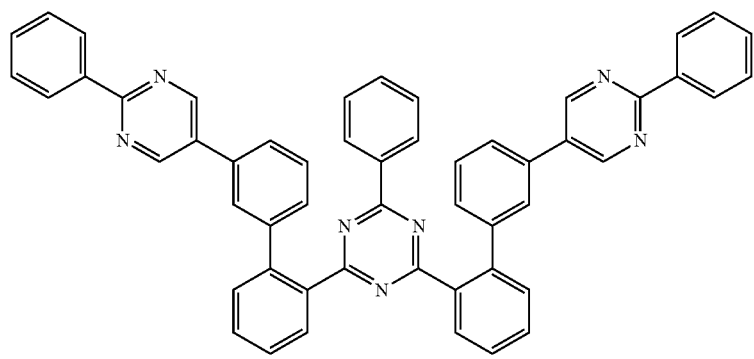
[A-139]
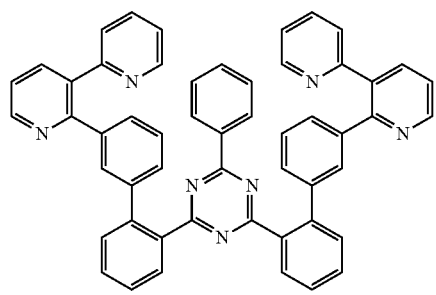
[A-140]
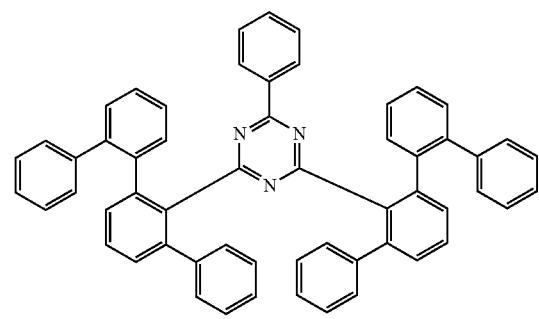
[A-141]
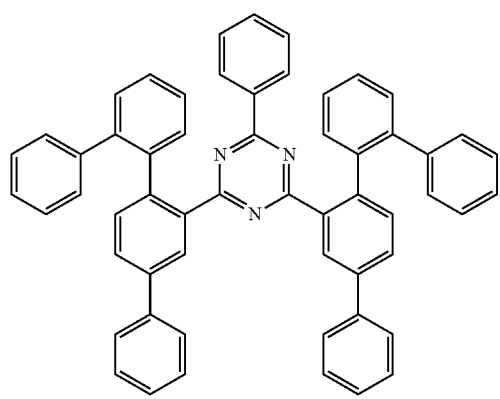
[A-142]
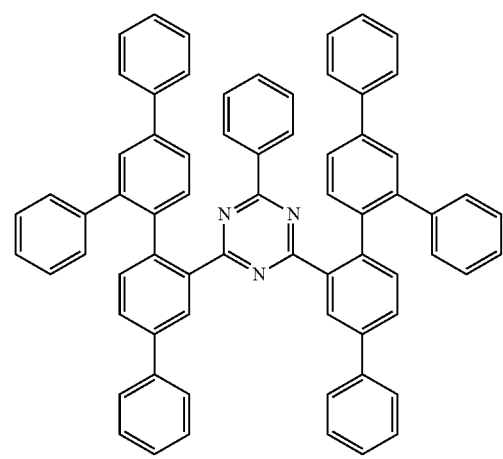
[A-143]

-continued
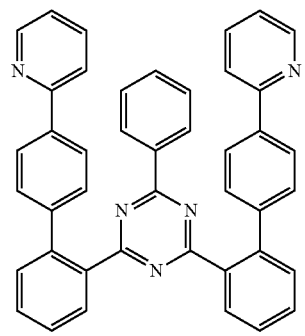
[A-144]
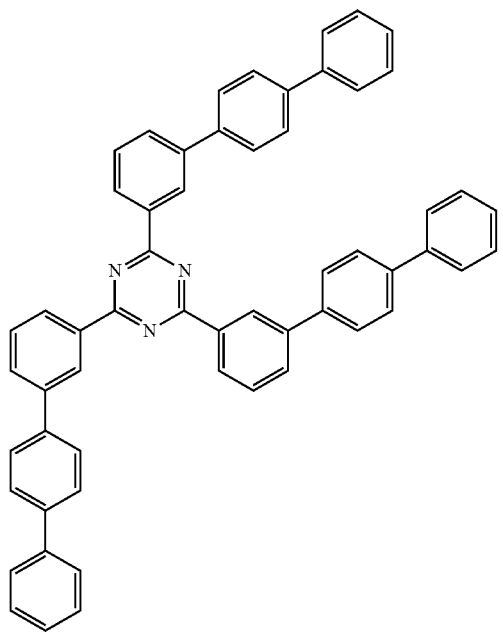
[A-145]
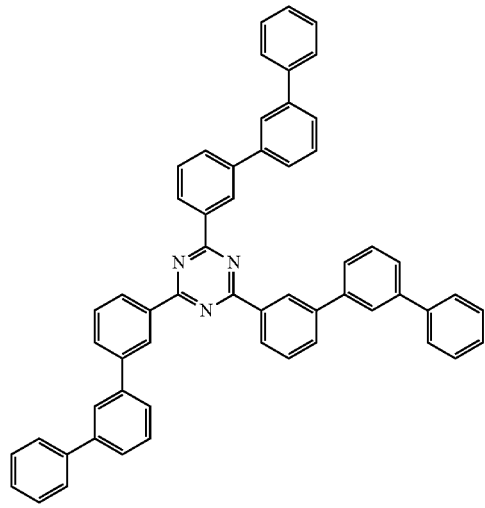
[A-146]
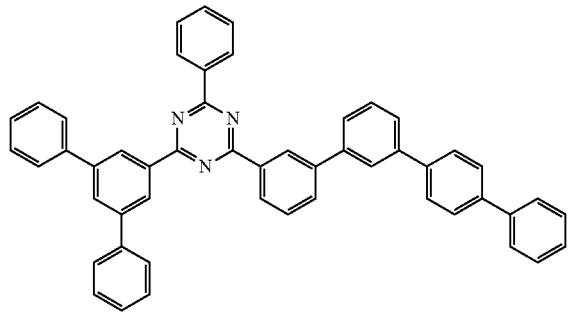
[A-147]
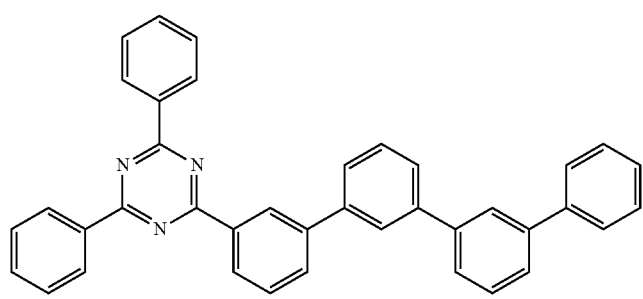
[A-148]

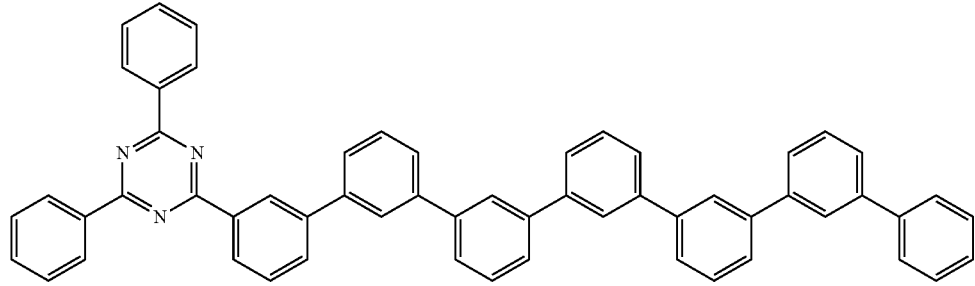
[A-149]
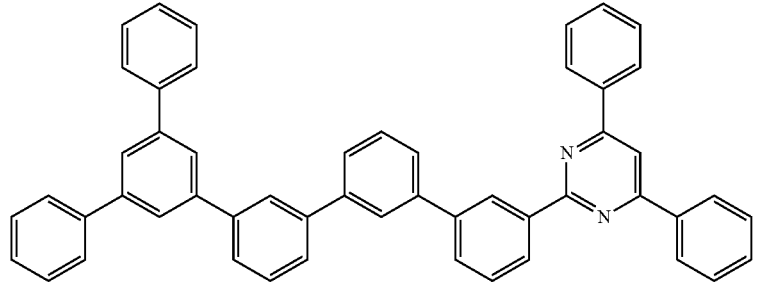
[A-150]
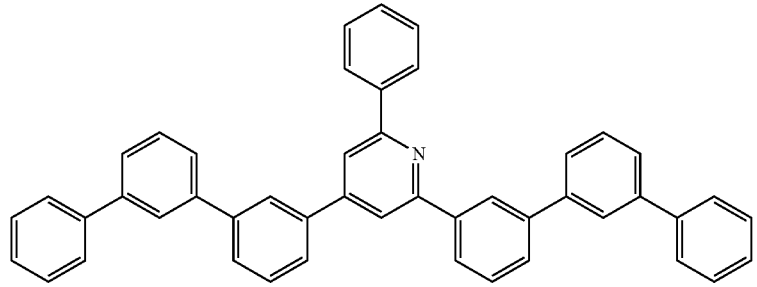
[A-151]
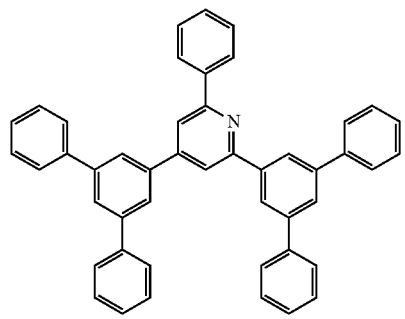
[A-152]
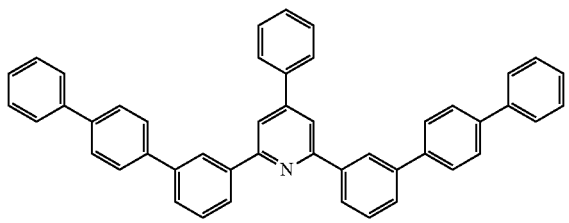
[A-153]
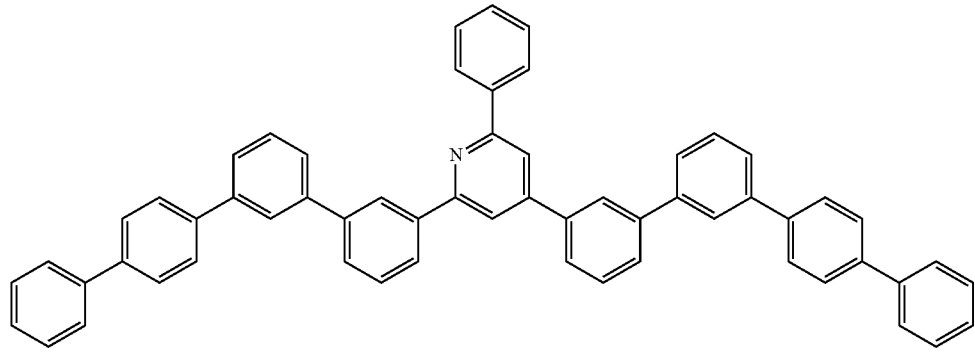
[A-154]

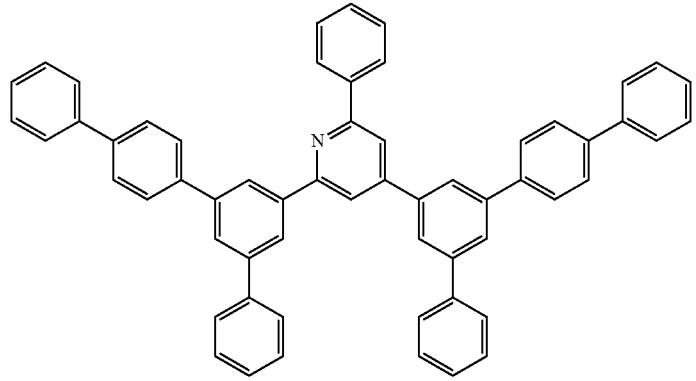 [A-155]
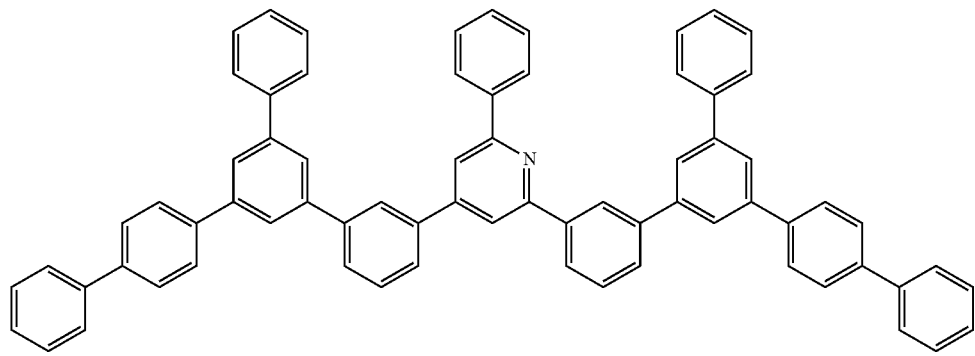 [A-156]
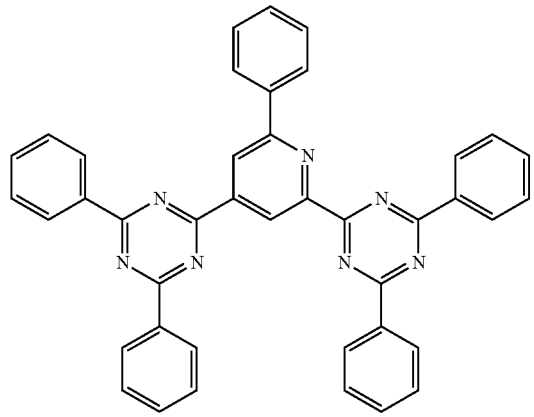 [A-157]
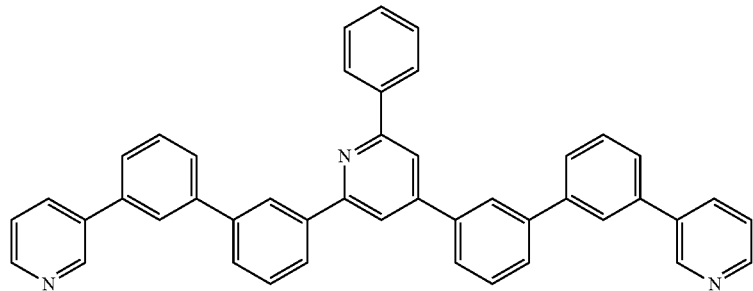 [A-158]

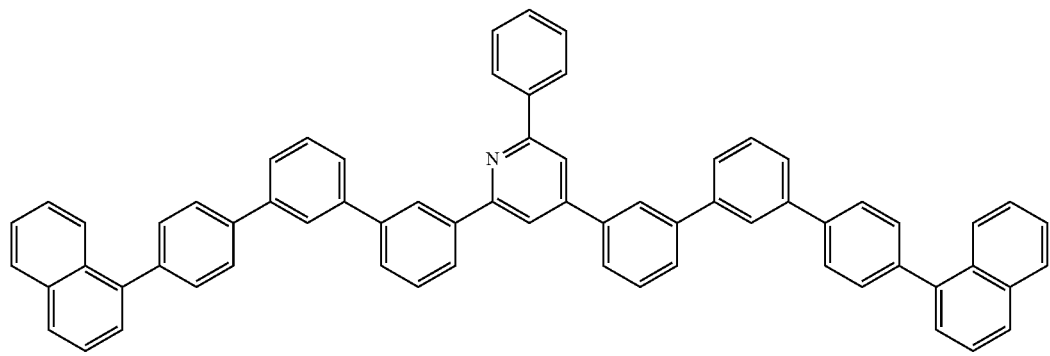
[A-159]
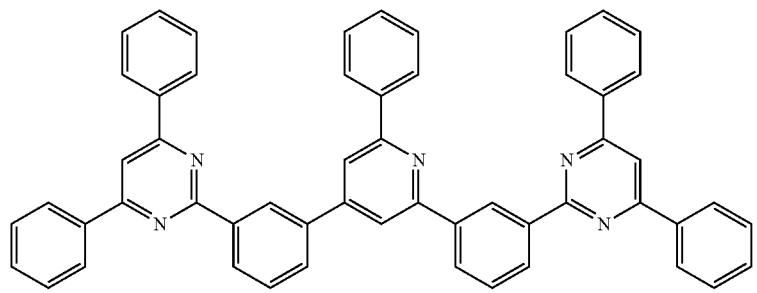
[A-160]
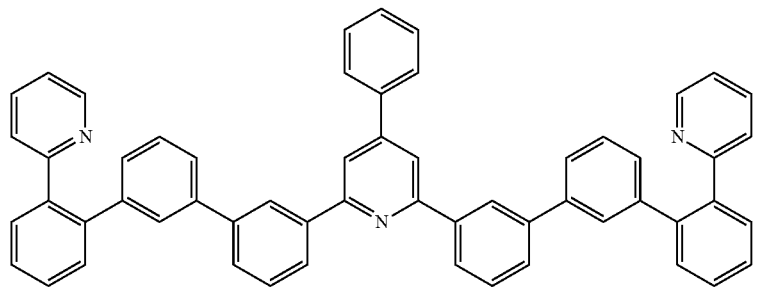
[A-161]
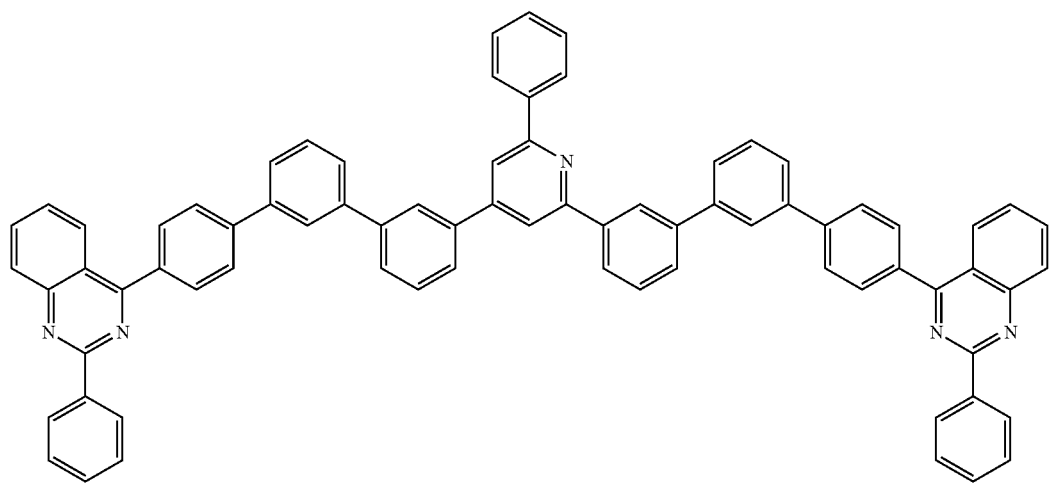
[A-162]

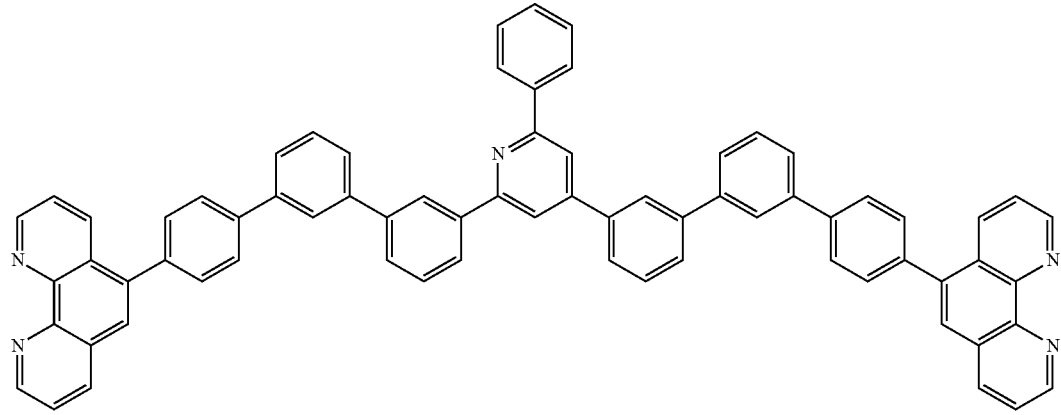
[A-163]
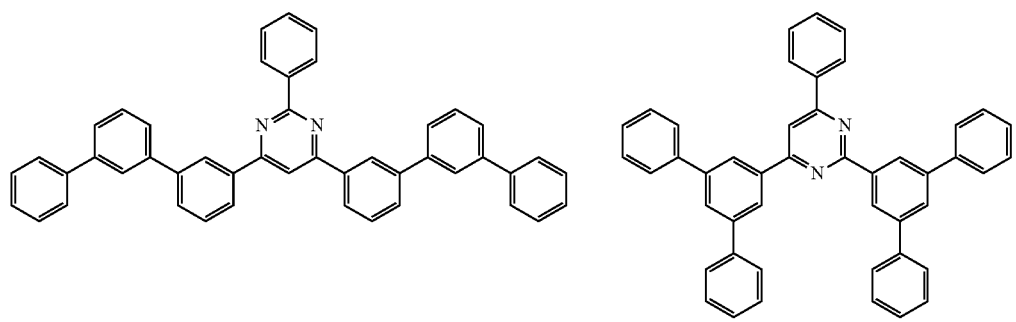
[A-164]  [A-165]
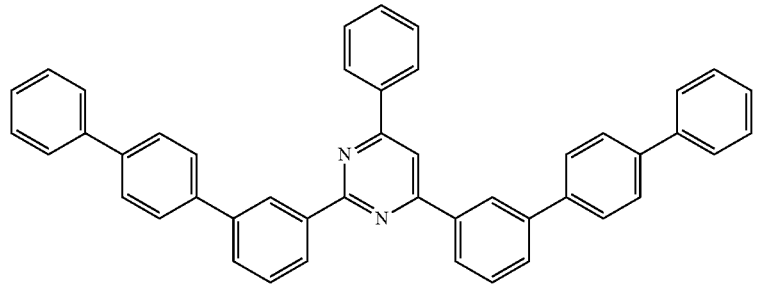
[A-166]
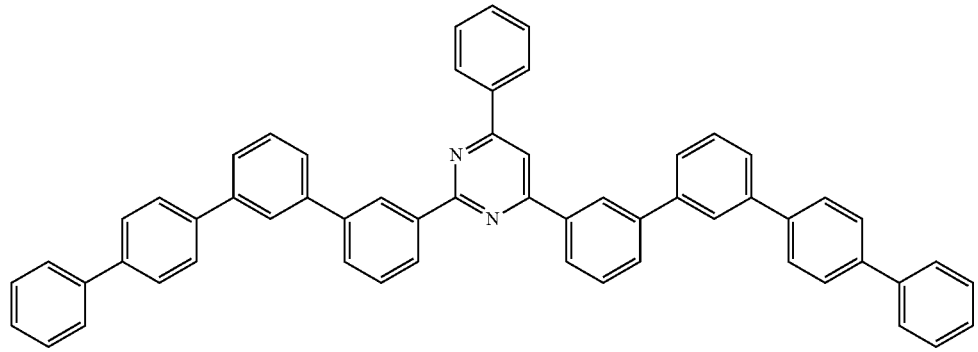
[A-167]

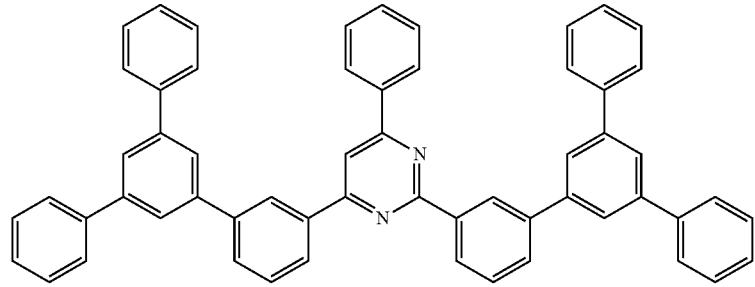
[A-168]
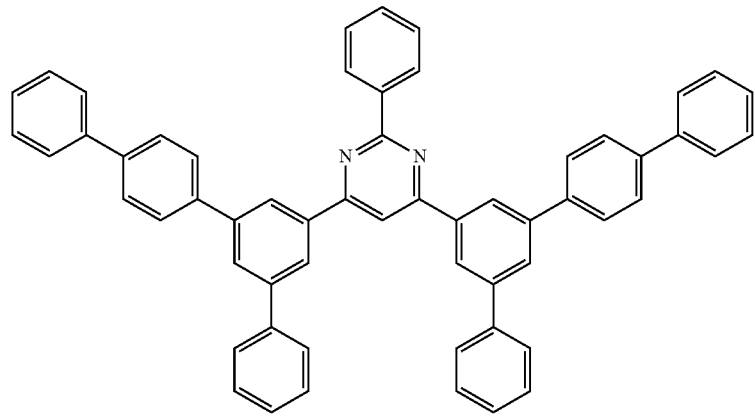
[A-169]
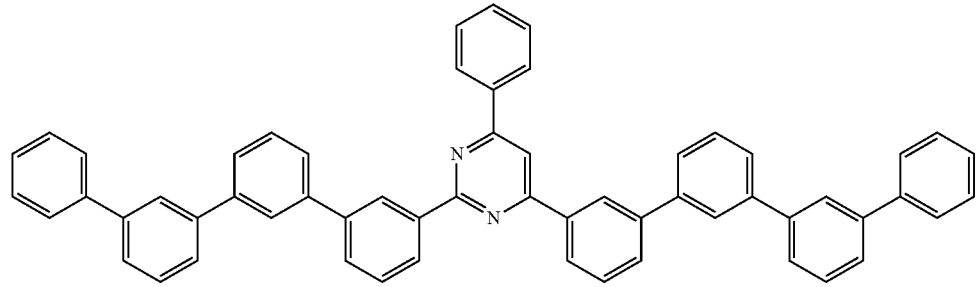
[A-170]
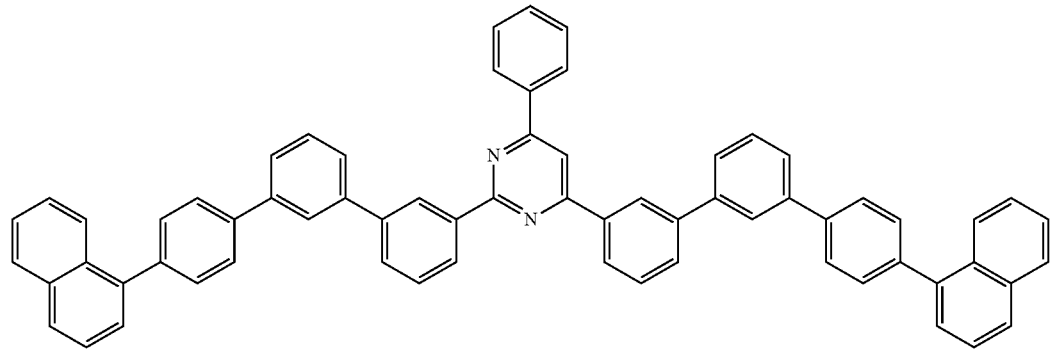
[A-171]

[A-172]
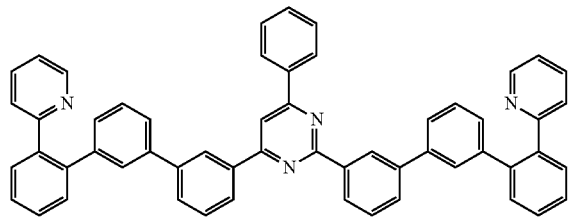
[A-173]
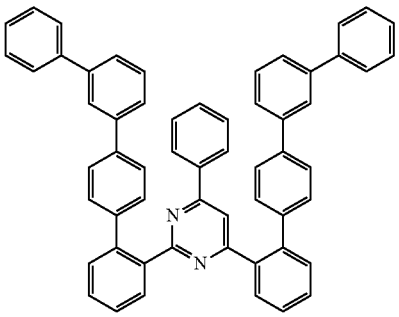
[A-174]
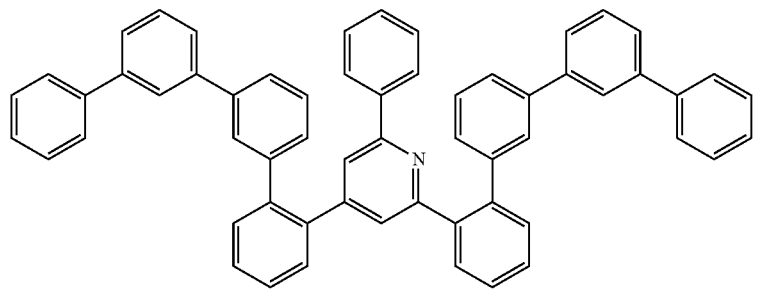
[A-175]
[A-176]
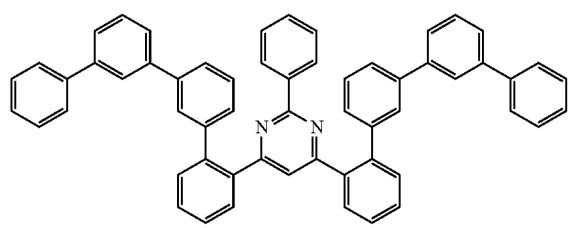
[A-177]
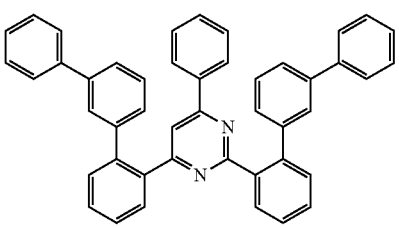
[A-178]
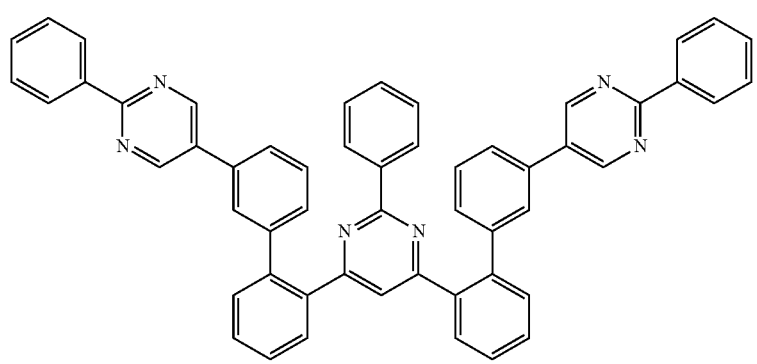
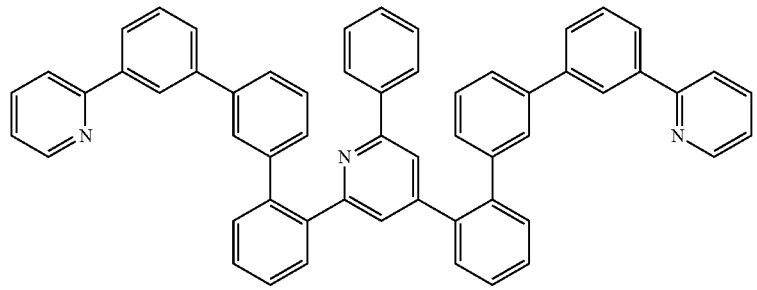

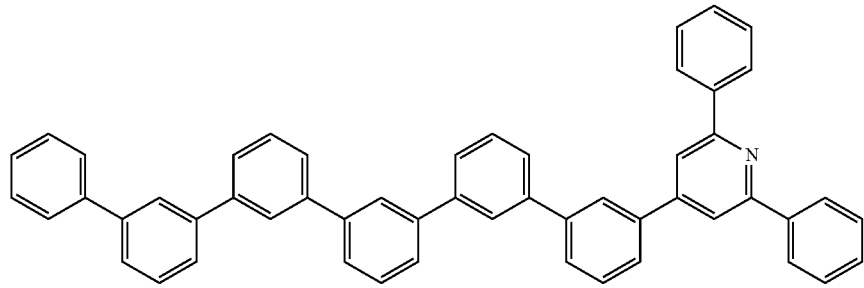
[A-179]
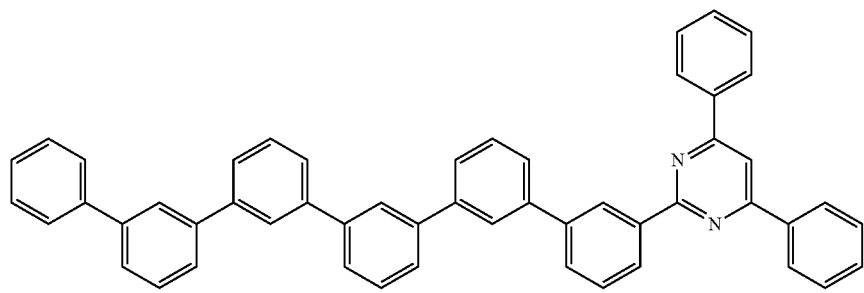
[A-180]
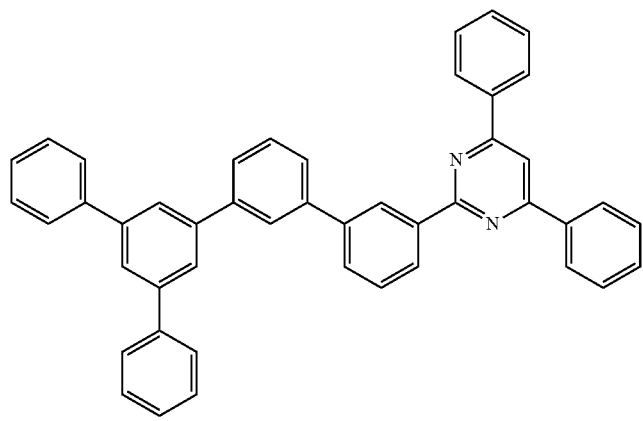
[A-181]
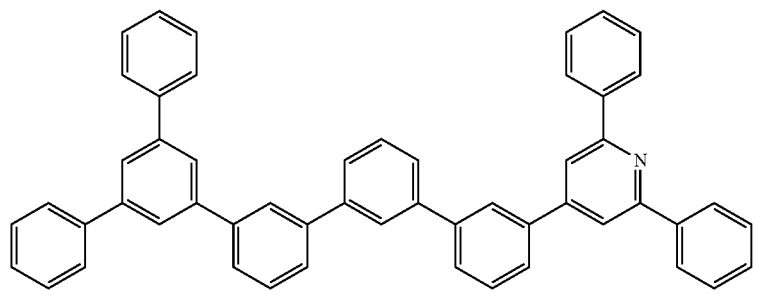
[A-182]

-continued
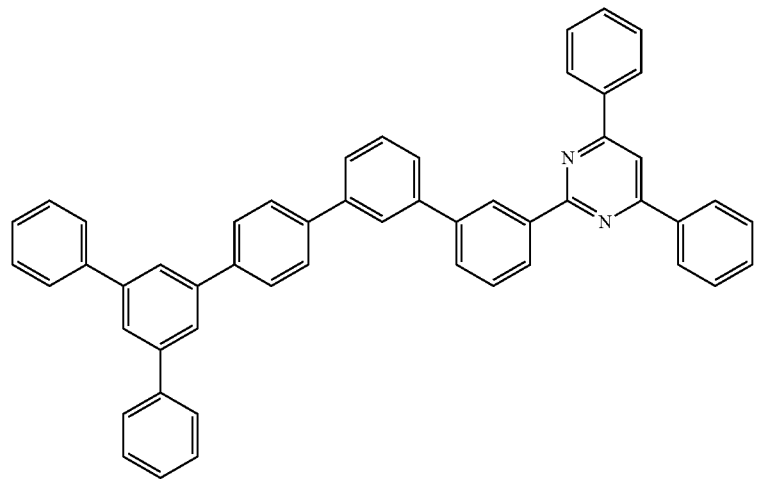
[A-183]
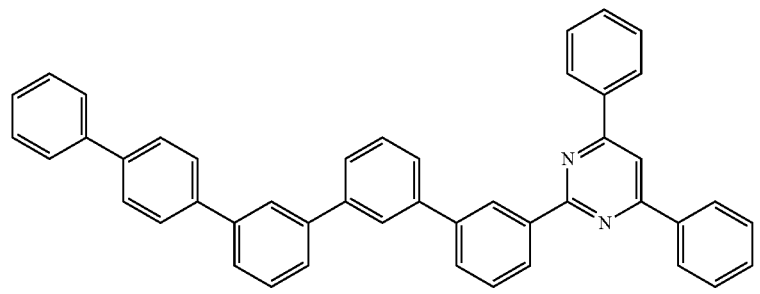
[A-184]
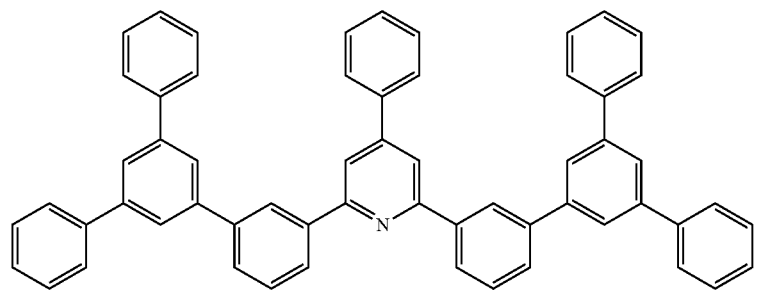
[A-185]
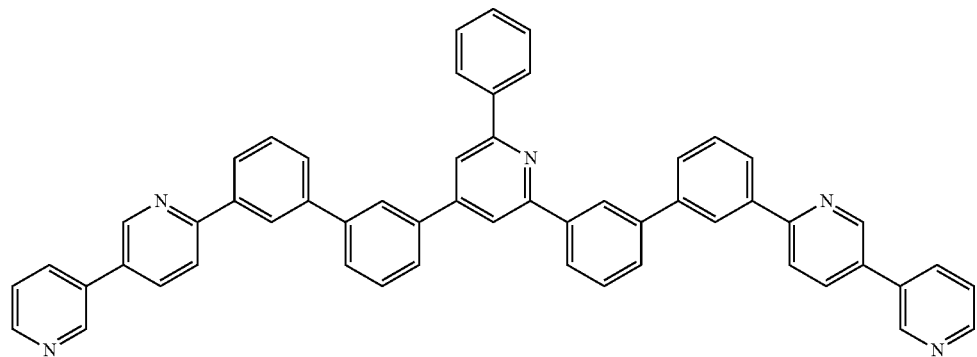
[A-186]

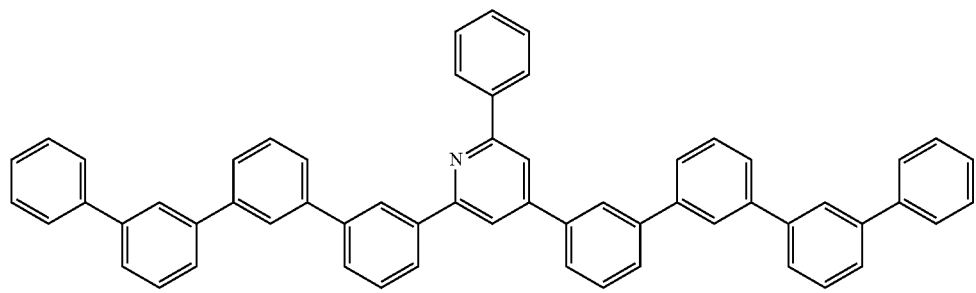
[A-187]
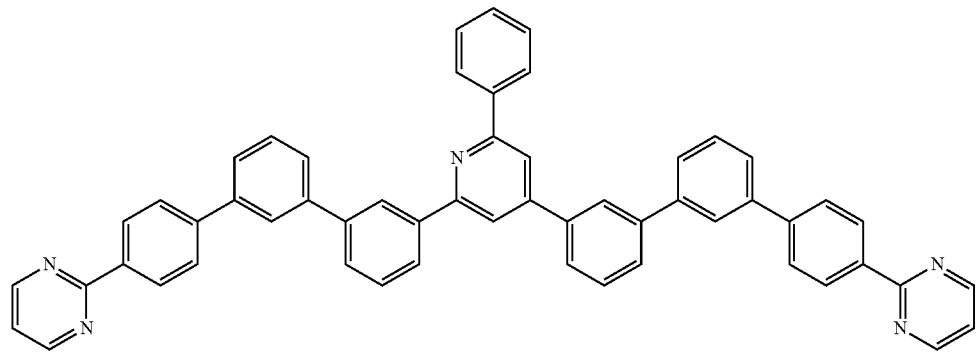
[A-188]
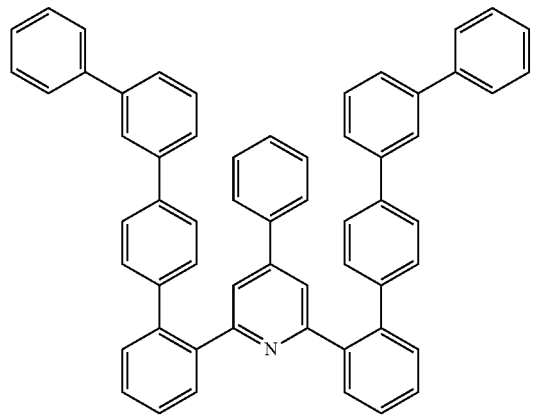
[A-189]
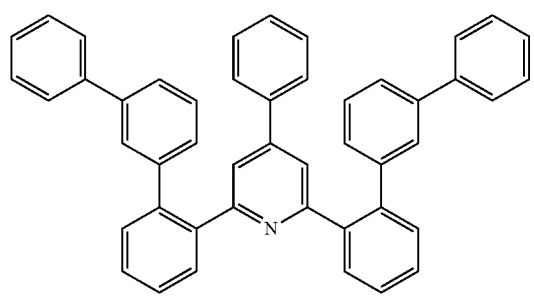
[A-190]
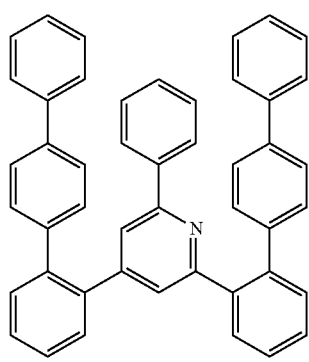
[A-191]

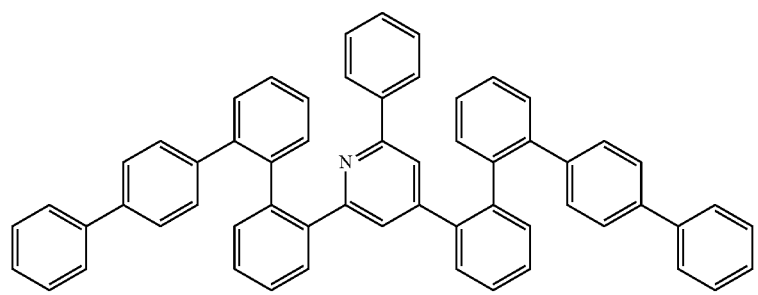
[A-192]
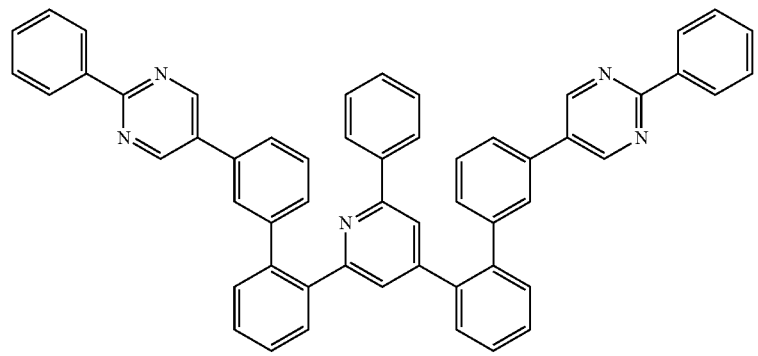
[A-193]
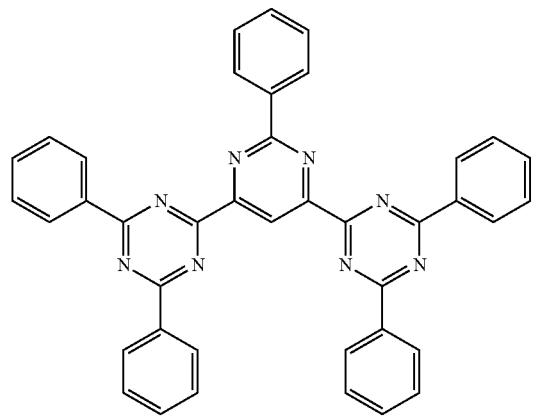
[A-194]
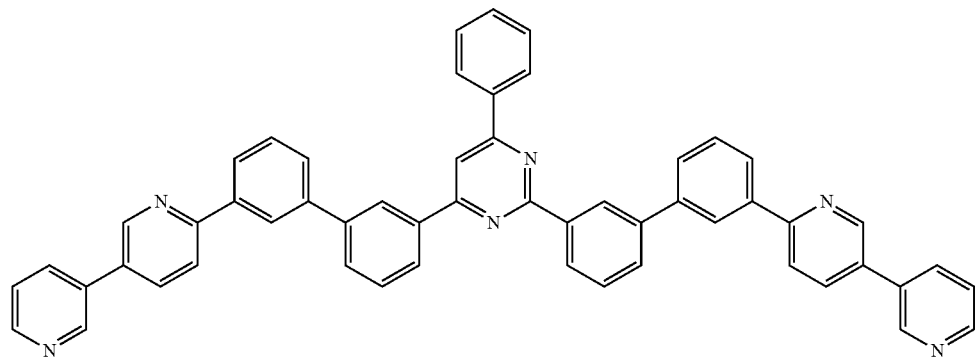
[A-195]

113
[A-196]
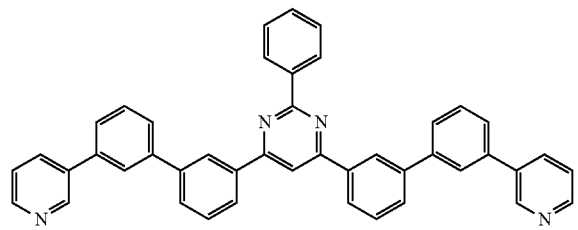
114
[A-197]
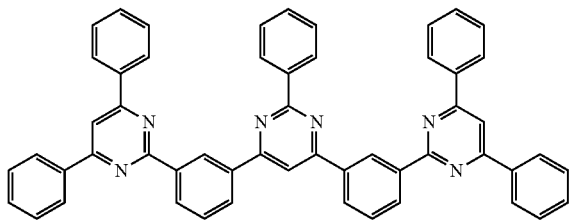
[A-198]
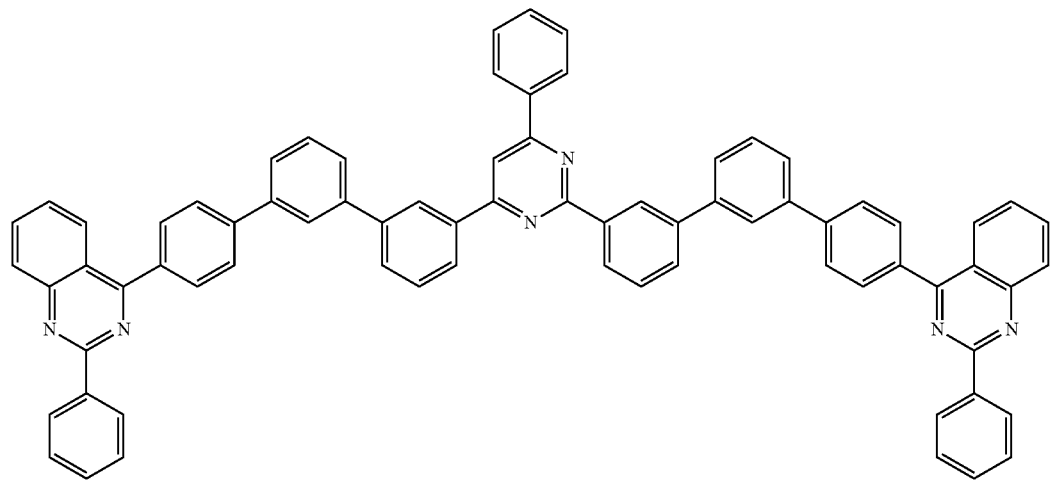
[A-199]
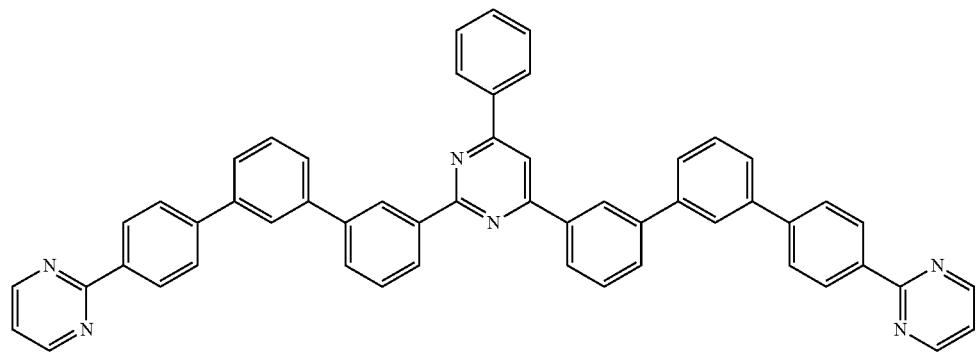
[A-200]
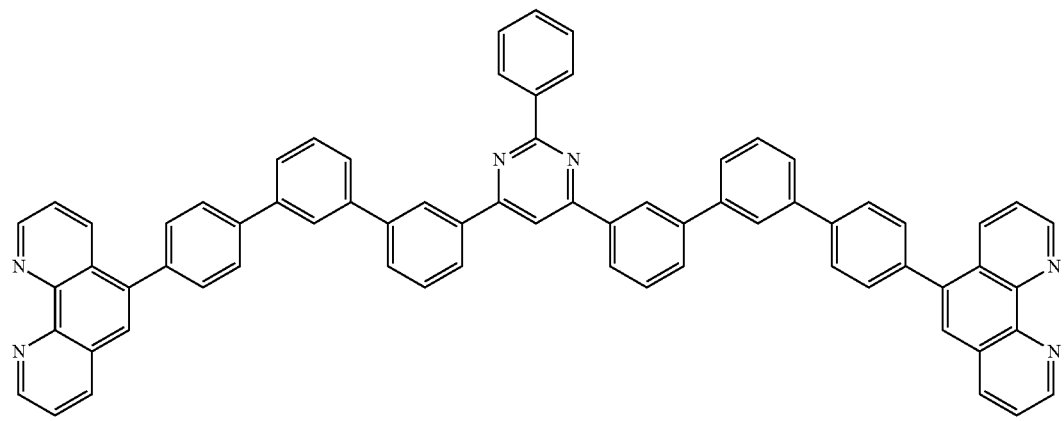

-continued
[A-201]
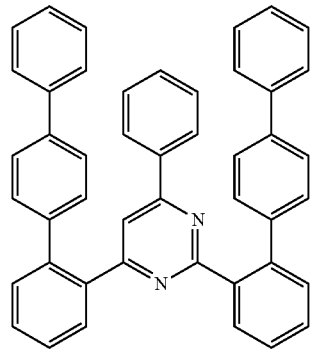
[A-202]
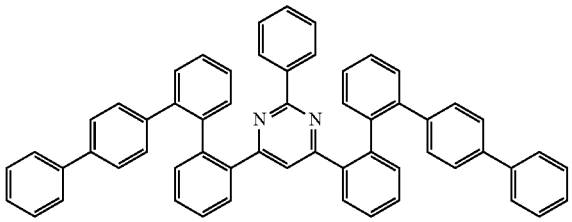
[A-203]
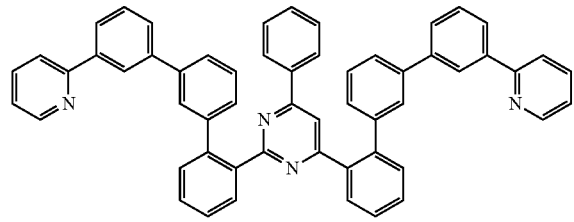
[A-204]
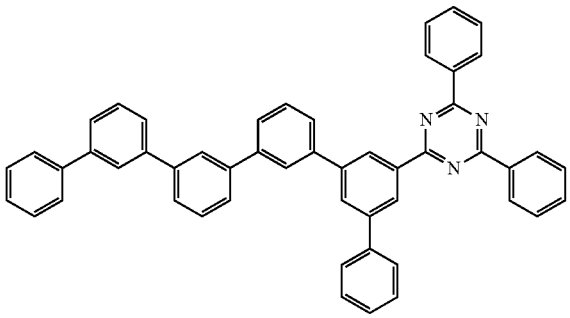
[A-205]
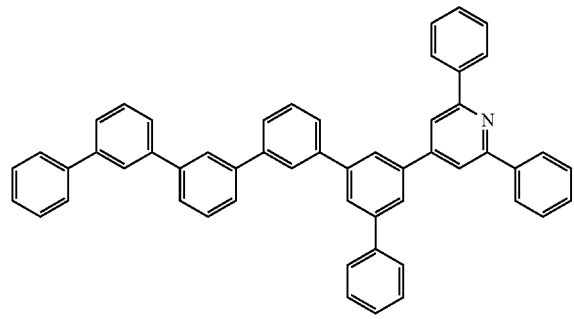
[A-206]
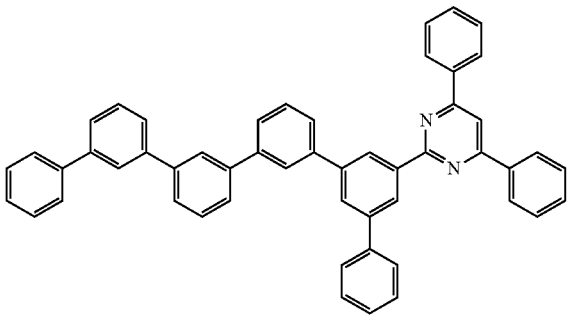
[A-207]
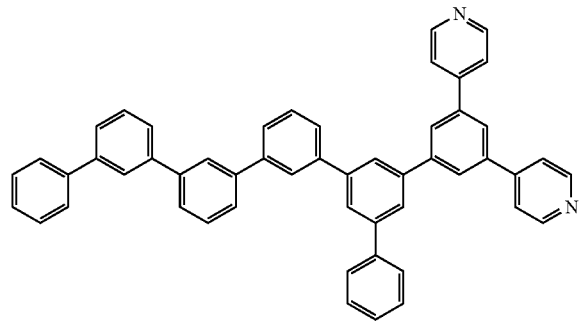
[A-208]
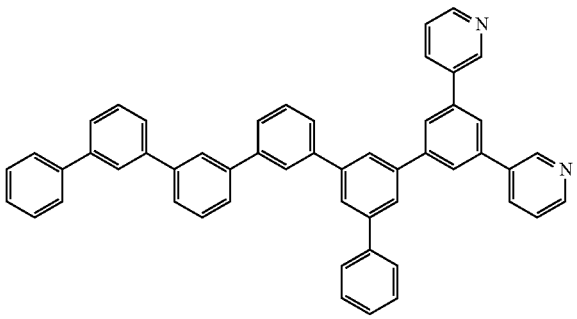

[A-209]
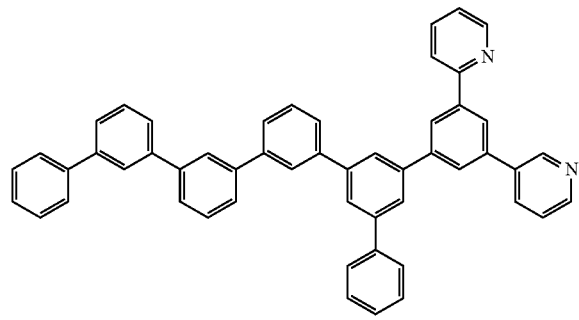
[A-210]
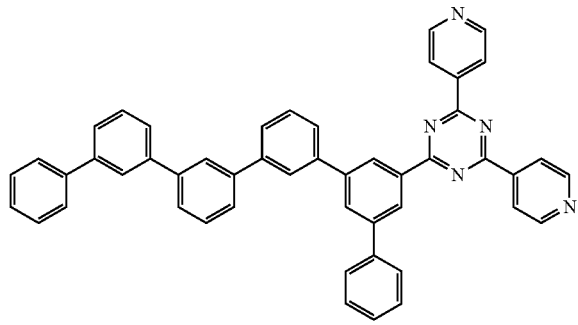
[A-211]
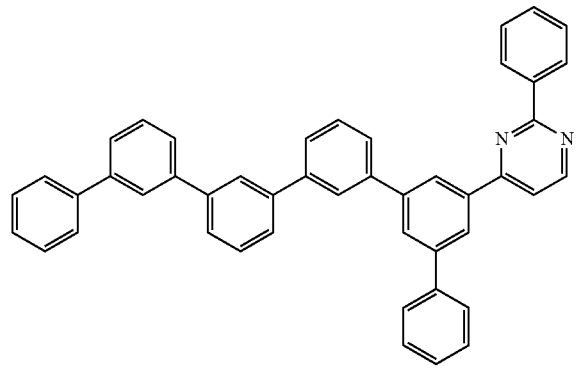
[A-212]
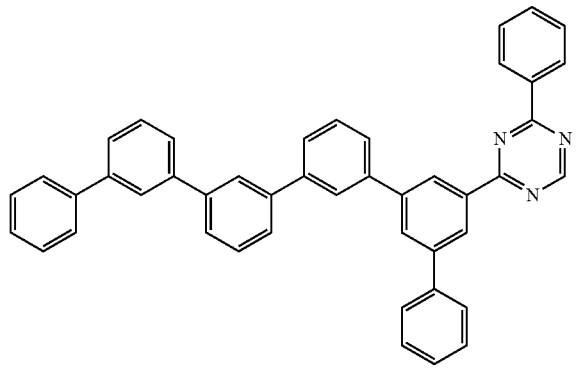
[A-213]
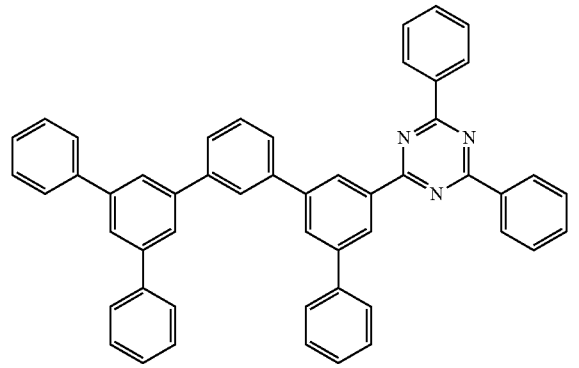
[A-214]
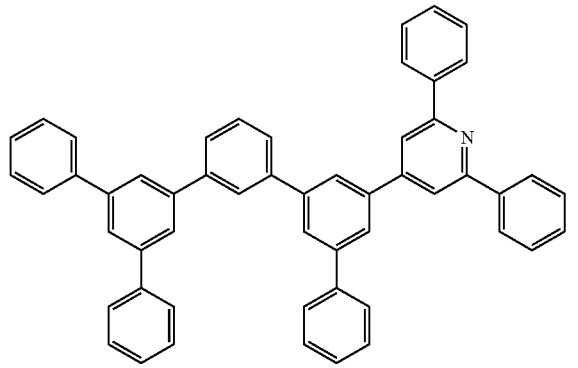
[A-215]
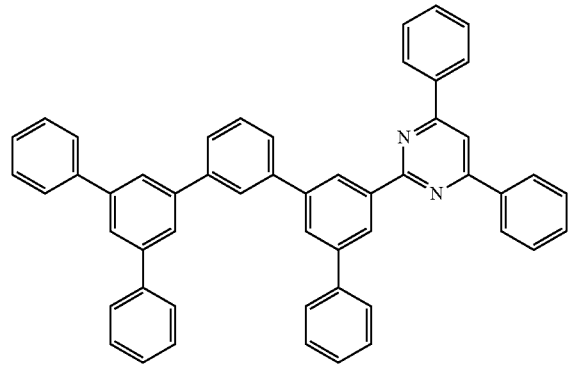
[A-216]
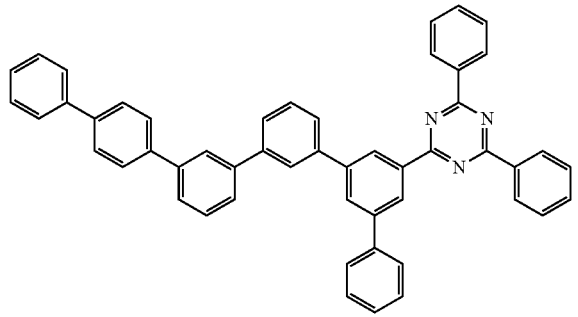

-continued
[A-217]
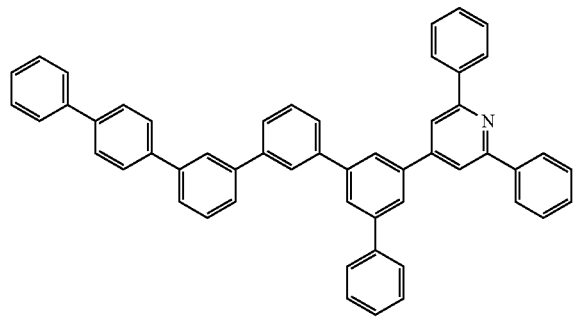
[A-218]
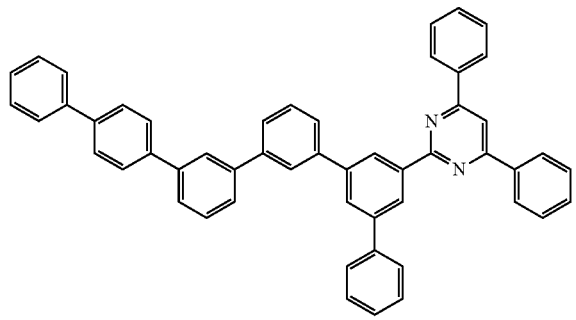
[A-219]
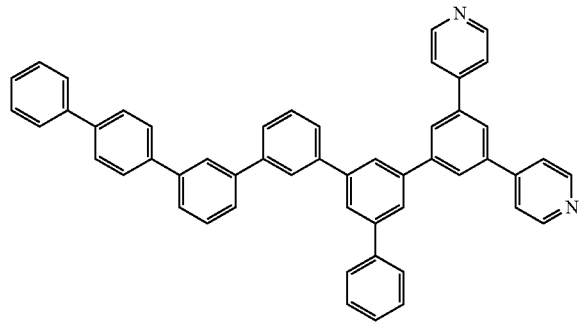
[A-220]
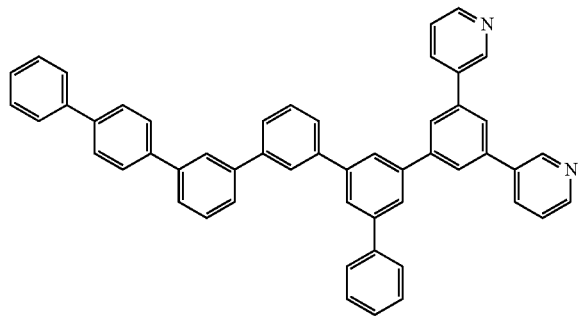
[A-221]
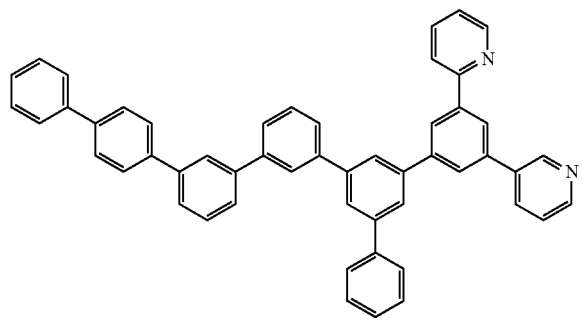
[A-222]
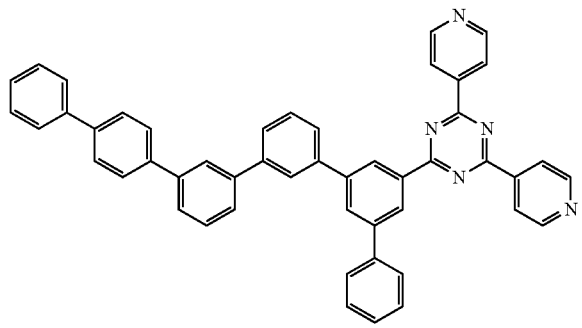
[A-223]
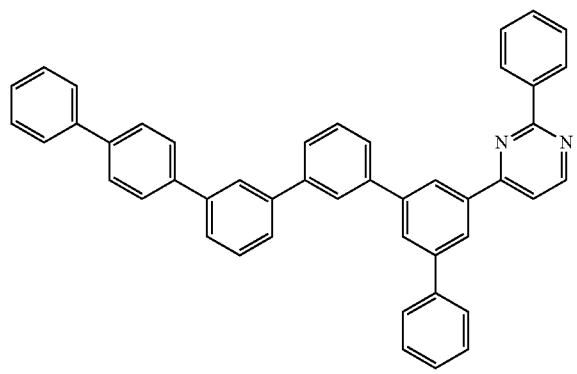
[A-224]
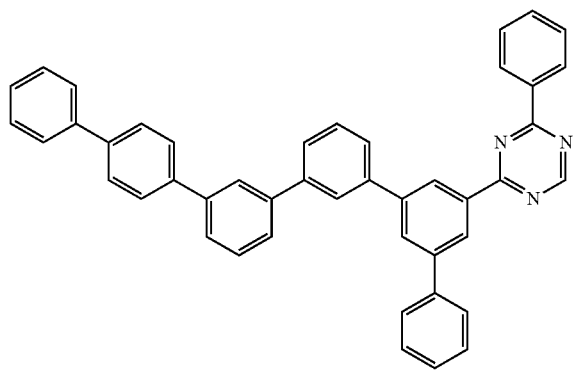

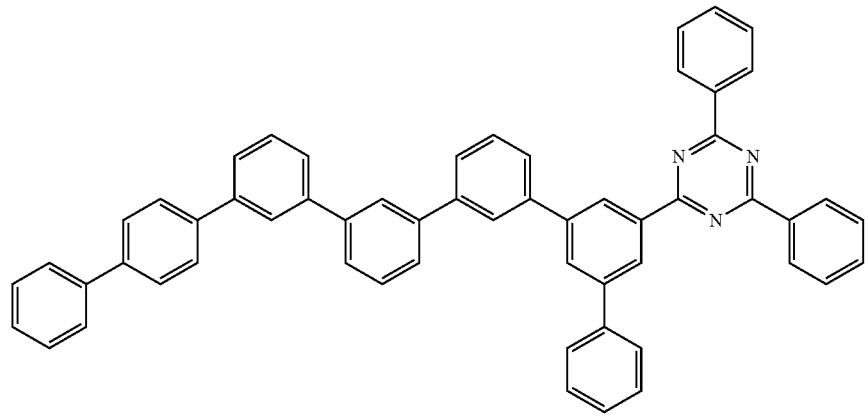
[A-225]
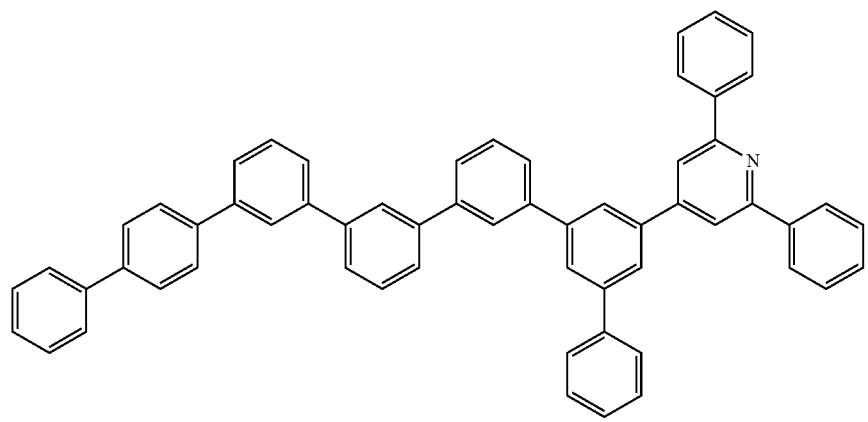
[A-226]
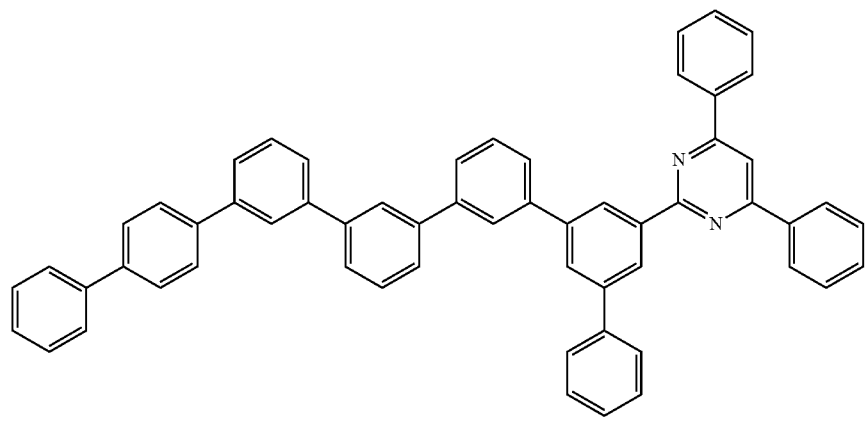
[A-227]

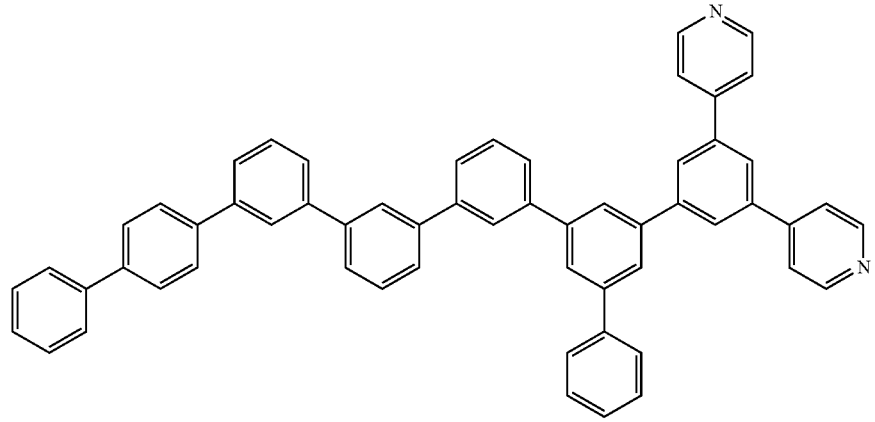
[A-228]
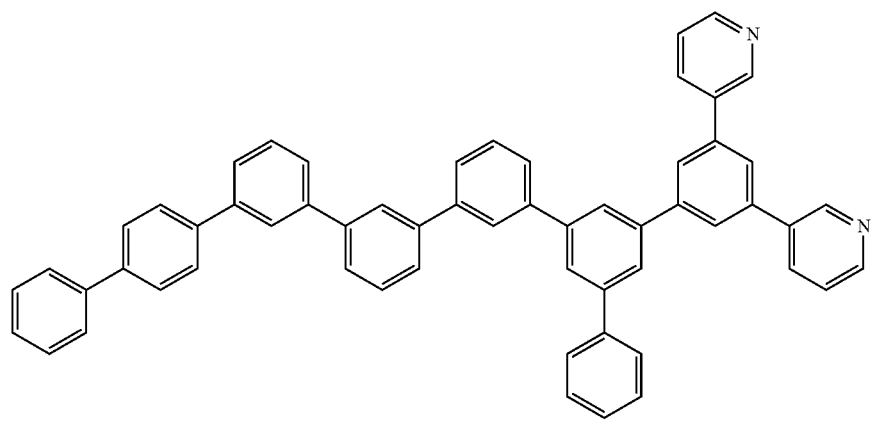
[A-229]
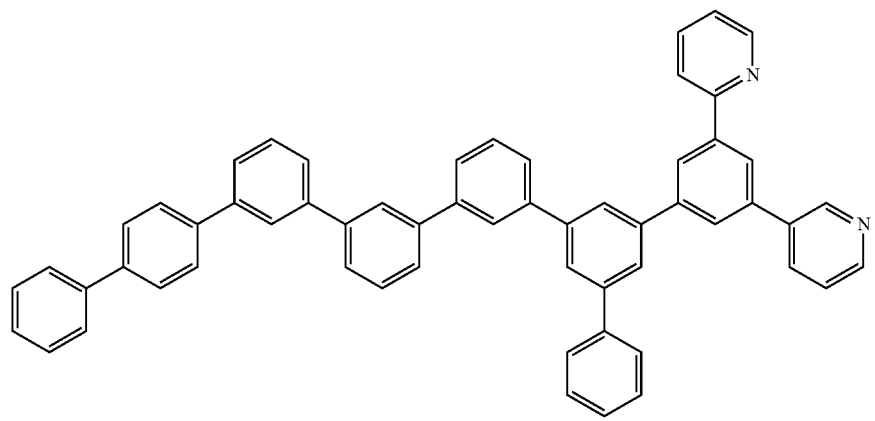
[A-230]

[A-231]
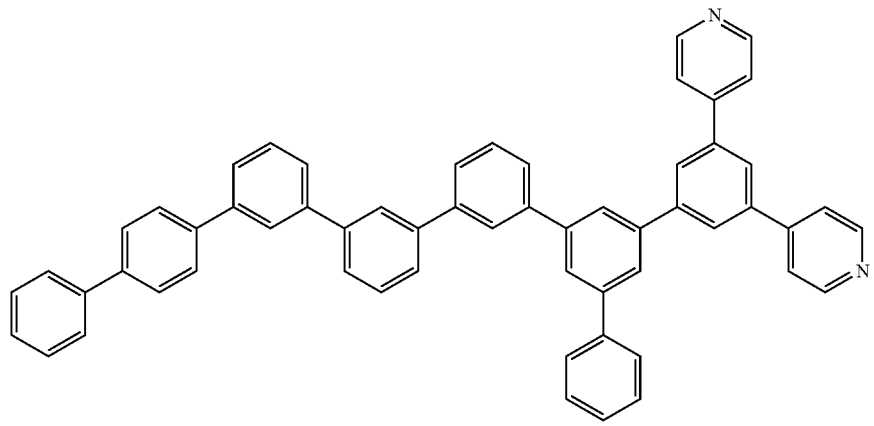
[A-232]
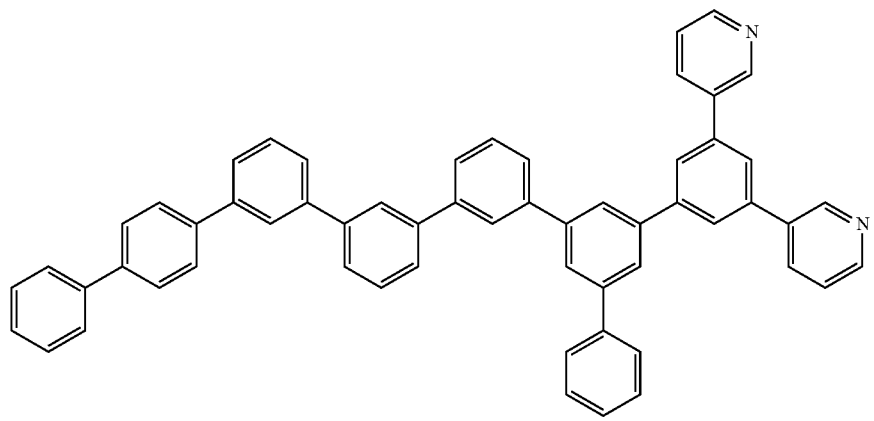
[A-233]
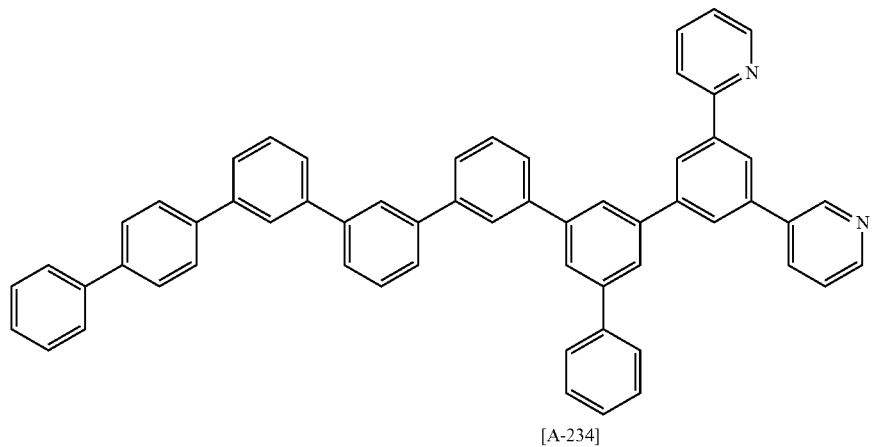
[A-234] [A-235]
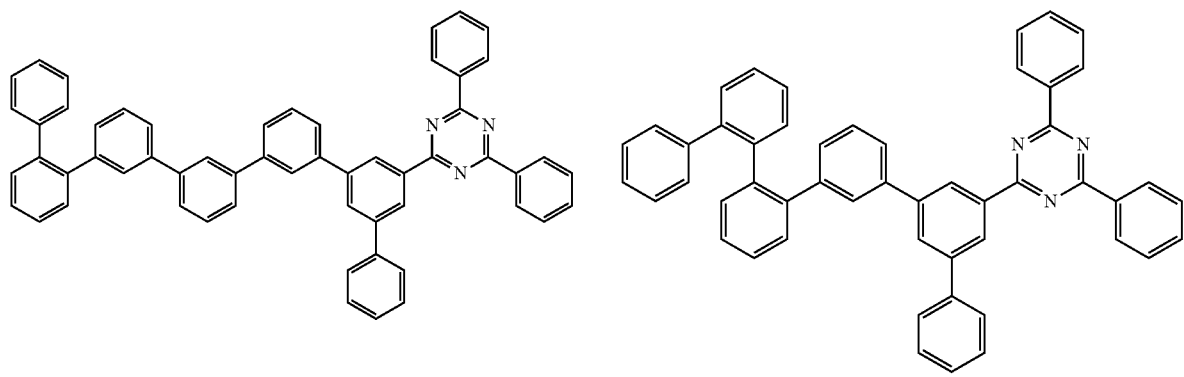

-continued
[A-236]
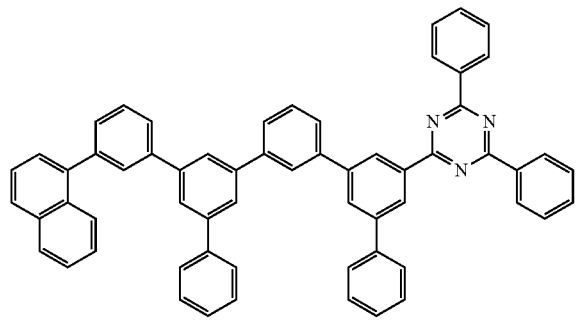
[A-237]
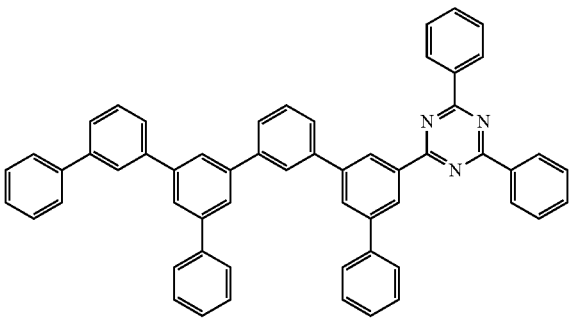
[A-238]
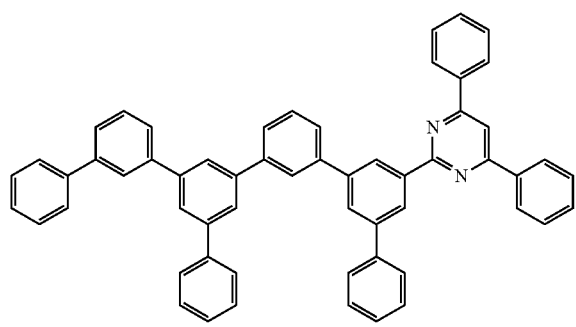
[A-239]
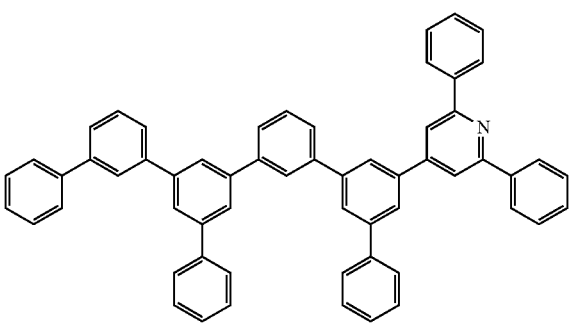
[A-240]
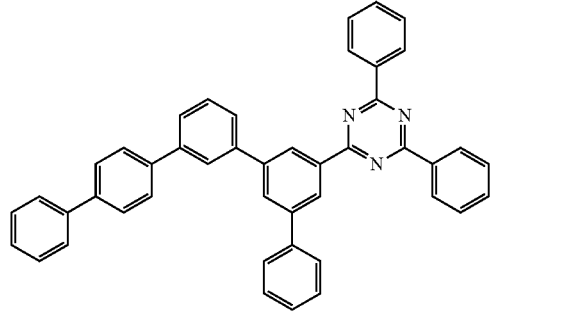
[A-241]
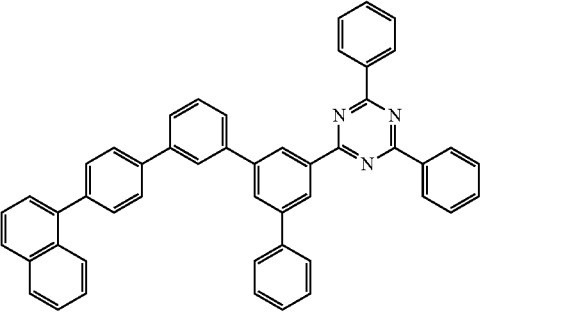
[A-242]
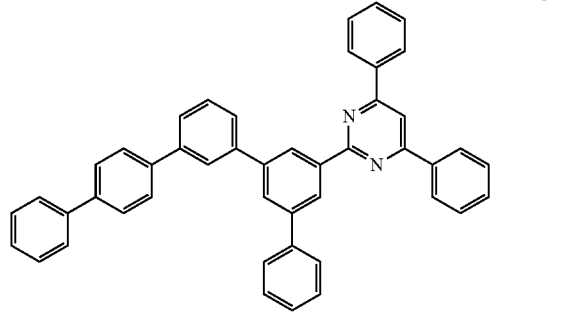
[A-243]
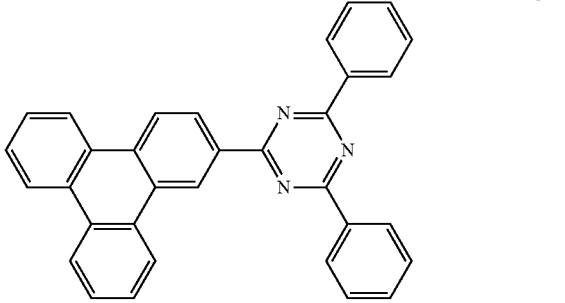
[A-244]
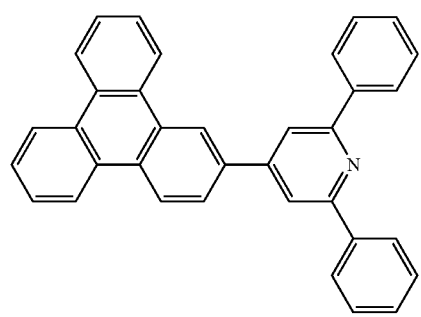
[A-245]
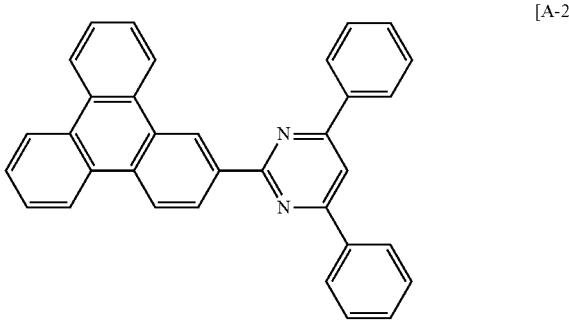

[A-246]
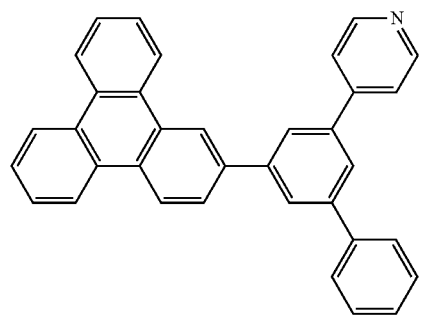
[A-247]
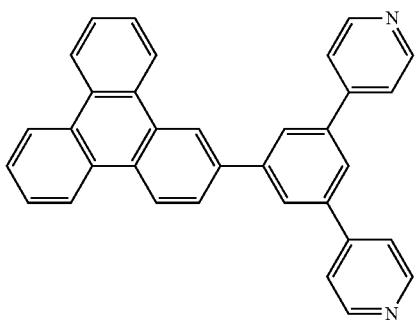
[A-248]
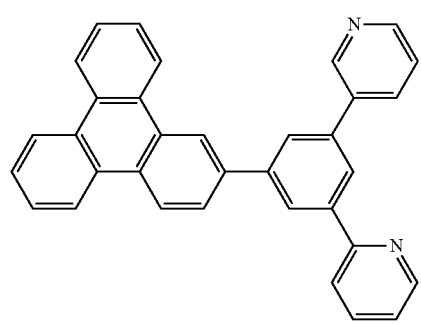
[A-249]
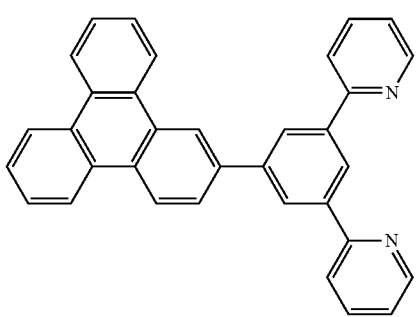
[A-250]
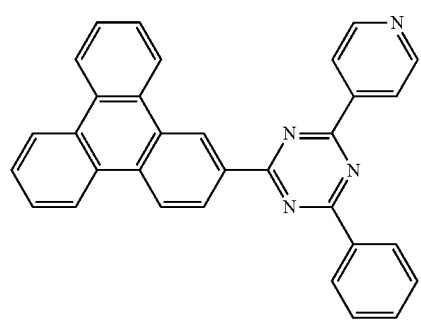
[A-251]
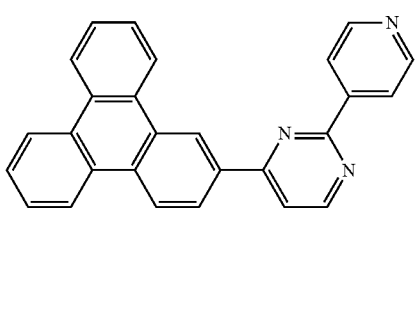
[A-252]
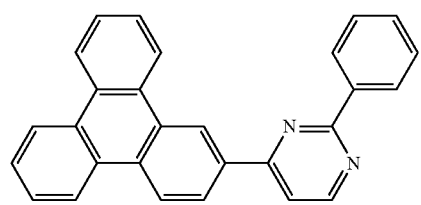
[A-253]
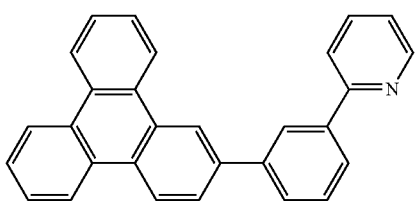
[A-254]
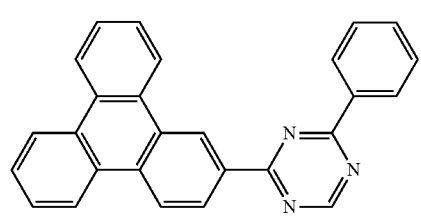
[A-255]
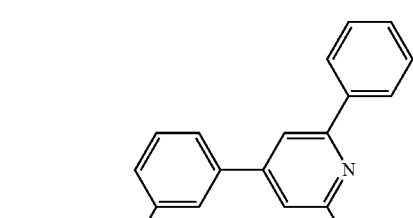
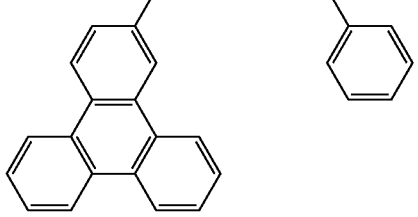

-continued
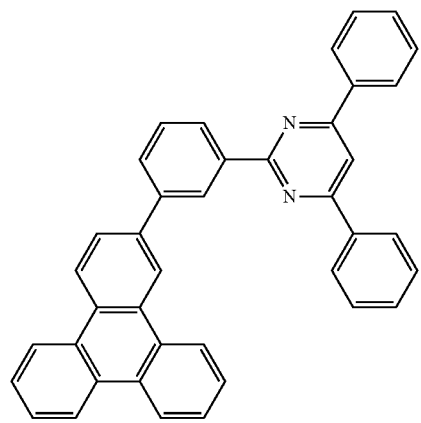
[A-256]
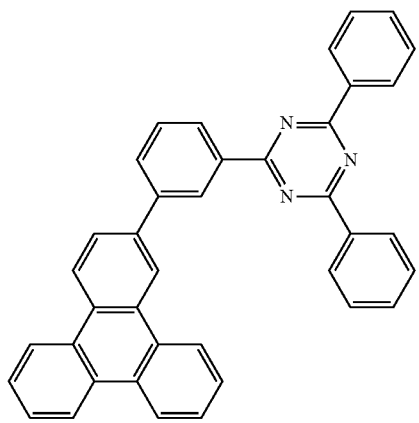
[A-257]
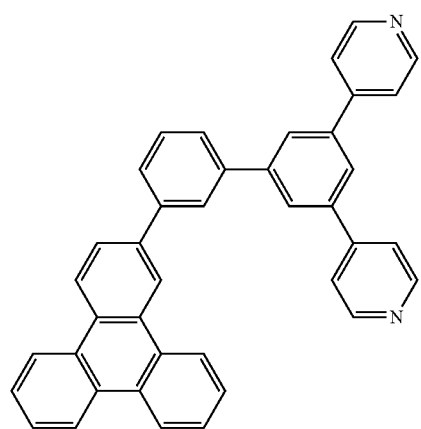
[A-258]
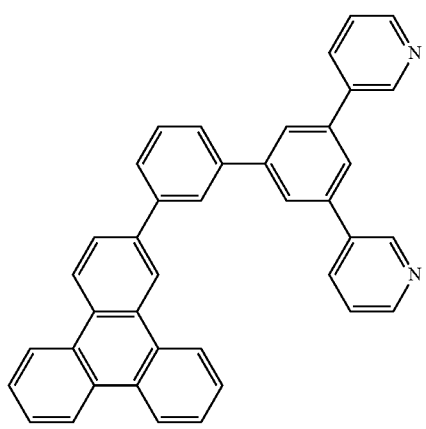
[A-259]
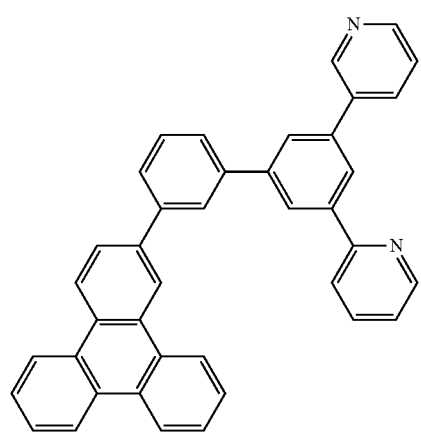
[A-260]
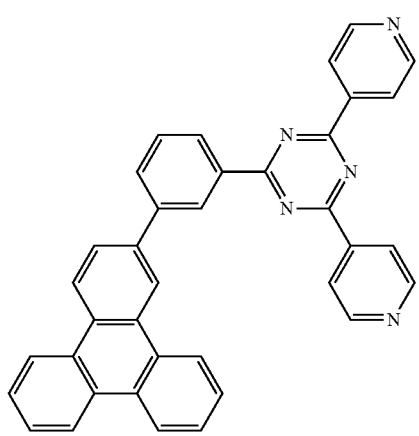
[A-261]

-continued
[A-262]
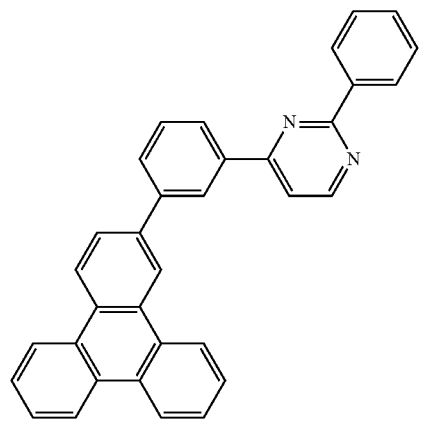
[A-263]
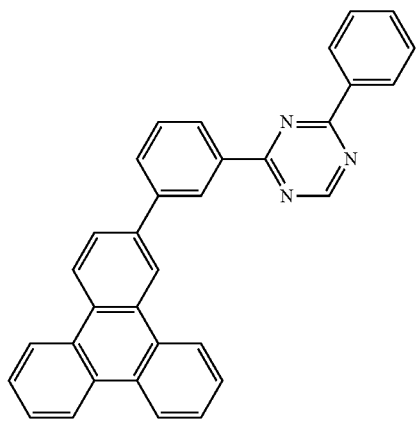
[A-264]
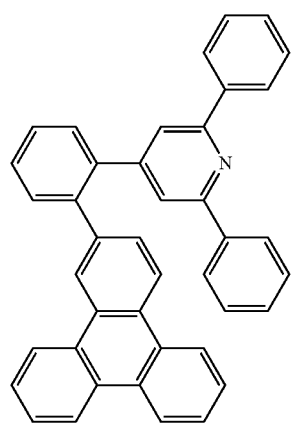
[A-265]
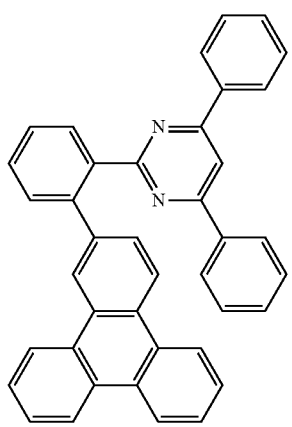
[A-266]
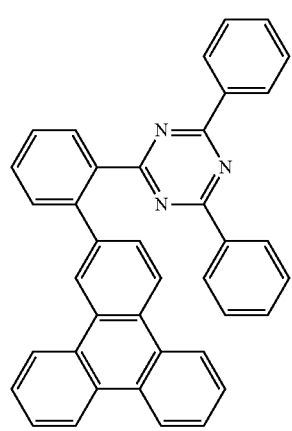
[A-267]
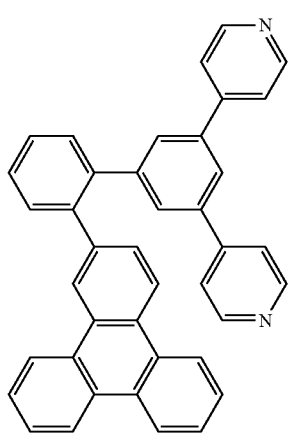

-continued
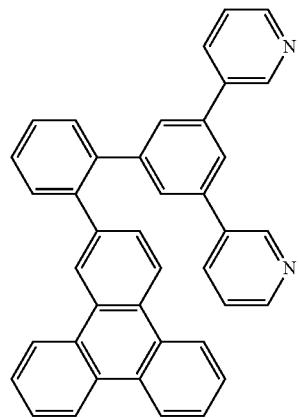
[A-268]
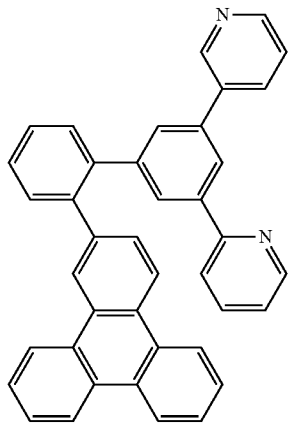
[A-269]
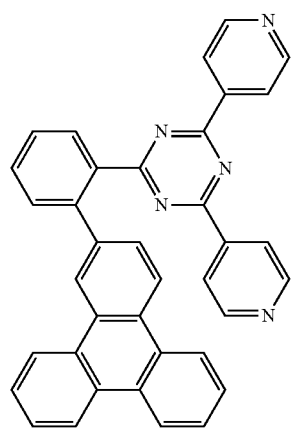
[A-270]
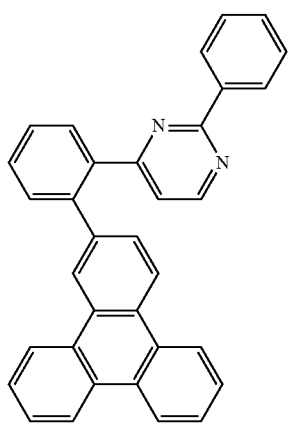
[A-271]
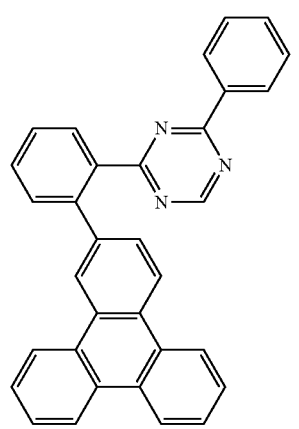
[A-272]
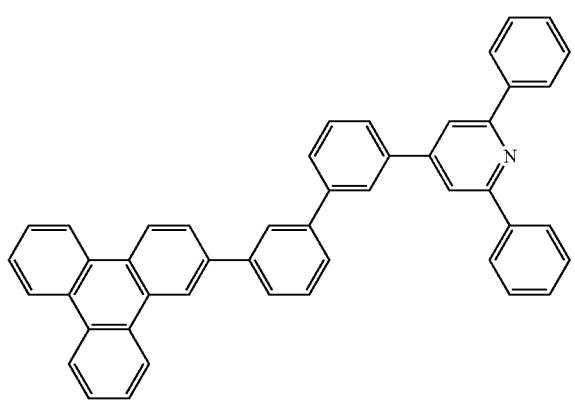
[A-273]

-continued
[A-274]
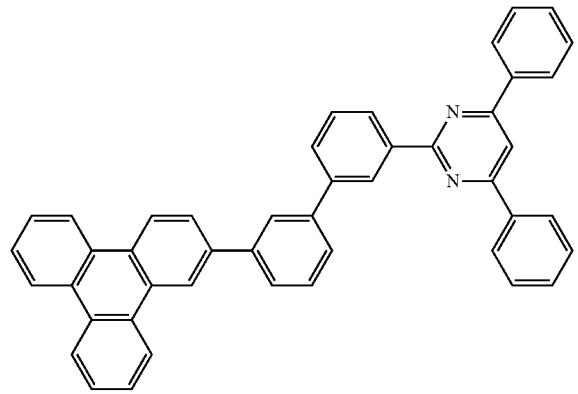
[A-275]
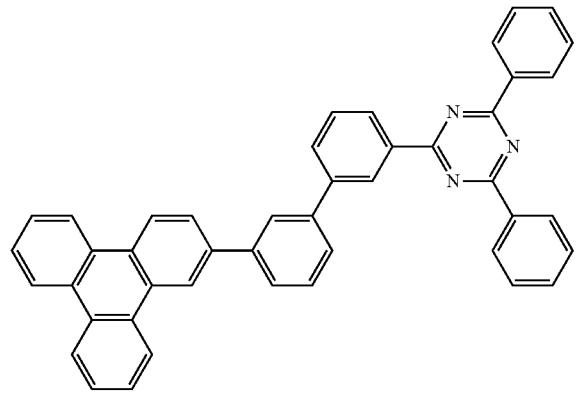
[A-276]
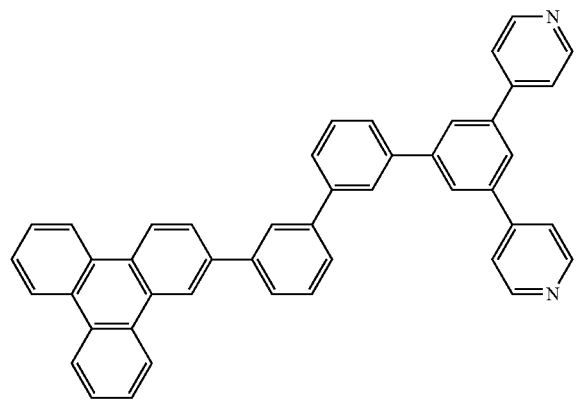
[A-277]
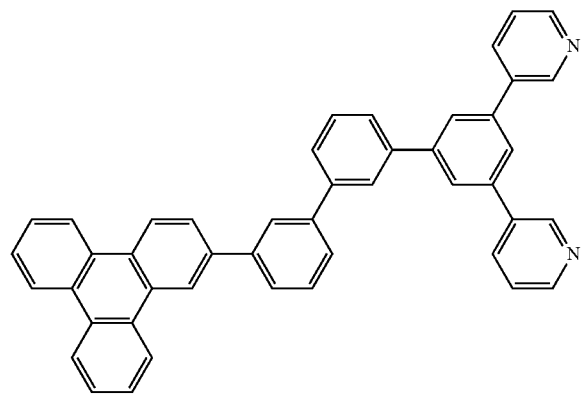
[A-278]
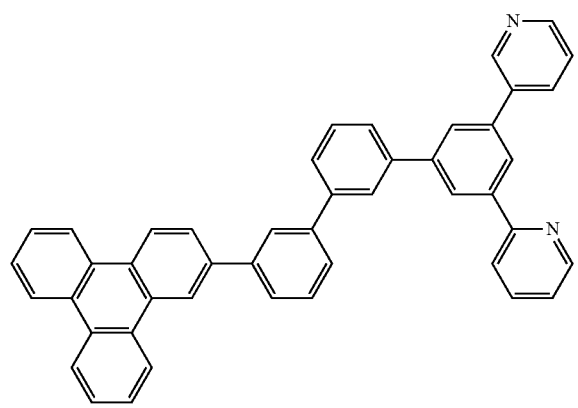
[A-279]
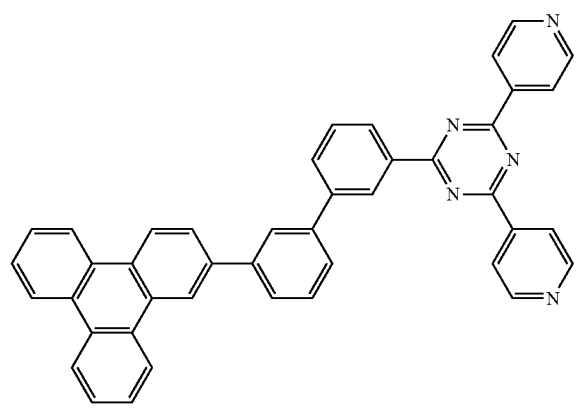

-continued
[A-280]
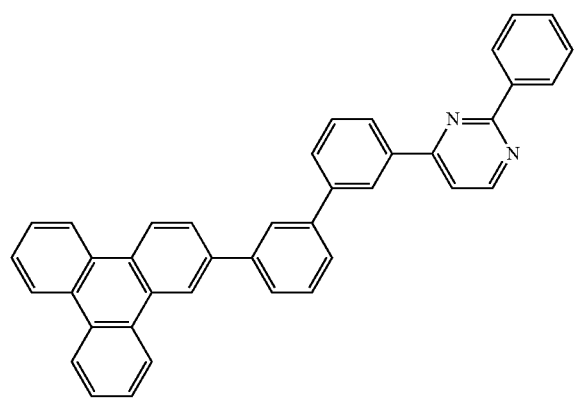
[A-281]
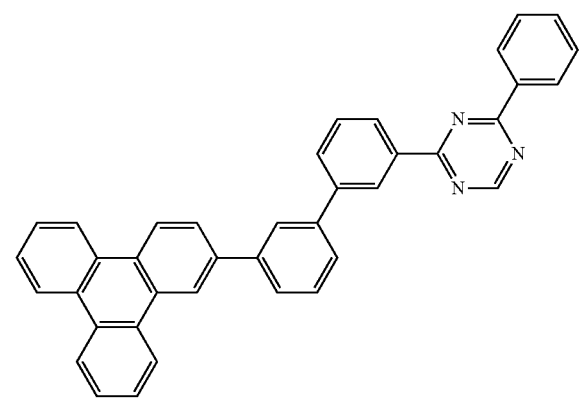
[A-282]
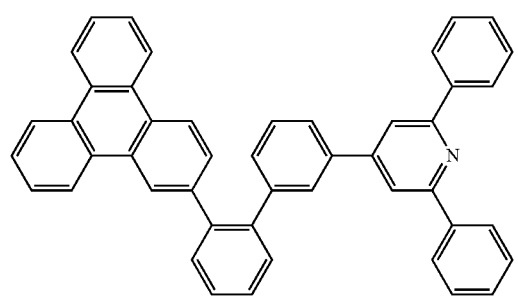
[A-283]
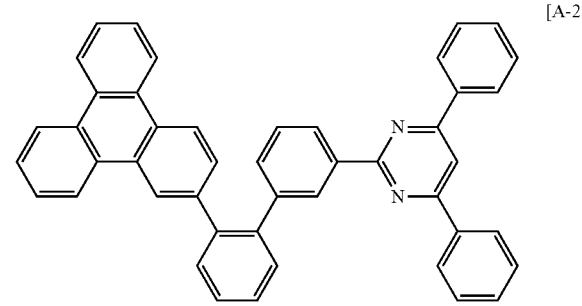
[A-284]
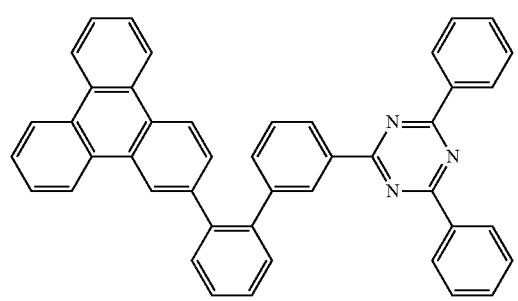
[A-285]
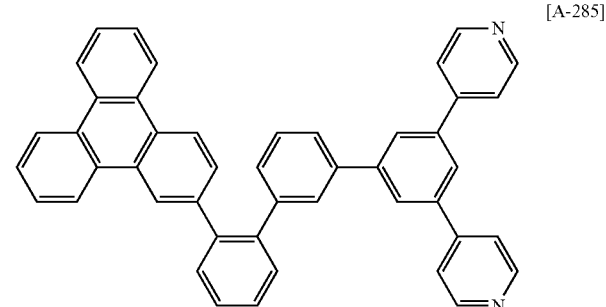
[A-286]
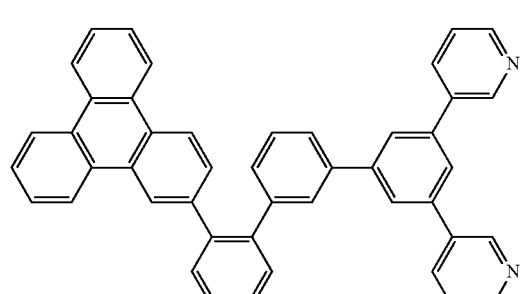
[A-287]
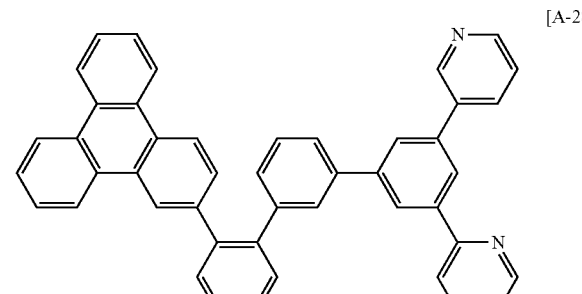
[A-288]
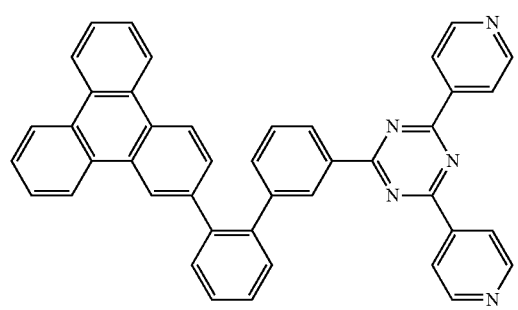
[A-289]
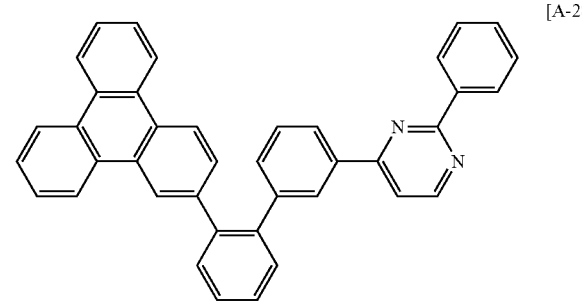

-continued
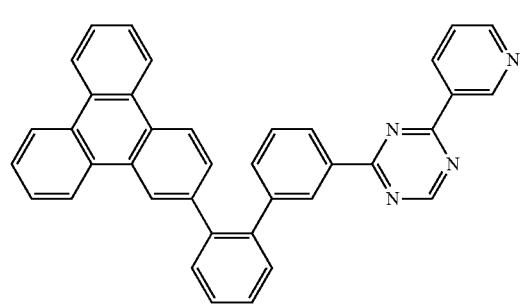 [A-290]
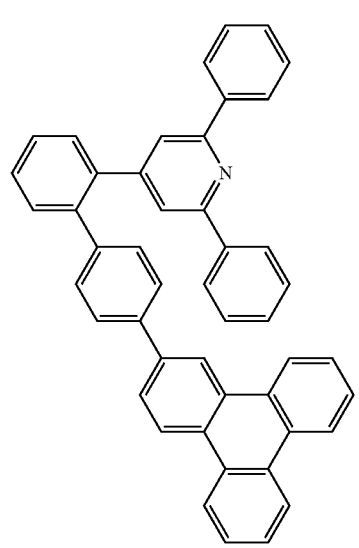 [A-291]
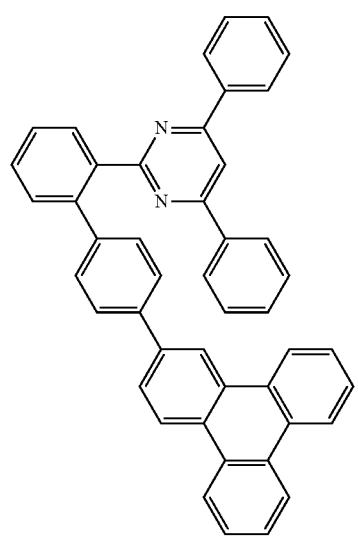 [A-292]
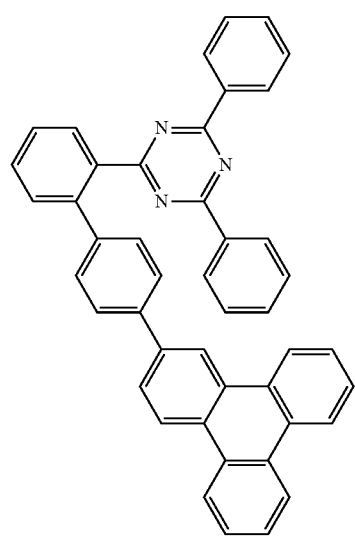 [A-293]
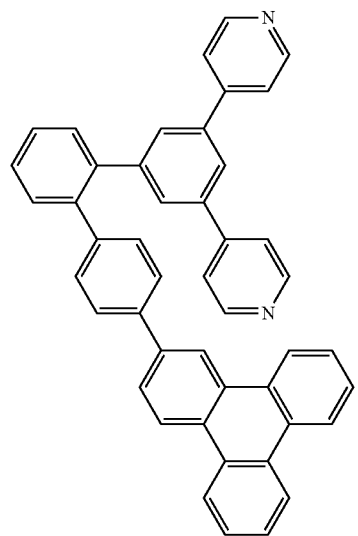 [A-294]
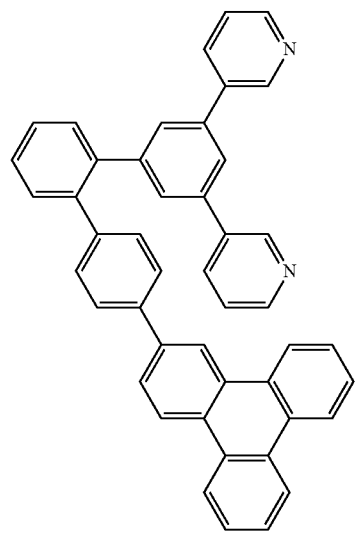 [A-295]

-continued
[A-296] [A-297]
[A-298] [A-299]
[A-300] [A-301]
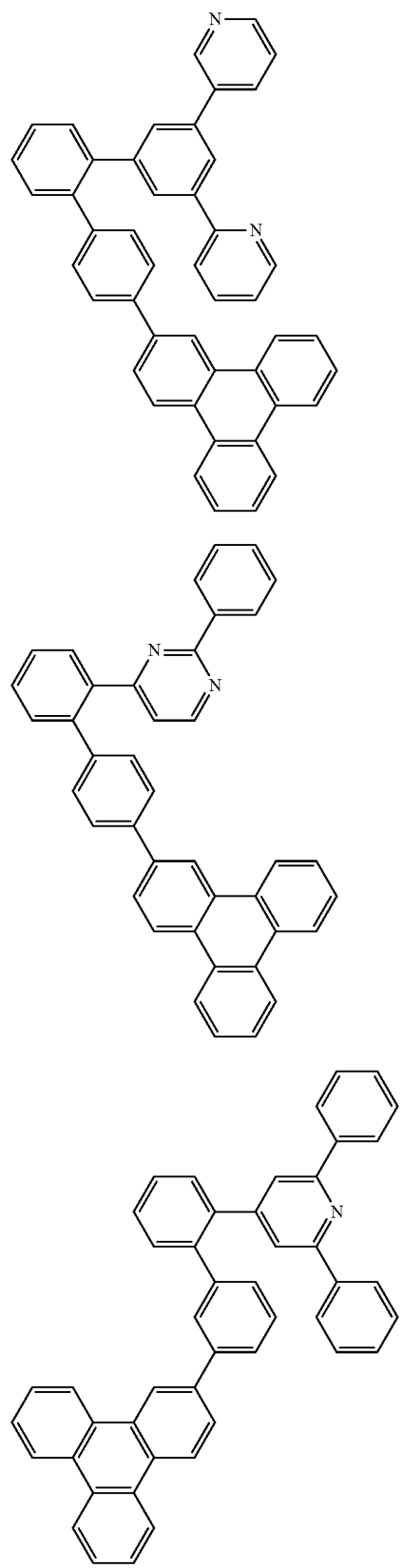
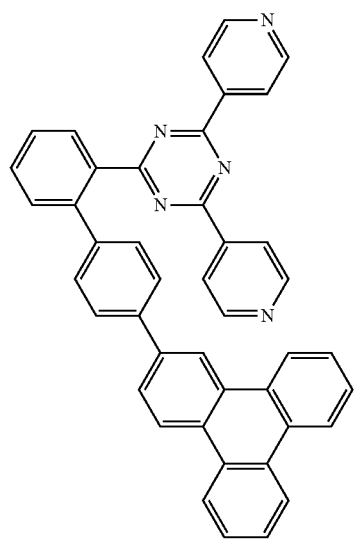

-continued
[A-302]
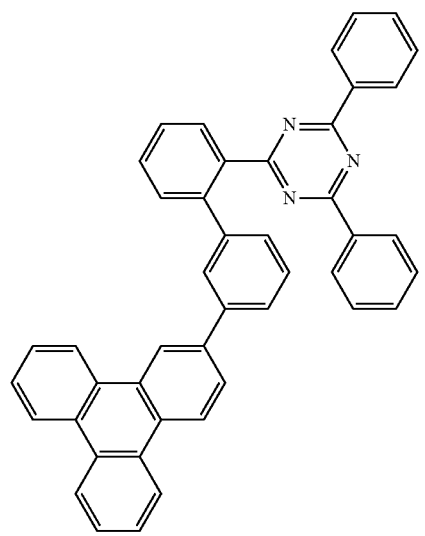
[A-303]
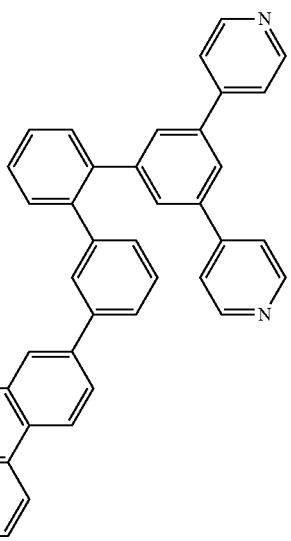
[A-304]
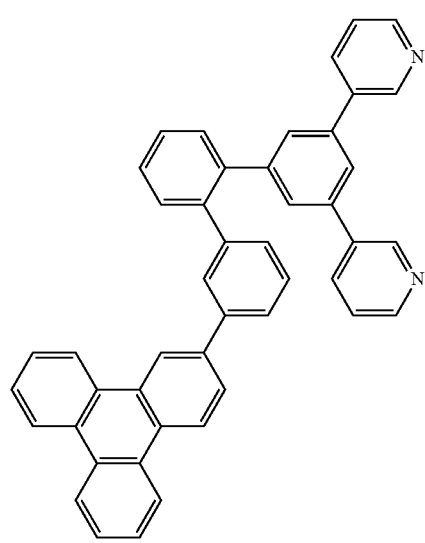
[A-305]
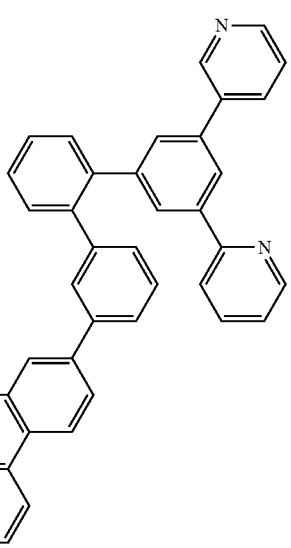
[A-306]
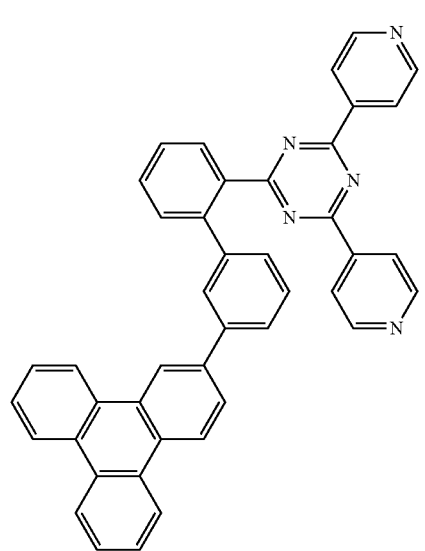
[A-307]
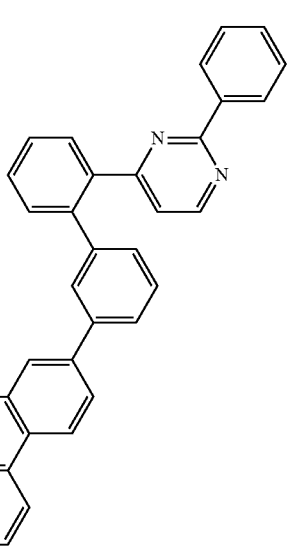

[A-308] 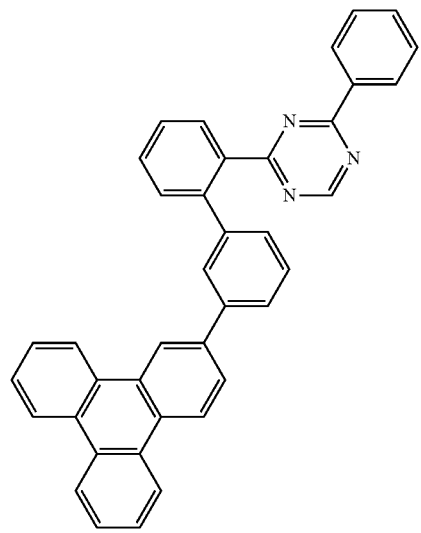
[A-309] 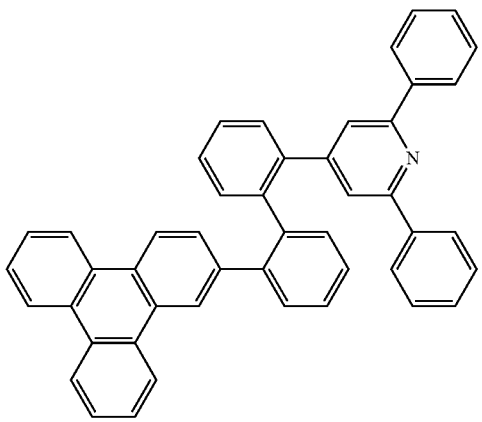
[A-310] 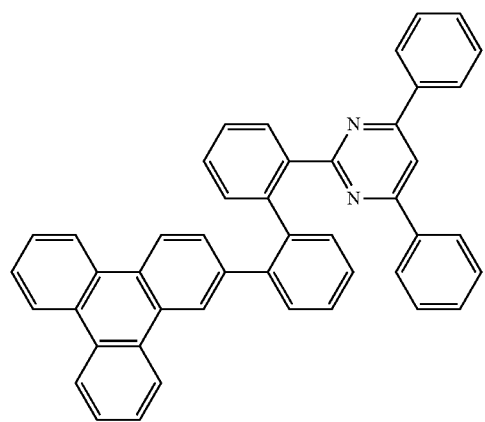
[A-311] 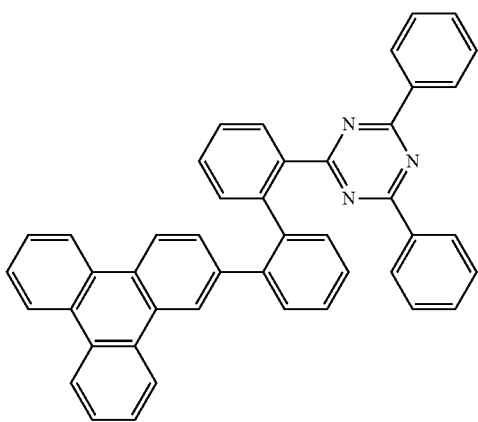
[A-312] 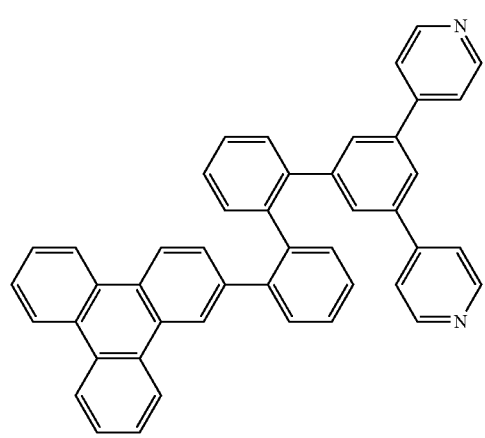
[A-313] 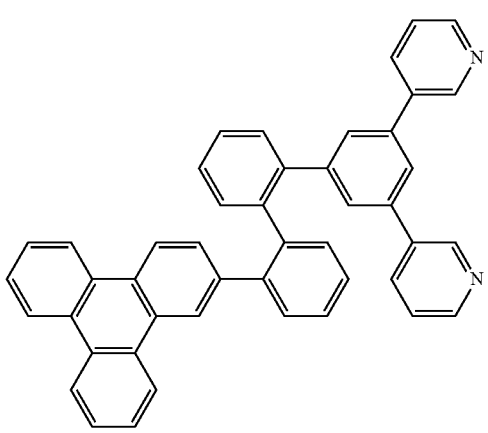

-continued
[A-314] 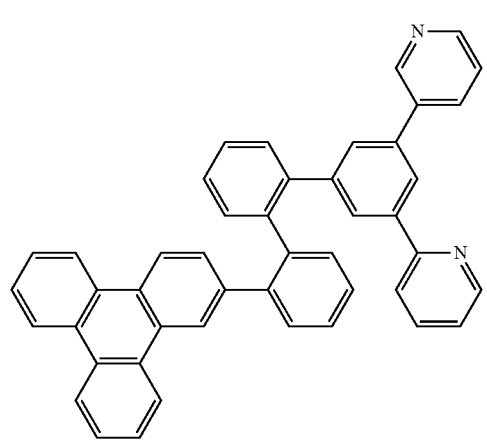
[A-315] 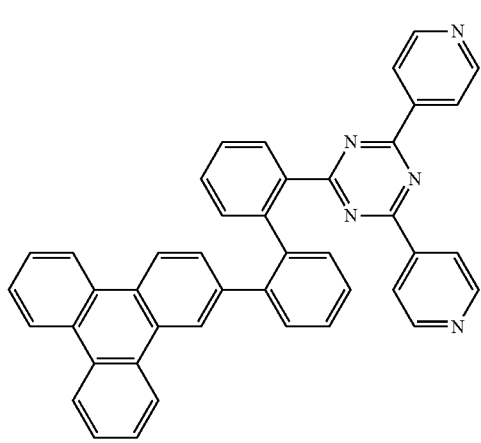
[A-316] 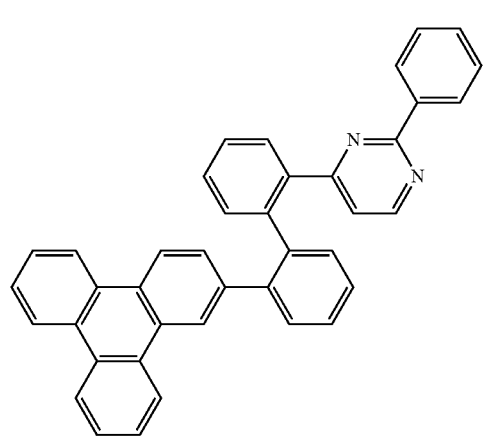
[A-317] 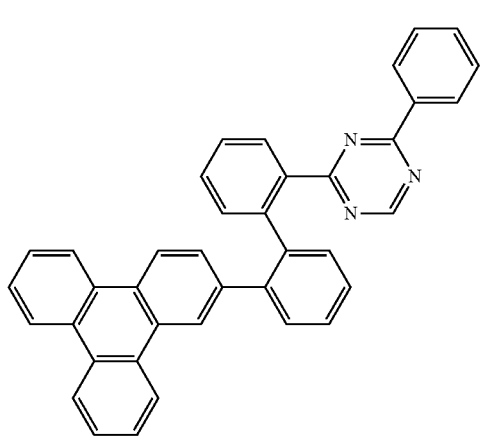
[A-318] 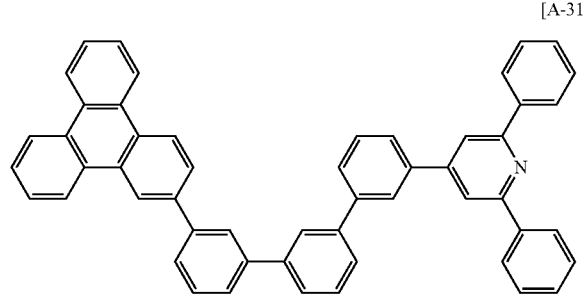
[A-319] 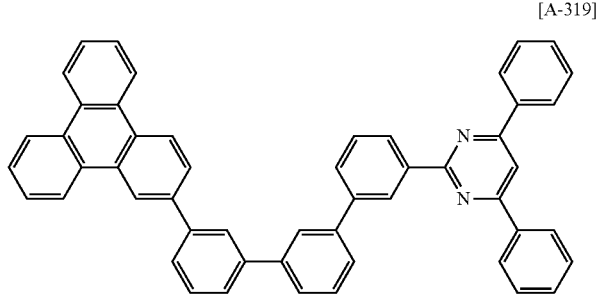
[A-320] 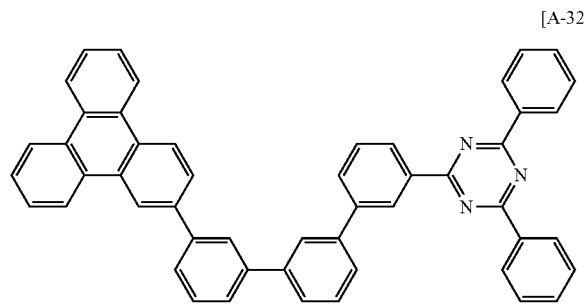
[A-321] 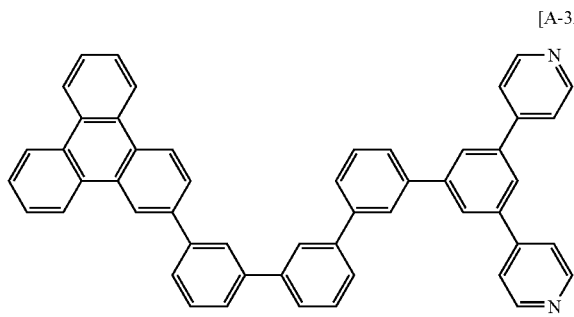

-continued
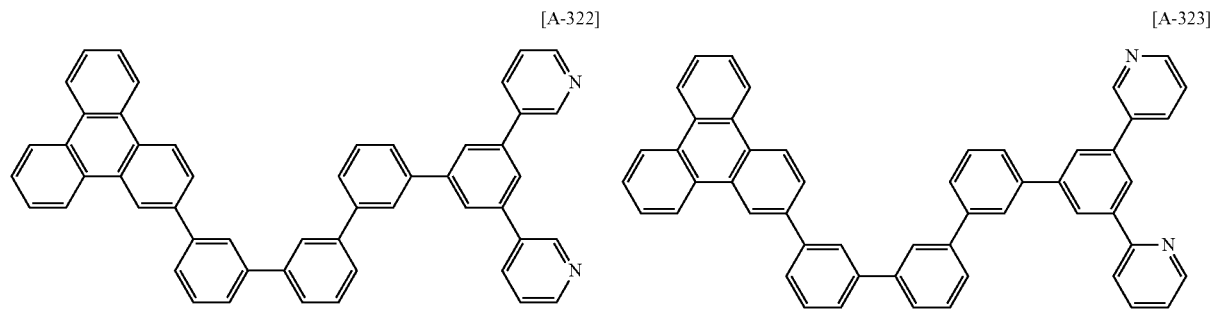
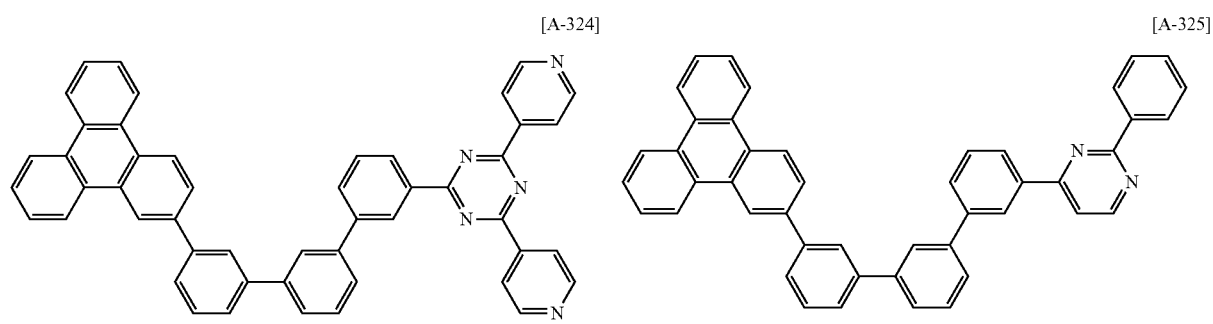
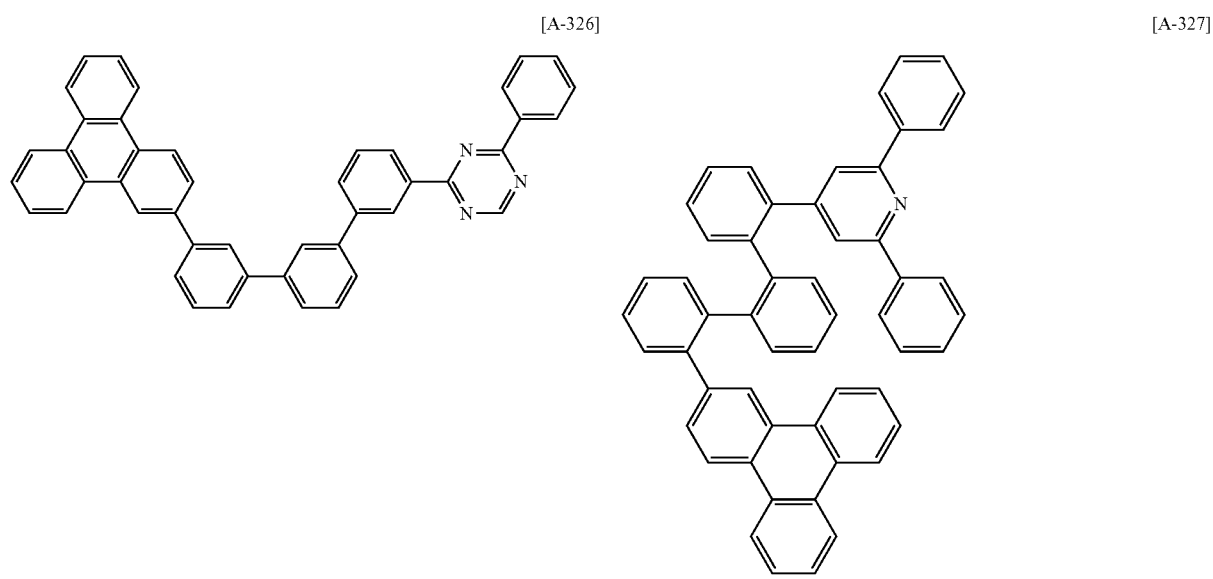

[A-328]
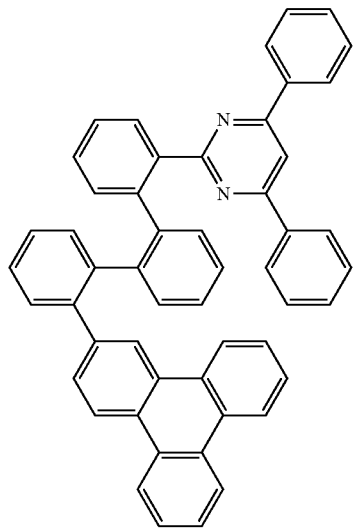
[A-329]
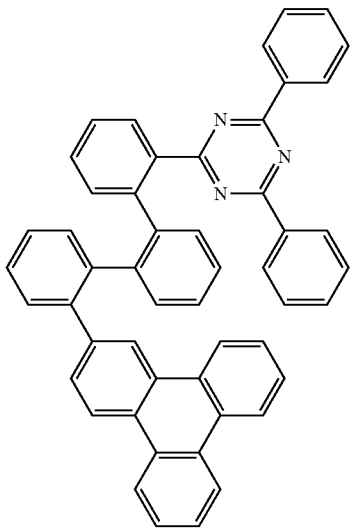
[A-330]
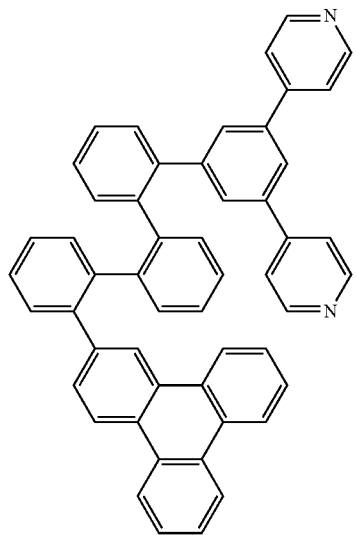
[A-331]
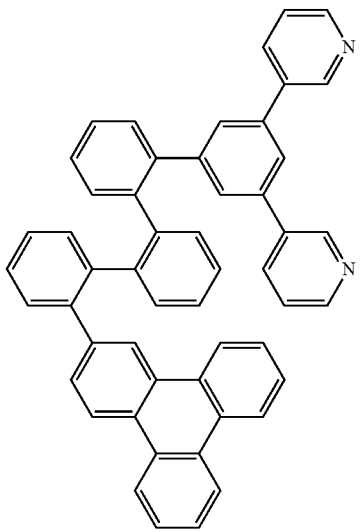
[A-332]
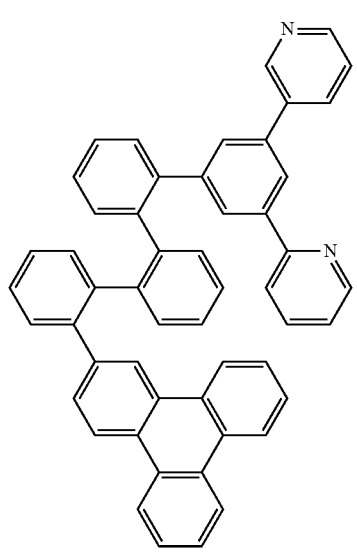
[A-333]
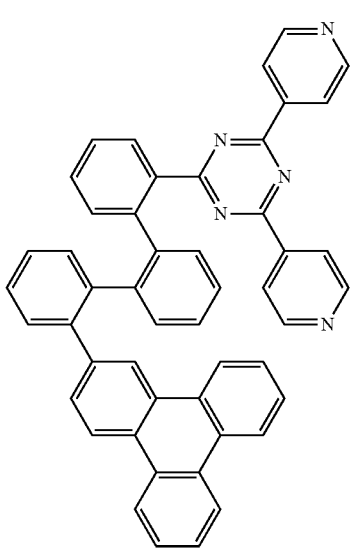

[A-334]
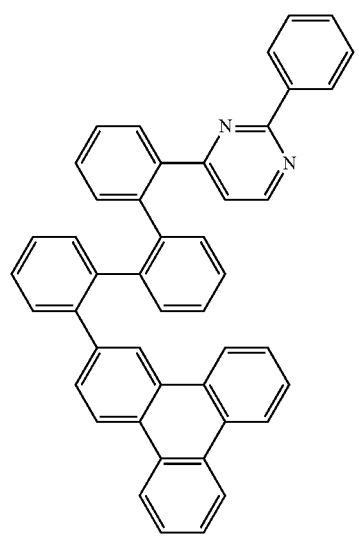
[A-335]
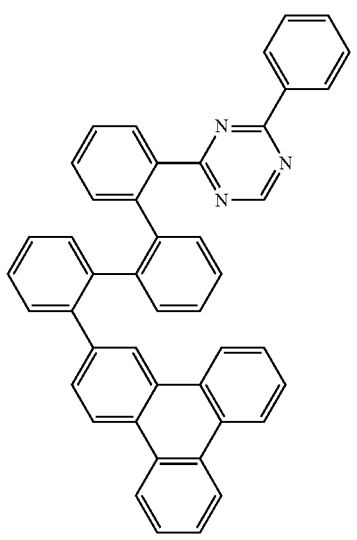
[A-336]
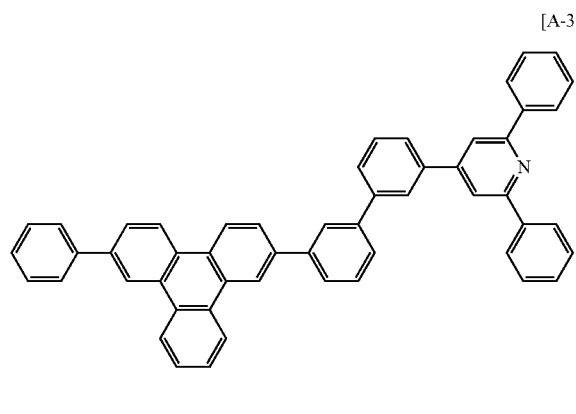
[A-337]
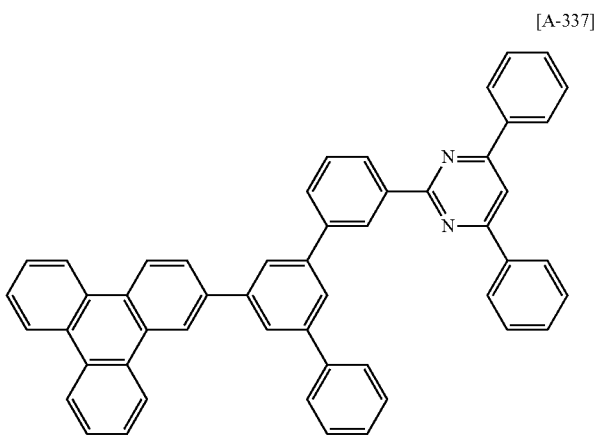
[A-338]
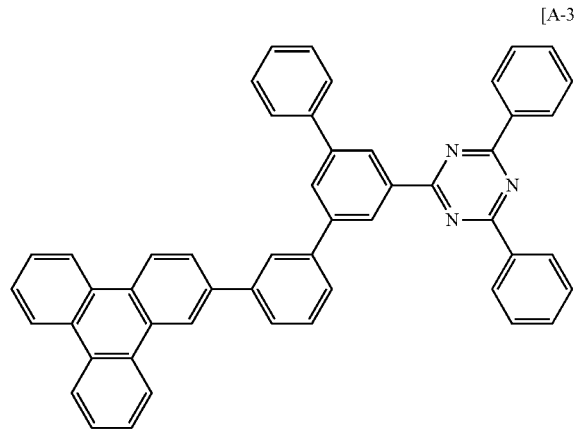
[A-339]
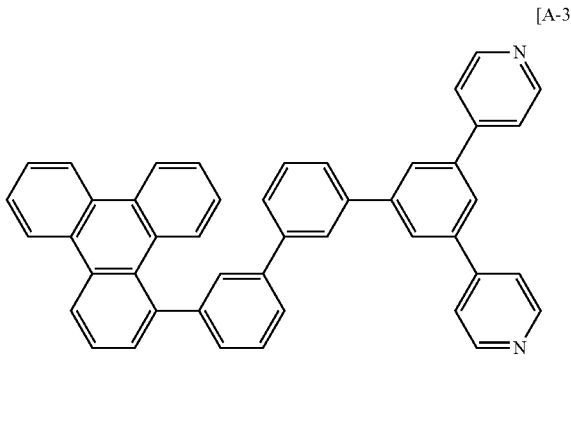

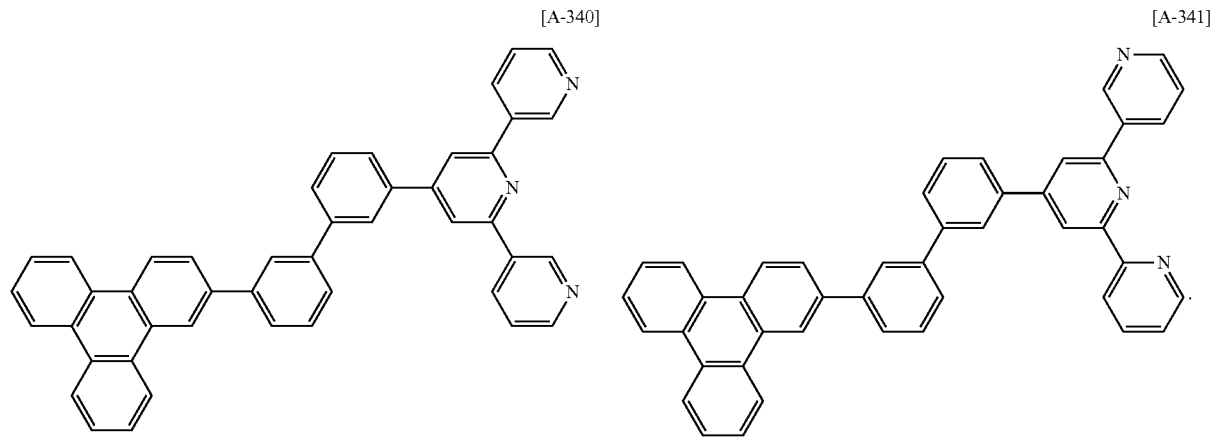

The first compound may be used along with at least one second compound having a carbazole moiety or a carbazole derivative in an emission layer.

The carbazole derivative has, for example, a structure derived based on the carbazole moiety and indicates a fused carbazole moiety consisting of a combination of the moiety represented by Chemical Formula 3 and the moiety represented by Chemical Formula 4.

The second compound may be represented by Chemical Formula 2.

$L^3$ to $L^6$ of Chemical Formula 2 according to an embodiment of the present invention may independently be a single bond, a substituted or unsubstituted C6 to C30 arylene group, a substituted or unsubstituted C2 to C30 heteroarylene group, and specifically a substituted or unsubstituted C6 to C30 arylene group. For example, they may be a single bond, a substituted or unsubstituted phenylene group, a substituted or unsubstituted biphenylene group, a substituted or unsubstituted terphenylene group, a substituted or unsubstituted quarterphenylene group, a substituted or unsubstituted naphthylene group, a substituted or unsubstituted anthracenylene group, a substituted or unsubstituted triphenylenyl group, or a substituted or unsubstituted phenanthrenylene group.

$R^7$ to $R^{10}$ of Chemical Formula 1 according to an embodiment of the present invention may independently be hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof as described above, and specifically, they may be hydrogen, deuterium, a substituted or unsubstituted C6 to C30 aryl group, or a substituted or unsubstituted C2 to C50 heterocyclic group. For example, $R^7$ to $R^{10}$ are independently hydrogen, a substituted or unsubstituted phenyl group, or a substituted or unsubstituted biphenyl group, a substituted or unsubstituted triphenylene group, a substituted or unsubstituted fluorenyl group, a substituted or unsubstituted carbazolyl group, a substituted or unsubstituted dibenzofuranyl group, a substituted or unsubstituted dibenzothiophenyl group, or a combination thereof, but is not limited thereto.

Chemical Formula 2 may be, for example represented by at least one of Chemical Formulae 2-I to 2-III.

[Chemical Formula 2-I]

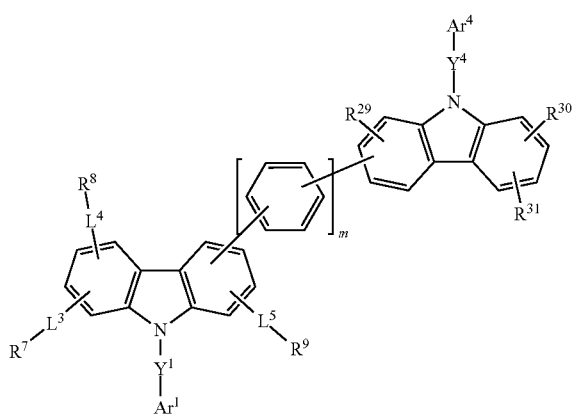

[Chemical Formula 2-II]

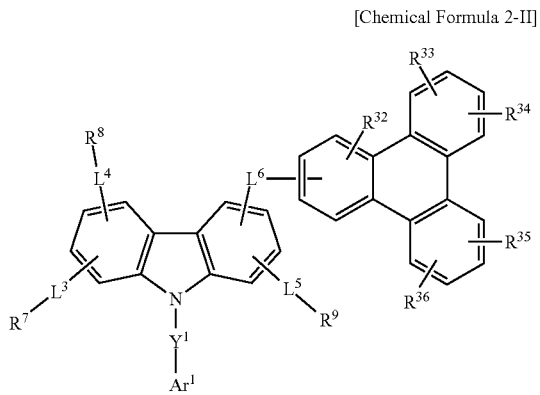

[Chemical Formula 2-III]

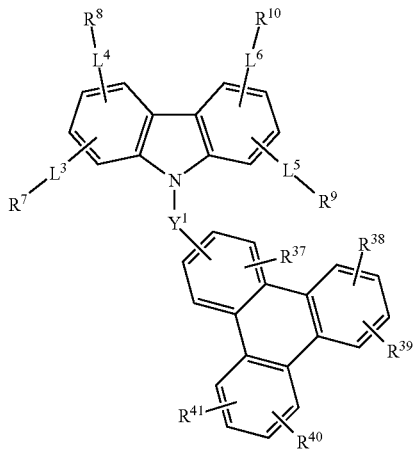

In Chemical Formula 2-I to 2-III, $L^3$ to $L^6$, $Y^1$ and $R^7$ to $R^{10}$ are the same as above, $R^{29}$ to $R^{41}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, $Y^4$ is a single bond, a substituted or unsubstituted C6 to C30 arylene group, a substituted or unsubstituted C2 to C30 heteroarylene group, or a combination thereof, $Ar^1$ and $Ar^4$ are independently substituted or unsubstituted C6 to C30 aryl group, a substituted or unsubstituted C2 to C30 heterocyclic group, or a combination thereof, m is an integer of 0 to 4, and wherein, "substituted" is the same as defined above.

Specifically, $Ar^1$ and $Ar^4$ of Chemical Formulae 2-I to 2-III are independently substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, a substituted or unsubstituted dibenzothiophenyl group, a substituted or unsubstituted dibenzofuranyl group, a substituted or unsubstituted pyridinyl group, or a combination thereof.

Specifically, Chemical Formula 2-I may be one of structures of Group 3 and the *—$Y^1$—$Ar^1$, *—$Y^4$—$Ar^4$ may be one of substituents of Group 4.

[Group 3]

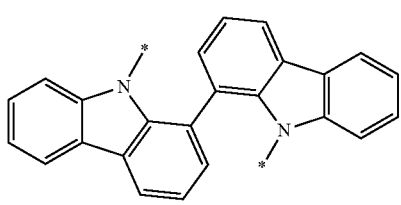

C-1

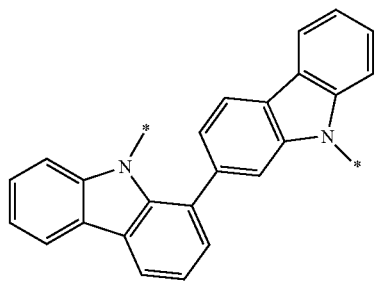

C-2

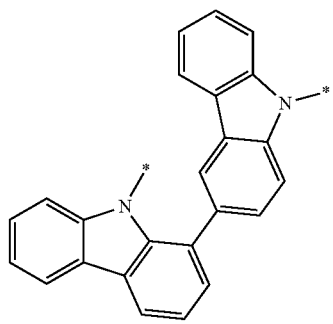

C-3

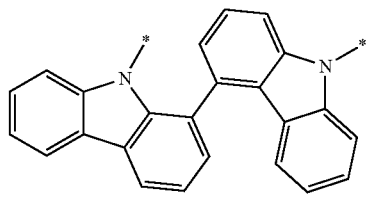

C-4

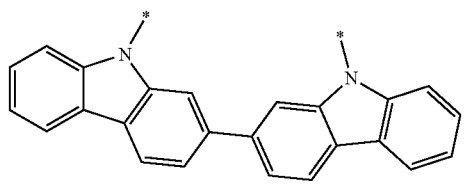

C-5

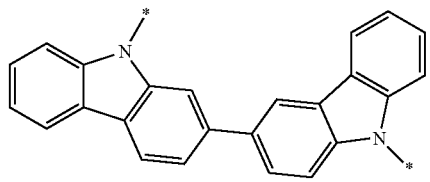

C-6

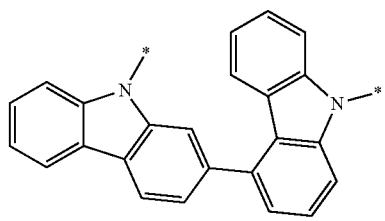

C-7

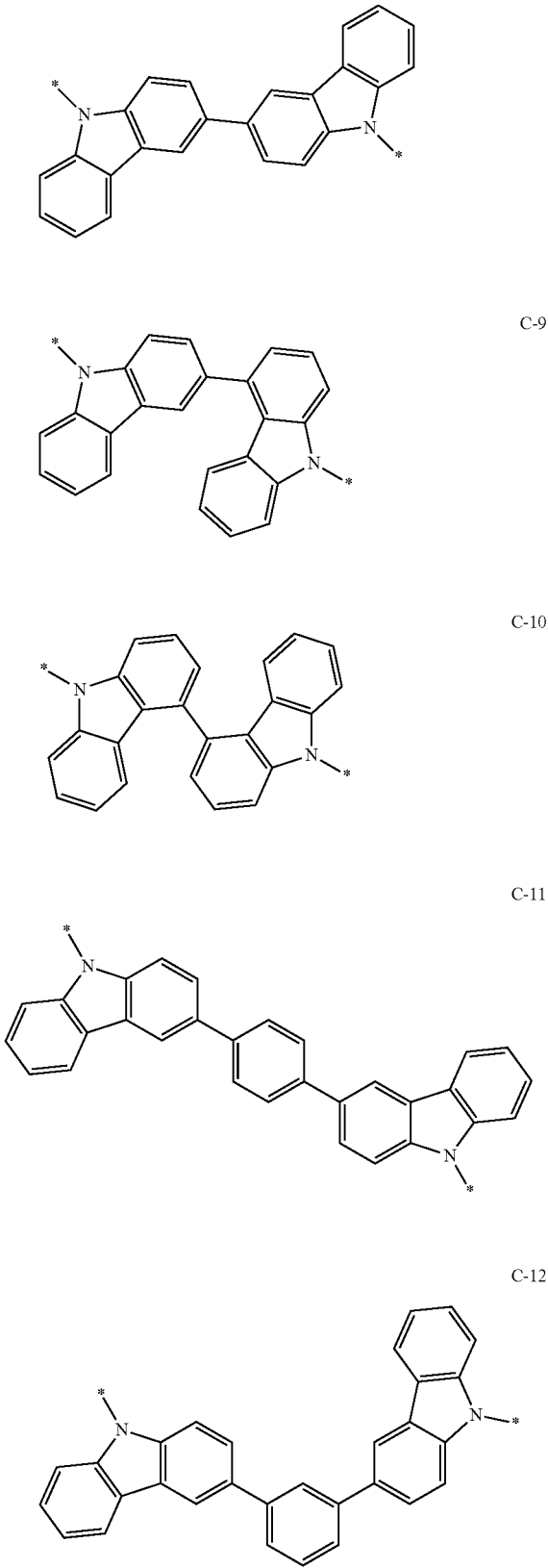

B-3 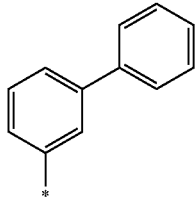
B-4 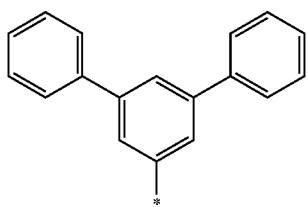
B-5 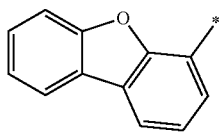
B-6 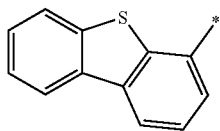
B-7 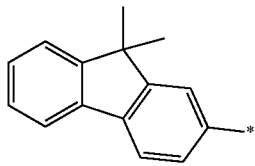
B-8 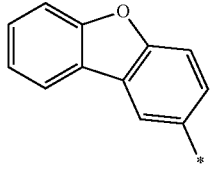
B-9 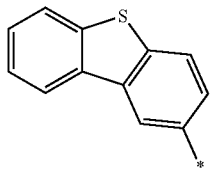
B-10 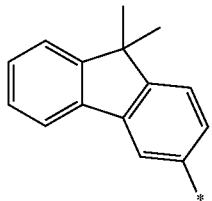
B-11 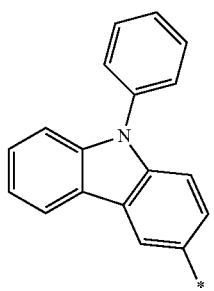
B-12 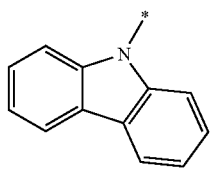
B-13 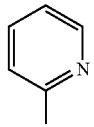
B-14 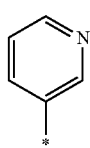
B-15 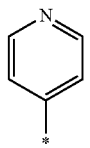
B-16 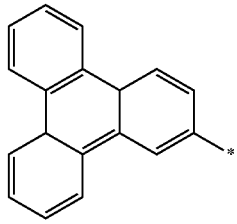
B-17 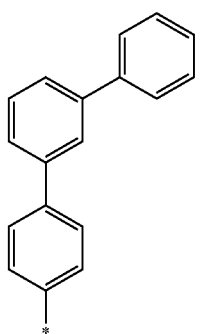

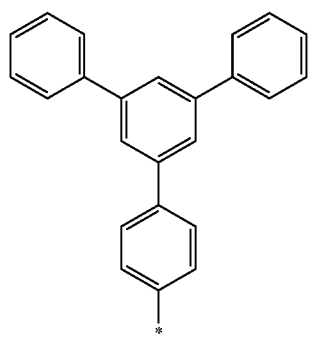
B-18
In Group 3 and Group 4, * is a linking point.
The second compound represented by Chemical Formula 2 may be, for example compounds of Group B to Group D, but is not limited thereto.
[Group B]
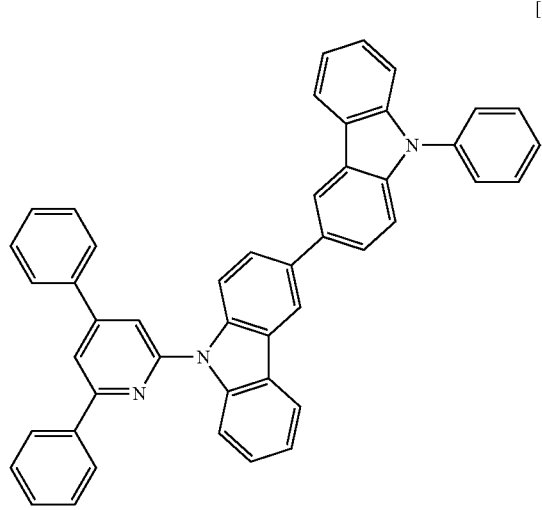
[B-1]
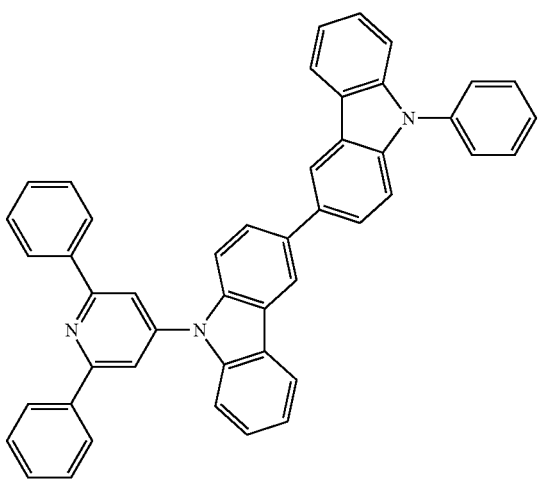
[B-2]
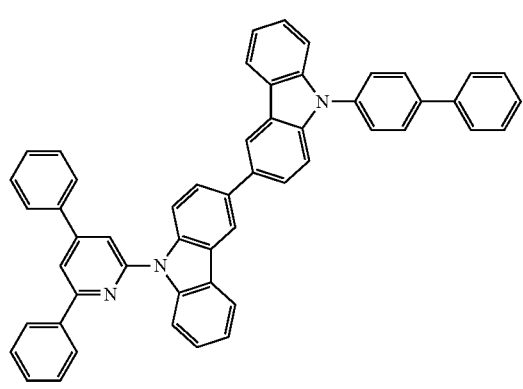
[B-3]
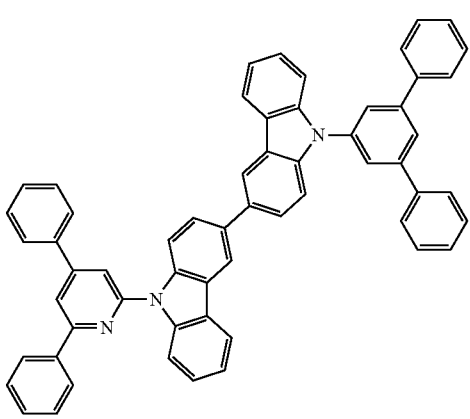
[B-4]

[B-5]
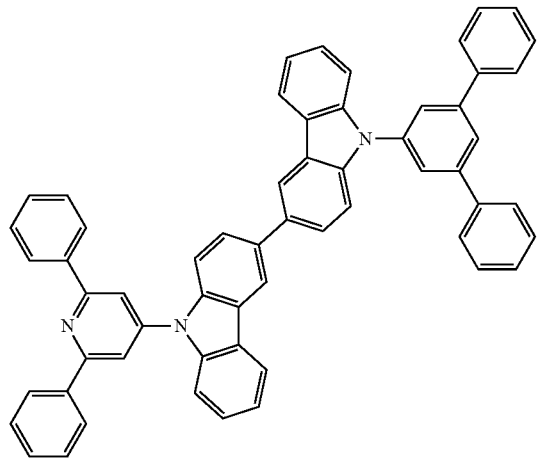
[B-6]
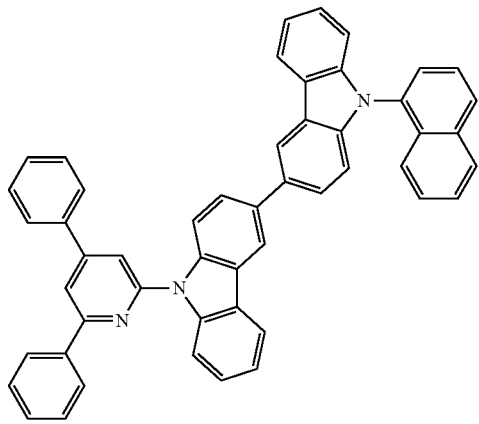
[B-7]
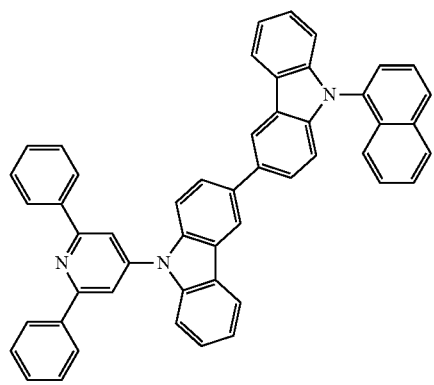
[B-8]
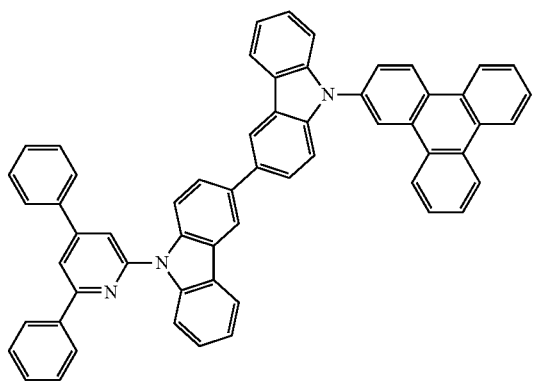
[B-9]
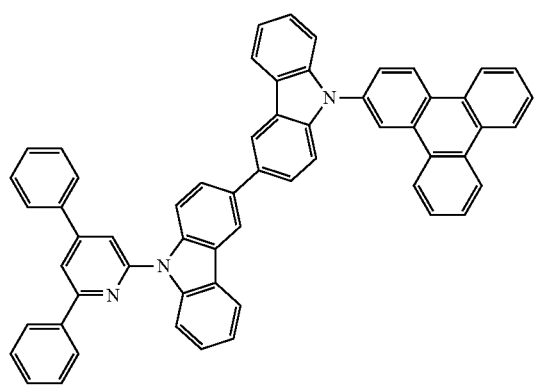
[B-10]
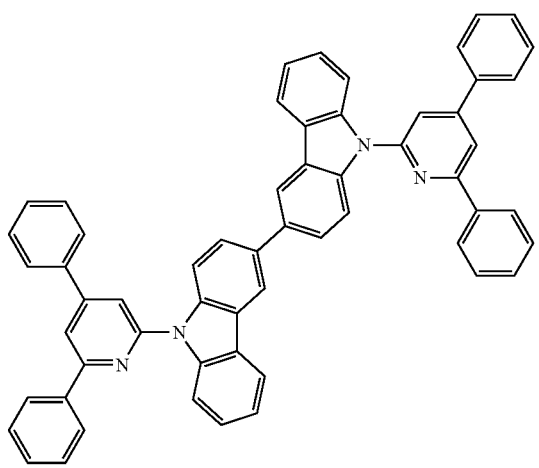

[B-11] 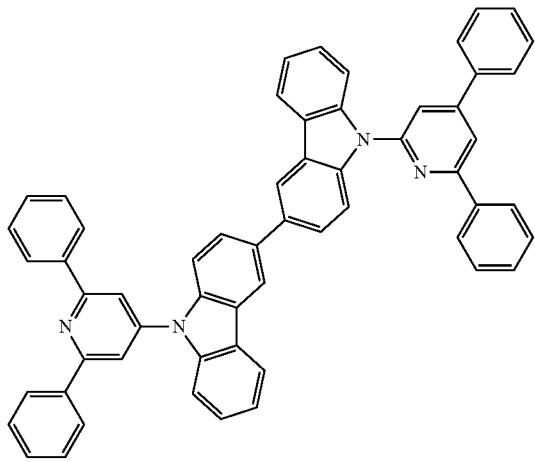
[B-12] 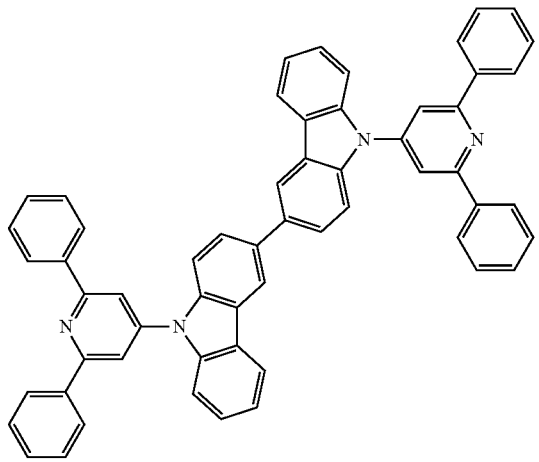
[B-13] 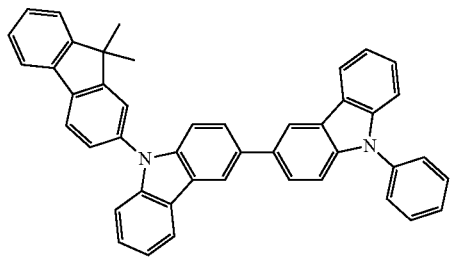
[B-14] 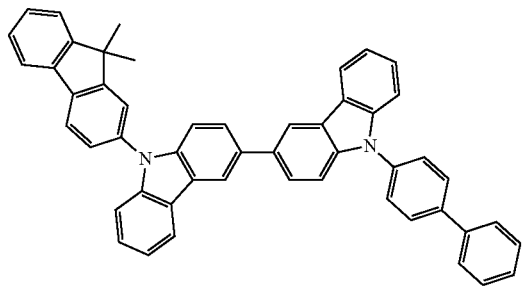
[B-15] 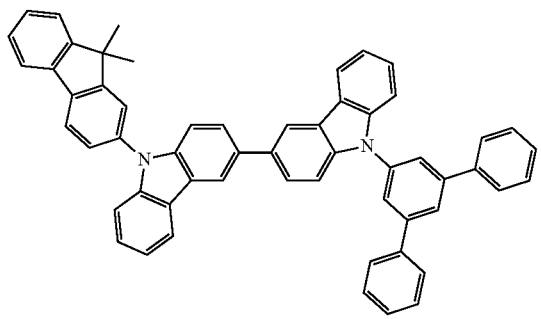
[B-16] 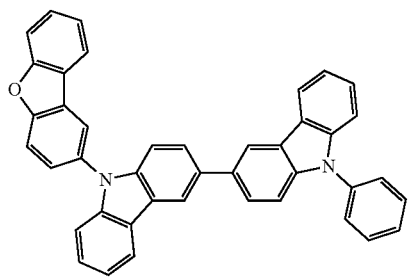
[B-17] 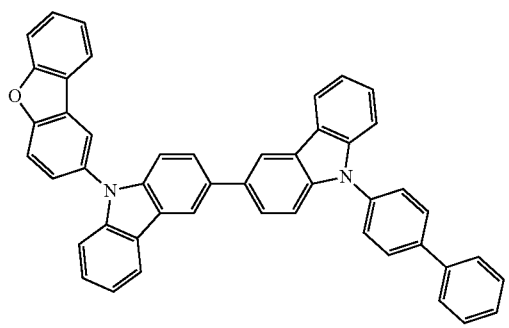
[B-18] 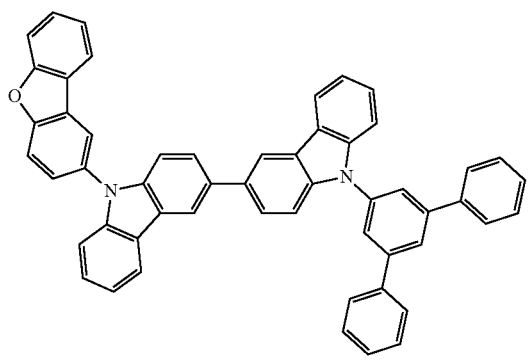

-continued
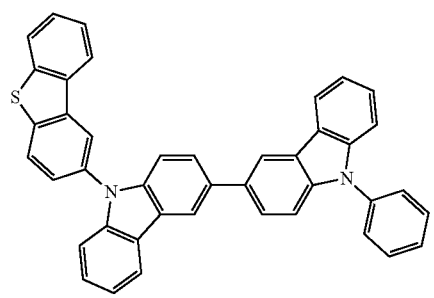
[B-19]
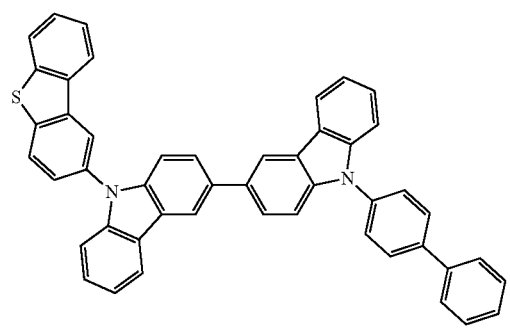
[B-20]
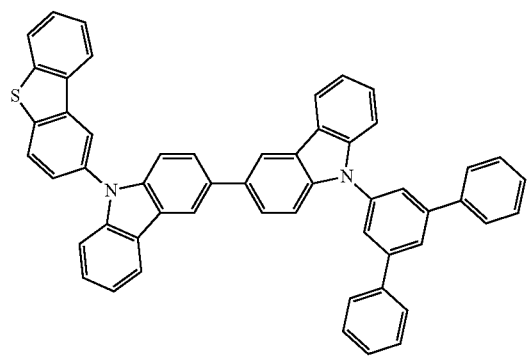
[B-21]
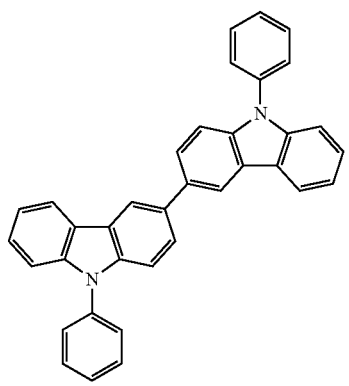
[B-22]
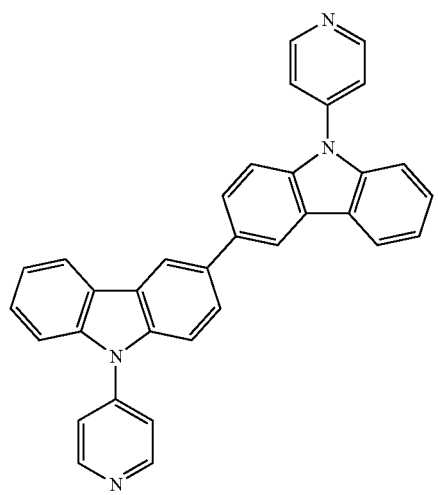
[B-23]
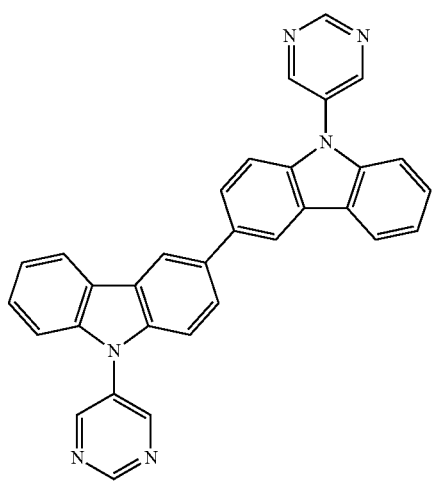
[B-24]

-continued
[B-25]
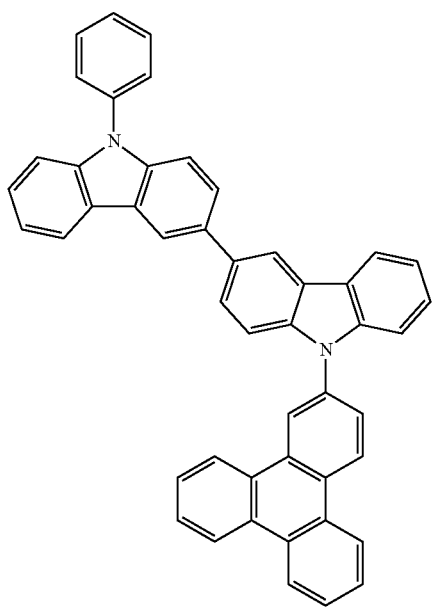
[B-26]
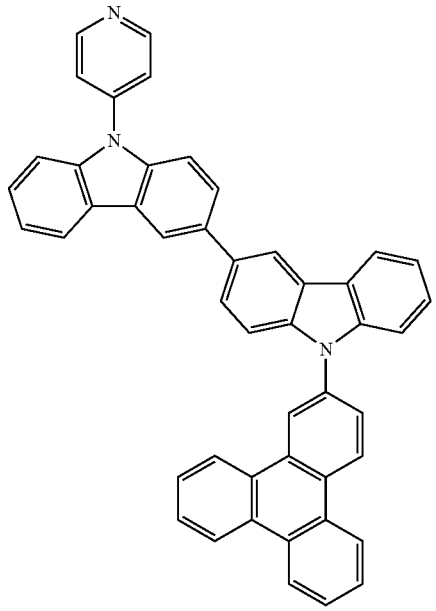
[B-27]
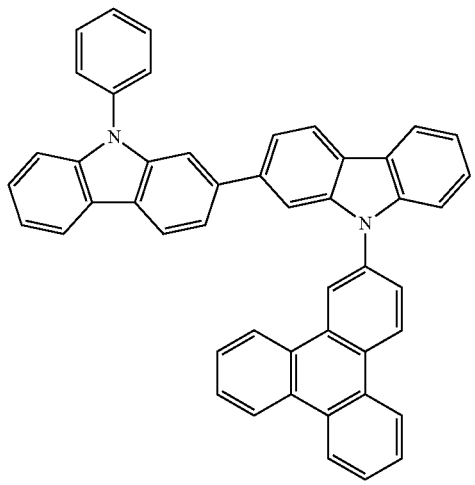
[B-28]
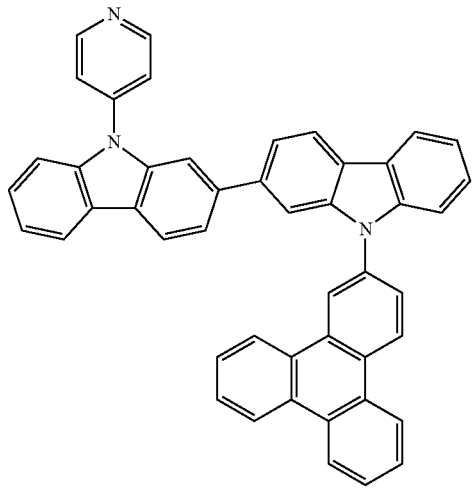
[B-29]
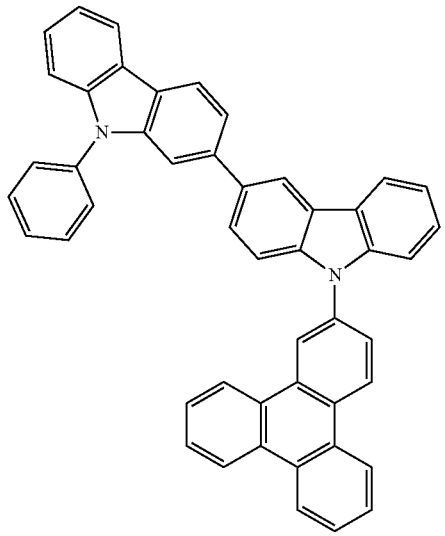
[B-30]
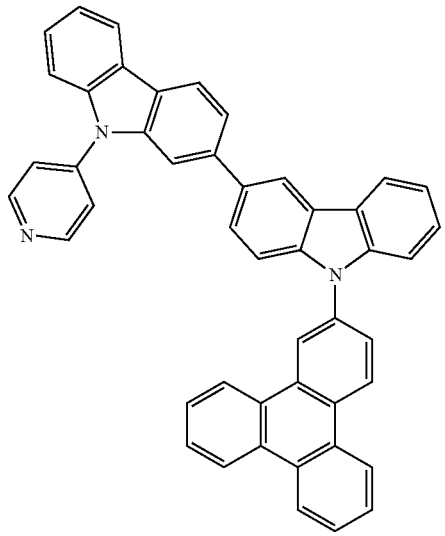

-continued
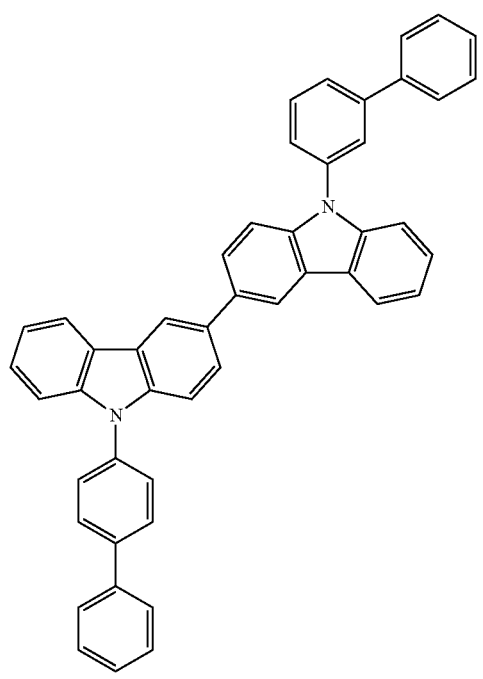
[B-31]
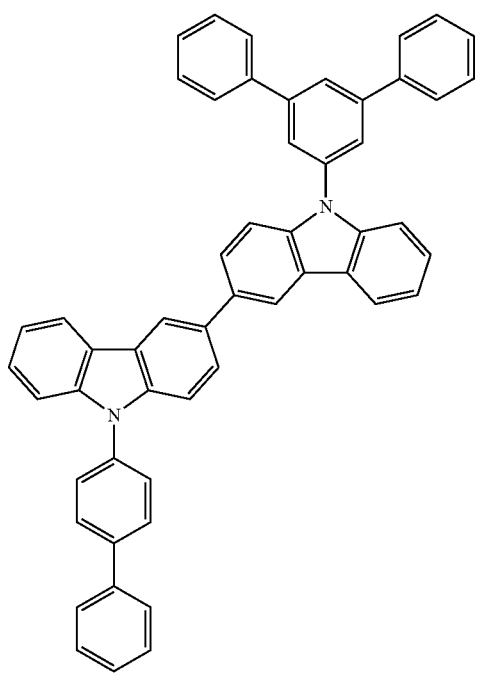
[B-32]
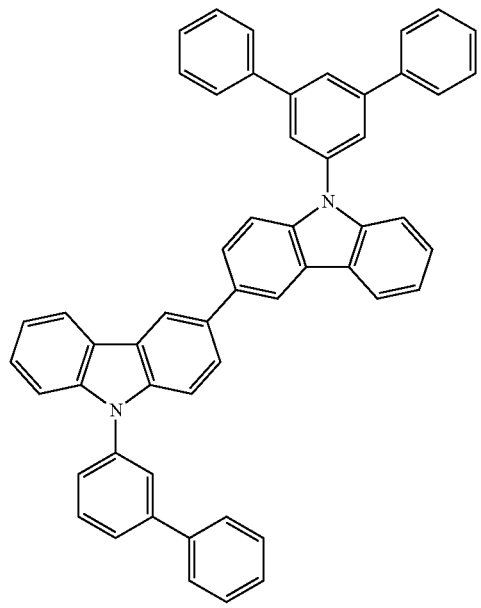
[B-33]
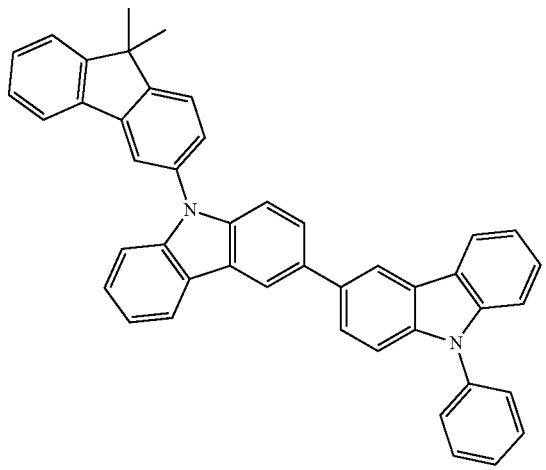
[B-34]

[B-35]
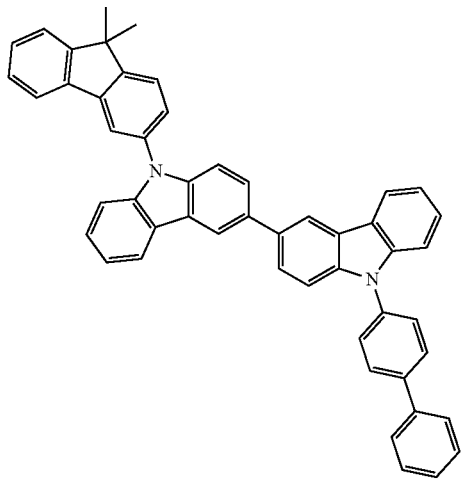
[B-36]
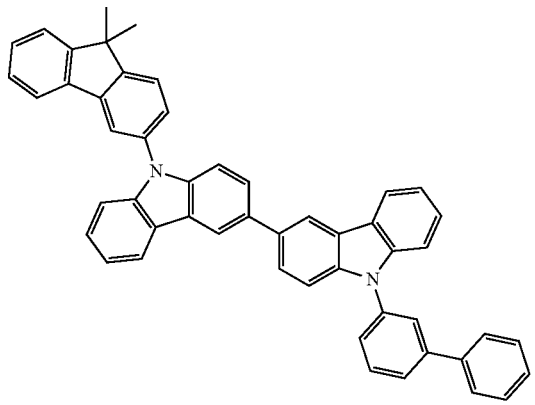
[B-37]
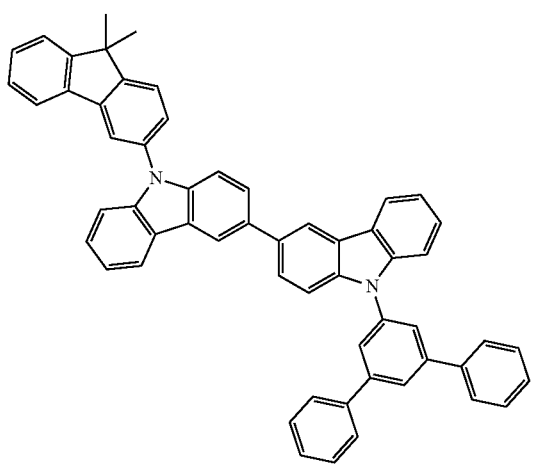
[B-38]
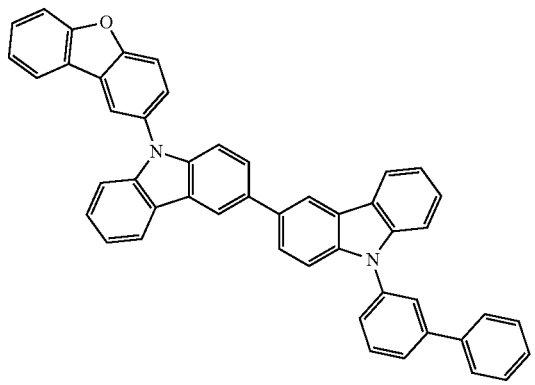
[B-39]
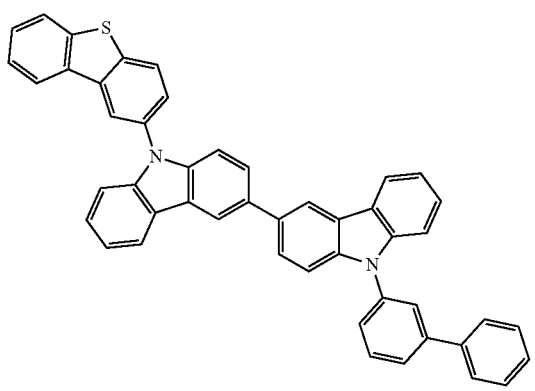
[B-40]
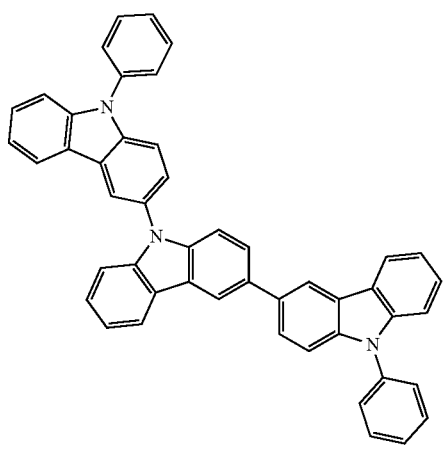

-continued
[B-41]
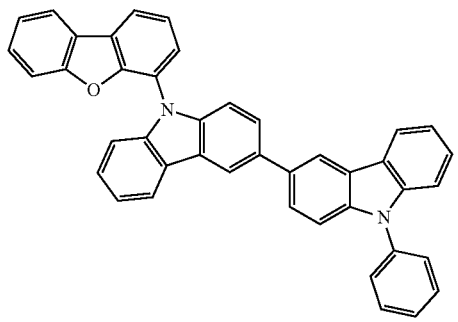
[B-42]
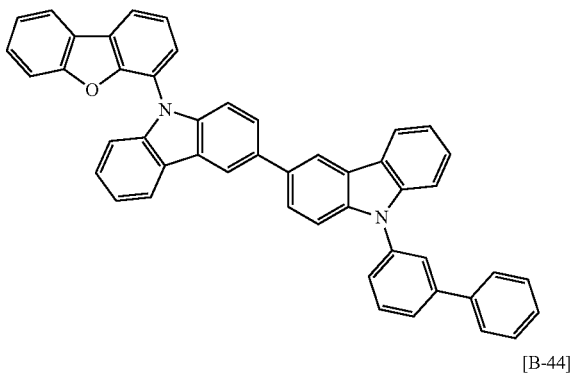
[B-43]
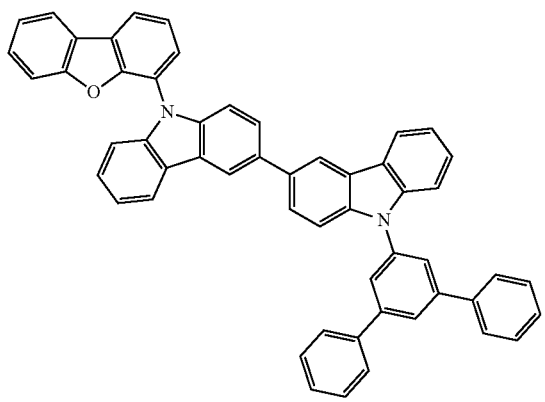
[B-44]
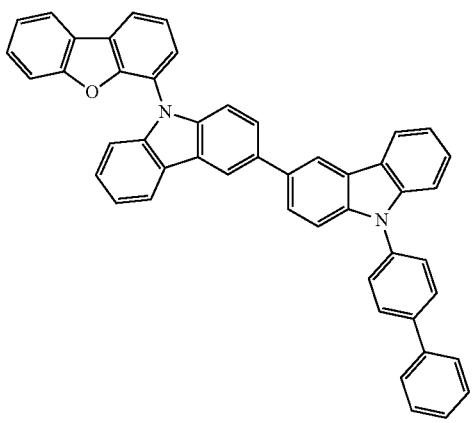
[B-45]
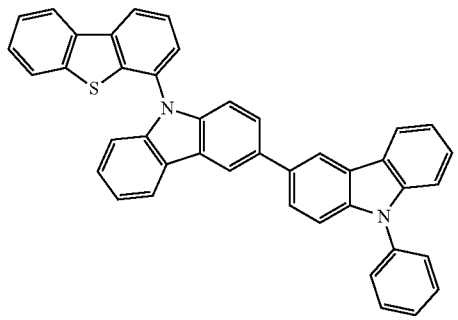
[B-46]
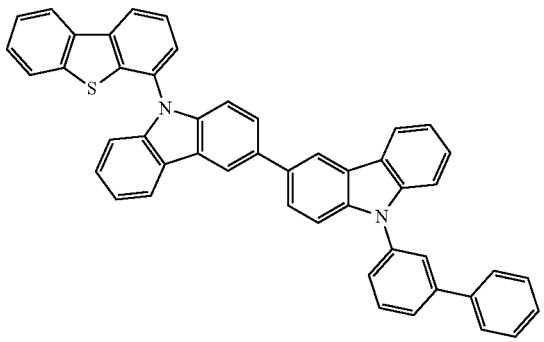
[B-47]
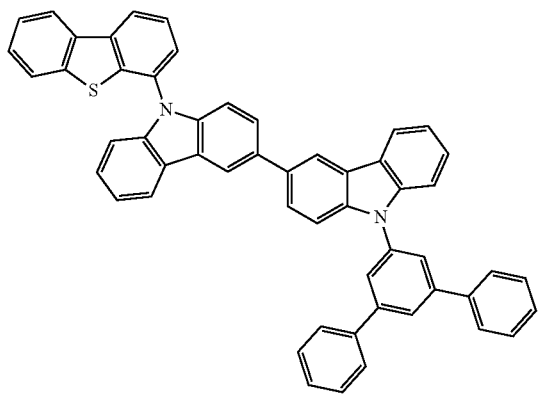
[B-48]
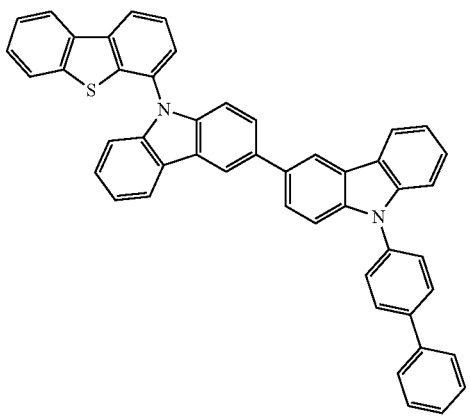

[B-49]
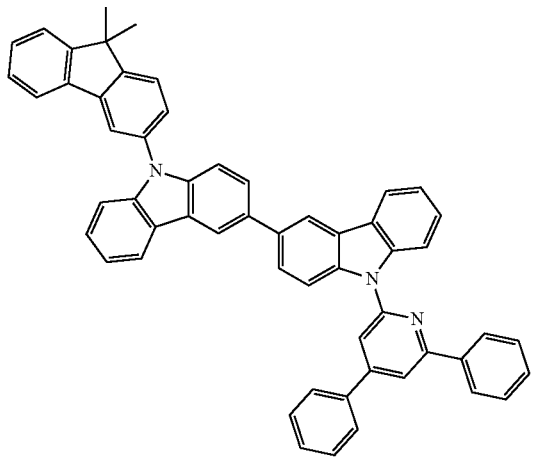
[B-50]
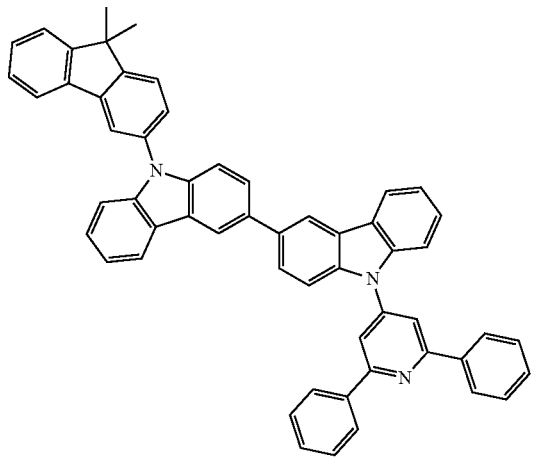
[B-51]
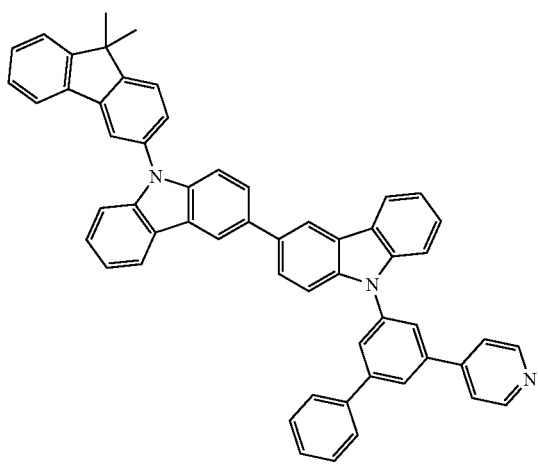
[B-52]
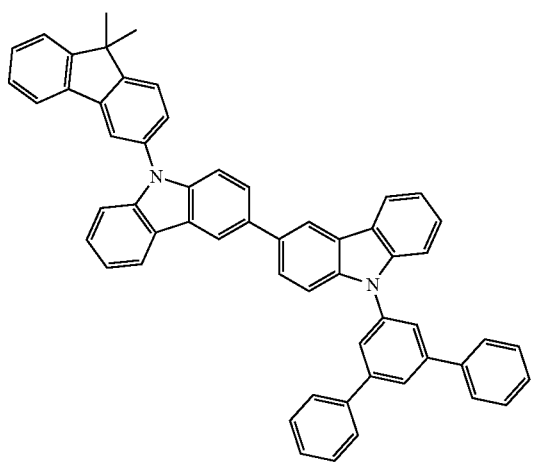
[B-53]
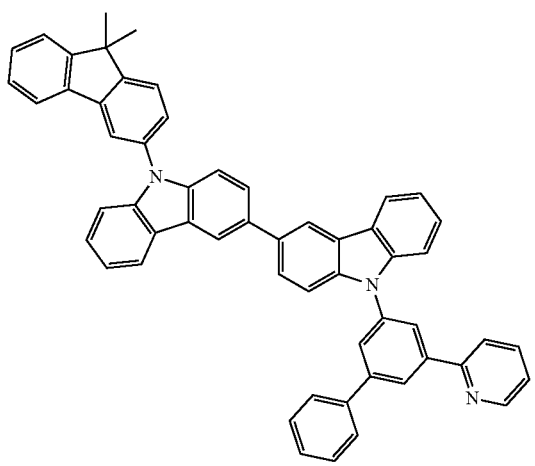
[B-54]
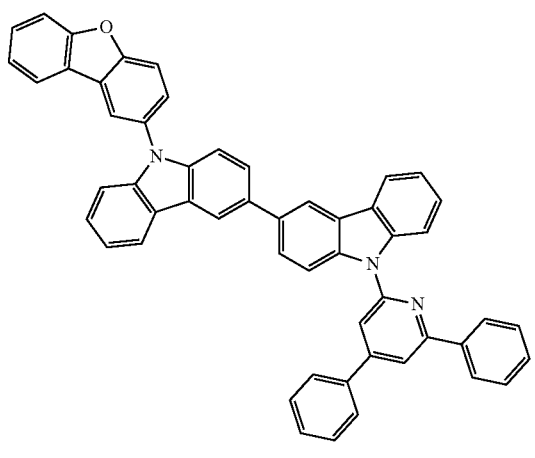

[B-55]
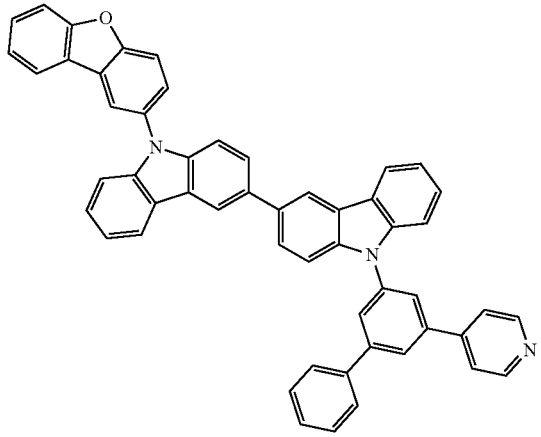
[B-56]
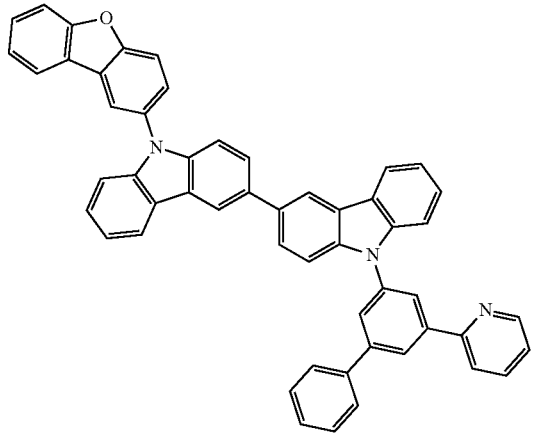
[B-57]
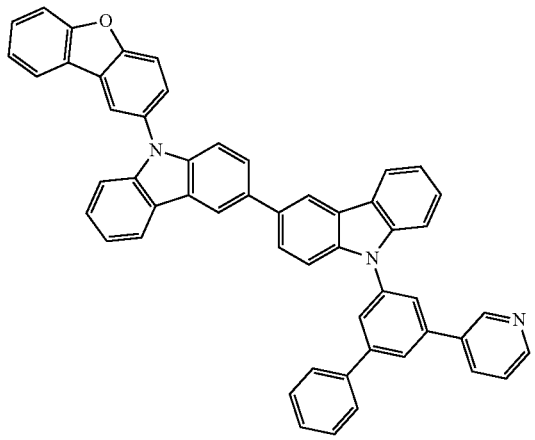
[B-58]
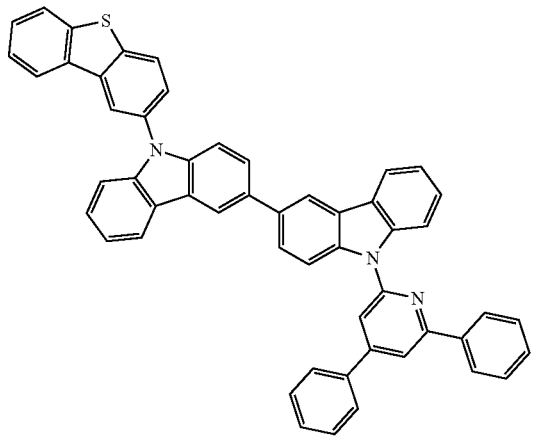
[B-59]
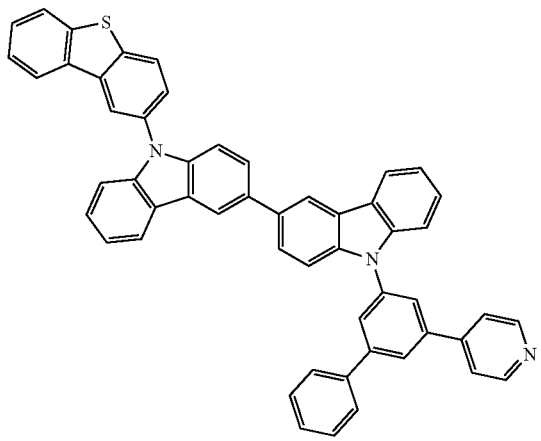
[B-60]
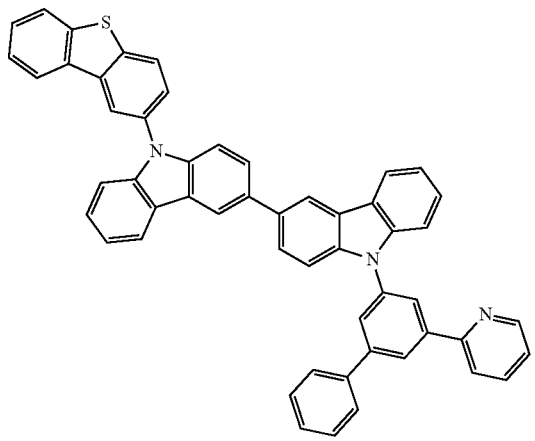

[B-61]
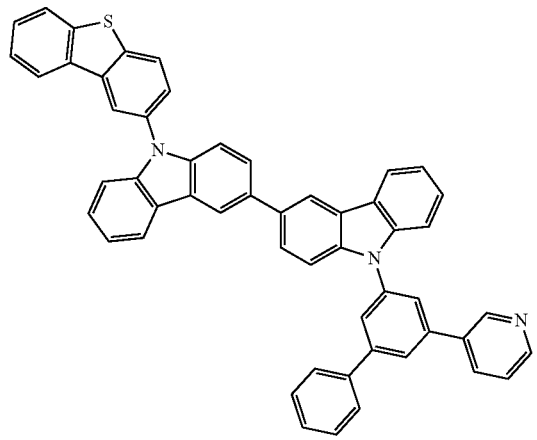
[B-62]
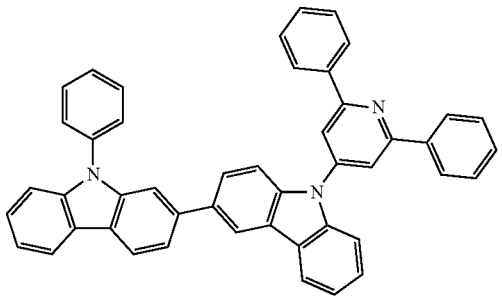
[B-63]
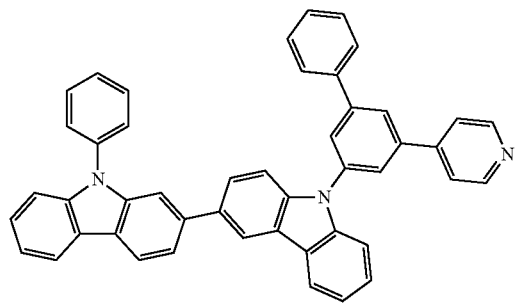
[B-64]
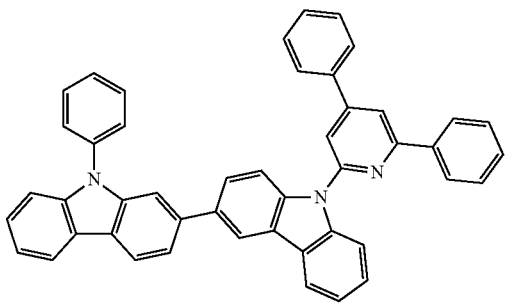
[B-65]
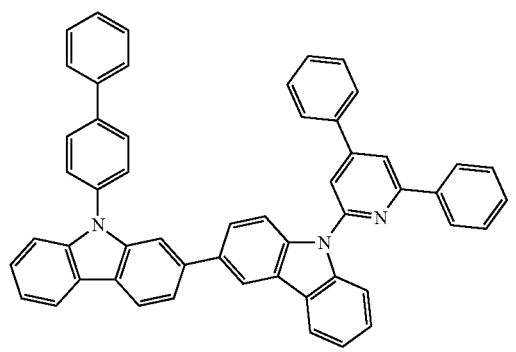
[B-66]
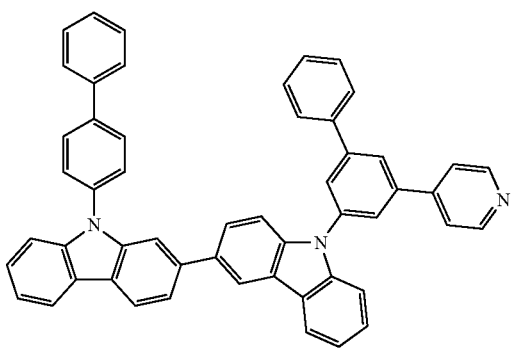
[B-67]
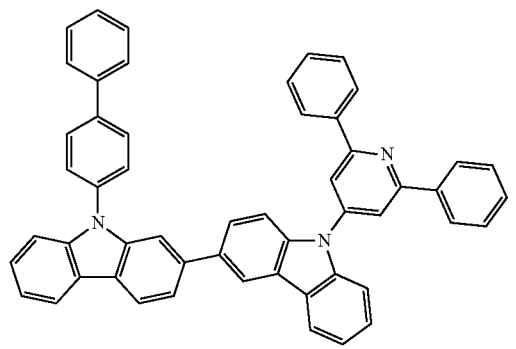
[B-68]
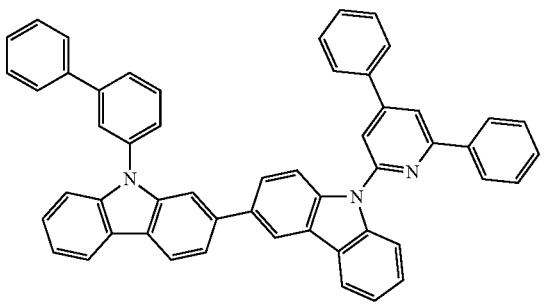

-continued
[B-69]
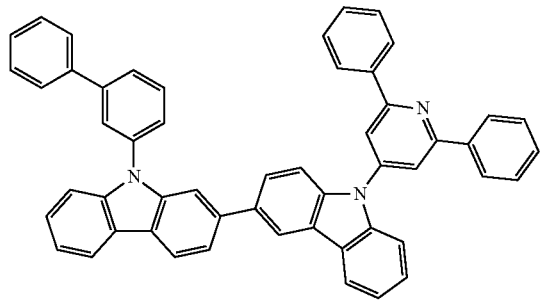
[B-70]
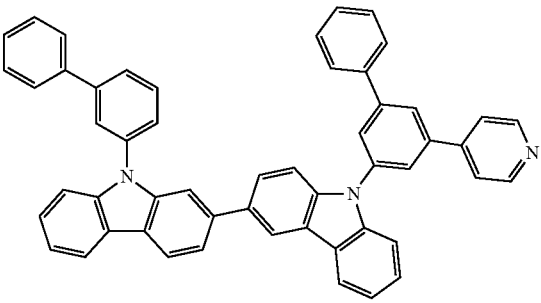
[B-71]
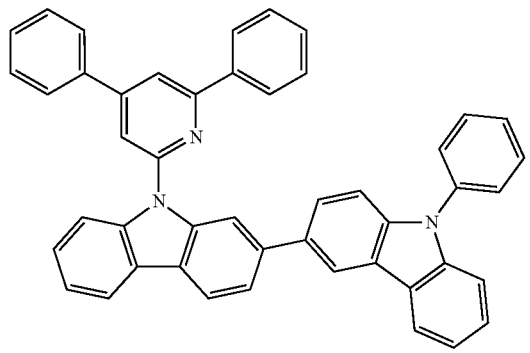
[B-72]
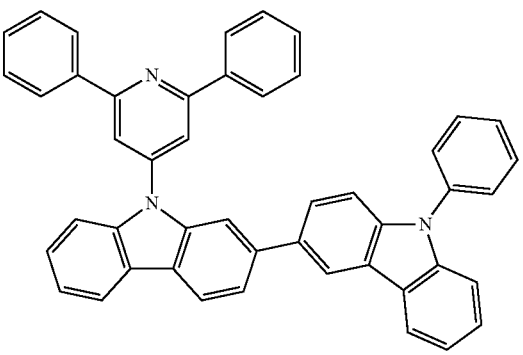
[B-73]
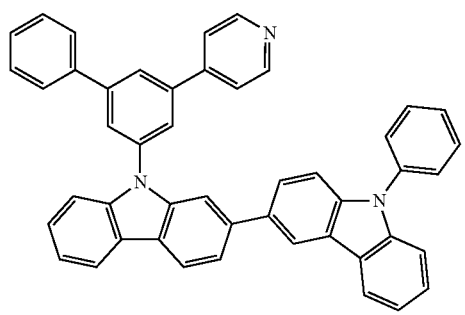
[B-74]
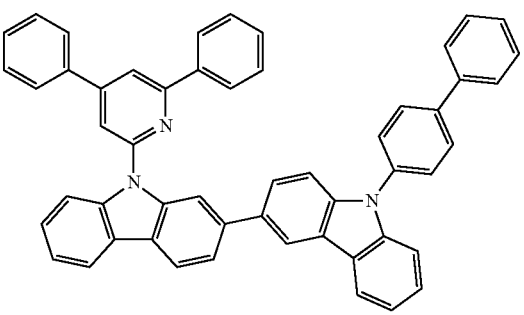
[B-75]
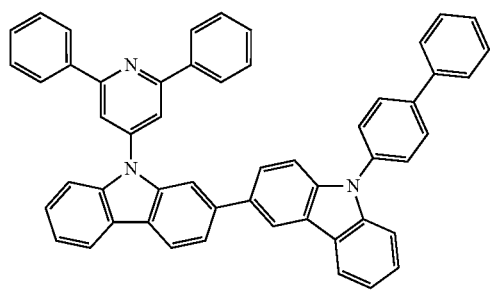
[B-76]
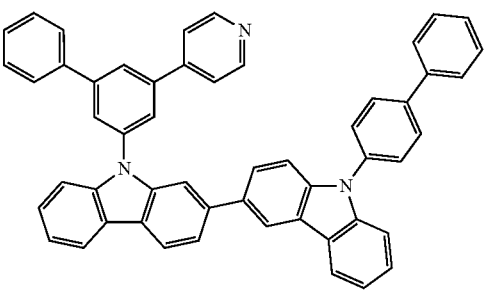
[B-77]
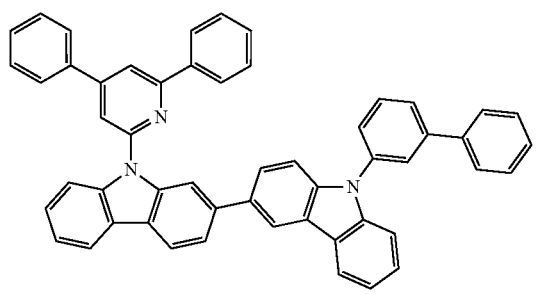
[B-78]
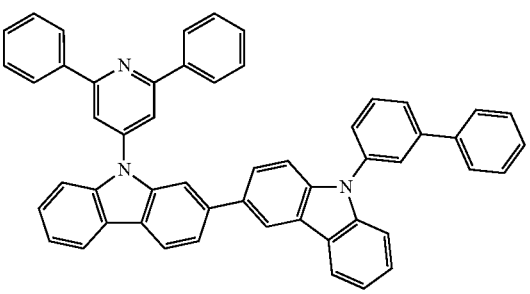

[B-79]
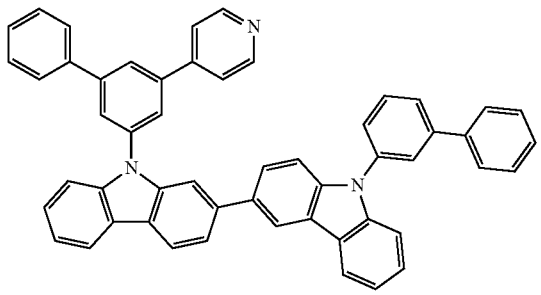
[B-80]
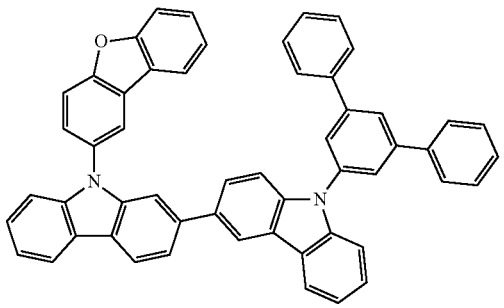
[B-81]
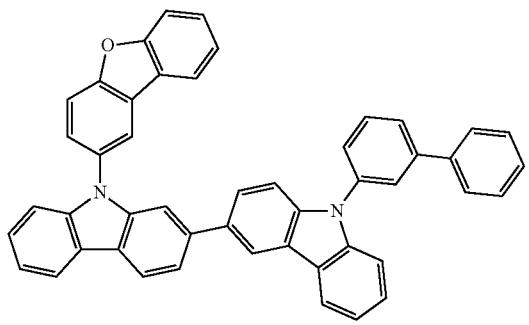
[B-82]
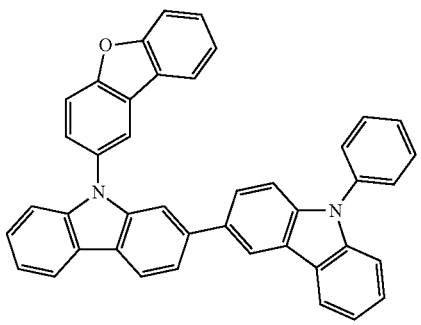
[B-83]
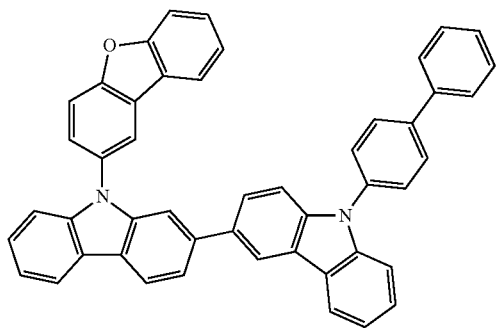
[B-84]
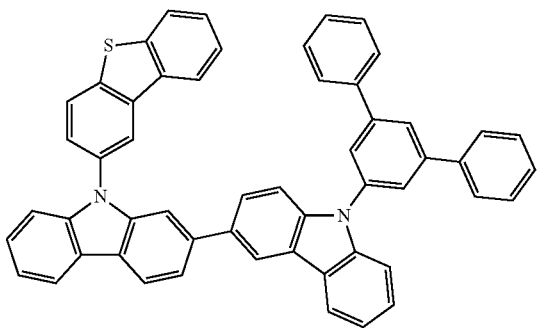
[B-85]
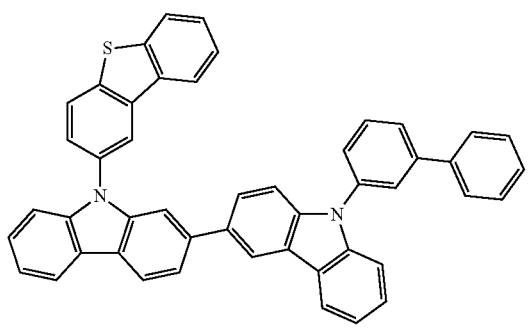
[B-86]
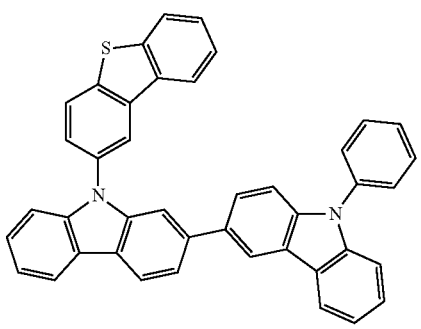

-continued
[B-87]
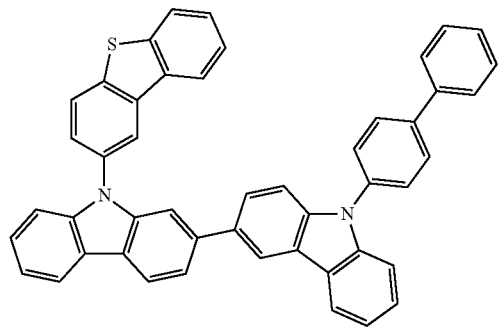
[B-88]
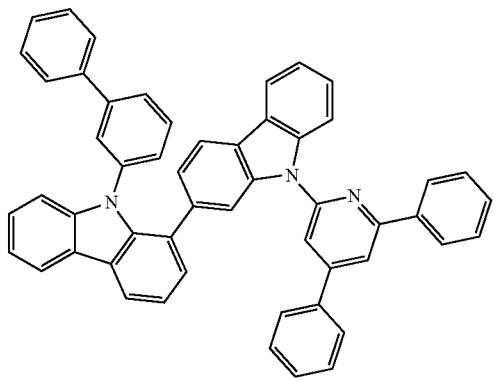
[B-89]
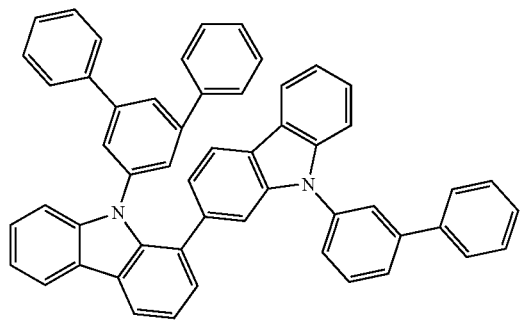
[B-90]
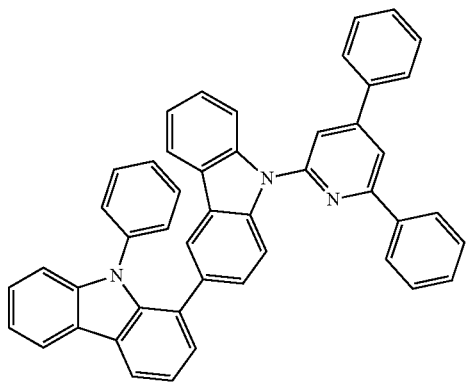
[B-91]
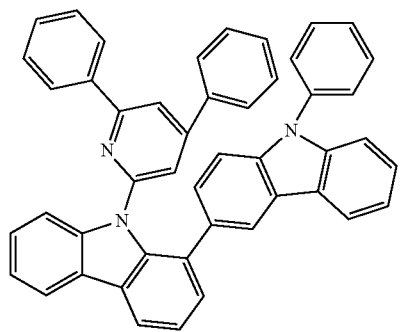
[B-92]
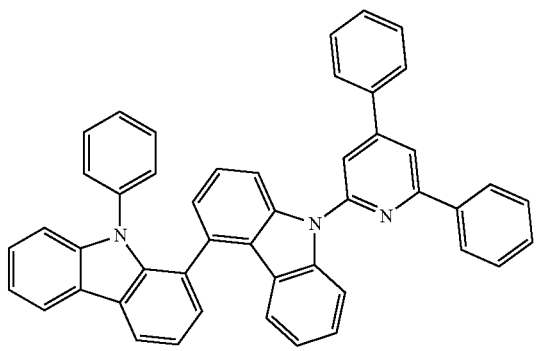
[B-93]
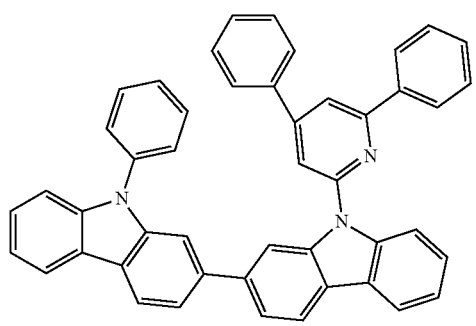
[B-94]
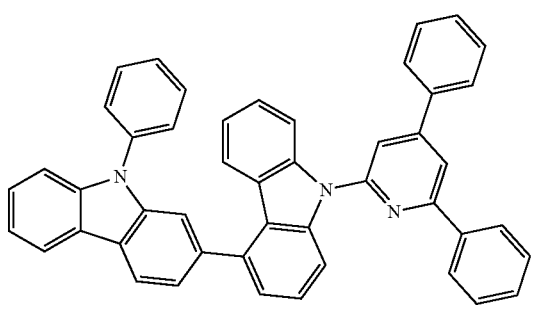

[B-95]
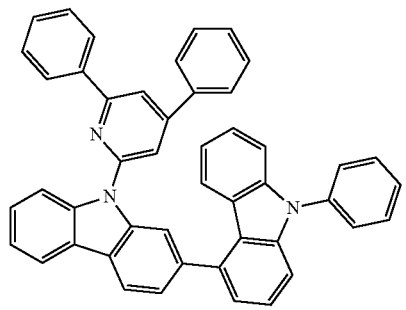
[B-96]
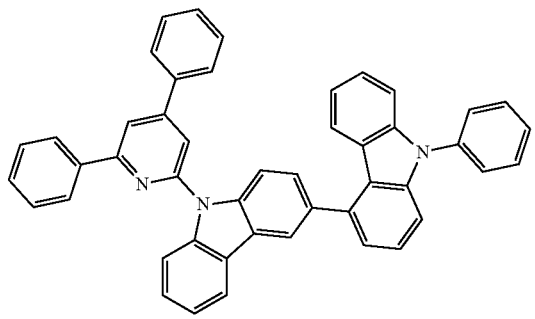
[B-97]
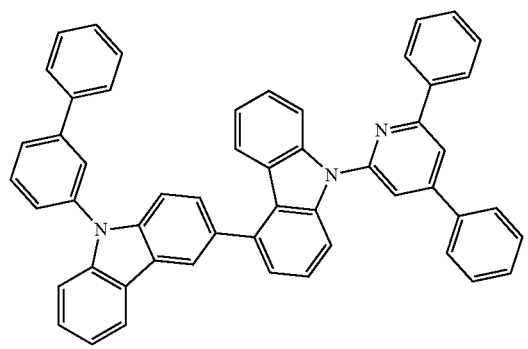
[B-98]
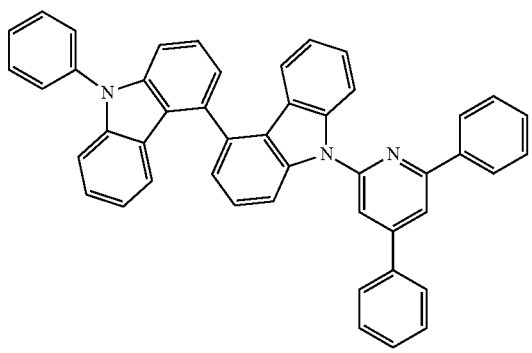
[B-99]
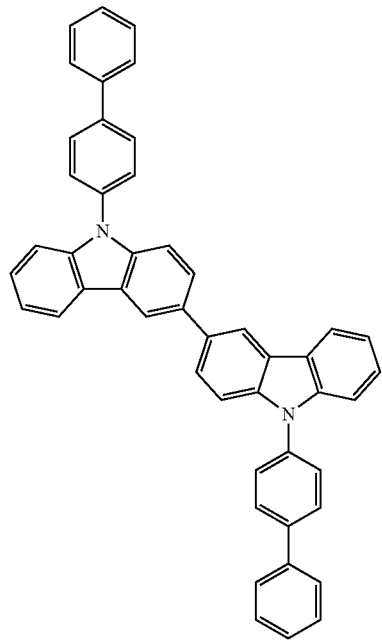
[B-100]
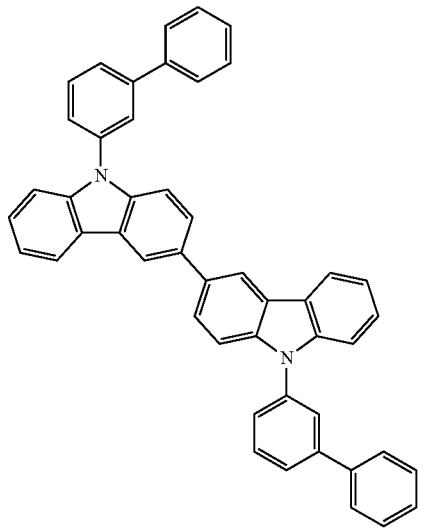

-continued
[B-101]
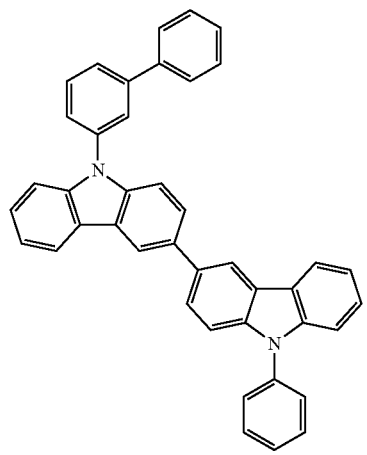
[B-102]
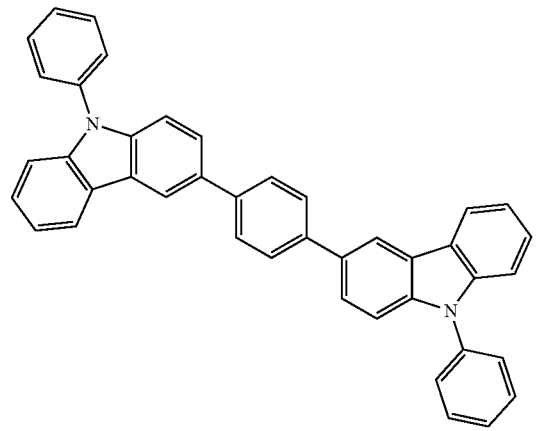
[B-103]
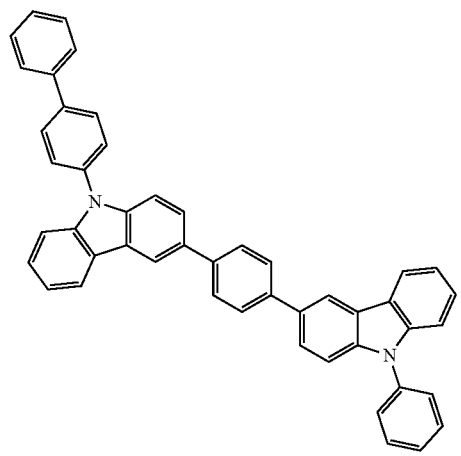
[B-104]
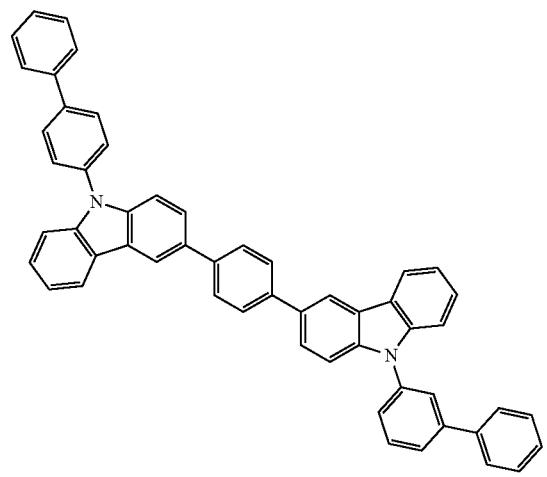
[B-105]
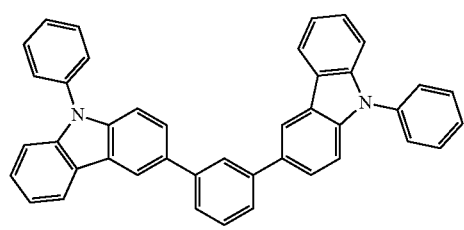
[B-106]
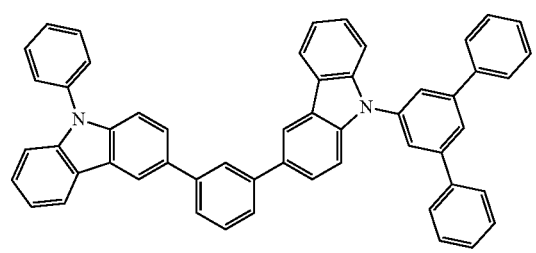

-continued
[B-107]
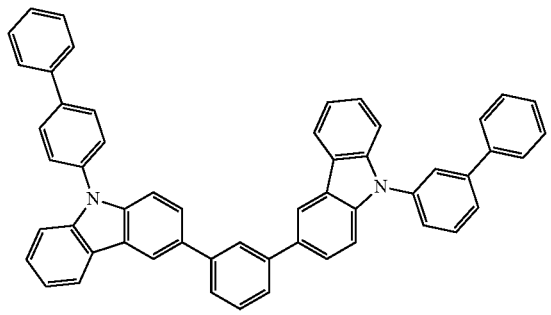
[B-108]
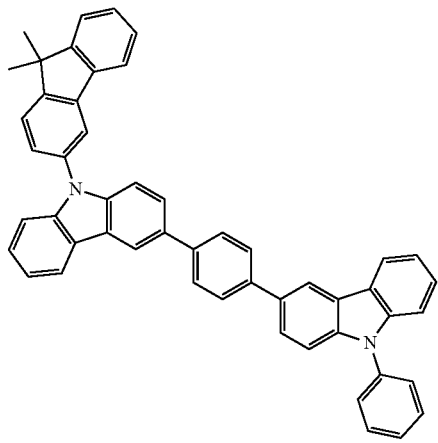
[B-109]
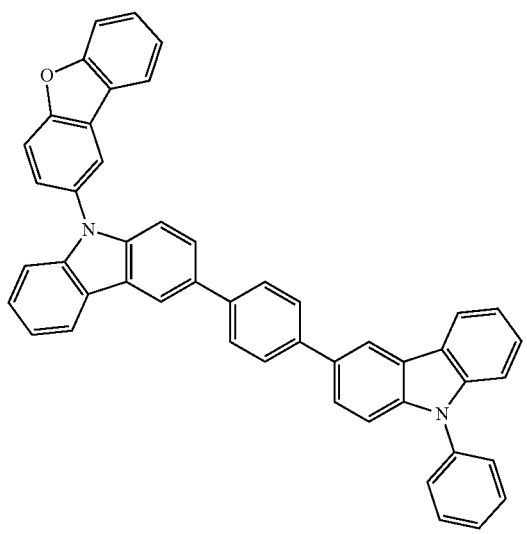
[B-110]
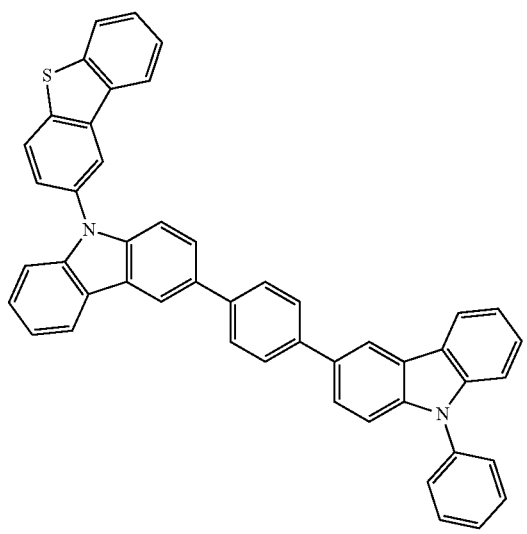
[B-111]
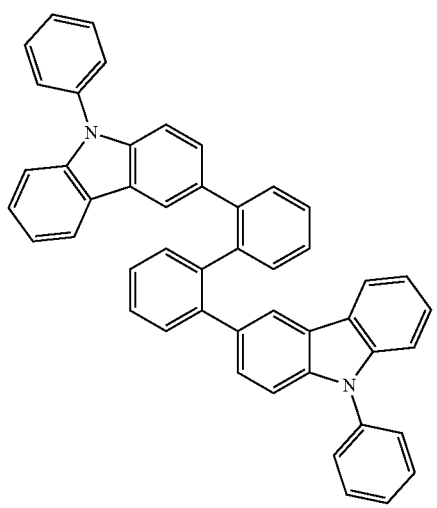
[B-112]
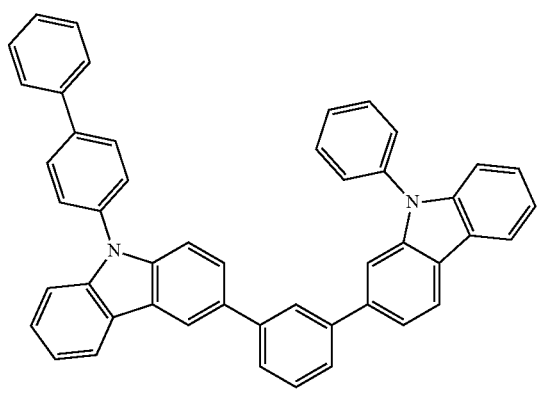

-continued
[B-113]
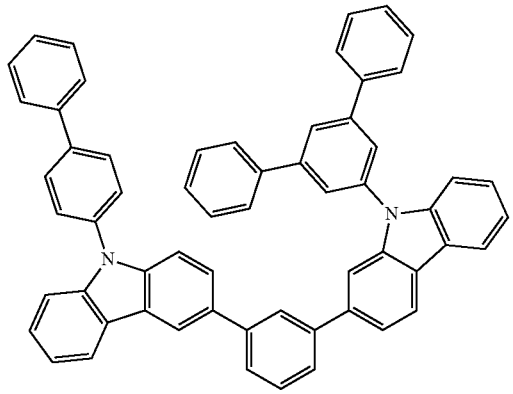
[B-114]
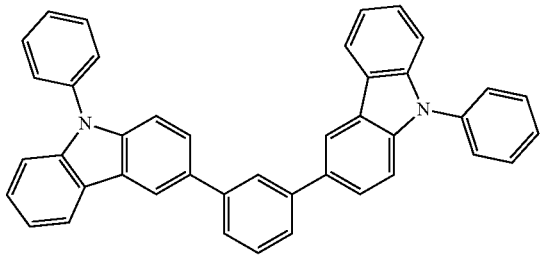
[B-115]
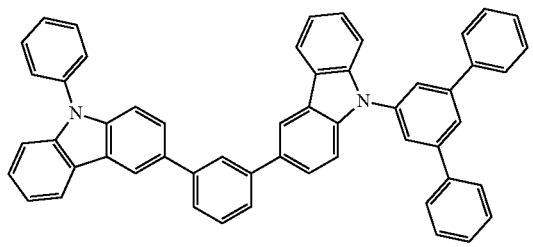
[B-116]
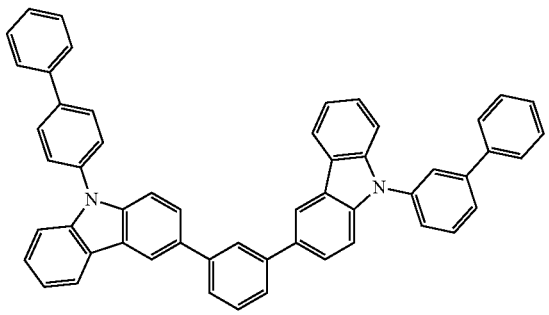
[B-117]
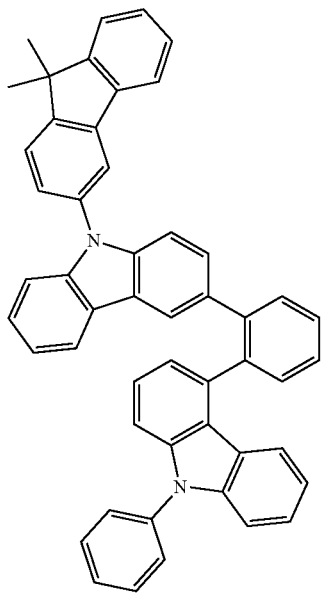
[B-118]
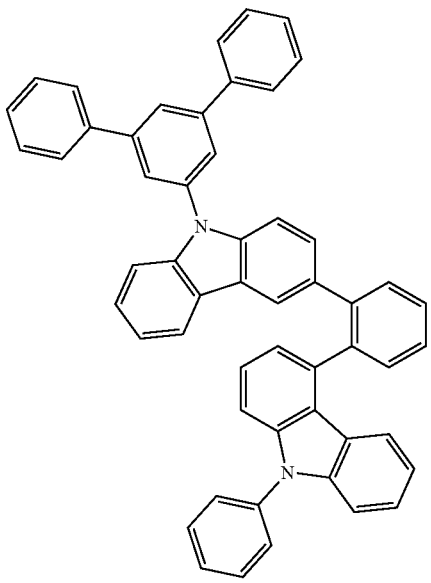

[B-119]
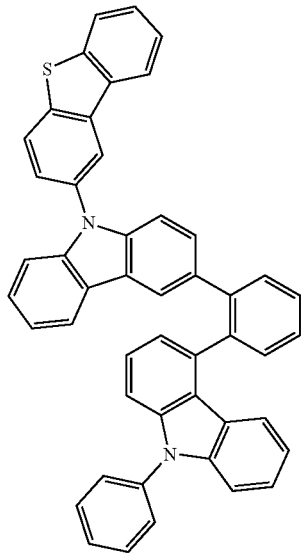
[B-120]
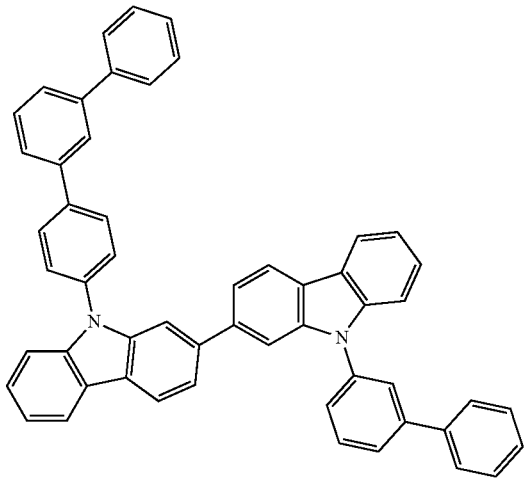
[B-121]
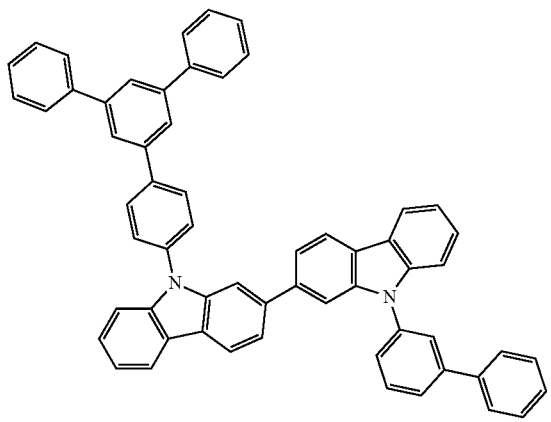
[B-122]
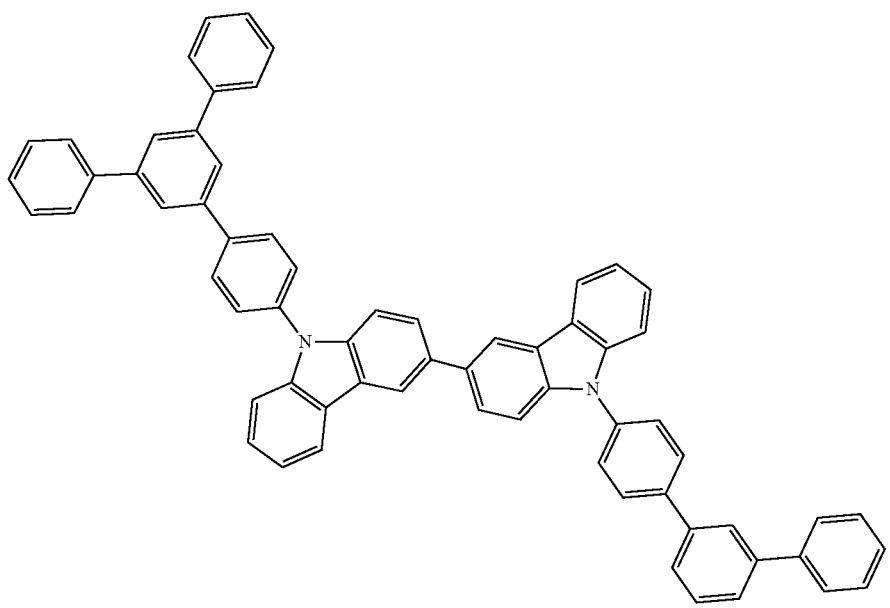

-continued
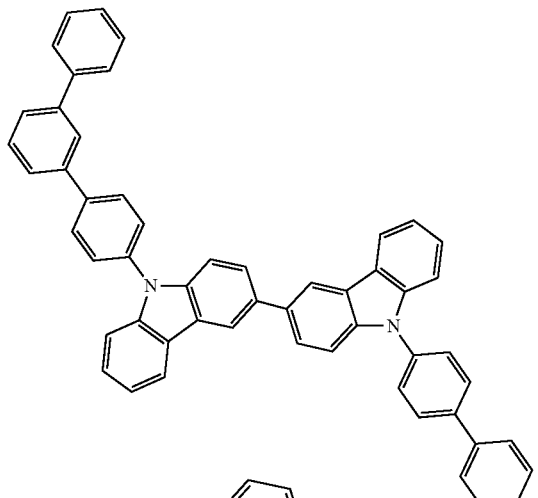
[B-123]
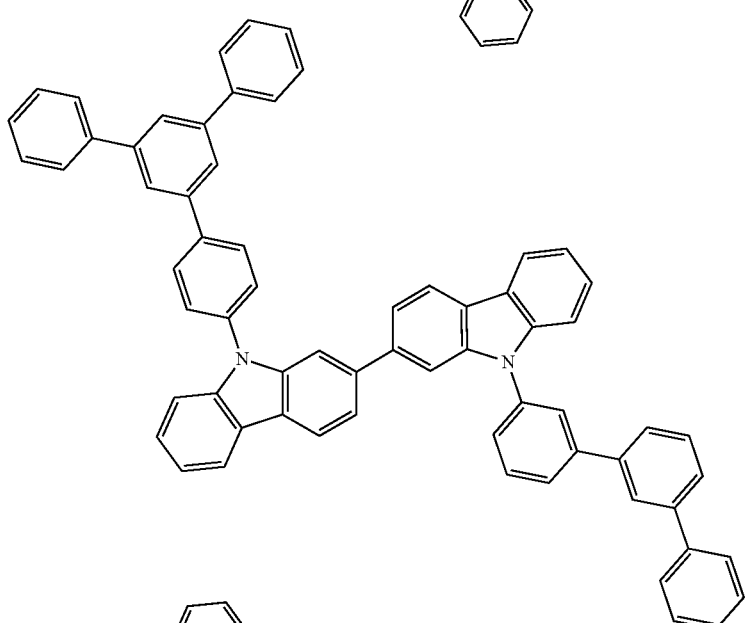
[B-125]
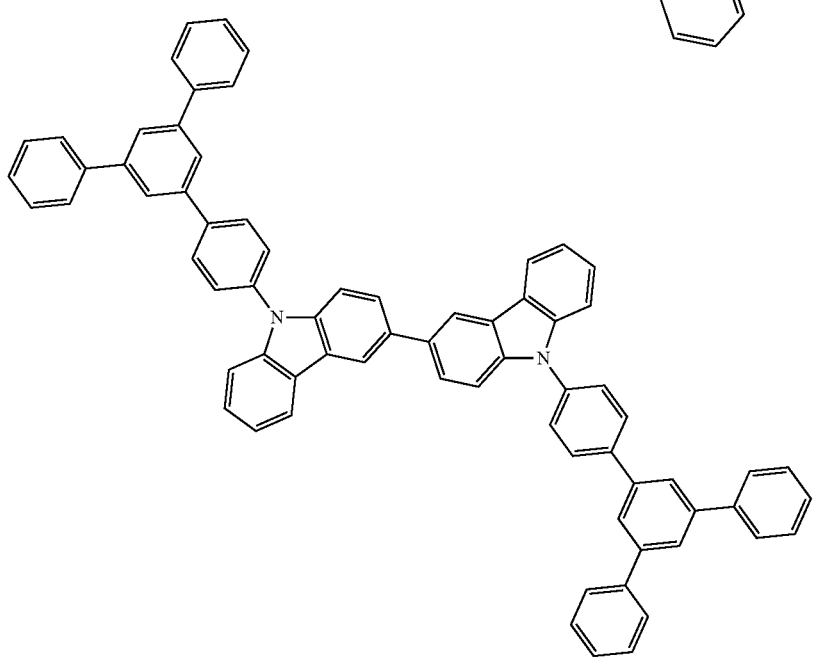
[B-125]

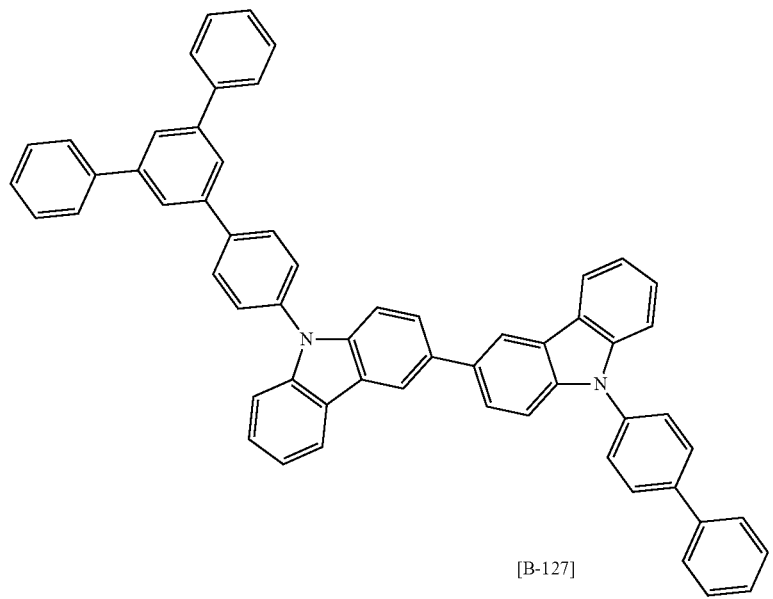
[B-126]
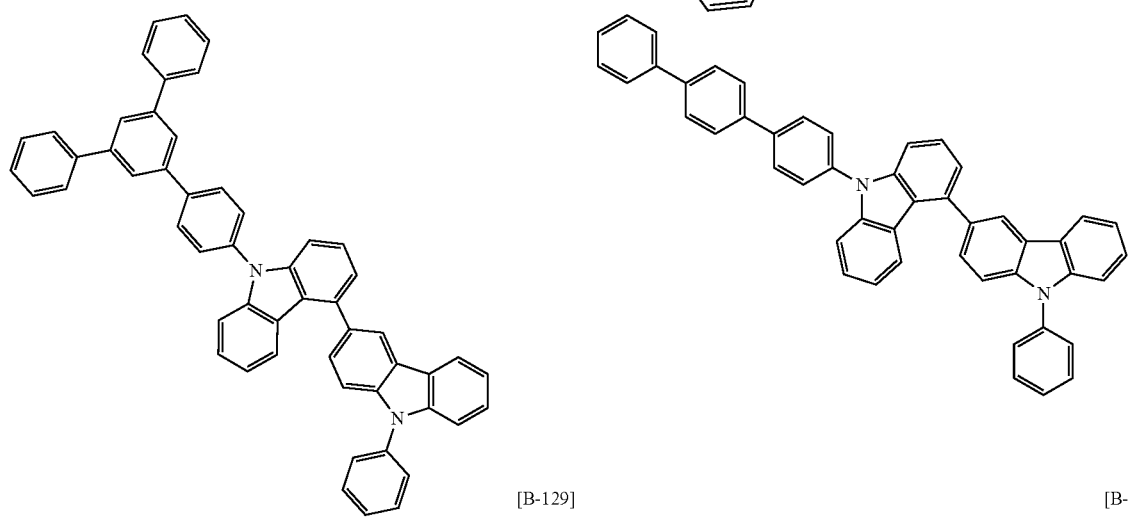
[B-127]
[B-128]
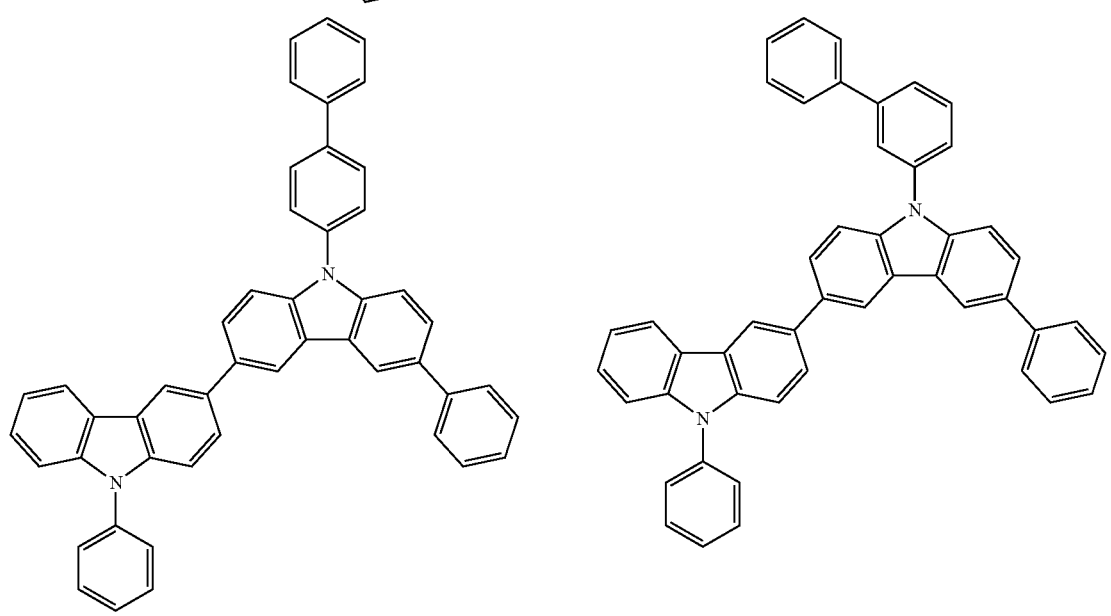
[B-129]
[B-130]

-continued
[B-131]
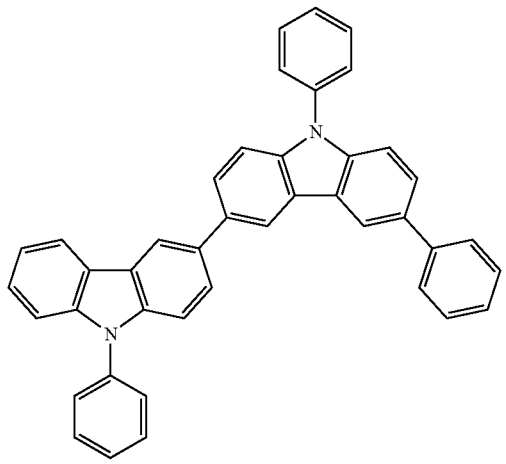
[B-132]
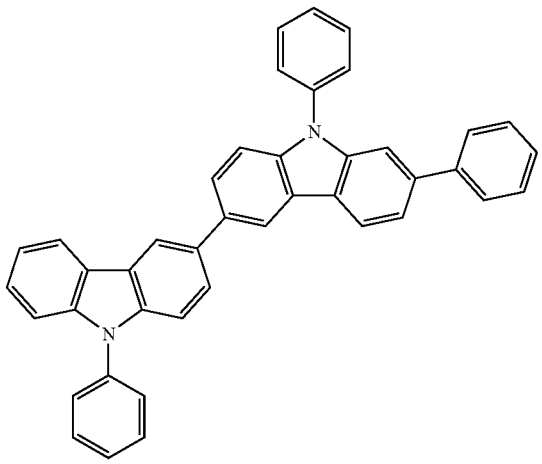
[B-133]
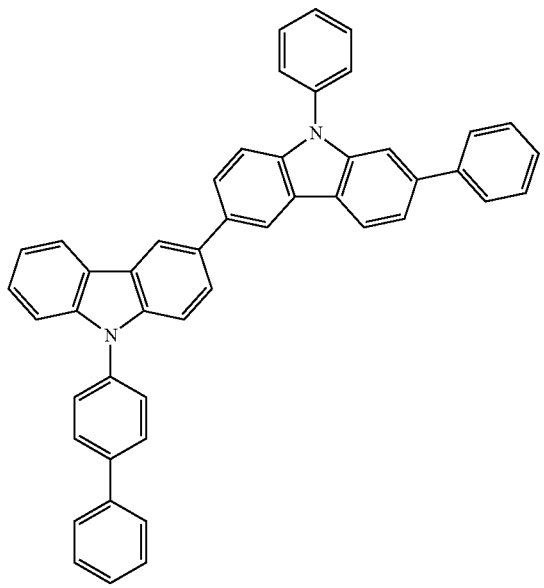
[B-134]
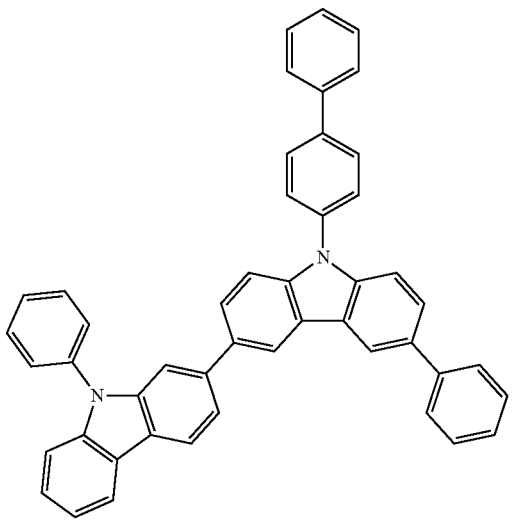
[B-135]
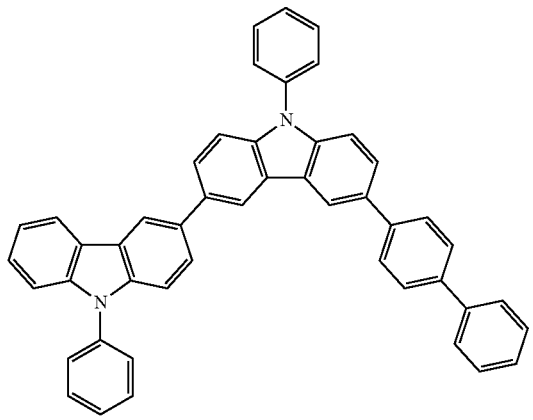
[B-136]
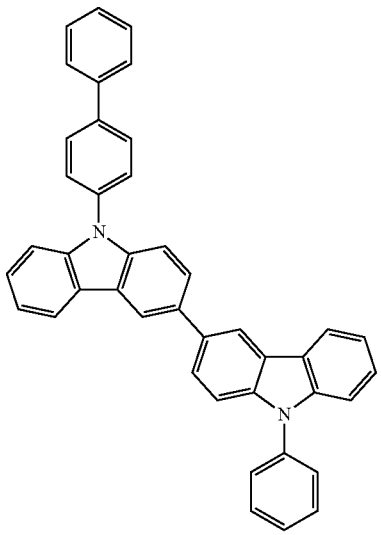

-continued
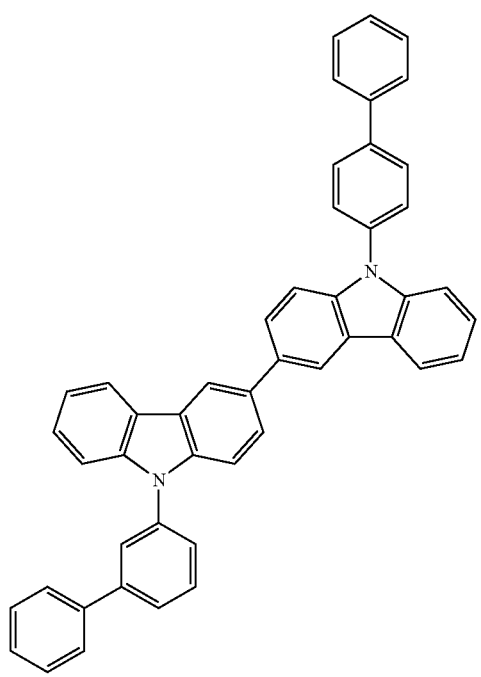
[B-137]
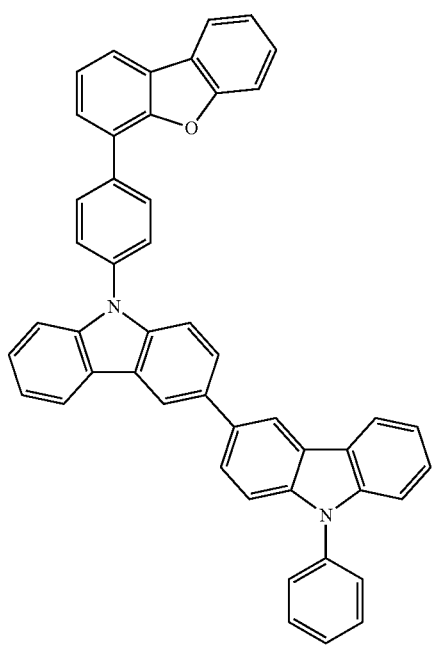
[B-138]
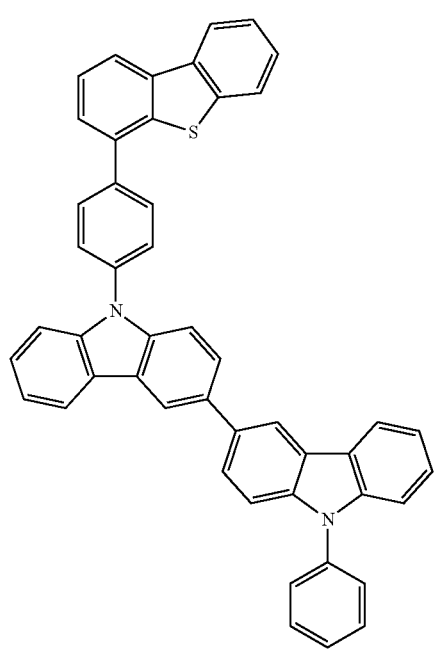
[B-139]

[Group C]
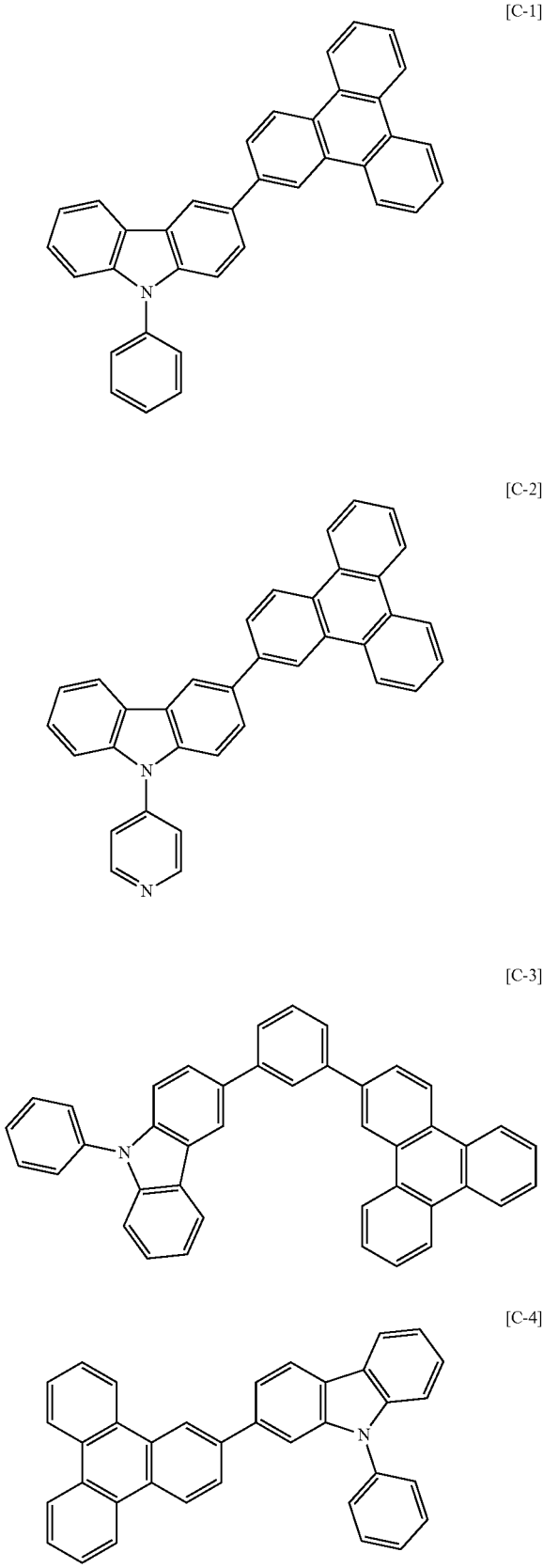

[C-9]
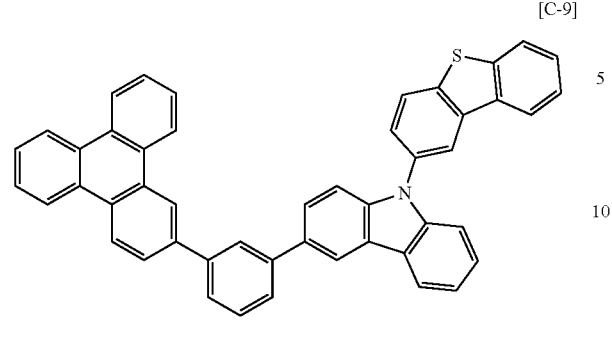
[C-10]
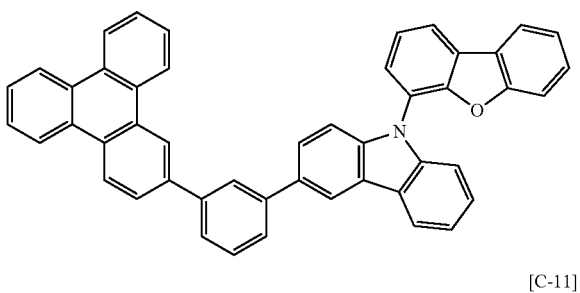
[C-11]
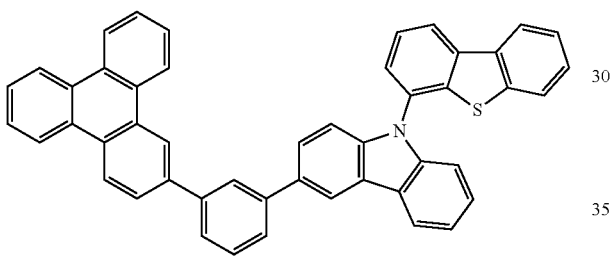
[C-12]
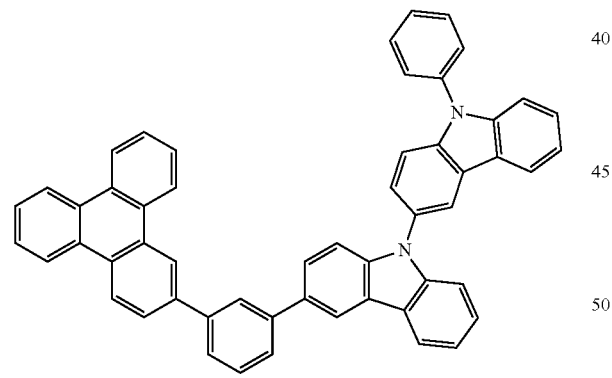
[C-13]
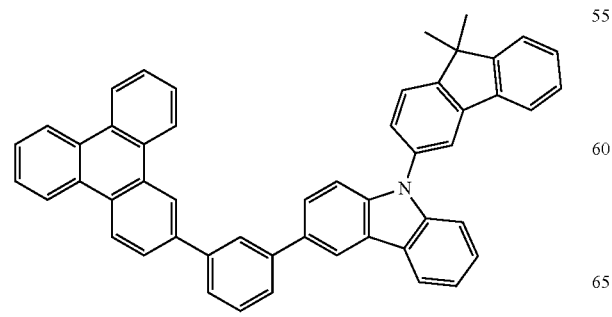
[C-14]
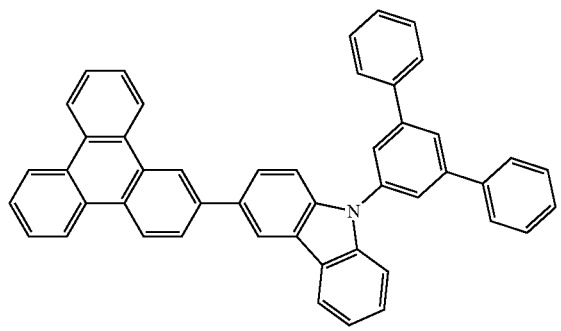
[C-15]
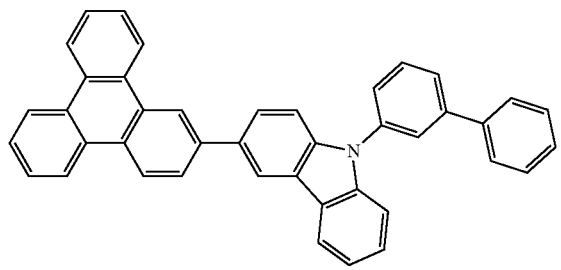
[C-16]
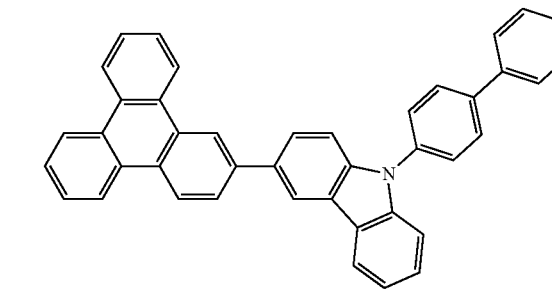
[C-17]
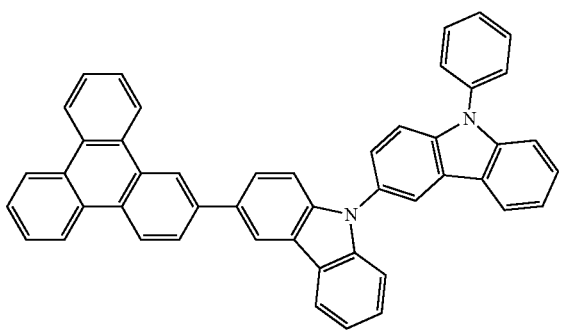
[C-18]
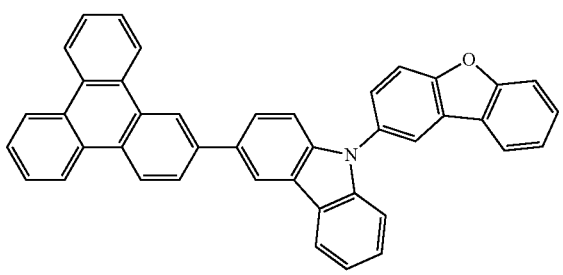

[C-19]
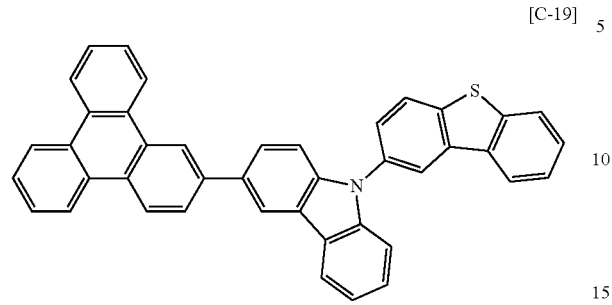
[C-20]
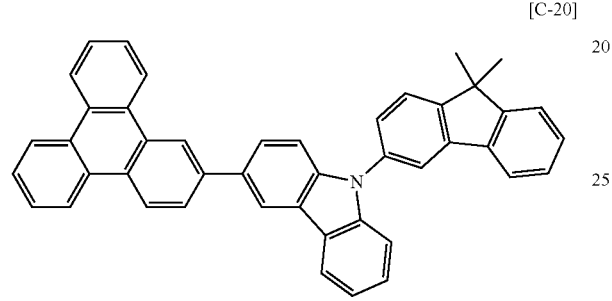
[C-21]
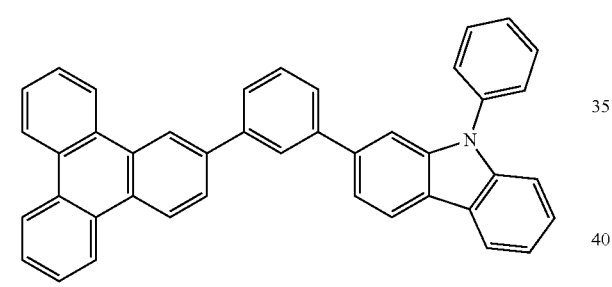
[C-22]
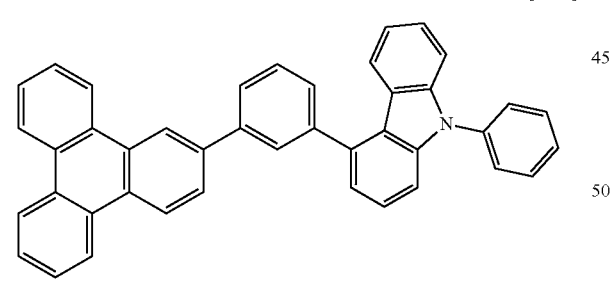
[C-23]
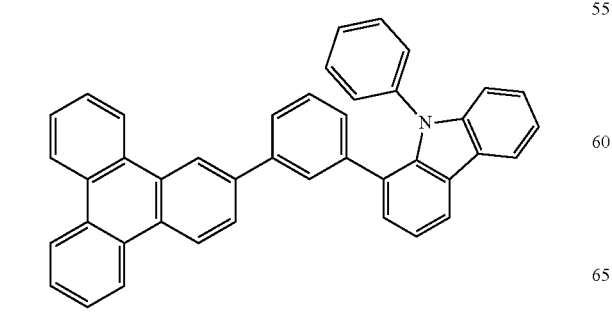
[C-24]
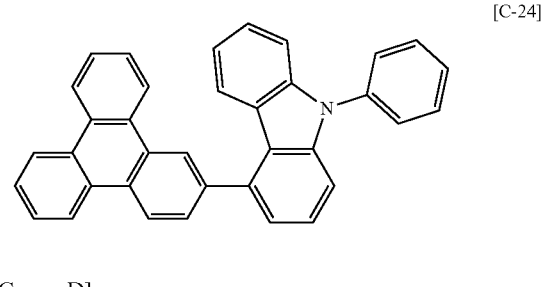
[Group D]
[D-1]
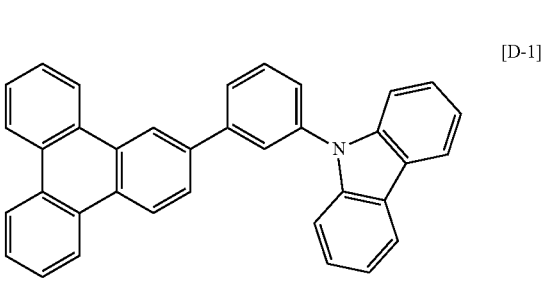
[D-2]
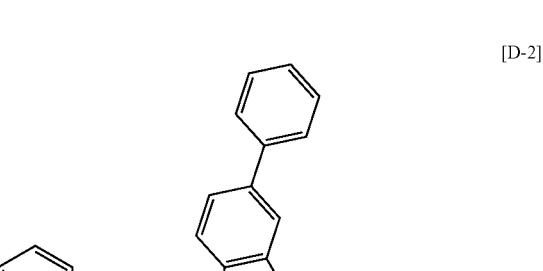
[D-3]
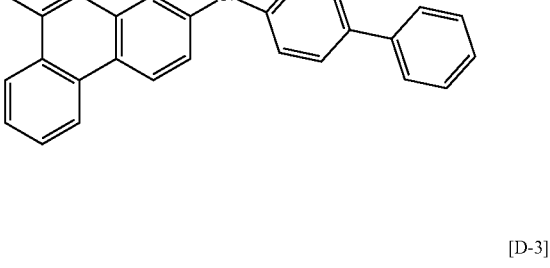
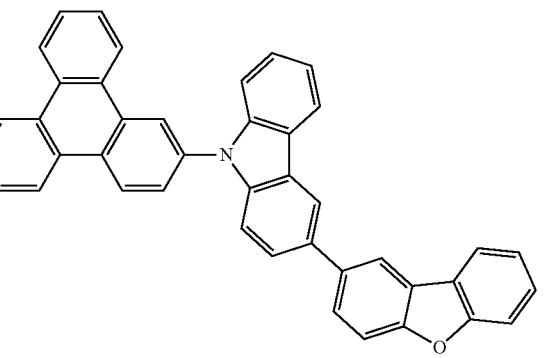

[D-4]
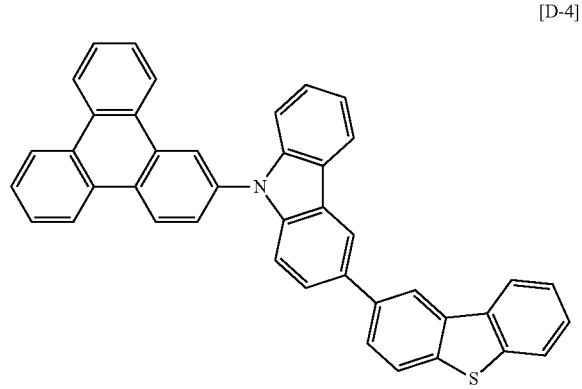
[D-6]
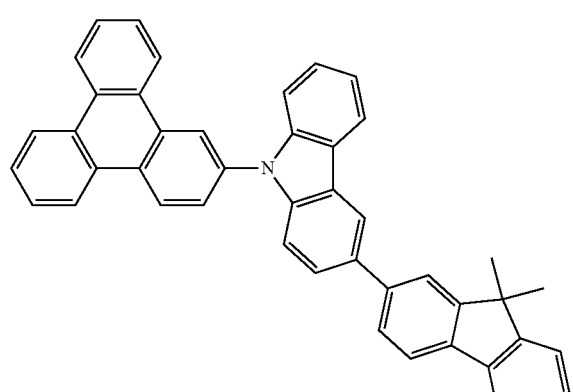
[D-7]
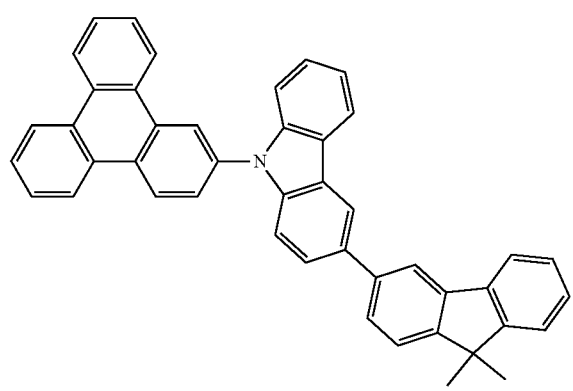
[D-8]
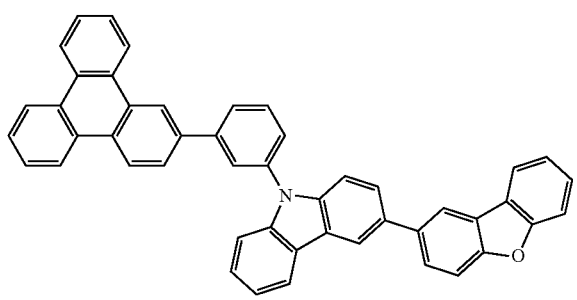
[D-9]
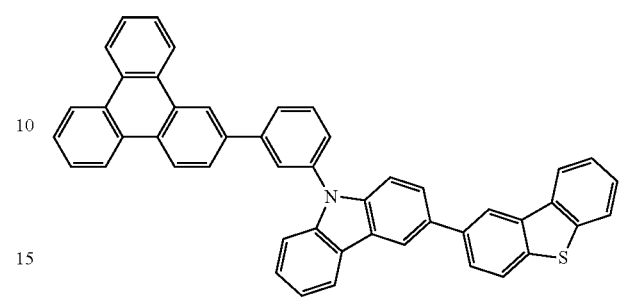
[D-10]
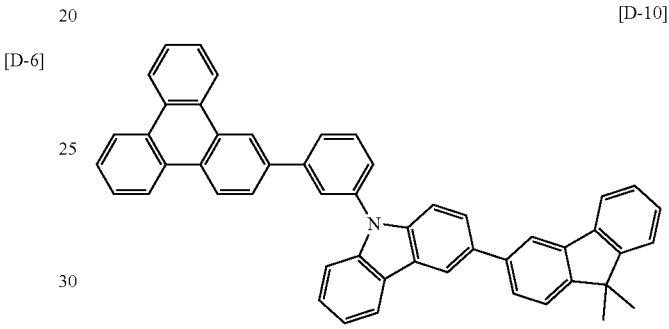
[D-11]
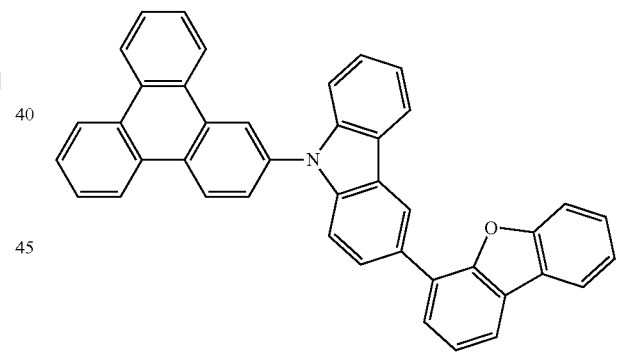
[D-12]
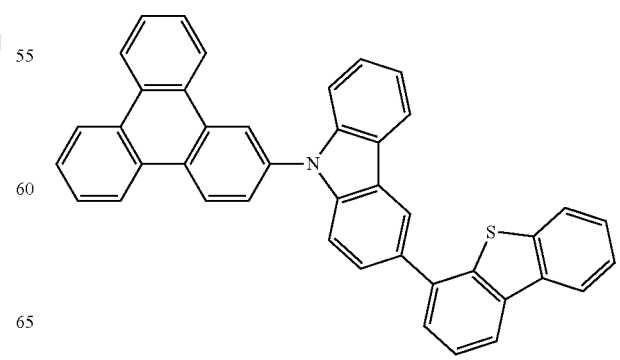

[D-13]

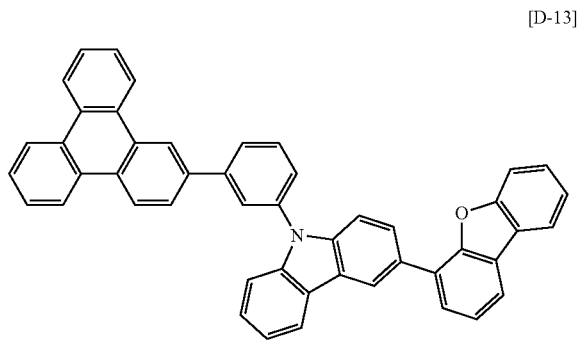

[D-14]

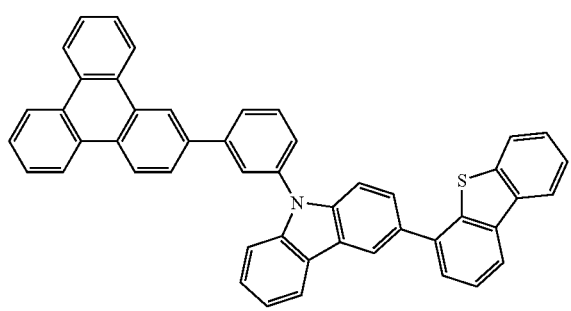

[D-15]

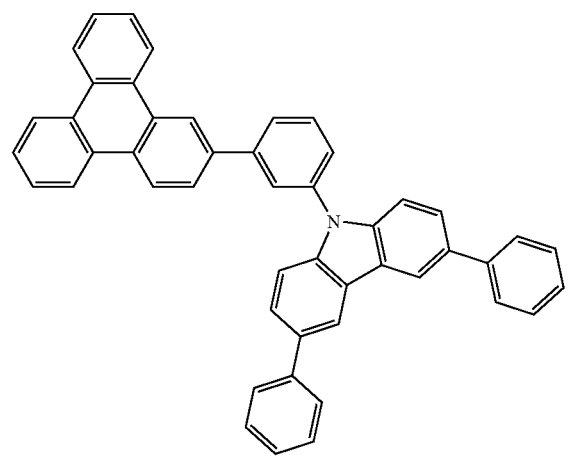

[D-16]

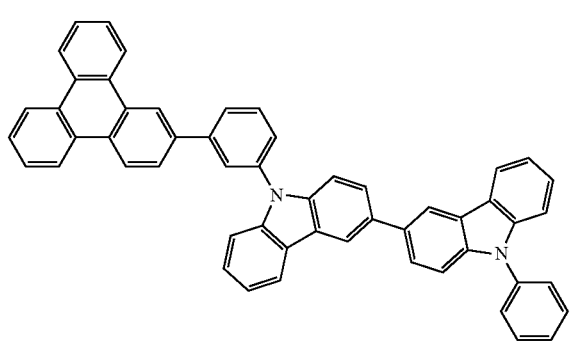

[D-17]

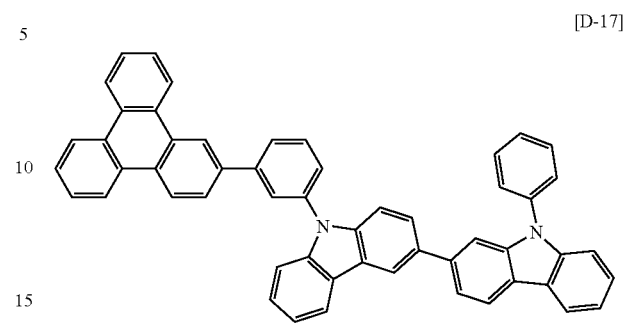

[D-18]

[D-19]

[D-20]

The second compound may be represented by a combination of the moiety represented by Chemical Formula 3 and the moiety represented by Chemical Formula 4.

The second compound consisting of a combination of the moiety represented by Chemical Formula 3 and the moiety represented by Chemical Formula 4 may be, for example, represented by at least one of Chemical Formulae 3-I to 3-V, but is not limited thereto.

[Chemical Formula 3-I]

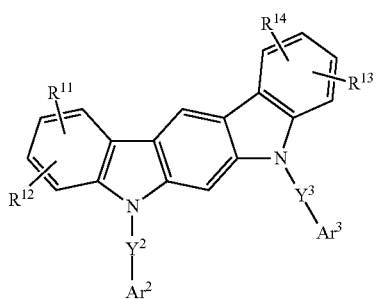

[Chemical Formula 3-II]

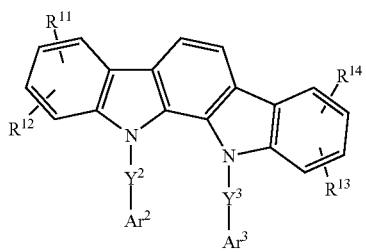

[Chemical Formula 3-III]

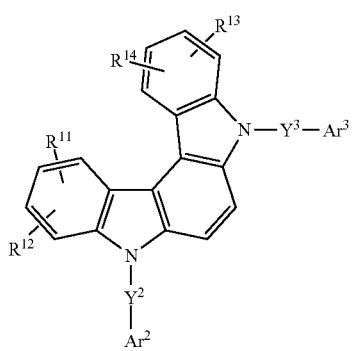

[Chemical Formula 3-VI]

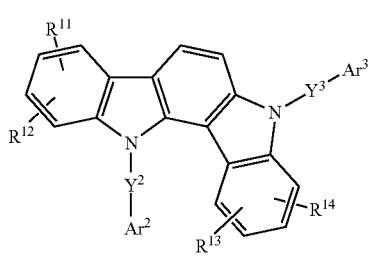

[Chemical Formula 3-V]

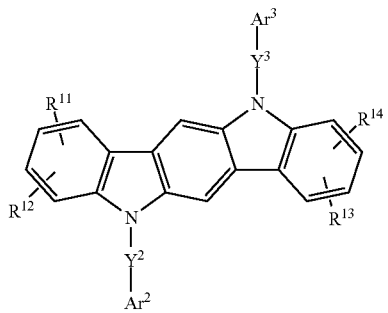

In Chemical Formulae 3-I to 3-V, $Y^2$, $Y^3$, $Ar^2$, and $R^{11}$ to $R^{14}$ are the same as described above. Ara is the same as $Ar^2$.

The second compound consisting of a combination of the moiety represented by Chemical Formula 3 and the moiety represented by Chemical Formula 4 may be, for example compounds of Group E, but is not limited thereto.

[Group E]

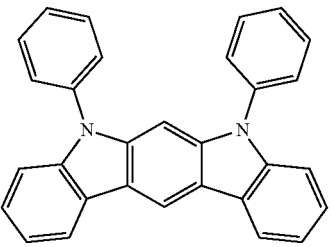
[E-1]

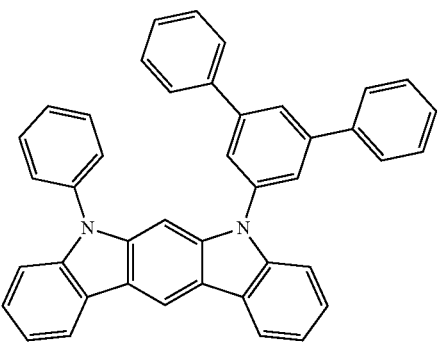
[E-2]

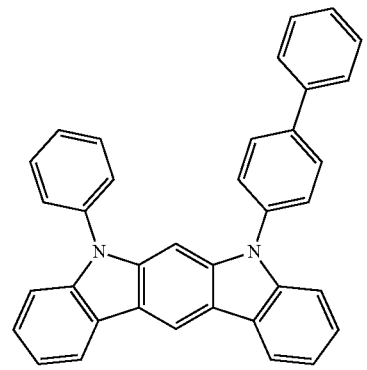
[E-3]

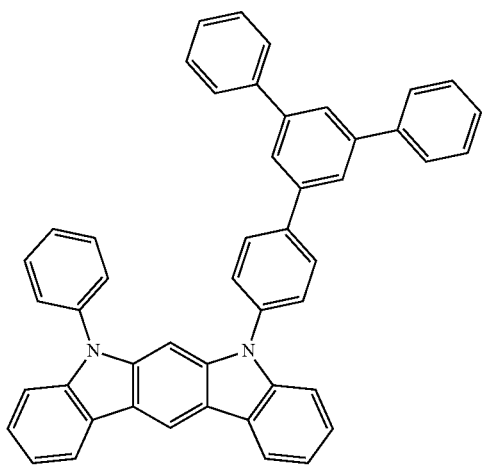
[E-4]

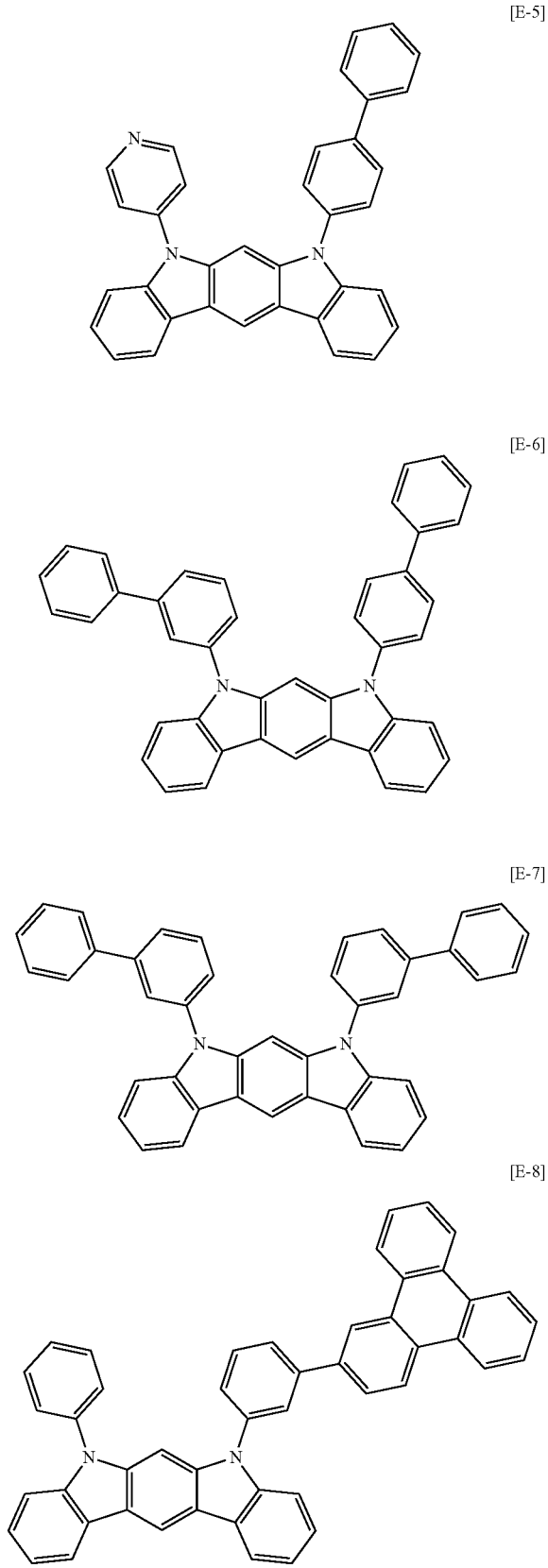
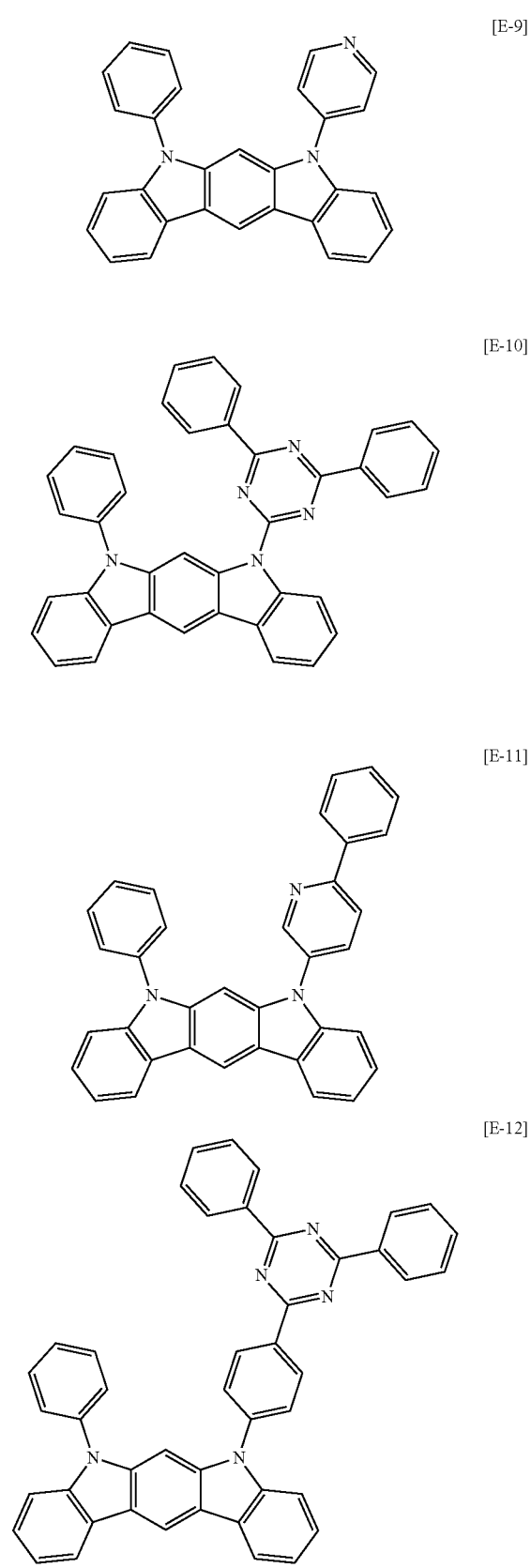

[E-13]
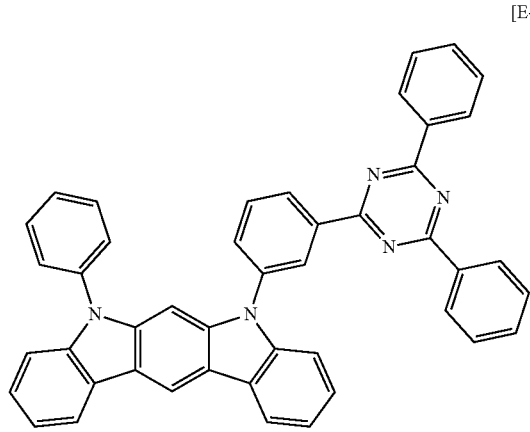
[E-14]
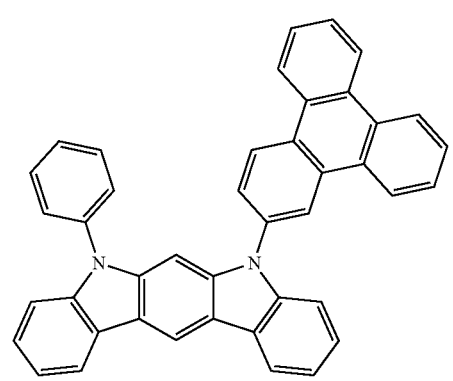
[E-15]
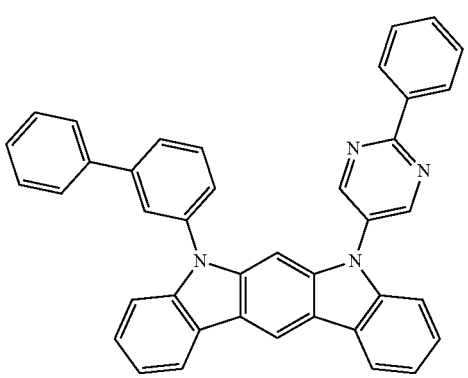
[E-16]
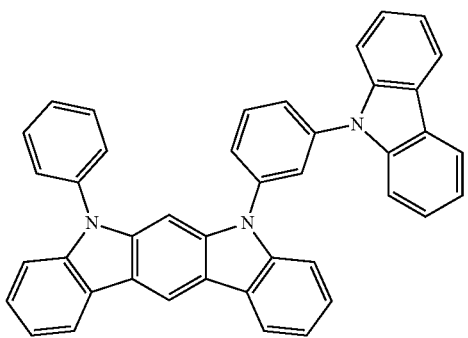
[E-17]
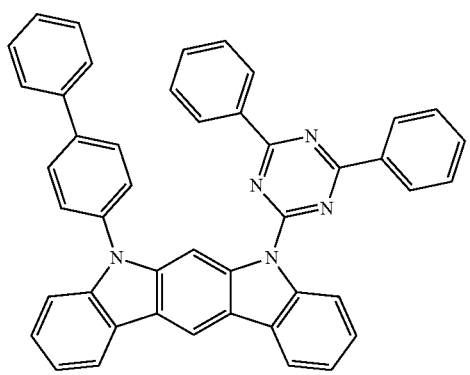
[E-18]
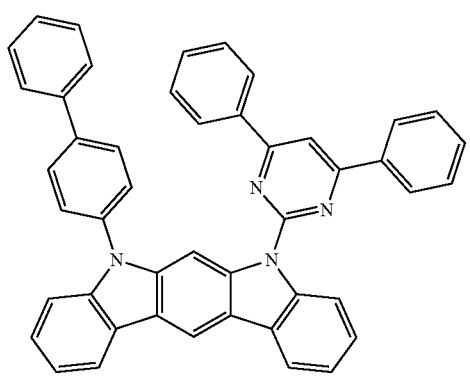
[E-19]
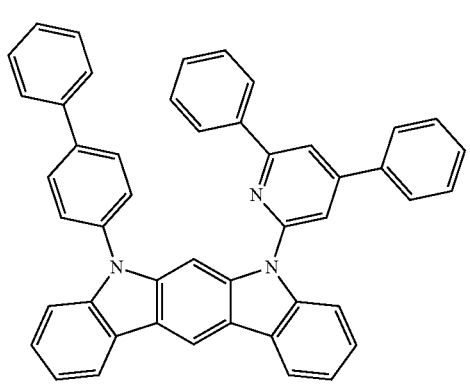
[E-20]
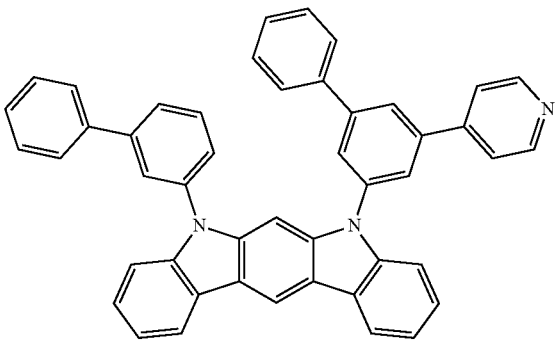

-continued
[E-21]
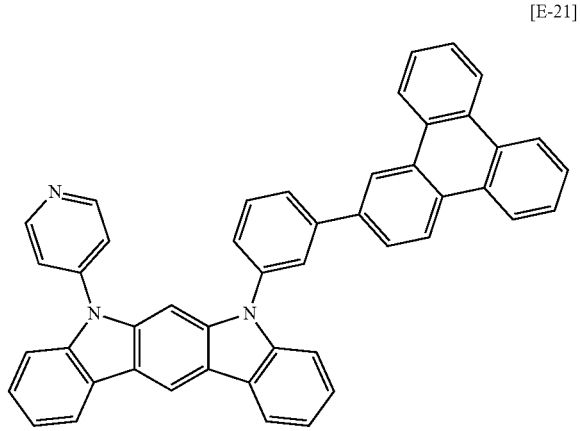
[E-22]
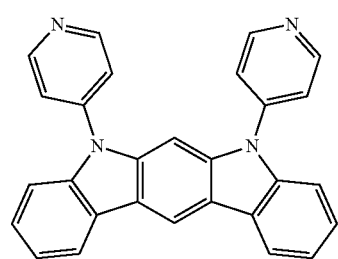
[E-23]
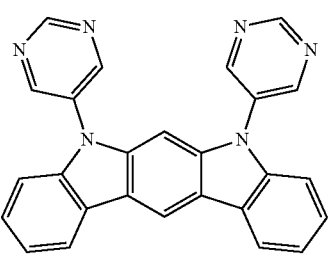
[E-24]
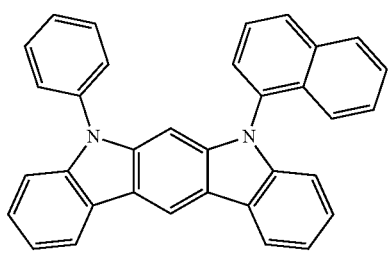
[E-25]
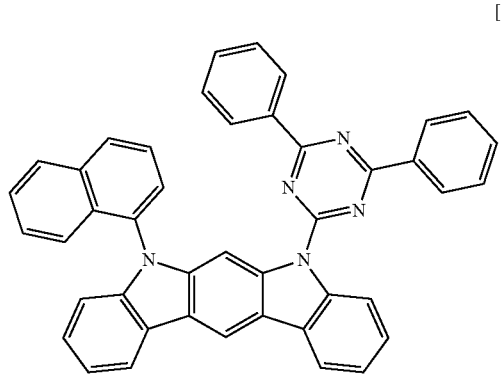
-continued
[E-26]
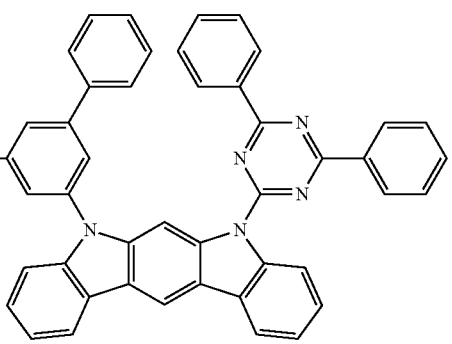
[E-27]
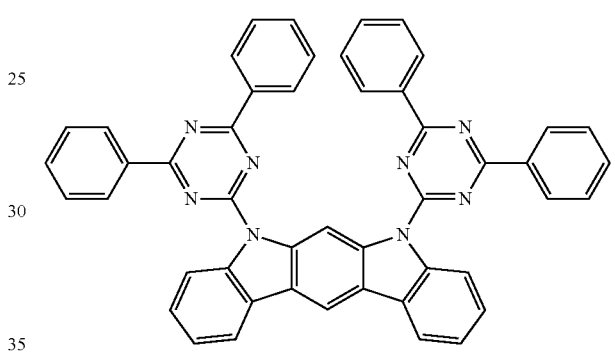
[E-28]
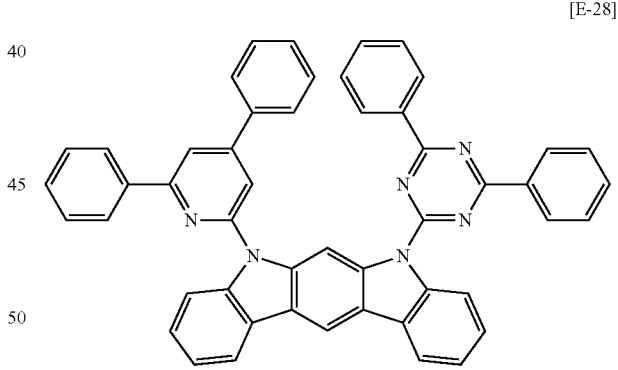
[E-29]
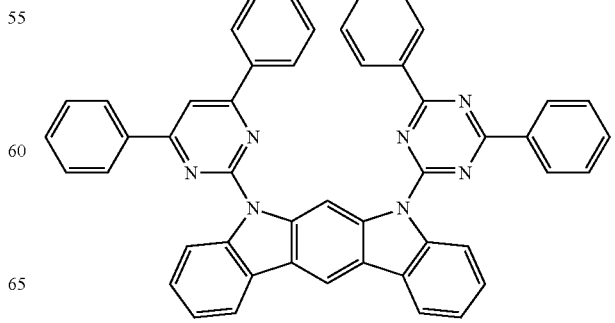

[E-30]
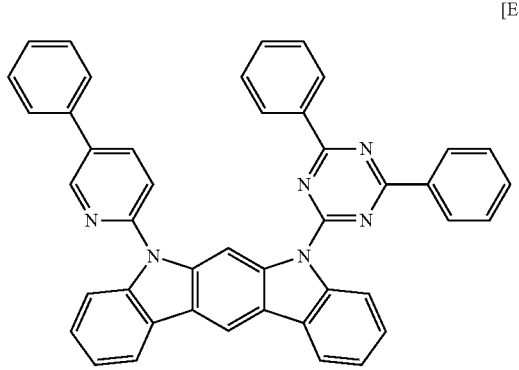
[E-34]
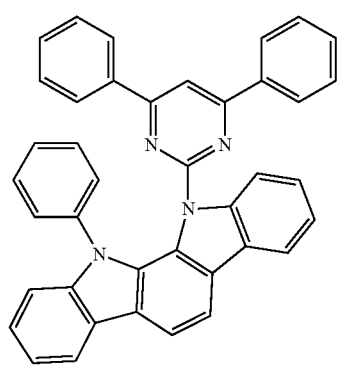
[E-31]
[E-35]
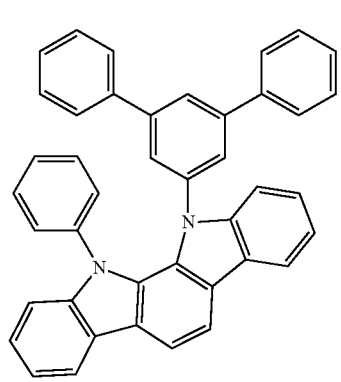
[E-32]
[E-36]
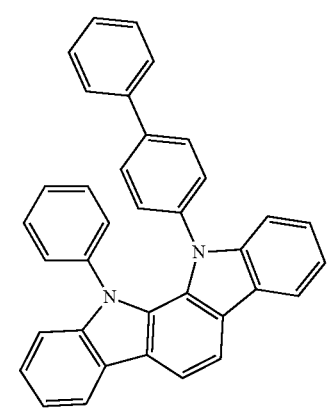
[E-33]
[E-37]
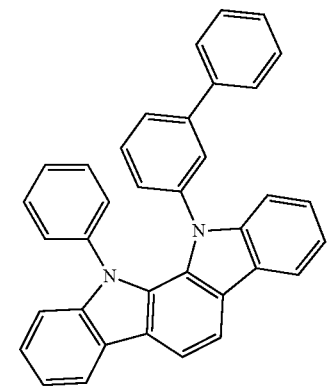

[E-38]
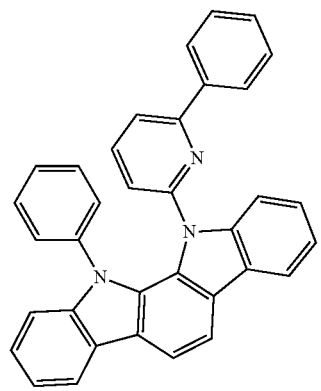

[E-39]
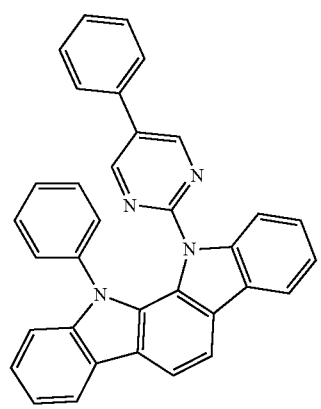

[E-40]
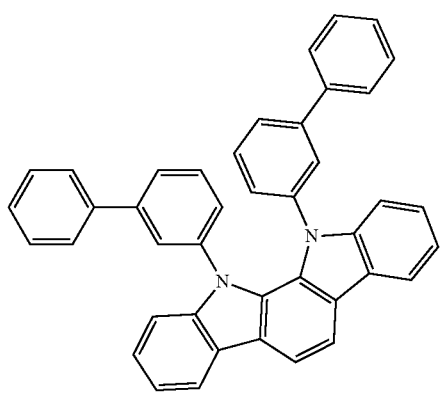

The second compound has bipolar characteristics in which hole characteristics are relatively strong and thus, may increase charge mobility and stability when used along with the first compound in an emission layer and resultantly improve luminous efficiency and life-span characteristics. In addition, the charge mobility may be adjusted by controlling a ratio between the second compound having hole characteristics and the first compound. Since the hole characteristics of the second compound are relatively determined in a relation with the first compound, the second compound may include a substituent having weak electron characteristics such as a substituted or unsubstituted pyridinyl group in one position of $R^7$ to $R^{10}$ and $Ar^1$ in Chemical Formula 2.

In addition, the first compound and the second compound may be, for example included in a weight ratio of about 1:9 to 9:1, and specifically in a weight ratio of 2:8 to 8:2, 3:7 to 7:3, 4:6 to 6:4, and 5:5. Within the ranges, bipolar characteristics are implemented and thereby efficiency and life-span may be simultaneously improved.

An emission layer 32 may further include a third compound in addition to the first compound and the second compound as a host.

The third compound may be represented by Chemical Formula 5.

$X^1$ to $X^{12}$ of Chemical Formula 3 may independently be N, C or $CR^d$, $R^d$ according to an embodiment of the present invention may independently be hydrogen, deuterium, a substituted or unsubstituted C1 to C30 alkyl group, a substituted or unsubstituted C1 to C30 alkenyl group, a substituted or unsubstituted C1 to C30 alkynyl group, a substituted or unsubstituted C6 to C30 aryl group, a substituted or unsubstituted C6 to C30 aryloxy group, a substituted or unsubstituted C6 to C30 arylthio group, a substituted or unsubstituted C2 to C30 heterocyclic group, a hydroxyl group, thiol group, or a combination thereof, as described above.

The $R^d$ may independently be present, and may be specifically hydrogen, deuterium, a substituted or unsubstituted C6 to C30 aryl group, a substituted or unsubstituted C2 to C30 heteroaryl group, or a combination thereof. For example, it may be selected from a substituted or unsubstituted phenyl group, or a substituted or unsubstituted biphenyl group, a substituted or unsubstituted terphenyl group, a substituted or unsubstituted pyridyl group, or a combination thereof, but is not limited thereto.

In addition, the adjacent $R^d$'s are linked to each other to form a ring, for example, a substituted or unsubstituted benzofuranpyrimidine, a substituted or unsubstituted benzothiophenepyrimidine, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted phthalazinyl group, or a substituted or unsubstituted phenanthrolinyl group, but is not limited thereto.

The Chemical Formula 5 may be, for example represented by one of Chemical Formulae 5-I to 5-III.

[Chemical Formula 5-I]
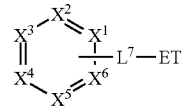

[Chemical Formula 5-II]
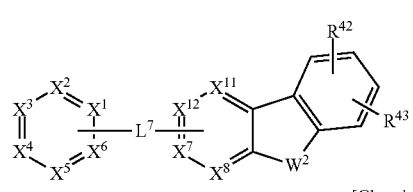

[Chemical Formula 5-III]
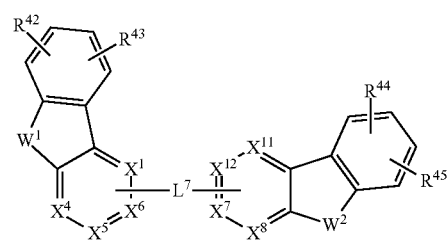

In Chemical Formulae 5-I to 5-III, $X^1$ to $X^8$, $X^{11}$, $X^{12}$, and $L^7$ are the same as above, at least one of $X^1$, $X^4$, $X^5$, and $X^6$ is N, and at least one of $X^7$, $X^8$, $X^{11}$, and $X^{12}$ is N, $W^1$ and $W^2$ are independently O or S, $R^{42}$ to $R^{45}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, ET is a substituted or unsubstituted pyridinyl group, a substituted or unsubstituted pyrimidinyl group, a substituted or unsubstituted triazinyl group, a substituted or unsubstituted pyrazinyl group, a substituted or unsubstituted quinoxalinyl group, a substituted or unsubstituted quinazolinyl group, a substituted or unsubstituted phenanthrolinyl group, or a combination thereof, and wherein, "substituted" is the same as defined above. Specifically, Chemical Formula 5-I may be, for example represented by one of Chemical Formulae 5-I-a to 5-I-g.

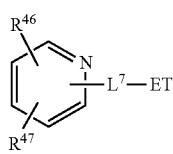

[Chemical Formula 5-I-a]

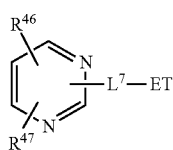

[Chemical Formula 5-I-b]

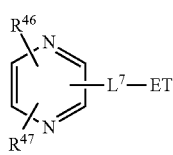

[Chemical Formula 5-I-c]

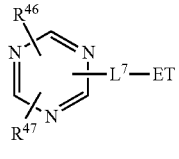

[Chemical Formula 5-I-d]

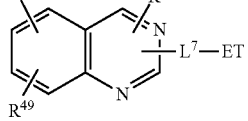

[Chemical Formula 5-I-e]

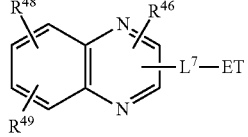

[Chemical Formula 5-I-f]

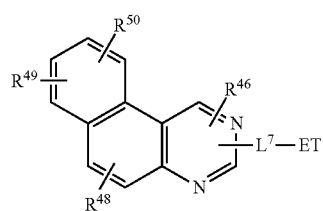

[Chemical Formula 5-I-g]

In Chemical Formulae 5-I-a to 5-I-g, L7 and ET are the same as above, $R^{46}$ to $R^{50}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof. Specifically, Chemical Formula 5-II may be, for example represented by one of Chemical Formulae 5-II-a to 5-II-n.

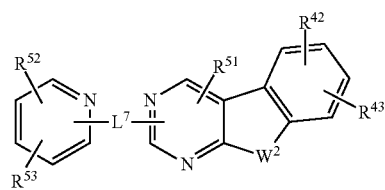

[Chemical Formula 5-II-a]

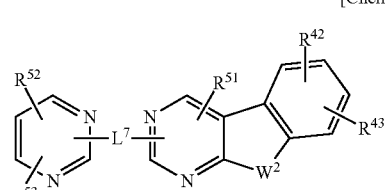

[Chemical Formula 5-II-b]

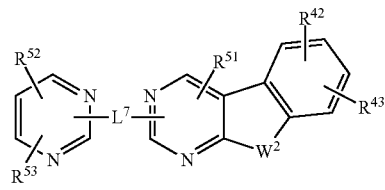

[Chemical Formula 5-II-c]

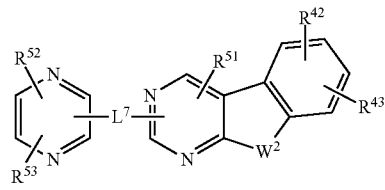

[Chemical Formula 5-II-d]

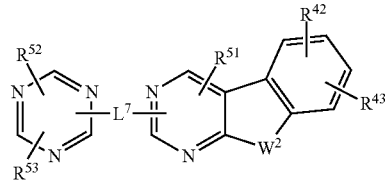

[Chemical Formula 5-II-e]

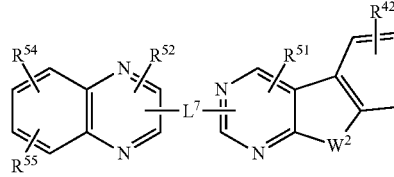

[Chemical Formula 5-II-f]

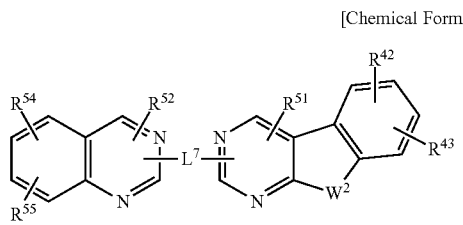

[Chemical Formula 5-II-g]

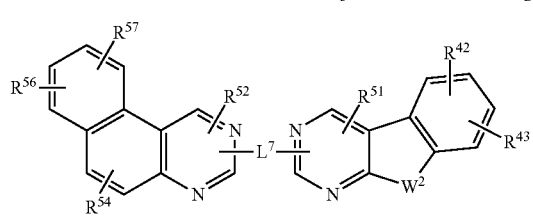

[Chemical Formula 5-II-h]

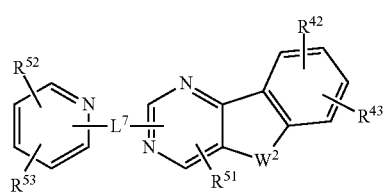

[Chemical Formula 5-II-i]

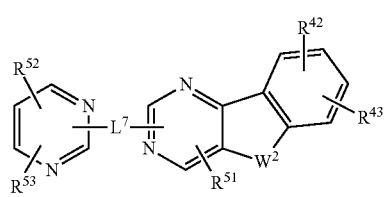

[Chemical Formula 5-II-j]

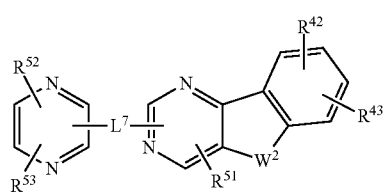

[Chemical Formula 5-II-k]

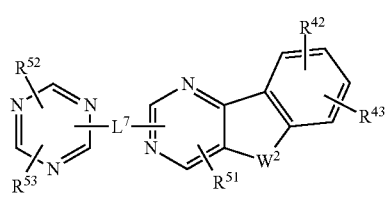

[Chemical Formula 5-II-l]

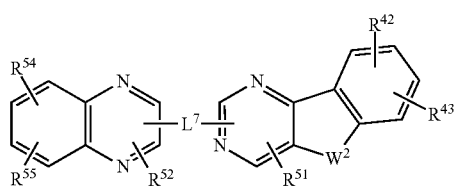

[Chemical Formula 5-II-m]

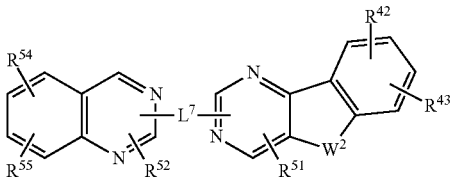

[Chemical Formula 5-II-n]

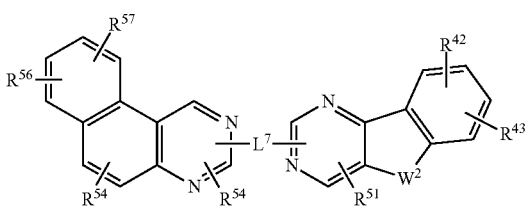

In Chemical Formulae 5-II-a to 5-II-n, $L^7$ and $W^2$, and $R^{42}$ and $R^{43}$ are the same as above, and $R^{51}$ to $R^{57}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof. Specifically, Chemical Formula 5-III may be, for example represented by one of Chemical Formulae 5-III-a to 5-III-c.

[Chemical Formula 5-III-a]

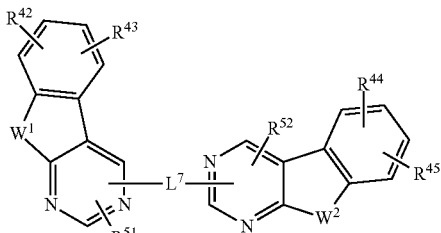

[Chemical Formula 5-III-b]

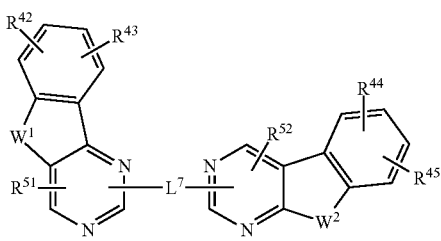

[Chemical Formula 5-III-c]

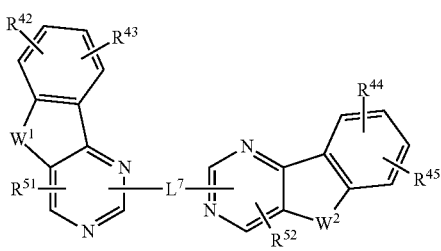

In Chemical Formulae 5-III-a to 5-III-c, $W^1$ and $W^2$, $R^{42}$ to $R^{45}$, $R^{51}$, $R^{52}$, and $L^7$ are the same as described above. In an embodiment of the present invention, $L^7$ may be, for example selected from substituted or unsubstituted groups of Group 2. The third compound represented by Chemical Formula 5 may be, for example, compounds of Groups F to H but is not limited thereto. [Group F] (in compound structure of Group F, heteroatoms are "N")
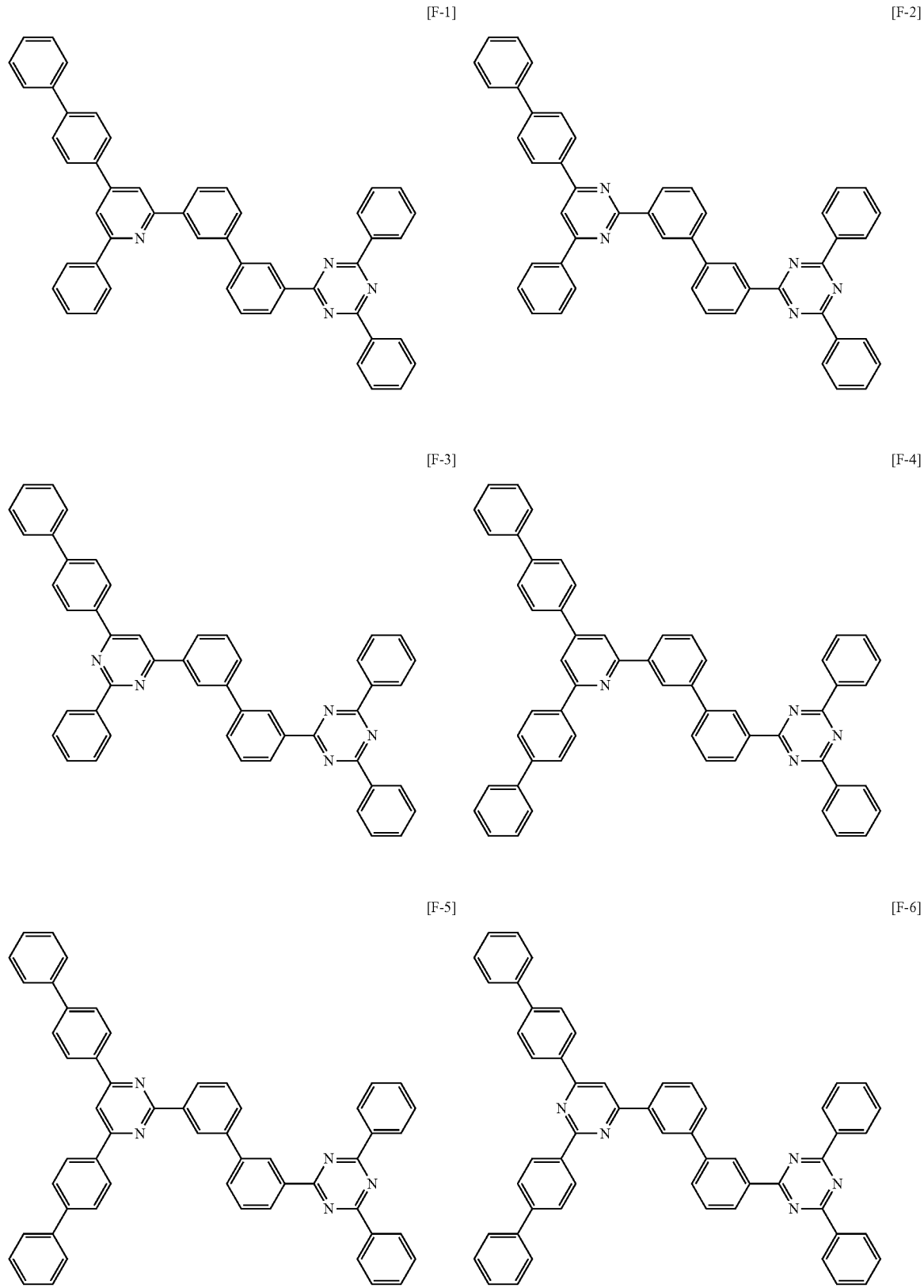

[F-7]
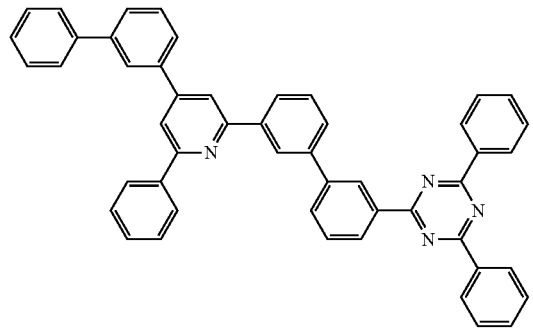
[F-8]
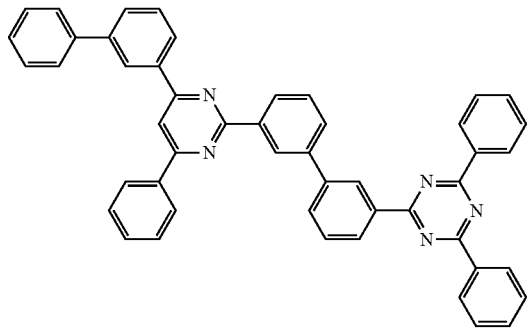
[F-9]
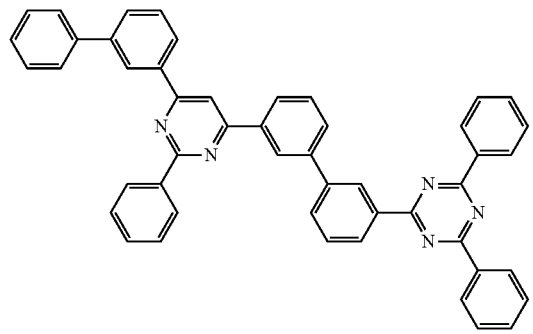
[F-10]
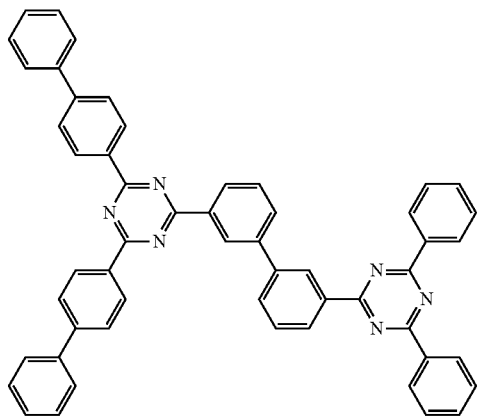
[F-11]
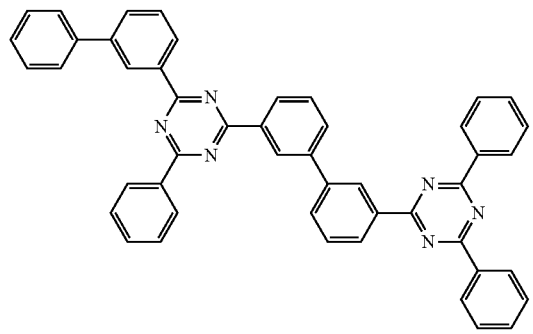
[F-12]
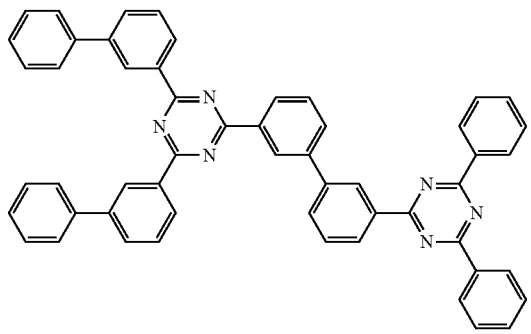
[F-13]
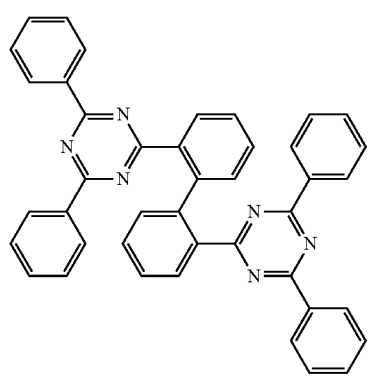
[F-14]
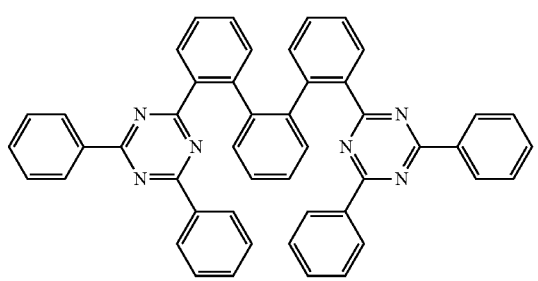

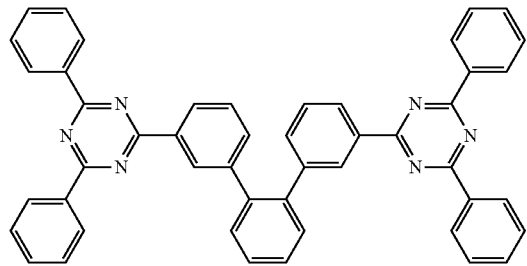
[F-15]
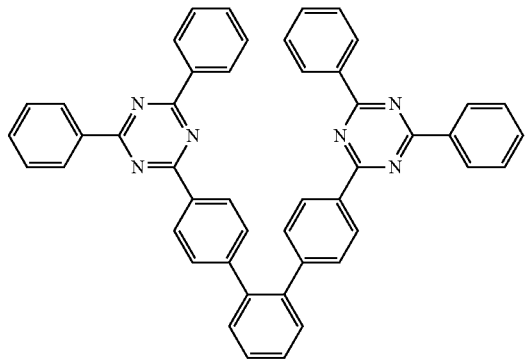
[F-16]
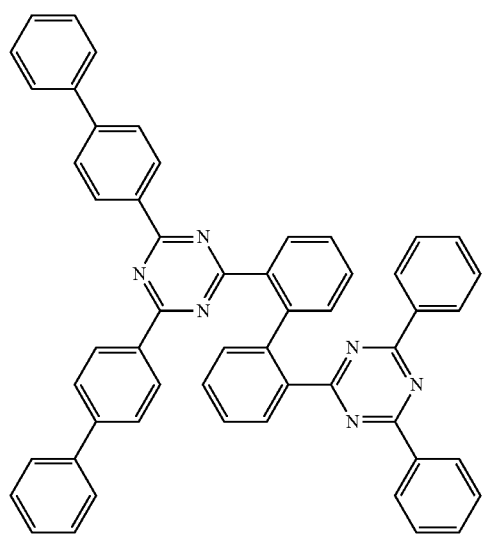
[F-17]
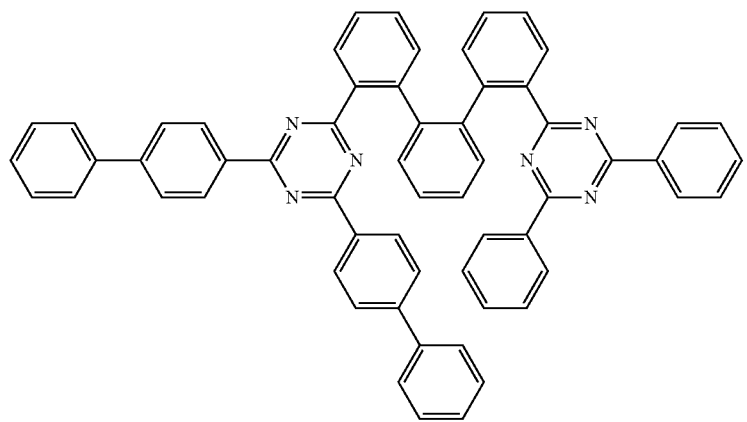
[F-18]

[F-19]
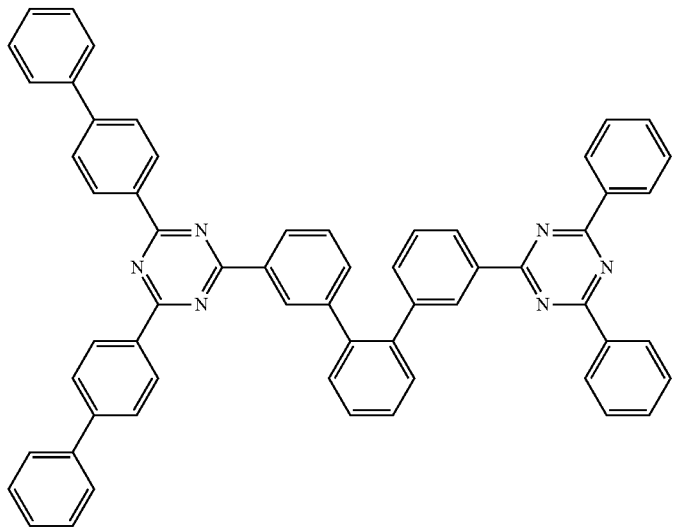
[F-20]
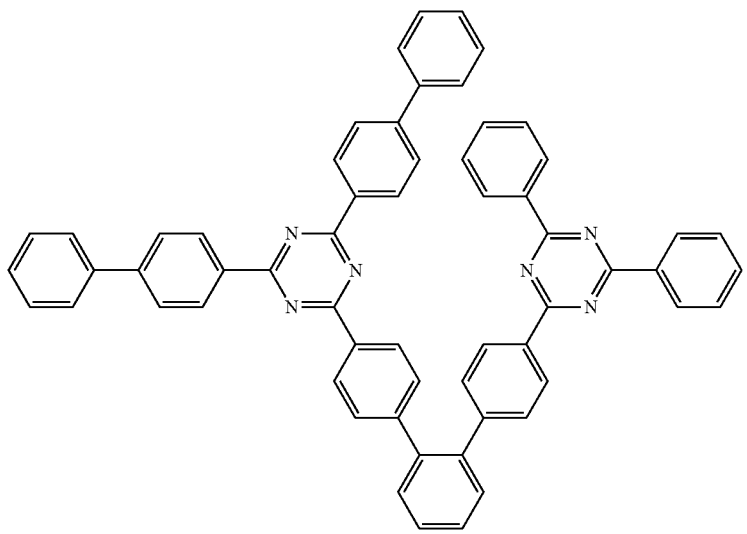
[Group G] (in compound structure of Group G, hetero atoms of 6-membered ring compound are "N" and hetero atoms of 5-membered ring are "O" or "S")
[G-1]
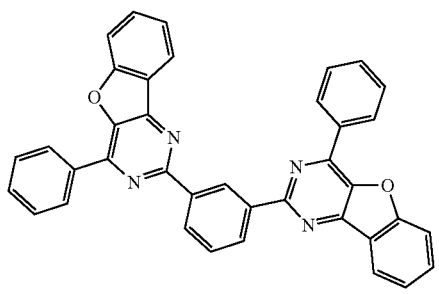
[G-2]
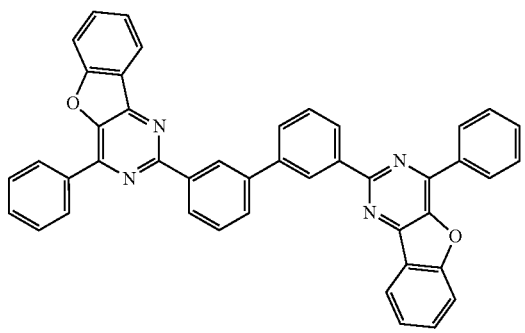

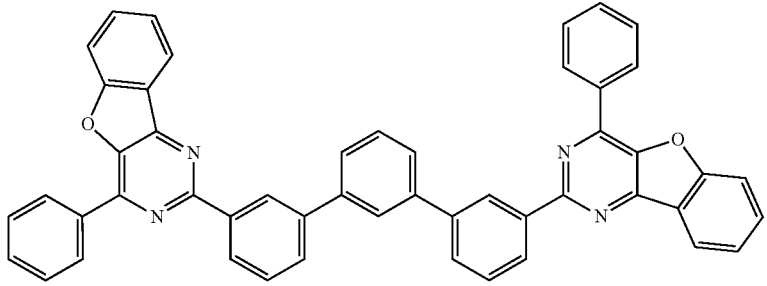
[G-3]
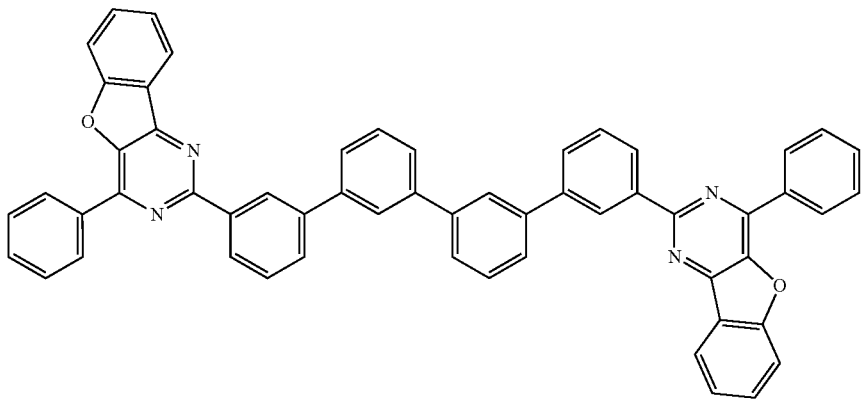
[G-4]
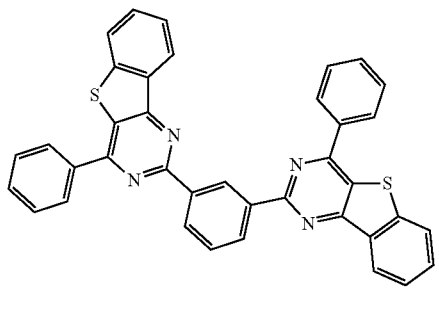
[G-5]
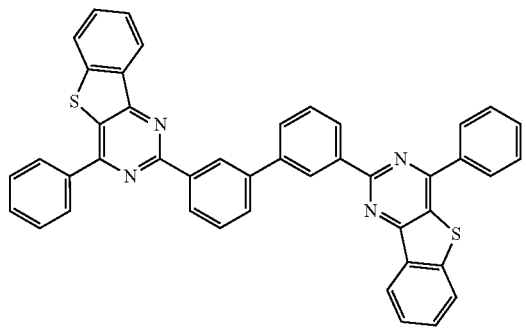
[G-6]
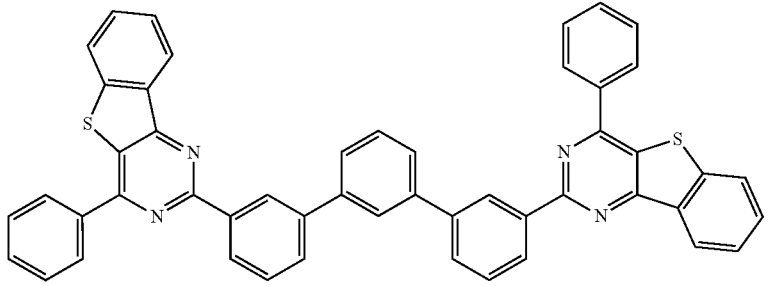
[G-7]

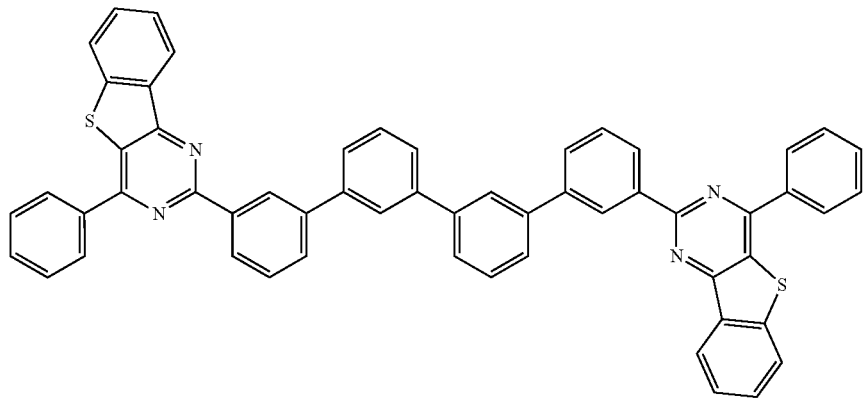
[G-8]
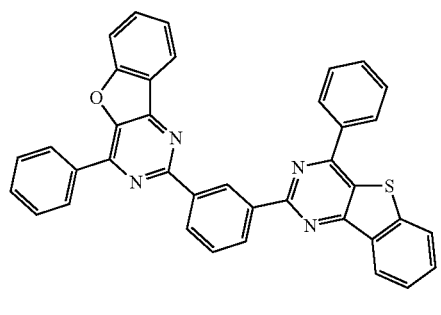
[G-9]
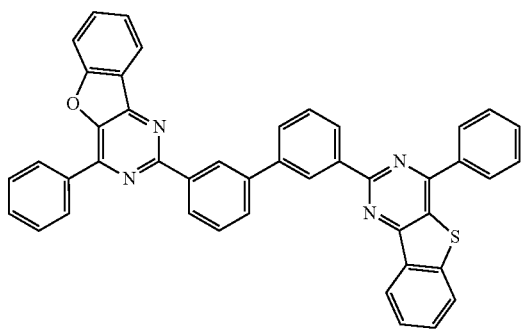
[G-10]
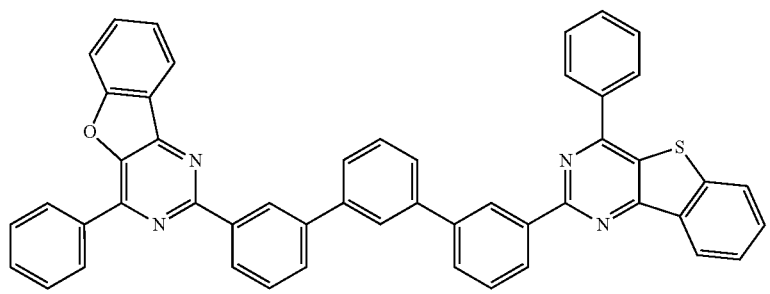
[G-11]
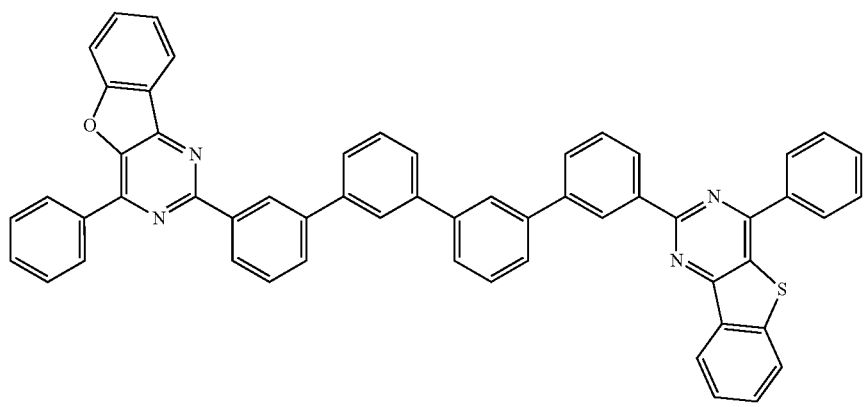
[G-12]

-continued
[G-13]
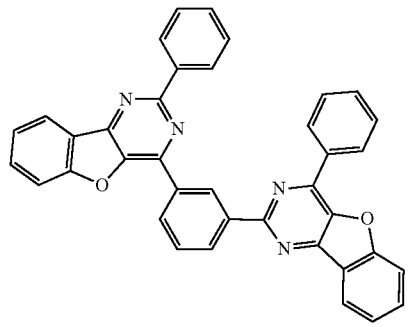
[G-14]
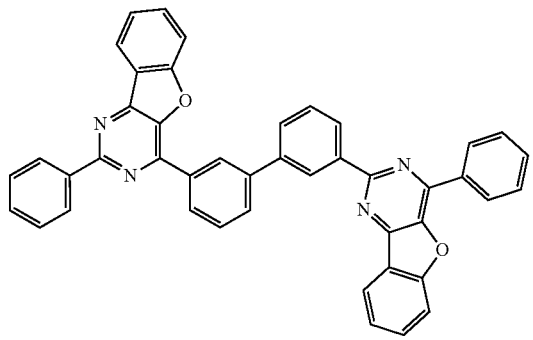
[G-15]
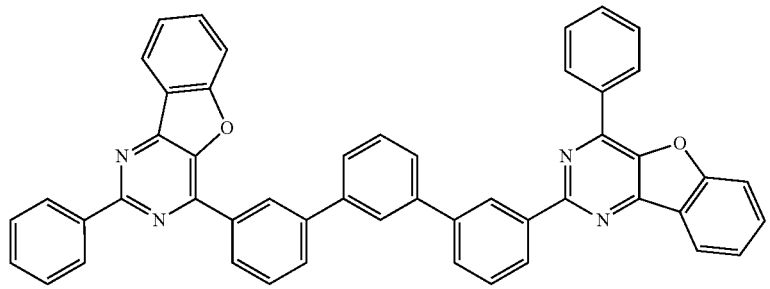
[G-16]
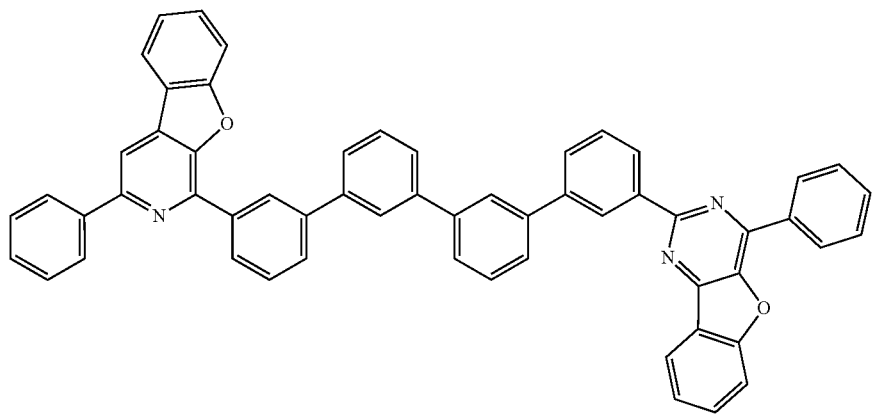
[G-17]
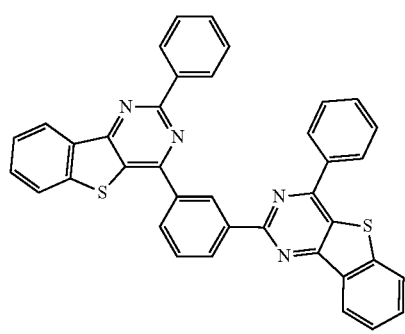
[G-18]
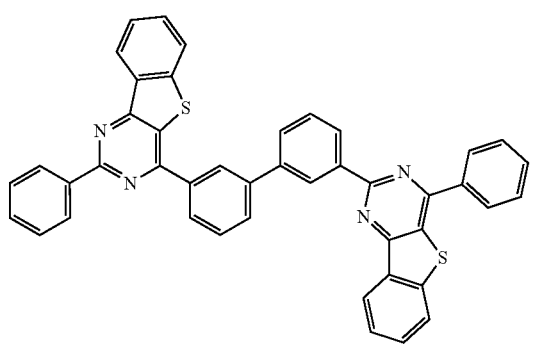

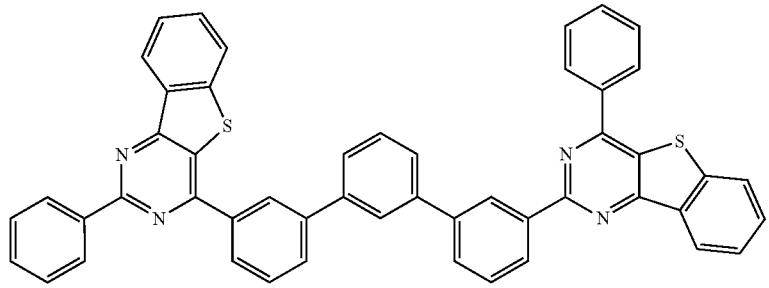
[G-19]
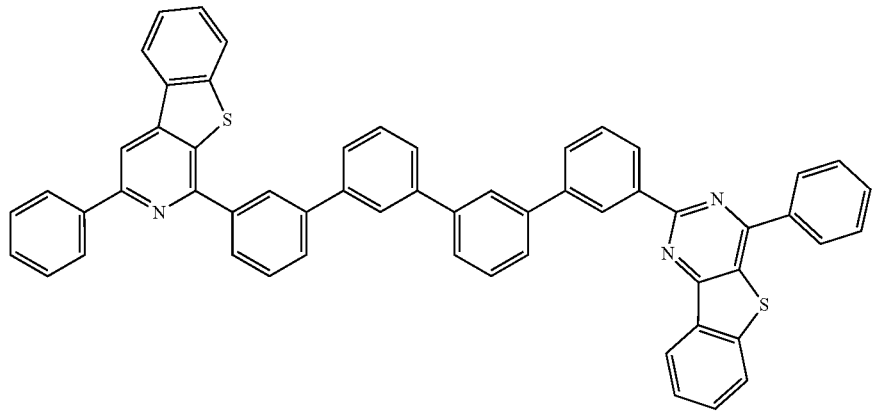
[G-20]
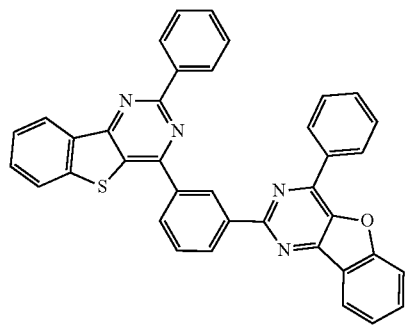
[G-21]
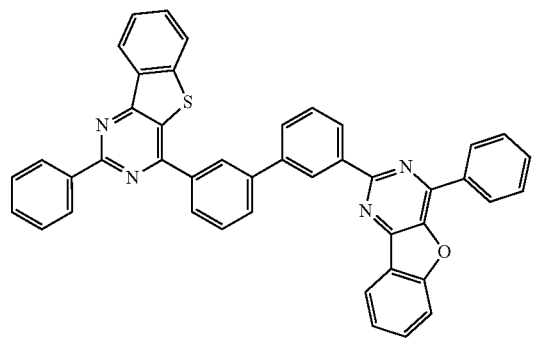
[G-22]
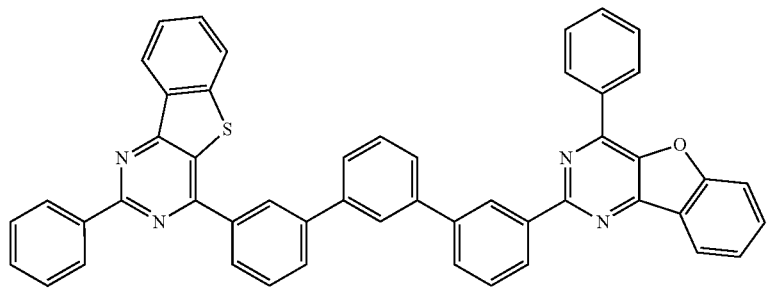
[G-23]

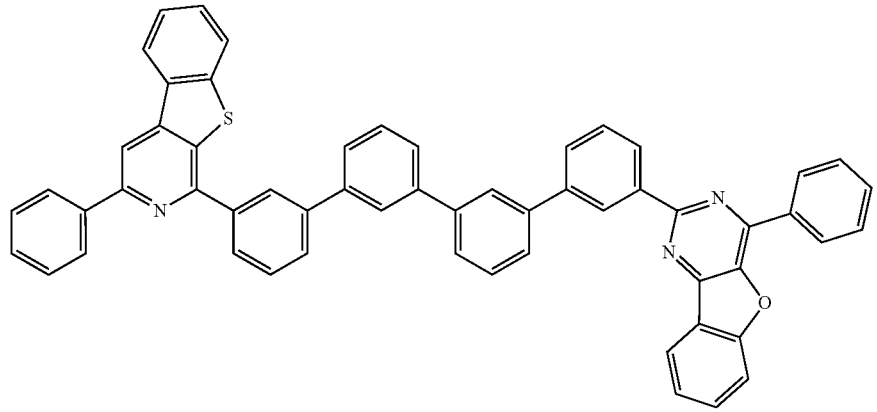
[G-24]
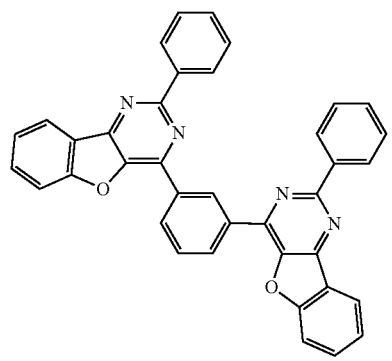
[G-25]
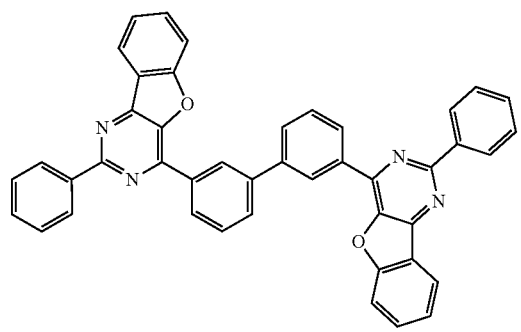
[G-26]
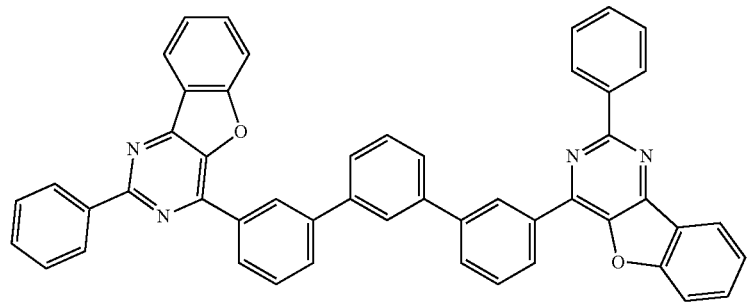
[G-27]
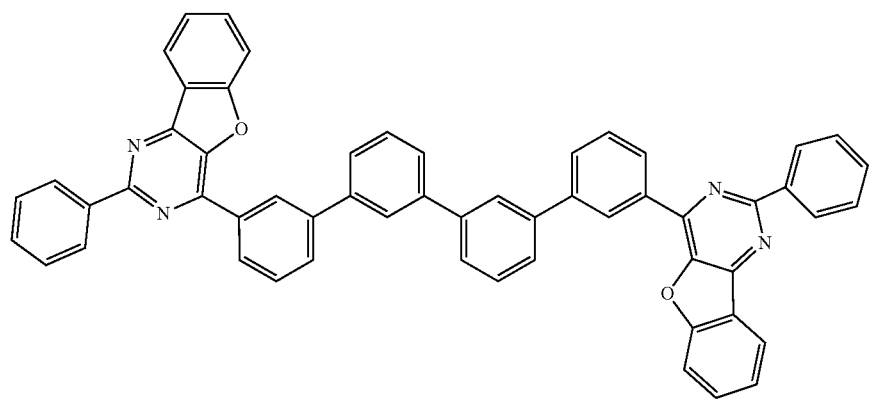
[G-28]

[G-29]
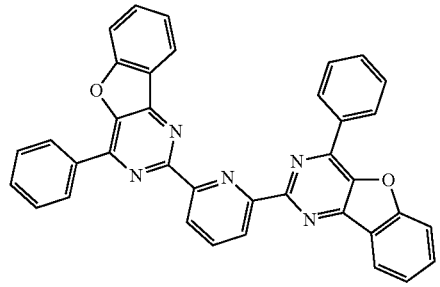
[G-30]
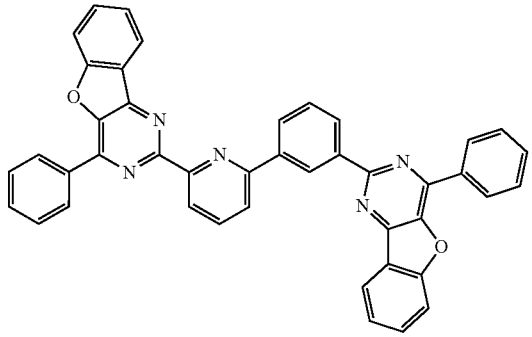
[G-31]
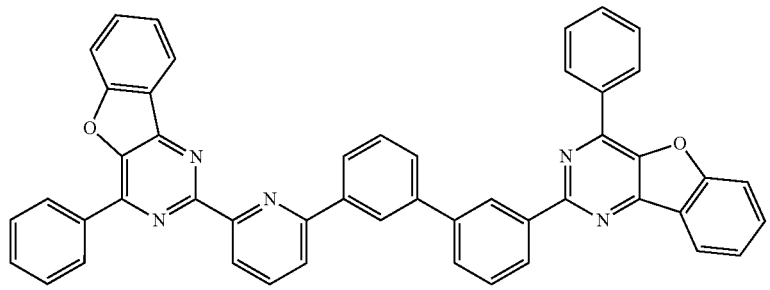
[G-32]
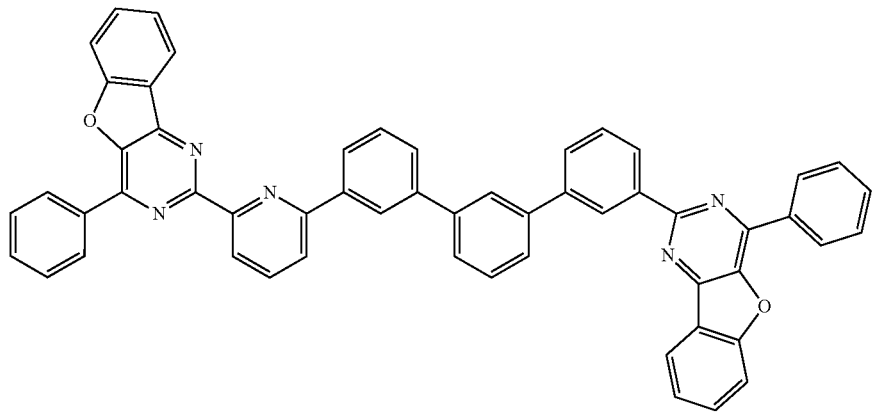
[G-33]
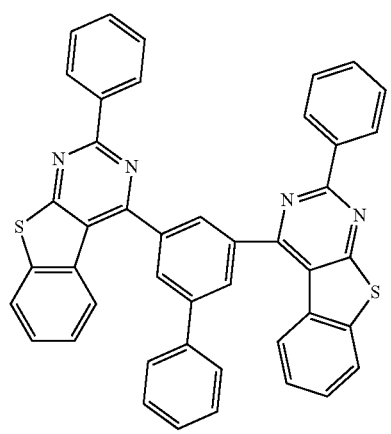
[G-34]
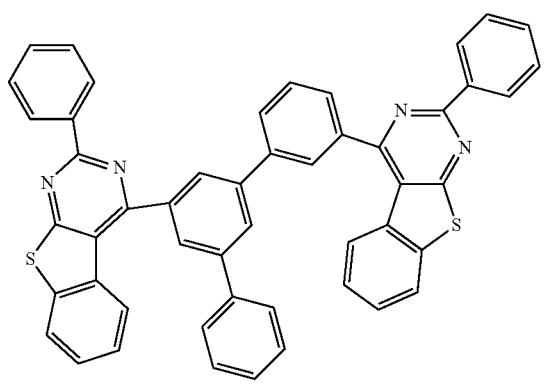

[G-35]
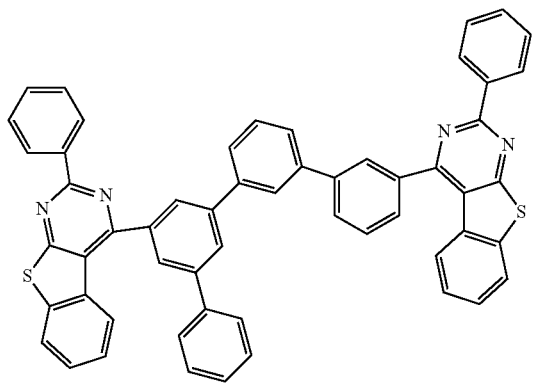
[G-36]
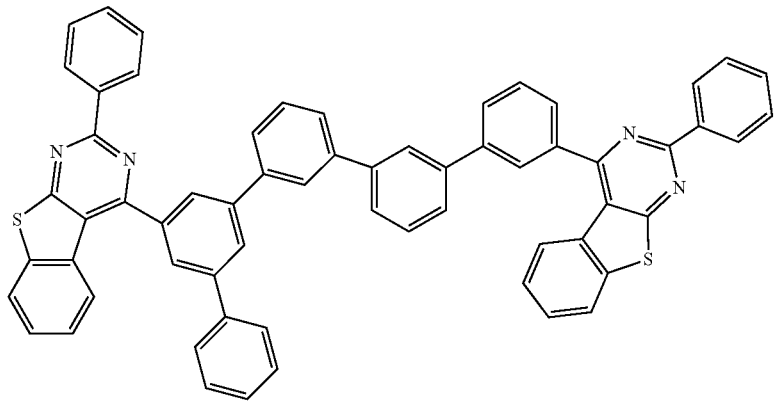
[Group H] (in compound structure of Group H, hetero atoms of 6-membered ring compound are "N" and hetero atoms of 5-membered ring are "O" or "S")
[H-1]
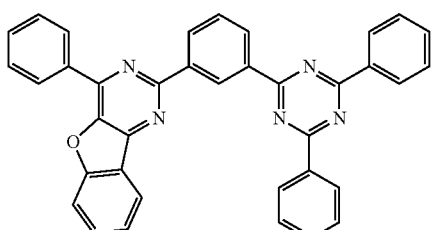
[H-2]
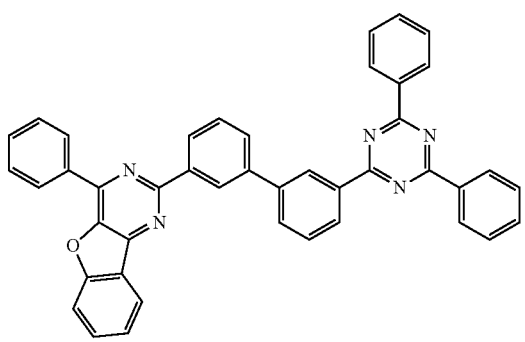
[H-3]
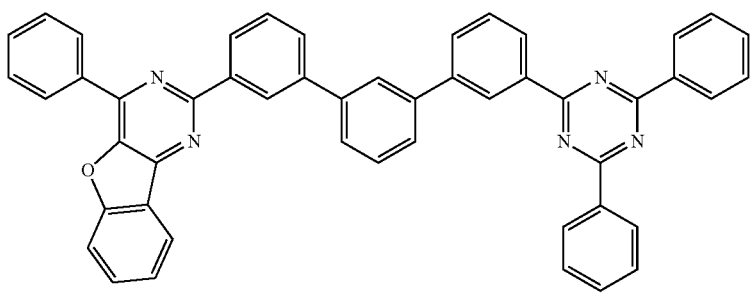

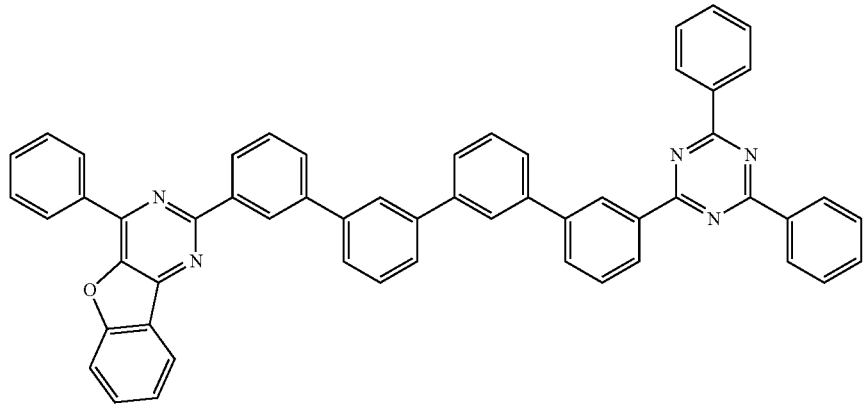
[H-4]
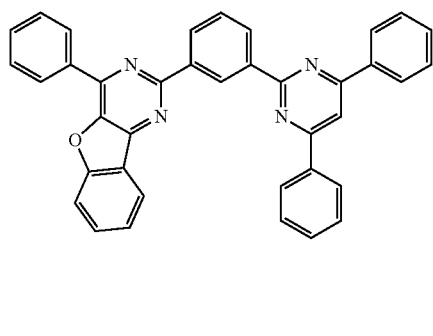
[H-5]
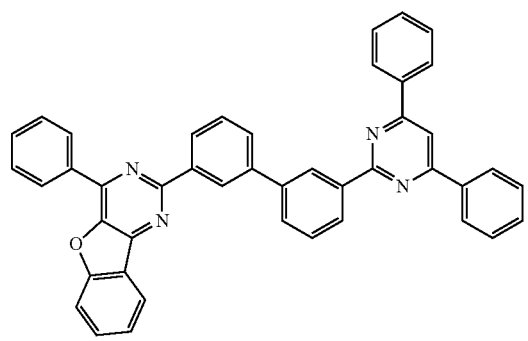
[H-6]
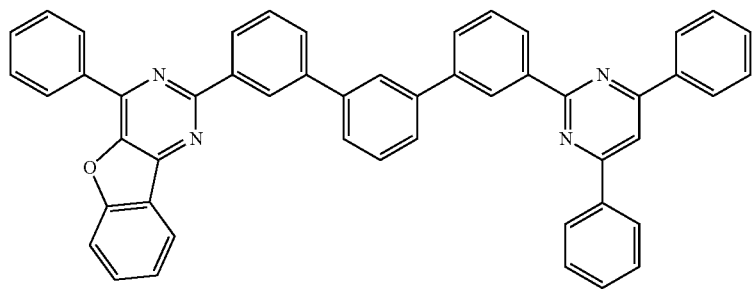
[H-7]
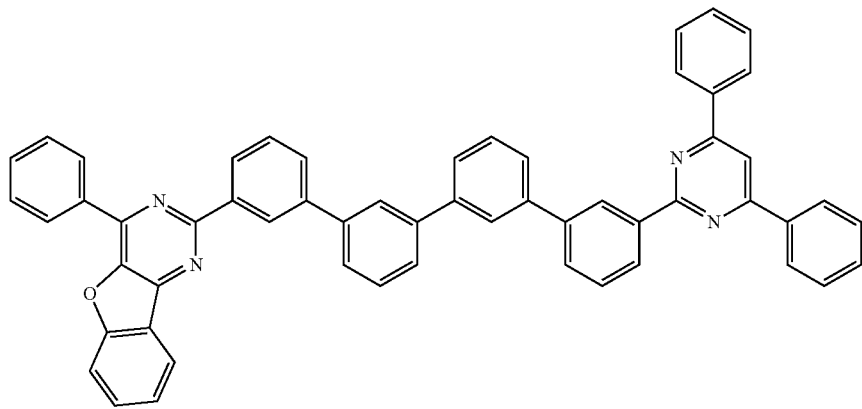
[H-8]

[H-9]
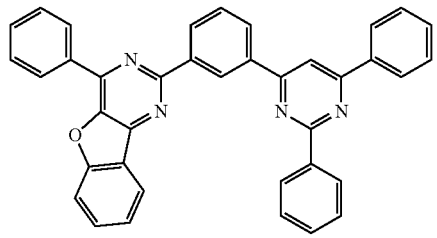
[H-10]
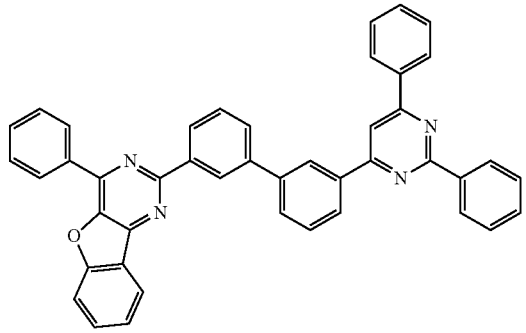
[H-11]
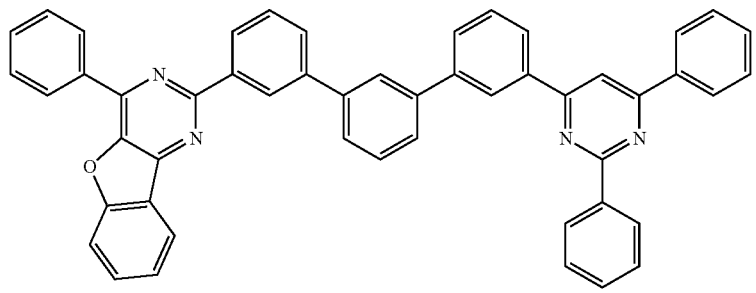
[H-12]
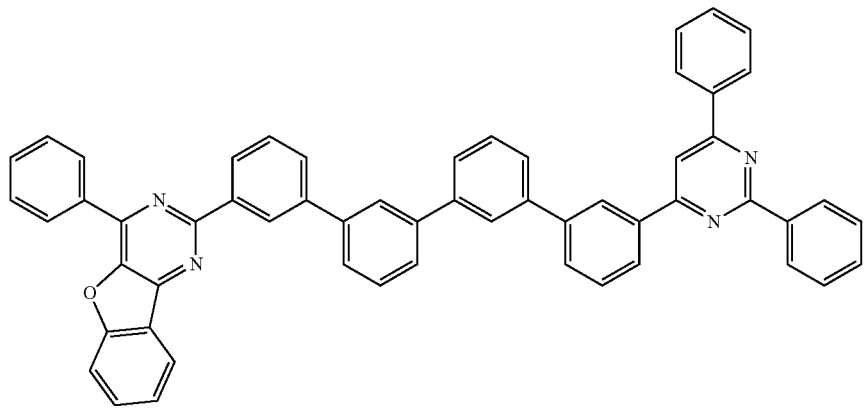
[H-13]
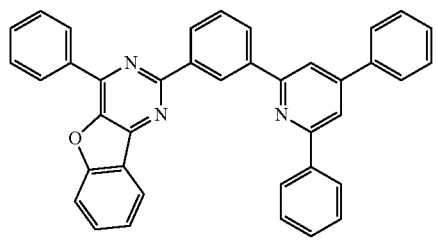
[H-14]
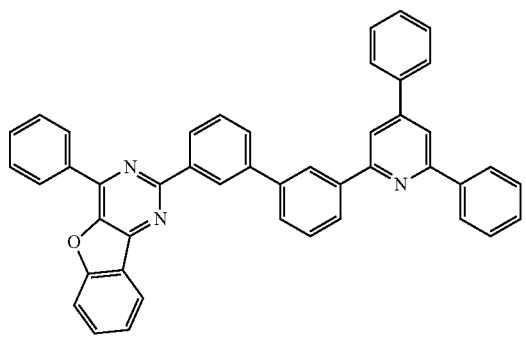

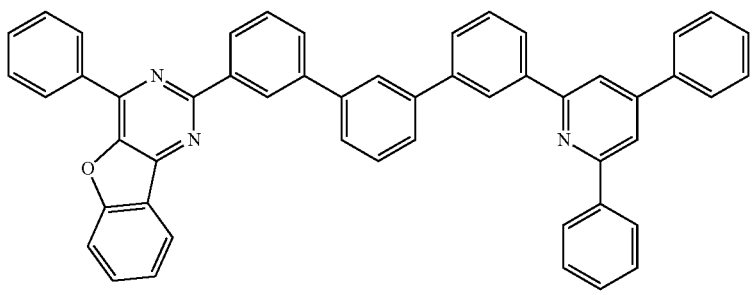
[H-15]
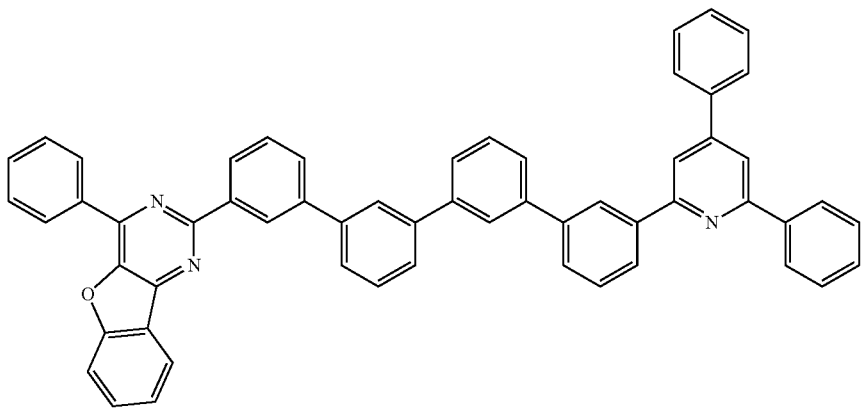
[H-16]
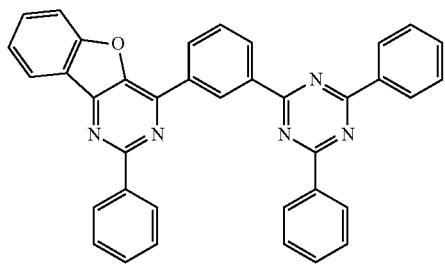
[H-17]
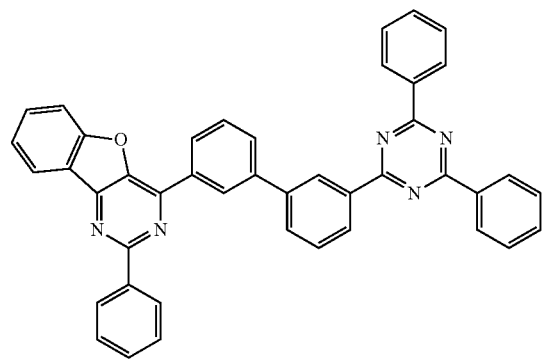
[H-18]
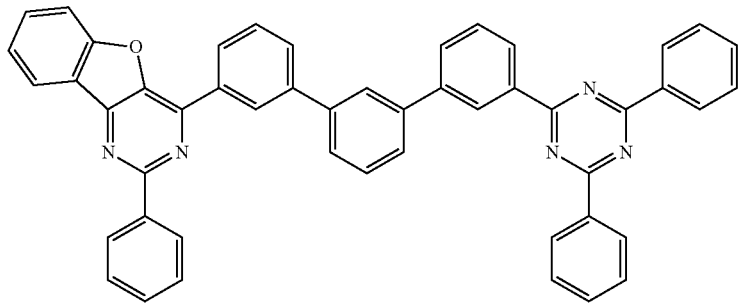
[H-19]

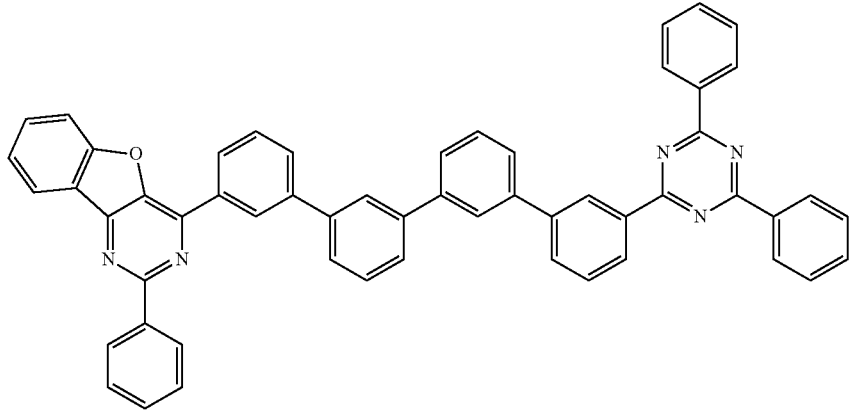
[H-20]
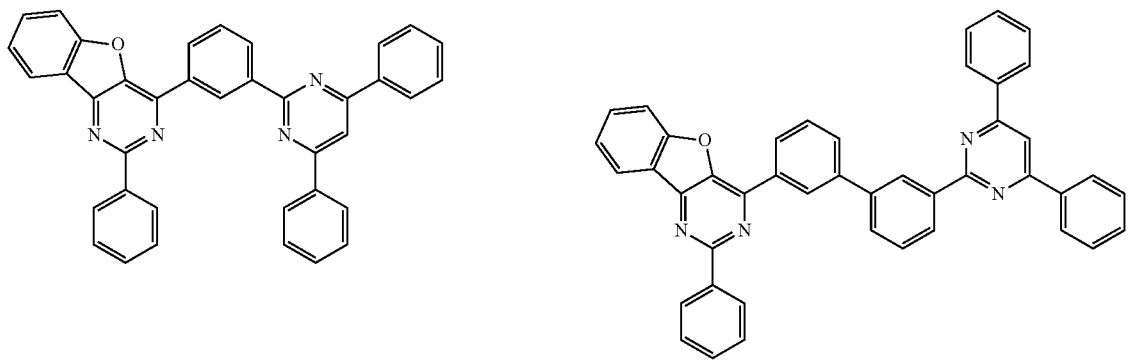
[H-21]
[H-22]
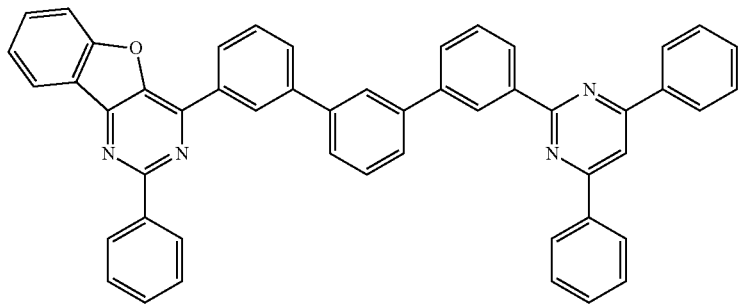
[H-23]
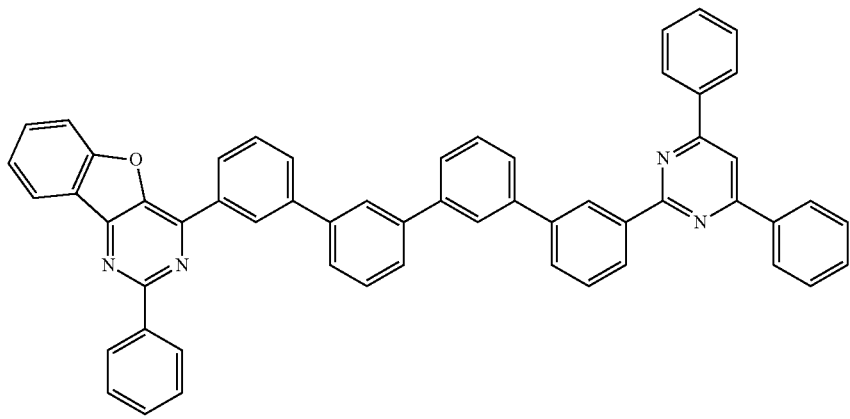
[H-24]

[H-25]
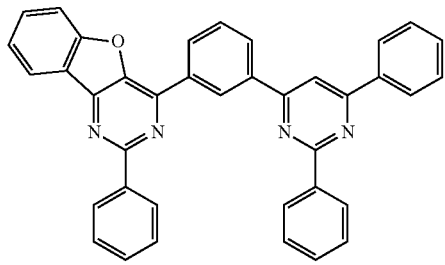
[H-26]
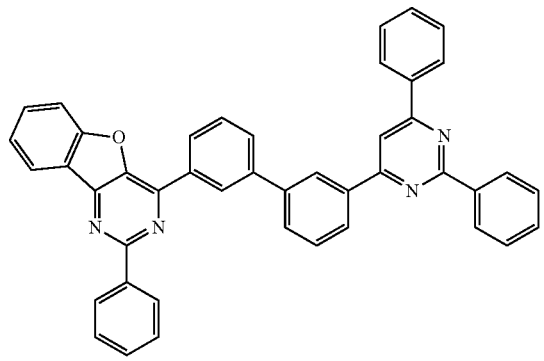
[H-27]
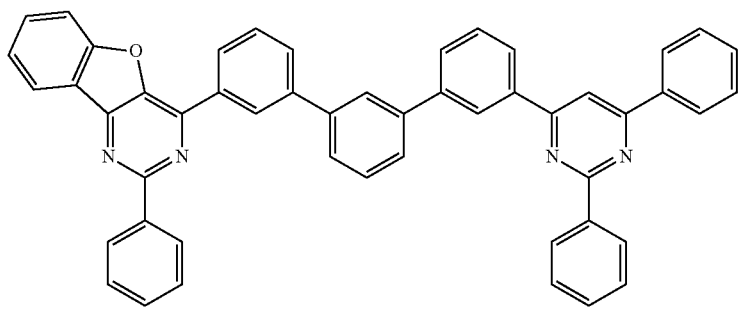
[H-28]
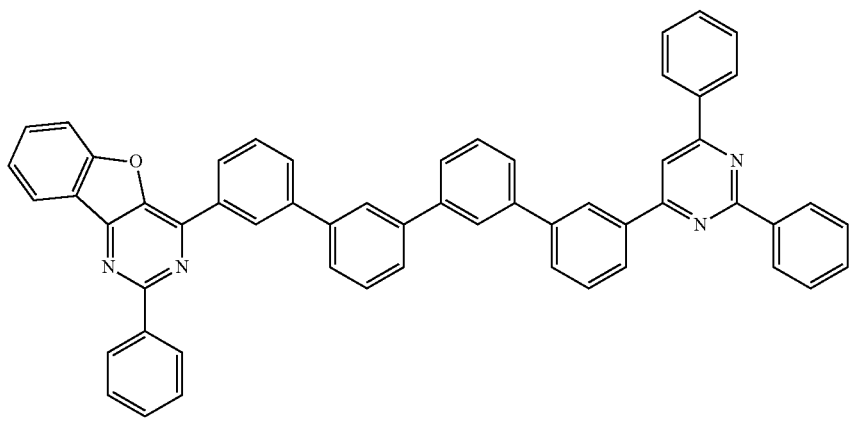
[H-29]
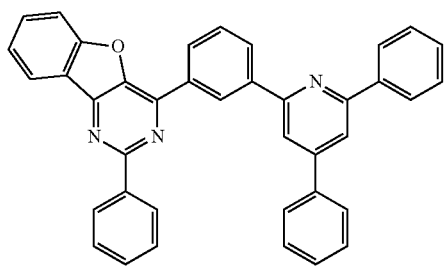
[H-30]
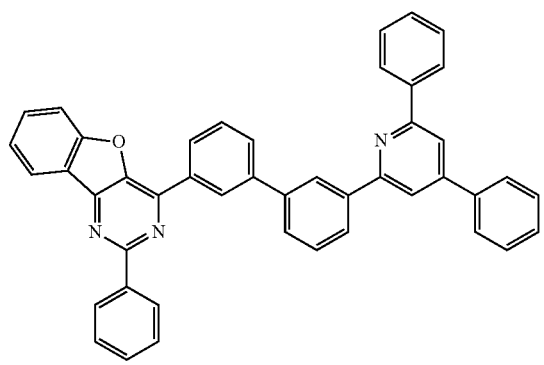

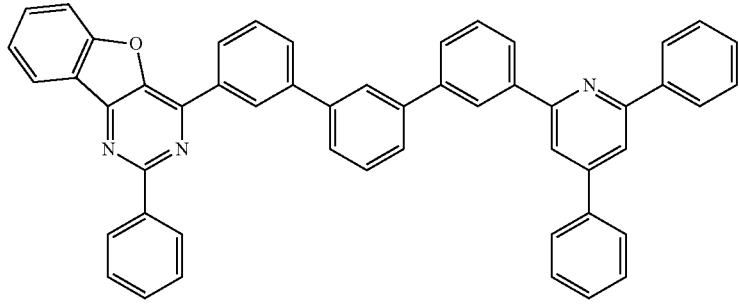
[H-31]
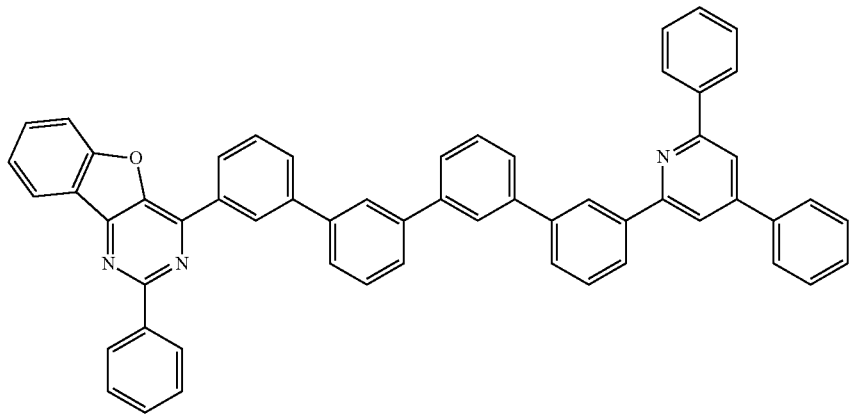
[H-32]
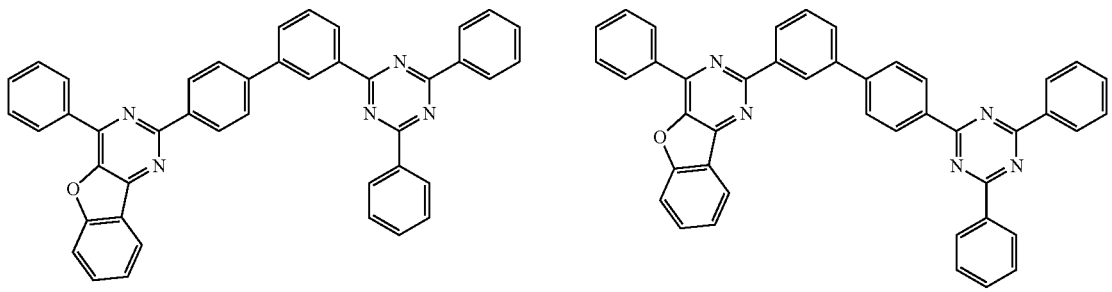
[H-33]  [H-34]
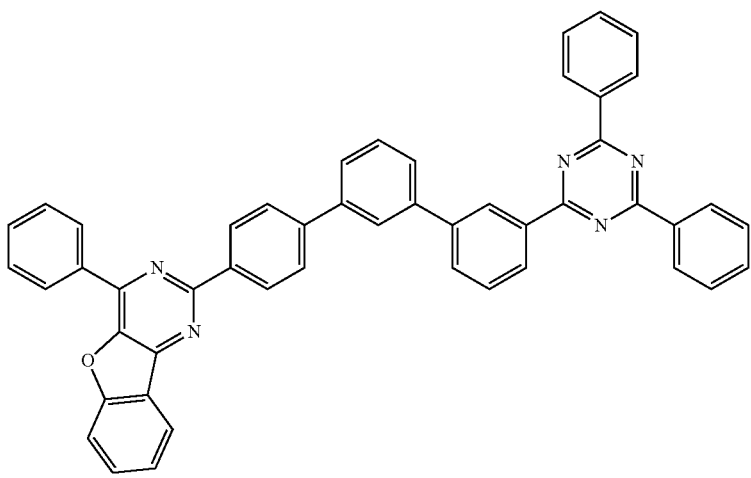
[H-35]

-continued
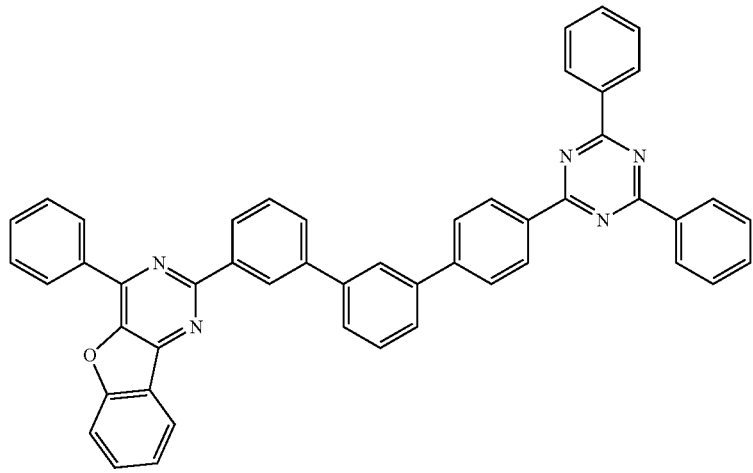
[H-36]
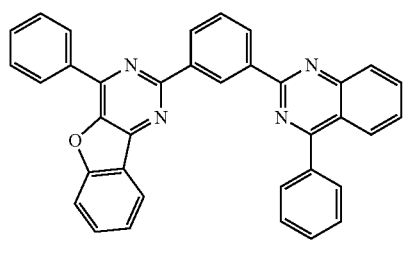
[H-37]
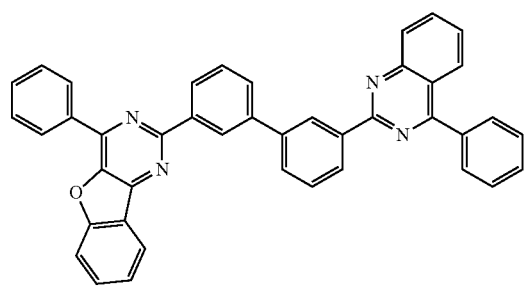
[H-38]
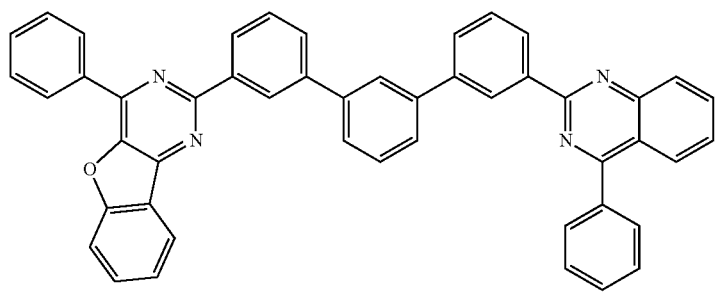
[H-39]
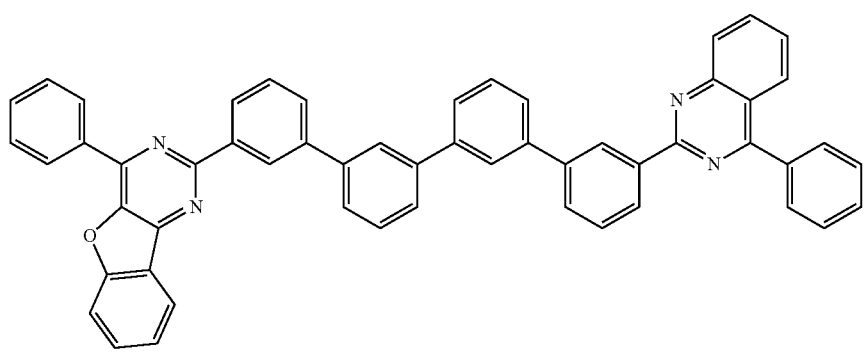
[H-40]

-continued
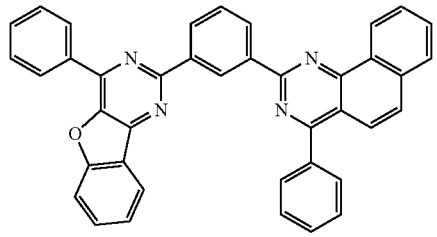
[H-41]
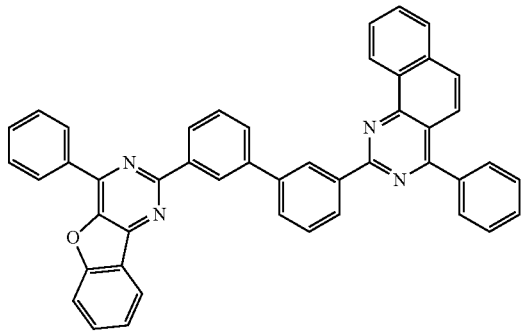
[H-42]
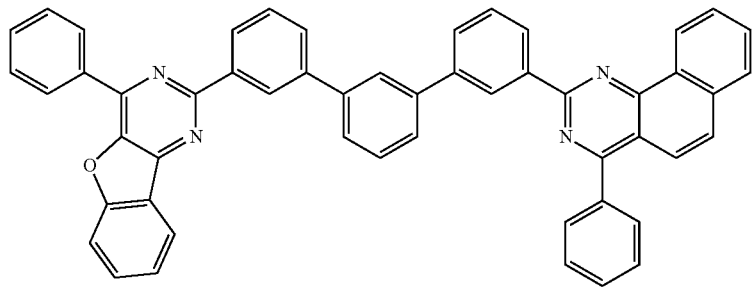
[H-43]
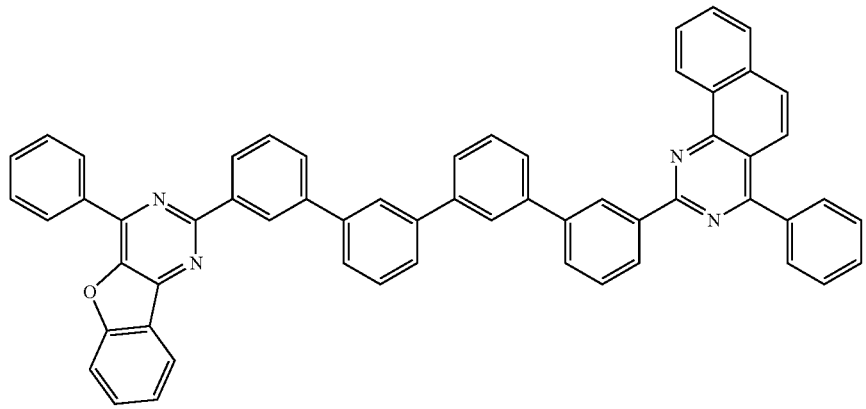
[H-44]
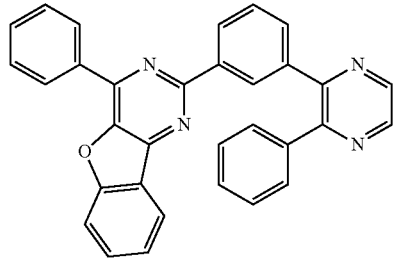
[H-45]
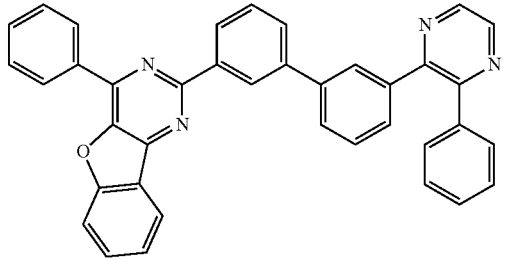
[H-46]
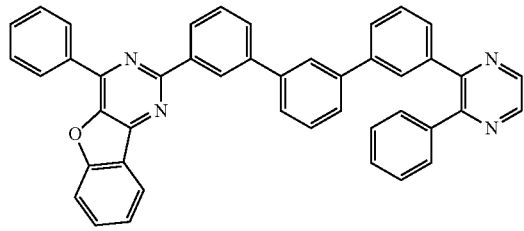
[H-47]

-continued
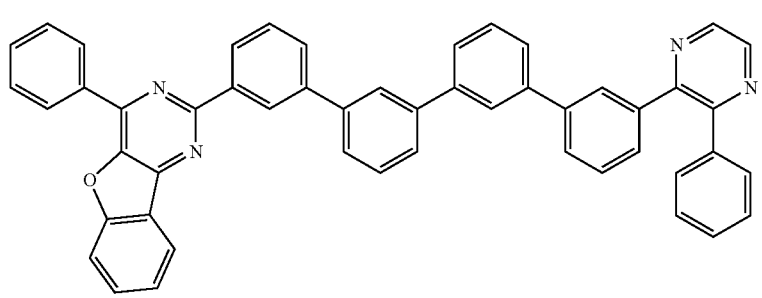
[H-48]
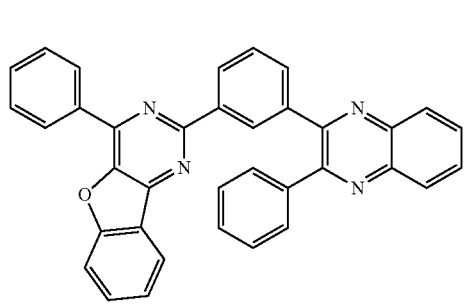
[H-49]
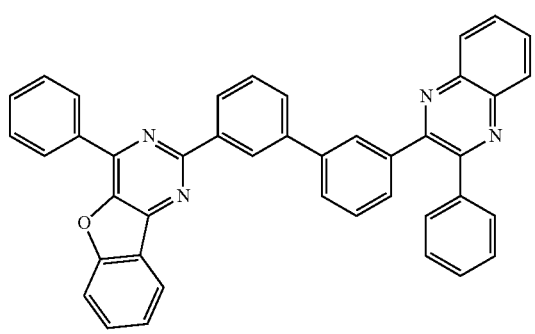
[H-50]
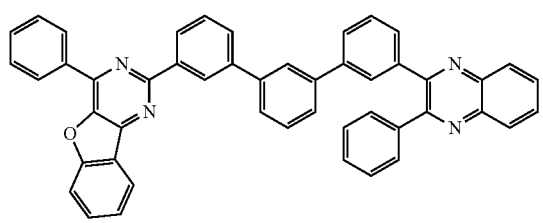
[H-51]
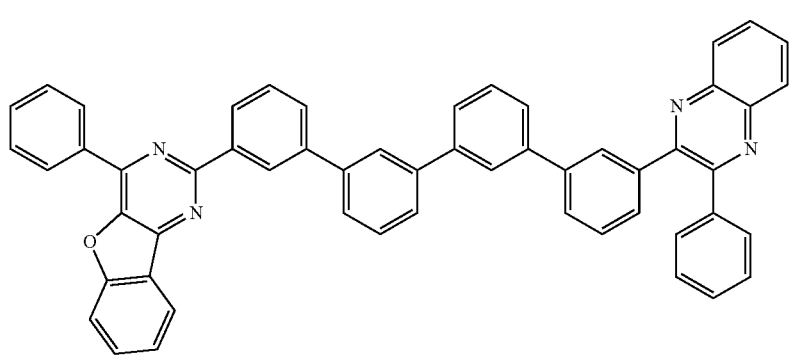
[H-52]

[H-53]
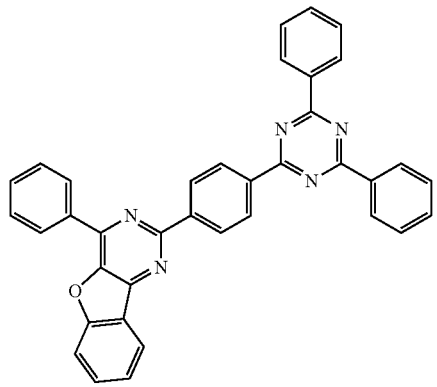
[H-54]
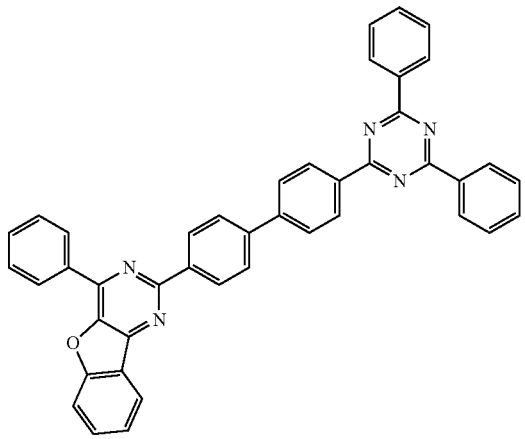
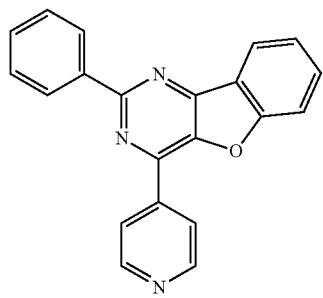
[H-55]
[H-56]
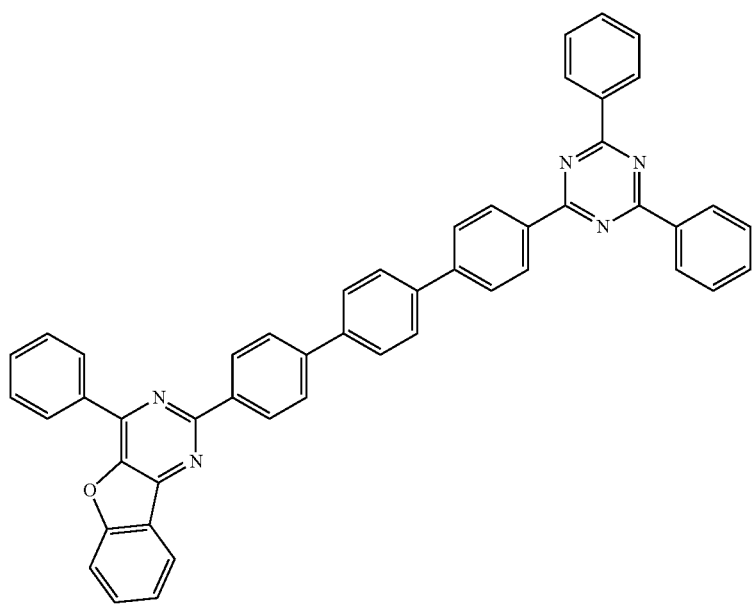

-continued
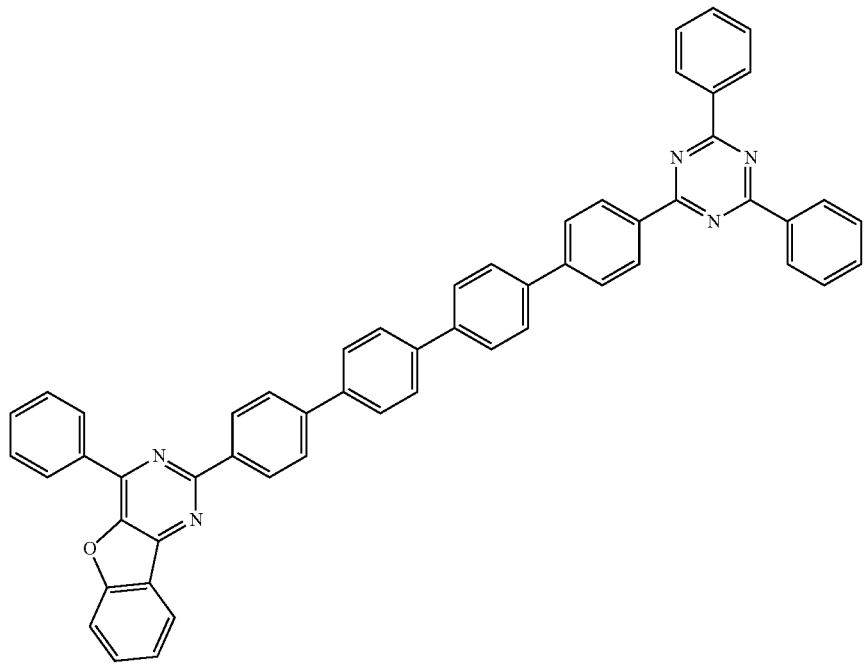
[H-57]
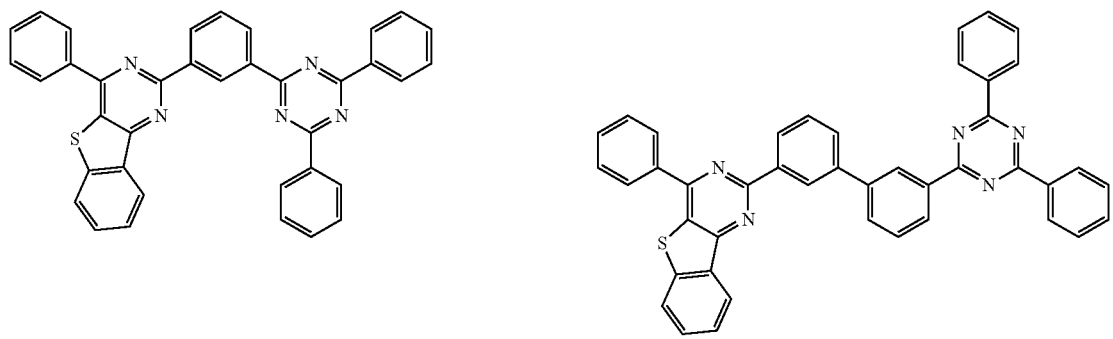
[H-58]  [H-59]
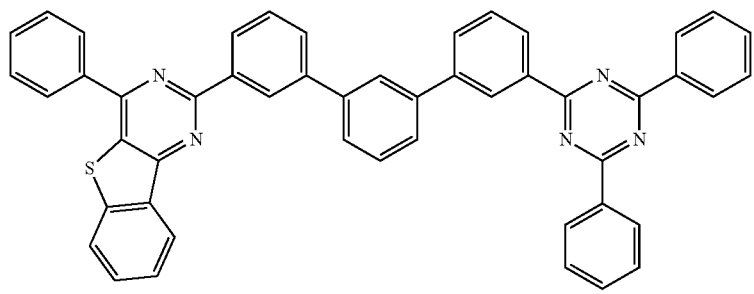
[H-60]

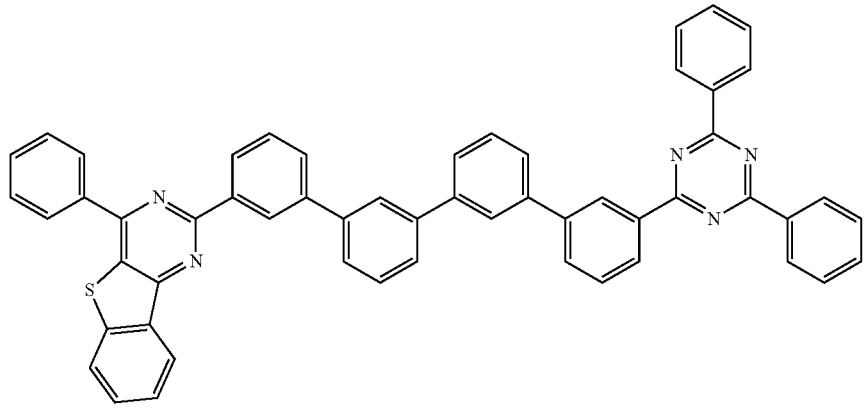
[H-61]
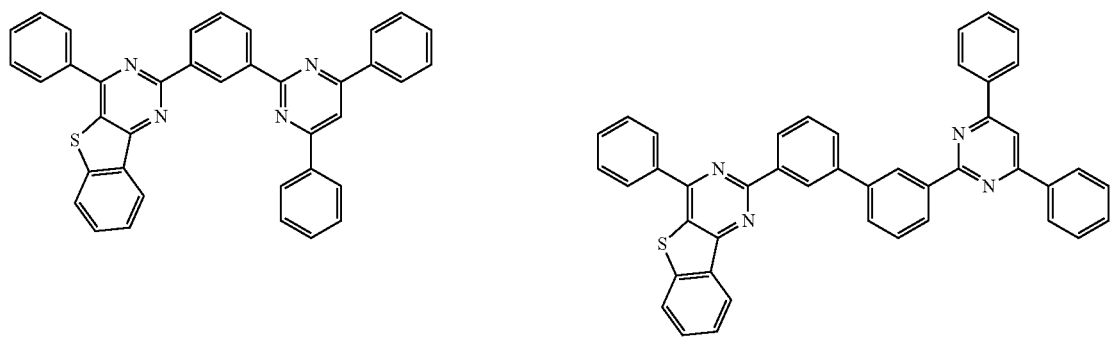
[H-62]
[H-63]
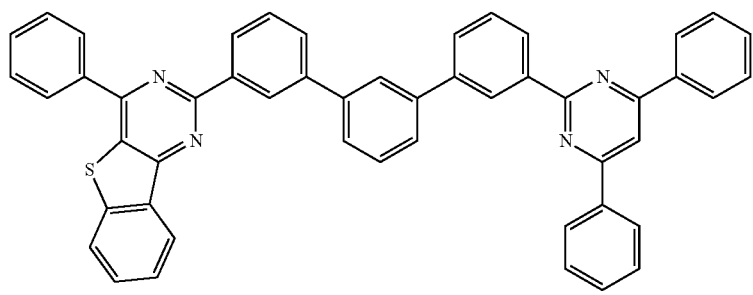
[H-64]
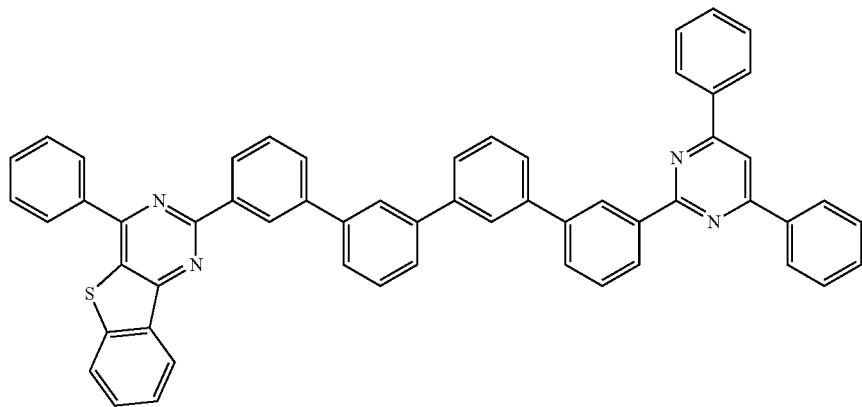
[H-65]

[H-66]
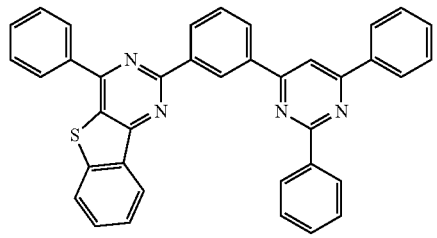
[H-67]
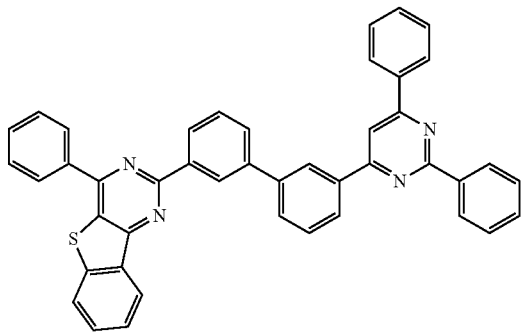
[H-68]
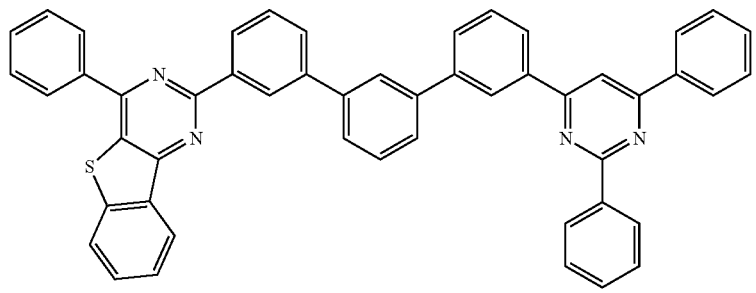
[H-69]
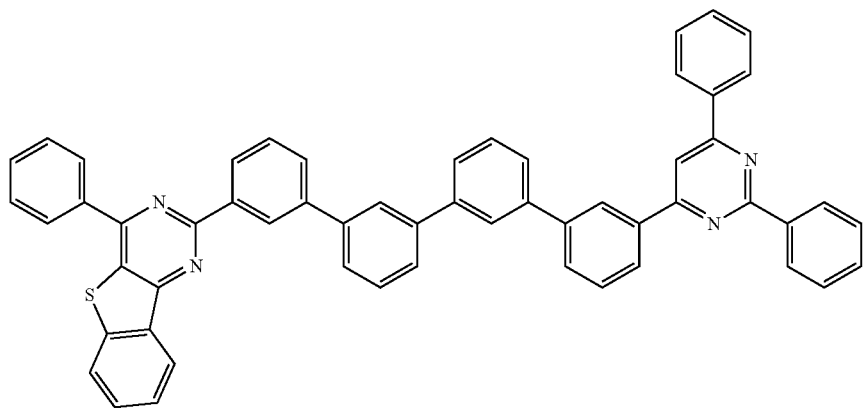
[H-70]
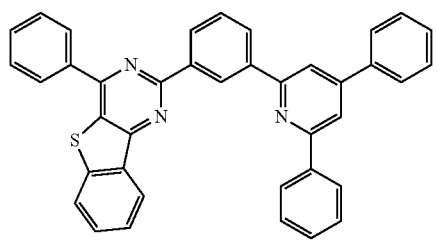
[H-71]
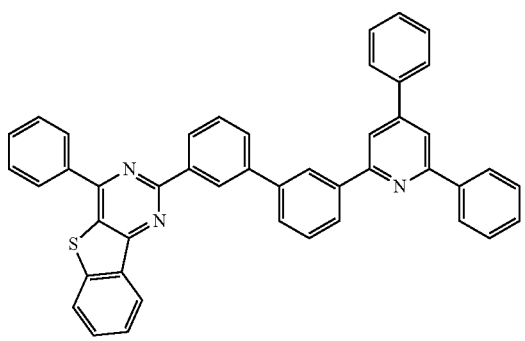

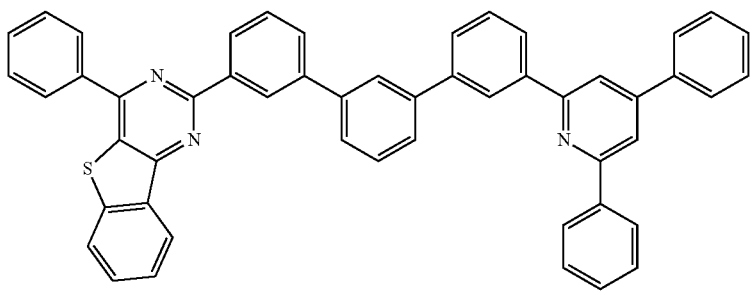
[H-72]
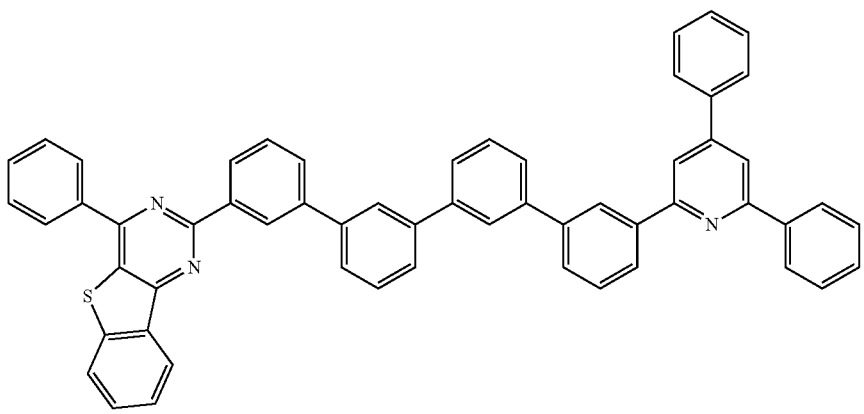
[H-73]
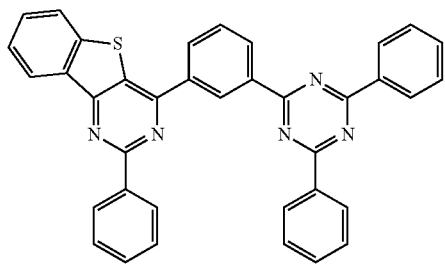
[H-74]
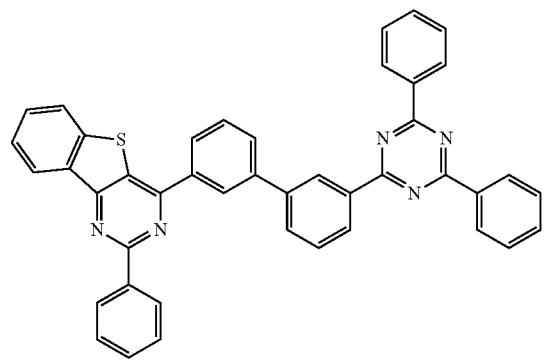
[H-75]
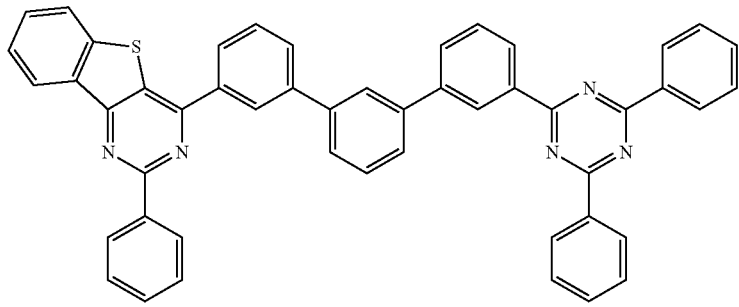
[H-76]

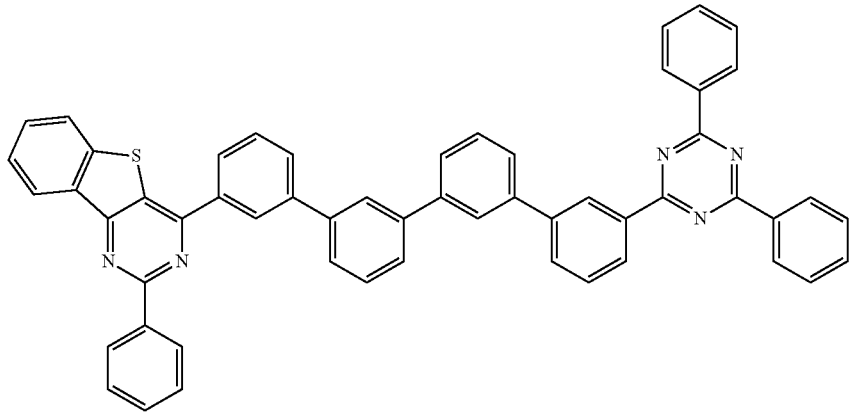
[H-77]
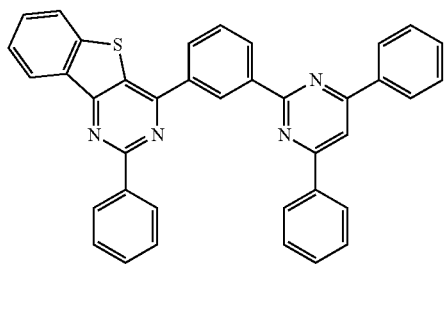
[H-78]
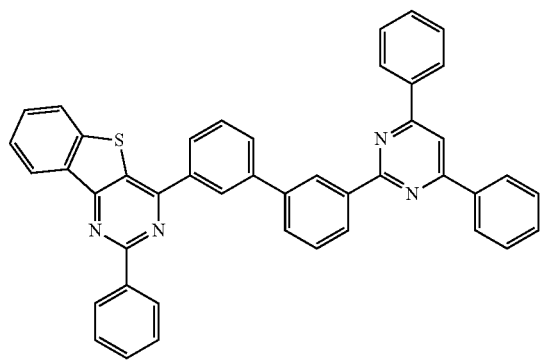
[H-79]
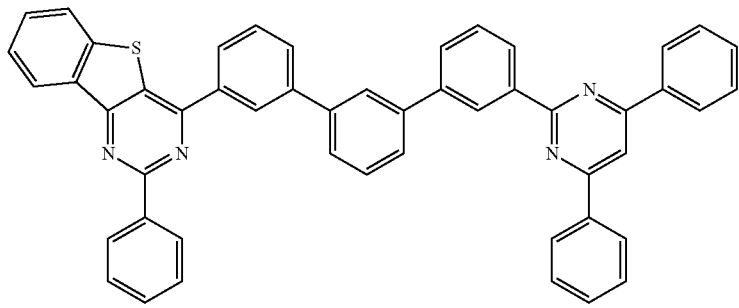
[H-80]
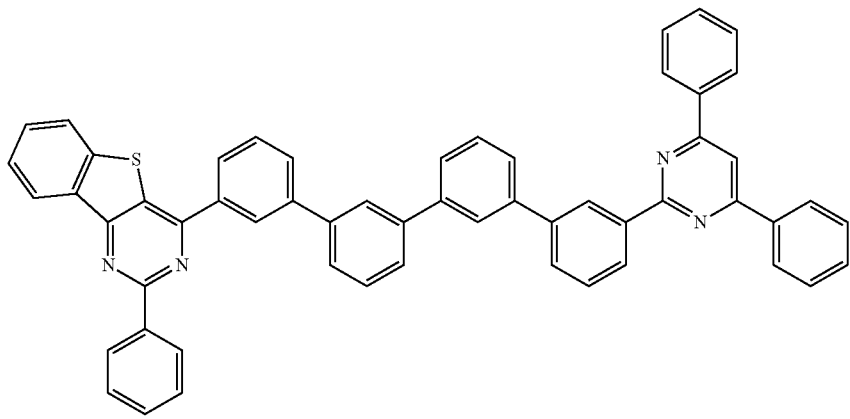
[H-81]

[H-82]
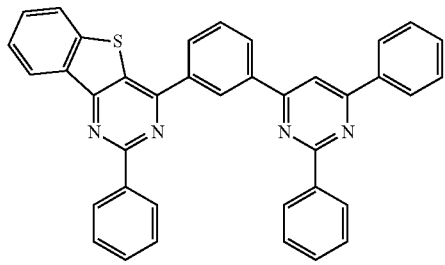
[H-83]
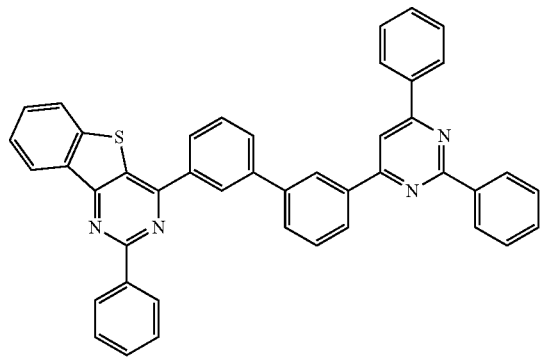
[H-84]
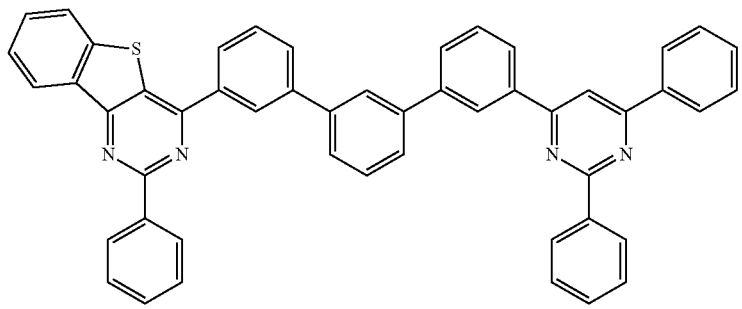
[H-85]
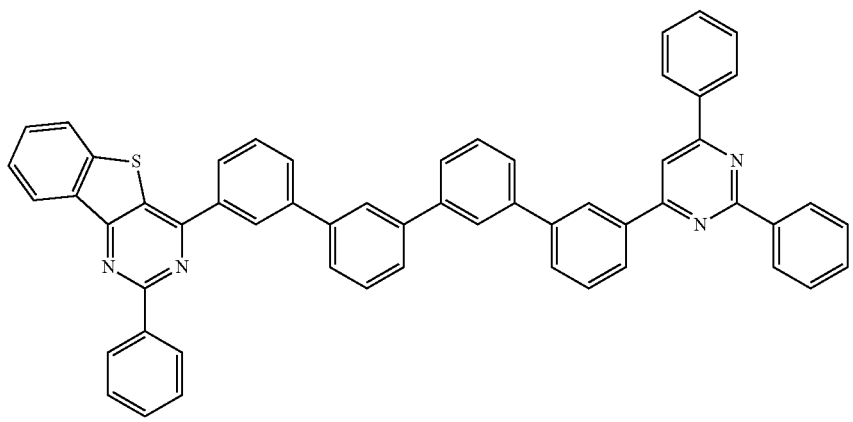
[H-86]
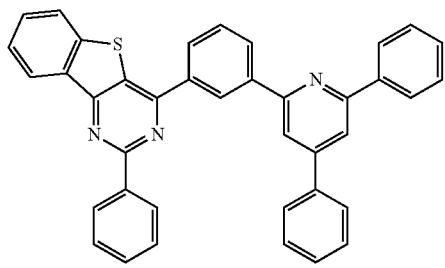
[H-87]
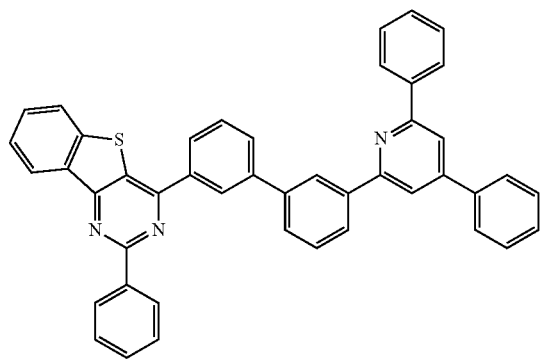

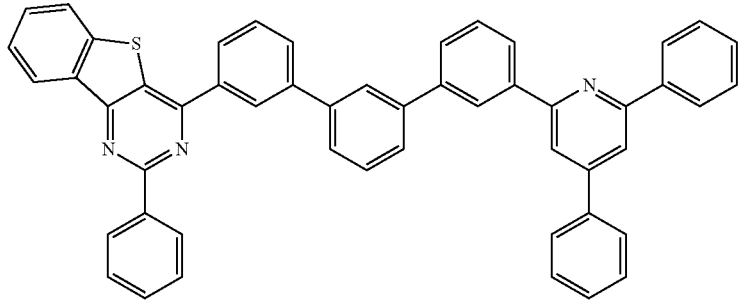
[H-88]
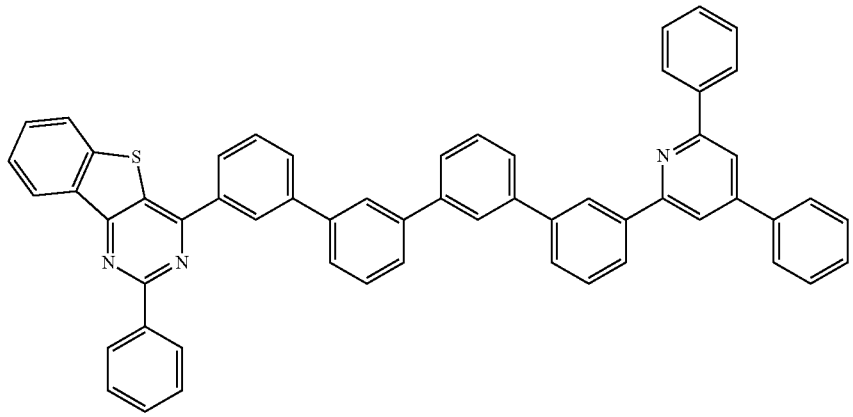
[H-89]
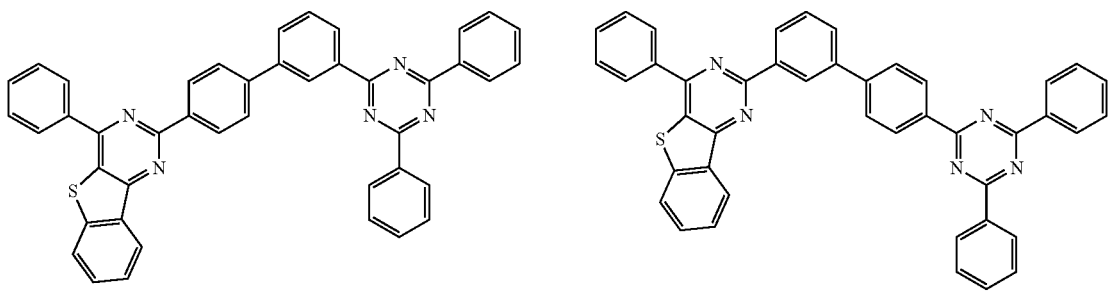
[H-90]  [H-91]
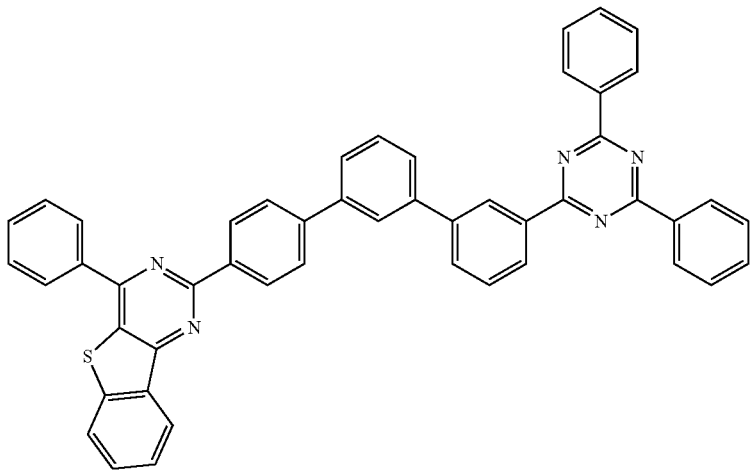
[H-92]

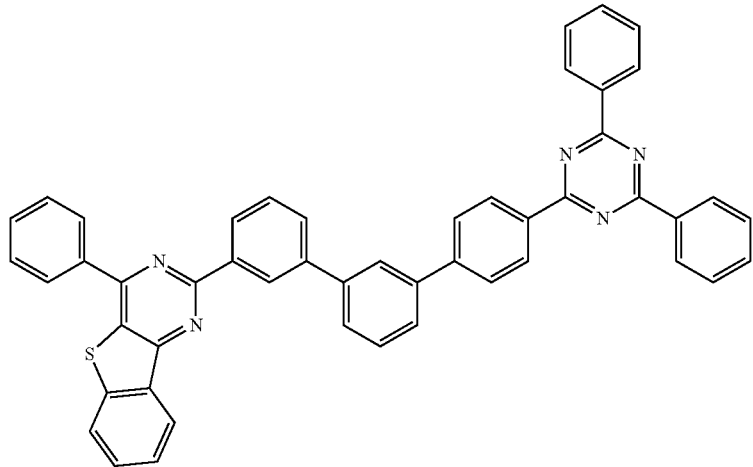
[H-93]
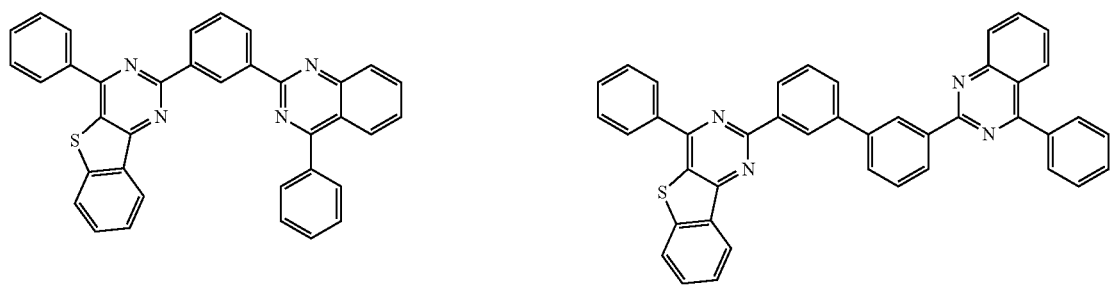
[H-94]
[H-95]
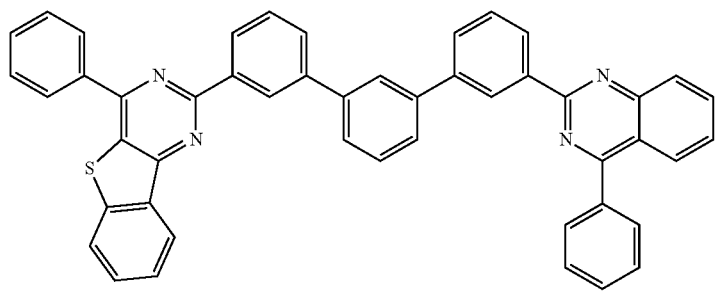
[H-96]
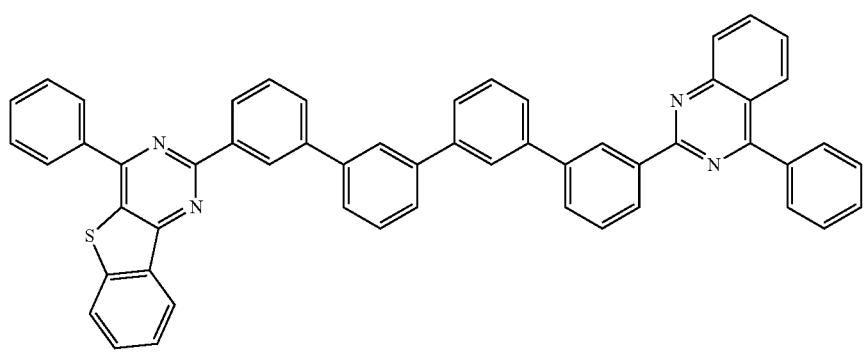
[H-97]

-continued
[H-98]
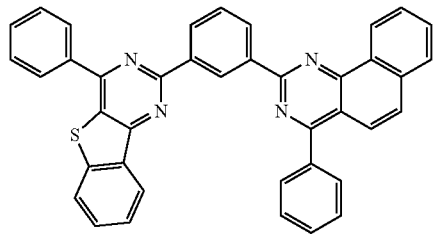
[H-99]
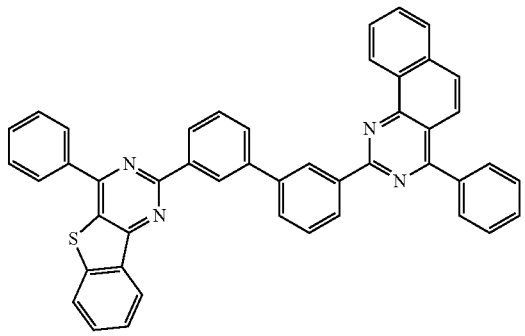
[H-100]
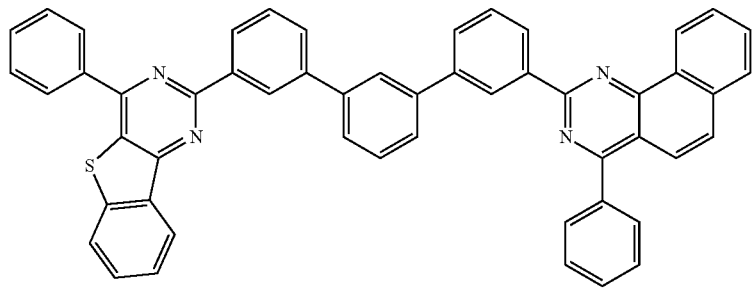
[H-101]
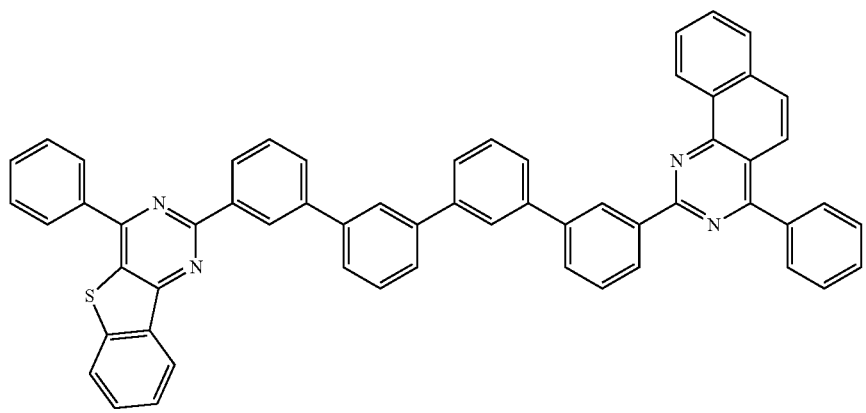
[H-102]
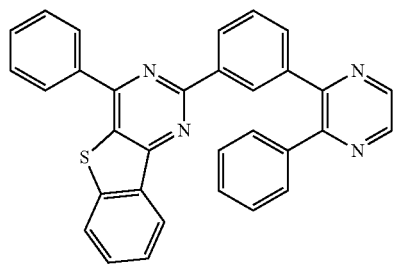
[H-103]
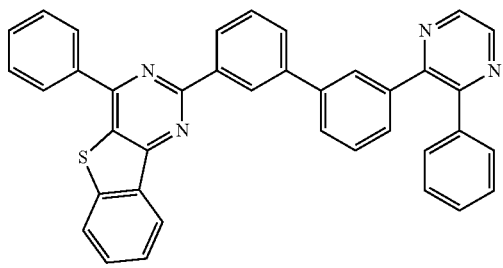
[H-104]
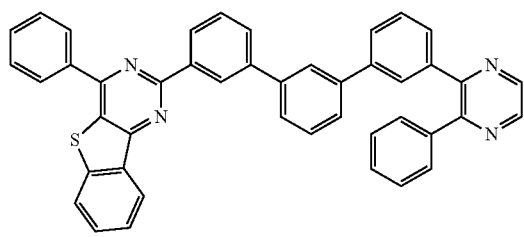

[H-105]
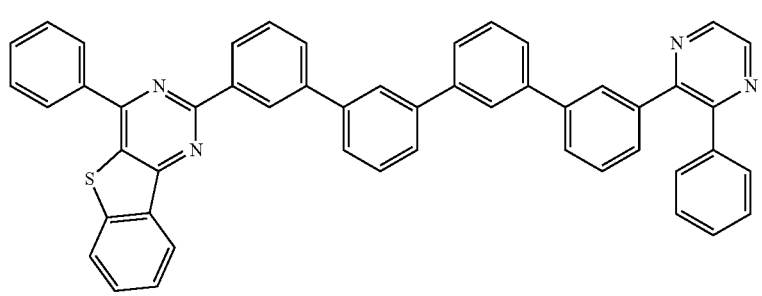
[H-106]
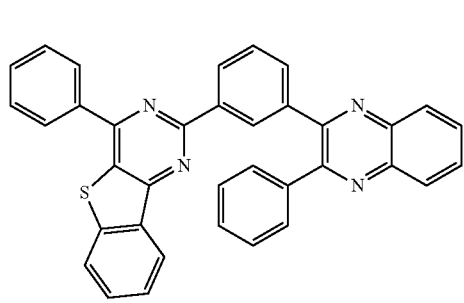
[H-107]
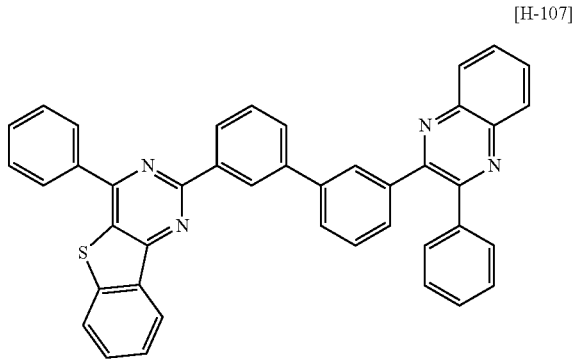
[H-108]
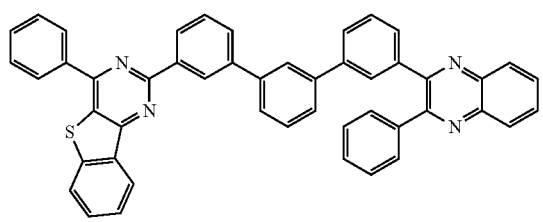
[H-109]
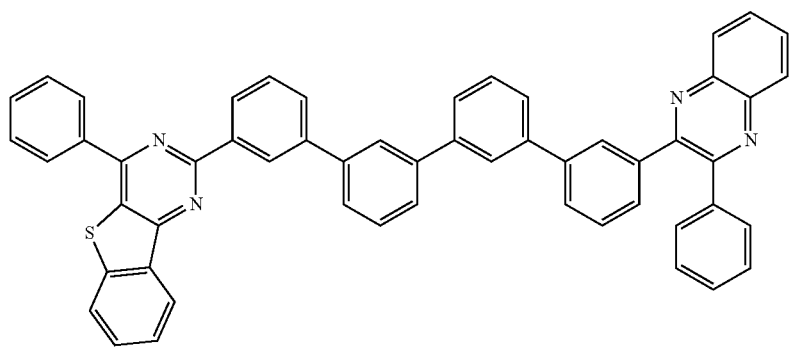

[H-110]
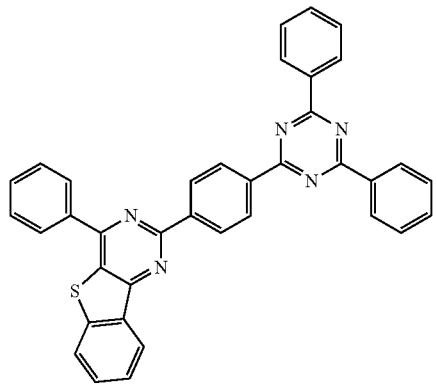
[H-111]
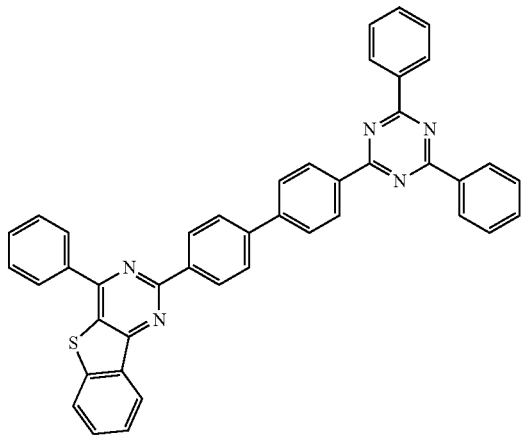
[H-112]
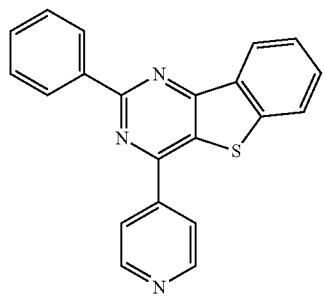
[H-113]
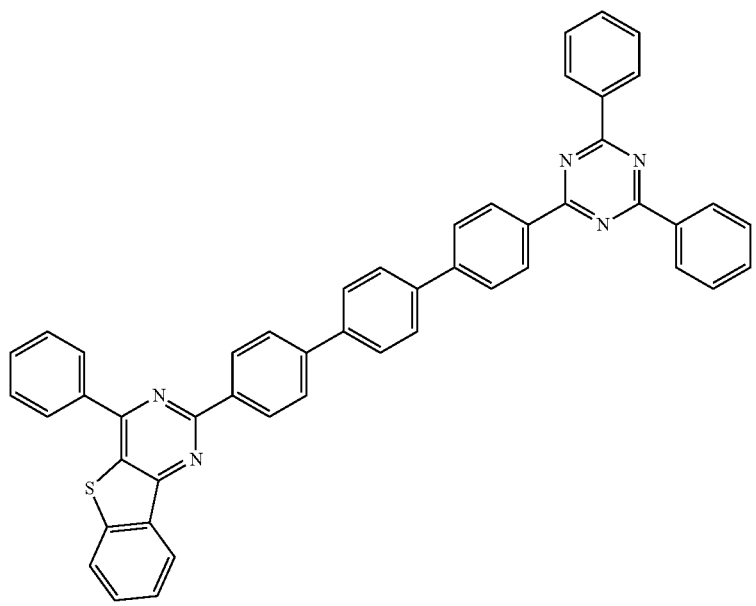

-continued
[H-114]
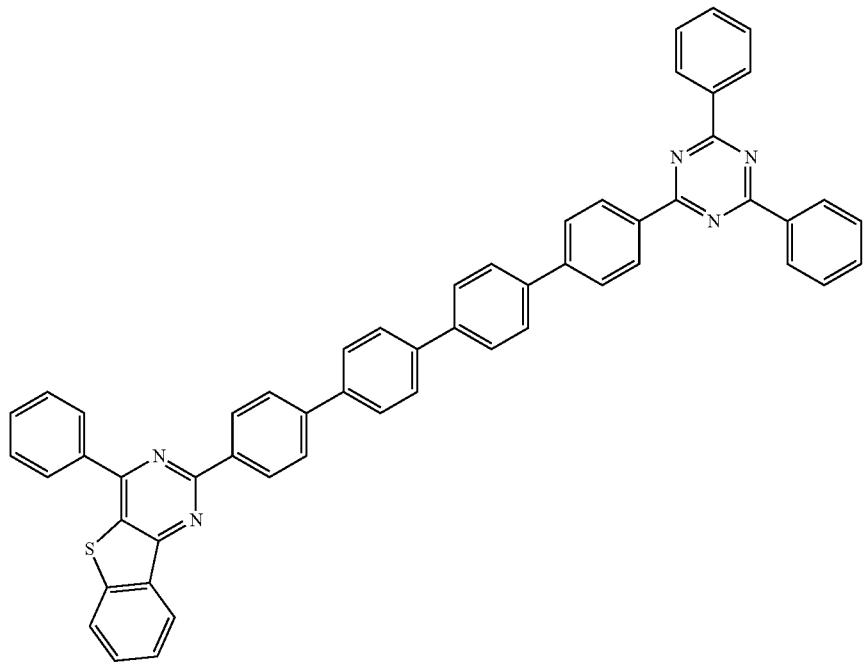
[H-115]
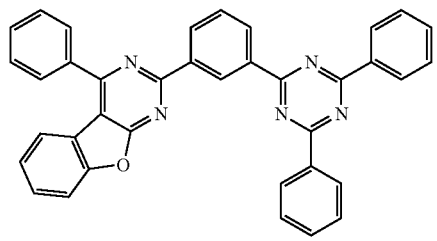
[H-116]
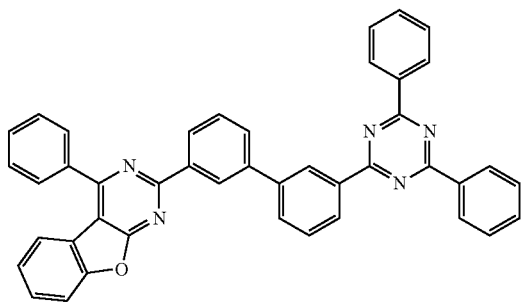
[H-117]
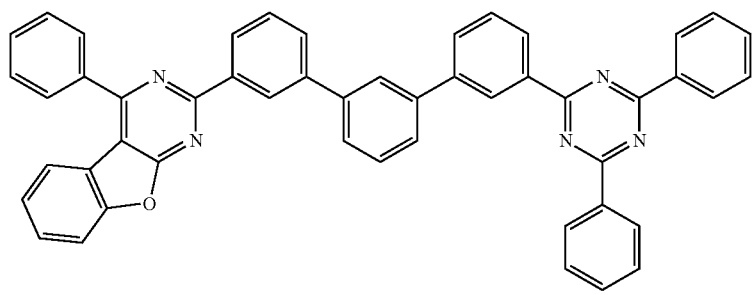
[H-118]
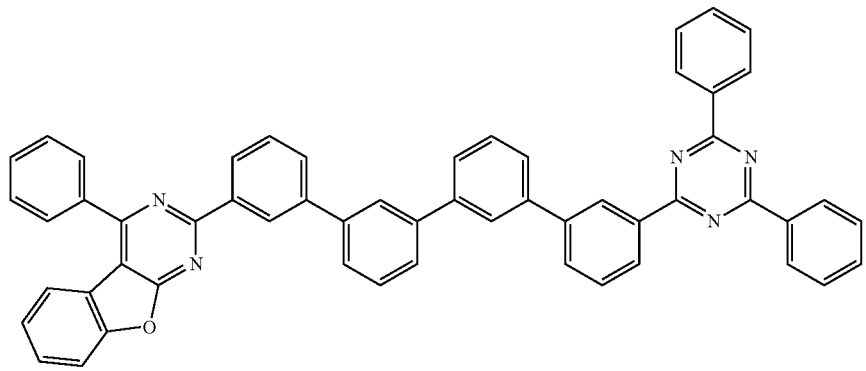

-continued
[H-119]
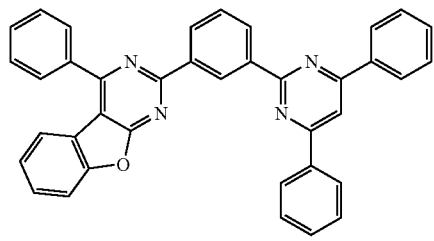
[H-120]
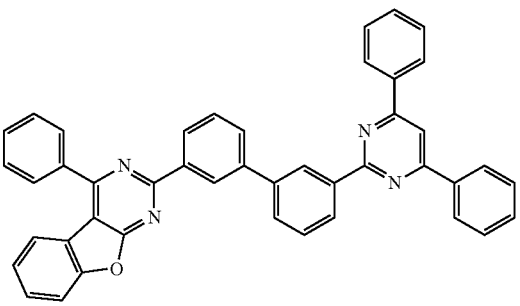
[H-121]
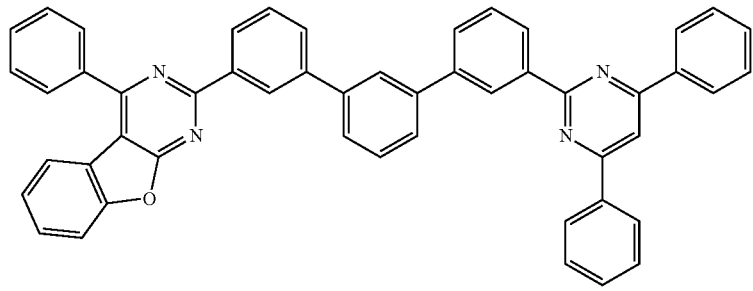
[H-122]
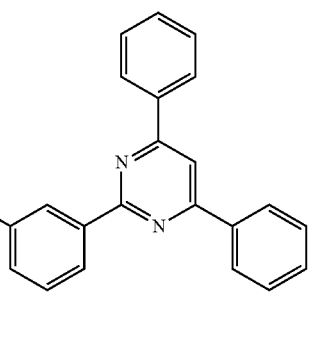
[H-123]
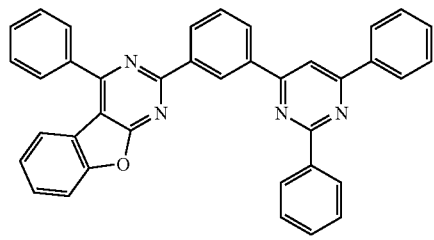
[H-124]
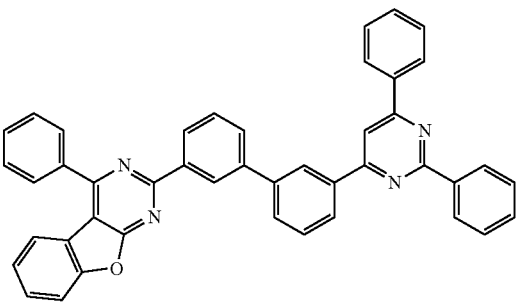
[H-125]
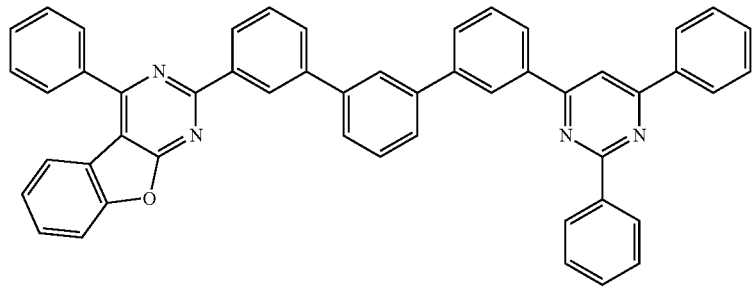

[H-126]
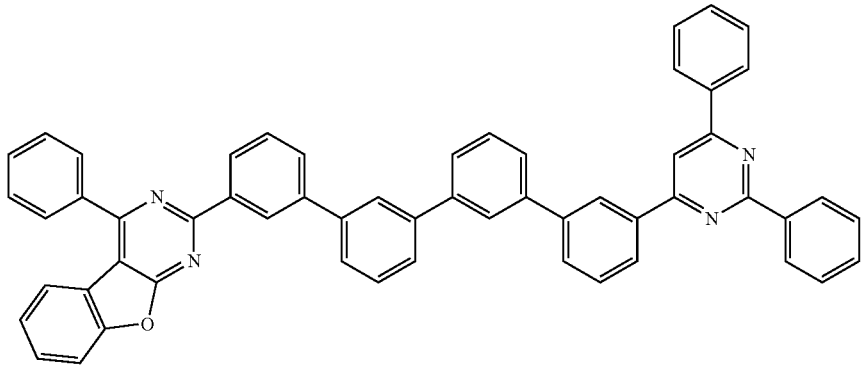
[H-127]
[H-128]
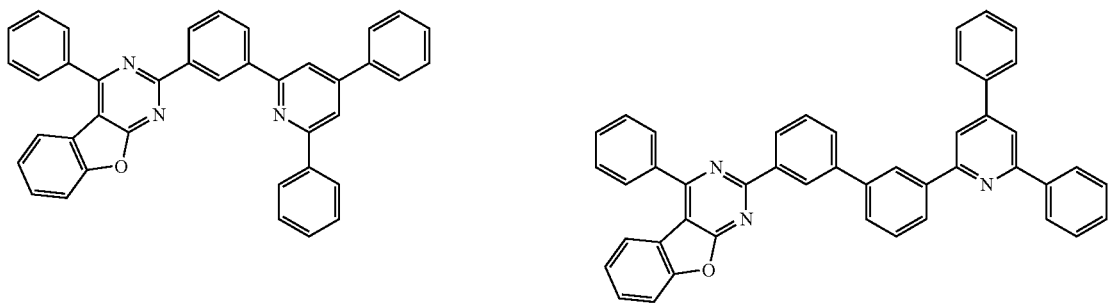
[H-129]
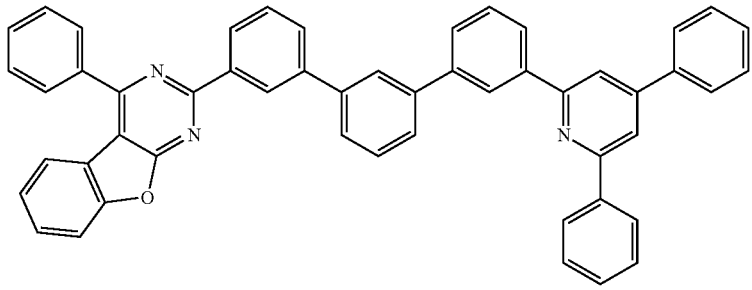
[H-130]
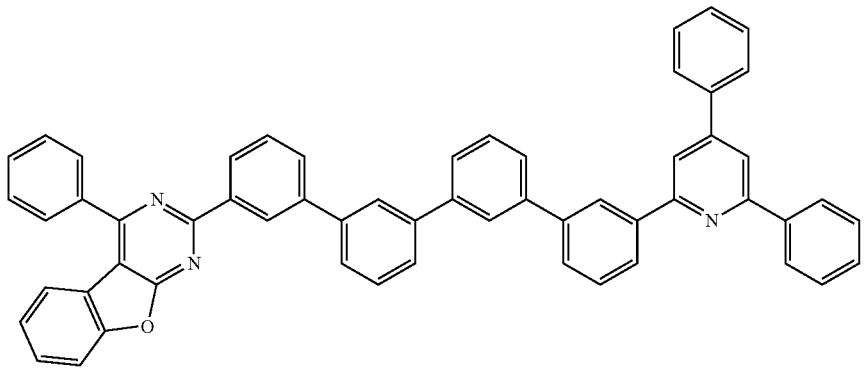

[H-131]
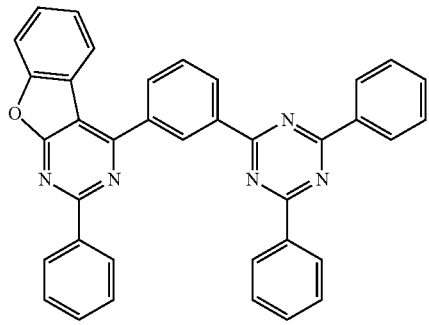
[H-132]
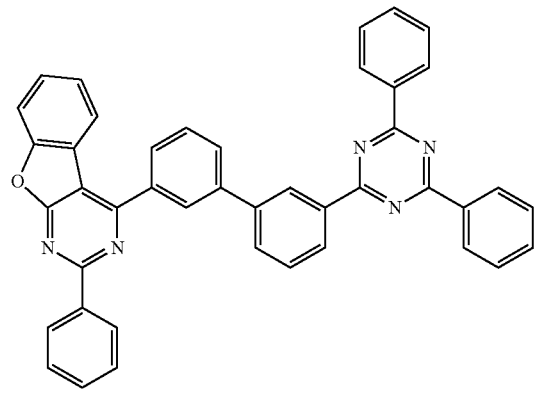
[H-133]
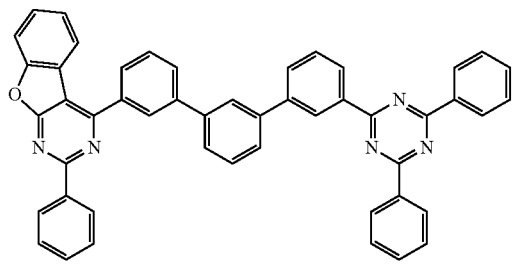
[H-134]
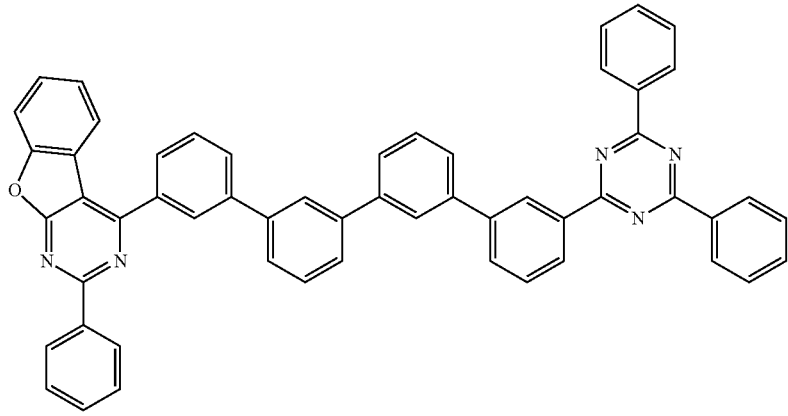
[H-135]
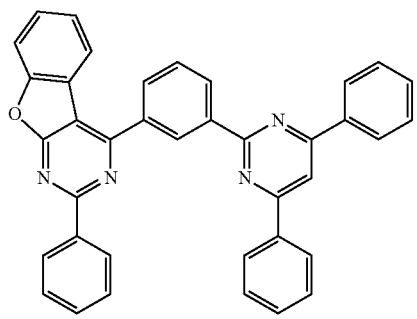
[H-136]
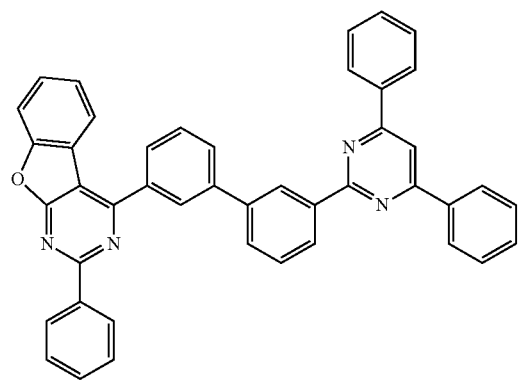

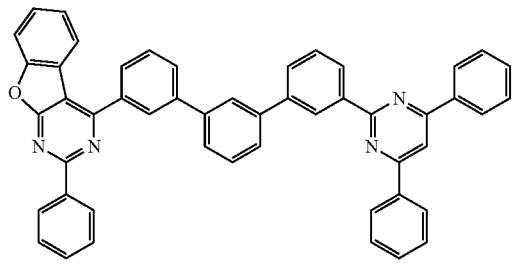
[H-137]
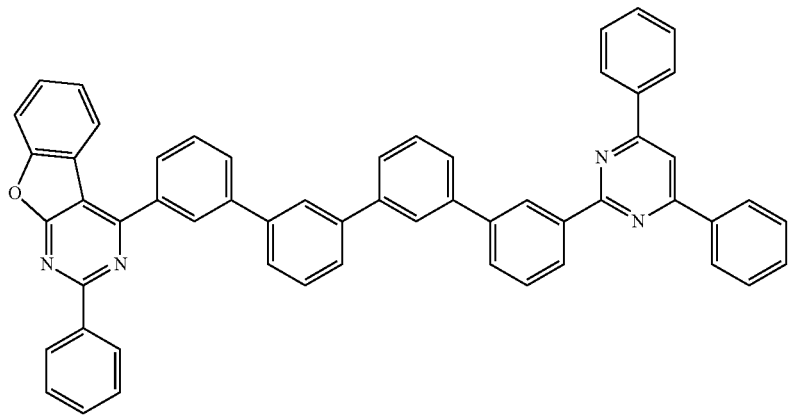
[H-138]
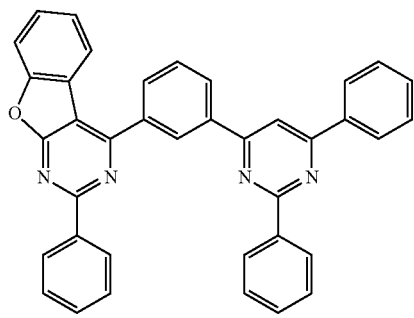
[H-139]
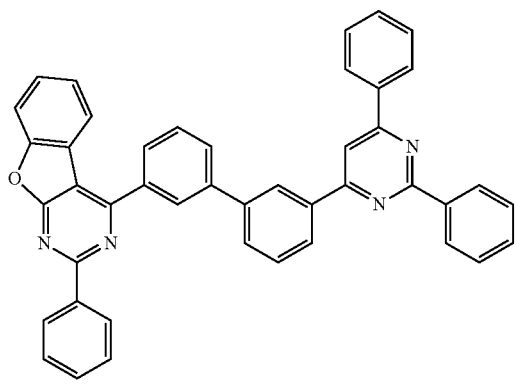
[H-140]
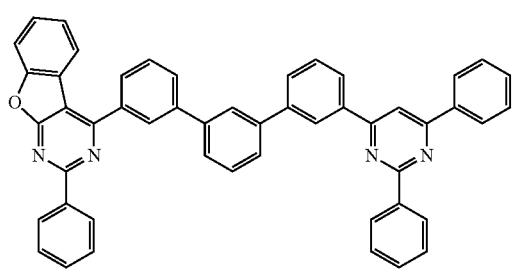
[H-141]

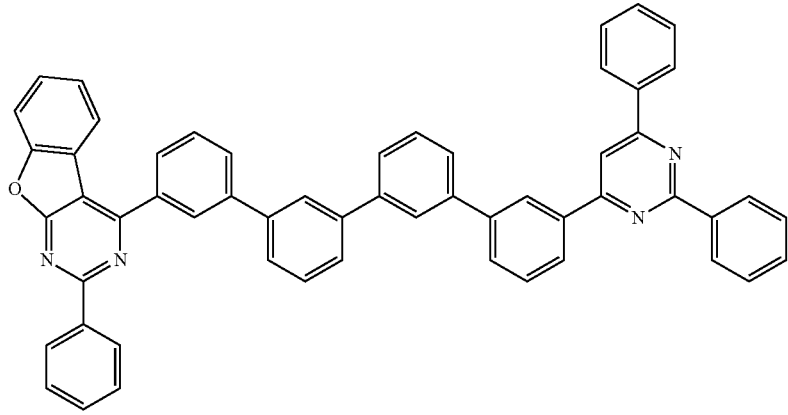
[H-142]
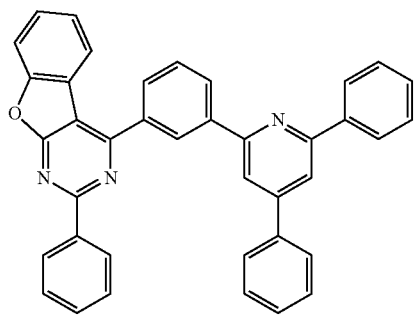
[H-143]
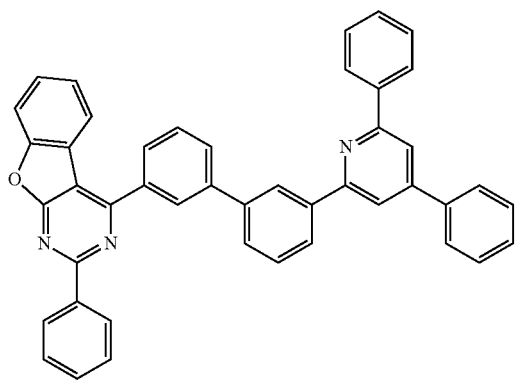
[H-144]
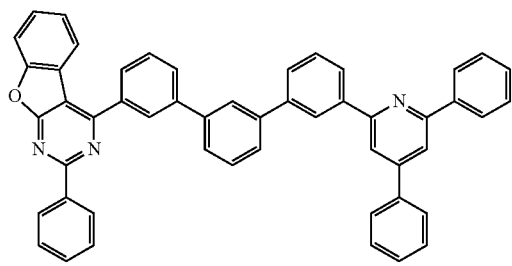
[H-145]
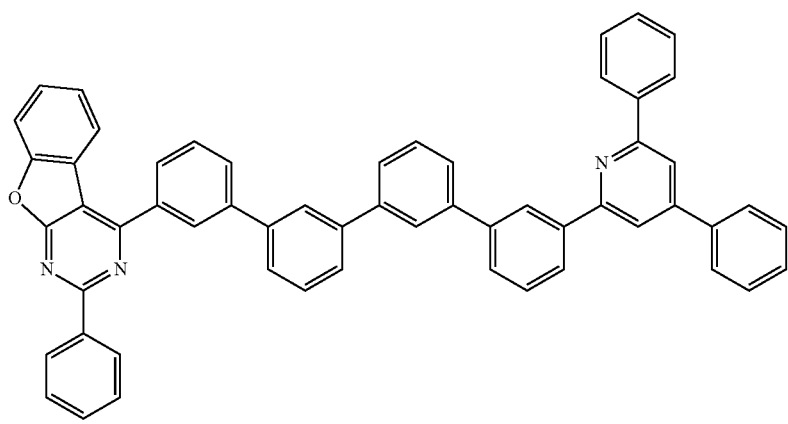
[H-146]

-continued
[H-147]
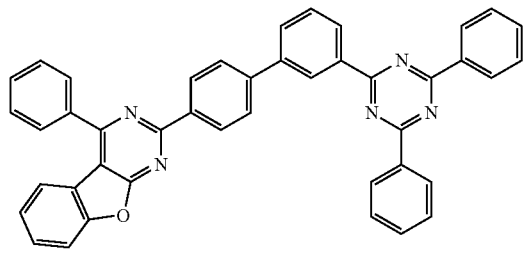
[H-148]
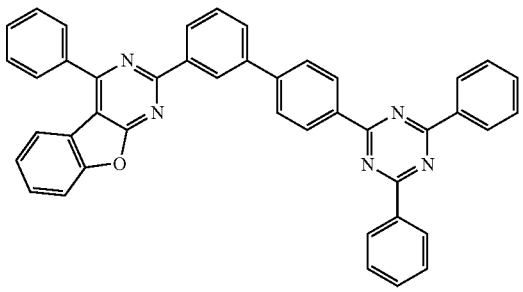
[H-149]
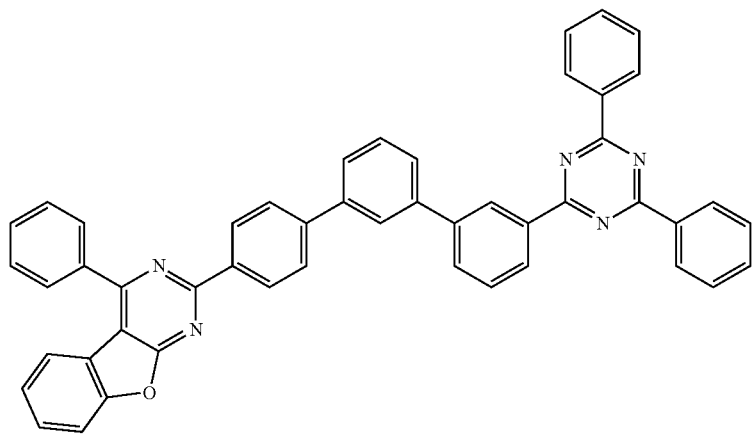
[H-150]
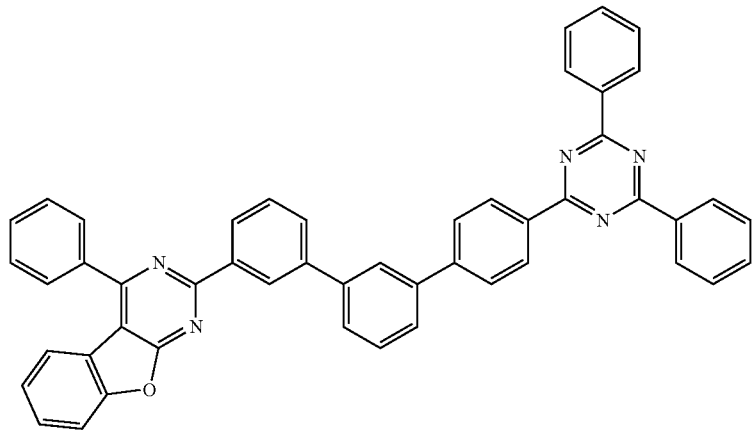
[H-151]
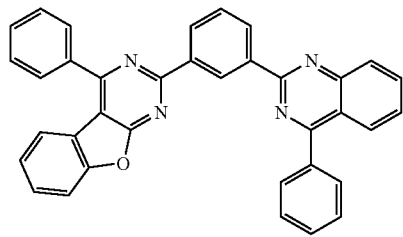
[H-152]
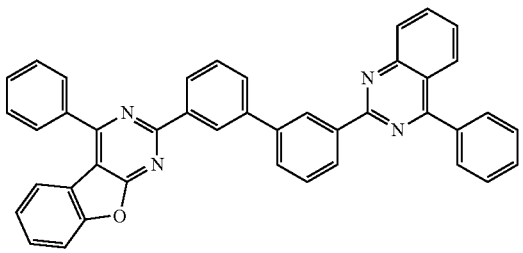

-continued
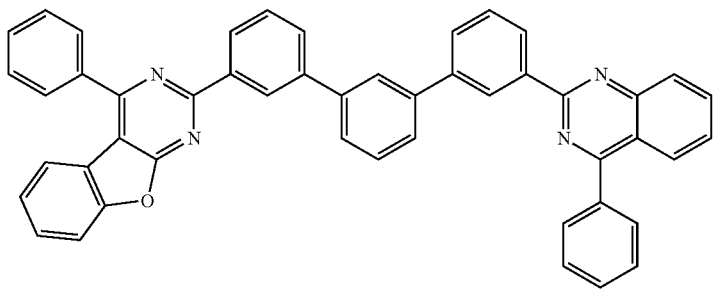
[H-153]
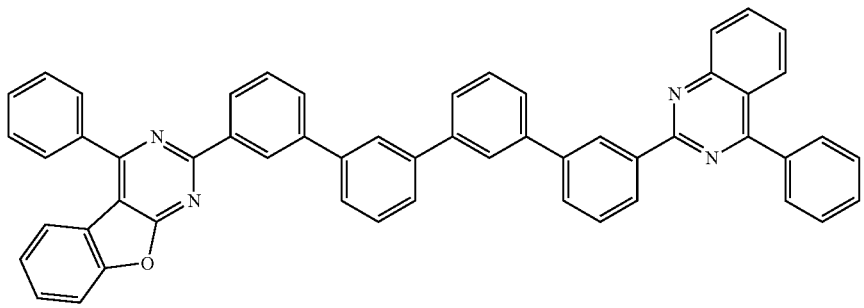
[H-154]
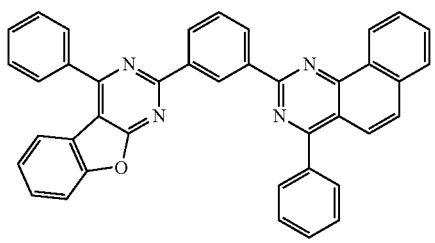
[H-155]
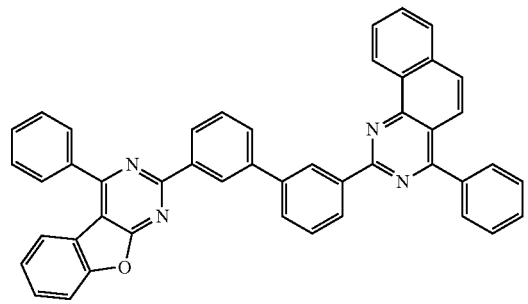
[H-156]
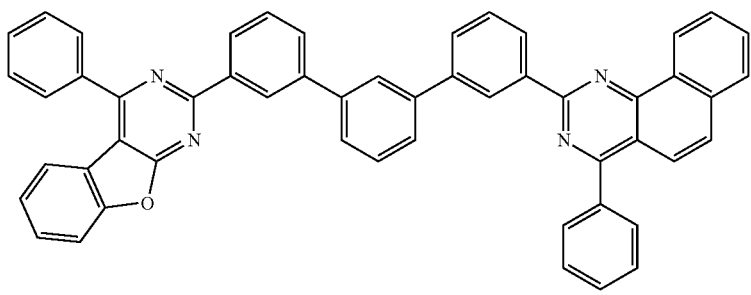
[H-157]
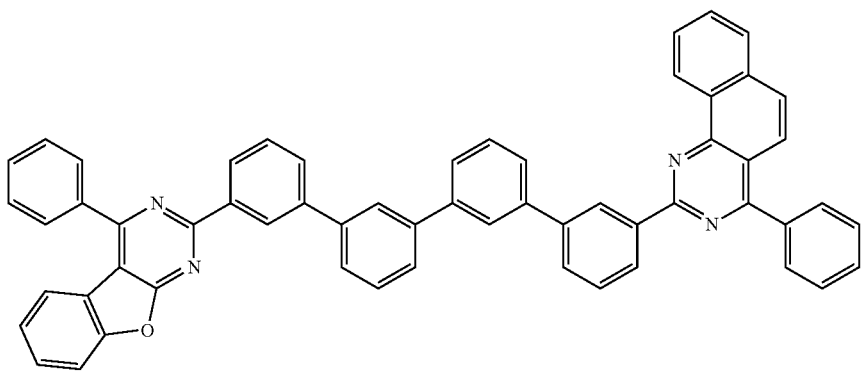
[H-158]

-continued
[H-159]
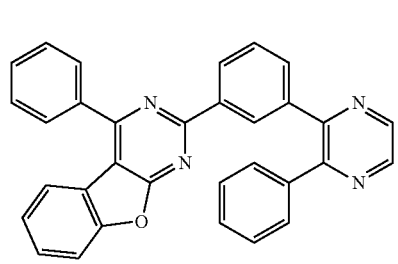
[H-160]
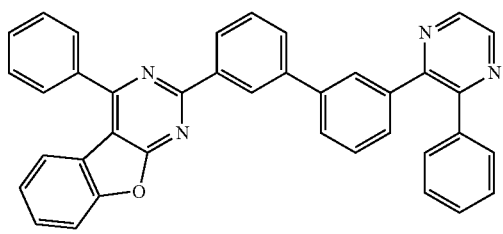
[H-161]
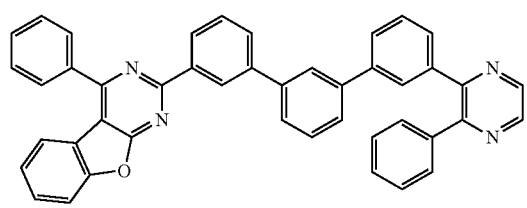
[H-162]
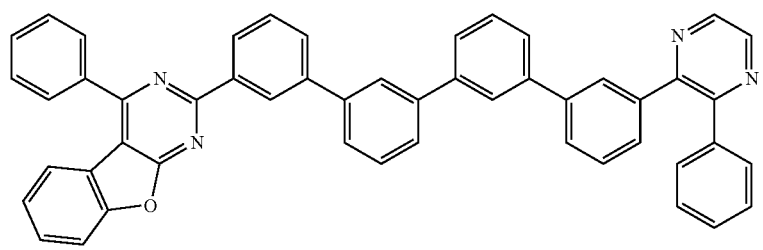
[H-163]
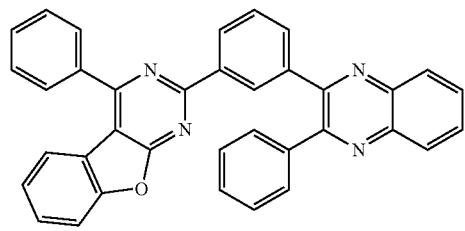
[H-164]
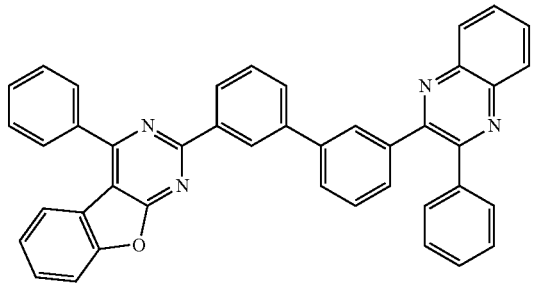
[H-165]
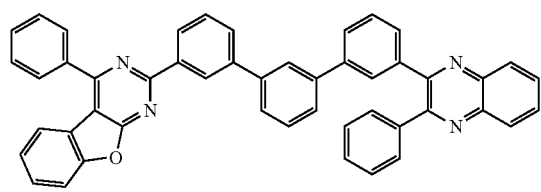
[H-166]
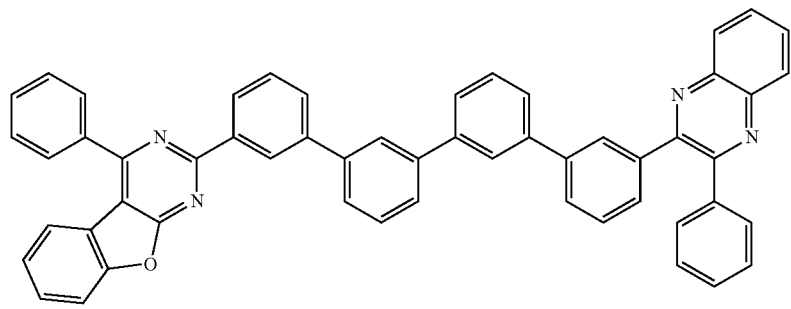

-continued
[H-167]
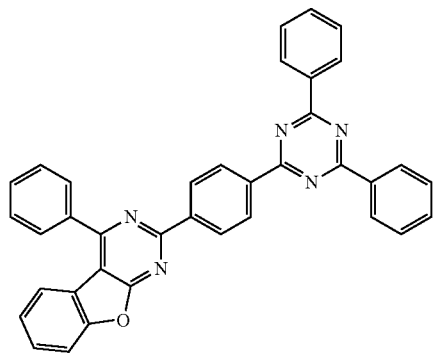
[H-168]
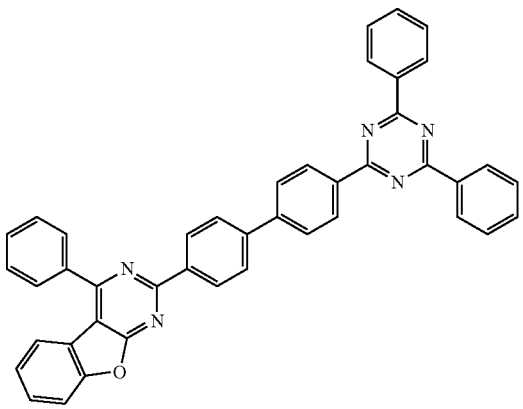
[H-169]
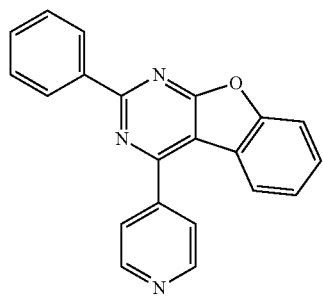
[H-170]
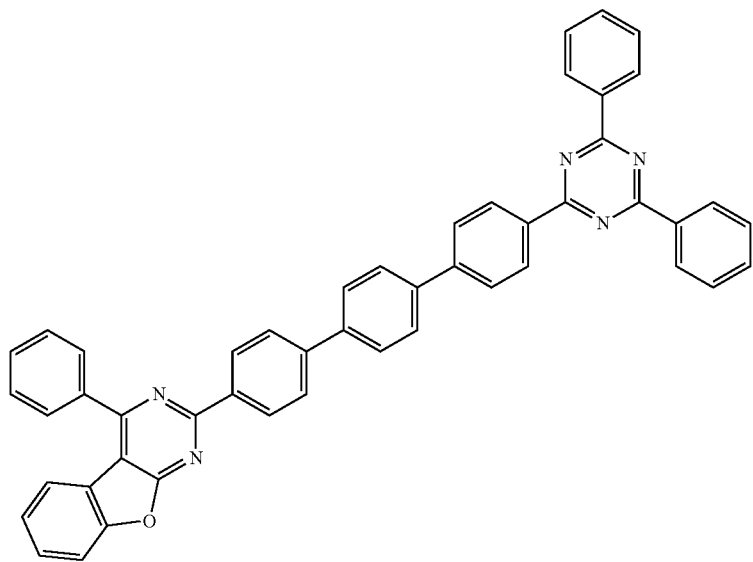

-continued
[H-171]
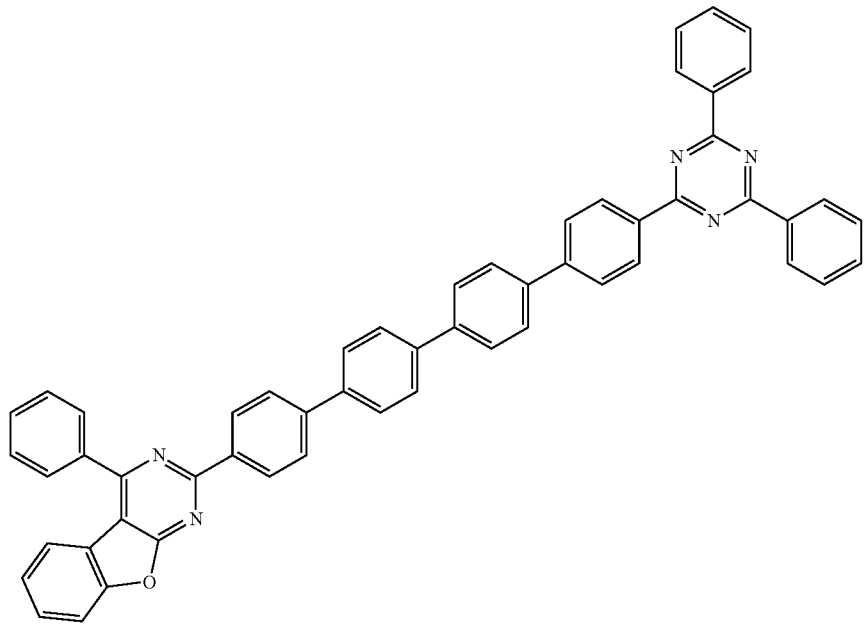
[H-172]
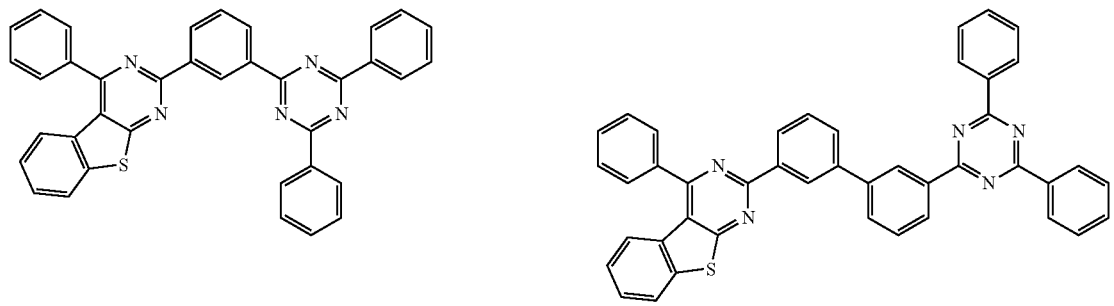
[H-173]
[H-174]
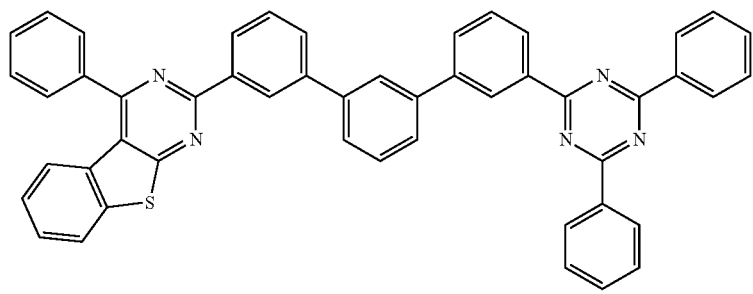
[H-175]
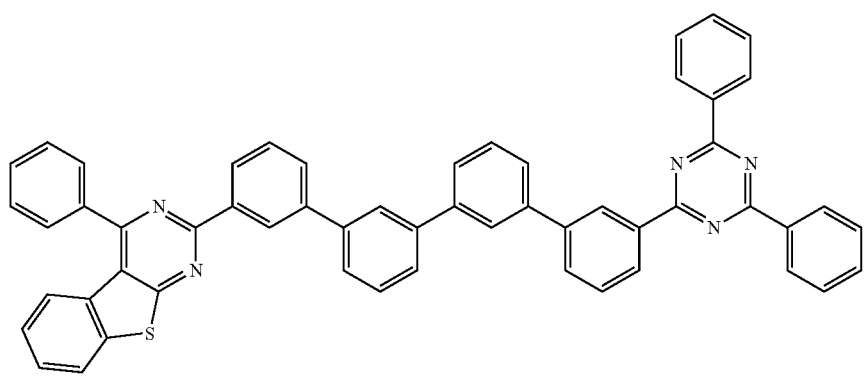

-continued
[H-176]
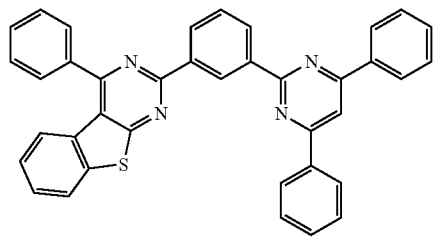
[H-177]
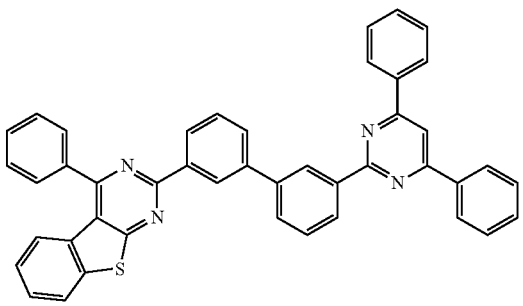
[H-178]
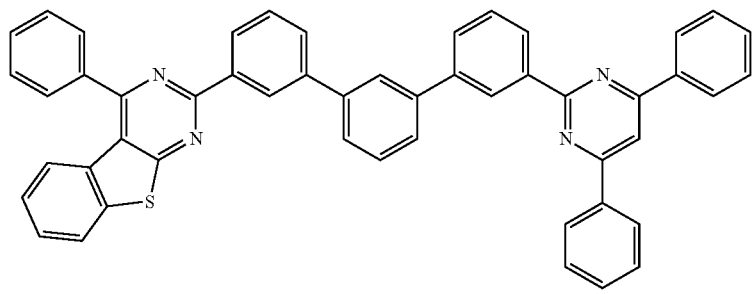
[H-179]
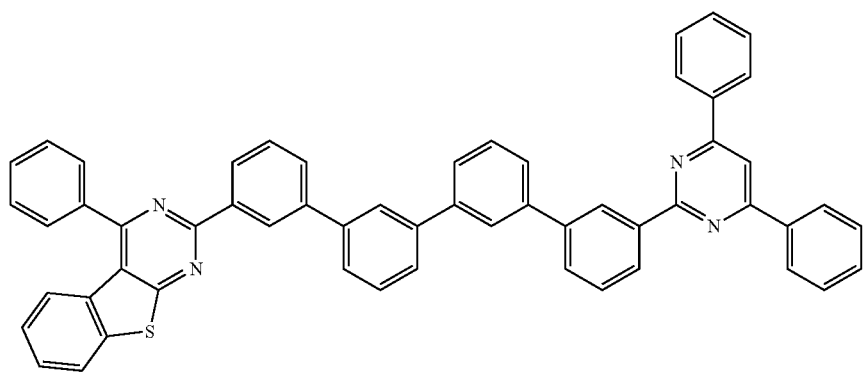
[H-180]
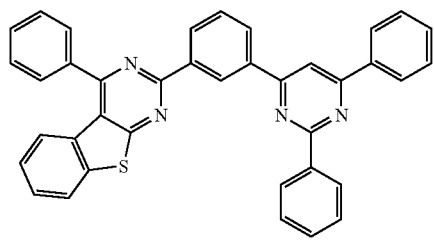
[H-181]
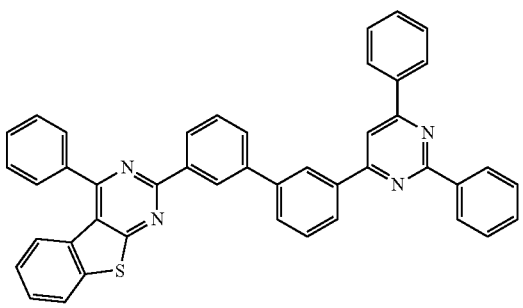
[H-182]
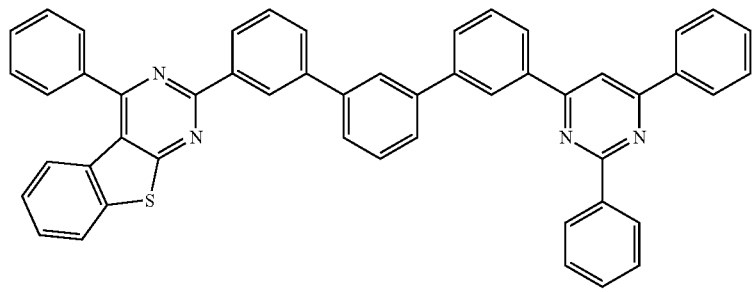

[H-183]
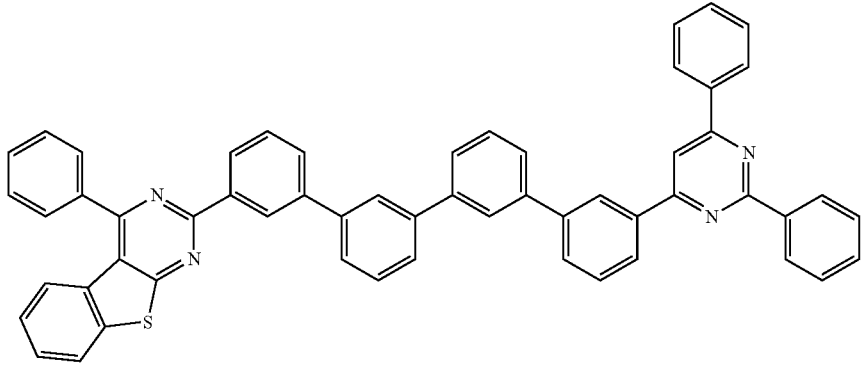
[H-184]
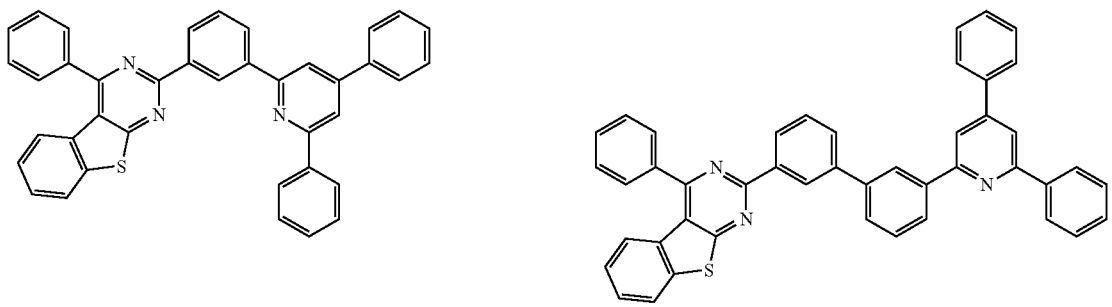
[H-185]
[H-186]
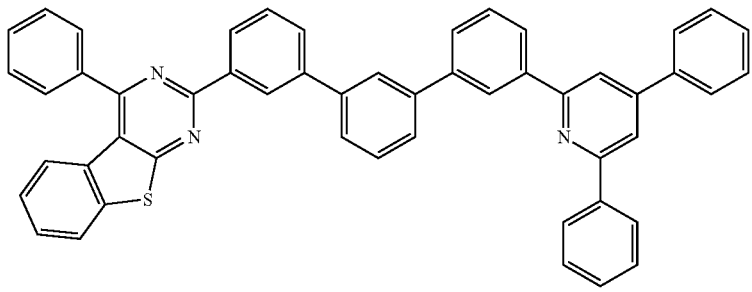
[H-187]
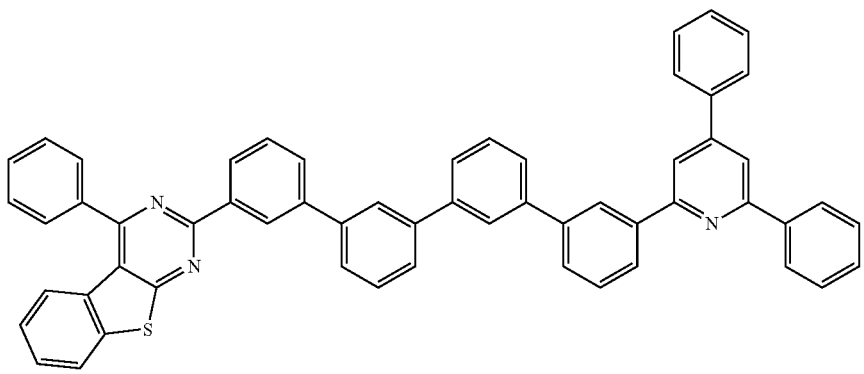

[H-188]
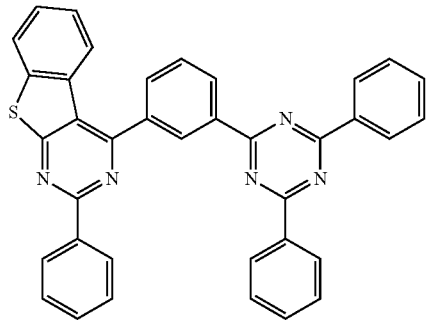
[H-189]
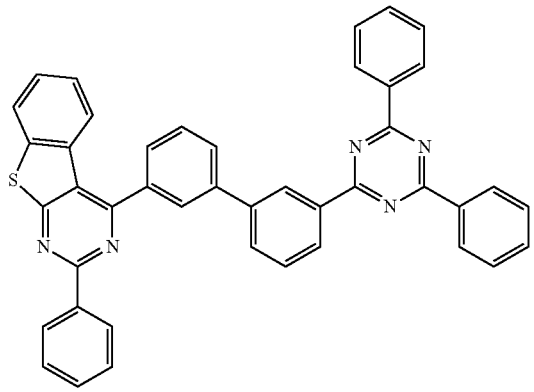
[H-190]
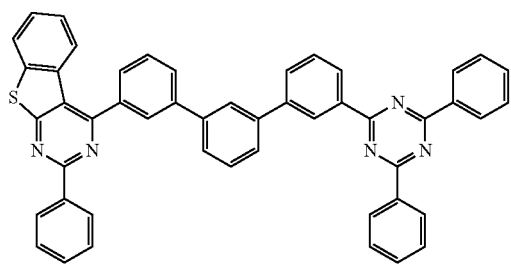
[H-191]
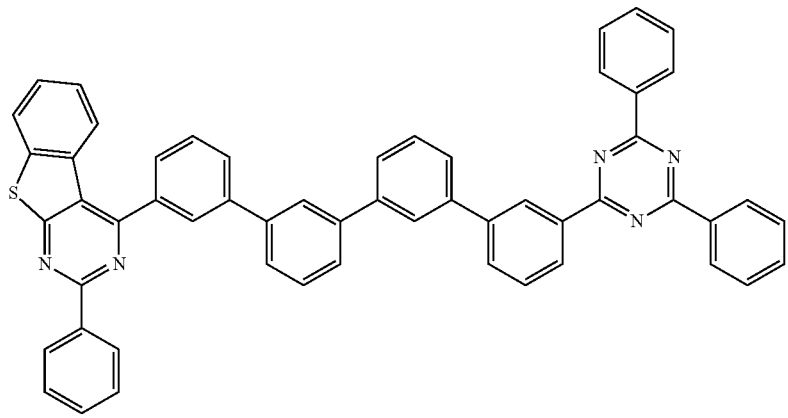
[H-192]
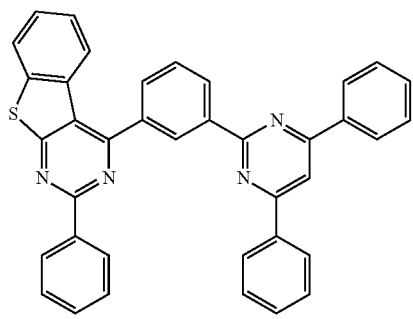
[H-193]
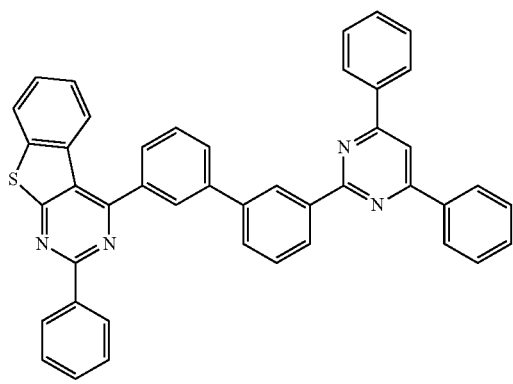

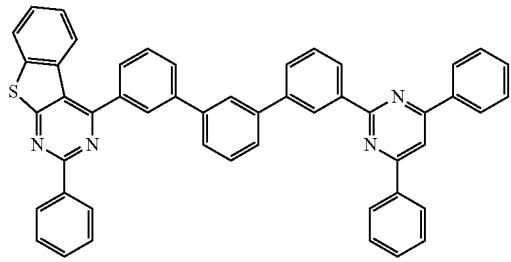
[H-194]
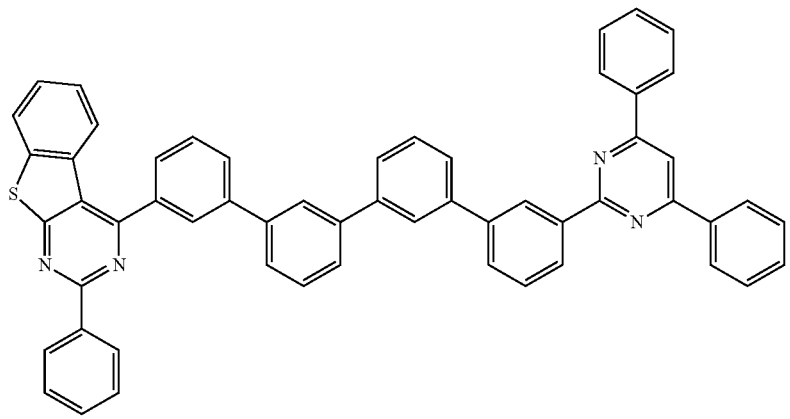
[H-195]
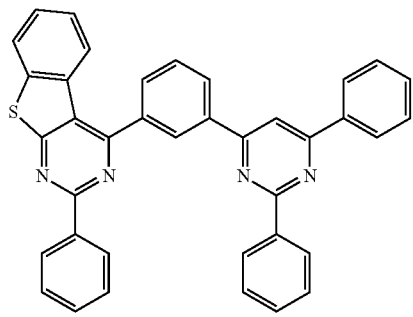
[H-196]
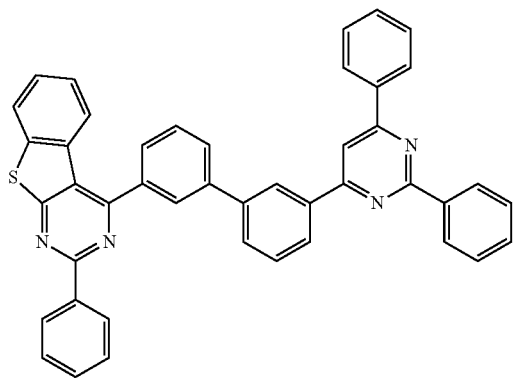
[H-197]
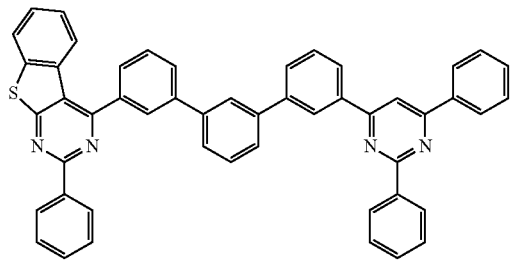
[H-198]

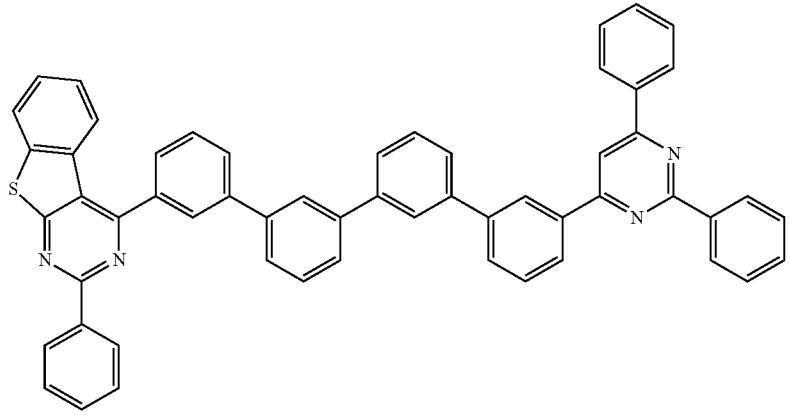
[H-199]
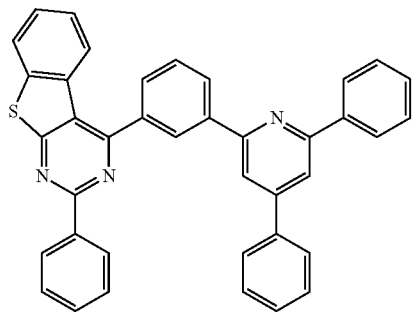
[H-200]
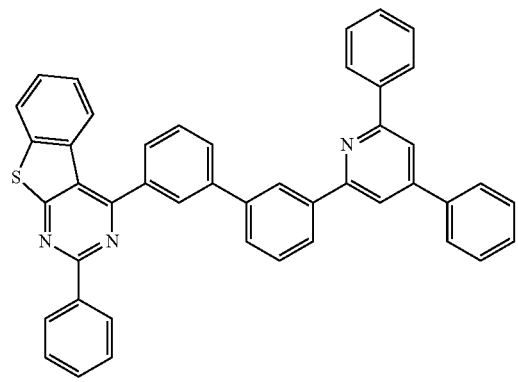
[H-201]
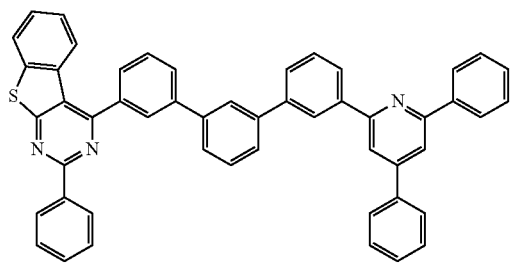
[H-202]
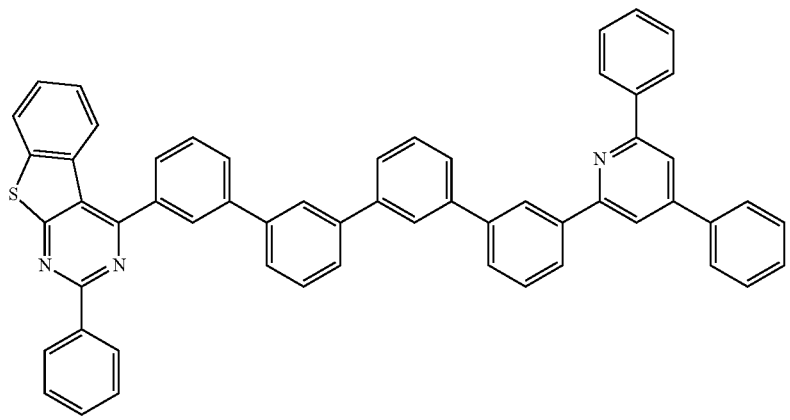
[H-203]

-continued
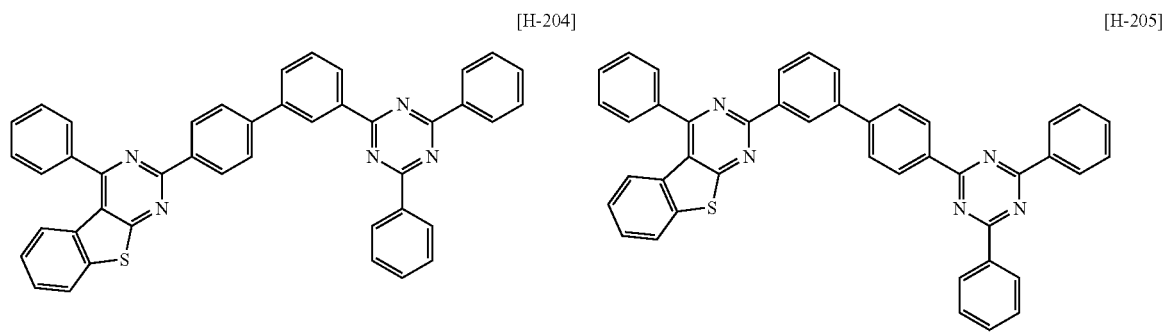
[H-204]
[H-205]
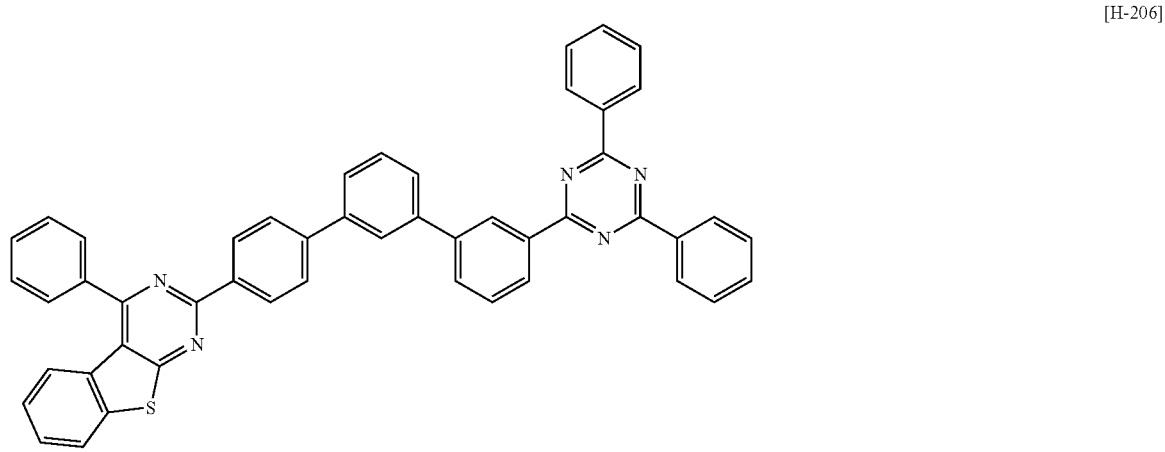
[H-206]
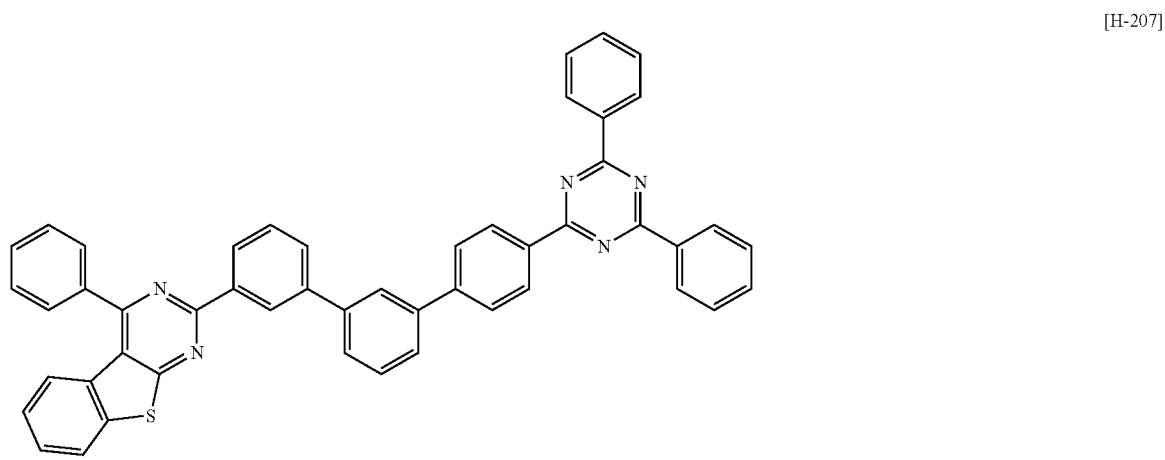
[H-207]
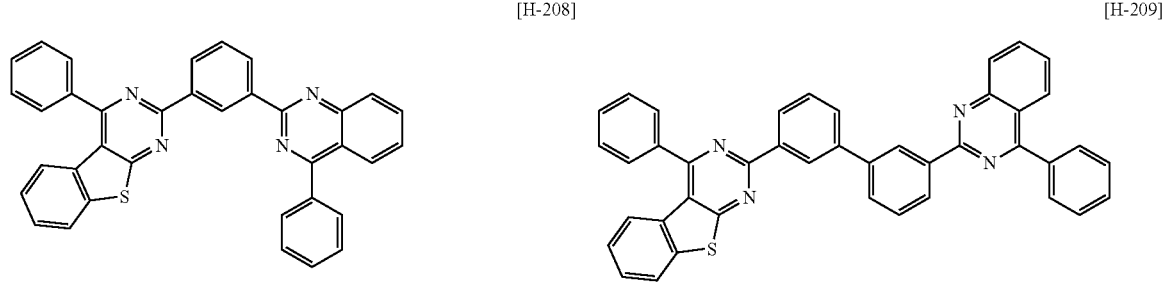
[H-208]
[H-209]

[H-210]
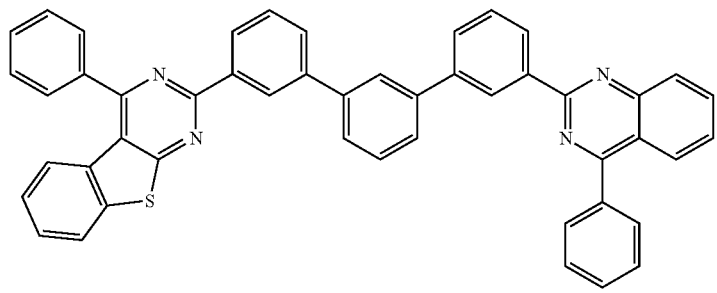
[H-211]
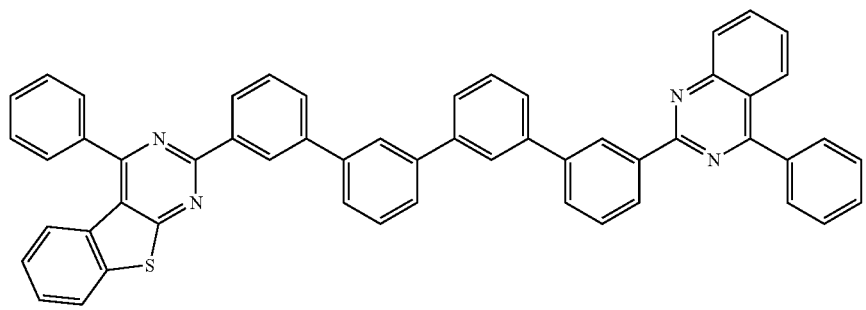
[H-212] [H-213]
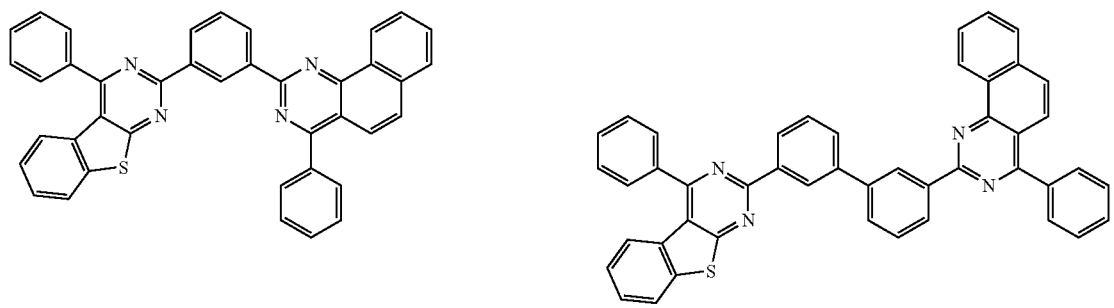
[H-214]
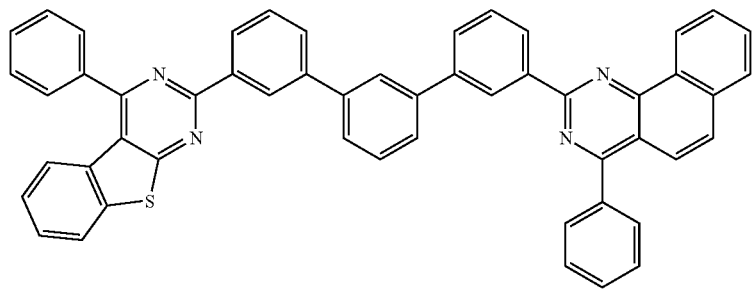
[H-215]
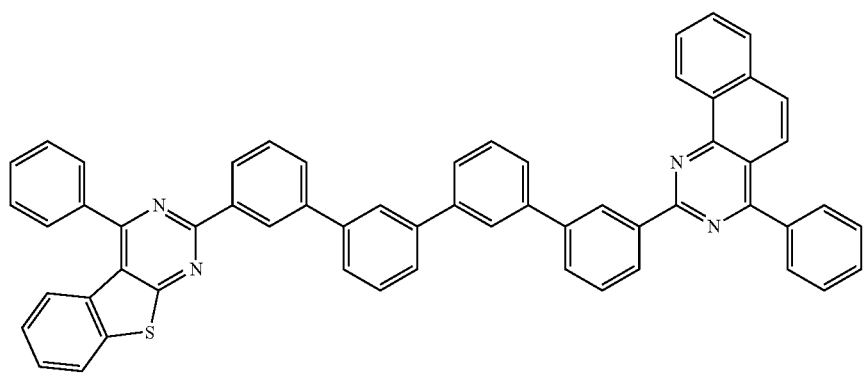

-continued
[H-216]
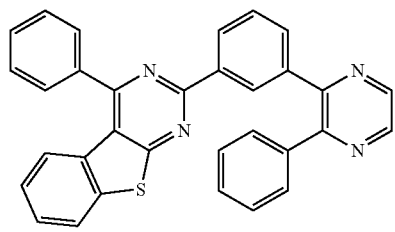
[H-217]
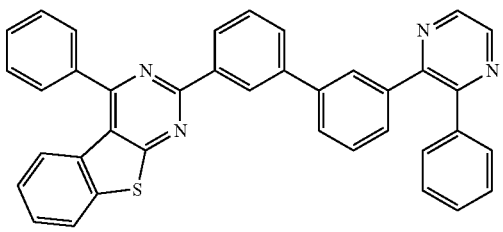
[H-218]
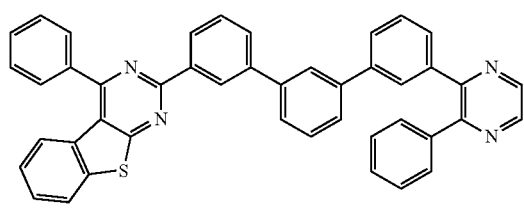
[H-219]
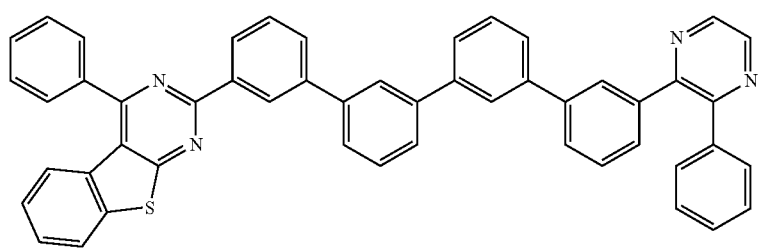
[H-220]
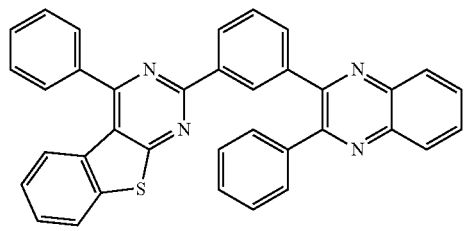
[H-221]
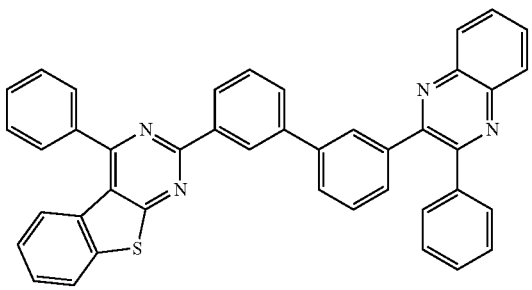
[H-222]
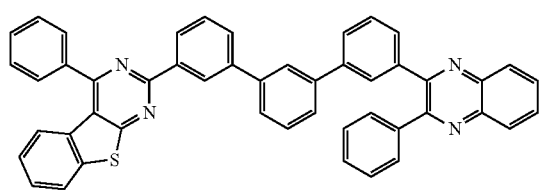
[H-223]
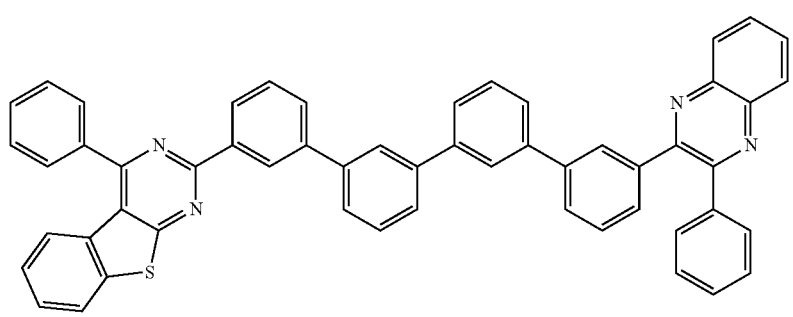

-continued
[H-224]
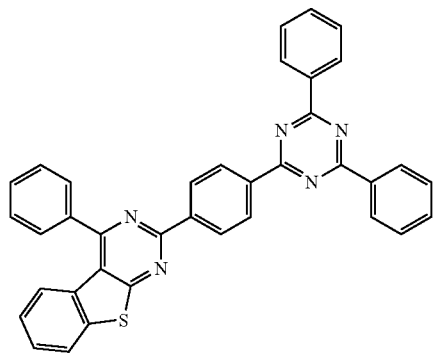
[H-225]
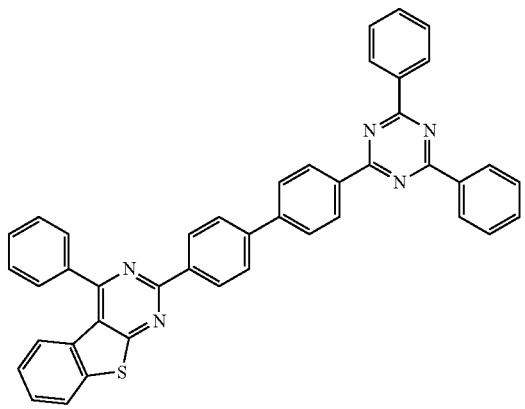
[H-226]
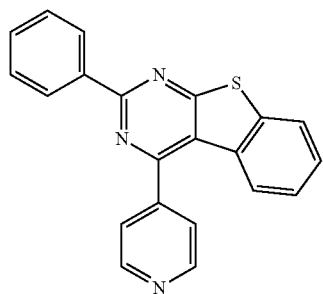
[H-227]
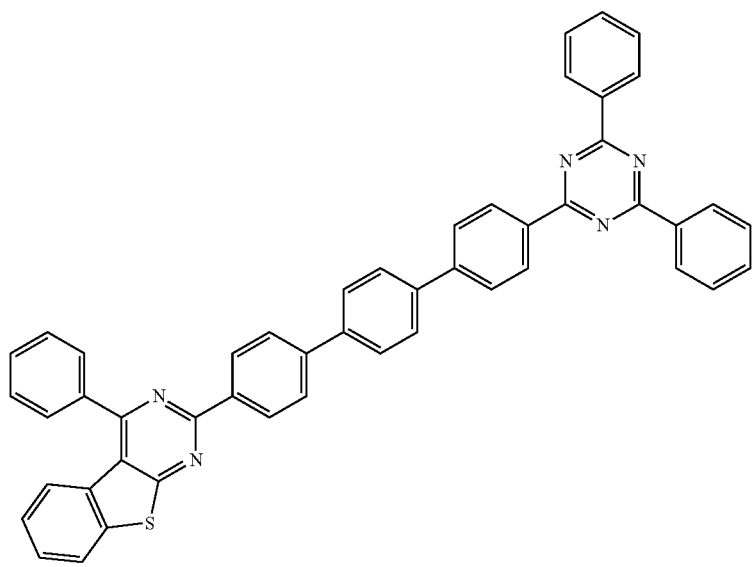

[H-228]
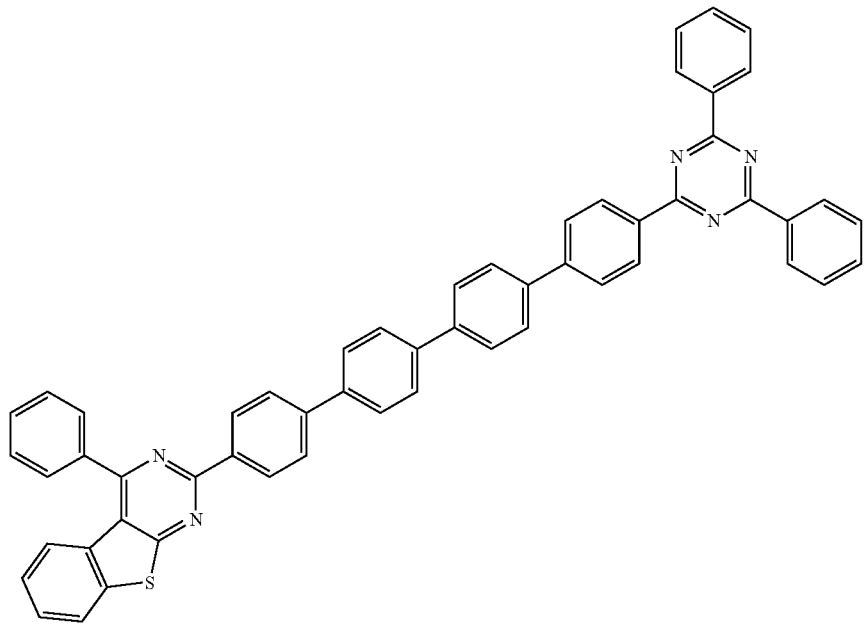
[H-229] [H-230]
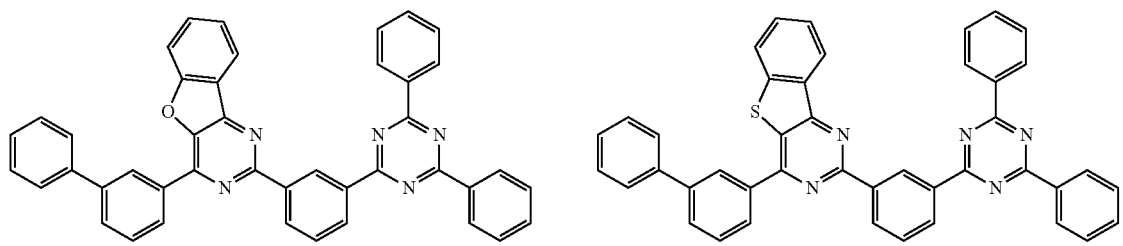
[H-231] [H-232]
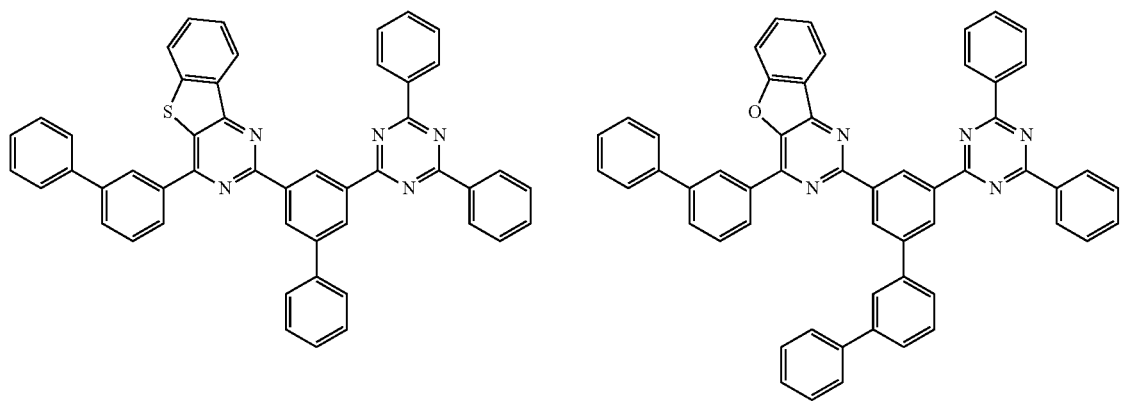

-continued

[H-233]
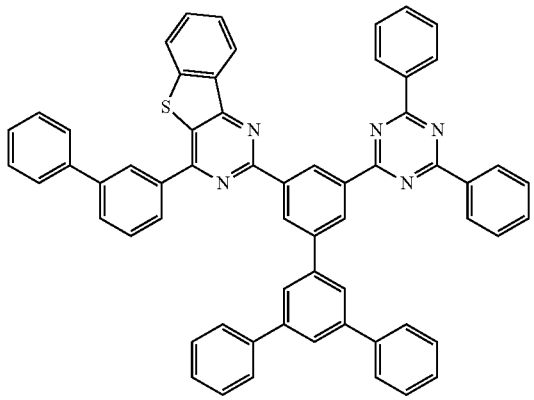

[H-234]
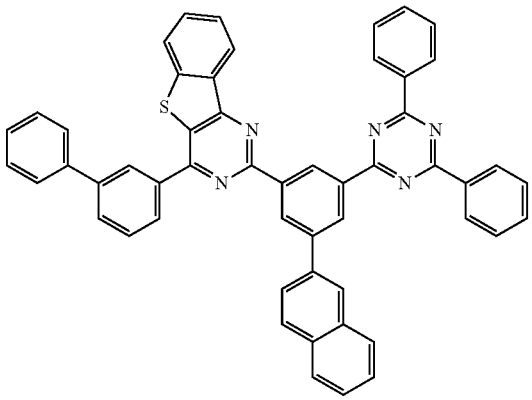

The composition for an organic optoelectronic device according to an embodiment of the present invention all includes the first compound having bipolar characteristics in which electron characteristics are relatively strong, the second compound having bipolar characteristics in which hole characteristics are relatively strong, and the third compound having excellent electron injection and transport capability in an emission layer and thus may realize an organic optoelectronic device having excellent efficiency and lifespan as well as remarkably decrease a driving voltage. In particular, the third compound may reduce or minimize a trap phenomenon between a dopant and a host and thus decrease the driving voltage. According to an embodiment of the present invention, an emission layer 32 includes the first compound, the second compound and the third compound simultaneously as a host, and the first compound may be, specifically represented by Chemical Formula 1-I or Chemical Formula 1-III, the second compound may be represented by Chemical Formula 2-I, and the third compound may be represented by Chemical Formula 5-I, or Chemical Formula 5-II. More specifically, the first compound may be represented by Chemical Formula 1-IB or 1-IIIA, and more specific examples of Chemical Formula 1-IB may be represented by Chemical Formula 1-I-3b. Third compound may be represented by Chemical Formula 5-I-b, Chemical Formula 5-I-d, or Chemical Formula 5-II-k. According to another embodiment of the present invention, the first compound may be, for example represented by Chemical Formula 1-I-c, or Chemical Formula 1-III-a, Chemical Formula 1-I-c may be represented by Chemical Formula 1-I-j, and Chemical Formula 1-III-a may be, more specifically represented by 1-III-g. A composition of the first compound and second compound and the third compound may be, for example included in a weight ratio of 90:10 to 10:90, and specifically in a weight ratio of 90:10 to 10:90, 85:15 to 15:85, 80:20 to 20:80, 70:30 to 30:70, 60:40 to 40:60, or 50:50. Preferably, the composition of the first compound and second compound and the third compound may be included in a weight ratio of 90:10, 85:15, 80:20 or 70:30. Within the ranges, bipolar characteristics may be effectively embodied, and thus efficiency and life-span may be simultaneously improved and a driving voltage may be remarkably lowered. Meanwhile, the first compound and second compound may be, for example included in a weight ratio of about 1:10 to 10:1, and specifically in a weight ratio of 2:8 to 8:2, 3:7 to 7:3, 4:6 to 6:4, and 5:5. Preferably, the first compound and second compound may be included in a weight ratio of 3:7, 4:6, or 5:5. The emission layer 32 may further include at least one compound in addition to the first compound and the second compound as a host. The emission layer 32 may further include a dopant. The dopant is mixed with a host in a small amount to cause light emission, and may be generally a material such as a metal complex that emits light by multiple excitation into a triplet or more. The dopant may be, for example an inorganic, organic, or organic/inorganic compound, and one or more kinds thereof may be used. The dopant may be a red, green, or blue dopant, for example phosphorescent dopant. Examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$L_2MX$ [Chemical Formula Z]

In Chemical Formula Z, M is a metal, and L and X are the same or different, and are a ligand to form a complex compound with M. The M may be, for example Ir, Pt, Os, Ti, Zr, Hf, Eu, Tb, Tm, Fe, Co, Ni, Ru, Rh, Pd or a combination thereof, and the L and X may be, for example a bidendate ligand. The composition may be applied to an organic layer of an organic optoelectronic device, for example an emission layer. For example, the composition may be applied as a host to an emission layer. The composition may be formed using a dry film formation method or a solution process. The dry film formation method may be, for example a chemical vapor deposition (CVD) method, sputtering, plasma plating, and ion plating, and two or more compounds may be simultaneously formed into a film or compound having the same deposition temperature may be mixed and formed into a film. The solution process may be, for example inkjet printing, spin coating, slit coating, bar coating and/or dip coating. Hereinafter, an organic optoelectronic device including the composition is described. The organic optoelectronic device may be any device to convert electrical energy into photoenergy and vice versa without particular limitation, and may be selected from an organic light emitting diode, an organic photoelectric device, an organic solar cell, an organic transistor, an organic photo conductor drum, and an organic memory device. The organic optoelectronic device includes an anode and a cathode facing each other, and at least one organic layer interposed between the anode and the cathode, wherein the organic layer includes the composition. Herein, an organic light emitting diode as one example of an organic optoelectronic device is described referring to drawings. FIG. 1 is a cross-sectional view of an organic light emitting diode according to an embodiment. Referring to FIG. 1, an organic light emitting diode 100 according to an embodiment includes an anode 120 and a cathode 110 facing each other and an organic layer 105 interposed between the anode 120 and cathode 110. The anode 120 may be made of a conductor having a large work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy) thiophene) (PEDT), polypyrrole, and polyaniline, but is not limited thereto. The cathode 110 may be made of a conductor having a small work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto. The organic layer 105 includes an emission layer 130 including composition. FIG. 2 is a cross-sectional view of an organic light emitting diode according to another embodiment. Referring to FIG. 2, an organic light emitting diode 200 according to the present embodiment includes an anode 120 and a cathode 110 facing each other and an organic layer 105 between the anode 120 and the cathode 110 like the above embodiment. The organic layer 105 includes an emission layer 130 and an auxiliary layer 140 between the emission layer 130 and the anode 120. The auxiliary layer 140 may help charge injection and transfer between the anode 120 and the emission layer 130. The auxiliary layer 140 may be, for example an electron transport layer (ETL), an electron injection layer (EIL), and/or an electron transport auxiliary layer. In FIGS. 1 and 2, at least one auxiliary layer between the anode 120 and the emission layer 130 may be further included as an organic layer 105. The organic light emitting diode may be applied to an organic light emitting diode (OLED) display. Hereinafter, the embodiments are illustrated in more detail with reference to examples. These examples, however, are not in any sense to be interpreted as limiting the scope of the invention. Hereinafter, a starting material and a reactant used in Synthesis Examples and Examples were purchased from Sigma-Aldrich Corporation or TCI Inc. unless there was particularly mentioned.

Synthesis of First Compound
(Synthesis of Intermediate)
Synthesis of intermediate I-1

[Reaction Scheme 1]

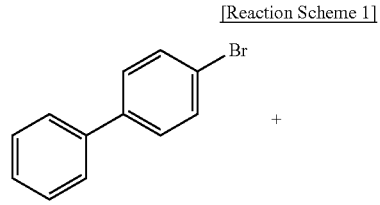

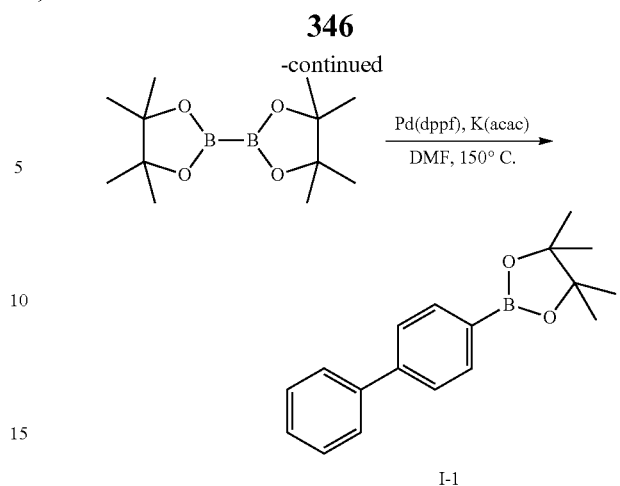

4-bromo-1,1'-biphenyl (20 g, 86 mmol) was dissolved in 1 L of dimethylformamide (DMF) under a nitrogen atmosphere, and bis(pinacolato)diboron (26 g, 103 mmol), (1,1'-bis(diphenylphosphine)ferrocene)dichloropalladium (II) (Pd(dppf)) (0.7 g, 0.86 mmol), and potassium acetate (K(acac)) (21 g, 215 mmol) were added thereto, and then heated and refluxed at 150° C. for 5 hours. When the reaction was completed, water was added to the reaction solution, and the mixture was filtered, and then dried in a vacuum oven. The obtained residue was separated and purified through flash column chromatography to obtain an intermediate I-1 (20 g, 85%). HRMS (70 eV, EI+): m/z calcd for C18H21BO2: 280.1635, found: 280.

Elemental Analysis: C, 77%; H, 8%.

Synthesis of Intermediate I-2

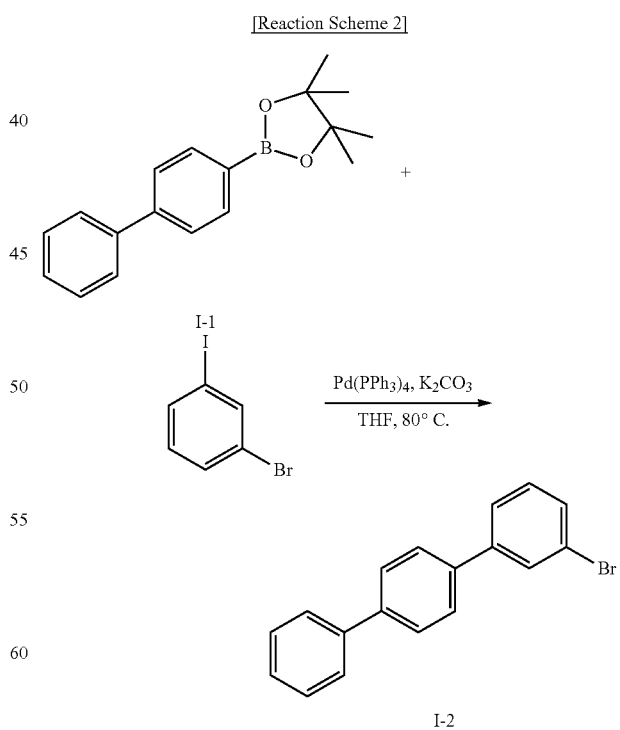

The intermediate I-1 (20 g, 71 mmol) was dissolved 1 L of THF under a nitrogen atmosphere, and then 1-bromo-3-iodobenzene (24 g, 85 mmol) and tetrakis(triphenylphosphine)palladium (Pd(PPh$_3$)$_4$) (0.8 mg, 0.7 mmol) were added thereto and then stirred. Potassium carbonate (K$_2$CO$_3$, 24.5 g, 177 mmol) saturated in water was added thereto, and the obtained mixture was heated and refluxed at 80° C. for 12 hours. When the reaction was completed, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain an intermediate I-2 (30 g, 90%). HRMS (70 eV, EI+): m/z calcd for C18H13Br: 309.1998, found 309 Elemental Analysis: C, 70%; H, 4%.

Synthesis of Intermediate I-3

[Reaction Scheme 3]

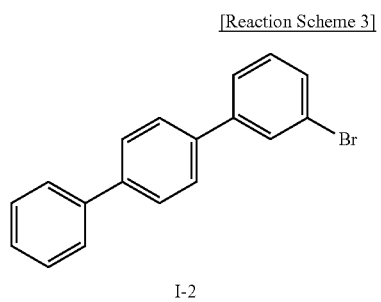

I-2

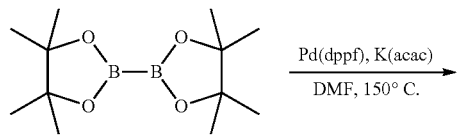

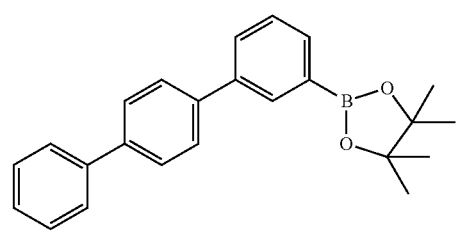

I-3

The intermediate I-2 (25 g, 81 mmol) was dissolved in 1 L of dimethylformamide (DMF) under a nitrogen atmosphere, and bis(pinacolato)diboron (25 g, 97 mmol), (1,1'-bis(diphenylphosphine)ferrocene)dichloropalladium (II) (Pd(dppf)) (0.7 g, 0.81 mmol), and potassium acetate (K(acac)) (20 g, 203 mmol) were added thereto, and then heated and refluxed at 150° C. for 5 hours. When the reaction was completed, water was added to the reaction solution, the mixture was filtered, and then dried in a vacuum oven. The obtained residue was separated and purified through flash column chromatography to obtain an intermediate I-3 (27 g, 93%). HRMS (70 eV, EI+): m/z calcd for C24H25BO2: 356.1948, found: 356.

Elemental Analysis: C, 81%; H, 7%.

Synthesis of Intermediate I-4

[Reaction Scheme 4]

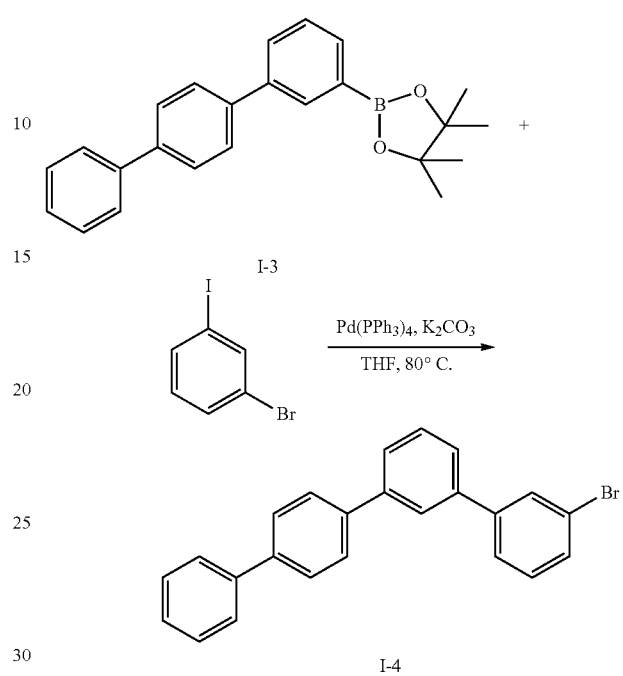

The intermediate I-3 (50 g, 140 mmol) was dissolved in 1 L of THF under a nitrogen atmosphere, and 1-bromo-3-iodobenzene (47 g, 168 mmol) and tetrakis(triphenylphosphine)palladium (Pd(PPh$_3$)$_4$) (1.6 g, 1.4 mmol) were added and then stirred. Potassium carbonate (K$_2$CO$_3$, 48 g, 350 mmol) saturated in water was added thereto, and the obtained mixture was heated and refluxed at 80° C. for 12 hours. When the reaction was completed, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain an intermediate I-4 (44 g, 89%). HRMS (70 eV, EI+): m/z calcd for C24H17Br: 384.0514, found 384 Elemental Analysis: C, 75%; H, 4%.

Synthesis of Intermediate I-5

[Reaction Scheme 5]

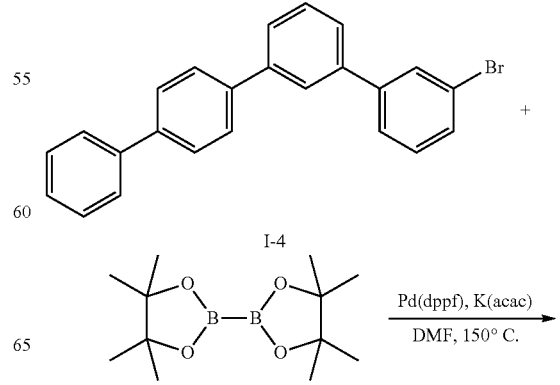

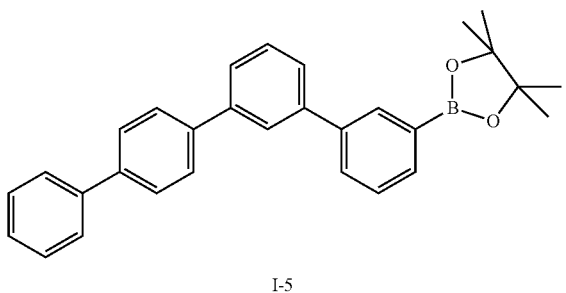

I-5

The intermediate I-4 (20 g, 52 mmol) was dissolved in 1 L of dimethylformamide (DMF) under a nitrogen atmosphere, and bis(pinacolato)diboron (16 g, 62.5 mmol), (1,1'-bis(diphenylphosphine)ferrocene)dichloropalladium (II) (Pd (dppf)) (0.4 g, 0.52 mmol), and potassium acetate (K(acac)) (13 g, 130 mmol) were added thereto, and then heated and refluxed at 150° C. for 5 hours. When the reaction was completed, water was added to the reaction solution, the mixture was filtered, and then dried in a vacuum oven. The obtained residue was separated and purified through flash column chromatography to obtain an intermediate I-5 (19 g, 85%). HRMS (70 eV, EI+): m/z calcd for C30H29BO2: 432.2261, found: 432.

Elemental Analysis: C, 83%; H, 7

Synthesis of Intermediate I-6

[Reaction Scheme 6]

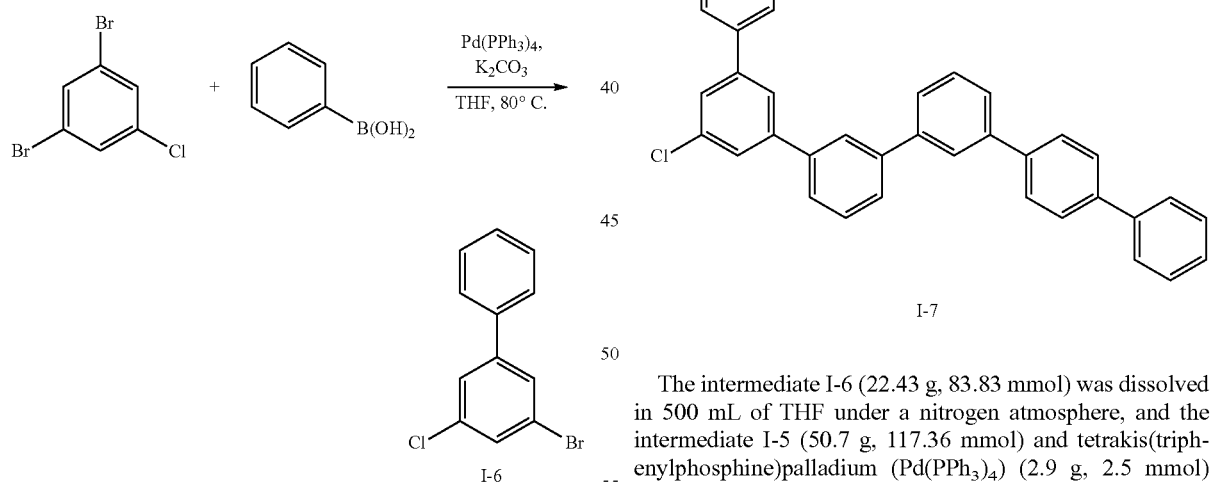

1,3-dibromo-5-chlorobenzene (100 g, 370 mmol) was dissolved in 2 L of THF under a nitrogen atmosphere, and phenylboronic acid (47.3 g, 388 mmol) and tetrakis(triphenylphosphine)palladium (Pd(PPh₃)₄) (1.5 g, 1.36 mmol) were added and then stirred. Potassium carbonate (K₂CO₃, 127 g, 925 mmol) saturated in water was added thereto, and the obtained mixture was heated and refluxed at 80° C. for 12 hours. When the reaction was completed, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain an intermediate I-6 (49 g, 50%). HRMS (70 eV, EI+): m/z calcd for C12H8BrCl: 265.9498, found 266 Elemental Analysis: C, 54%; H, 3%.

Synthesis of Intermediate I-7

[Reaction Scheme 7]

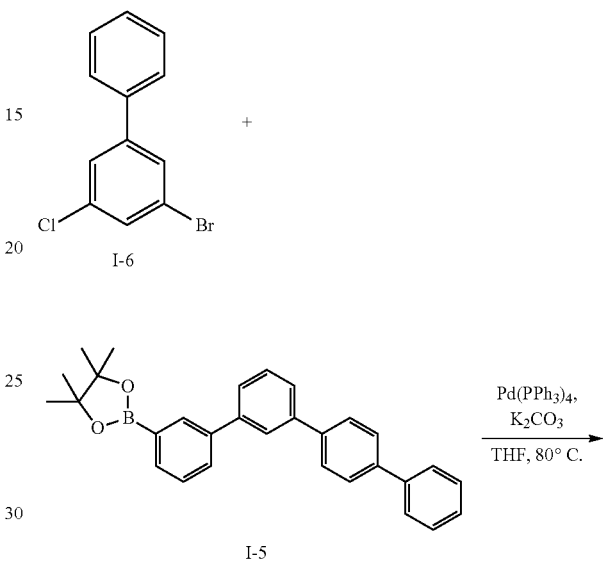

The intermediate I-6 (22.43 g, 83.83 mmol) was dissolved in 500 mL of THF under a nitrogen atmosphere, and the intermediate I-5 (50.7 g, 117.36 mmol) and tetrakis(triphenylphosphine)palladium (Pd(PPh₃)₄) (2.9 g, 2.5 mmol) were added and then stirred. Potassium carbonate (K₂CO₃, 46 g, 335.31 mmol) saturated in water was added thereto, and the obtained mixture was heated and refluxed at 80° C. for 12 hours. When the reaction was completed, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain an intermediate I-7 (33 g and 81%). HRMS (70 eV, EI+): m/z calcd for C36H25Cl: 492.1645, found 492 Elemental Analysis: C, 88%; H, 5%.

Synthesis of Intermediate I-8

[Reaction Scheme 8]

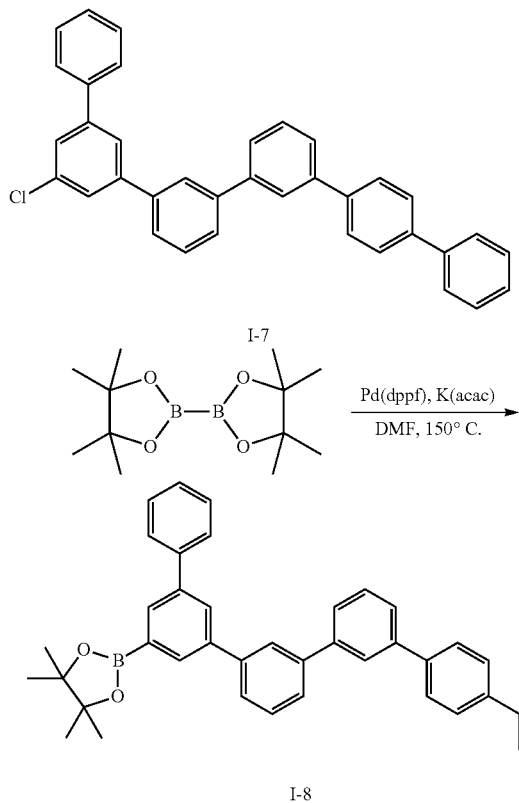

The intermediate I-7 (42 g, 85.8 mmol) was dissolved in 1 L of dimethylformamide (DMF) under a nitrogen atmosphere, and bis(pinacolato)diboron (26 g, 103 mmol), (1,1'-bis(diphenylphosphine)ferrocene)dichloropalladium (II) (Pd(dppf)) (0.7 g, 0.85 mmol), and potassium acetate (K(acac)) (58 g, 595 mmol) were added thereto, and then heated and refluxed at 150° C. for 5 hours. When the reaction was completed, water was added to the reaction solution, and the mixture was filtered, and then dried in a vacuum oven. The obtained residue was separated and purified through flash column chromatography to obtain an intermediate I-8 (42 g, 85%). HRMS (70 eV, EI+): m/z calcd for C42H37BO2: 584.2887, found: 584. Elemental Analysis: C, 86%; H, 6%.

Synthesis of Intermediate I-9

[Reaction Scheme 9]

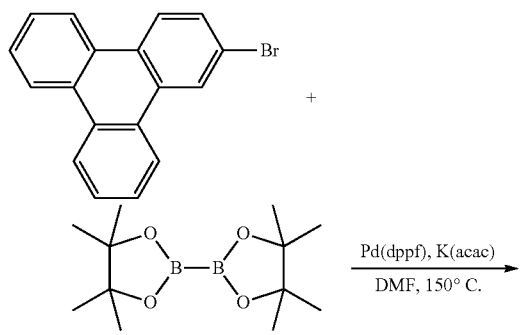

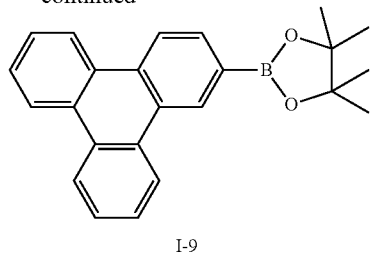

2-bromotriphenylene (100 g, 326 mmol) was dissolved in 1 L of dimethylformamide (DMF) under a nitrogen atmosphere, and bis(pinacolato)diboron (99.2 g, 391 mmol), (1,1'-bis(diphenylphosphine)ferrocene)dichloropalladium (II) (2.66 g, 3.26 mmol), and potassium acetate (80 g, 815 mmol) were added thereto, and then heated and refluxed at 150° C. for 5 hours. When the reaction was completed, water was added to the reaction solution, the mixture was filtered, and then dried in a vacuum oven. The obtained residue was separated and purified through flash column chromatography to obtain an intermediate I-9 (113 g, 98%). HRMS (70 eV, EI+): m/z calcd for C24H23BO2: 354.1791, found: 354. Elemental Analysis: C, 81%; H, 7%.

Synthesis of Intermediate I-10

[Reaction Scheme 10]

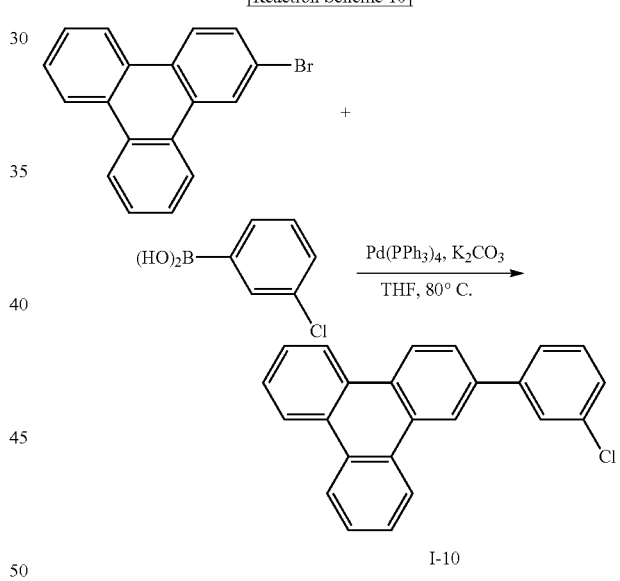

2-bromotriphenylene (32.7 g, 107 mmol) was dissolved in 0.3 L of tetrahydrofuran (THF) under a nitrogen atmosphere, and 3-chloro phenylboronic acid (20 g, 128 mmol) and tetrakis(triphenylphosphine)palladium (1.23 g, 1.07 mmol) were added and then stirred. Potassium carbonate (36.8 g, 267 mmol) saturated in water was added thereto, and the obtained mixture was heated and refluxed at 80° C. for 24 hours. When the reaction was completed, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain an intermediate I-10 (22.6 g, 63%). HRMS (70 eV, EI+): m/z calcd for C24H15Cl: 338.0862, found: 338. Elemental Analysis: C, 85%; H, 5%.

Synthesis of Intermediate I-11

[Reaction Scheme 11]

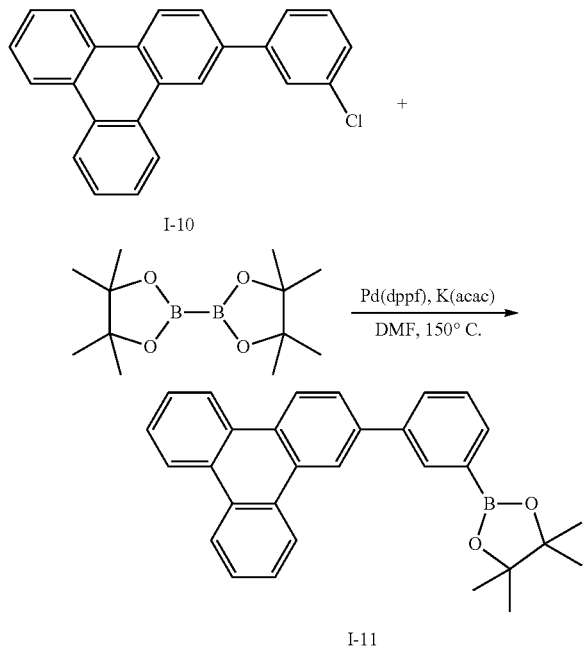

The intermediate I-10 (22.6 g, 66.7 mmol) was dissolved in 0.3 L of dimethylformamide (DMF) 0.3 L under a nitrogen atmosphere, and bis(pinacolato)diboron (25.4 g, 100 mmol), (1,1'-bis(diphenylphosphine)ferrocene)dichloropalladium(II) (0.54 g, 0.67 mmol), and potassium acetate (16.4 g, 167 mmol) was added thereto, and the obtained mixture was heated and refluxed at 150° C. for 48 hours. When the reaction was completed, water was added to the reaction solution, and the mixture was filtered, and then dried in a vacuum oven. The obtained residue was separated and purified through flash column chromatography to obtain an intermediate I-11 (18.6 g, 65%). HRMS (70 eV, EI+): m/z calcd for C30H27BO2: 430.2104, found: 430. Elemental Analysis: C, 84%; H, 6%.

Synthesis of Intermediate I-12

[Reaction Scheme 12]

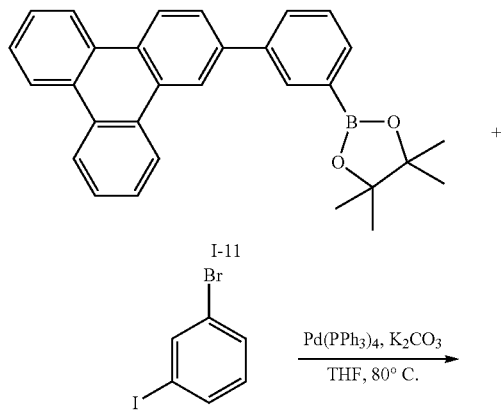

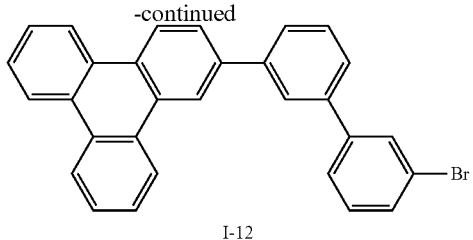

The intermediate I-11 (50 g, 116 mmol) was dissolved in 0.5 L of tetrahydrofuran (THF) under a nitrogen atmosphere, and 1-bromo-3-iodobenzene (39.4 g, 139 mmol) and tetrakis(triphenylphosphine)palladium (1.34 g, 1.16 mmol) were added and then stirred. Potassium carbonate (40.1 g, 290 mmol) saturated in water was added thereto, and the obtained mixture was heated and refluxed at 80° C. for 12 hours. When the reaction was completed, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain an intermediate I-12 (42.6 g, 80%). HRMS (70 eV, EI+): m/z calcd for C30H19Br: 458.0670, found: 458. Elemental Analysis: C, 78%; H, 4%.

Synthesis of Intermediate I-13

[Reaction Scheme 13]

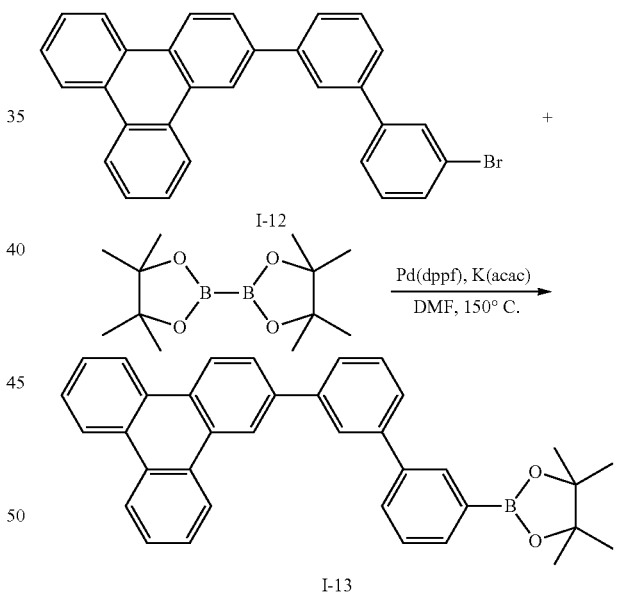

The intermediate I-12 (40 g, 87.1 mmol) was dissolved in 0.3 L of dimethylformamide (DMF) under a nitrogen atmosphere, and bis(pinacolato)diboron (26.5 g, 104 mmol), (1,1'-bis(diphenylphosphine)ferrocene)dichloropalladium (II) (0.71 g, 0.87 mmol), and potassium acetate (21.4 g, 218 mmol) were added thereto, and then heated and refluxed at 150° C. for 26 hours. When the reaction was completed, water was added to the reaction solution, and the mixture was filtered, and then dried in a vacuum oven. The obtained residue was separated and purified through flash column chromatography to obtain 34 g (77%) of an intermediate I-13. HRMS (70 eV, EI+): m/z calcd for C36H31BO2: 506.2417, found: 506. Elemental Analysis: C, 85%; H, 6%.

(Synthesis of Final Compound)

Synthesis Example 1: Synthesis of Compound A-275

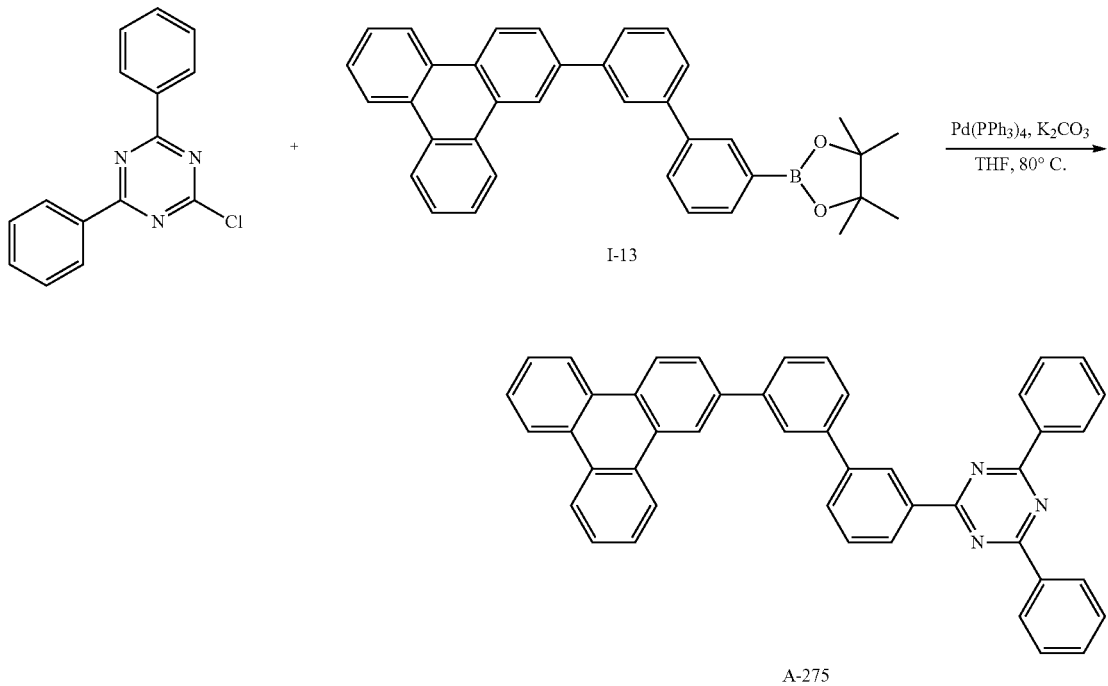

2-chloro-4,6-diphenyl-1,3,5-triazine (10.6 g, 39.5 mmol) was dissolved in 1 L of THF under a nitrogen atmosphere, and the intermediate I-13 (20 g, 39.5 mmol) and tetrakis(triphenylphosphine)palladium (Pd(PPh$_3$)$_4$) (0.46 g, 0.4 mmol) were added and then stirred. Potassium carbonate (K$_2$CO$_3$, 13.6 g, 98.8 mmol) saturated in water was added thereto, and the obtained mixture was heated and refluxed at 80° C. for 12 hours. When the reaction was completed, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain an compound A-275 (17.9 g, 74%). HRMS (70 eV, EI+): m/z calcd for C45H29N3: 611.2361, found 611 Elemental Analysis: C, 88%; H, 5%.

Synthesis Example 2: Synthesis of Compound A-216

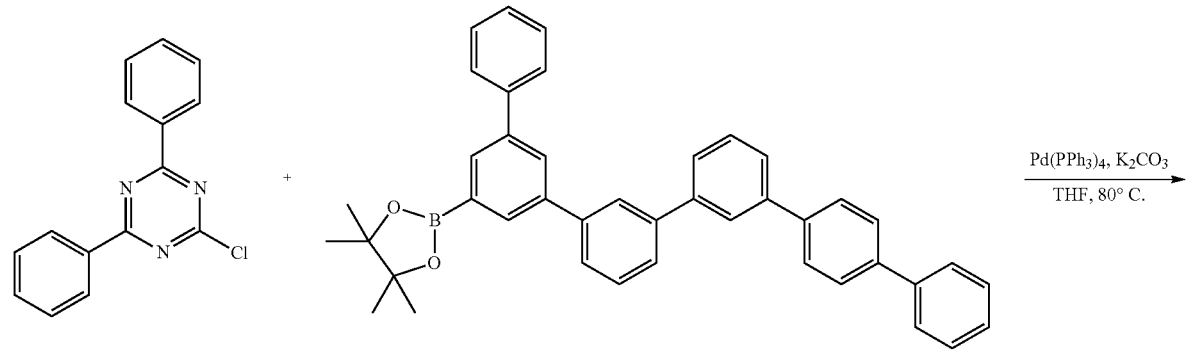

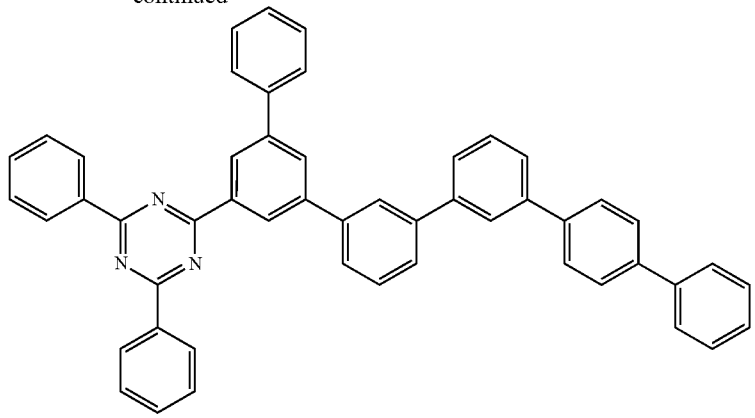

A-216

2-chloro-4,6-diphenyl-1,3,5-triazine (32 g, 76 mmol) was dissolved in 1 L of THF under a nitrogen atmosphere, and the intermediate I-8 (44 g, 76 mmol) and tetrakis(triphenylphosphine)palladium (Pd(PPh$_3$)$_4$) (0.88 g, 0.76 mmol) were added and then stirred. Potassium carbonate (K$_2$CO$_3$, 26 g, 190 mmol) saturated in water was added thereto, and the obtained mixture was heated and refluxed at 80° C. for 12 hours. When the reaction was completed, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound A-216 (41 g, 80%). HRMS (70 eV, EI+): m/z calcd for C51H35N3: 689.2831, found 689 Elemental Analysis: C, 89%; H, 5%.

Synthesis of Second Compound

Synthesis Example 3: Synthesis of Compound B-30

[Reaction Scheme 16]

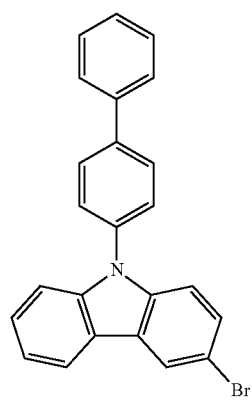

+

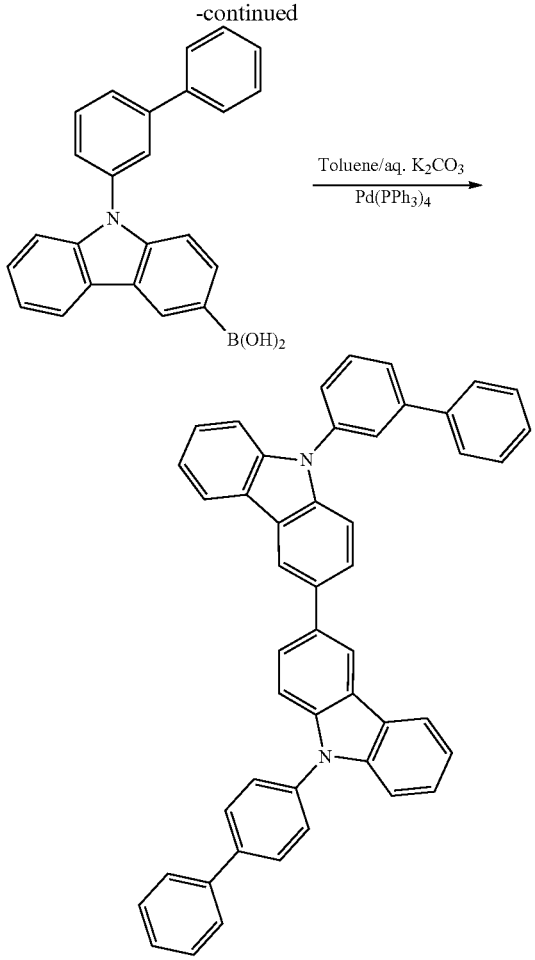

The compound 9-(4-(4,4'-biphenyl)carbazole)-3-yl bromide (12.33 g, 30.95 mmol) was dissolved in 0.2 L of toluene under a nitrogen atmosphere, and (9-(3-(4-phenyl)phenyl)carbazole-3-yl boronic acid (12.37 g, 34.05 mmol) and tetrakis(triphenylphosphine)palladium (1.07 g, 0.93 mmol) were added and then stirred. Potassium carbonate (12.83 g, 92.86 mmol) saturated in water was heated and refluxed at 120° C. for 12 hours. When the reaction was completed, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound B-30 (18.7 g, 92%). HRMS (70 eV, EI+): m/z calcd for C48H32N2 636.26, found: 636.

Elemental Analysis: C, 91%; H, 5%

Synthesis Example 4: Synthesis of Compound B-129

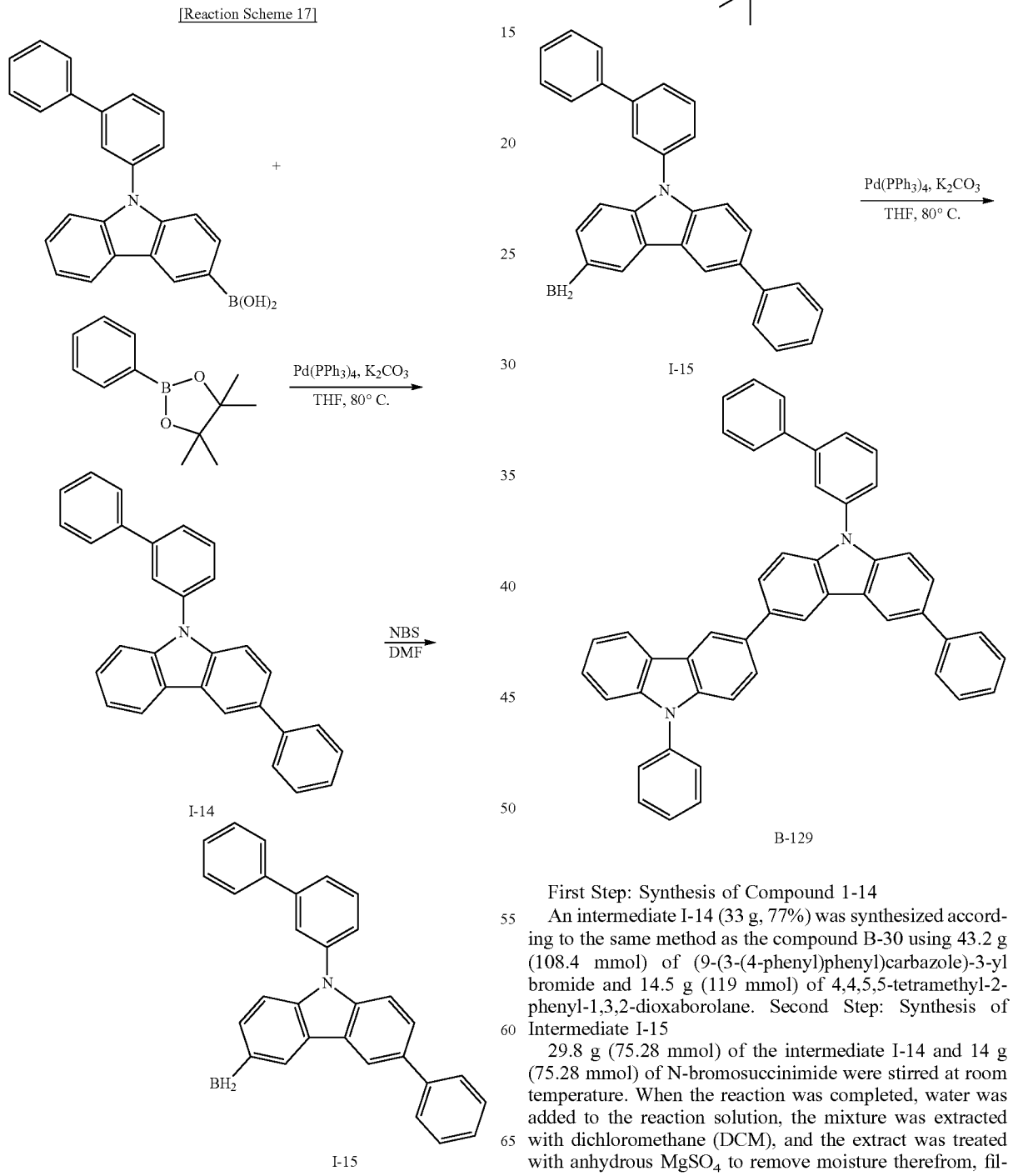

First Step: Synthesis of Compound 1-14

An intermediate I-14 (33 g, 77%) was synthesized according to the same method as the compound B-30 using 43.2 g (108.4 mmol) of (9-(3-(4-phenyl)phenyl)carbazole)-3-yl bromide and 14.5 g (119 mmol) of 4,4,5,5-tetramethyl-2-phenyl-1,3,2-dioxaborolane. Second Step: Synthesis of Intermediate I-15

29.8 g (75.28 mmol) of the intermediate I-14 and 14 g (75.28 mmol) of N-bromosuccinimide were stirred at room temperature. When the reaction was completed, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain an intermediate I-15 (29 g, 81%). Third Step: Synthesis of Compound B-129

A compound B-129 (17 g, 79%) was obtained according to the same method as the compound B-30 using 9.7 g (33.65 mmol) of 9-phenyl-3-(4,4,5,5-tetramethyl-1,3,2-dioxaborolan-2-yl)-9H-carbazole and 16 g (33.65 mmol) of the intermediate I-15. HRMS (70 eV, EI+): m/z calcd for C48H32N2 636.2565, found: 636.

Elemental Analysis: C, 90%; H, 5%.

Synthesis of Third Compound
Synthesis of Intermediate A

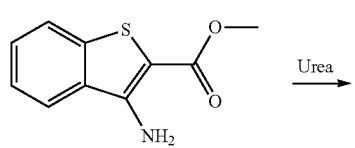

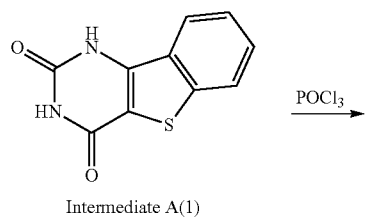

Intermediate A(1)

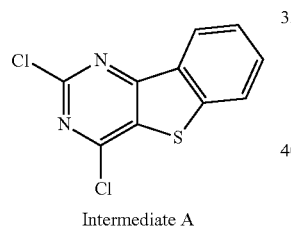

Intermediate A

Synthesis of Intermediate A (1) (benzo-1H-thieno[3,2-d]pyrimidine-2,4-dione)

A mixture of methyl 3-amino-benzo2-thiophenecarboxylate (237.5 g, 1.15 mol) and urea (397.0 g, 5.75 mol) was put in a 2 L round flask and stirred at 200° C. for 2 hours. The reaction mixture at the high temperature was cooled down to room temperature and poured into a sodium hydroxide solution, the obtained mixture was filtered to remove impurities therefrom, the reactant therefrom was acidized (HCl, 2N), and a precipitate therefrom was dried to obtain an intermediate A (1) (175 g, 75%). calcd. $C_{10}H_6N_2O_2S$: C, 55.04; H, 2.77; N, 12.84; O, 14.66; S, 14.69; found: C, 55.01; H, 2.79; N, 12.81; O, 14.69; S, 14.70.

Synthesis of Intermediate A (benzo-2,4-dichloro-thieno[3,2-d]pyrimidine)

A mixture of the intermediate A (1) (benzo-1H-thieno[3,2-d]pyrimidine-2,4-dione) (175 g, 0.80 mol) and phosphorus oxychloride (1000 mL) was stirred and refluxed in a 3000 mL round flask for 8 hours. The reaction mixture was cooled down to room temperature and poured into ice/water while strongly stirred to produce a precipitate. Then, a reactant obtained therefrom was filtered to obtain an intermediate A (benzo-2,4-dichloro-thieno[3,2-d]pyrimidine) (175 g, 85%, a white solid). The element analysis result of the intermediate A is provided as follows. calcd. $C_{10}H_4Cl_2N_2S$: C, 47.08; H, 1.58; Cl, 27.79; N, 10.98; S, 12.57; found: C, 47.03; H, 1.61; Cl, 27.81; N, 10.98; S, 12.60.

Synthesis of Intermediate B

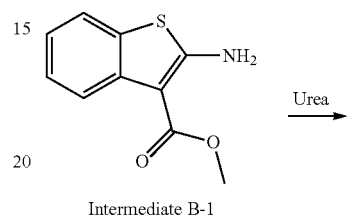

Intermediate B-1

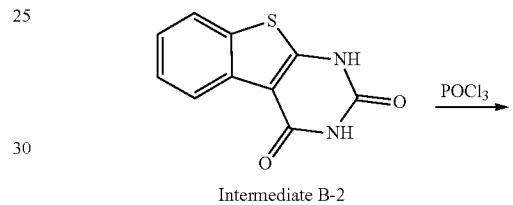

Intermediate B-2

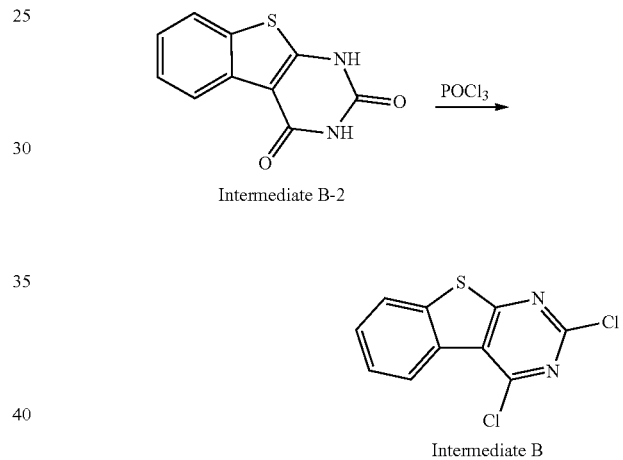

Intermediate B

Synthesis of Intermediate B-2

A mixture of the intermediate B-1 (35.0 g, 0.17 mol) and urea (50.7 g, 0.84 mol) was stirred at 200° C. for 2 hours in a 250 mL round flask. The reaction mixture at the high temperature was cooled down to room temperature and then, poured into a sodium hydroxide solution, the obtained mixture was filtered to remove impurities, the reactant therefrom was acidized (HCl, 2N), and a precipitate therefrom was dried to obtain an intermediate B-2 (18.9 g, 51%). calcd. C10H6N2O2S: C, 55.04; H, 2.77; N, 12.84; O, 14.66; S, 14.69; found: C, 55.01; H, 2.77; N, 12.83; O, 14.65; S, 14.63.

Synthesis of Intermediate B

A mixture of the intermediate B-2 (18.9 g, 99.2 mmol) and phosphorus oxychloride (100 mL) was stirred and refluxed in a 250 mL round flask for 6 hours. The reaction mixture was cooled down to room temperature and then, poured into ice/water while strongly stirred to produce a precipitate. A reactant obtained therefrom was filtered to obtain an intermediate B. (17.5 g, 85%, a white solid) calcd. C10H4Cl2N2S: C, 47.08; H, 1.58; Cl, 27.79; N, 10.98; S, 12.57; found: C, 47.04; H, 1.53; Cl, 27.74; N, 10.96; S, 12.44.

Synthesis Example 5: Synthesis of Compound H-59
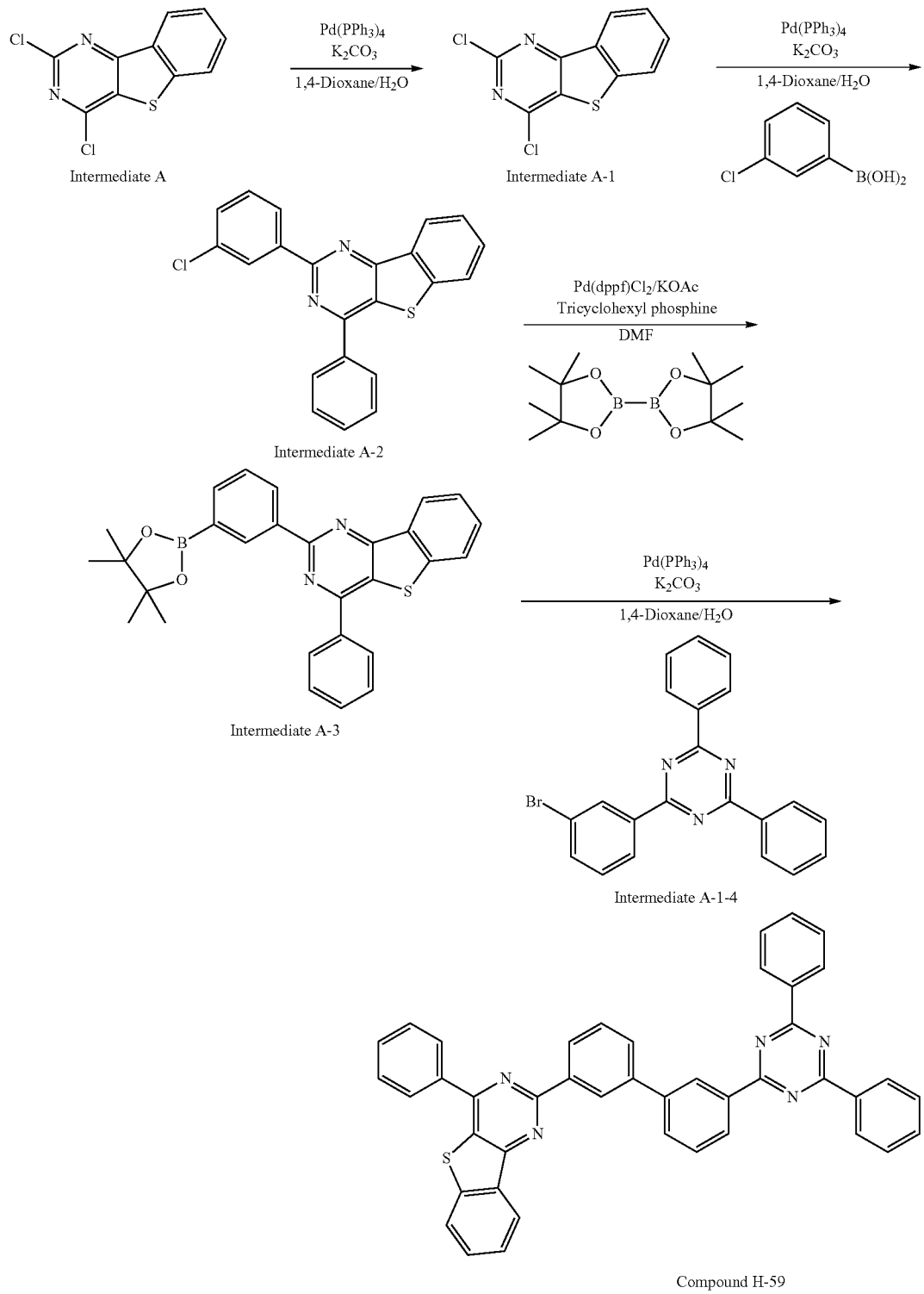
Synthesis of Intermediate A-1-1
70.0 g (274.4 mmol) of the intermediate A, 33.5 g (274.4 mmol) of phenylboronic acid, 94.8 g (686.0 mmol) of potassium carbonate, and 15.9 g (13.7 mmol) of tetrakis (triphenylphosphine) palladium (0) were added to 800 mL of 1,4-dioxane and 400 mL of water in a 2000 mL flask, and the mixture was heated under a nitrogen stream for 24 hours at 50° C. The obtained mixture was added to 3000 mL of methanol, a crystallized solid was filtered, dissolved in monochlorobenzene, and filtered with silica gel/Celite, and then, recrystallized with methanol after removing an appropriate amount of an organic solvent to obtain an intermediate A-1-1 (59.4 g, 73% of a yield). calcd. C16H9ClN2S: C, 64.75; H, 3.06; Cl, 11.95; N, 9.44; S, 10.80; found: C, 64.70; H, 3.02; Cl, 11.93; N, 9.40; S, 10.73.

Synthesis of Intermediate A-1-2

59.0 g (198.8 mmol) of the intermediate A-1-1, 31.1 g (198.8 mmol) of 3-chlorophenyl boronic acid, 68.7 g (497.0 mmol) of potassium carbonate, and 11.5 g (9.9 mmol) of tetrakis(triphenylphosphine) palladium (0) were added to 600 mL of 1,4-dioxane and 300 mL of water in a 2 L round flask, and the mixture was heated and refluxed under a nitrogen stream for 16 hours. The obtained mixture was added to 2000 mL of methanol, a crystallized solid therein was filtered, dissolved in monochlorobenzene, filtered with silica gel/Celite, and then, recrystallized with methanol after removing an appropriate amount of an organic solvent to obtain an intermediate A-1-2 (51.2 g, 69% of a yield). calcd. C22H13ClN2S: C, 70.87; H, 3.51; Cl, 9.51; N, 7.51; S, 8.60; found C, 70.84; H, 3.46; Cl, 9.50; N, 7.47; S, 8.58.

Synthesis of Intermediate A-1-3

The intermediate A-1-2 (50.0 g, 134.1 mmol), 4,4,4',4',5,5,5',5'-octamethyl-2,2'-bi(1,3,2-dioxaborolane) (40.9 g, 160.9 mmol), potassium acetate (KOAc, 39.5 g, 402.3 mmol), and 1,1'-bis(diphenylphosphino) ferrocene-palladium(II)dichloride (6.6 g, 8.1 mmol), and tricyclohexylphosphine (5.6 g, 20.1 mmol) were added to 500 mL of N,N-dimethylformamide in a 1 L flask, and the mixture was stirred at 130° C. for 24 hours. When a reaction was complete, the reaction solution was extracted with water and EA to obtain an organic layer, the organic layer was concentrated after removing moisture with magnesium sulfate and purified through column chromatography to obtain an intermediate A-1-3 as a white solid (40.3 g, a yield=69%). calcd. C28H25BN2O2S: C, 72.42; H, 5.43; B, 2.33; N, 6.03; O, 6.89; S, 6.90; found: C, 72.40; H, 5.42; B, 2.32; N, 6.00; O, 6.82; S, 6.85.

Synthesis of Compound H-59

5.0 g (10.8 mmol) of the intermediate A-1-3, 4.2 g (10.8 mmol) of the intermediate A-1-4 (obtained by reacting a product through a pinacolboron reaction of 2-chloro-4,6-diphenyl-1,3,5-triazine as a starting material like in a synthesis method of the intermediate I-8 with 1-bromo-3-iodobenzene in a synthesis method of the intermediate I-12), 3.7 g (27.0 mmol) of potassium carbonate, and 0.6 g (0.5 mmol) of tetrakis(triphenylphosphine) palladium (0) were added to 40 mL of 1,4-dioxane and 20 mL of water in a 100 mL flask and then, heated and refluxed under a nitrogen stream for 16 hours. The obtained mixture was added to 150 mL of methanol, a solid crystallized therein was filtered, dissolved in monochlorobenzene, filtered with silica gel/Celite, and then, recrystallized with methanol after removing an appropriate amount of an organic solvent to obtain a compound H-59 (4.7 g, 68% of a yield). calcd. C43H27N5S: C, 79.98; H, 4.21; N, 10.84; S, 4.97; found: C, 79.95; H, 4.20; N, 10.81; S, 4.92.

Synthesis Example 6: Synthesis of Compound H-90

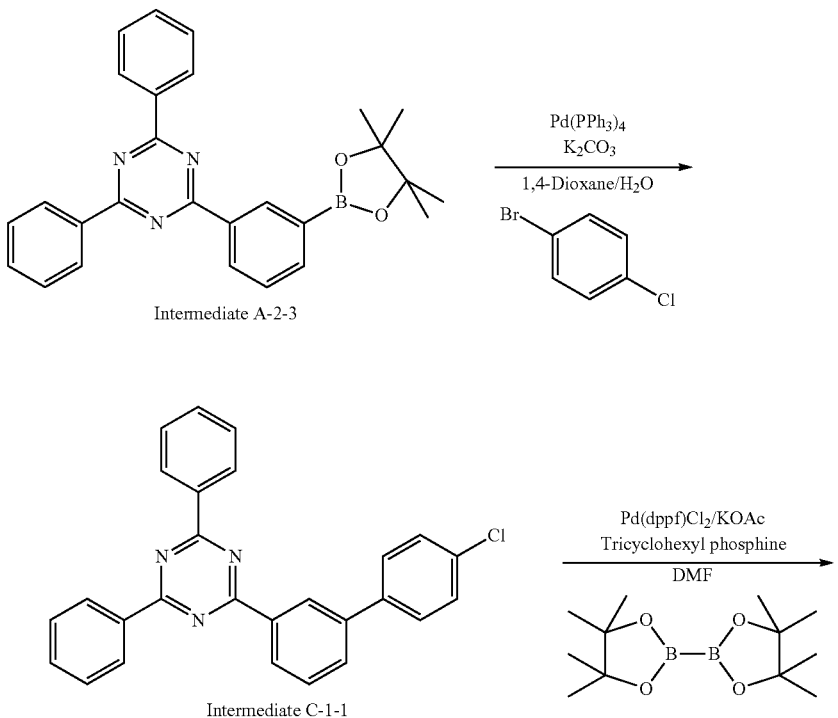

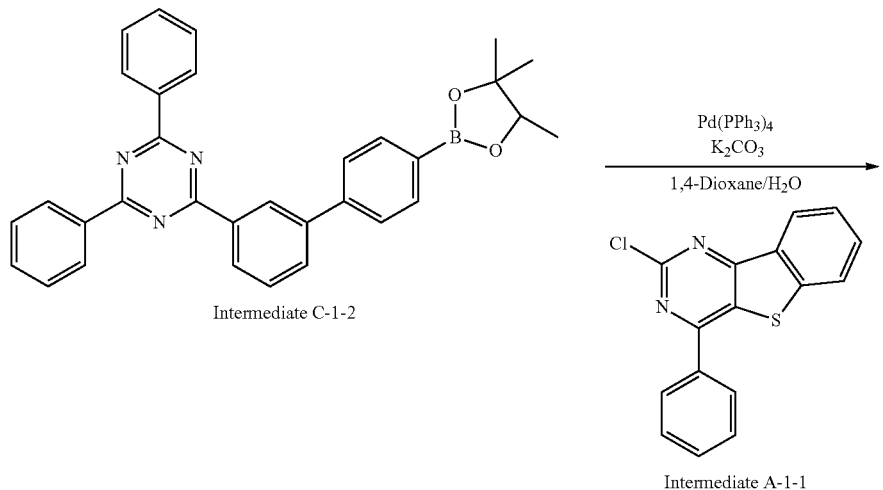

Intermediate C-1-2

Intermediate A-1-1

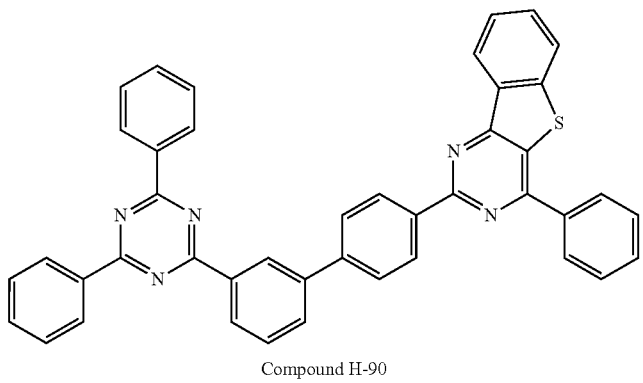

Compound H-90

Synthesis of Intermediate C-1-1

23.0 g (64.3 mmol) of the intermediate A-2-3 (prepared by reacting the intermediate A-1-4 as a starting material in a synthesis method of the intermediate I-13), 13.6 g (70.8 mmol) of 1-bromo-4-chlorobenzene, 17.8 g (128.6 mmol) of potassium carbonate, and 2.2 g (1.93 mmol) of tetrakis(triphenylphosphine) palladium (0) were added to 300 mL of 1,4-dioxane and 150 mL of water in a 1000 mL flask, and the mixture was refluxed under a nitrogen stream for 24 hours. The obtained mixture was added to 1000 mL of methanol, and a solid crystallized therein was filtered and washed with water, methanol, and hexane. Then, the solid was dried to obtain an intermediate C-1-1 as a white solid (26.8 g, 99% of a yield). calcd. C27H18ClN3: C, 77.23; H, 4.32; Cl, 8.44; N, 10.01; found: C, 77.25; H, 4.30; Cl, 8.42; N, 10.03.

Synthesis of Intermediate C-1-2

The intermediate C-1-1 (26.8 g, 63.8 mmol), 4,4,4',4',5,5,5',5'-octamethyl-2,2'-bi(1,3,2-dioxaborolane) (19.5 g, 76.6 mmol), potassium acetate (KOAc, 18.8 g, 191.5 mmol), 1,1'-bis(diphenylphosphino)ferrocene-palladium(II)dichloride (3.1 g, 3.8 mmol), and tricyclohexylphosphine (4.3 g, 15.3 mmol) were added to N,N-dimethylformamide (300 mL) in a 500 mL flask, and the mixture was stirred at 130° C. for 24 hours. When a reaction was complete, the reaction solution was treated with water and EA, an organic layer obtained therefrom was concentrated after removing moisture by using magnesium sulfate and purified through column chromatography to obtain an intermediate C-1-2 as a white solid (22.5 g, a yield=69%). calcd. C33H30BN3O2: C, 77.50; H, 5.91; B, 2.11; N, 8.22; O, 6.26; found: C, 77.52; H, 5.89; B, 2.13; N, 8.18; O, 6.28.

Synthesis of Compound H-90

20.0 g (39.1 mmol) of the intermediate C-1-2, 12.8 g (43.0 mmol) of the intermediate A-1-1, 10.8 g (78.2 mmol) of potassium carbonate, and 1.4 g (1.2 mmol) of tetrakis(triphenylphosphine) palladium (0) were added to 200 mL of 1,4-dioxane and 100 mL of water in a 500 mL flask, and the mixture was heated and refluxed under a nitrogen stream for 12 hours. The obtained mixture was added to 150 mL of methanol, a solid crystallized therein was filtered, dissolved in dichlorobenzene, filtered with silica gel/Celite, and then, recrystallized with methanol after removing an appropriate amount of an organic solvent to obtain a compound H-90 (22.4 g, 89% of a yield). calcd. C43H27N5S: C, 79.98; H, 4.21; N, 10.84; S, 4.97; found: C, 79.96; H, 4.23; N, 10.82; S, 4.99.

Synthesis Example 7: Synthesis of Compound H-91
[Reaction Scheme 20]
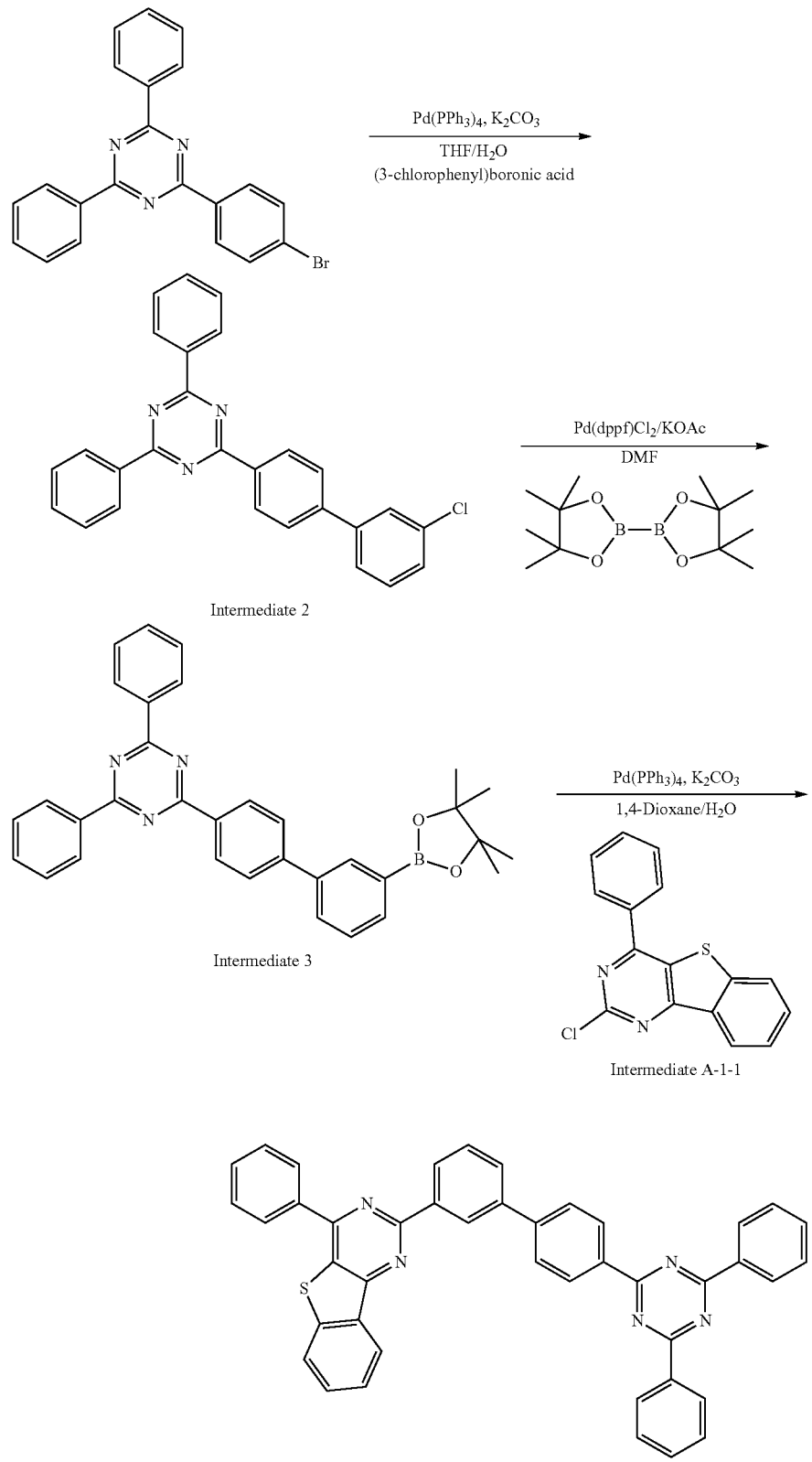

Synthesis of Intermediate 2

The compound, 2-(4-bromophenyl)-4,6-diphenyl-1,3,5-triazine (50 g, 128 mmol) was dissolved in 1 L of THF under a nitrogen atmosphere, and (4-chlorophenyl)boronic acid (24 g, 155 mmol) and tetrakis(triphenylphosphine)palladium (1.5 g, 1.3 mmol) were added and then stirred. Potassium carbonate (44 g, 320 mmol) saturated in water was added thereto, and the obtained mixture was heated and refluxed at 80° C. for 12 hours. When the reaction was completed, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain an intermediate 2 (2-(3'-chloro-[1,1'-biphenyl]-4-yl)-4,6-diphenyl-1,3,5-triazine) (51 g, 95%). HRMS (70 eV, EI+): m/z calcd for C27H18ClN3: 419.1189, found: 419. Elemental Analysis: C, 77%; H, 4%.

Synthesis of Intermediate 3

The intermediate 2 (50 g, 119 mmol) was dissolved in 1 L of dimethylformamide (DMF) under a nitrogen atmosphere, and bis(pinacolato)diboron (36 g, 142 mmol), bis(diphenylphosphine)ferrocene)dichloropalladium(II) (1 g, 1.19 mmol) and potassium acetate (29 g, 298 mmol) were added thereto, and the obtained mixture was heated and refluxed at 150° C. for 48 hours. When the reaction was completed, water was added to the reaction solution, the mixture was filtered and then, dried in a vacuum oven. The obtained residue was separated and purified through flash column chromatography to obtain an intermediate 3 (54 g, 88%). HRMS (70 eV, EI+): m/z calcd for C33H30BN3O2: 511.2431, found: 511.

Elemental Analysis: C, 77%; H, 6%

Synthesis of Compound H-91

The intermediate 3 (20 g, 39 mmol) was dissolved in 0.2 L of 1,4 dioxane under a nitrogen atmosphere, and the intermediate A-1-1 (11.5 g, 39 mmol) and tetrakis(triphenylphosphine)palladium (0.45 g, 0.39 mmol) were added and then stirred. Potassium carbonate (13.5 g, 97 mmol) saturated in water was heated and refluxed at 80° C. for 20 hours. When the reaction was completed, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain a compound H-91 (19 g, 79%). HRMS (70 eV, EI+): m/z calcd for C43H27N5S: 645.1987, found: 645.

Elemental Analysis: C, 80%; H, 4%

Synthesis Example 8: Synthesis of Compound H-173

[Reaction Scheme 21]

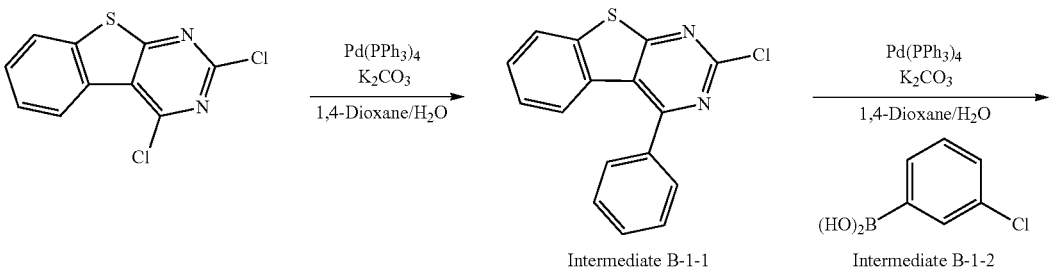

Intermediate B-1-1       Intermediate B-1-2

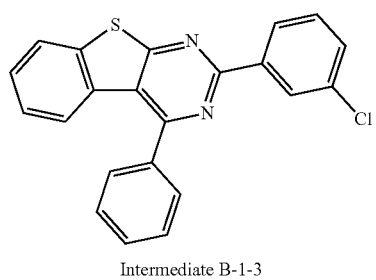

Intermediate B-1-3

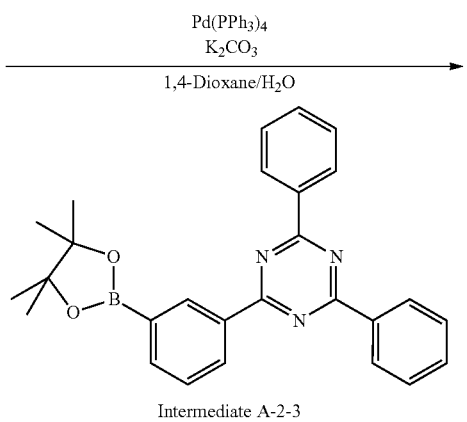

Intermediate A-2-3

-continued

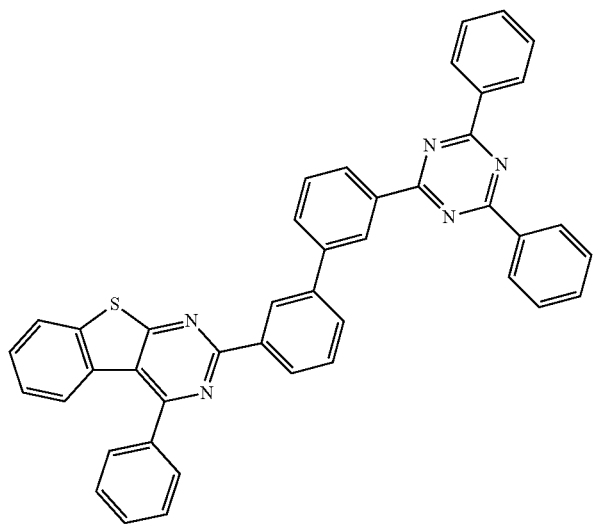

Synthesis of Intermediate B-1-1

10.0 g (39.2 mmol) of the intermediate B, 5.3 g (43.1 mmol) of phenylboronic acid, 13.5 g (98.0 mmol) of potassium carbonate, and 2.3 g (2.0 mmol) of tetrakis(triphenylphosphine) palladium (0) were added to 140 mL of 1,4-dioxane and 70 mL of water in a 500 mL flask, and the mixture was heated under a nitrogen stream for 10 hours at 60° C. The obtained mixture was added to 450 mL of methanol, and a solid crystallized therein was filtered, dissolved in monochlorobenzene, filtered with silica gel/Celite, and then, recrystallized with methanol after removing an appropriate amount of an organic solvent to obtain an intermediate B-1-1 (8.0 g, 69% of a yield). calcd. C16H9ClN2S: C, 64.75; H, 3.06; Cl, 11.95; N, 9.44; S, 10.80; found: C, 64.72; H, 3.06; Cl, 11.94; N, 9.42; S, 10.77.

Synthesis of Intermediate B-1-3

An intermediate B-1-3 (10.3 g, 65% of a yield) was synthesized according to the same synthesis method as the method of synthesizing the intermediate A-1-2 according to Synthesis Example 5 except for using the intermediate B-1-1 instead of the intermediate A-1-1. calcd. C22H13ClN2S: C, 70.87; H, 3.51; Cl, 9.51; N, 7.51; S, 8.60; found: C, 70.83; H, 3.49; Cl, 9.47; N, 7.50; S, 8.54.

Synthesis of Compound H-173

A compound H-173 (4.1 g, 39% of a yield) was synthesized by using the same synthesis method as the method of synthesizing the compound intermediate A-1-3 according to Synthesis Example 5 except for using the intermediate B-1-3 instead of the intermediate A-1-2 and treating a product therefrom in the same synthesis method as the method of synthesizing the compound H-59 according to Synthesis Example 5. calcd. C43H27N5S: C, 79.98; H, 4.21; N, 10.84; S, 4.97; found: C, 79.94; H, 4.17; N, 10.82; S, 4.95.

Synthesis Example 9: Synthesis of Compound H-230

[Reaction Scheme 22]

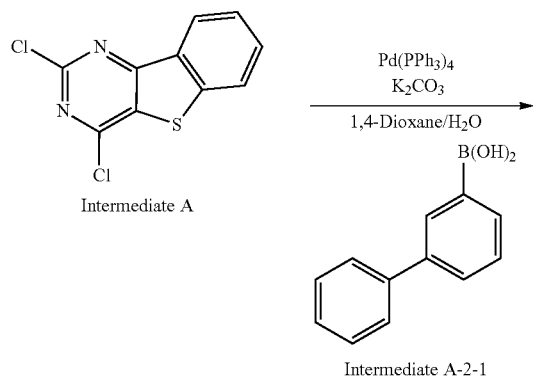

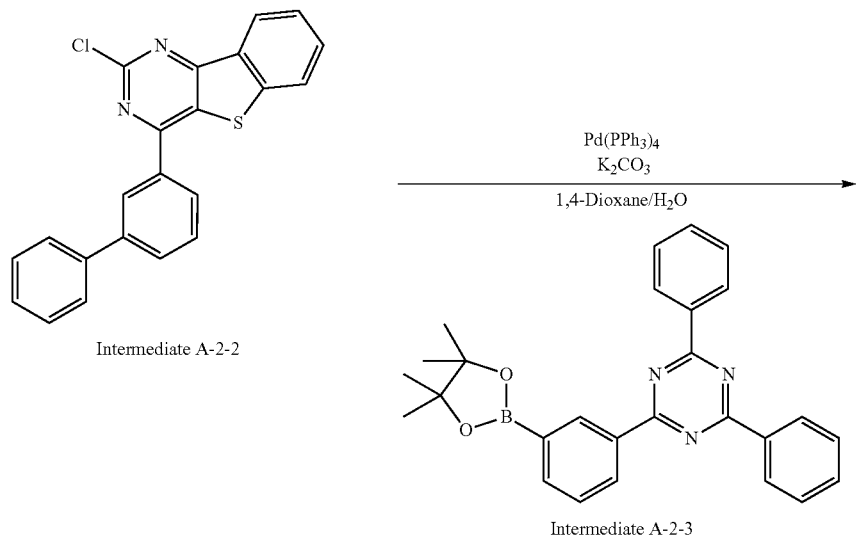

Intermediate A-2-2

Intermediate A-2-3

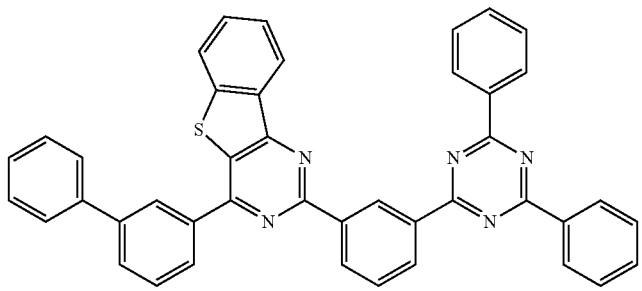

Synthesis of Intermediate A-2-2

10.0 g (39.2 mmol) of the intermediate A, 12.1 g (43.1 mmol) of the intermediate A-2-1, 13.5 g (98.0 mmol) of potassium carbonate, and 2.3 g (43.1 mmol) of tetrakis (triphenylphosphine) palladium (0) were added to 140 mL of 1,4-dioxane and 70 mL of water in a 500 mL flask, and the mixture was heated under a nitrogen stream for 12 hours at 60° C. The obtained mixture was added to 500 mL of methanol, and a solid crystallized therein was filtered, dissolved in monochlorobenzene, filtered through silica gel/Celite, and then, recrystallized with methanol after removing an appropriate amount of an organic solvent to obtain an intermediate A-2-2 (10.1 g, 69% of a yield). calcd. $C_{22}H_{13}ClN_2S$: C, 70.87; H, 3.51; Cl, 9.51; N, 7.51; S, 8.60; found: C, 70.80; H, 3.50; Cl, 9.47; N, 7.49; S, 8.60.

Synthesis of Compound H-230

10.0 g (26.8 mmol) of the intermediate A-2-2, 11.7 g (26.8 mmol) of the intermediate A-2-3, 9.3 g (67.1 mmol) of potassium carbonate, and 1.6 g (1.3 mmol) of tetrakis (triphenylphosphine) palladium (0) were added to 90 mL of 1,4-dioxane and 45 mL of water in a 250 mL flask, and the mixture was heated under a nitrogen stream for 12 hours at 70° C. The obtained mixture was added to 250 mL of methanol, and a solid crystallized therein was filtered, dissolved in monochlorobenzene, filtered with silica gel/Celite, and then, recrystallized with methanol after removing an appropriate amount of an organic solvent to obtain a compound H-230 (12.4 g, 72% of a yield). calcd. $C_{43}H_{27}N_5S$: C, 79.98; H, 4.21; N, 10.84; S, 4.97; found: C, 79.97; H, 4.19; N, 10.81; S, 4.96.

Synthesis Example 10: Synthesis of Compound F-2

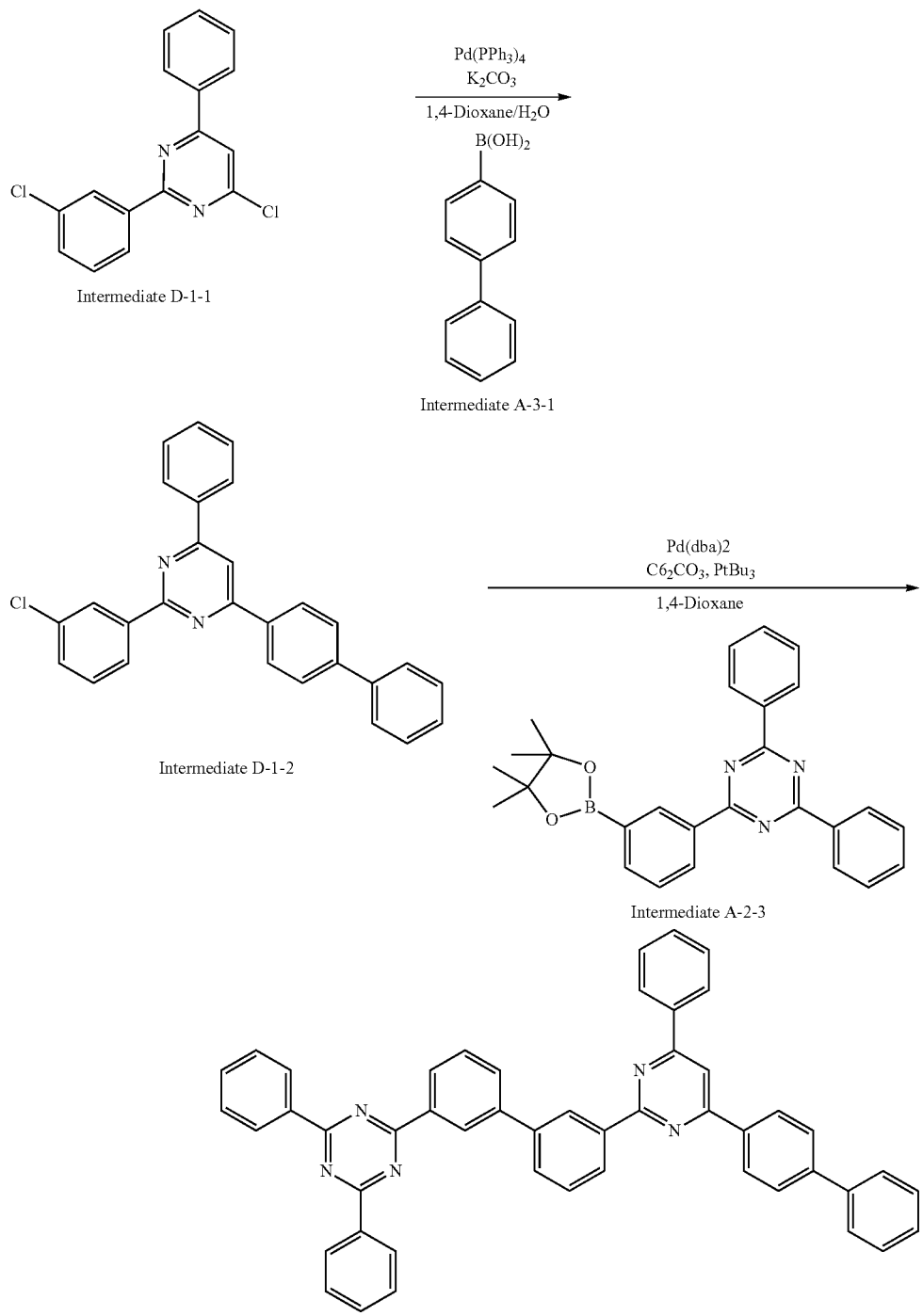

Synthesis of Intermediate D-1-2

11.8 g (39.2 mmol) of the intermediate D-1-1 (commercially available, Aurora Building Blocks), 12.1 g (43.1 mmol) of the intermediate A-3-1, 13.5 g (98.0 mmol) of potassium carbonate, and 2.3 g (43.1 mmol) of tetrakis (triphenylphosphine) palladium (0) were added to 140 mL of 1,4-dioxane and 70 mL of water in a 500 mL flask, and the mixture was heated under a nitrogen stream for 12 hours at 60° C. The obtained mixture was added to 500 mL of methanol, and a solid crystallized therein was filtered, dissolved in monochlorobenzene, filtered with silica gel/Celite, and then, recrystallized with methanol after removing an appropriate amount of an organic solvent to obtain an intermediate D-1-2 (13.1 g, 80% of a yield). calcd.

C28H19ClN2: C, 80.28; H, 4.57; Cl, 8.46; N, 6.69; found: C, 80.25; H, 4.55; Cl, 8.41; N, 6.68.

Synthesis of Compound F-2

12.0 g (28.6 mmol) of the intermediate D-1-2, 12.5 g (28.6 mmol) of the intermediate A-2-3, 23.3 g (71.5 mmol) of cesiumcarbonate ($Cs_2CO_3$), 1.1 g (0.6 mmol) of tris (dibenzylidene-acetone) dipalladium (0), and 0.9 mL of tri t-butylphosphine (50% in toluene) were added to 120 mL of 1,4-dioxane in a 250 mL flask, and the mixture was heated under a nitrogen stream for 18 hours at 110° C. The obtained mixture was added to 250 mL of methanol, and a solid crystallized therein was filtered, dissolved in monochlorobenzene, filtered with silica gel/Celite, and then, recrystallized with methanol after removing an appropriate of an organic solvent to obtain a compound F-2 (13.8 g, 70% of a yield). calcd. C49H33N5: C, 85.07; H, 4.81; N, 10.12; found: C, 85.09; H, 4.80; N, 10.10.

Manufacture of Organic Light Emitting Diode

Example 1

A glass substrate coated with ITO (indium tin oxide) as a 1500 Å-thick thin film was ultrasonic wave-washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700Å-thick hole injection layer was formed on the ITO substrate by vacuum depositing the compound A, and a hole transport layer was formed on the injection layer by depositing the compound B to be 50Å thick and the compound C to be 1020Å thick. A 400 Å thick emission layer was formed on the hole transport layer (HTL) by vacuum depositing a first compound A-275 of Synthesis Example 1, a second compound B-30 of Synthesis Example 3, and a third compound H-59 of Synthesis Example 5 simultaneously as a host and 10 wt % of tris(2-phenylpyridine)iridium(III) [$Ir(ppy)_3$] doped as a dopant. Herein the compound A-275 and the compound B-30 was used in a weight ratio of 3:7, and a composition of the compound A-275 and the compound B-30 and the compound H-59 were used in a weight ratio of 8:2. Subsequently, on the emission layer, a 300 Å-thick electron transport layer was formed by simultaneously vacuum-depositing the compound D and Liq in a ratio of 1:1, and on the electron transport layer, Liq and Al were sequentially vacuum-deposited to be 15 Å thick and 1200 Å thick, manufacturing an organic light emitting diode. The organic light emitting diode had a structure of 5-layered organic thin films specifically as follows. The structure was as follows: ITO/Compound A 700 Å/Compound B 50 Å/Compound C 1020 Å/EML[{(Compound A-275:Compound B-30=3:7 wt %):Compound H-59}=8:2]:$Ir(ppy)_3$=X: X:10%] 400 Å/Compound D:Liq 300 Å/Liq 15 Å/AI 1200 Å. (X=a weight ratio)

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Example 2

An organic light emitting diode was manufactured according to the same method as Example 1 except for changing the mixing ration of the composition of the compounds A-275 and B-30 and the compound H-59 into 7:3.

Example 3

An organic light emitting diode was manufactured according to the same method as Example 1 except for using the compound H-90 according to Synthesis Example 6 as a third compound instead of the third compound H-59 in an emission layer.

Example 4

An organic light emitting diode was manufactured according to the same method as Example 1 except for using the compound H-91 according to Synthesis Example 7 as a third compound instead of the third compound H-59 in an emission layer.

Example 5

An organic light emitting diode was manufactured according to the same method as Example 1 except for using the compound H-173 according to Synthesis Example 8 as a third compound instead of the third compound H-59 in an emission layer.

Example 6

An organic light emitting diode was manufactured according to the same method as Example 1 except for using the compound H-230 according to Synthesis Example 9 as a third compound instead of the third compound H-59 in an emission layer.

Example 7

An organic light emitting diode was manufactured according to the same method as Example 1 except for changing the mixing ration of the composition of the compounds A-275 and B-30 and the compound H-230 into 85:15.

Example 8

An organic light emitting diode was manufactured according to the same method as Example 1 except for using the compound F-2 according to Synthesis Example 10 as a third compound instead of the third compound H-59 in an emission layer.

Example 9

An organic light emitting diode was manufactured according to the same method as Example 2 except for using the compound B-129 according to Synthesis Example 4 as a third compound instead of the second compound B-30 in an emission layer.

Example 10

An organic light emitting diode was manufactured according to the same method as Example 9 except for using the compound A-216 according to Synthesis Example 2 as a first compound instead of the first compound A-275 in an emission layer.

Reference Example 1

An organic light emitting diode was manufactured according to the same method as Example 9 except for using no third compound.

Reference Example 2

An organic light emitting diode was manufactured according to the same method as Example 10 except for using no third compound.

Comparative Example 1

An organic light emitting diode was manufactured according to the same method as Example 1 except for using no third compound.

Evaluation

Driving voltages and luminous efficiency characteristics of organic light emitting diodes according to Examples 1 to 10, Reference Examples 1 and 2 and Comparative Example 1 were evaluated. The measurements were specifically performed in the following methods, and the results are shown in Table 1.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Power efficiency (lm/W) at the same current density (10 mA/cm$^2$) was calculated by using the luminance, current density, and voltages (V) from the items (1) and (2).

(4) Measurement of Driving Voltage

Driving voltages of each device were measured at 15 mA/cm$^2$ using a current-voltage meter (Keithley 2400).

Referring to Table 1, when the third host was introduced according to the present invention, Examples showed a sharply deteriorated driving voltage and simultaneously, remarkably increased power efficiency compared with Comparative Example 1 consisting of only the first and second hosts. This result may be obtained by adding the third compound having excellent electron injection and transport capability as a host according to the present invention and thus minimizing a trap phenomenon due to a LUMO energy level between a dopant and a host, and accordingly, an organic optoelectronic device having excellent efficiency and life-span as well as a low driving voltage may be manufactured. While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A composition for an organic optoelectronic device, the composition comprising a mixture of:
   at least one first compound represented by Chemical Formula 1,
   at least one second compound selected from a compound represented by Chemical Formula 2, and a compound consisting of a combination of a moiety represented by Chemical Formula 3 and a moiety represented by Chemical Formula 4, and
   at least one third compound,

[Chemical Formula 1]

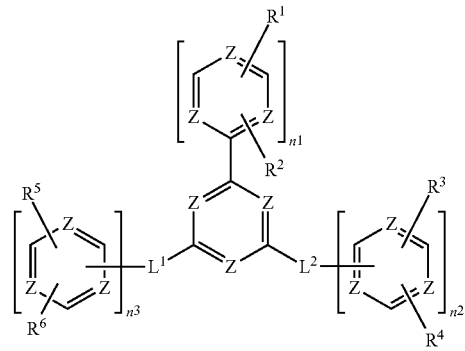

TABLE 1

| Nos. | First host | Second host | Ratio of first host:second host | Third host | Composition of first host and second host:third host | Driving Voltage (Vd) | Δ Driving voltage (%) | Power Efficiency (lm/W) | Δ Power efficiency (%) |
|---|---|---|---|---|---|---|---|---|---|
| Example 1 | A-275 | B-30 | 30:70 | H-59 | 80:20 | 3.83 | 84 | 40.2 | 122% |
| Example 2 | A-275 | B-30 | 30:70 | H-59 | 70:30 | 3.79 | 77 | 39.2 | 119% |
| Example 3 | A-275 | B-30 | 30:70 | H-90 | 80:20 | 3.93 | 80 | 39.6 | 120% |
| Example 4 | A-275 | B-30 | 30:70 | H-91 | 80:20 | 3.99 | 81 | 38.4 | 117% |
| Example 5 | A-275 | B-30 | 30:70 | H-173 | 80:20 | 4.12 | 83 | 37.2 | 113% |
| Example 6 | A-275 | B-30 | 30:70 | H-230 | 80:20 | 4.03 | 82 | 39.7 | 121% |
| Example 7 | A-275 | B-30 | 30:70 | H-230 | 85:15 | 4.14 | 84 | 39.0 | 119% |
| Example 8 | A-275 | B-30 | 30:70 | F-2 | 80:20 | 4.07 | 82 | 38.4 | 117% |
| Example 9 | A-275 | B-129 | 30:70 | H-59 | 70:30 | 4.13 | 93 | 40.9 | 122% |
| Example 10 | A-216 | B-129 | 30:70 | H-59 | 70:30 | 4.07 | 93 | 40.7 | 128% |
| Reference Example 1 | A-275 | B-129 | 30:70 | — | — | 4.72 | 100 | 33.5 | 100% |
| Reference Example 2 | A-216 | B-129 | 30:70 | — | — | 4.37 | 100 | 31.9 | 100% |
| Comparative Example 1 | A-275 | B-30 | 30:70 | — | — | 4.94 | 100 | 32.9 | 100% | wherein, in Chemical Formula 1,

Z is independently N, C, or $CR^a$, at least one of Z is N, $R^1$ to $R^6$ and $R^a$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^1$ to $R^6$ and $R^a$ are independently present or adjacent groups are linked to each other to form a ring, $L^1$ and $L^2$ are independently a single bond, a substituted or unsubstituted C6 to C30 arylene group, a substituted or unsubstituted C2 to C30 heteroarylene group, or a combination thereof, n1 is 1, n2 and n3 are independently an integer of 0 or 1, and $1 \leq n2+n3 \leq 2$;

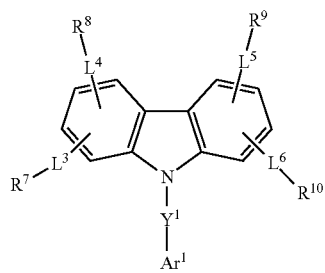

[Chemical Formula 2]

wherein, in Chemical Formula 2, $L^3$ to $L^6$ and $Y^1$ are independently, a single bond, a substituted or unsubstituted C6 to C30 arylene group, a substituted or unsubstituted C2 to C30 heteroarylene group, or a combination thereof, $Ar^1$ is a substituted or unsubstituted C6 to C30 aryl group, a substituted or unsubstituted C2 to C30 heterocyclic group, or a combination thereof, $R^7$ to $R^{10}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and at least one of $R^7$ to $R^{10}$ and $Ar^1$ includes a substituted or unsubstituted triphenylene group or a substituted or unsubstituted carbazole group,

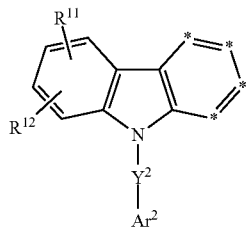

[Chemical Formula 3]

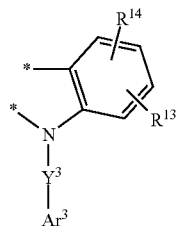

[Chemical Formula 4]

wherein, in Chemical Formulae 3 and 4, $Y^2$ and $Y^3$ are independently a single bond, a substituted or unsubstituted C6 to C30 arylene group, a substituted or unsubstituted C2 to C30 heteroarylene group, or a combination thereof, $Ar^2$ and $Ar^3$ are independently substituted or unsubstituted C6 to C30 aryl group, a substituted or unsubstituted C2 to C30 heterocyclic group, or a combination thereof, $R^{11}$ to $R^{14}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, two adjacent *'s of Chemical Formula 3 is combined with two *'s of Chemical Formula 4 to form a fused ring and in Chemical Formula 3, *'s not forming the fused ring are independently $CR^c$, and $R^c$ is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;

wherein the at least one third compound is selected from the following compounds:

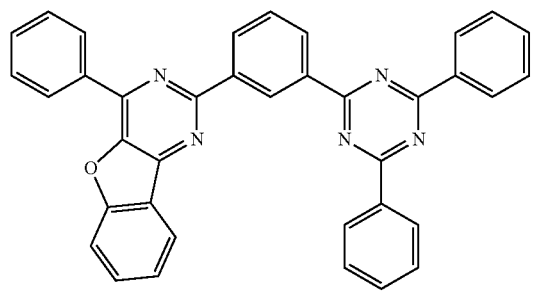

[H-1]

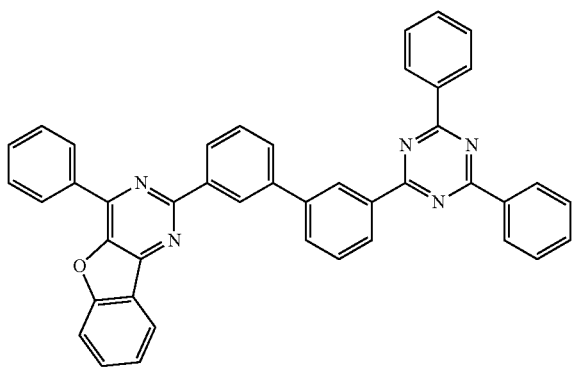

[H-2]

-continued
[H-3]
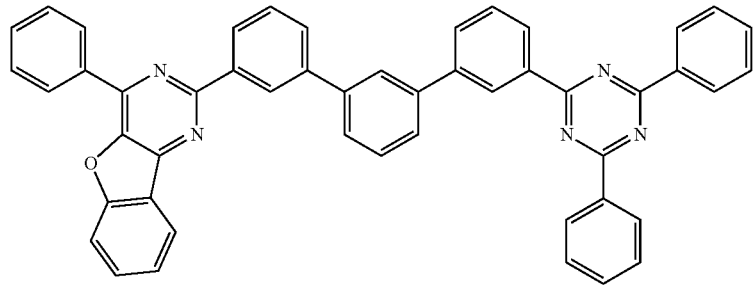
[H-4]
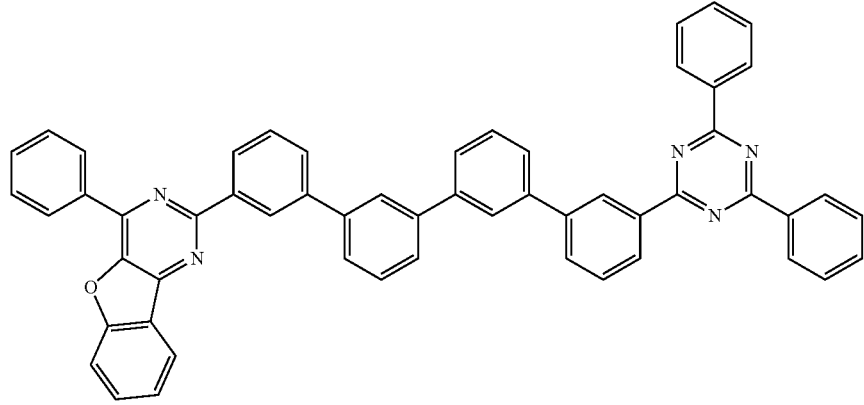
[H-33]
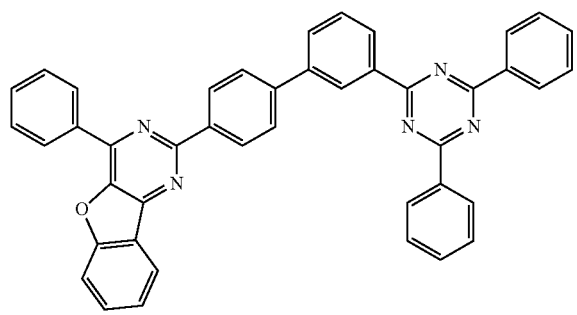
[H-53]
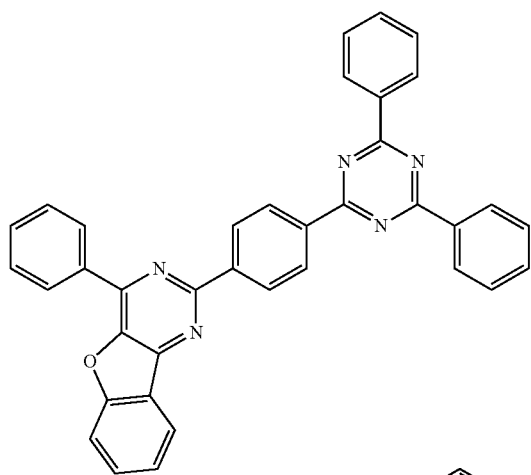
[H-54]
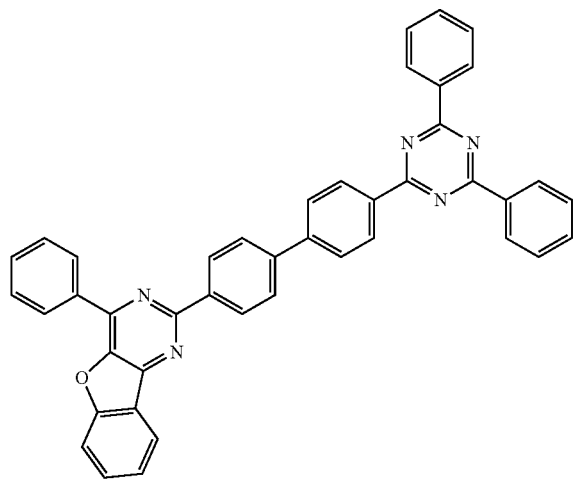
[H-56]
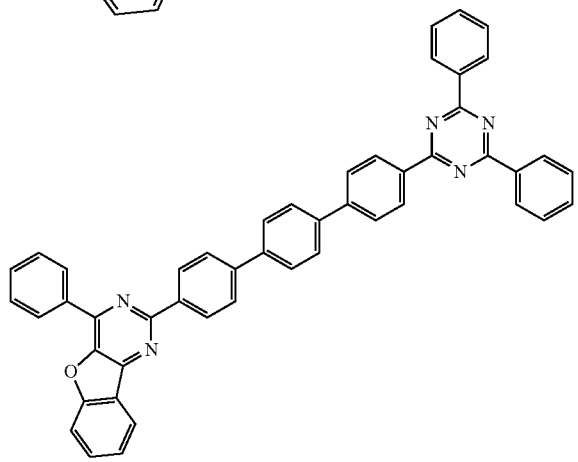

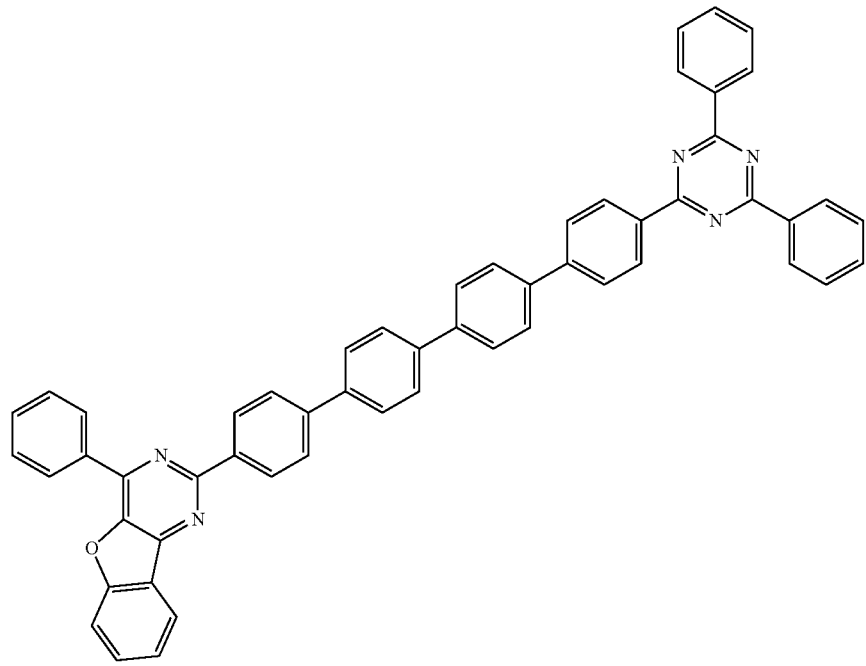
[H-57]
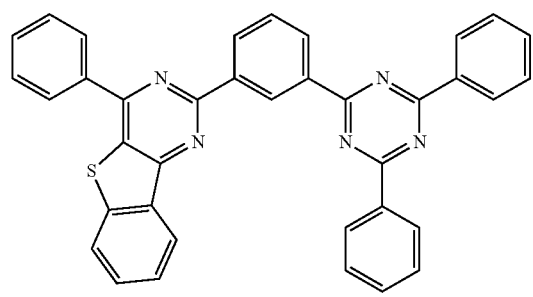
[H-58]
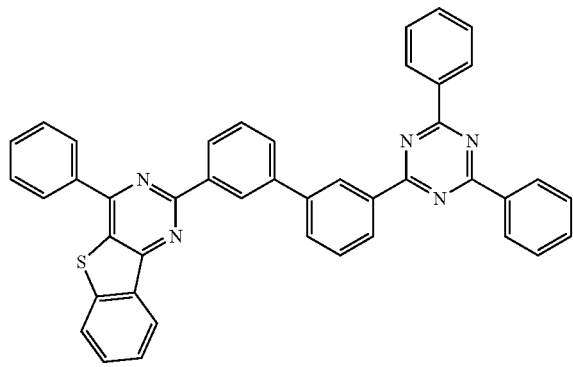
[H-59]
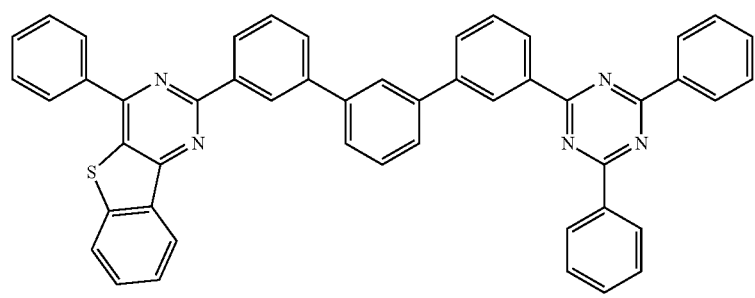
[H-60]

-continued
[H-61]
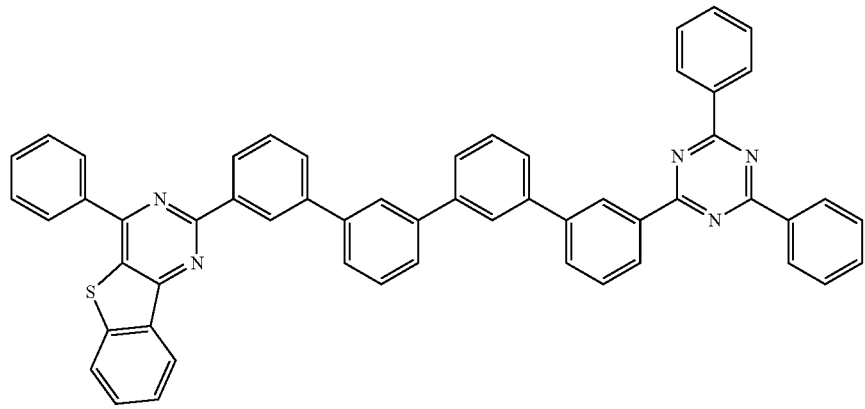
[H-90] [H-91]
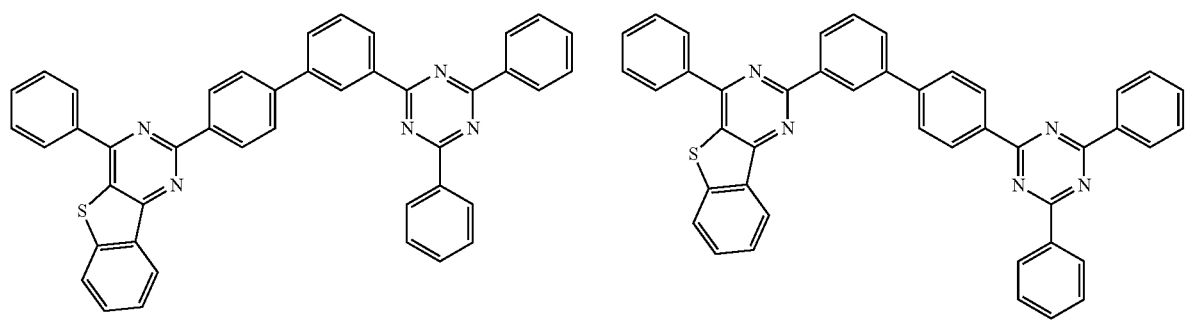
[H-92] [H-93]
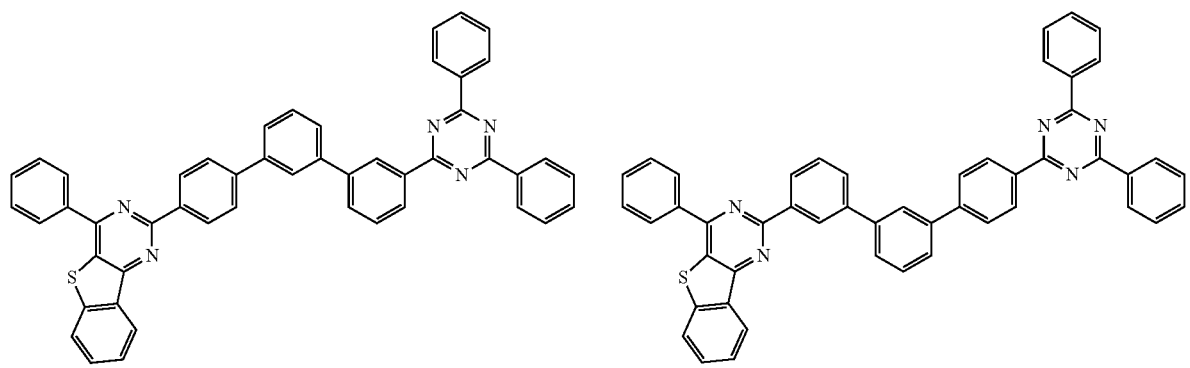
[H-110] [H-111]
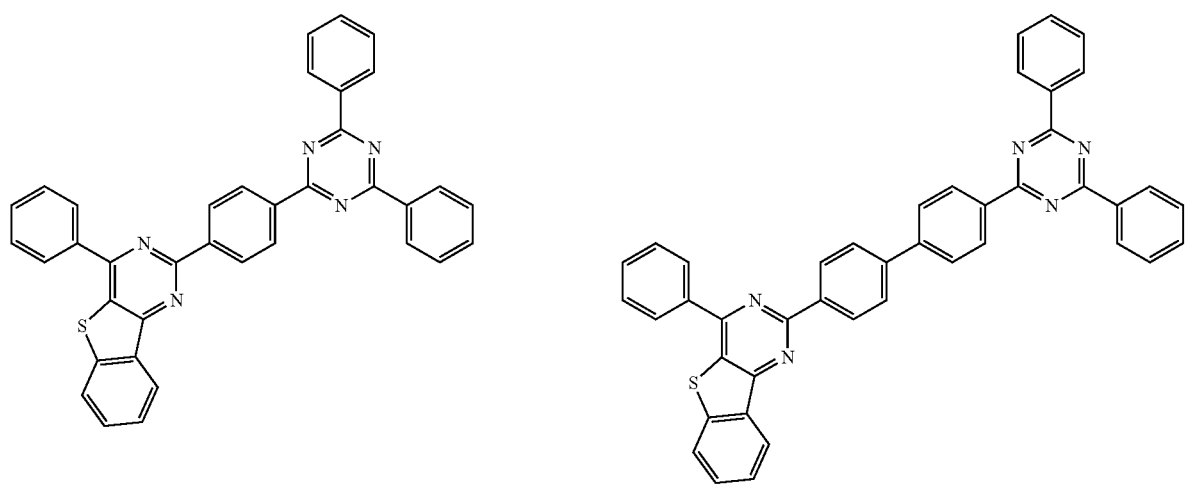

[H-113]
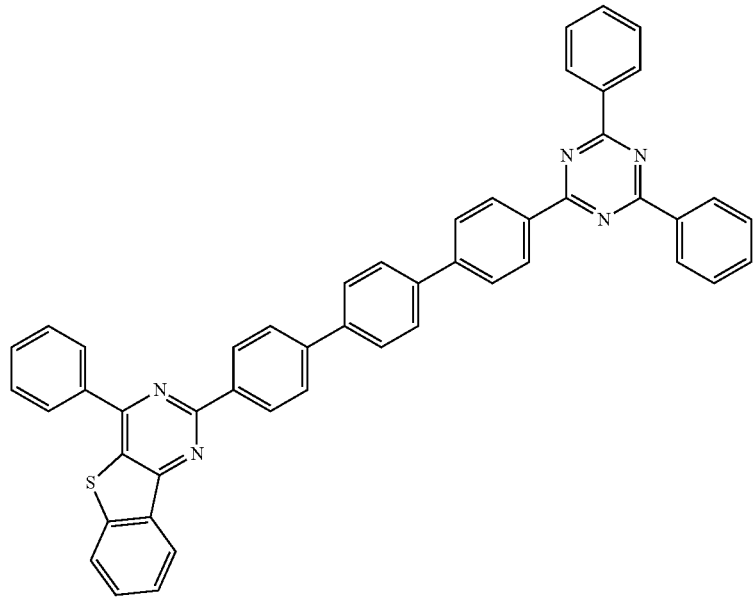
[H-114]
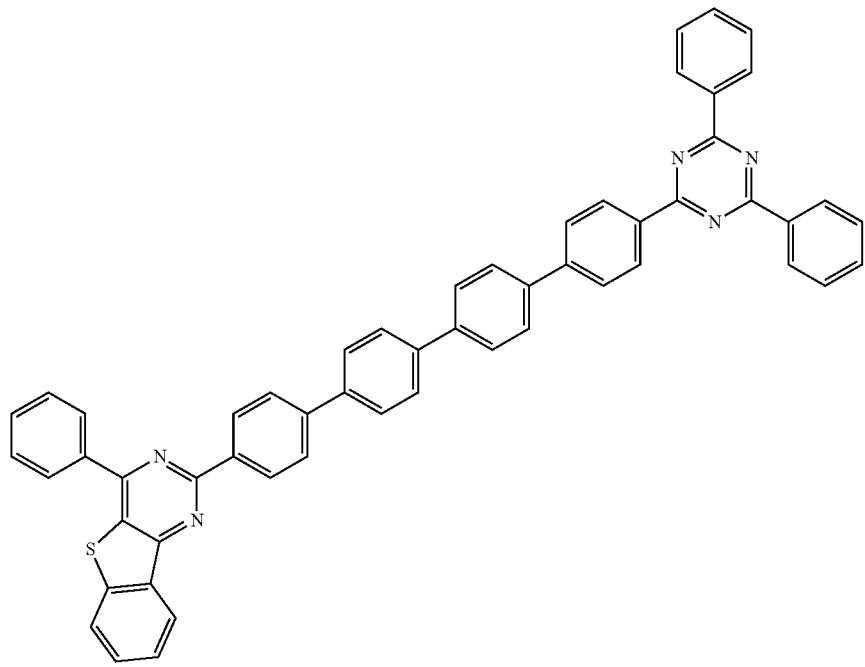
[H-229] [H-230]
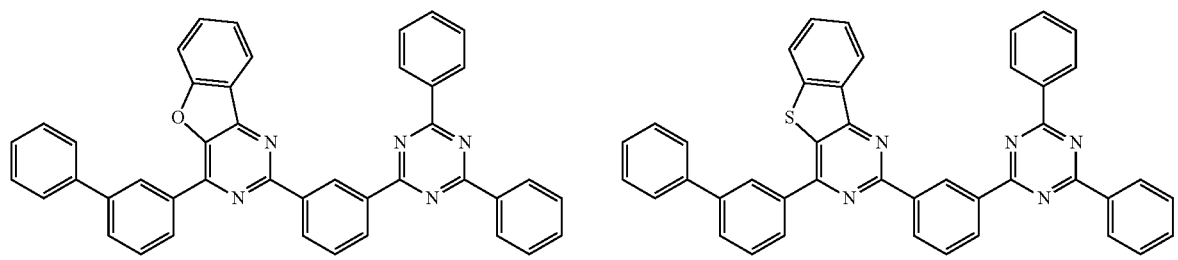

[H-231] 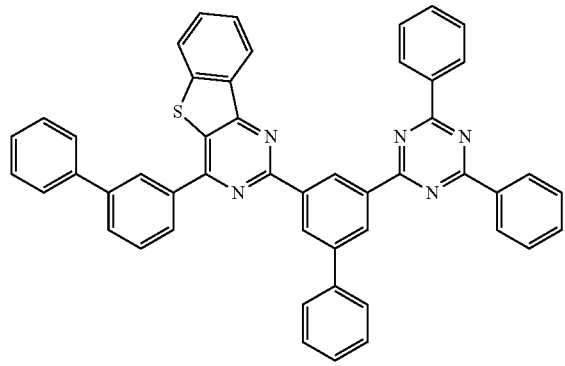
[H-232] 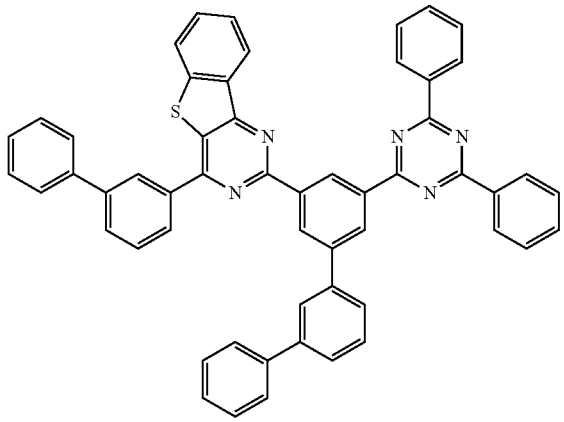
[H-233] 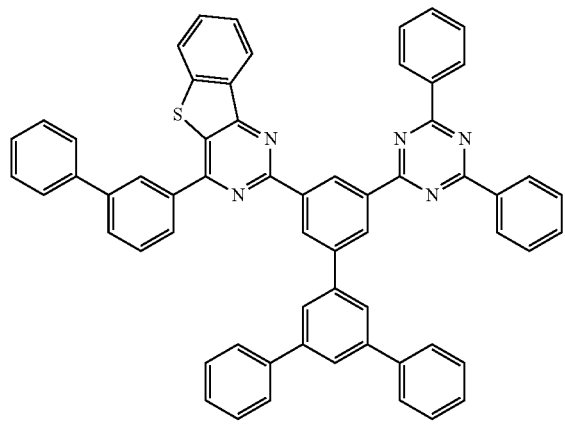
[H-234] 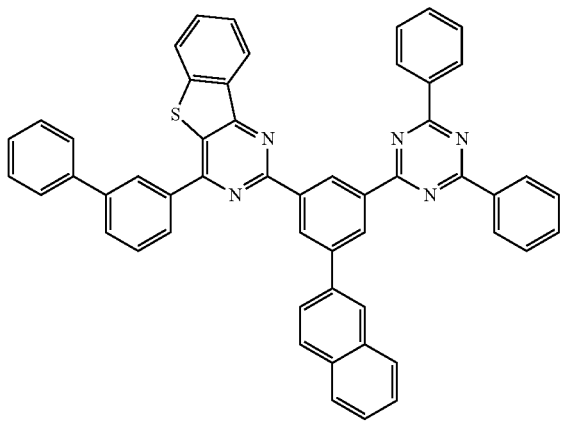
2. The composition for an organic optoelectronic device of claim 1, wherein Chemical Formula 1 is represented by one of Chemical Formulae 1-I to 1-III:
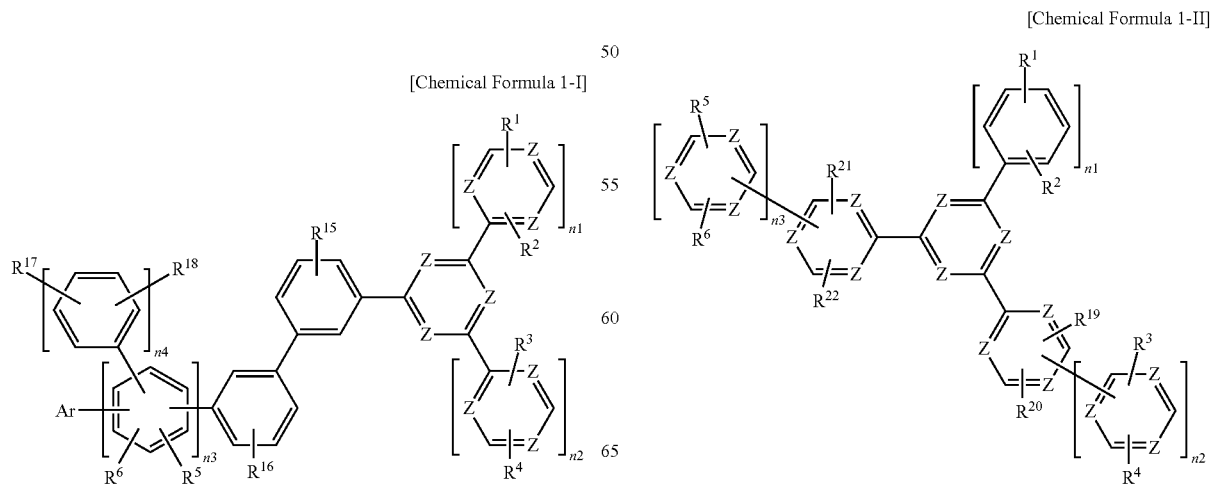

[Chemical Formula 1-III]

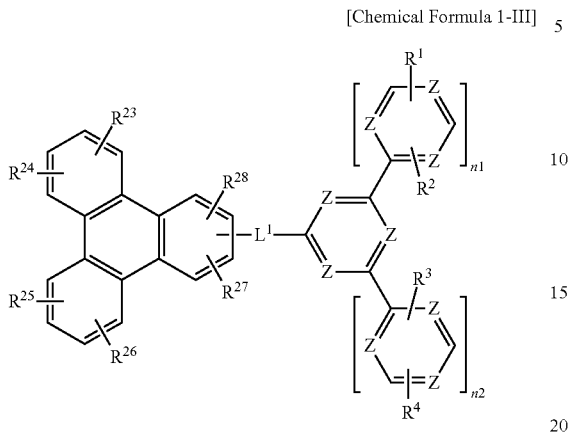

[Chemical Formula 1-IA]

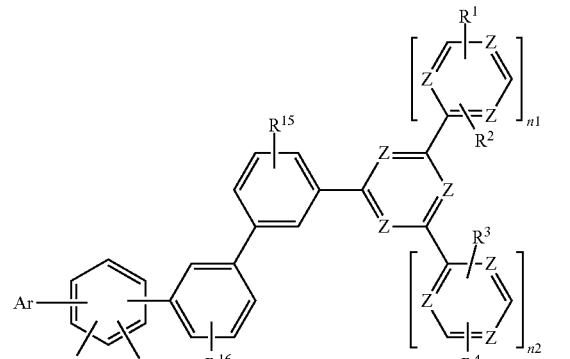

[Chemical Formula 1-IB]

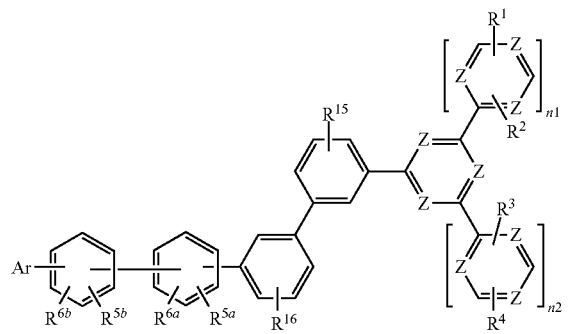

[Chemical Formula 1-IC]

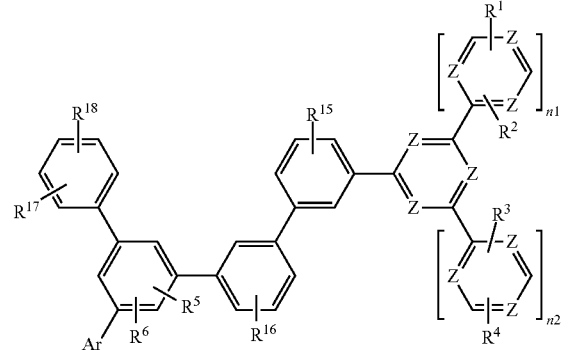

wherein, in Chemical Formulae 1-I to 1-III,

Z is independently N, C, or $CR^a$, at least one of Z is N, $R^1$ to $R^6$, $R^{15}$ to $R^{28}$, and $R^a$ are independently hydrogen, deuterium, a substituted or unsubstituted C1 to C10 alkyl group, a substituted or unsubstituted C6 to C12 aryl group, a substituted or unsubstituted C2 to C30 heteroaryl group, or a combination thereof, Ar is a substituted or unsubstituted C6 to C30 aryl group, a substituted or unsubstituted C2 to C30 heterocyclic group, or a combination thereof, $R^1$ to $R^6$, $R^a$, $R^{17}$, and $R^{18}$ are independently present or adjacent groups are linked to each other to form a ring, $L^1$ is a single bond, a substituted or unsubstituted C6 to C30 arylene group, a substituted or unsubstituted C2 to C30 heteroarylene group, or a combination thereof, n1 is an integer of 1, n2 is an integer of 0 or 1, n3 and n4 are independently an integer ranging from 0 to 2, 1≤n2+n3≤2, and "substituted" refers to replacement of at least one hydrogen by deuterium, a halogen, a hydroxyl group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

3. The composition for an organic optoelectronic device of claim 2, wherein Chemical Formula 1 is represented by Chemical Formula 1-I, and Chemical Formula 1-I is represented by one of Chemical Formulae 1-IA to 1-IC:

wherein, in above Chemical Formulae 1-IA to 1-IC,

Z is independently N, C, or $CR^a$, at least one of Z is N, $R^1$ to $R^6$, $R^a$, $R^{5a}$, $R^{6a}$, $R^{5b}$, $R^{6b}$, and $R^{15}$ to $R^{18}$ are independently hydrogen, deuterium, a substituted or unsubstituted C1 to C10 alkyl group, a substituted or unsubstituted C6 to C12 aryl group, a substituted or unsubstituted C2 to C30 heteroaryl group, or a combination thereof, $R^1$ to $R^6$, $R^a$, $R^{5a}$, $R^{6a}$, $R^{5b}$, $R^{6b}$, $R^{17}$, and $R^{18}$ are independently present or adjacent groups are linked to each other to form a ring, Ar is a substituted or unsubstituted C6 to C30 aryl group, a substituted or unsubstituted C2 to C30 heterocyclic group, or a combination thereof, n1 is an integer of 1, n2 is an integer of 0 or 1, and "substituted" refers to replacement of at least one hydrogen by deuterium, a halogen, a hydroxyl group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

4. The composition for an organic optoelectronic device of claim 2, wherein Chemical Formula 1 is represented by Chemical Formula 1-II, and Chemical Formula 1-II is represented by Chemical Formula 1-IIA or 1-IIB:

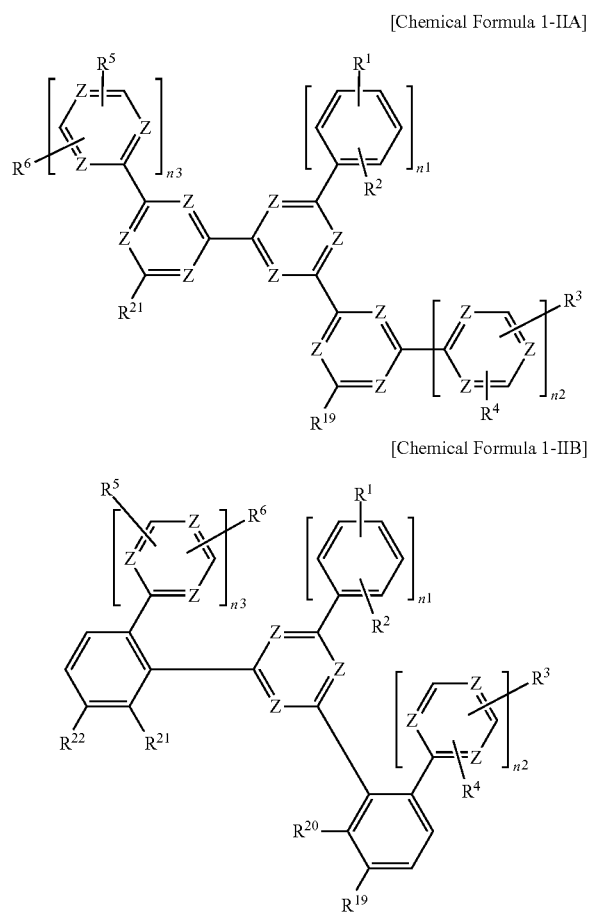

5. The composition for an organic optoelectronic device of claim 2, wherein Chemical Formula 1 is represented by Chemical Formula 1-III, and Chemical Formula 1-III is represented by Chemical Formula 1-IIIA or 1-IIIB:

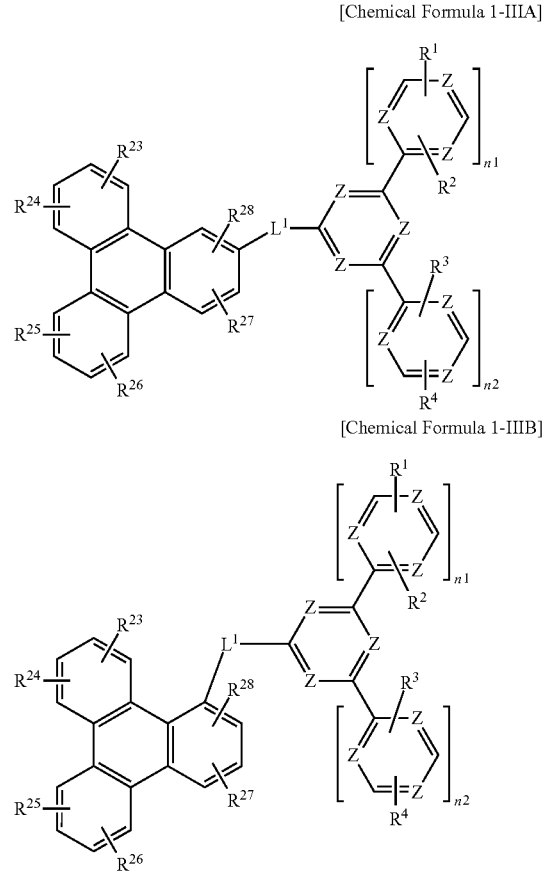

wherein, in Chemical Formulae 1-IIA and 1-IIB,
Z is independently N, C, or $CR^a$,
at least one of Z is N,
$R^1$ to $R^6$, $R^{19}$ to $R^{22}$, and $R^a$ are independently hydrogen, deuterium, a substituted or unsubstituted C1 to C10 alkyl group, a substituted or unsubstituted C6 to C12 aryl group, a substituted or unsubstituted C2 to C30 heteroaryl group, or a combination thereof,
$R^1$ to $R^6$, $R^{19}$ to $R^{22}$, and $R^a$ are independently present or adjacent groups are linked to each other to form a ring,
n1 is an integer of 1,
n2 and n3 are independently an integer of 0 or 1,
$1 \leq n2+n3 \leq 2$, and
"substituted" refers to replacement of at least one hydrogen by deuterium, a halogen, a hydroxyl group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

wherein, in Chemical Formulae 1-IIIA and 1-IIIB,
Z is independently N, C, or $CR^a$,
at least one of Z is N,
$R^1$ to $R^4$, $R^{23}$ to $R^{28}$, and $R^a$ are independently hydrogen, deuterium, a substituted or unsubstituted C1 to C10 alkyl group, a substituted or unsubstituted C6 to C12 aryl group, a substituted or unsubstituted C2 to C30 heteroaryl group, or a combination thereof,
$R^1$ to $R^4$ and $R^a$ are independently present or adjacent groups are linked to each other to form a ring,
$L^1$ is a single bond, a substituted or unsubstituted phenylene group, a substituted or unsubstituted biphenylene group or a substituted or unsubstituted terphenylene group,
n1 is an integer of 1,
n2 is an integer of 0 or 1, and
"substituted" refers to replacement of at least one hydrogen by deuterium, a halogen, a hydroxyl group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

6. The composition for an organic optoelectronic device of claim 1, wherein Chemical Formula 2 is represented by one of Chemical Formulae 2-I to 2-III:

[Chemical Formula 2-I]

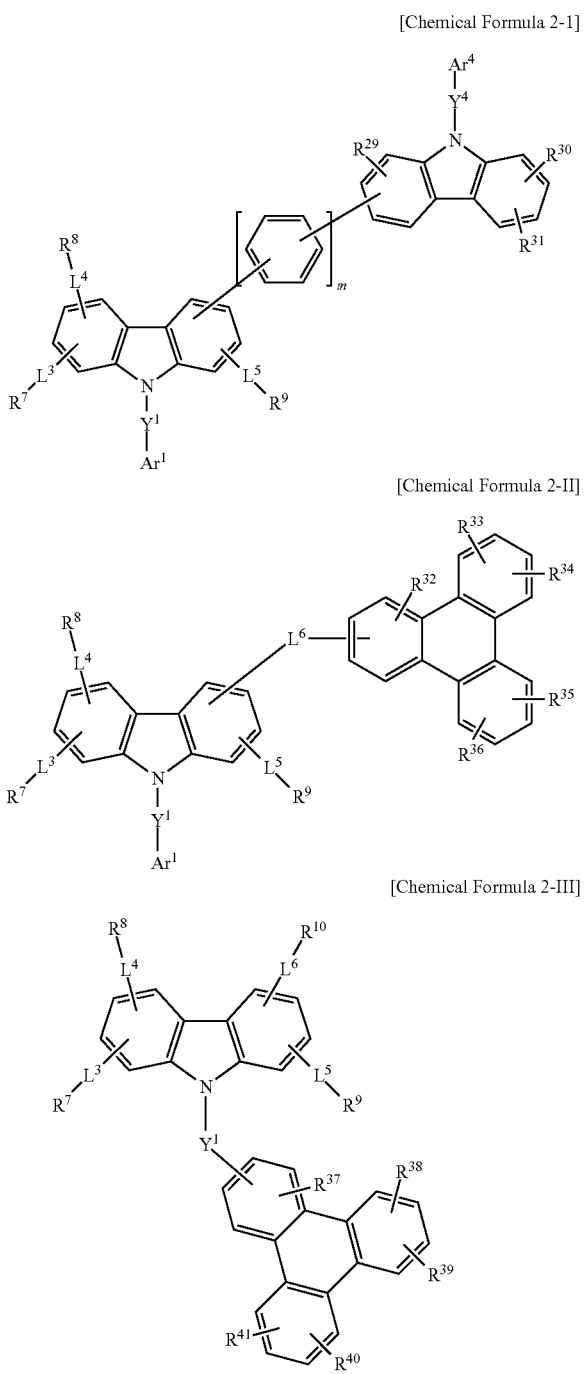

[Chemical Formula 2-II]

[Chemical Formula 2-III]

wherein, in Chemical Formula 2-I to 2-III,
L³ to L⁶, Y¹, and Y⁴ are independently a single bond, a substituted or unsubstituted C6 to C30 arylene group, a substituted or unsubstituted C2 to C30 heteroarylene group, or a combination thereof,
Ar¹ and Ar⁴ are independently substituted or unsubstituted C6 to C30 aryl group, a substituted or unsubstituted C2 to C30 heterocyclic group, or a combination thereof,
R⁷ to R¹⁰ and R²⁹ to R⁴¹ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, m is an integer of 0 to 4, and
"substituted" refers to replacement of at least one hydrogen by deuterium, a halogen, a hydroxyl group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

7. The composition for an organic optoelectronic device of claim 6, wherein Ar¹ and Ar⁴ of Chemical Formulae 2-I to 2-III are independently, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, a substituted or unsubstituted dibenzofuranyl group, a substituted or unsubstituted dibenzothiophenyl group, a substituted or unsubstituted pyridinyl group, or a combination thereof.

8. The composition for an organic optoelectronic device of claim 6, wherein Chemical Formula 2 is represented by Chemical Formula 2-I, and Chemical Formula 2-I comprises one of structures of Group 3 and the *—Y¹—Ar¹, *Y⁴—Ar⁴ are one of substituents of Group 4:

[Group 3]

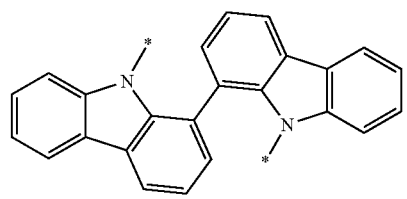
C-1

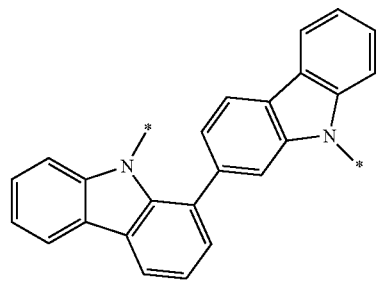
C-2

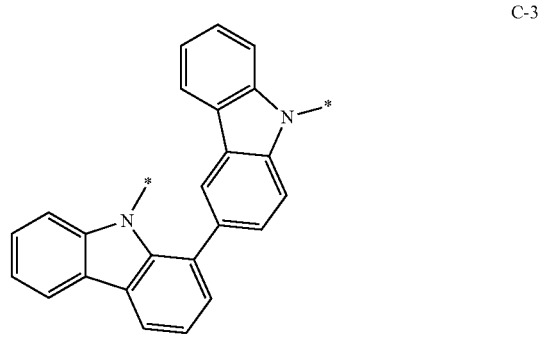
C-3

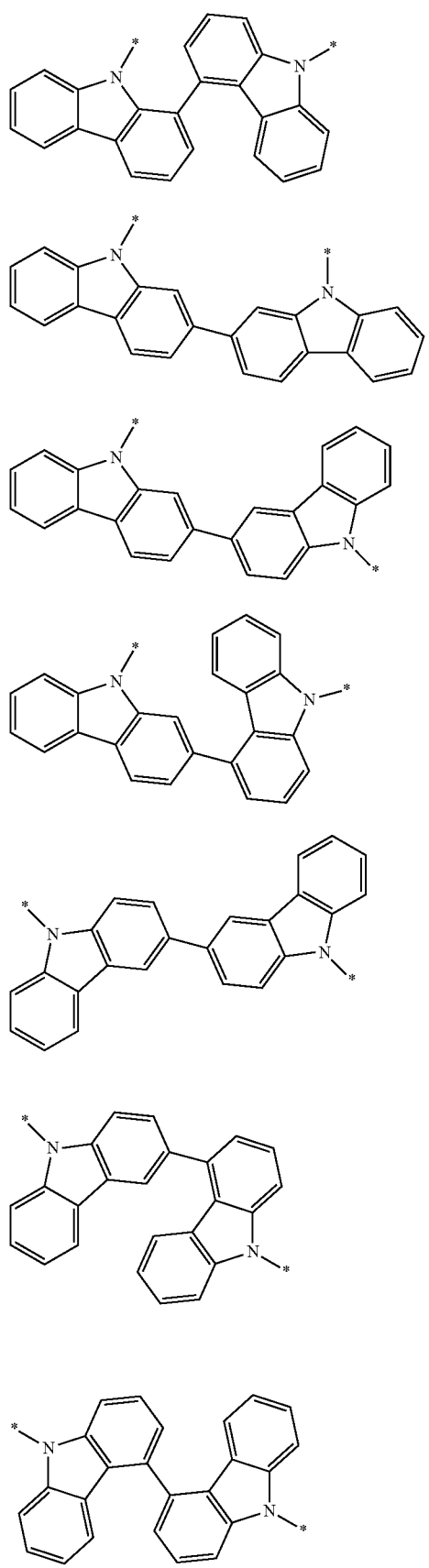
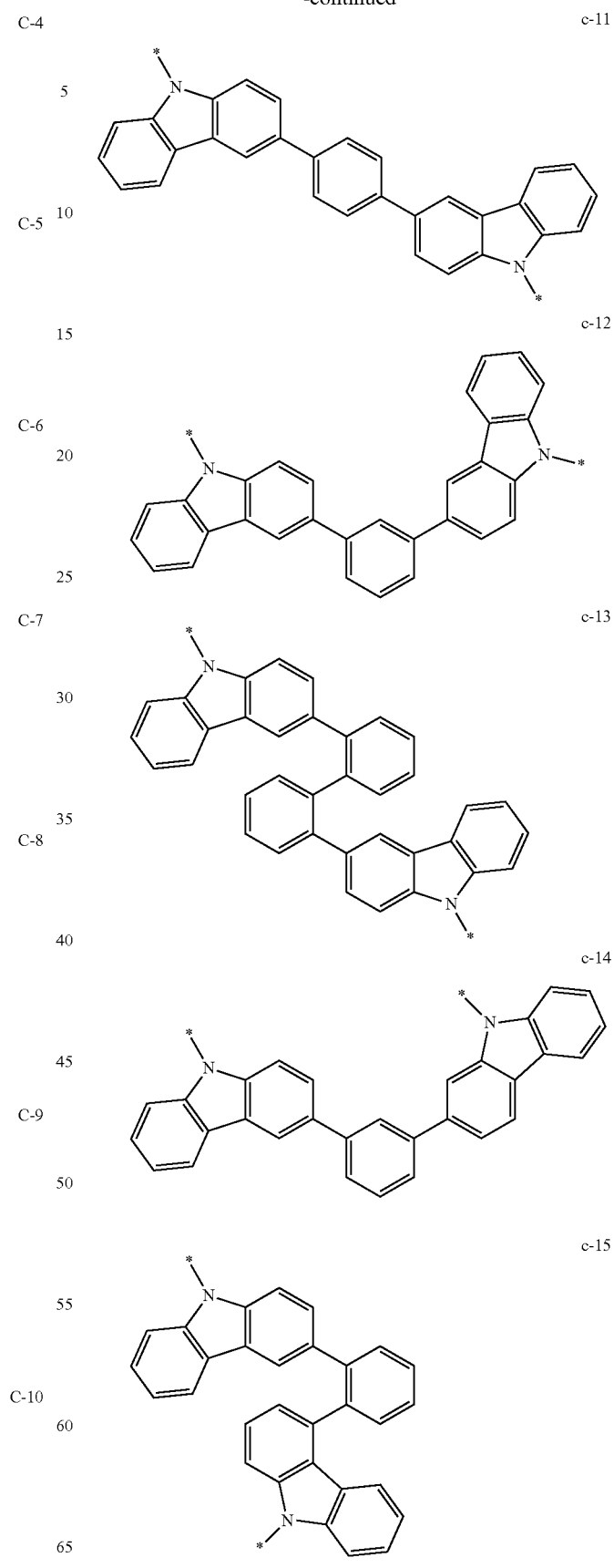

[Group 4]
B-1 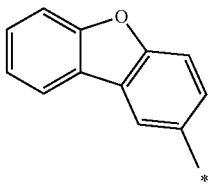
B-2 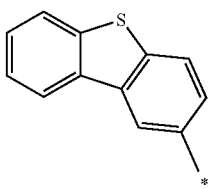
B-3 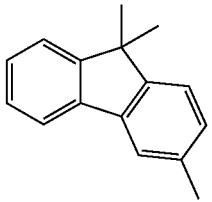
B-4 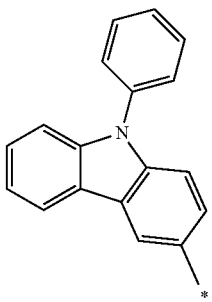
B-5 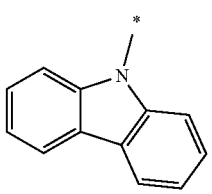
B-6 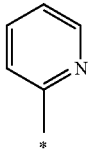
B-7 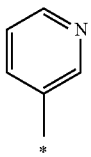
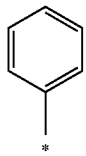
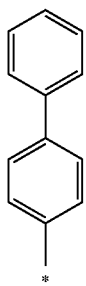
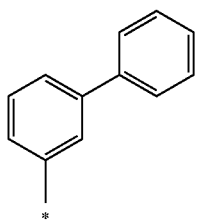
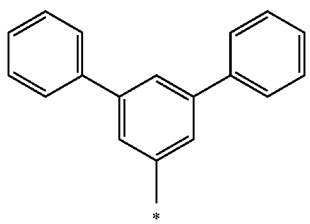
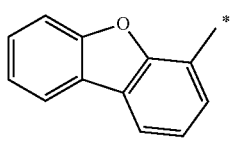
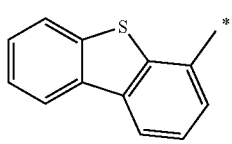
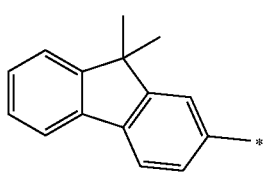
B-8
B-9
B-10
B-11
B-12
B-13
B-14

-continued

B-15 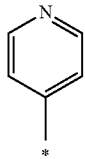

B-16 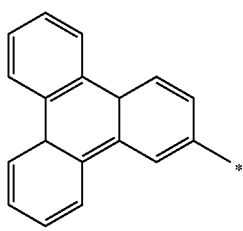

B-17 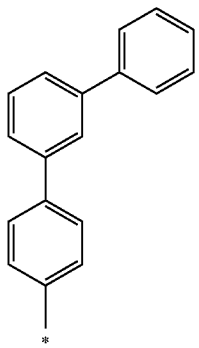

B-18 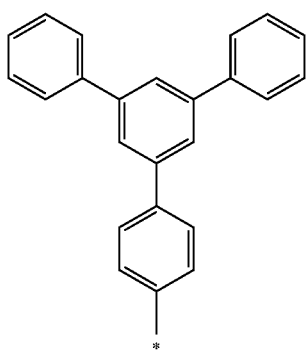

wherein, in Group 3 and Group 4, * is a linking point.

9. The composition for an organic optoelectronic device of claim 1, wherein the second compound consists of a combination of the moiety represented by Chemical Formula 3 and the moiety represented by Chemical Formula 4, and the second compound consisting of a combination of the moiety represented by Chemical Formula 3 and the moiety represented by Chemical Formula 4 is represented by at least one of Chemical Formulae 3-I to 3-V:

[Chemical Formula 3-I]
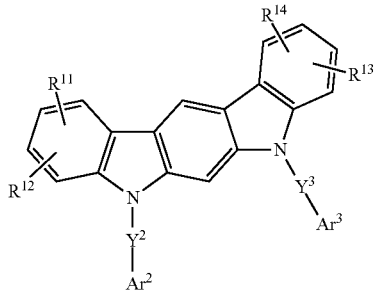

[Chemical Formula 3-II]
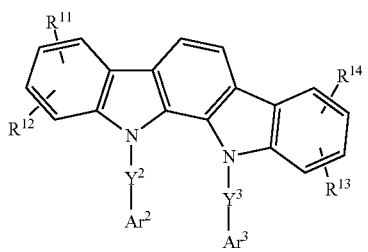

[Chemical Formula 3-III]
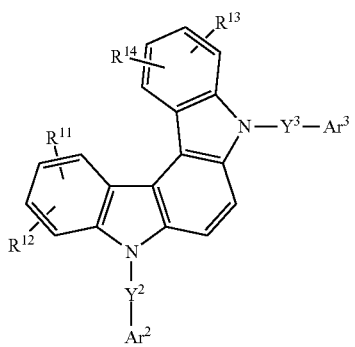

[Chemical Formula 3-VI]
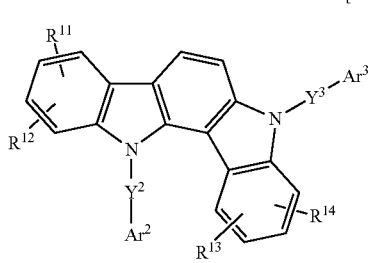

[Chemical Formula 3-V]
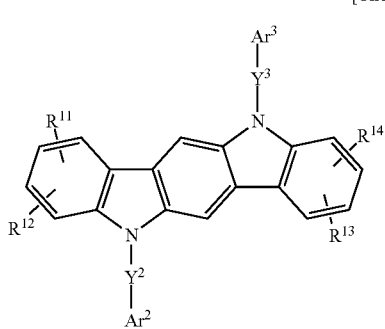

wherein, in Chemical Formulae 3-I to 3-V,
$Y^2$ and $Y^3$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^2$ and $Ar^3$ are independently substituted or unsubstituted C6 to C30 aryl group, a substituted or unsubstituted C2 to C30 heterocyclic group, or a combination thereof, $R^{11}$ to $R^{14}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and "substituted" refers to replacement of at least one hydrogen by deuterium, a halogen, a hydroxyl group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

10. The composition for an organic optoelectronic device of claim 1, wherein:
the first compound is represented by Chemical Formula 1-I or Chemical Formula 1-III, and
the second compound is represented by Chemical Formula 2-I:

[Chemical Formula 1-I]

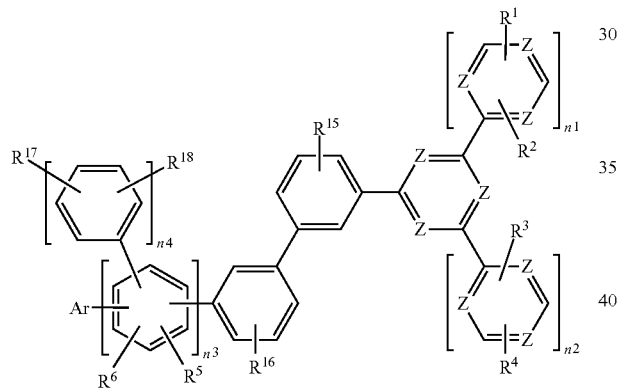

[Chemical Formula 1-III]

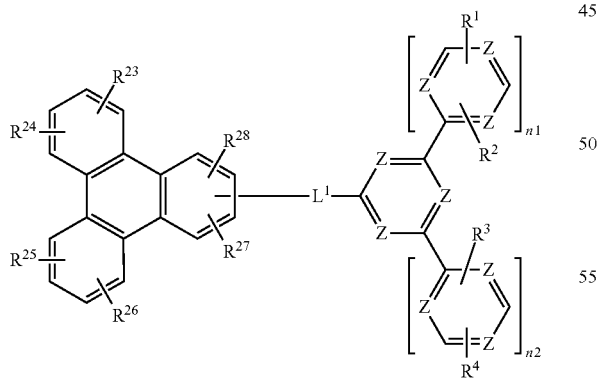

wherein, in Chemical Formulae 1-I and 1-III,
Z is independently N, C, or $CR^a$,
at least one of Z is N,
$R^1$ to $R^6$, $R^{15}$ to $R^{18}$, $R^{23}$ to $R^{28}$, and $R^a$ are independently hydrogen, deuterium, a substituted or unsubstituted C1 to C10 alkyl group, or a substituted or unsubstituted C6 to C12 aryl group, Ar is independently a substituted or unsubstituted C6 to C30 aryl group, a substituted or unsubstituted C2 to C30 heterocyclic group, or a combination thereof, $R^1$ to $R^6$, $R^{15}$ to $R^{18}$, $R^{23}$ to $R^{28}$, and $R^a$ are independently present or adjacent groups are linked to each other to form a ring, $L^1$ is a single bond, a substituted or unsubstituted phenylene group, a substituted or unsubstituted biphenylene group, a substituted or unsubstituted terphenylene group, a substituted or unsubstituted quarterphenylene group, a substituted or unsubstituted naphthylene group, a substituted or unsubstituted anthracenylene group, a substituted or unsubstituted triphenylenyl group, or a substituted or unsubstituted phenanthrenylene group, n1 is an integer of 1, n2 and n3 are independently an integer of 0 or 1, and n4 is an integer ranging from 0 to 2;

[Chemical Formula 2-I]

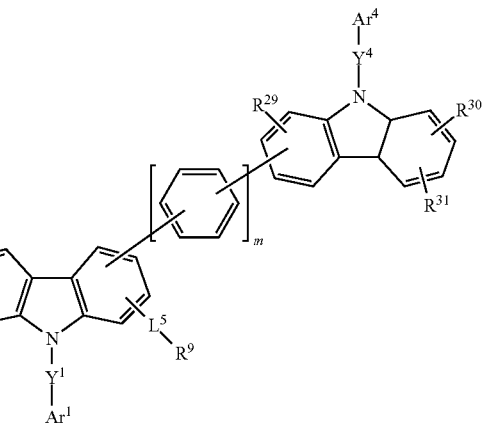

wherein, in Chemical Formula 2-I, $L^3$ to $L^5$, $Y^1$, and $Y^4$ are independently a single bond, or a substituted or unsubstituted C6 to C30 arylene group, $Ar^1$ and $Ar^4$ are independently substituted or unsubstituted C6 to C30 aryl group, a substituted or unsubstituted C2 to C30 heterocyclic group, or a combination thereof, $R^7$ to $R^9$ and $R^{29}$ to $R^{31}$ are independently hydrogen, deuterium, a substituted or unsubstituted C1 to C20 alkyl group, or a substituted or unsubstituted C6 to C50 aryl group, and m is an integer of 0 or 1; and "substituted" refers to replacement of at least one hydrogen by deuterium, a halogen, a hydroxyl group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

11. The composition for an organic optoelectronic device of claim 10, wherein the first compound is represented by Chemical Formula 1-IB or 1-IIIA:

[Chemical Formula 1-IB]

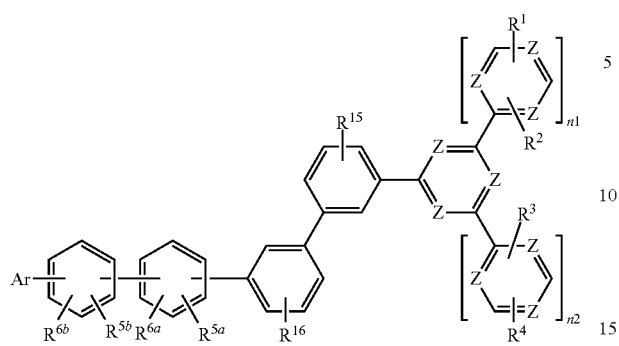

wherein, in Chemical Formula 1-IB,
Z is independently N, C, or $CR^a$,
at least one of Z is N,
$R^1$ to $R^4$, $R^{15}$, $R^{16}$, $R^{5a}$, $R^{6a}$, $R^{5b}$, and $R^{6b}$ are independently hydrogen, deuterium, a substituted or unsubstituted C1 to C10 alkyl group, or a substituted or unsubstituted C6 to C12 aryl group,
Ar is independently a substituted or unsubstituted C6 to C30 aryl group, a substituted or unsubstituted C2 to C30 heterocyclic group, or a combination thereof,
$R^{5a}$ and $R^{6a}$ and $R^{5b}$ and $R^{6b}$ are independently present or adjacent groups are linked to each other to form a ring,
n1 is an integer of 1, and
n2 is an integer of 0 or 1;

[Chemical Formula 1-IIIA]

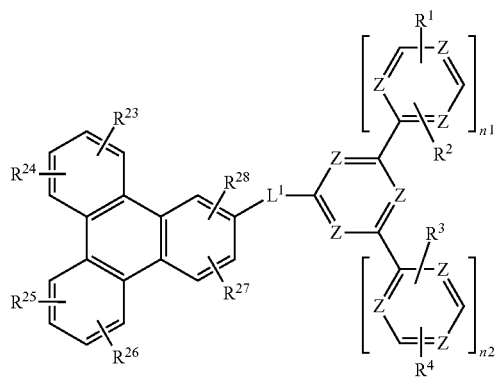

wherein, in Chemical Formula 1-IIIA,
Z is independently N, C, or $CR^a$,
at least one of Z is N,
$R^1$ to $R^4$, $R^{23}$ to $R^{28}$ and $R^a$ are independently hydrogen, deuterium, a substituted or unsubstituted C1 to C10 alkyl group, a substituted or unsubstituted C6 to C12 aryl group, a substituted or unsubstituted C2 to C30 heteroaryl group, or a combination thereof,
$R^1$ to $R^4$ and $R^a$ are independently present or adjacent groups are linked to each other to form a ring,
$L^1$ is a single bond, a substituted or unsubstituted phenylene group, a substituted or unsubstituted biphenylene group, a substituted or unsubstituted terphenylene group, a substituted or unsubstituted quarterphenylene group, a substituted or unsubstituted naphthylene group, a substituted or unsubstituted anthracenylene group, a substituted or unsubstituted triphenylenyl group, or a substituted or unsubstituted phenanthrenylene group,
n1 is an integer of 1,
n2 is an integer of 0 or 1; and
"substituted" refers to replacement of at least one hydrogen by deuterium, a halogen, a hydroxyl group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

12. The composition for an organic optoelectronic device of claim 1, which further comprises a phosphorescent dopant.

13. An organic optoelectronic device comprising
an anode and a cathode facing each other, and
at least one organic layer interposed between the anode and the cathode wherein the organic layer includes the composition for an organic optoelectronic device of claim 1.

14. A display device comprising the organic optoelectronic device of claim 13.

* * * * *